(12) United States Patent
Chenard et al.

(10) Patent No.: US 10,519,158 B2
(45) Date of Patent: *Dec. 31, 2019

(54) INHIBITING THE TRANSIENT RECEPTOR POTENTIAL A1 ION CHANNEL

(71) Applicant: Eli Lilly and Company, Indianapolis, IN (US)

(72) Inventors: Bertrand L. Chenard, Waterford, CT (US); Xinyuan Wu, Newton, MA (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/234,809

(22) Filed: Dec. 28, 2018

(65) Prior Publication Data

US 2019/0330212 A1 Oct. 31, 2019

Related U.S. Application Data

(63) Continuation of application No. 15/512,213, filed as application No. PCT/US2015/051063 on Sep. 18, 2015, now Pat. No. 10,221,177.

(60) Provisional application No. 62/052,678, filed on Sep. 19, 2014.

(51) Int. Cl.
| | |
|---|---|
| *C07D 473/06* | (2006.01) |
| *A61K 31/52* | (2006.01) |
| *C07D 473/08* | (2006.01) |
| *C07K 14/705* | (2006.01) |
| *A61K 9/20* | (2006.01) |
| *A61K 31/00* | (2006.01) |

(52) U.S. Cl.
CPC .......... *C07D 473/08* (2013.01); *A61K 9/2018* (2013.01); *A61K 31/52* (2013.01); *C07D 473/06* (2013.01); *C07K 14/705* (2013.01); *A61K 9/20* (2013.01); *A61K 31/00* (2013.01)

(58) Field of Classification Search
CPC .............................. C07D 473/06; A61K 31/52
See application file for complete search history.

(56) References Cited

U.S. PATENT DOCUMENTS

| 10,221,177 B2* | 3/2019 | Chenard .............. C07D 473/06 |
| 2017/0050966 A1 | 2/2017 | Lippa et al. |
| 2018/0230149 A1 | 8/2018 | Lippa et al. |

FOREIGN PATENT DOCUMENTS

| WO | 2009002933 A1 | 12/2008 |
| WO | 2009140517 A1 | 11/2009 |
| WO | 2010036821 A1 | 4/2010 |
| WO | 2013023102 A1 | 2/2013 |
| WO | 2014/113671 A1 | 7/2014 |
| WO | 2014189466 A1 | 11/2014 |

OTHER PUBLICATIONS

Chen et al. "TRPA1 as a drug target—promises and challenges," Naunyn-Schmiedeberg's Arch Pharmacol, 2015, 388:451-463.
International Search Report and Written Opinion from corresponding International Application No. PCT/US2015/051063 dated Dec. 15, 2015.
WEBMD. "What is inflammation," 2016. Web: <http://www.webmd.com/arthritis/about-inflammation#2>.
Patani, George A. and Edmond J. LaVoie, "Bioisosterism: A Rational Approach in Drug Design," Chem. Rev. 1996, 96, 3147-3176.

* cited by examiner

*Primary Examiner* — Emily A Bernhardt
*Assistant Examiner* — Laura M Daniel
(74) *Attorney, Agent, or Firm* — Nelsen L Lentz

(57) ABSTRACT

The present invention relates to pharmaceutical compounds of the Formula (I), or a pharmaceutically acceptable salt or composition thereof, and methods of their use for the treatment of pain, respiratory conditions, as well as inhibiting the Transient Receptor Potential A1 ion channel (TRPA1).

20 Claims, No Drawings

INHIBITING THE TRANSIENT RECEPTOR POTENTIAL A1 ION CHANNEL

CROSS-REFERENCE TO RELATED APPLICATIONS

This application is a continuation of U.S. patent application Ser. No. 15/512,213, filed Mar. 17, 2017, which is a U.S. National Phase Application under 35 U.S.C. § 371 of International Application No. PCT/US2015/051063, filed Sep. 18, 2015, which claims the benefit of U.S. Provisional Application 62/052,678 filed on Sep. 19, 2014. The entire contents of these applications are incorporated herein by reference in their entirety.

TECHNICAL FIELD

The present invention relates to pharmaceutical compounds, compositions, and methods for the treatment of pain, respiratory conditions, as well as inhibiting the Transient Receptor Potential A1 ion channel (TRPA1).

BACKGROUND

Transient Receptor Potential A1(herein, "TRPA1") is a non-selective cation channel related to pain sensation in humans. TRPA1 is found in sensory neurons and functions as a detector that helps link detection of noxious chemicals, tissue damage, and inflammation to pain. Activation of TRPA1 is believed to cause pain by inducing firing of nociceptive neurons and driving central sensitization in the spinal cord. TRPA1 stimulation can also increase firing of sensory neurons, leading to the release of pro-inflammatory neuropeptides such as NK-A, substance P and CGRP (which induce vasodilation and help recruit immune cells). A variety of endogenous reactive compounds produced during inflammation activate TRPA1 (including 4-hydroxynonenal released during liposome peroxidation; cyclopentane prostaglandins synthesized by COX enzymes; hydrogen peroxide produced by oxidative stress). Activation of TRPA1 also sensitizes TRPA1 to cold. Furthermore, a gain-of-function mutation in TRPA1 causes familial episodic pain syndrome; patients suffering from this condition have episodic pain that may be triggered by cold. Thus, TRPA1 is considered to play a role in pain related to nerve damage, cold allodynia, and inflammatory pain.

Compounds that inhibit the TRPA1 ion channel can be useful, for example, in treating conditions ameliorated, eliminated or prevented by inhibition of the TRPA1 ion channel. For example, pharmaceutical compositions that inhibit TRPA1 can be used to treat pain. Inhibition of TRPA1 (e.g., by genetic ablation and chemical antagonism) has been shown to result in reduced pain behavior in mice and rats. Knockout mice lacking functional TRPA1 have diminished nociceptive responses to TRPA1 activators (including AITC, formalin, acrolein, 4-hydroxynonenal) and, in addition, have greatly reduced thermal and mechanical hypersensitivity in response to the inflammatory mediator bradykinin (e.g., Kwan, K. Y. et al. Neuron 2006, 50, 277-289; Bautista, D. M. et al. Cell 2006, 124, 1269-1282). In animal pain models, down regulation of TRPA1 expression by gene specific antisenses prevented and reversed cold hyperalgesia induced by inflammation and nerve injury (See, e.g., Obata, K. et al., Journal of Clinical Investigation 2005, 115, 2393-2401; Jordt, S. E. et al., Nature 2004, 427, 260-265; Katsura, H. et al., Exploratory Neurology 2006, 200, 112-123). TRPA1 inhibitor compounds are effective in a variety of rodent pain models. TRPA1 inhibitors have been shown to reduce mechanical hypersensitivity and cold allodynia following inflammation induced by Complete Freund's Adjuvant (without altering normal cold sensation in naïve animals) and also to improve function in the rat mono-iodoacetate osteoarthritis model. Materazzi, S et al., European Journal of Physiology 2012, 463(4):561-9; Wei H et al., Anesthesiology 2012, 117(1):137-48; Koivisto, A et al., Pharmacol Res. 2012,65(1):149-58. TRPA1 inhibitor compounds have demonstrated reduced pain behavior in rodents injected with AITC (mustard oil), formalin, cinnamaldehyde, acrolein, and other TRPA1 activators. TRPA1 inhibitor compounds have also demonstrated efficacy in rodent models for post-operative pain, see, for example, Wei et al., Anesthesiology 2012, 117(1):137-48; chemotherapy induced peripheral neuropathy, see, for example, Trevisan, et al., Cancer Res. 2013 May 15;73(10):3120-31 Online Mar. 11, 2013; and painful diabetic neuropathy, see, for example, Koivisto et al., Pharmacol Res (2011).

SUMMARY OF THE INVENTION

The present invention provides compounds of the Formula (I) and pharmaceutically acceptable salts thereof:

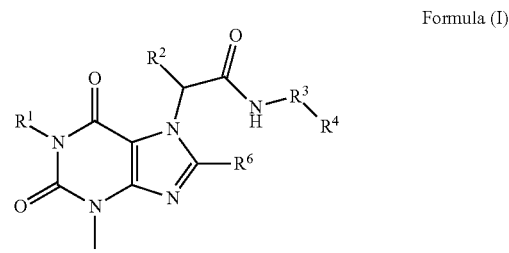

Formula (I)

wherein each of the variables above are as described herein, for example, in the detailed description below.

The present invention further provides compositions comprising a compound of Formula (I) and a pharmaceutically acceptable excipient, diluent or carrier.

The compounds and compositions described herein can be used to treat various disorders in a subject. For example, described herein are methods of treatment such as a method of treating a TRPA1 mediated disorder in a subject, the method comprising administering an effective amount of a compound of Formula (I), or a pharmaceutically acceptable salt thereof. Methods of treating pain in a subject, the method comprising administering an effective amount of a compound of Formula (I), or a pharmaceutically acceptable salt thereof are also described herein. Exemplary types of pain include neuropathic pain, e.g., painful diabetic neuropathy, chemotherapy-induced peripheral neuropathy, lower back pain, trigeminal neuralgia, post-herpetic neuralgia, sciatica, and complex regional pain syndrome; inflammatory pain, e.g., from rheumatoid arthritis, osteoarthritis, temperomandibular disorder; PDN or CIPN; visceral pain, e.g., from pancreatitis, inflammatory bowel disease, colitis, Crohn's disease, endometriosis, pelvic pain, and angina; pain selected from the group: cancer pain, burn pain, oral pain, crush and injury-induced pain, incisional pain, bone pain, sickle cell disease pain, fibromyalgia and musculo-skeletal pain; or pain from hyperalgesia or allodynia.

DETAILED DESCRIPTION

The present invention provides compounds of Formula I:

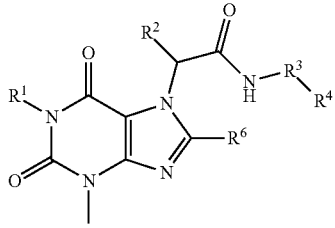

Formula (I)

or a pharmaceutically acceptable salt thereof, wherein:

$R^1$ is $C_2$-$C_6$ alkyl, $C_2$-$C_6$ alkenyl, $C_2$-$C_6$ alkynyl, —$C_1$-$C_6$ alkyl-O—$C_0$-$C_6$ alkyl, —$C_0$-$C_6$ alkyl-O—$C_1$-$C_6$ alkyl, —$C_1$-$C_6$ alkyl-C(O)—$C_0$-$C_6$ alkyl, —$C_0$-$C_6$ alkyl-C(O)—$C_1$-$C_6$ alkyl, —$C_1$-$C_6$ alkyl-C(O)N($R^8$)$_2$, —$C_1$-$C_6$ alkyl-CN, —$C_1$-$C_6$ haloalkyl, aryl, heteroaryl, heterocyclyl, heteroarylalkyl, or heterocyclylalkyl, each of which is substituted with ($R^7$)$_{1-7}$;

$R^2$ is H or $C_1$-$C_6$ alkyl;

$R^3$ is a 3 to 8-membered cycloalkyl, aryl, heterocyclyl, or heteroaryl, each of which is substituted with ($R^4$)$_{1-2}$;

$R^4$ is independently H, $C_1$-$C_3$ alkyl, $C_1$-$C_3$ alkoxy, $C_1$-$C_3$ haloalkyl, —$C_1$-$C_6$ alkyl-O—$C_0$-$C_6$ alkyl, —$C_0$-$C_6$ alkyl-O—$C_1$-$C_6$ alkyl, —N($R^8$)$_2$, 3 to 8-membered cycloalkyl, aryl, heterocyclyl, heterocyclylalkyl, heteroaryl, cyano, or halo, or two $R^4$ together with the atoms to which they are attached may form an optionally substituted 3 to 7-membered ring each of which is optionally substituted with ($R^5$)$_{1-3}$;

$R^5$ is independently H, $C_3$-$C_{10}$ heterocyclyl, $C_1$-$C_3$ alkyl, $C_1$-$C_3$ alkoxy, —$C_1$-$C_6$ alkyl-O—$C_0$-$C_6$ alkyl, —$C_0$-$C_6$ alkyl-O—$C_1$-$C_6$ alkyl, —N($C_1$-$C_3$ alkyl)$_2$, $C_1$-$C_6$ haloalkyl, —$C_1$-$C_3$ alkyl-N($R^8$)$_2$, heterocyclylalkyl, halo, cyano, or keto, each of which is optionally substituted with ($R^7$)$_{1-3}$;

$R^6$ is H or $C_1$-$C_6$ alkyl;

$R^7$ is independently H, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, hydroxy, aryl, heteroaryl, heterocyclyl, arylalkyl, aryloxy, heteroaryloxy, arylalkoxy, heteroarylalkoxy, heterarylalkyl, haloalkyl, keto, cyano, or halo, or two $R^6$ together with the atoms to which they are attached may form an optionally substituted 3 to 7-membered ring; and $R^8$ is H, $C_1$-$C_6$ alkyl, or $C_1$-$C_6$ haloalkyl.

In a second embodiment, in the general Formula I, $R^2$, $R^3$, $R^4$, $R^5$, $R^6$, $R^7$, and $R^8$ have the meaning as defined in the preceding embodiments and $R^1$ is $C_2$-$C_5$ alkyl, $C_2$-$C_4$ alkynyl, —$C_1$-$C_4$ alkyl-O—$C_0$-$C_4$ alkyl, —$C_0$-$C_4$ alkyl-O—$C_1$-$C_4$ alkyl, —$C_0$-$C_4$ alkyl-C(O)—$C_1$-$C_5$ alkyl-, —$C_1$-$C_4$ alkyl-C(O)—$C_0$-$C_5$ alkyl, $C_1$-$C_2$ alkyl-C(O)N($R^8$)$_2$, —$C_1$-$C_6$ haloalkyl-CF$_3$, —$C_2$-$C_4$ alkyl-CN, heteroarylalkyl, or heterocyclylalkyl, each of which is optionally substituted with ($R^7$)$_{1-4}$.

In another embodiment, in the general Formula I, $R^2$, $R^3$, $R^4$, $R^5$, $R^6$, $R^7$, and $R^8$ have the meaning as defined in any of the preceding embodiments, and $R^1$ is hydroxypropyl, hydroxyethyl, ketopentyl, hydroxymethyl, pyridinylmethyl, oxazolylmethyl, oxetanylmethyl, methylisooxazolylmethyl, oxadiazolylmethyl, methoxyethyl, hydroxymethoxypropyl, methyloxadiazolylmethyl, methoxyketopropyl, ketomethylbutyl, ketopropyl, ketobutyl, acetamido, cyanomethyl, methylacetamido, trifluoroethyl, trifluoropropyl, or butynyl.

In another embodiment, in the general Formula I, $R^2$, $R^3$, $R^4$, $R^5$, $R^6$, $R^7$, and $R^8$ have the meaning as defined in any of the preceding embodiments, and $R^1$ is

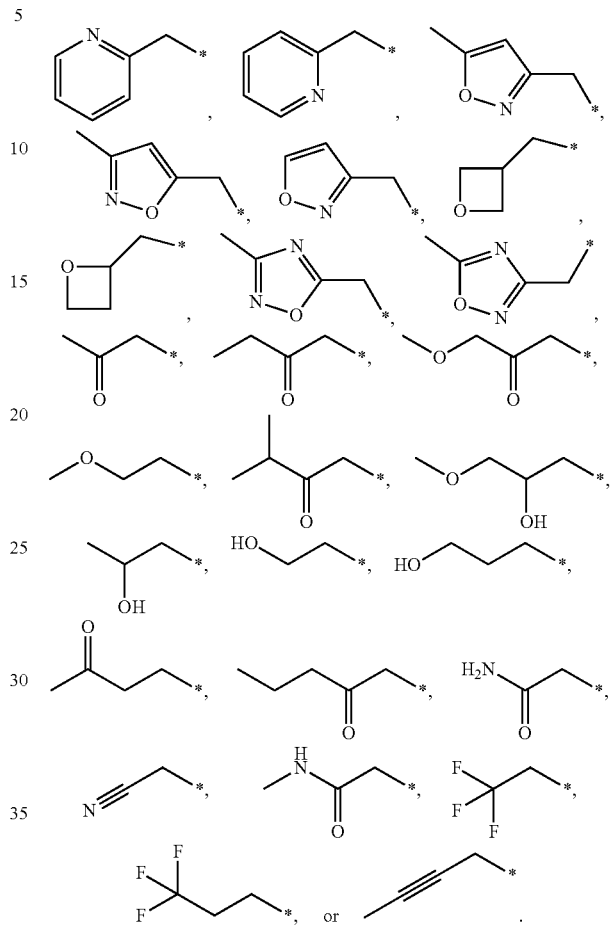

In another embodiment, in the general Formula I, $R^1$, $R^3$, $R^4$, $R^5$, $R^6$, $R^7$, and $R^8$ have the meaning as defined in any of the preceding embodiments, and $R^2$ is methyl.

In another embodiment, in the general Formula I, $R^1$, $R^3$, $R^4$, $R^5$, $R^6$, $R^7$, and $R^8$ have the meaning as defined in any of the preceding embodiments, and $R^2$ is H.

In another embodiment, in the general Formula I, $R^1$, $R^2$, $R^4$, $R^5$, $R^6$, $R^7$, and $R^8$ have the meaning as defined in any of the preceding embodiments, and $R^3$ is aryl or heteroaryl, each of which is substituted with ($R^4$)$_{1-2}$.

In another embodiment, in the general Formula I, $R^1$, $R^2$, $R^4$, $R^5$, $R^6$, $R^7$, and $R^8$ have the meaning as defined in any of the preceding embodiments, and $R^3$ is phenyl, pyridyl, pyrimidinyl, pyrazinyl, or thiazolyl, each of which is substituted with ($R^4$)$_{1-2}$.

In another embodiment, in the general Formula I, $R^1$, $R^2$, $R^4$, $R^5$, $R^6$, $R^7$, and $R^8$ have the meaning as defined in any of the preceding embodiments, and $R^3$ is

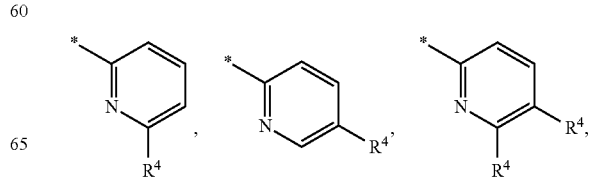

-continued

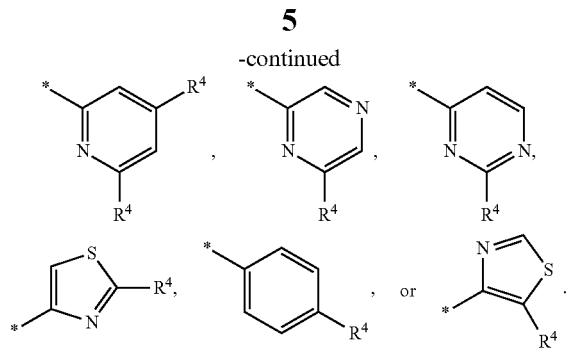

In another embodiment, in the general Formula I, $R^1$, $R^2$, $R^4$, $R^5$, $R^6$, $R^7$, and $R^8$ have the meaning as defined in any of the preceding embodiments, and $R^4$ is independently H, $C_1$-$C_3$ alkyl, $C_1$-$C_3$ alkoxy, $C_1$-$C_3$ haloalkyl, —N$(R^8)_2$, 3 to 8-membered cycloalkyl, aryl, heterocyclyl, heteroaryl, cyano, or halo, or two $R^4$ together with the atoms to which they are attached may form an optionally substituted 3 to 7-membered ring each of which is optionally substituted with $(R^5)_{1-3}$.

In another embodiment, in the general Formula I, $R^1$, $R^2$, $R^4$, $R^5$, $R^6$, $R^7$, and $R^8$ have the meaning as defined in any of the preceding embodiments, and $R^4$ is independently H, methyl, ethyl, propyl, —N$(R^8)_2$, phenyl, halo, cyano, haloalkyl, methoxy, pyridinyl, pyrimidinyl, oxadiazolyl, piperdinyl, azetidinyl, pyrazinyl, azabicyclohexyl, piperazinyl, or pyrrolidinyl, each of which is substituted with $(R^5))_{1-2}$.

In another embodiment, in the general Formula I, $R^1$, $R^2$, $R^4$, $R^5$, $R^6$, $R^7$, and $R^8$ have the meaning as defined in any of the preceding embodiments, and $R^4$ is independently H, methyl, ethyl, propyl, cyano, methoxy, chlorine, fluorine, bromine, —CF$_3$, —CF$_2$,

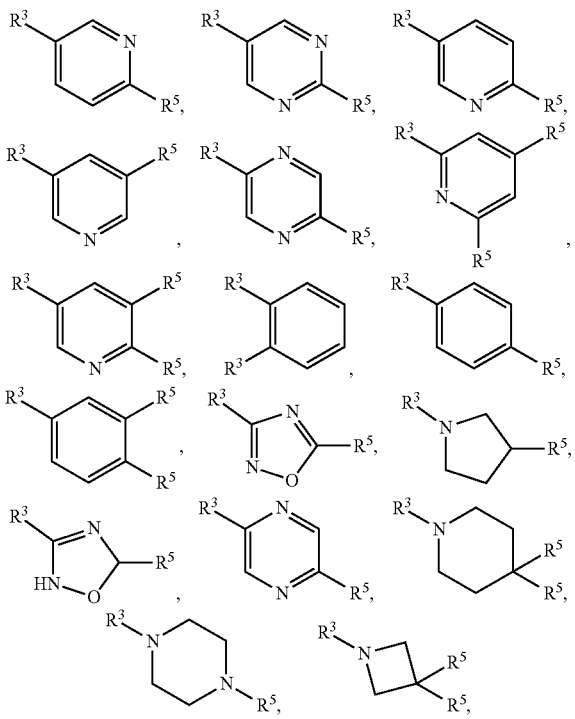

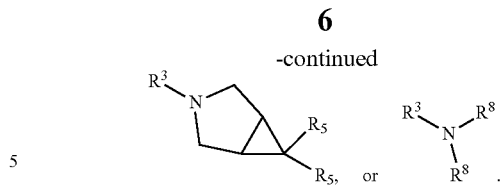

In another embodiment, in the general Formula I, $R^1$, $R^2$, $R^3$, $R^4$, $R^6$, $R^7$, and $R^8$ have the meaning as defined in any of the preceding embodiments, and $R^5$ is independently H, pyrrolidinyl, trifluoroethyl, halo, haloalkyl, methyl, isopropyl, cyano, propyl, ethyl, trifluoromethyl, azabicyclohexyl, difluoroazabicyclohexyl, keto, methoxy, methoxyethyl, dialkylamino, or ethoxy, each of which is optionally substituted with $(R^6)_{1-3}$.

In another embodiment, in the general Formula I, $R^1$, $R^2$, $R^3$, $R^4$, $R^6$, $R^7$, and $R^8$ have the meaning as defined in any of the preceding embodiments, and $R^5$ is independently H, —CF$_3$, cyanomethyl, bromine, chlorine, fluorine, methyl, ethyl, isopropyl, cyano, keto,

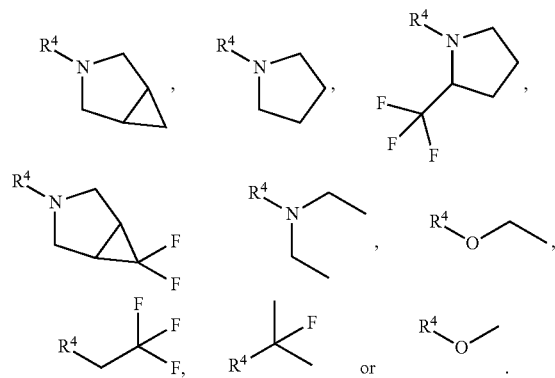

In another embodiment, in the general Formula I, $R^1$, $R^2$, $R^4$, $R^5$, $R^6$, $R^7$, and $R^8$ have the meaning as defined in any of the preceding embodiments, and $R^6$ is H.

In another embodiment, in the general Formula I, $R^1$, $R^2$, $R^4$, $R^5$, $R^6$, $R^7$, and $R^8$ have the meaning as defined in any of the preceding embodiments, and $R^6$ is methyl.

In another embodiment, in the general Formula I, $R^1$, $R^2$, $R^4$, $R^5$, $R^6$, $R^7$, and $R^8$ have the meaning as defined in any of the preceding embodiments, and $R^8$ is H, methyl, ethyl, or CF$_3$.

A further embodiment of the present invention comprises compounds of formula I in which
$R^1$ is

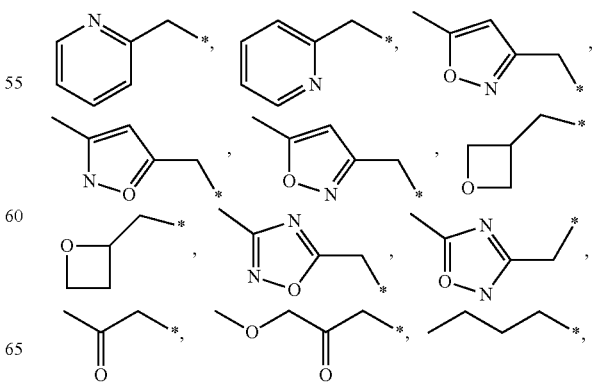

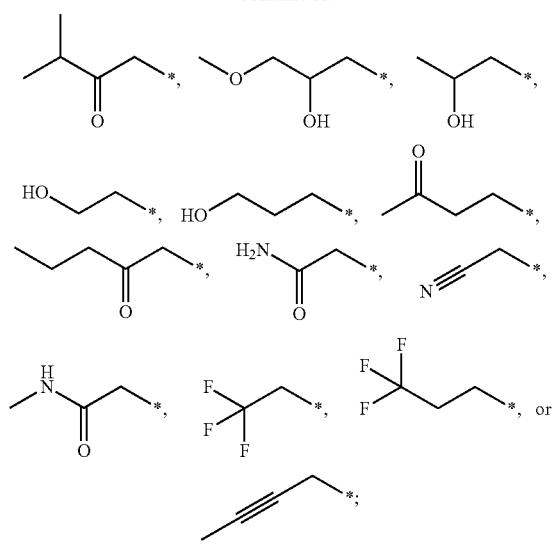

$R^2$ is H or methyl;
$R^3$ is

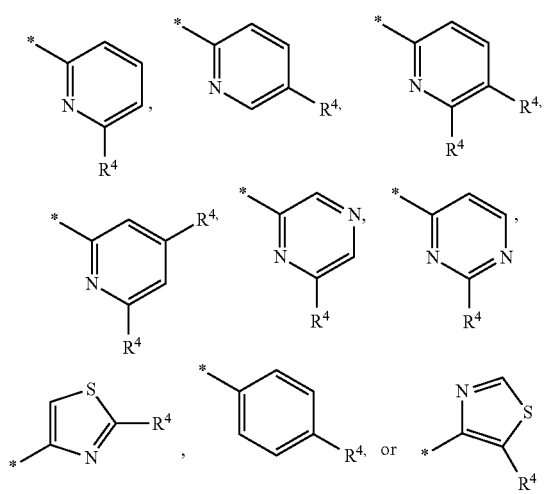

$R^4$ is is independently H, methyl, ethyl, propyl, cyano, methoxy, chlorine, fluorine, bromine, —$CF_3$, —$CF_2$,

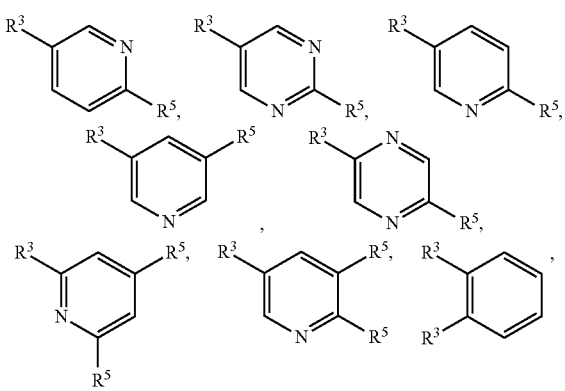

$R^5$ is independently H, —$CF_3$, cyanomethyl, bromine, chlorine, fluorine, methyl, ethyl, isopropyl, cyano, keto, $R^6$ is H or methyl; and
$R^8$ is H, methyl, ethyl, or $CF_3$.

In an embodiment, $R^4$ is independently $C_1$-$C_3$ alkyl, $C_1$-$C_3$ alkoxy, $C_1$-$C_3$ haloalkyl, —$C_1$-$C_6$ alkyl-O—$C_0$-$C_6$ alkyl, —$C_0$-$C_6$ alkyl-O—$C_1$-$C_6$ alkyl, —$N(R^8)_2$, 3 to 8-membered cycloalkyl, aryl, heterocyclyl, heterocyclylalkyl, heteroaryl, cyano, or halo, or two $R^4$ together with the atoms to which they are attached may form an optionally substituted 3 to 7-membered ring each of which is optionally substituted with $(R^5)_{1-3}$.

In an embodiment, $R^5$ is independently $C_3$-$C_{10}$ heterocyclyl, $C_1$-$C_3$ alkyl, $C_1$-$C_3$ alkoxy, —$C_1$-$C_6$ alkyl-O—$C_0$-$C_6$ alkyl, —$C_0$-$C_6$ alkyl-O—$C_1$-$C_6$ alkyl, —$N(C_1$-$C_3$ alkyl$)_2$, —$C_1$-$C_6$ haloalkyl, —$C_1$-$C_6$ alkyl-$N(R^8)_2$, heterocyclylalkyl, halo, or cyano, each of which is optionally substituted with $(R^7)_{1-3}$.

In an embodiment, $R^7$ is independently H, $C_1$-$C_6$ alkyl, $C_2$-$C_6$ alkenyl, $C_2$-$C_6$ alkynyl, $C_1$-$C_6$ alkoxy, $C_1$-$C_6$ hydroxy, aryl, heteroaryl, heterocyclyl, arylalkyl, aryloxy, heteroaryloxy, arylalkoxy, heteroarylalkoxy, heterarylalkyl, haloalkyl, keto, cyano, or halo, or two $R^6$ together with the atoms to which they are attached may form an optionally substituted 3 to 7-membered ring.

In an embodiment, $R^8$ is H, methyl, ethyl, or $CF_3$.

In another aspect, the present invention provides compounds of Formula I:

Formula (I)

or a pharmaceutically acceptable salt thereof, wherein:

$R^1$ is $C_2$-$C_6$ alkyl, $C_1$-$C_6$ alkenyl, $C_1$-$C_6$ alkynyl, —$C_1$-$C_6$ alkyl-O—$C_0$-$C_6$ alkyl, —$C_0$-$C_6$ alkyl-O—$C_1$-$C_6$ alkyl, —$C_1$-$C_6$ alkyl-C(O)—$C_0$-$C_6$ alkyl, —$C_0$-$C_6$ alkyl-C(O)—$C_1$-$C_6$ alkyl, —$C_1$-$C_6$ alkyl-C(O)N($R^8$)$_2$, —$C_1$-$C_6$ alkyl-CN, —$C_1$-$C_6$ haloalkyl, aryl, heteroaryl, heterocyclyl, heteroarylalkyl, heterocyclylalkyl, each of which is substituted with ($R^7$)$_{1-7}$;

$R^2$ is H or $C_1$-$C_6$ alkyl;

$R^3$ is a 3 to 8-member cycloalkyl, aryl, heterocyclyl, or heteroaryl, each of which is substituted with ($R^4$)$_{1-2}$;

$R^4$ is independently H, $C_1$-$C_3$ alkyl, $C_1$-$C_3$ alkoxy, $C_1$-$C_3$ haloalkyl, —$C_1$-$C_6$ alkyl-O—$C_0$-$C_6$ alkyl, —$C_0$-$C_6$ alkyl-O—$C_1$-$C_6$ alkyl, —N($R^8$)$_2$, 3 to 8-member cycloalkyl, aryl, heterocyclyl, heterocyclylalkyl, heteroaryl, cyano, halo, or two $R^4$ together with the atoms to which they are attached may form an optionally substituted 3 to 7-member ring each of which is optionally substituted with ($R^5$)$_{1-3}$;

$R^5$ is independently H, $C_3$-$C_{10}$ heterocyclyl, $C_1$-$C_3$ alkyl, $C_1$-$C_3$ alkoxy, —$C_1$-$C_6$ alkyl-O—$C_0$-$C_6$ alkyl, —$C_0$-$C_6$ alkyl-O—$C_1$-$C_6$ alkyl, —N($C_1$-$C_3$ alkyl)$_2$, —$C_1$-$C_6$ haloalkyl, —$C_1$-$C_3$ alkyl-N($R^8$)$_2$, heterocyclylalkyl, halo, cyano, each of which is optionally substituted with ($R^7$)$_{1-3}$;

$R^6$ is H or $C_1$-$C_6$ alkyl;

$R^7$ is independently H, $C_1$-$C_6$ alkyl, $C_1$-$C_6$ alkenyl, $C_1$-$C_6$ alkynyl, $C_1$-$C_6$ alkoxy, $C_1$-$C_6$ hydroxy, aryl, heteroaryl, heterocyclyl, arylalkyl, aryloxy, heteroaryloxy, arylalkoxy, heteroarylalkoxy, hetearylalkyl, haloalkyl, keto, cyano, halo, or two $R^6$ together with the atoms to which they are attached may form an optionally substituted 3 to 7-member ring; and $R^8$ is H or $C_1$-$C_6$ alkyl.

In a embodiment, in the general Formula I, $R^2$, $R^3$, $R^4$, $R^5$, $R^6$, and $R^7$ have the meaning as defined in the preceding embodiments and $R^1$ is $C_2$-$C_5$ alkyl, $C_2$-$C_4$ alkynyl, —$C_1$-$C_4$ alkyl-O—$C_0$-$C_4$ alkyl, —$C_0$-$C_4$ alkyl-O—$C_1$-$C_4$ alkyl, —$C_0$-$C_4$ alkyl-C(O)—$C_1$-$C_5$ alkyl-, —$C_1$-$C_4$ alkyl-C(O)—$C_0$-$C_5$ alkyl, $C_1$-$C_2$ alkyl-C(O)N($R^8$)$_2$, —$C_1$-$C_6$ alkyl-CF$_3$, —$C_2$-$C_4$ alkyl-CN, heteroarylalkyl, heterocyclylalkyl, each of which is optionally substituted with ($R^7$)$_{1-4}$.

In another embodiment, in the general Formula I, $R^2$, $R^3$, $R^4$, $R^5$, $R^6$, and $R^7$ have the meaning as defined in any of the preceding embodiments, and $R^1$ is is hydroxypropyl, ketopentyl, hydroxymethyl, pyridinylmethyl, oxazolylmethyl, oxetanylmethyl, oxadiazolylmethyl, methoxyethyl, hydroxymethoxypropyl, methoxyketopropyl, ketomethylbutyl, ketopropyl, ketobutyl, acetamido, cyanomethyl, methylacetamido, trifluoroethyl, trifluoropropyl, or butynyl.

In another embodiment, in the general Formula I, $R^2$, $R^3$, $R^4$, $R^5$, $R^6$, and $R^7$ have the meaning as defined in any of the preceding embodiments, and $R^1$ is In another embodiment, in the general Formula I, $R^1$, $R^3$, $R^4$, $R^5$, $R^6$, and $R^7$ have the meaning as defined in any of the preceding embodiments, and $R^2$ is methyl.

In another embodiment, in the general Formula I, $R^1$, $R^3$, $R^4$, $R^5$, $R^6$, and $R^7$ have the meaning as defined in any of the preceding embodiments, and $R^2$ is H.

In another embodiment, in the general Formula I, $R^1$, $R^3$, $R^4$, $R^5$, $R^6$, and $R^7$ have the meaning as defined in any of the preceding embodiments, and $R^3$ is aryl or heteroaryl, each of which is substituted with ($R^4$)$_{1-2}$.

In another embodiment, in the general Formula I, $R^1$, $R^3$, $R^4$, $R^5$, $R^6$, and $R^7$ have the meaning as defined in any of the preceding embodiments, and $R^3$ is phenyl, pyridyl, pyridazinyl, pyrimidinyl, pyrazinyl, or thiazolyl each of which is substituted with ($R^4$)$_{1-2}$.

In another embodiment, in the general Formula I, $R^1$, $R^3$, $R^4$, $R^5$, $R^6$, and $R^7$ have the meaning as defined in any of the preceding embodiments, and $R^3$ is

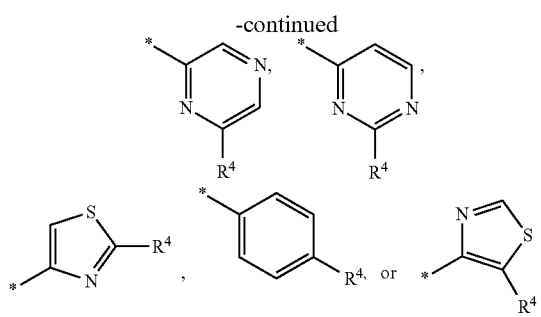

In another embodiment, in the general Formula I, $R^1$, $R^2$, $R^3$, $R^5$, $R^6$, and $R^7$ have the meaning as defined in any of the preceding embodiments, and $R^4$ is independently H, methyl, ethyl, propyl, —N($R^8$)$_2$, phenyl, halo, cyano, haloalkyl, methoxy, pyridinyl, pyrimidinyl, oxadiazolyl, piperdinyl, azetidinyl, pyrazinyl, azabicyclohexyl, piperazinyl, or pyrrolidinyl, each of which is substituted with $(R^5)_{1-2}$.

In another embodiment, in the general Formula I, $R^1$, $R^2$, $R^3$, $R^5$, $R^6$, and $R^7$ have the meaning as defined in any of the preceding embodiments, and $R^4$ is independently H, methyl, ethyl, propyl, cyano, methoxy, chlorine, fluorine, bromine, —CF$_3$, —C$_2$F,

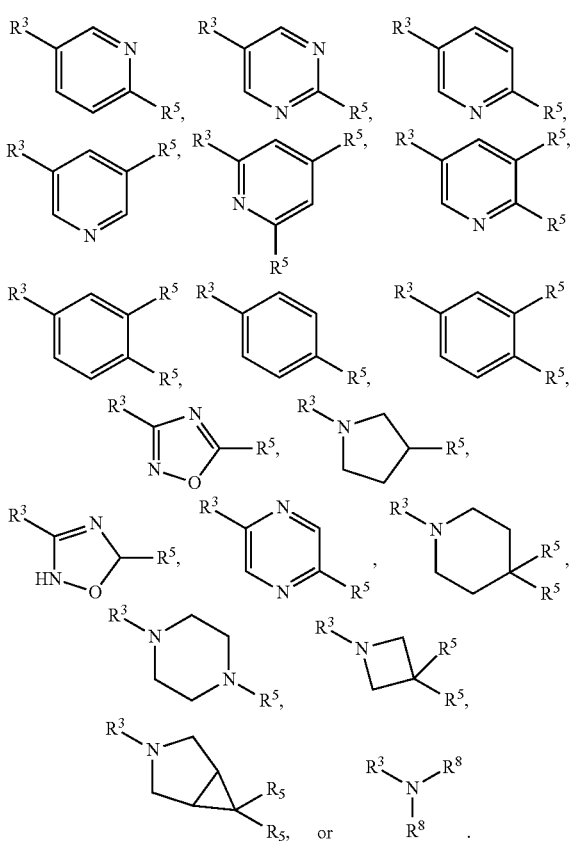

In another embodiment, in the general Formula I, $R^1$, $R^2$, $R^3$, $R^5$, $R^6$, and $R^7$ have the meaning as defined in any of the preceding embodiments, and $R^5$ is independently H, pyrrolidinyl, trifluoroethyl, halo, haloalkyl, methyl, isopropyl, cyano, propyl, ethyl, trifluoromethyl, azabicyclohexyl, difluoroazabicyclohexyl, ketone, methanol, methoxy, or methoxyethyl, dialkylamino, ethoxy, each of which is optionally substituted with $(R^6)_{1-3}$.

In another embodiment, in the general Formula I, $R^1$, $R^2$, $R^3$, $R^5$, $R^6$, and $R^7$ have the meaning as defined in any of the preceding embodiments, and $R^5$ is independently H, —CF$_3$, cyanomethyl, bromine, chlorine, fluorine, methyl, ethyl, isopropyl, cyano, ketone,

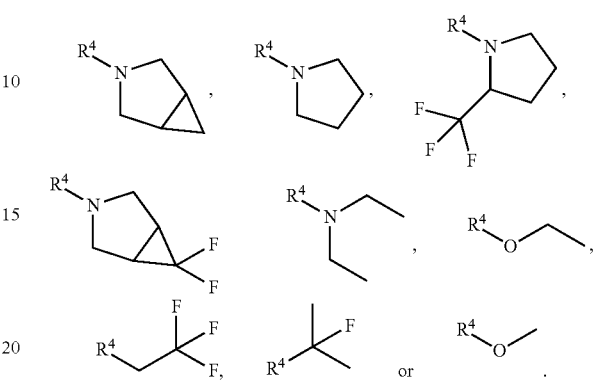

In another embodiment, in the general Formula I, $R^1$, $R^2$, $R^3$, $R^5$, $R^6$, and $R^7$ have the meaning as defined in any of the preceding embodiments, and $R^6$ is H.

In another embodiment, in the general Formula I, $R^1$, $R^2$, $R^3$, $R^5$, $R^6$, and $R^7$ have the meaning as defined in any of the preceding embodiments, and $R^6$ is methyl.

A further embodiment of the present invention comprises compounds of formula I in which
$R^1$ is

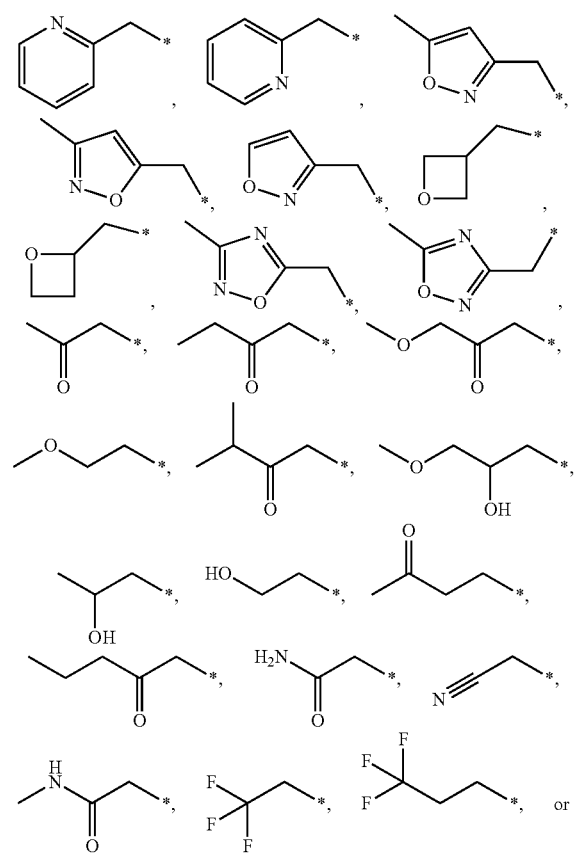

-continued

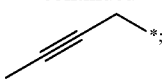

$R^2$ is H or methyl;
$R^3$ is

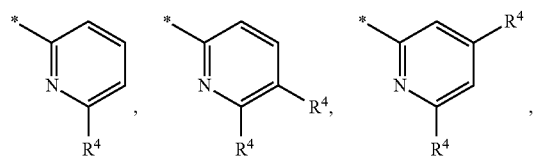

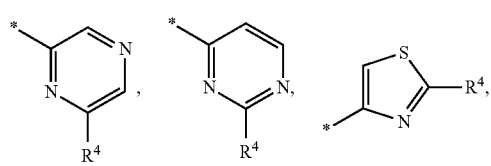

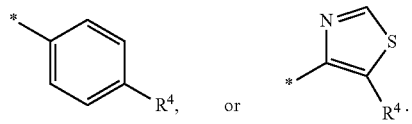

$R^4$ is is independently H, methyl, ethyl, propyl, cyano, methoxy, chlorine, fluorine, bromine, —CF$_3$, —C$_2$F,

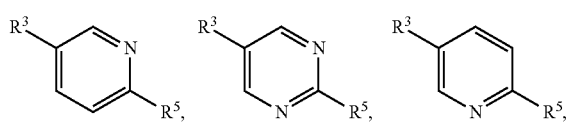

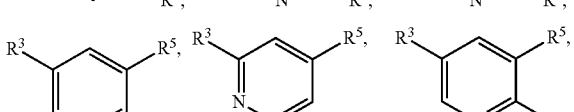

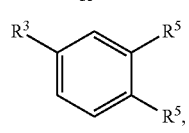

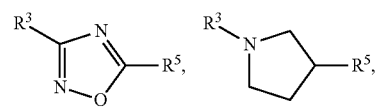

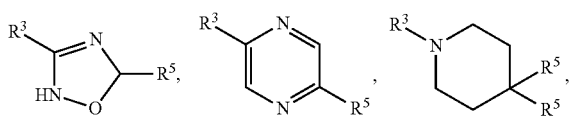

-continued

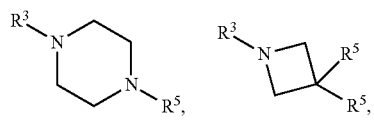

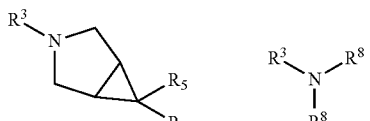

$R^5$ is independently H, —CF$_3$, cyanomethyl, bromine, chlorine, fluorine, methyl, ethyl, isopropyl, cyano, ketone,

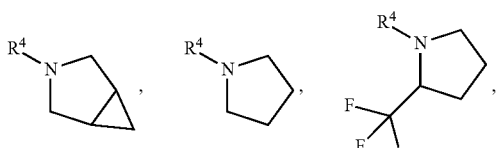

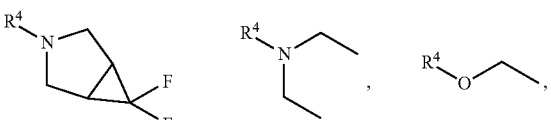

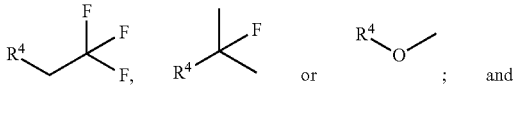

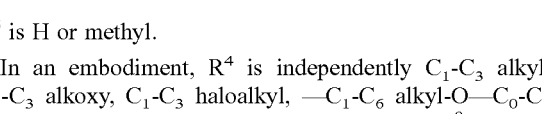

$R^6$ is H or methyl.

In an embodiment, $R^4$ is independently $C_1$-$C_3$ alkyl, $C_1$-$C_3$ alkoxy, $C_1$-$C_3$ haloalkyl, —$C_1$-$C_6$ alkyl-O—$C_0$-$C_6$ alkyl, —$C_0$-$C_6$ alkyl-O—$C_1$-$C_6$ alkyl, —N($R^8$)$_2$, 3 to 8-member cycloalkyl, aryl, heterocyclyl, heterocyclylalkyl, heteroaryl, cyano, halo, or two $R^4$ together with the atoms to which they are attached may form an optionally substituted 3 to 7-member ring each of which is optionally substituted with ($R^5$)$_{1-3}$.

In an embodiment, $R^5$ is independently $C_3$-$C_{10}$ heterocyclyl, $C_1$-$C_3$ alkyl, $C_1$-$C_3$ alkoxy, —$C_1$-$C_6$ alkyl-O—$C_0$-$C_6$ alkyl, —$C_0$-$C_6$ alkyl-O—$C_1$-$C_6$ alkyl,—N($C_1$-$C_3$ alkyl)$_2$, —$C_1$-$C_6$ haloalkyl , —$C_1$-$C_3$ alkyl-N($R^8$)$_2$, heterocyclylalkyl, halo, cyano, each of which is optionally substituted with ($R^7$)$_{1-3}$.

In an embodiment, $R^7$ is independently H, $C_1$-$C_6$ alkyl, $C_1$-$C_6$ alkenyl, $C_1$-$C_6$ alkynyl, $C_1$-$C_6$ alkoxy, $C_1$-$C_6$ hydroxy, aryl, heteroaryl, heterocyclyl, arylalkyl, aryloxy, heteroaryloxy, arylalkoxy, heteroarylalkoxy, heterarylalkyl, haloalkyl, keto, cyano, halo, or two $R^6$ together with the atoms to which they are attached may form an optionally substituted 3 to 7-member ring.

In certain embodiments, exemplary compounds of Formula (I) include the compounds described in Table 1 and in the Examples.

TABLE 1

| Compound # | Structure |
|---|---|
| 1 | 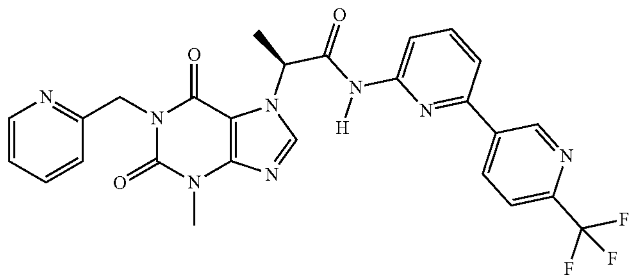 [SMILES: C[C@@H](C(=O)Nc1cccc(-c2ccc(C(F)(F)F)nc2)n1)n1cnc2c1c(=O)n(Cc1ccccn1)c(=O)n2C] |
| 2 | 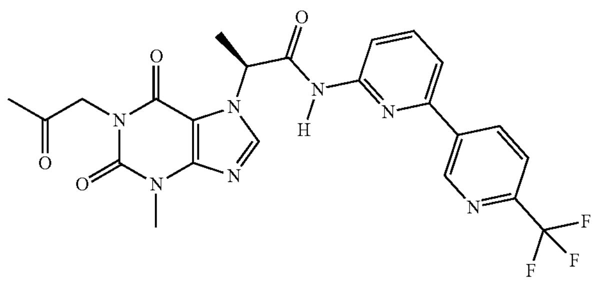 [SMILES: CC(=O)Cn1c(=O)c2c(ncn2[C@@H](C)C(=O)Nc2cccc(-c3ccc(C(F)(F)F)nc3)n2)n(C)c1=O] |
| 3 | 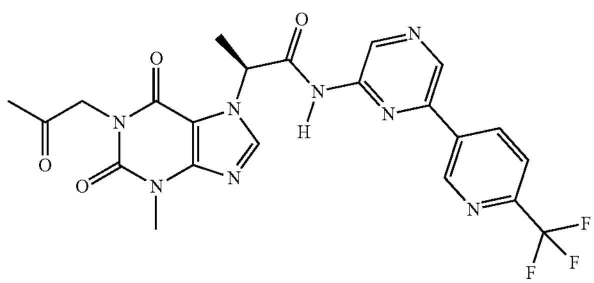 [SMILES: CC(=O)Cn1c(=O)c2c(ncn2[C@@H](C)C(=O)Nc2cncc(-c3ccc(C(F)(F)F)nc3)n2)n(C)c1=O] |
| 4 | 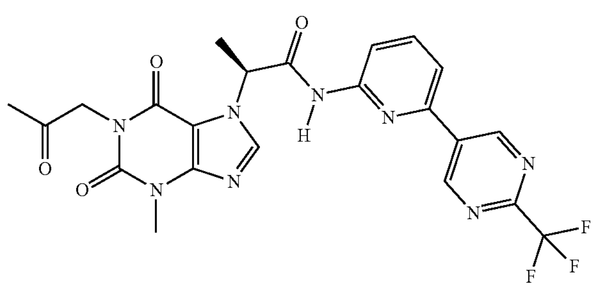 [SMILES: CC(=O)Cn1c(=O)c2c(ncn2[C@@H](C)C(=O)Nc2cccc(-c3cnc(C(F)(F)F)nc3)n2)n(C)c1=O] |
| 5 | 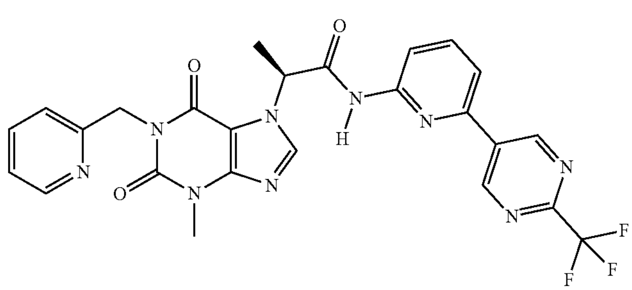 [SMILES: C[C@@H](C(=O)Nc1cccc(-c2cnc(C(F)(F)F)nc2)n1)n1cnc2c1c(=O)n(Cc1ccccn1)c(=O)n2C] |

TABLE 1-continued

| Compound # | Structure |
|---|---|
| 6 | 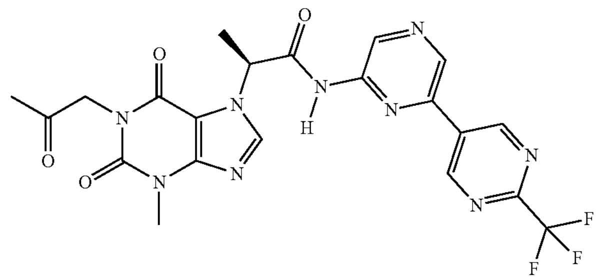 [SMILES: CC(=O)Cn1c(=O)c2c(ncn2[C@@H](C)C(=O)Nc2cncc(-c3cnc(C(F)(F)F)nc3)n2)n(C)c1=O] |
| 7 | 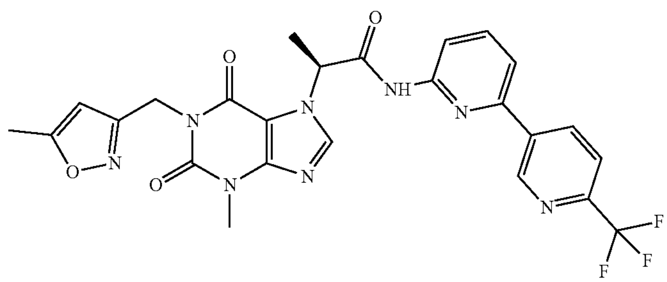 [SMILES: Cc1cc(Cn2c(=O)c3c(ncn3[C@@H](C)C(=O)Nc3cccc(-c4ccc(C(F)(F)F)nc4)n3)n(C)c2=O)no1] |
| 8 | 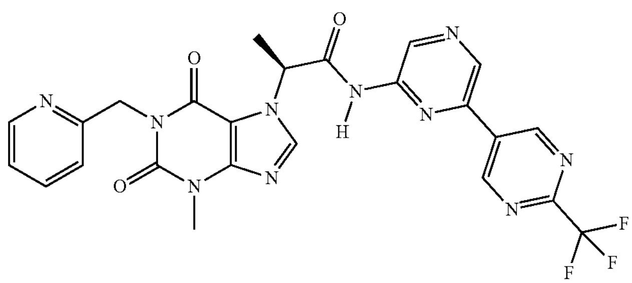 [SMILES: C[C@@H](C(=O)Nc1cncc(-c2cnc(C(F)(F)F)nc2)n1)n1cnc2c1c(=O)n(Cc1ccccn1)c(=O)n2C] |
| 9 | 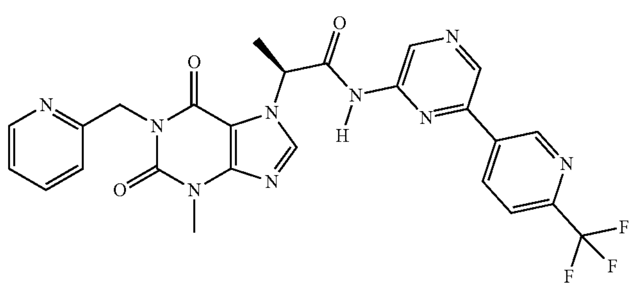 [SMILES: C[C@@H](C(=O)Nc1cncc(-c2ccc(C(F)(F)F)nc2)n1)n1cnc2c1c(=O)n(Cc1ccccn1)c(=O)n2C] |
| 10 | 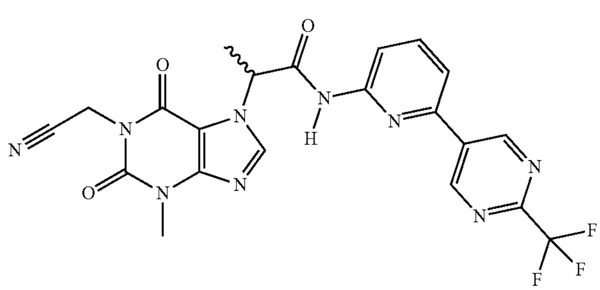 [SMILES: CC(C(=O)Nc1cccc(-c2cnc(C(F)(F)F)nc2)n1)n1cnc2c1c(=O)n(CC#N)c(=O)n2C] |

TABLE 1-continued

| Compound # | Structure |
|---|---|
| 11 | 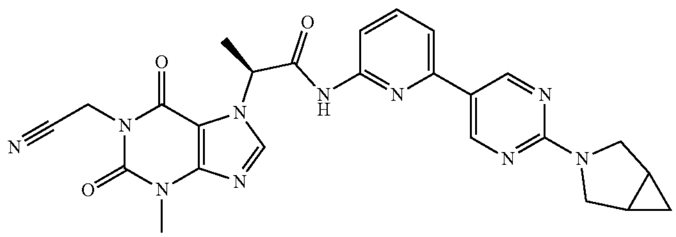 [SMILES: C[C@@H](C(=O)Nc1cccc(-c2cnc(N3CC4CC4C3)nc2)n1)n1cnc2c1c(=O)n(CC#N)c(=O)n2C] |
| 12 | 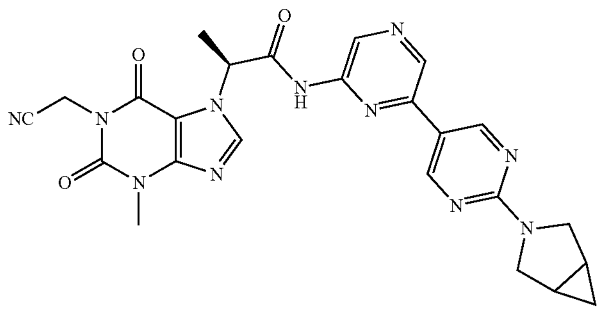 [SMILES: C[C@@H](C(=O)Nc1cncc(-c2cnc(N3CC4CC4C3)nc2)n1)n1cnc2c1c(=O)n(CC#N)c(=O)n2C] |
| 13 | 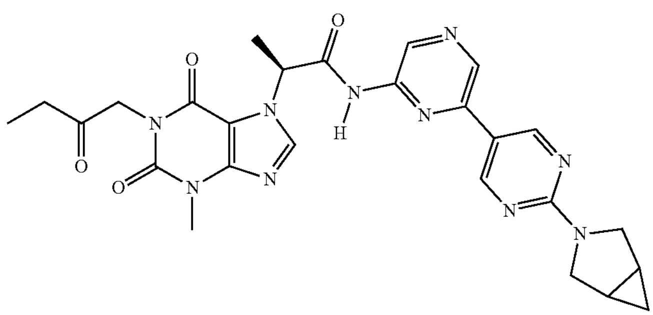 [SMILES: CCC(=O)Cn1c(=O)c2c(ncn2[C@@H](C)C(=O)Nc2cncc(-c3cnc(N4CC5CC5C4)nc3)n2)n(C)c1=O] |
| 14 | 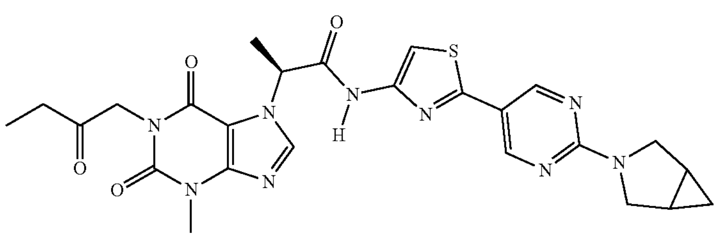 [SMILES: CCC(=O)Cn1c(=O)c2c(ncn2[C@@H](C)C(=O)Nc2csc(-c3cnc(N4CC5CC5C4)nc3)n2)n(C)c1=O] |
| 15 | 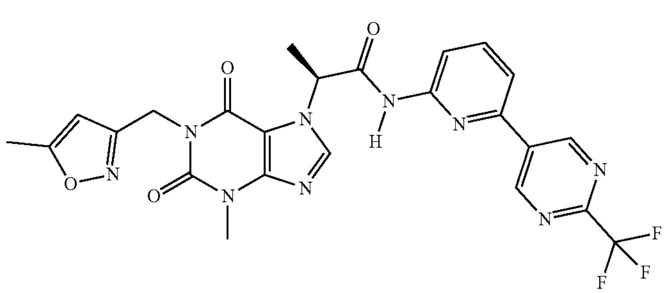 [SMILES: Cc1cc(Cn2c(=O)c3c(ncn3[C@@H](C)C(=O)Nc3cccc(-c4cnc(C(F)(F)F)nc4)n3)n(C)c2=O)no1] |

TABLE 1-continued

| Compound # | Structure |
|---|---|
| 16 | 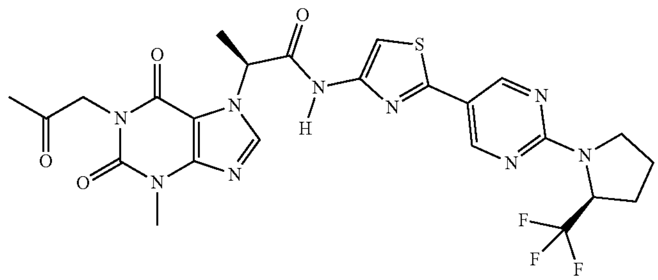 [SMILES: CC(=O)Cn1c(=O)c2c(ncn2[C@@H](C)C(=O)Nc2csc(-c3cnc(N4CCC[C@H]4C(F)(F)F)nc3)n2)n(C)c1=O] |
| 17 | 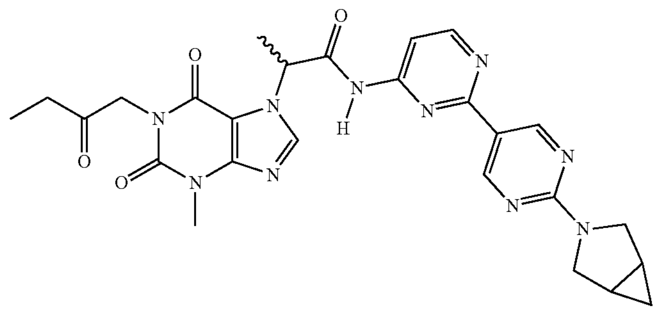 [SMILES: CCC(=O)Cn1c(=O)c2c(ncn2C(C)C(=O)Nc2ccnc(-c3cnc(N4CC5CC5C4)nc3)n2)n(C)c1=O] |
| 18 | 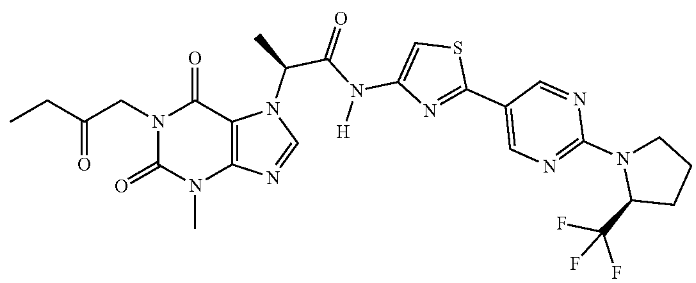 [SMILES: CCC(=O)Cn1c(=O)c2c(ncn2[C@@H](C)C(=O)Nc2csc(-c3cnc(N4CCC[C@H]4C(F)(F)F)nc3)n2)n(C)c1=O] |
| 19 | 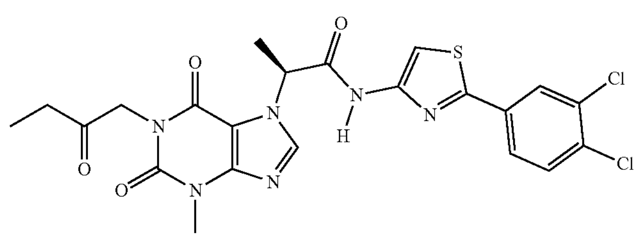 [SMILES: CCC(=O)Cn1c(=O)c2c(ncn2[C@@H](C)C(=O)Nc2csc(-c3ccc(Cl)c(Cl)c3)n2)n(C)c1=O] |
| 20 | 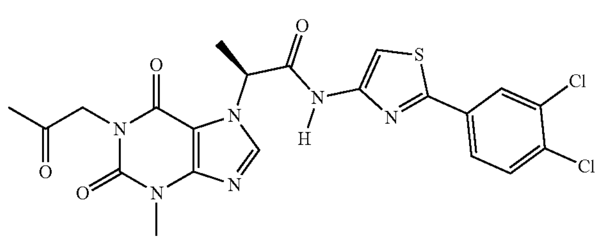 [SMILES: CC(=O)Cn1c(=O)c2c(ncn2[C@@H](C)C(=O)Nc2csc(-c3ccc(Cl)c(Cl)c3)n2)n(C)c1=O] |

TABLE 1-continued

| Compound # | Structure |
|---|---|
| 21 | 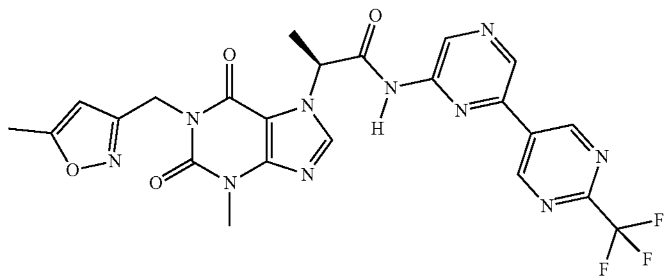 [SMILES: Cc1cc(Cn2c(=O)c3c(ncn3[C@@H](C)C(=O)Nc3cncc(-c4cnc(C(F)(F)F)nc4)n3)n(C)c2=O)no1] |
| 22 | 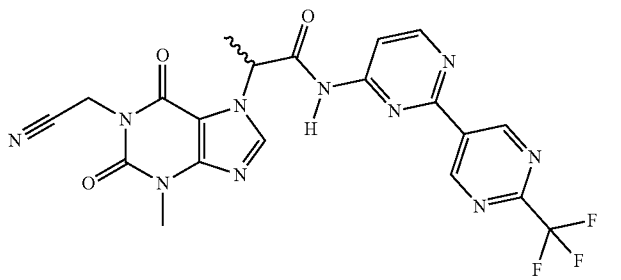 [SMILES: CC(C(=O)Nc1ccnc(-c2cnc(C(F)(F)F)nc2)n1)n1cnc2c1c(=O)n(CC#N)c(=O)n2C] |
| 23 | 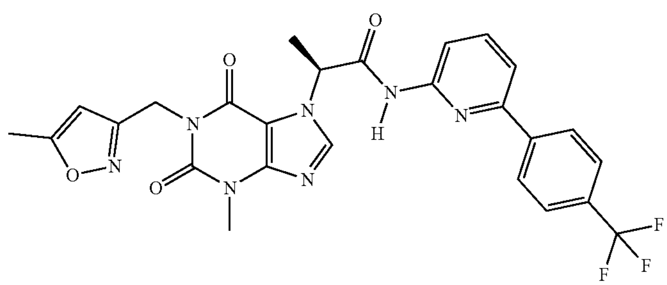 [SMILES: Cc1cc(Cn2c(=O)c3c(ncn3[C@@H](C)C(=O)Nc3cccc(-c4ccc(C(F)(F)F)cc4)n3)n(C)c2=O)no1] |
| 24 | 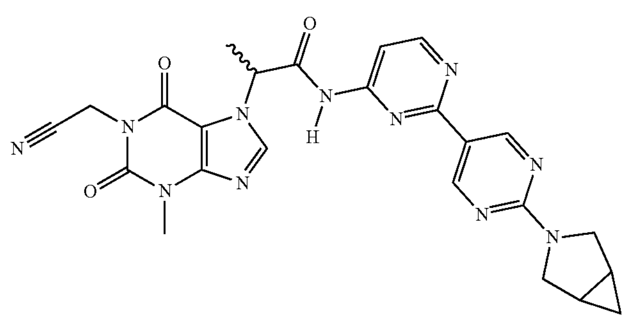 [SMILES: CC(C(=O)Nc1ccnc(-c2cnc(N3CC4CC4C3)nc2)n1)n1cnc2c1c(=O)n(CC#N)c(=O)n2C] |
| 25 | 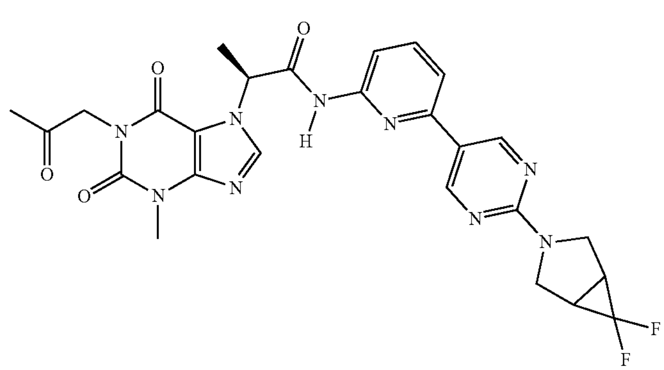 [SMILES: CC(=O)Cn1c(=O)c2c(ncn2[C@@H](C)C(=O)Nc2cccc(-c3cnc(N4CC5C(C4)C5(F)F)nc3)n2)n(C)c1=O] |

TABLE 1-continued

| Compound # | Structure |
|---|---|
| 26 | 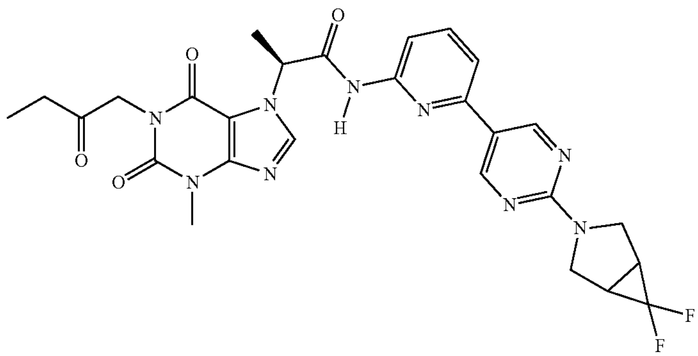 [SMILES: CCC(=O)Cn1c(=O)c2c(ncn2[C@@H](C)C(=O)Nc2cccc(-c3cnc(N4CC5C(C4)C5(F)F)nc3)n2)n(C)c1=O] |
| 27 | 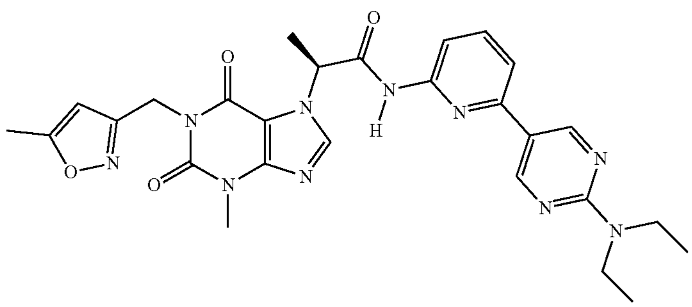 [SMILES: CCN(CC)c1ncc(-c2cccc(NC(=O)[C@H](C)n3cnc4c3c(=O)n(Cc3cc(C)on3)c(=O)n4C)n2)cn1] |
| 28 | 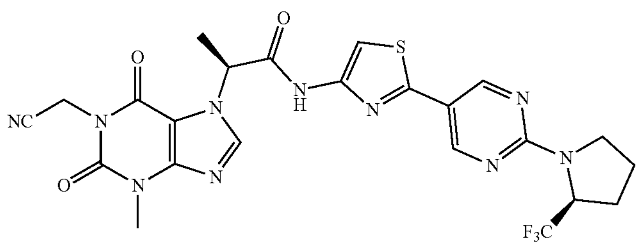 [SMILES: C[C@@H](C(=O)Nc1csc(-c2cnc(N3CCC[C@H]3C(F)(F)F)nc2)n1)n1cnc2c1c(=O)n(CC#N)c(=O)n2C] |
| 29 | 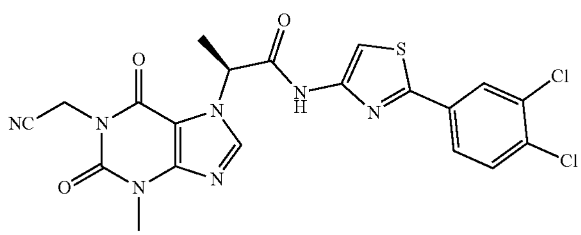 [SMILES: C[C@@H](C(=O)Nc1csc(-c2ccc(Cl)c(Cl)c2)n1)n1cnc2c1c(=O)n(CC#N)c(=O)n2C] |
| 30 | 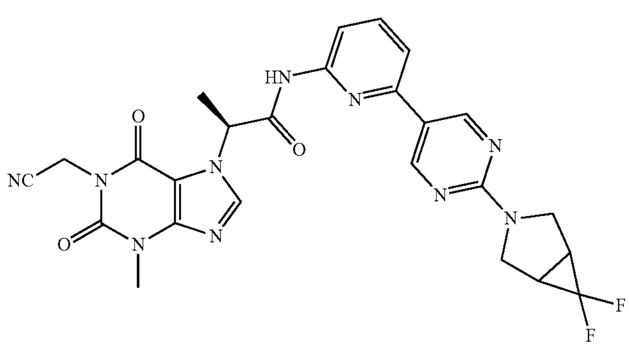 [SMILES: C[C@@H](C(=O)Nc1cccc(-c2cnc(N3CC4C(C3)C4(F)F)nc2)n1)n1cnc2c1c(=O)n(CC#N)c(=O)n2C] |

TABLE 1-continued

| Compound # | Structure |
|---|---|
| 31 | 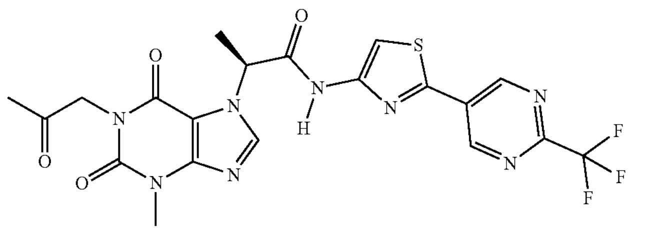 [SMILES: CC(=O)Cn1c(=O)c2c(ncn2[C@@H](C)C(=O)Nc2csc(-c3cnc(C(F)(F)F)nc3)n2)n(C)c1=O] |
| 32 | 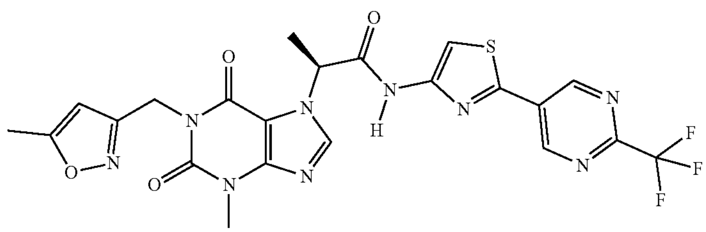 [SMILES: Cc1cc(Cn2c(=O)c3c(ncn3[C@@H](C)C(=O)Nc3csc(-c4cnc(C(F)(F)F)nc4)n3)n(C)c2=O)no1] |
| 33 | 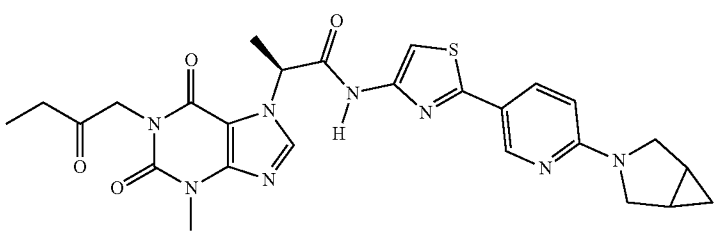 [SMILES: CCC(=O)Cn1c(=O)c2c(ncn2[C@@H](C)C(=O)Nc2csc(-c3ccc(N4CC5CC5C4)nc3)n2)n(C)c1=O] |
| 34 | 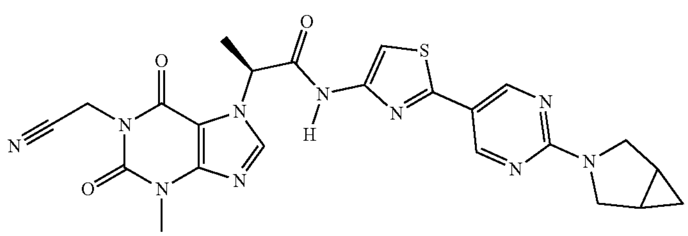 [SMILES: C[C@@H](C(=O)Nc1csc(-c2cnc(N3CC4CC4C3)nc2)n1)n1cnc2c1c(=O)n(CC#N)c(=O)n2C] |
| 35 | 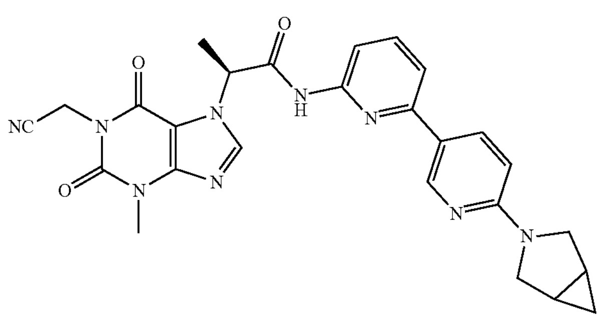 [SMILES: C[C@@H](C(=O)Nc1cccc(-c2ccc(N3CC4CC4C3)nc2)n1)n1cnc2c1c(=O)n(CC#N)c(=O)n2C] |
| 36 | 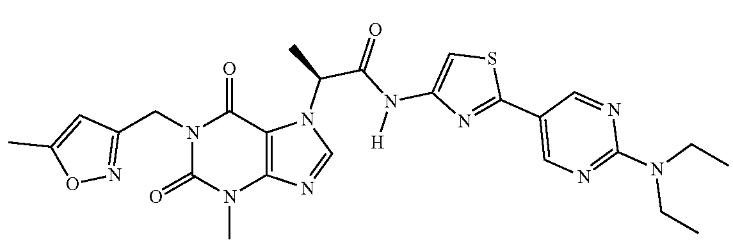 [SMILES: CCN(CC)c1ncc(-c2nc(NC(=O)[C@H](C)n3cnc4c3c(=O)n(Cc3cc(C)on3)c(=O)n4C)cs2)cn1] |

TABLE 1-continued

| Compound # | Structure |
|---|---|
| 37 | 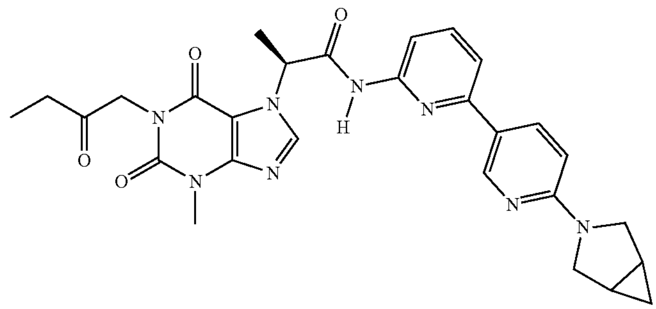 [SMILES: CCC(=O)Cn1c(=O)c2c(ncn2[C@@H](C)C(=O)Nc2cccc(-c3ccc(N4CC5CC5C4)nc3)n2)n(C)c1=O] |
| 38 | 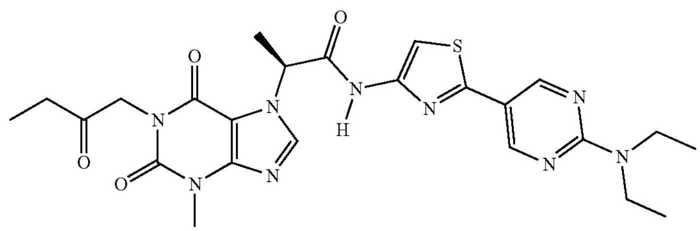 [SMILES: CCC(=O)Cn1c(=O)c2c(ncn2[C@@H](C)C(=O)Nc2csc(-c3cnc(N(CC)CC)nc3)n2)n(C)c1=O] |
| 39 | 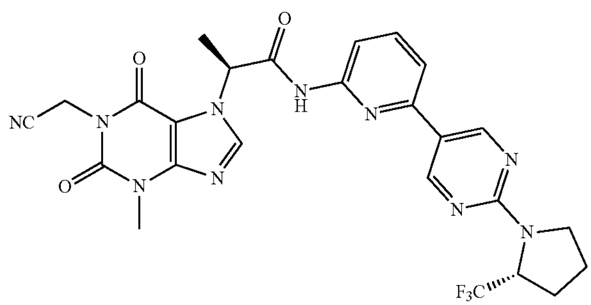 |
| 40 | 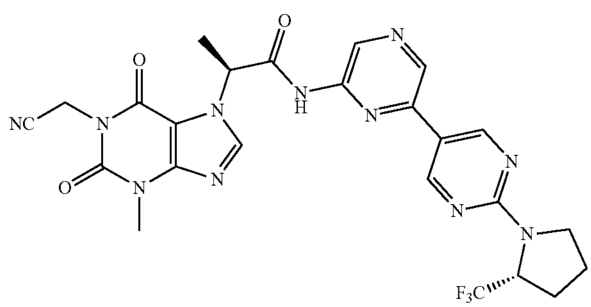 [SMILES: C[C@@H](C(=O)Nc1cccc(-c2cnc(N3CCC[C@@H]3C(F)(F)F)nc2)n1)n1cnc2c1c(=O)n(CC#N)c(=O)n2C] |
| 41 | 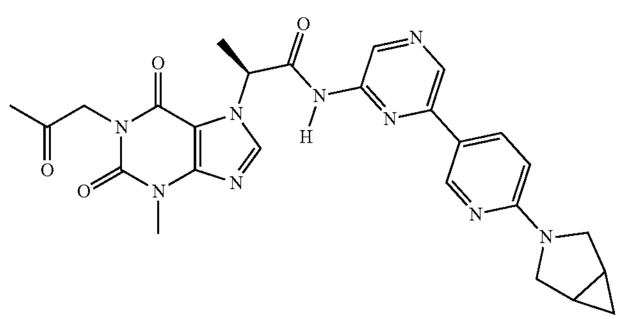 [SMILES: CC(=O)Cn1c(=O)c2c(ncn2[C@@H](C)C(=O)Nc2cncc(-c3ccc(N4CC5CC5C4)nc3)n2)n(C)c1=O] |

TABLE 1-continued
| Compound # | Structure |
|---|---|
| 42 | 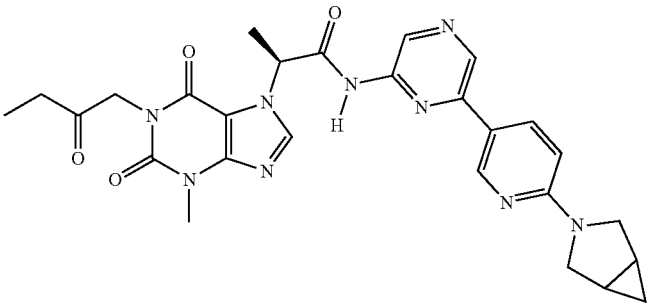 [SMILES: CCC(=O)Cn1c(=O)c2c(ncn2[C@@H](C)C(=O)Nc2cncc(-c3ccc(N4CC5CC5C4)nc3)n2)n(C)c1=O] |
| 43 | 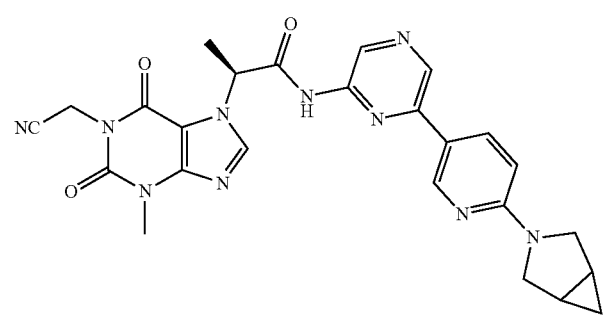 [SMILES: C[C@@H](C(=O)Nc1cncc(-c2ccc(N3CC4CC4C3)nc2)n1)n1cnc2c1c(=O)n(CC#N)c(=O)n2C] |
| 44 | 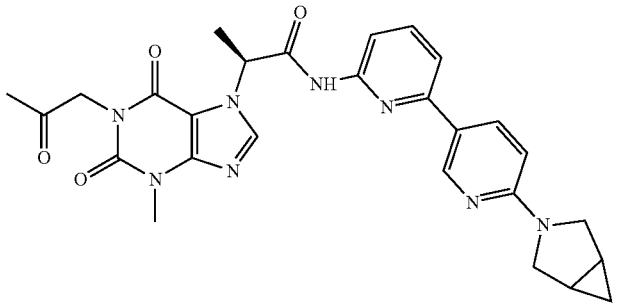 [SMILES: CC(=O)Cn1c(=O)c2c(ncn2[C@@H](C)C(=O)Nc2cccc(-c3ccc(N4CC5CC5C4)nc3)n2)n(C)c1=O] |
| 45 | 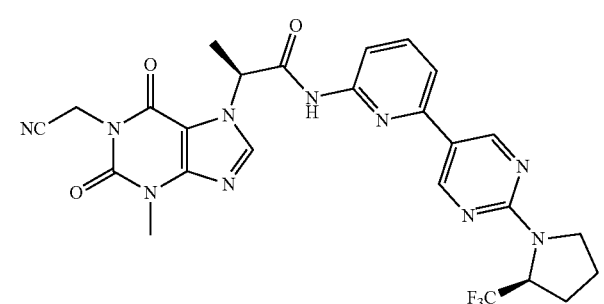 |
| 46 | 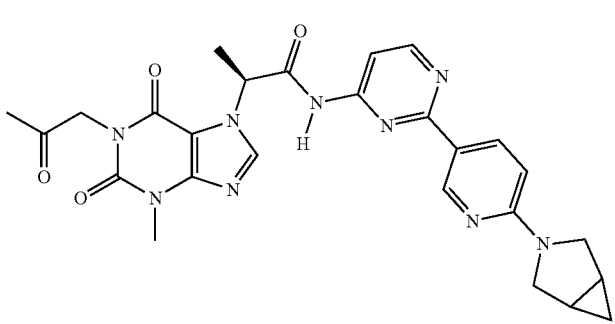 [SMILES: CC(=O)Cn1c(=O)c2c(ncn2[C@@H](C)C(=O)Nc2ccnc(-c3ccc(N4CC5CC5C4)nc3)n2)n(C)c1=O] |

TABLE 1-continued

| Compound # | Structure |
|---|---|
| 47 | 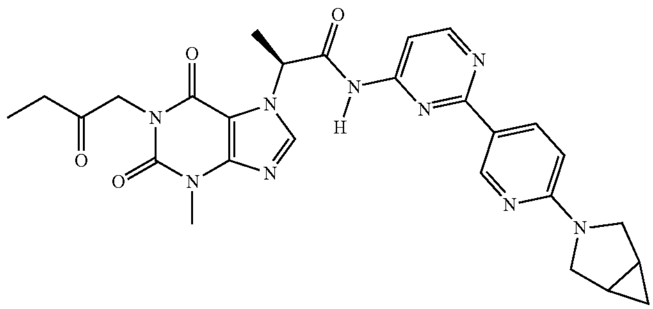 [SMILES: CCC(=O)Cn1c(=O)c2c(ncn2[C@@H](C)C(=O)Nc2ccnc(-c3ccc(N4CC5CC5C4)nc3)n2)n(C)c1=O] |
| 48 | 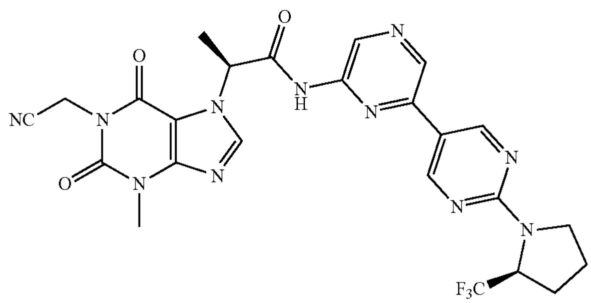 [SMILES: C[C@@H](C(=O)Nc1cncc(-c2cnc(N3CCC[C@H]3C(F)(F)F)nc2)n1)n1cnc2c1c(=O)n(CC#N)c(=O)n2C] |
| 49 | 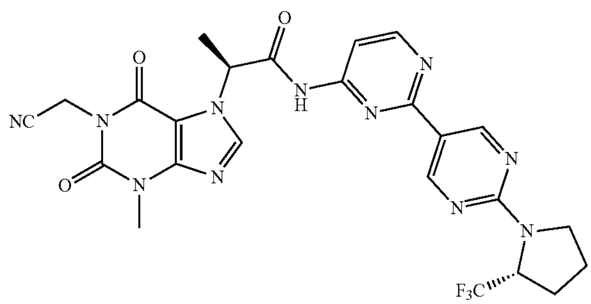 [SMILES: C[C@@H](C(=O)Nc1ccnc(-c2cnc(N3CCC[C@@H]3C(F)(F)F)nc2)n1)n1cnc2c1c(=O)n(CC#N)c(=O)n2C] |
| 50 | 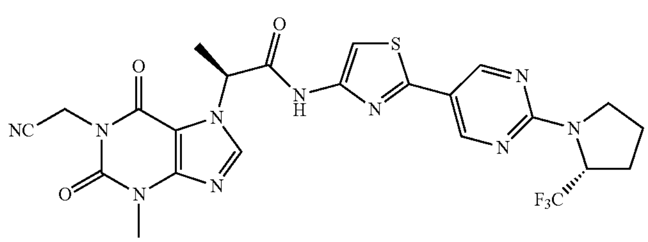 [SMILES: C[C@@H](C(=O)Nc1csc(-c2cnc(N3CCC[C@@H]3C(F)(F)F)nc2)n1)n1cnc2c1c(=O)n(CC#N)c(=O)n2C] |
| 51 | 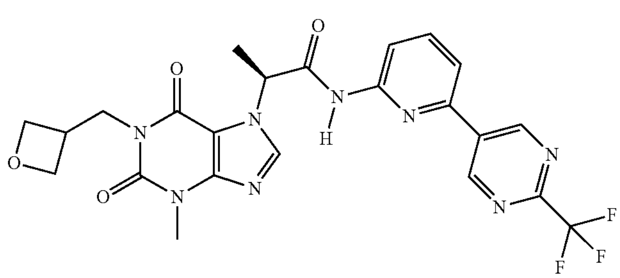 [SMILES: C[C@@H](C(=O)Nc1cccc(-c2cnc(C(F)(F)F)nc2)n1)n1cnc2c1c(=O)n(CC1COC1)c(=O)n2C] |

TABLE 1-continued

| Compound # | Structure |
|---|---|
| 52 | 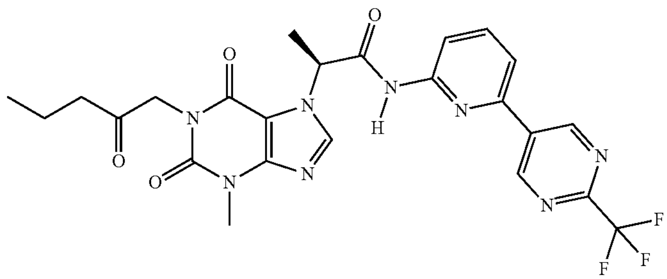 [SMILES: CCCC(=O)Cn1c(=O)c2c(ncn2[C@@H](C)C(=O)Nc2cccc(-c3cnc(C(F)(F)F)nc3)n2)n(C)c1=O] |
| 53 | 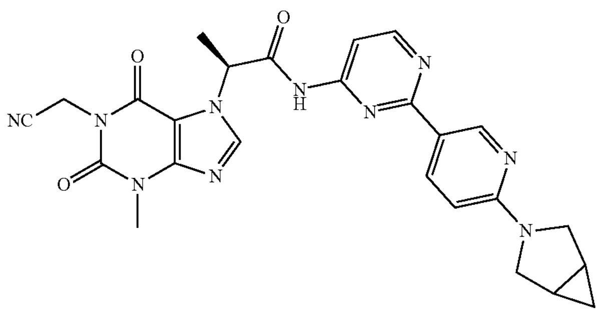 [SMILES: C[C@@H](C(=O)Nc1ccnc(-c2ccc(N3CC4CC4C3)nc2)n1)n1cnc2c1c(=O)n(CC#N)c(=O)n2C] |
| 54 | 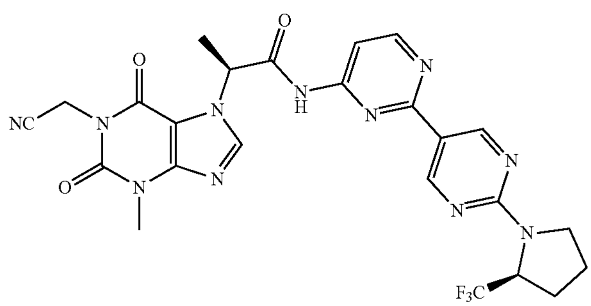 |
| 55 | 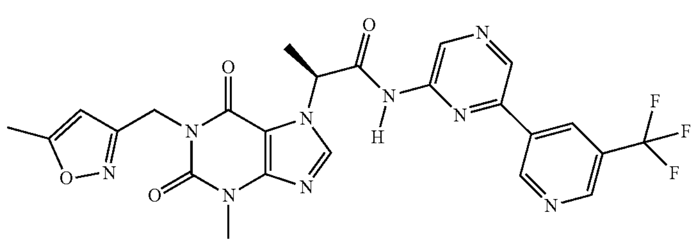 [SMILES: Cc1cc(Cn2c(=O)c3c(ncn3[C@@H](C)C(=O)Nc3cncc(-c4cncc(C(F)(F)F)c4)n3)n(C)c2=O)no1] |
| 56 | 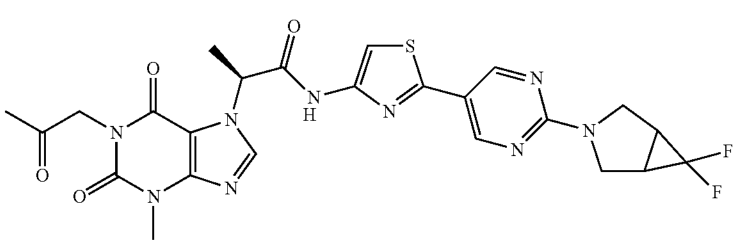 |

TABLE 1-continued

| Compound # | Structure |
|---|---|
| 57 | 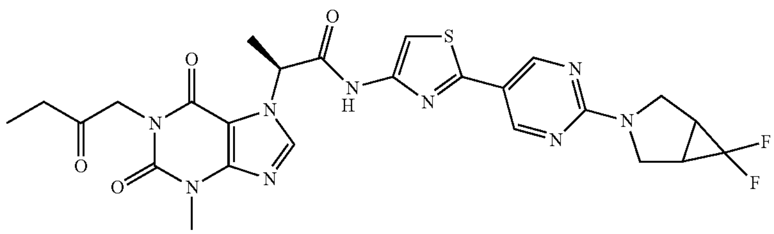 |
| 58 | 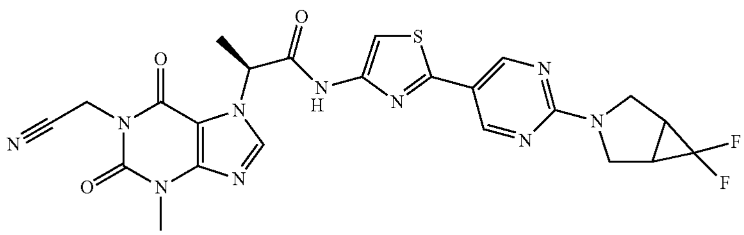 |
| 59 | 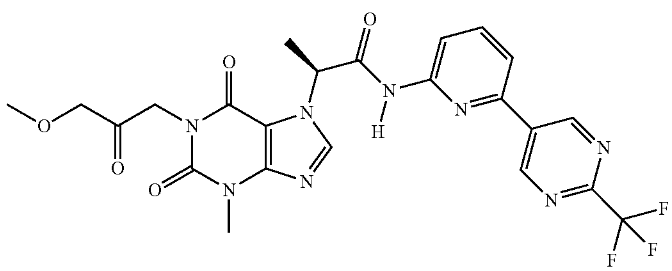 [SMILES: COCC(=O)Cn1c(=O)c2c(ncn2[C@@H](C)C(=O)Nc2cccc(-c3cnc(C(F)(F)F)nc3)n2)n(C)c1=O] |
| 60 | 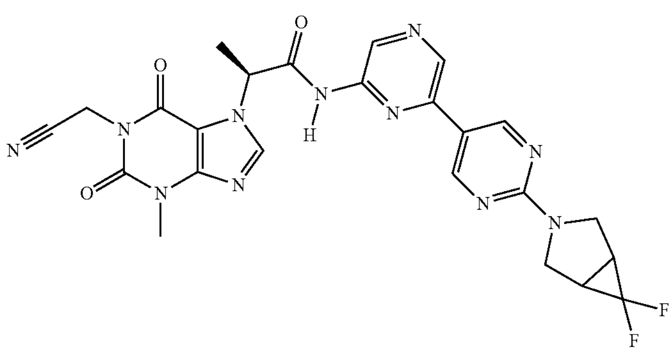 [SMILES: C[C@@H](C(=O)Nc1cncc(-c2cnc(N3CC4C(C3)C4(F)F)nc2)n1)n1cnc2c1c(=O)n(CC#N)c(=O)n2C] |
| 61 | 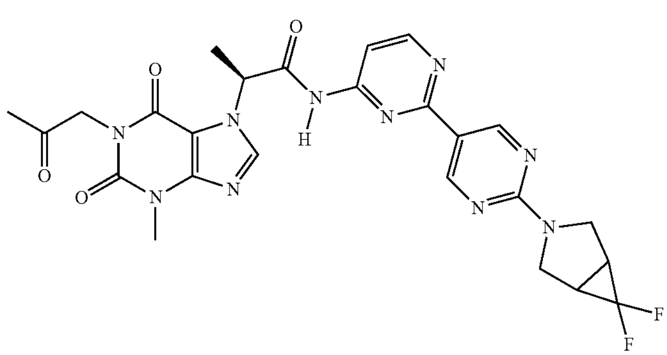 [SMILES: CC(=O)Cn1c(=O)c2c(ncn2[C@@H](C)C(=O)Nc2ccnc(-c3cnc(N4CC5C(C4)C5(F)F)nc3)n2)n(C)c1=O] |

TABLE 1-continued

| Compound # | Structure |
|---|---|
| 62 | 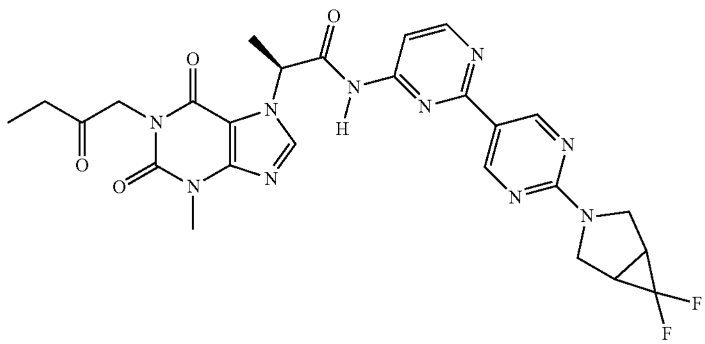 [SMILES: CCC(=O)Cn1c(=O)c2c(ncn2[C@@H](C)C(=O)Nc2ccnc(-c3cnc(N4CC5C(C4)C5(F)F)nc3)n2)n(C)c1=O] |
| 63 | 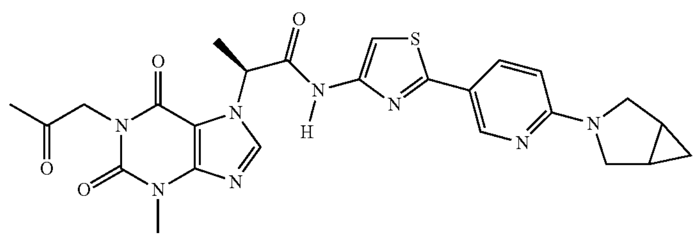 [SMILES: CC(=O)Cn1c(=O)c2c(ncn2[C@@H](C)C(=O)Nc2csc(-c3ccc(N4CC5CC5C4)nc3)n2)n(C)c1=O] |
| 64 | 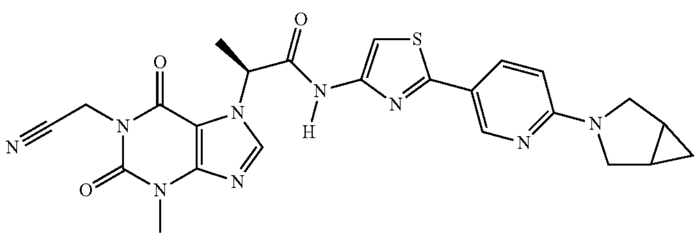 [SMILES: C[C@@H](C(=O)Nc1csc(-c2ccc(N3CC4CC4C3)nc2)n1)n1cnc2c1c(=O)n(CC#N)c(=O)n2C] |
| 65 | 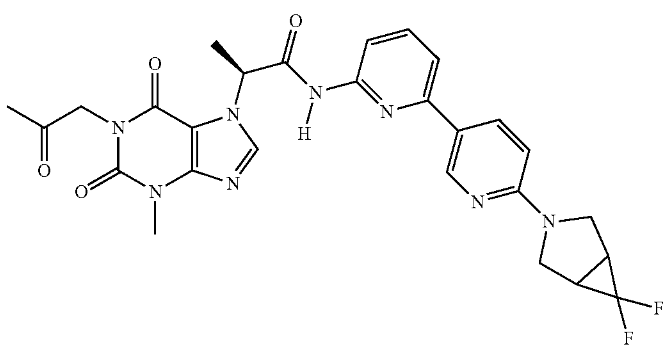 [SMILES: CC(=O)Cn1c(=O)c2c(ncn2[C@@H](C)C(=O)Nc2cccc(-c3ccc(N4CC5C(C4)C5(F)F)nc3)n2)n(C)c1=O] |
| 66 | 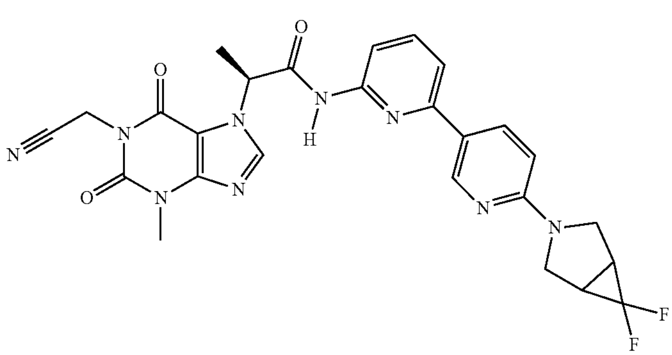 [SMILES: C[C@@H](C(=O)Nc1cccc(-c2ccc(N3CC4C(C3)C4(F)F)nc2)n1)n1cnc2c1c(=O)n(CC#N)c(=O)n2C] |

TABLE 1-continued
| Compound # | Structure |
|---|---|
| 67 | 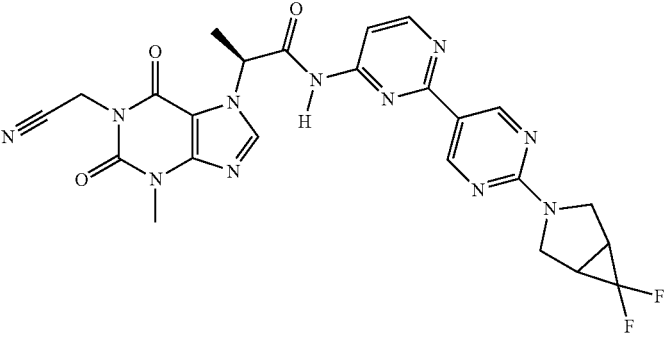 [SMILES: C[C@@H](C(=O)Nc1ccnc(-c2cnc(N3CC4C(C3)C4(F)F)nc2)n1)n1cnc2c1c(=O)n(CC#N)c(=O)n2C] |
| 68 | 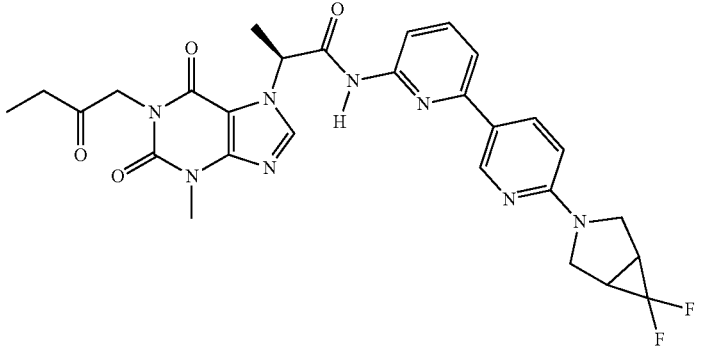 [SMILES: CCC(=O)Cn1c(=O)c2c(ncn2[C@@H](C)C(=O)Nc2cccc(-c3ccc(N4CC5C(C4)C5(F)F)nc3)n2)n(C)c1=O] |
| 69 | 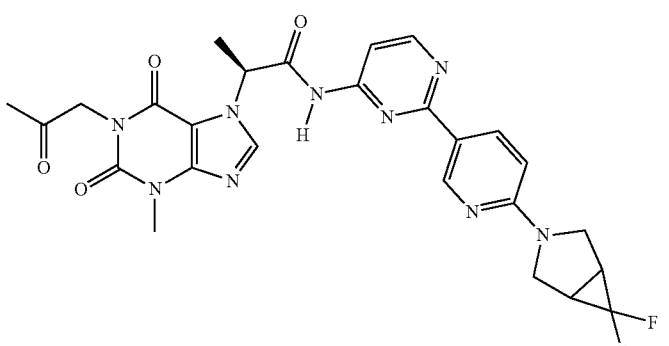 |
| 70 | 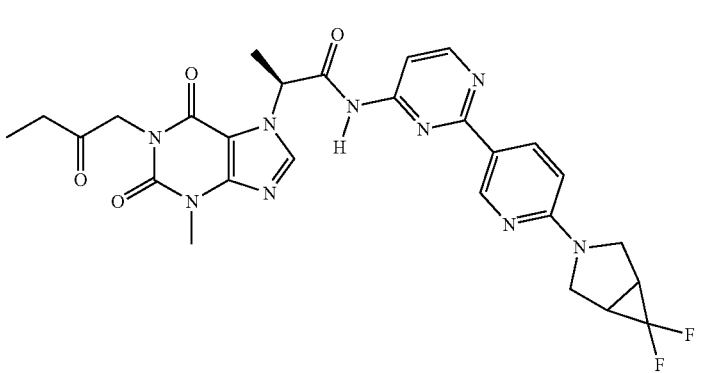 [SMILES: CCC(=O)Cn1c(=O)c2c(ncn2[C@@H](C)C(=O)Nc2ccnc(-c3ccc(N4CC5C(C4)C5(F)F)nc3)n2)n(C)c1=O] |

TABLE 1-continued

| Compound # | Structure |
|---|---|
| 71 | 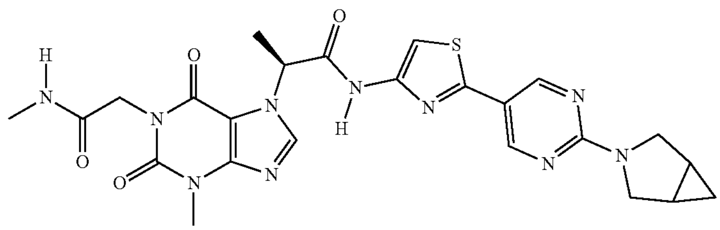 [SMILES: CNC(=O)Cn1c(=O)c2c(ncn2[C@@H](C)C(=O)Nc2csc(-c3cnc(N4CC5CC5C4)nc3)n2)n(C)c1=O] |
| 72 | 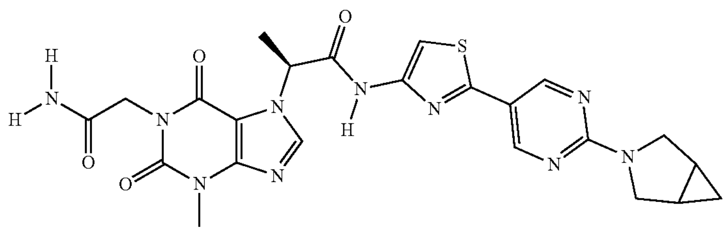 [SMILES: C[C@@H](C(=O)Nc1csc(-c2cnc(N3CC4CC4C3)nc2)n1)n1cnc2c1c(=O)n(CC(N)=O)c(=O)n2C] |
| 73 | 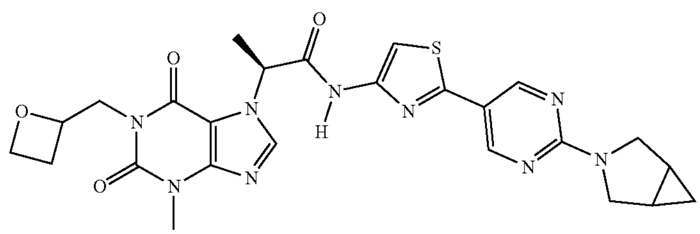 [SMILES: C[C@@H](C(=O)Nc1csc(-c2cnc(N3CC4CC4C3)nc2)n1)n1cnc2c1c(=O)n(CC1CCO1)c(=O)n2C] |
| 74 | 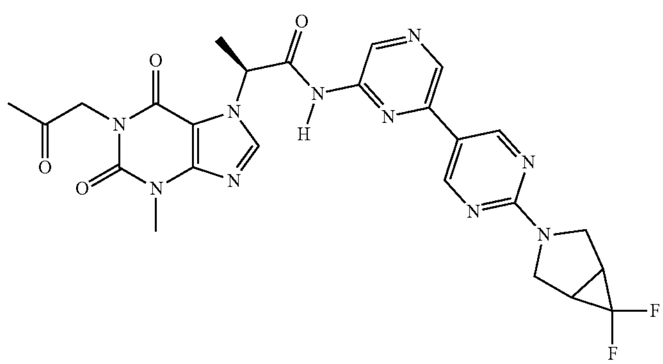 [SMILES: CC(=O)Cn1c(=O)c2c(ncn2[C@@H](C)C(=O)Nc2cncc(-c3cnc(N4CC5C(C4)C5(F)F)nc3)n2)n(C)c1=O] |
| 75 | 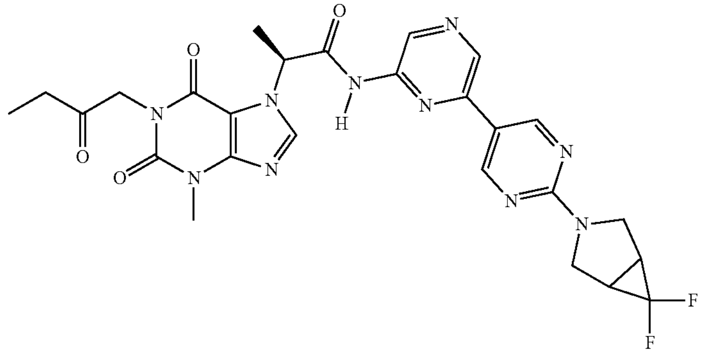 [SMILES: CCC(=O)Cn1c(=O)c2c(ncn2[C@@H](C)C(=O)Nc2cncc(-c3cnc(N4CC5C(C4)C5(F)F)nc3)n2)n(C)c1=O] |

TABLE 1-continued

| Compound # | Structure |
|---|---|
| 76 | 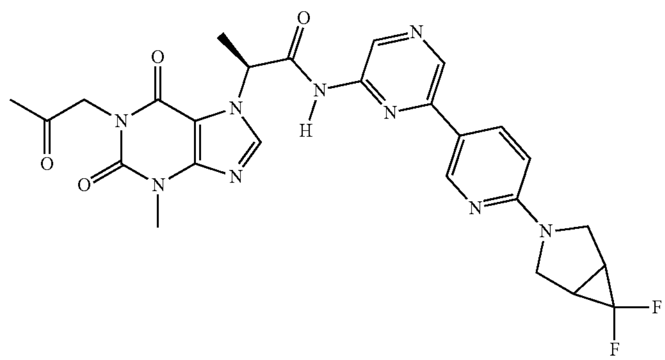 [SMILES: CC(=O)Cn1c(=O)c2c(ncn2[C@@H](C)C(=O)Nc2cncc(-c3ccc(N4CC5C(C4)C5(F)F)nc3)n2)n(C)c1=O] |
| 77 | 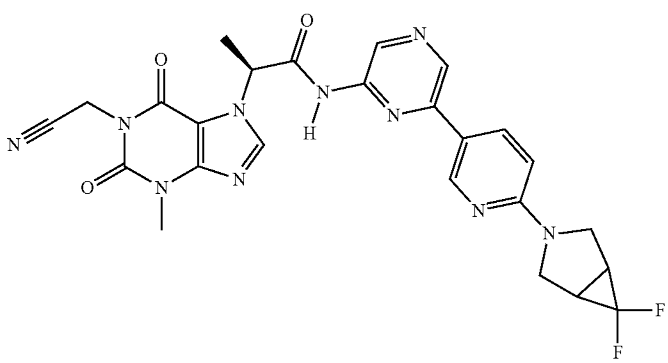 [SMILES: C[C@@H](C(=O)Nc1cncc(-c2ccc(N3CC4C(C3)C4(F)F)nc2)n1)n1cnc2c1c(=O)n(CC#N)c(=O)n2C] |
| 78 | 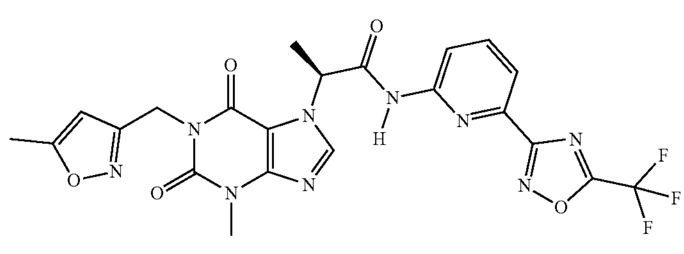 [SMILES: Cc1cc(Cn2c(=O)c3c(ncn3[C@@H](C)C(=O)Nc3cccc(-c4noc(C(F)(F)F)n4)n3)n(C)c2=O)no1] |
| 79 | 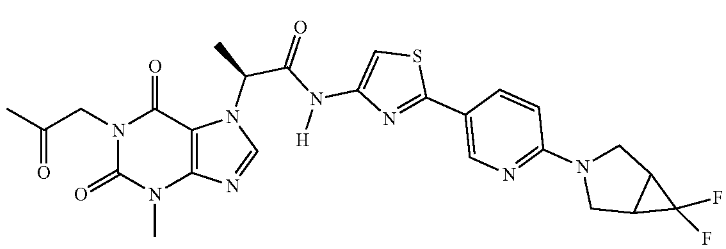 [SMILES: CC(=O)Cn1c(=O)c2c(ncn2[C@@H](C)C(=O)Nc2csc(-c3ccc(N4CC5C(C4)C5(F)F)nc3)n2)n(C)c1=O] |
| 80 | 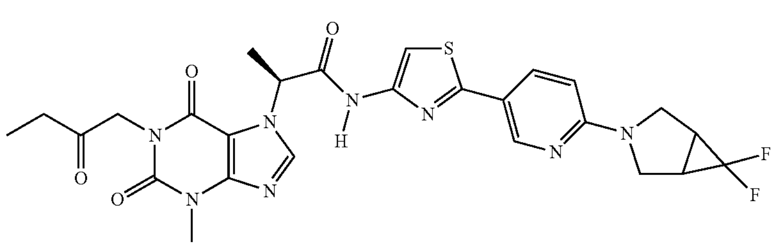 [SMILES: CCC(=O)Cn1c(=O)c2c(ncn2[C@@H](C)C(=O)Nc2csc(-c3ccc(N4CC5C(C4)C5(F)F)nc3)n2)n(C)c1=O] |

TABLE 1-continued
| Compound # | Structure |
|---|---|
| 81 | 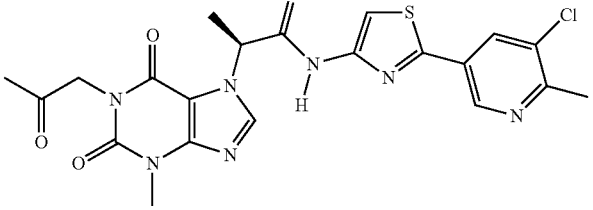 |
| 82 | 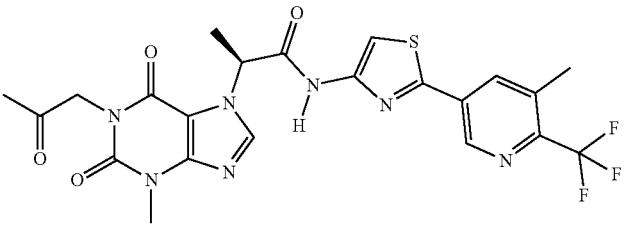 [SMILES: CC(=O)Cn1c(=O)c2c(ncn2[C@@H](C)C(=O)Nc2csc(-c3cnc(C(F)(F)F)c(C)c3)n2)n(C)c1=O] |
| 83 | 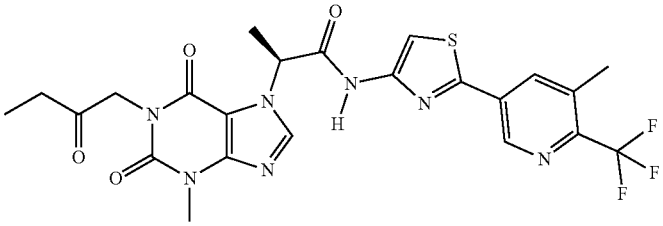 [SMILES: CCC(=O)Cn1c(=O)c2c(ncn2[C@@H](C)C(=O)Nc2csc(-c3cnc(C(F)(F)F)c(C)c3)n2)n(C)c1=O] |
| 84 | 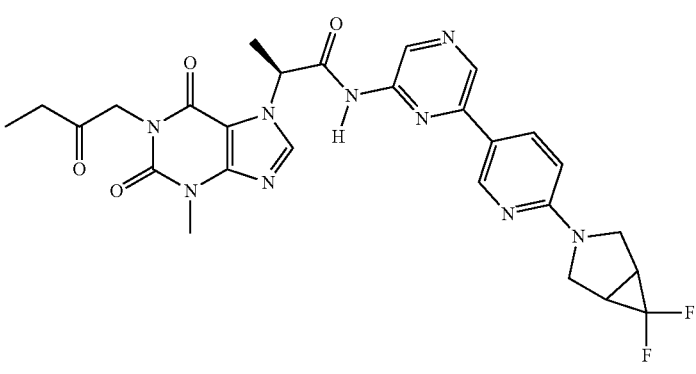 [SMILES: CCC(=O)Cn1c(=O)c2c(ncn2[C@@H](C)C(=O)Nc2cncc(-c3ccc(N4CC5C(C4)C5(F)F)nc3)n2)n(C)c1=O] |
| 85 | 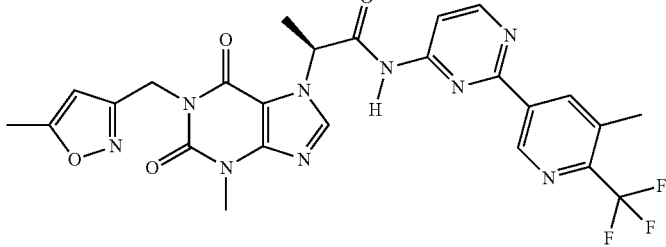 |
| 86 | 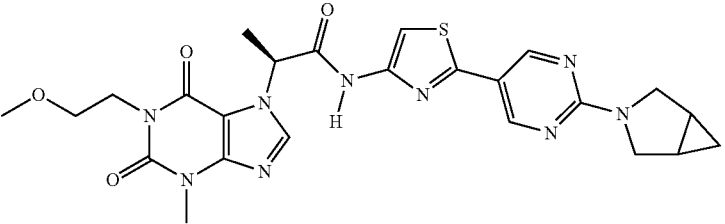 [SMILES: COCCn1c(=O)c2c(ncn2[C@@H](C)C(=O)Nc2csc(-c3cnc(N4CC5CC5C4)nc3)n2)n(C)c1=O] |

TABLE 1-continued

| Compound # | Structure |
|---|---|
| 87 | 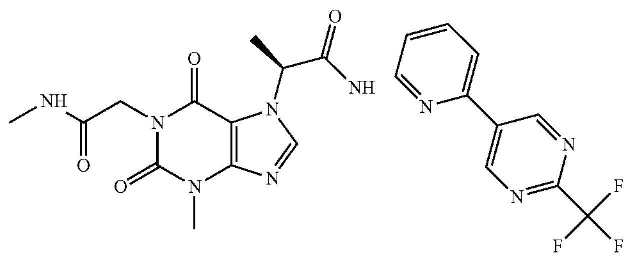 |
| 88 | 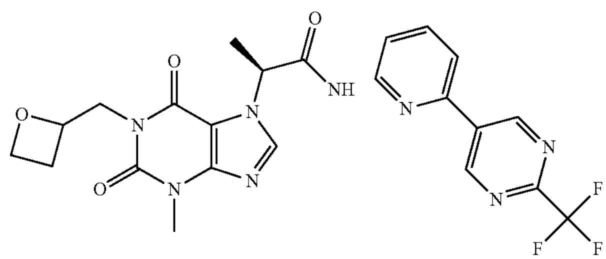 |
| 89 | 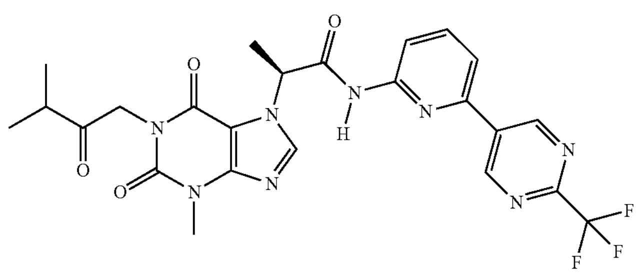 [SMILES: CC(C)C(=O)Cn1c(=O)c2c(ncn2[C@@H](C)C(=O)Nc2cccc(-c3cnc(C(F)(F)F)nc3)n2)n(C)c1=O] |
| 90 | 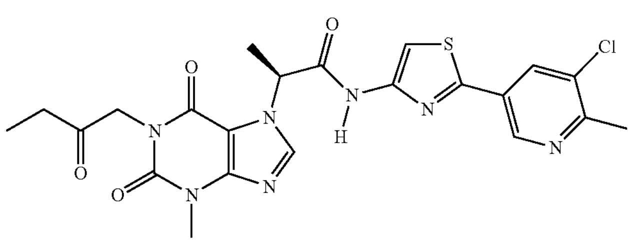 |
| 91 | 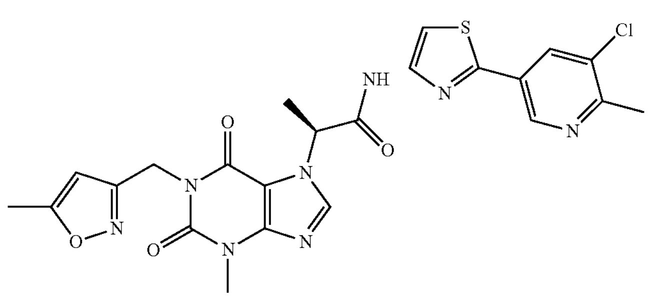 |
| 92 | 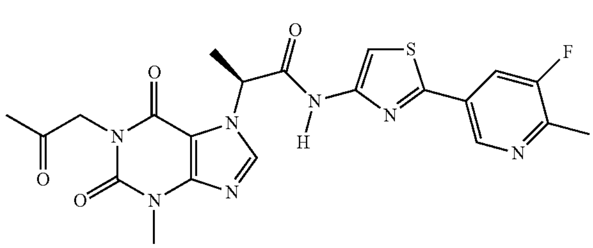 [SMILES: CC(=O)Cn1c(=O)c2c(ncn2[C@@H](C)C(=O)Nc2csc(-c3cnc(C)c(F)c3)n2)n(C)c1=O] |

TABLE 1-continued

| Compound # | Structure |
|---|---|
| 93 | 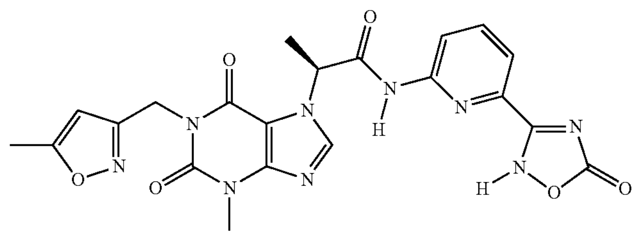 [SMILES: Cc1cc(Cn2c(=O)c3c(ncn3[C@@H](C)C(=O)Nc3cccc(-c4nc(=O)o[nH]4)n3)n(C)c2=O)no1] |
| 94 | 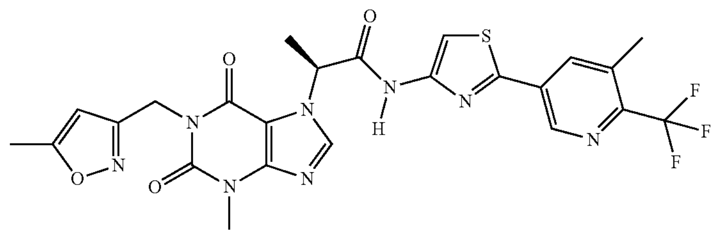 [SMILES: Cc1cc(Cn2c(=O)c3c(ncn3[C@@H](C)C(=O)Nc3csc(-c4cnc(C(F)(F)F)c(C)c4)n3)n(C)c2=O)no1] |
| 95 | 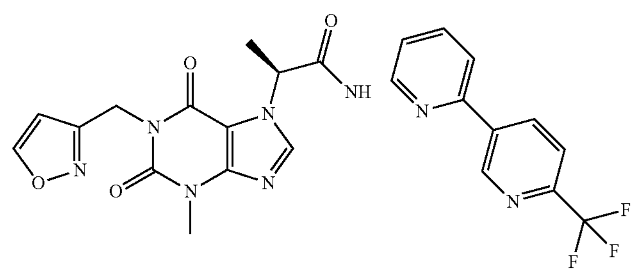 |
| 96 | 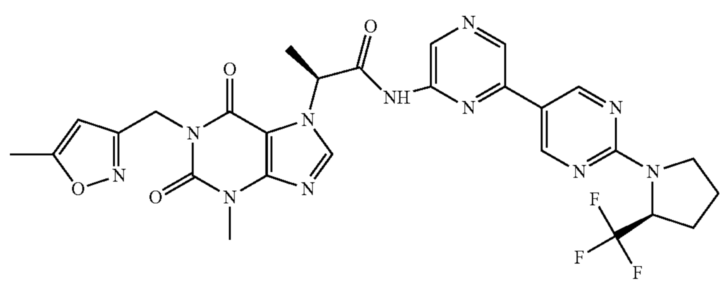 [SMILES: Cc1cc(Cn2c(=O)c3c(ncn3[C@@H](C)C(=O)Nc3cncc(-c4cnc(N5CCC[C@H]5C(F)(F)F)nc4)n3)n(C)c2=O)no1] |
| 97 | 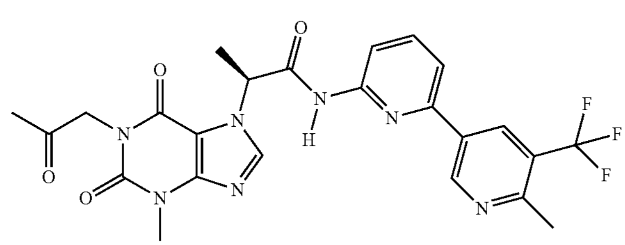 [SMILES: CC(=O)Cn1c(=O)c2c(ncn2[C@@H](C)C(=O)Nc2cccc(-c3cnc(C)c(C(F)(F)F)c3)n2)n(C)c1=O] |
| 98 | 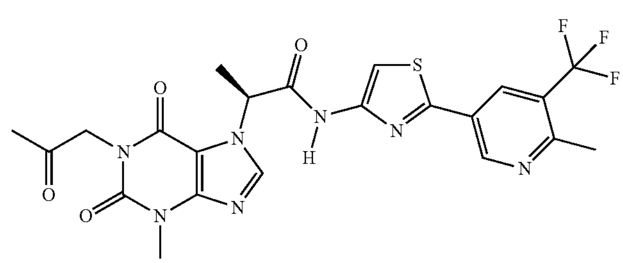 [SMILES: CC(=O)Cn1c(=O)c2c(ncn2[C@@H](C)C(=O)Nc2csc(-c3cnc(C)c(C(F)(F)F)c3)n2)n(C)c1=O] |

TABLE 1-continued

| Compound # | Structure |
|---|---|
| 99 | 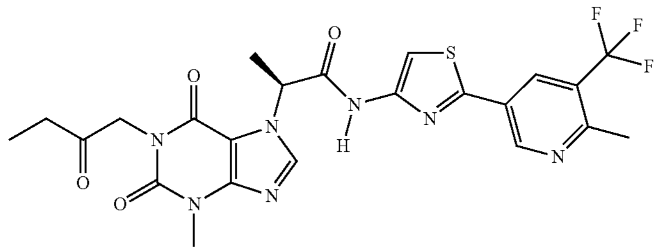 [SMILES: CCC(=O)Cn1c(=O)c2c(ncn2[C@@H](C)C(=O)Nc2csc(-c3cnc(C)c(C(F)(F)F)c3)n2)n(C)c1=O] |
| 100 | 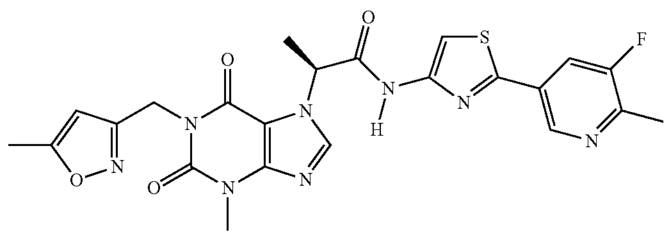 |
| 101 | 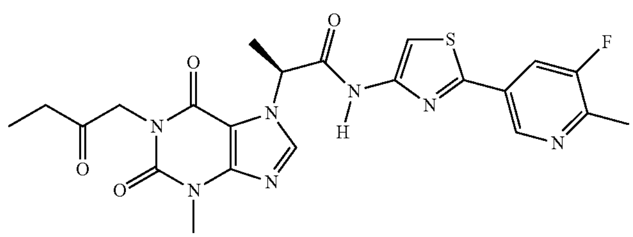 [SMILES: CCC(=O)Cn1c(=O)c2c(ncn2[C@@H](C)C(=O)Nc2csc(-c3cnc(C)c(F)c3)n2)n(C)c1=O] |
| 102 | 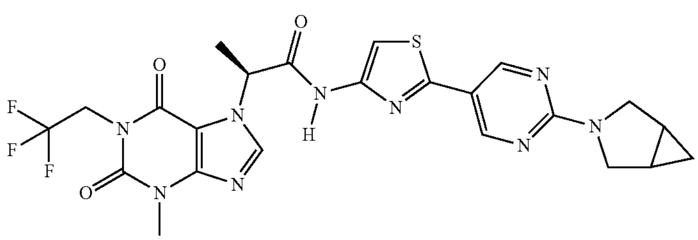 [SMILES: C[C@@H](C(=O)Nc1csc(-c2cnc(N3CC4CC4C3)nc2)n1)n1cnc2c1c(=O)n(CC(F)(F)F)c(=O)n2C] |
| 103 | 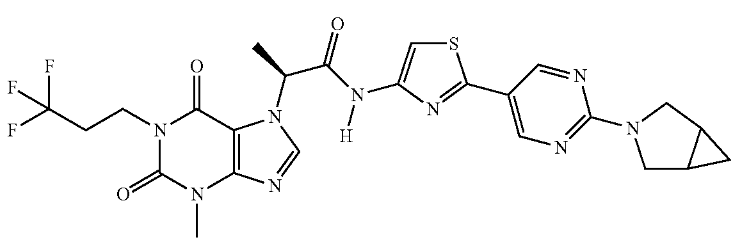 [SMILES: C[C@@H](C(=O)Nc1csc(-c2cnc(N3CC4CC4C3)nc2)n1)n1cnc2c1c(=O)n(CCC(F)(F)F)c(=O)n2C] |
| 104 | 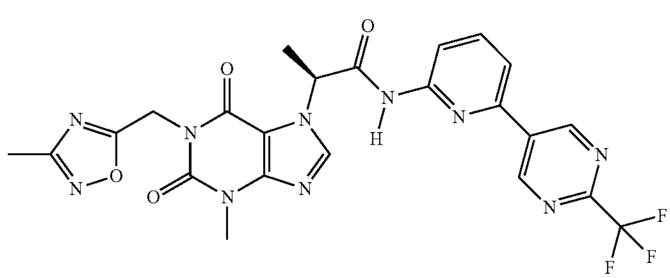 [SMILES: Cc1noc(Cn2c(=O)c3c(ncn3[C@@H](C)C(=O)Nc3cccc(-c4cnc(C(F)(F)F)nc4)n3)n(C)c2=O)n1] |

TABLE 1-continued

| Compound # | Structure |
|---|---|
| 105 | 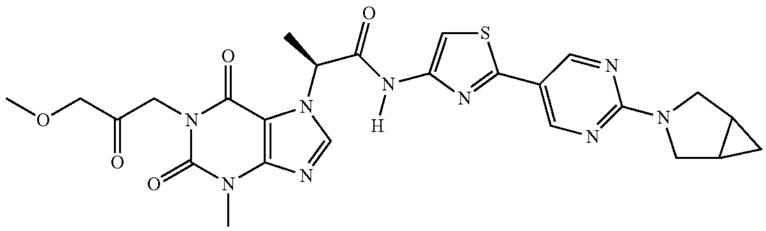 [SMILES: COCC(=O)Cn1c(=O)c2c(ncn2[C@@H](C)C(=O)Nc2csc(-c3cnc(N4CC5CC5C4)nc3)n2)n(C)c1=O] |
| 106 | 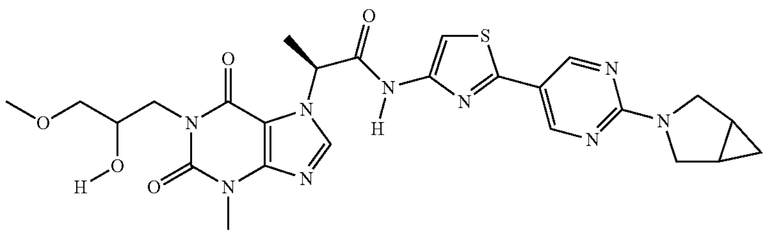 [SMILES: COCC(O)Cn1c(=O)c2c(ncn2[C@@H](C)C(=O)Nc2csc(-c3cnc(N4CC5CC5C4)nc3)n2)n(C)c1=O] |
| 107 | 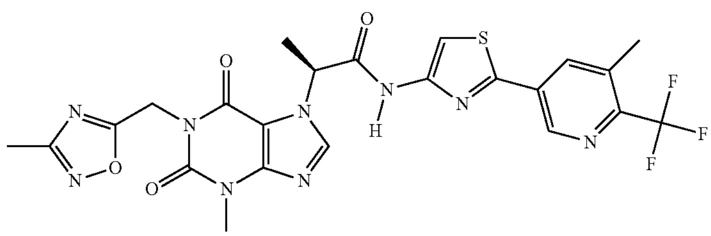 [SMILES: Cc1noc(Cn2c(=O)c3c(ncn3[C@@H](C)C(=O)Nc3csc(-c4cnc(C(F)(F)F)c(C)c4)n3)n(C)c2=O)n1] |
| 108 | 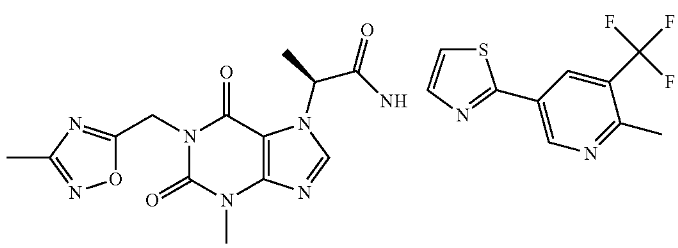 |
| 109 | 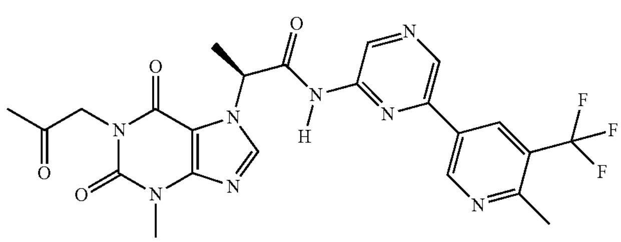 [SMILES: CC(=O)Cn1c(=O)c2c(ncn2[C@@H](C)C(=O)Nc2cncc(-c3cnc(C)c(C(F)(F)F)c3)n2)n(C)c1=O] |
| 110 | 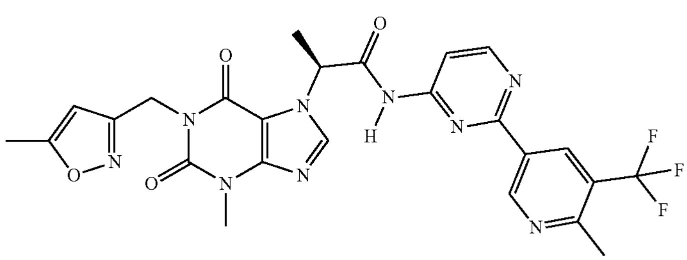 [SMILES: Cc1cc(Cn2c(=O)c3c(ncn3[C@@H](C)C(=O)Nc3ccnc(-c4cnc(C)c(C(F)(F)F)c4)n3)n(C)c2=O)no1] |

TABLE 1-continued
| Compound # | Structure |
|---|---|
| 111 | 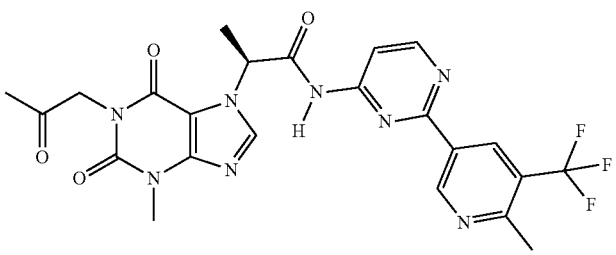 [SMILES: CC(=O)Cn1c(=O)c2c(ncn2[C@@H](C)C(=O)Nc2ccnc(-c3cnc(C)c(C(F)(F)F)c3)n2)n(C)c1=O] |
| 112 | 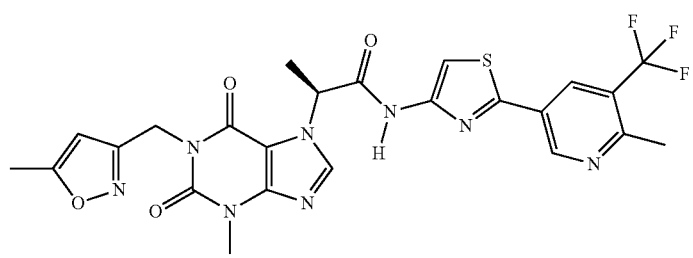 [SMILES: Cc1cc(Cn2c(=O)c3c(ncn3[C@@H](C)C(=O)Nc3csc(-c4cnc(C)c(C(F)(F)F)c4)n3)n(C)c2=O)no1] |
| 113 | 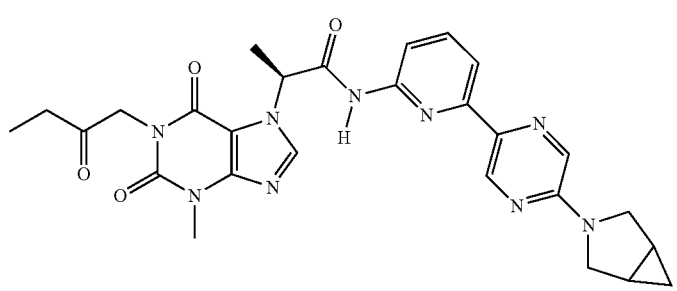 [SMILES: CCC(=O)Cn1c(=O)c2c(ncn2[C@@H](C)C(=O)Nc2cccc(-c3cnc(N4CC5CC5C4)cn3)n2)n(C)c1=O] |
| 114 | 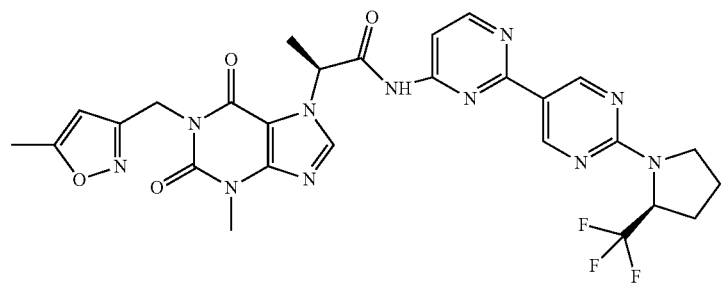 [SMILES: Cc1cc(Cn2c(=O)c3c(ncn3[C@@H](C)C(=O)Nc3ccnc(-c4cnc(N5CCC[C@H]5C(F)(F)F)nc4)n3)n(C)c2=O)no1] |
| 115 | 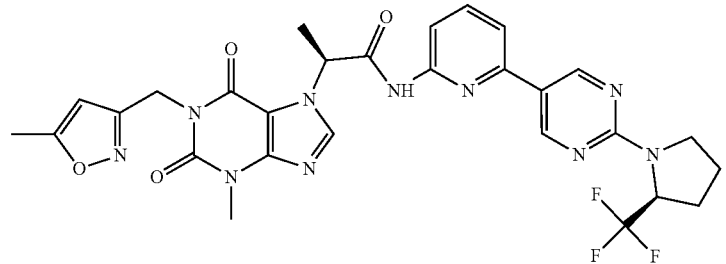 [SMILES: Cc1cc(Cn2c(=O)c3c(ncn3[C@@H](C)C(=O)Nc3cccc(-c4cnc(N5CCC[C@H]5C(F)(F)F)nc4)n3)n(C)c2=O)no1] |

TABLE 1-continued

| Compound # | Structure |
|---|---|
| 116 | 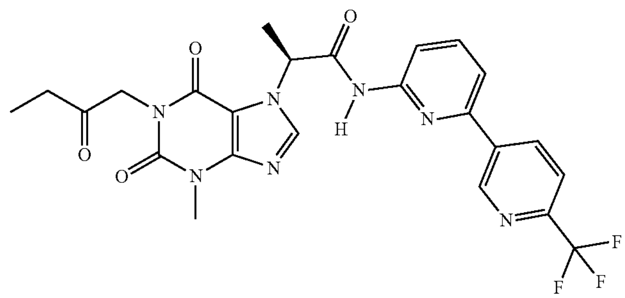 [SMILES: CCC(=O)Cn1c(=O)c2c(ncn2[C@@H](C)C(=O)Nc2cccc(-c3ccc(C(F)(F)F)nc3)n2)n(C)c1=O] |
| 117 | 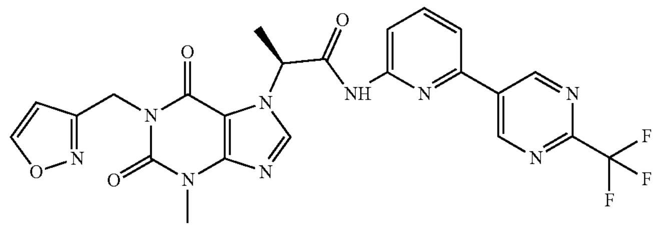 [SMILES: C[C@@H](C(=O)Nc1cccc(-c2cnc(C(F)(F)F)nc2)n1)n1cnc2c1c(=O)n(Cc1ccon1)c(=O)n2C] |
| 118 | 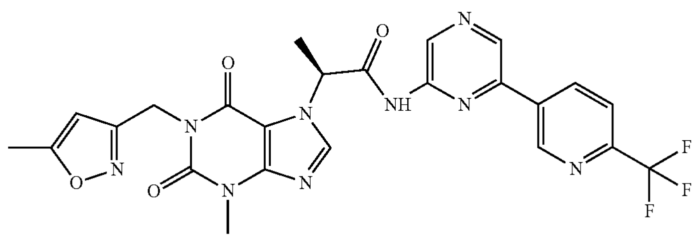 [SMILES: Cc1cc(Cn2c(=O)c3c(ncn3[C@@H](C)C(=O)Nc3cncc(-c4ccc(C(F)(F)F)nc4)n3)n(C)c2=O)no1] |
| 119 | 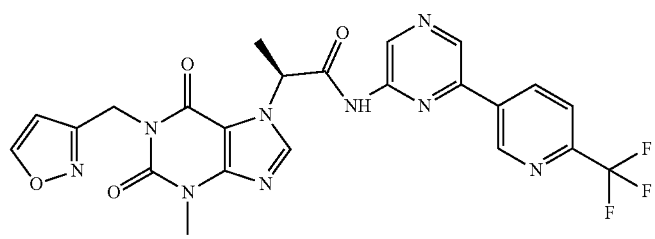 [SMILES: C[C@@H](C(=O)Nc1cncc(-c2ccc(C(F)(F)F)nc2)n1)n1cnc2c1c(=O)n(Cc1ccon1)c(=O)n2C] |
| 120 | 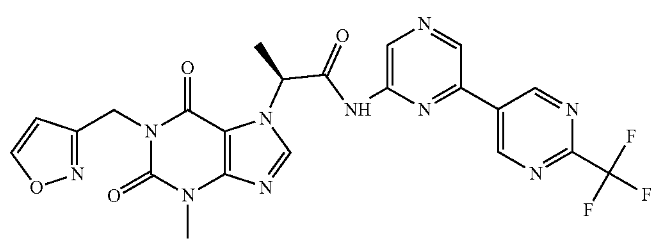 [SMILES: C[C@@H](C(=O)Nc1cncc(-c2cnc(C(F)(F)F)nc2)n1)n1cnc2c1c(=O)n(Cc1ccon1)c(=O)n2C] |
| 121 | 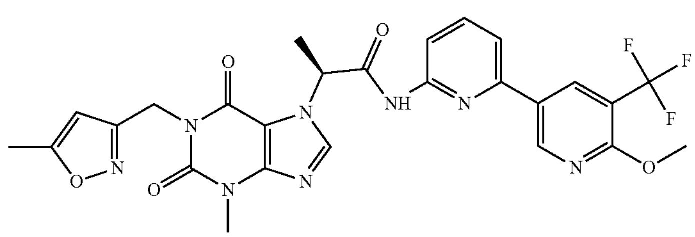 |

TABLE 1-continued

| Compound # | Structure |
|---|---|
| 122 | 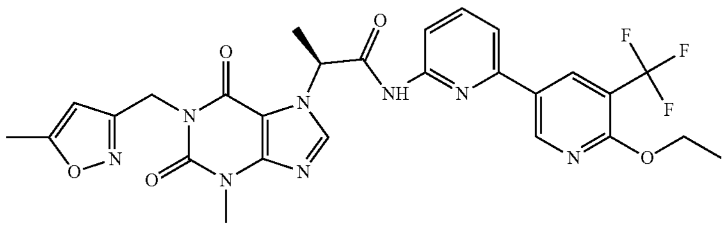 [SMILES: CCOc1ncc(-c2cccc(NC(=O)[C@H](C)n3cnc4c3c(=O)n(Cc3cc(C)on3)c(=O)n4C)n2)cc1C(F)(F)F] |
| 123 | 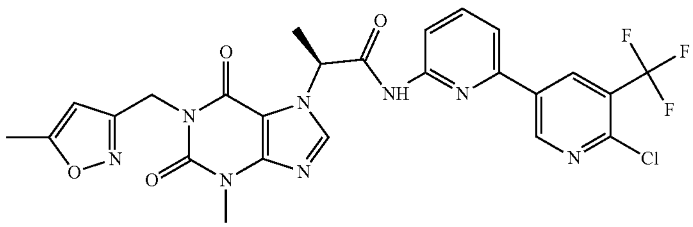 [SMILES: Cc1cc(Cn2c(=O)c3c(ncn3[C@@H](C)C(=O)Nc3cccc(-c4cnc(Cl)c(C(F)(F)F)c4)n3)n(C)c2=O)no1] |
| 124 | 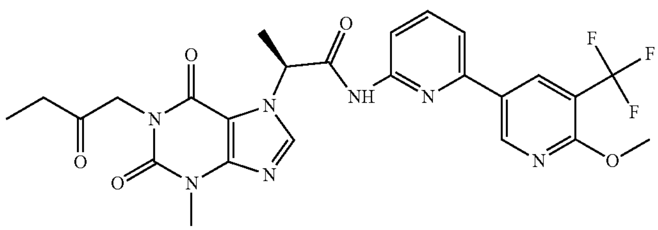 [SMILES: CCC(=O)Cn1c(=O)c2c(ncn2[C@@H](C)C(=O)Nc2cccc(-c3cnc(OC)c(C(F)(F)F)c3)n2)n(C)c1=O] |
| 125 | 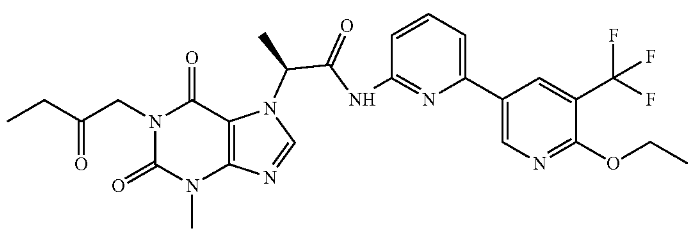 [SMILES: CCOc1ncc(-c2cccc(NC(=O)[C@H](C)n3cnc4c3c(=O)n(CC(=O)CC)c(=O)n4C)n2)cc1C(F)(F)F] |
| 126 | 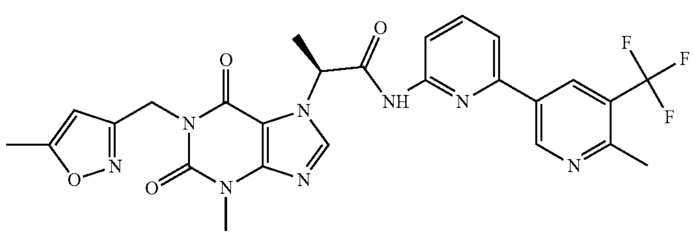 [SMILES: Cc1cc(Cn2c(=O)c3c(ncn3[C@@H](C)C(=O)Nc3cccc(-c4cnc(C)c(C(F)(F)F)c4)n3)n(C)c2=O)no1] |
| 127 | 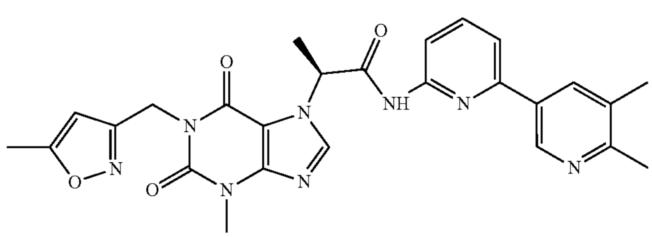 |

TABLE 1-continued
| Compound # | Structure |
|---|---|
| 128 | 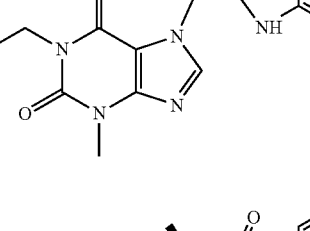 |
| 129 | 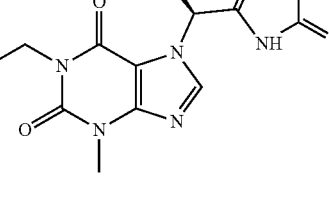 |
| 130 | 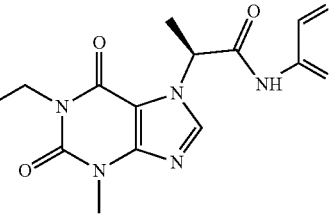 |
| 131 | 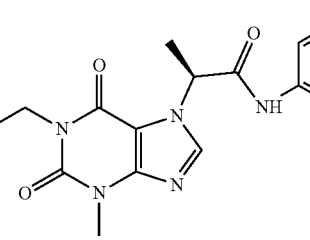 |
| 132 | 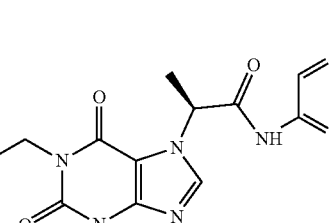 |
| 133 | 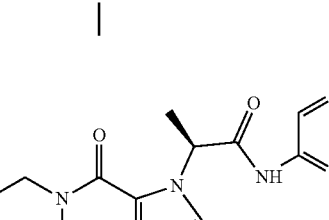 |

TABLE 1-continued

| Compound # | Structure |
|---|---|
| 134 | 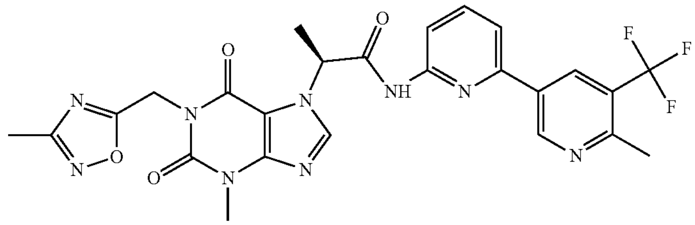 [SMILES: Cc1noc(Cn2c(=O)c3c(ncn3[C@@H](C)C(=O)Nc3cccc(-c4cnc(C)c(C(F)(F)F)c4)n3)n(C)c2=O)n1] |
| 135 | 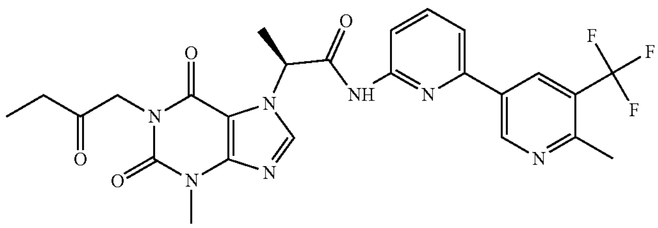 [SMILES: CCC(=O)Cn1c(=O)c2c(ncn2[C@@H](C)C(=O)Nc2cccc(-c3cnc(C)c(C(F)(F)F)c3)n2)n(C)c1=O] |
| 136 | 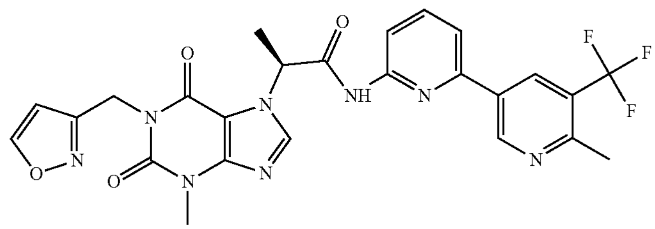 [SMILES: Cc1ncc(-c2cccc(NC(=O)[C@H](C)n3cnc4c3c(=O)n(Cc3ccon3)c(=O)n4C)n2)cc1C(F)(F)F] |
| 137 | 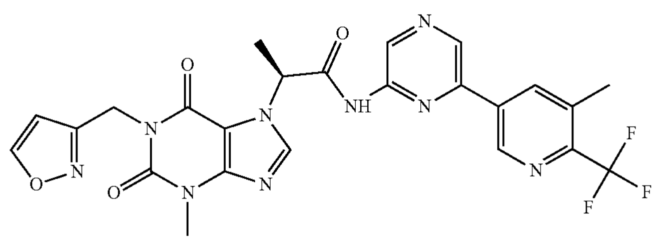 [SMILES: Cc1cc(-c2cncc(NC(=O)[C@H](C)n3cnc4c3c(=O)n(Cc3ccon3)c(=O)n4C)n2)cnc1C(F)(F)F] |
| 139 | 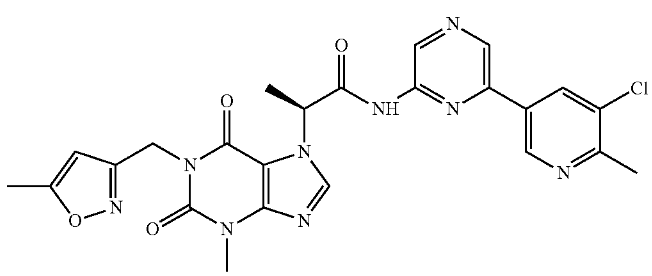 |
| 140 | 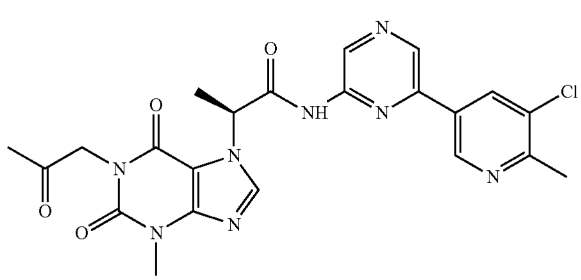 [SMILES: CC(=O)Cn1c(=O)c2c(ncn2[C@@H](C)C(=O)Nc2cncc(-c3cnc(C)c(Cl)c3)n2)n(C)c1=O] |

TABLE 1-continued
| Compound # | Structure |
|---|---|
| 141 | 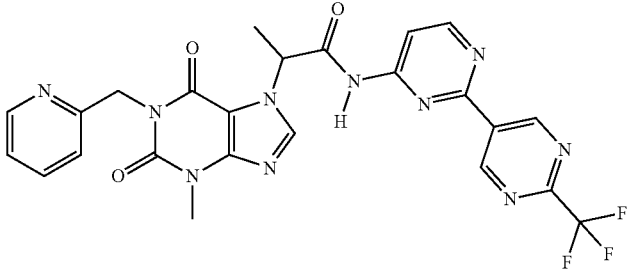 [SMILES: CC(C(=O)Nc1ccnc(-c2cnc(C(F)(F)F)nc2)n1)n1cnc2c1c(=O)n(Cc1ccccn1)c(=O)n2C] |
| 142 | 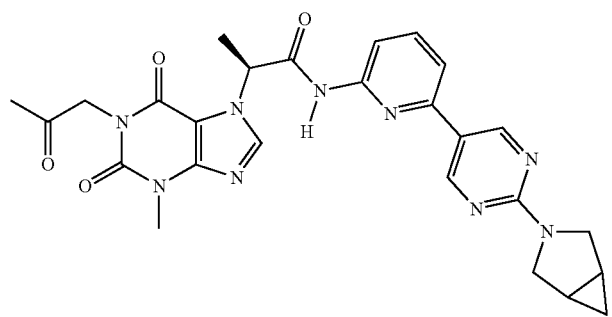 [SMILES: CC(=O)Cn1c(=O)c2c(ncn2[C@@H](C)C(=O)Nc2cccc(-c3cnc(N4CC5CC5C4)nc3)n2)n(C)c1=O] |
| 143 | 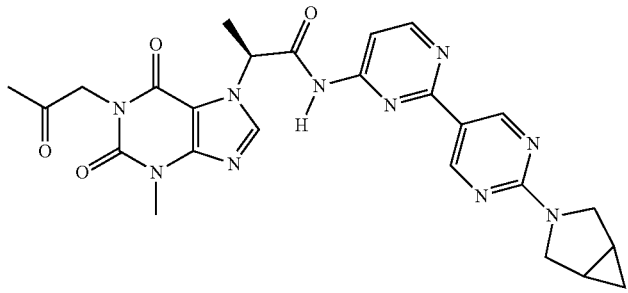 [SMILES: CC(=O)Cn1c(=O)c2c(ncn2[C@@H](C)C(=O)Nc2ccnc(-c3cnc(N4CC5CC5C4)nc3)n2)n(C)c1=O] |
| 144 | 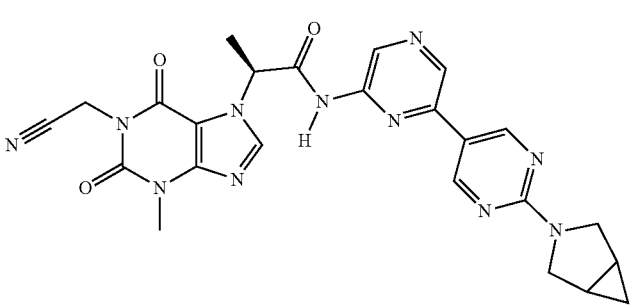 [SMILES: C[C@@H](C(=O)Nc1cncc(-c2cnc(N3CC4CC4C3)nc2)n1)n1cnc2c1c(=O)n(CC#N)c(=O)n2C] |
| 145 | 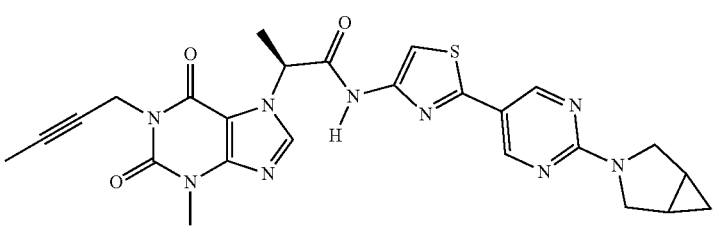 [SMILES: CC#CCn1c(=O)c2c(ncn2[C@@H](C)C(=O)Nc2csc(-c3cnc(N4CC5CC5C4)nc3)n2)n(C)c1=O] |

TABLE 1-continued
| Compound # | Structure |
|---|---|
| 146 | 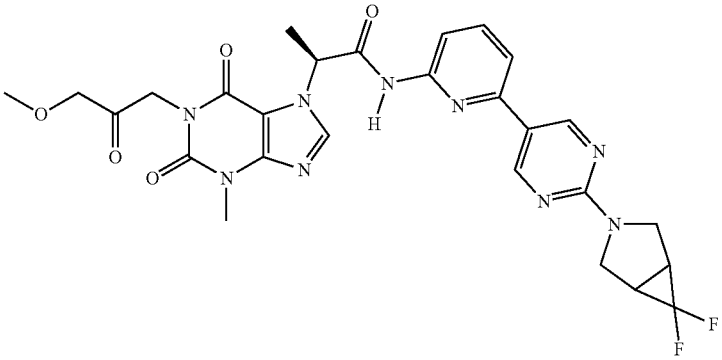 [SMILES: COCC(=O)Cn1c(=O)c2c(ncn2[C@@H](C)C(=O)Nc2cccc(-c3cnc(N4CC5C(C4)C5(F)F)nc3)n2)n(C)c1=O] |
| 147 | 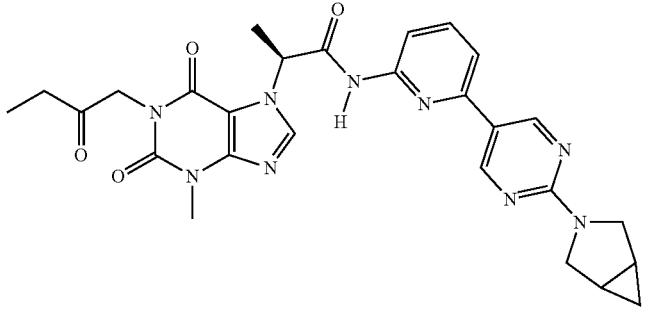 [SMILES: CCC(=O)Cn1c(=O)c2c(ncn2[C@@H](C)C(=O)Nc2cccc(-c3cnc(N4CC5CC5C4)nc3)n2)n(C)c1=O] |
| 148 | 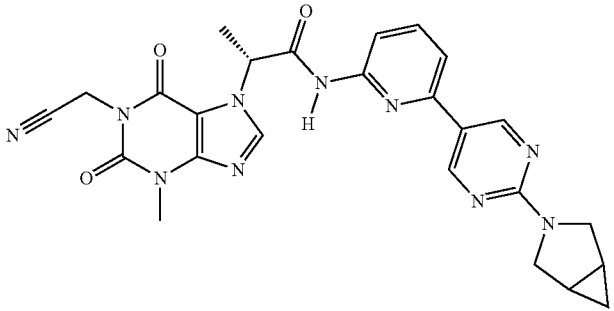 [SMILES: C[C@H](C(=O)Nc1cccc(-c2cnc(N3CC4CC4C3)nc2)n1)n1cnc2c1c(=O)n(CC#N)c(=O)n2C] |
| 149 | 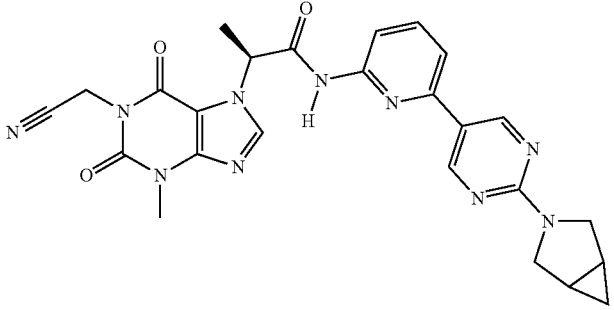 [SMILES: C[C@@H](C(=O)Nc1cccc(-c2cnc(N3CC4CC4C3)nc2)n1)n1cnc2c1c(=O)n(CC#N)c(=O)n2C] |

TABLE 1-continued

| Compound # | Structure |
|---|---|
| 150 | 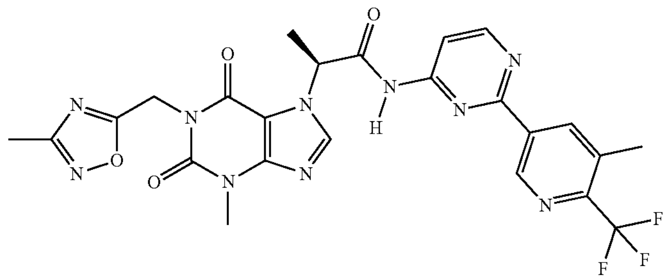 [SMILES: Cc1noc(Cn2c(=O)c3c(ncn3[C@@H](C)C(=O)Nc3ccnc(-c4cnc(C(F)(F)F)c(C)c4)n3)n(C)c2=O)n1] |
| 151 | 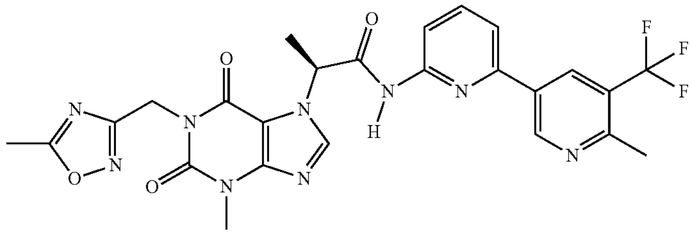 [SMILES: Cc1nc(Cn2c(=O)c3c(ncn3[C@@H](C)C(=O)Nc3cccc(-c4cnc(C)c(C(F)(F)F)c4)n3)n(C)c2=O)no1] |
| 152 | 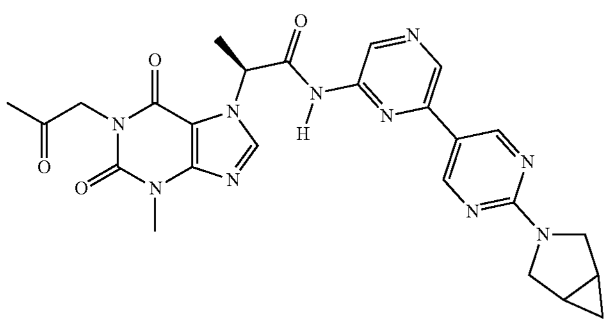 [SMILES: CC(=O)Cn1c(=O)c2c(ncn2[C@@H](C)C(=O)Nc2cncc(-c3cnc(N4CC5CC5C4)nc3)n2)n(C)c1=O] |
| 153 | 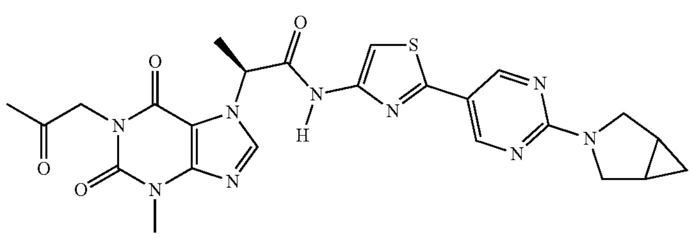 [SMILES: CC(=O)Cn1c(=O)c2c(ncn2[C@@H](C)C(=O)Nc2csc(-c3cnc(N4CC5CC5C4)nc3)n2)n(C)c1=O] |
| 154 | 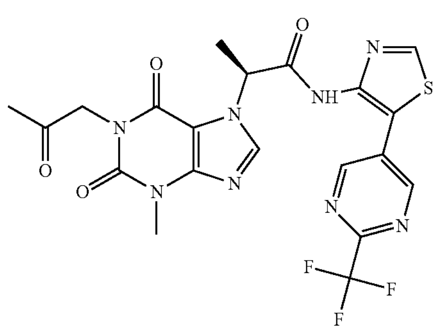 [SMILES: CC(=O)Cn1c(=O)c2c(ncn2[C@@H](C)C(=O)Nc2ncsc2-c2cnc(C(F)(F)F)nc2)n(C)c1=O] |

TABLE 1-continued

| Compound # | Structure |
|---|---|
| 155 | 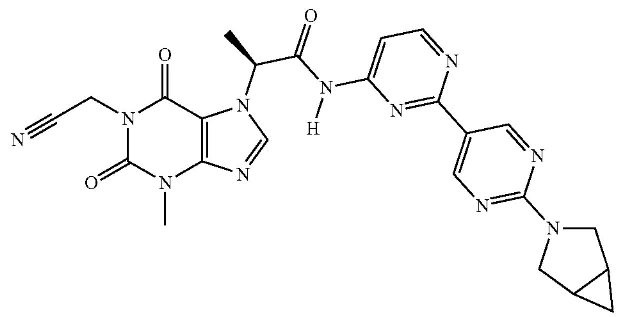 [SMILES: C[C@@H](C(=O)Nc1ccnc(-c2cnc(N3CC4CC4C3)nc2)n1)n1cnc2c1c(=O)n(CC#N)c(=O)n2C] |
| 156 | 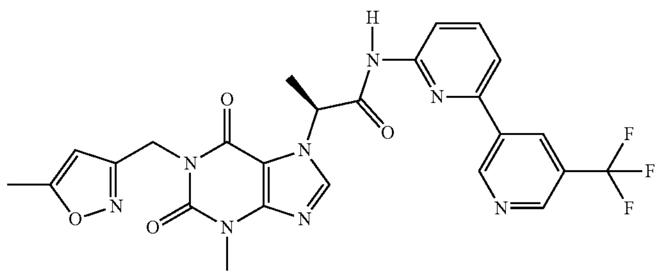 [SMILES: Cc1cc(Cn2c(=O)c3c(ncn3[C@@H](C)C(=O)Nc3cccc(-c4cncc(C(F)(F)F)c4)n3)n(C)c2=O)no1] |
| 157 | 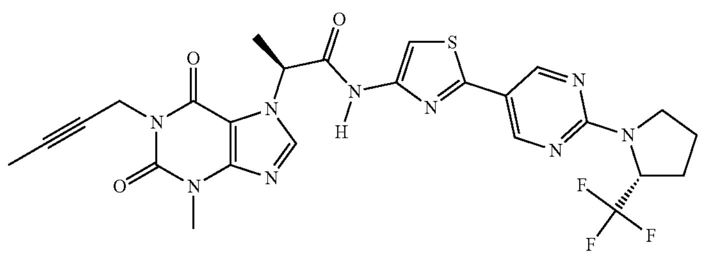 [SMILES: CC#CCn1c(=O)c2c(ncn2[C@@H](C)C(=O)Nc2csc(-c3cnc(N4CCC[C@@H]4C(F)(F)F)nc3)n2)n(C)c1=O] |
| 158 | 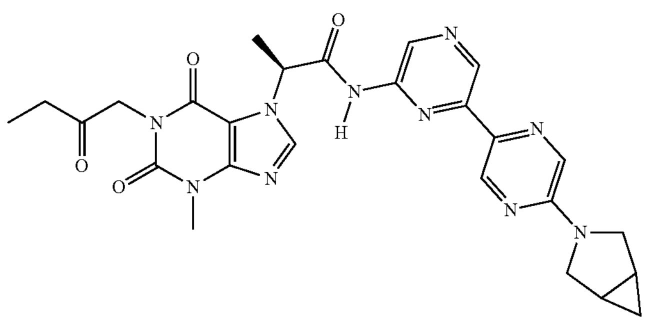 [SMILES: CCC(=O)Cn1c(=O)c2c(ncn2[C@@H](C)C(=O)Nc2cncc(-c3cnc(N4CC5CC5C4)cn3)n2)n(C)c1=O] |
| 159 | 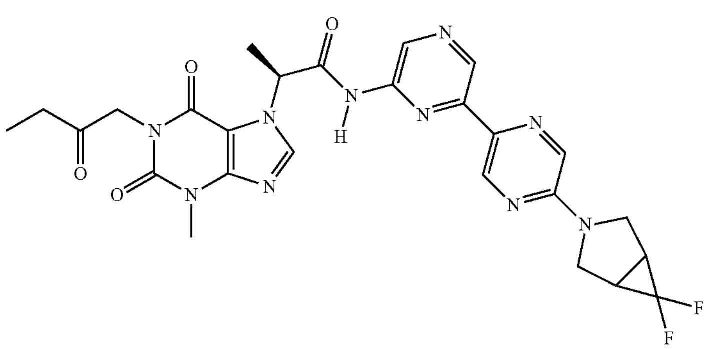 [SMILES: CCC(=O)Cn1c(=O)c2c(ncn2[C@@H](C)C(=O)Nc2cncc(-c3cnc(N4CC5C(C4)C5(F)F)cn3)n2)n(C)c1=O] |

TABLE 1-continued

| Compound # | Structure |
|---|---|
| 160 | 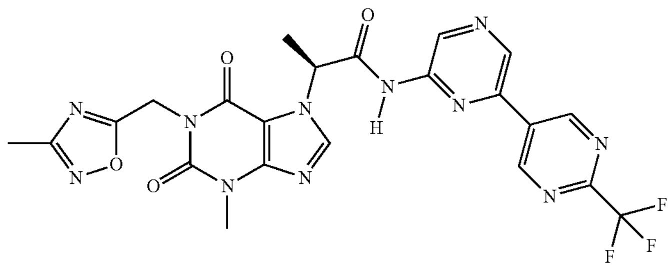 |
| 161 | 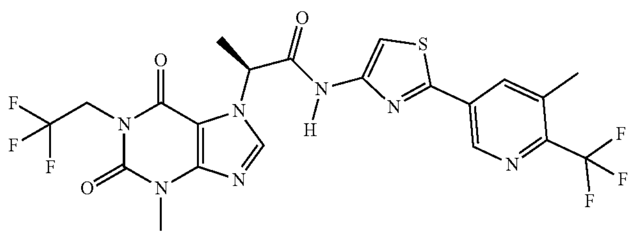 [SMILES: Cc1cc(-c2nc(NC(=O)[C@H](C)n3cnc4c3c(=O)n(CC(F)(F)F)c(=O)n4C)cs2)cnc1C(F)(F)F] |
| 162 | 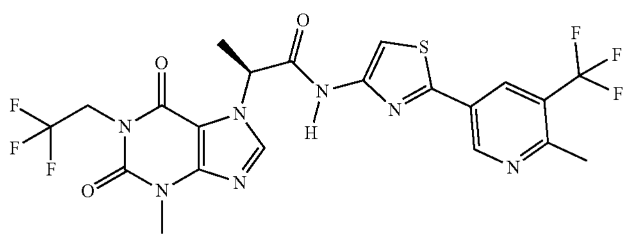 [SMILES: Cc1ncc(-c2nc(NC(=O)[C@H](C)n3cnc4c3c(=O)n(CC(F)(F)F)c(=O)n4C)cs2)cc1C(F)(F)F] |
| 163 | 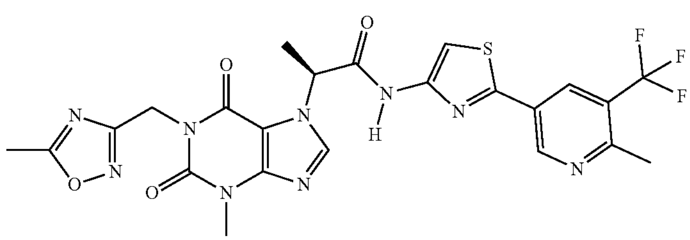 [SMILES: Cc1nc(Cn2c(=O)c3c(ncn3[C@@H](C)C(=O)Nc3csc(-c4cnc(C)c(C(F)(F)F)c4)n3)n(C)c2=O)no1] |
| 164 | 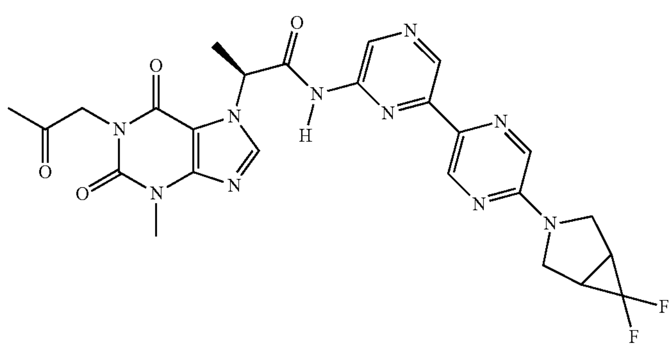 [SMILES: CC(=O)Cn1c(=O)c2c(ncn2[C@@H](C)C(=O)Nc2cncc(-c3cnc(N4CC5C(C4)C5(F)F)cn3)n2)n(C)c1=O] |

TABLE 1-continued

| Compound # | Structure |
|---|---|
| 165 | 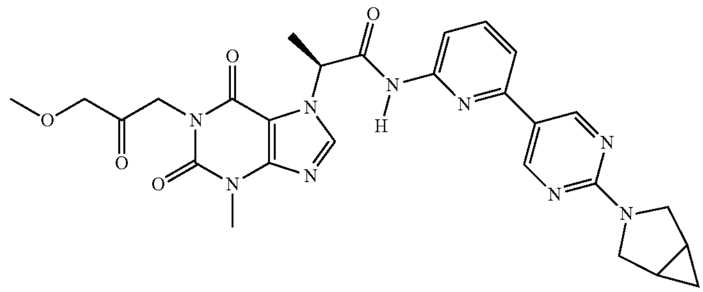 [SMILES: COCC(=O)Cn1c(=O)c2c(ncn2[C@@H](C)C(=O)Nc2cccc(-c3cnc(N4CC5CC5C4)nc3)n2)n(C)c1=O] |
| 166 | 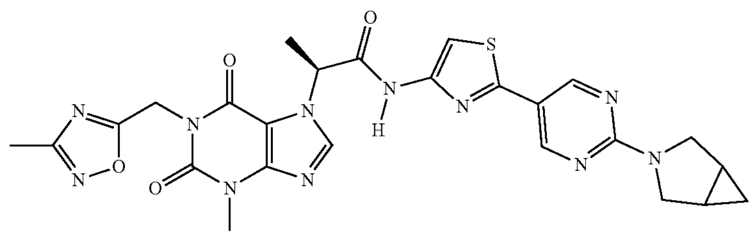 [SMILES: Cc1noc(Cn2c(=O)c3c(ncn3[C@@H](C)C(=O)Nc3csc(-c4cnc(N5CC6CC6C5)nc4)n3)n(C)c2=O)n1] |
| 167 | 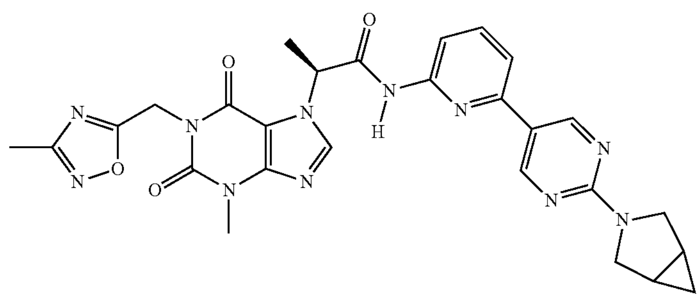 [SMILES: Cc1noc(Cn2c(=O)c3c(ncn3[C@@H](C)C(=O)Nc3cccc(-c4cnc(N5CC6CC6C5)nc4)n3)n(C)c2=O)n1] |
| 168 | 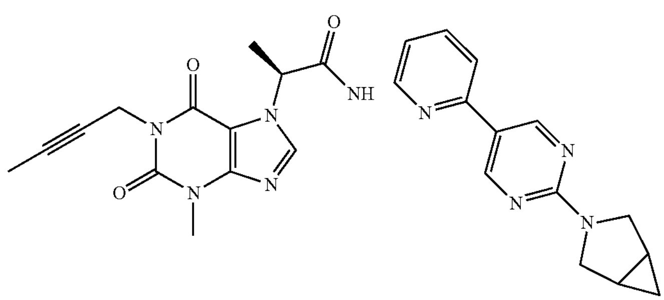 |
| 169 | 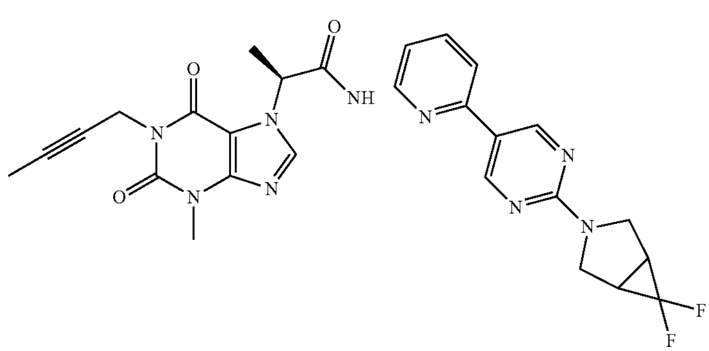 |

TABLE 1-continued

| Compound # | Structure |
|---|---|
| 170 | 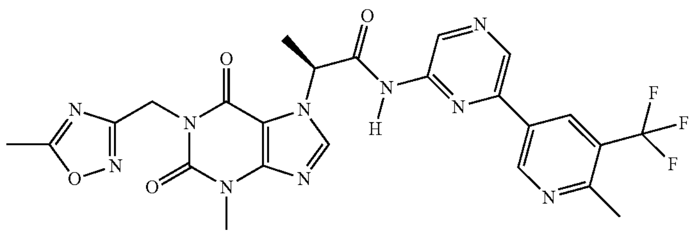 [SMILES: Cc1nc(Cn2c(=O)c3c(ncn3[C@@H](C)C(=O)Nc3cncc(-c4cnc(C)c(C(F)(F)F)c4)n3)n(C)c2=O)no1] |
| 171 | 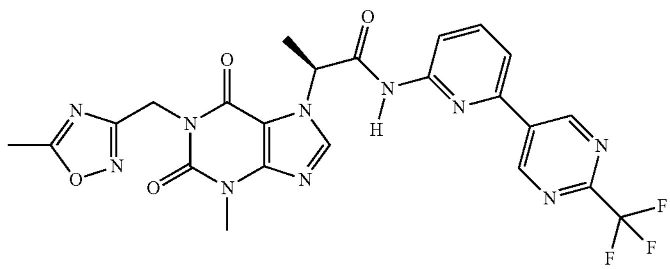 [SMILES: Cc1nc(Cn2c(=O)c3c(ncn3[C@@H](C)C(=O)Nc3cccc(-c4cnc(C(F)(F)F)nc4)n3)n(C)c2=O)no1] |
| 172 | 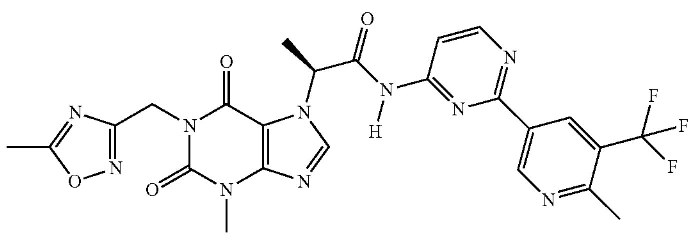 [SMILES: Cc1nc(Cn2c(=O)c3c(ncn3[C@@H](C)C(=O)Nc3ccnc(-c4cnc(C)c(C(F)(F)F)c4)n3)n(C)c2=O)no1] |
| 173 | 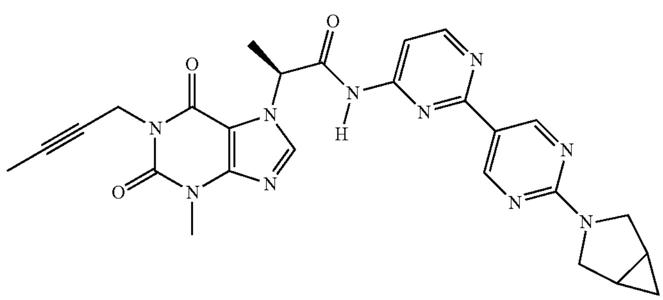 [SMILES: CC#CCn1c(=O)c2c(ncn2[C@@H](C)C(=O)Nc2ccnc(-c3cnc(N4CC5CC5C4)nc3)n2)n(C)c1=O] |
| 174 | 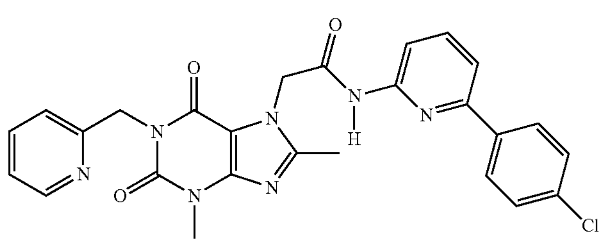 [SMILES: Cc1nc2c(c(=O)n(Cc3ccccn3)c(=O)n2C)n1CC(=O)Nc1cccc(-c2ccc(Cl)cc2)n1] |
| 175 | 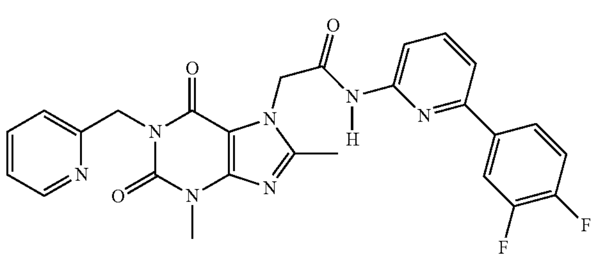 [SMILES: Cc1nc2c(c(=O)n(Cc3ccccn3)c(=O)n2C)n1CC(=O)Nc1cccc(-c2ccc(F)c(F)c2)n1] |

TABLE 1-continued
| Compound # | Structure |
|---|---|
| 176 | 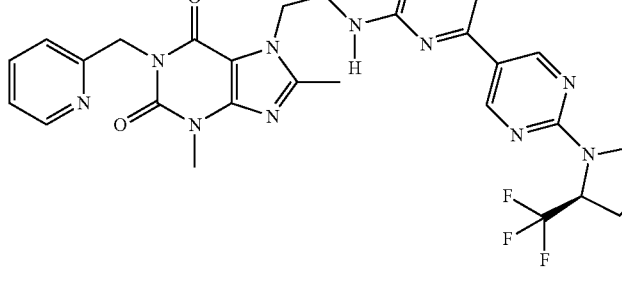 |
| 177 | 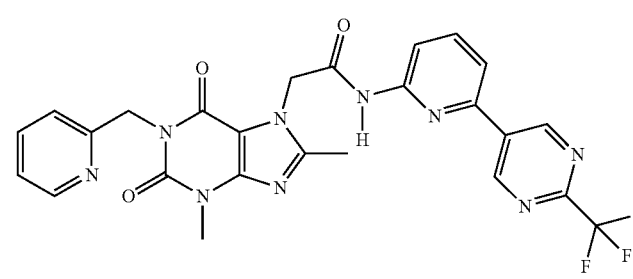 |
| 178 | 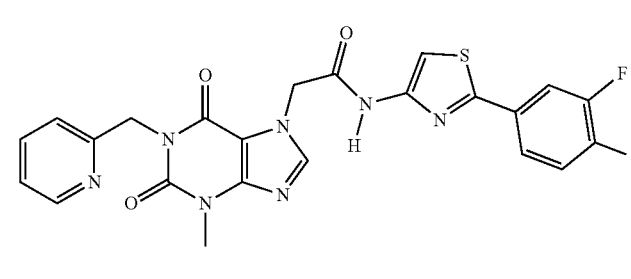 |
| 181 | 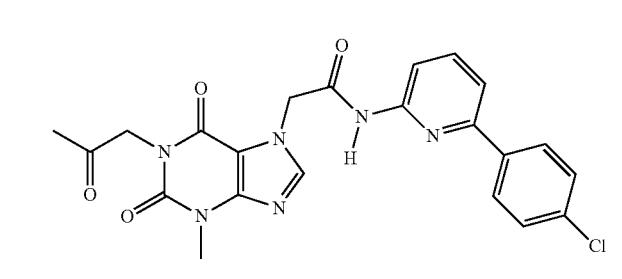 [SMILES: CC(=O)Cn1c(=O)c2c(ncn2CC(=O)Nc2cccc(-c3ccc(Cl)cc3)n2)n(C)c1=O] |
| 182 | 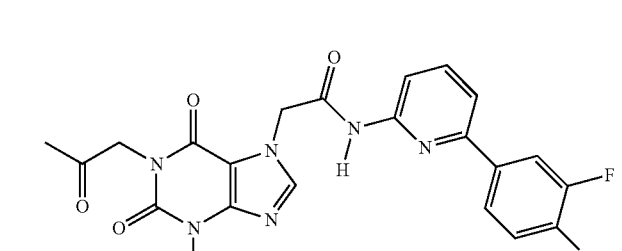 |

TABLE 1-continued

| Compound # | Structure |
|---|---|
| 183 | 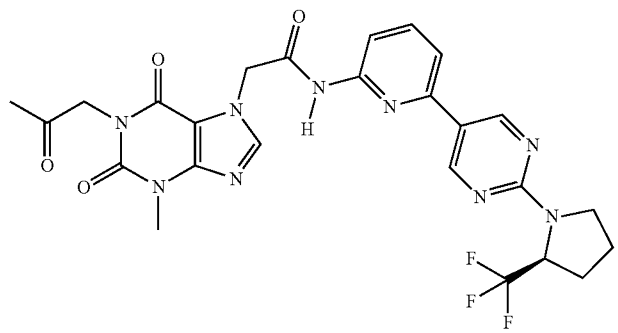 [SMILES: CC(=O)Cn1c(=O)c2c(ncn2CC(=O)Nc2cccc(-c3cnc(N4CCC[C@H]4C(F)(F)F)nc3)n2)n(C)c1=O] |
| 184 | 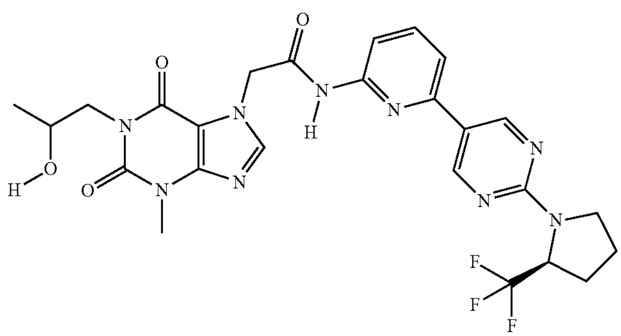 [SMILES: CC(O)Cn1c(=O)c2c(ncn2CC(=O)Nc2cccc(-c3cnc(N4CCC[C@H]4C(F)(F)F)nc3)n2)n(C)c1=O] |
| 185 | 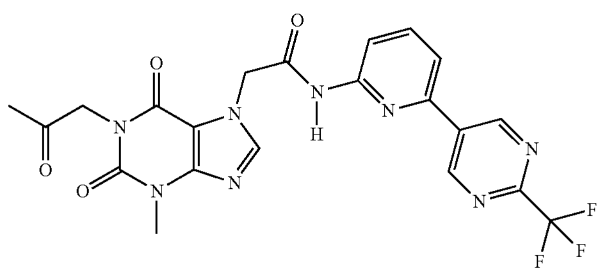 [SMILES: CC(=O)Cn1c(=O)c2c(ncn2CC(=O)Nc2cccc(-c3cnc(C(F)(F)F)nc3)n2)n(C)c1=O] |
| 186 | 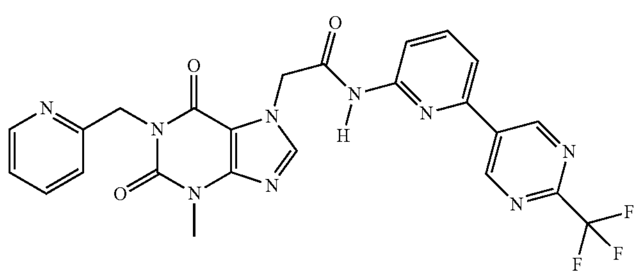 [SMILES: Cn1c(=O)n(Cc2ccccn2)c(=O)c2c1ncn2CC(=O)Nc1cccc(-c2cnc(C(F)(F)F)nc2)n1] |
| 187 | 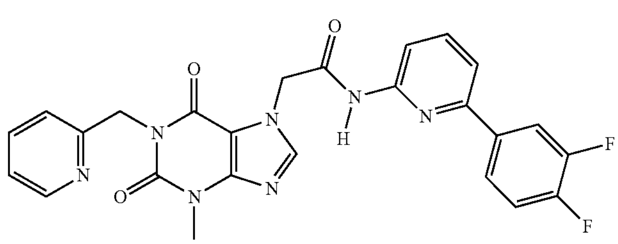 [SMILES: Cn1c(=O)n(Cc2ccccn2)c(=O)c2c1ncn2CC(=O)Nc1cccc(-c2ccc(F)c(F)c2)n1] |

TABLE 1-continued
| Compound # | Structure |
|---|---|
| 188 | 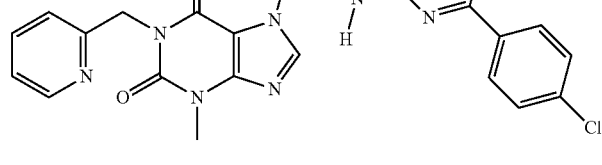 |
| 189 | 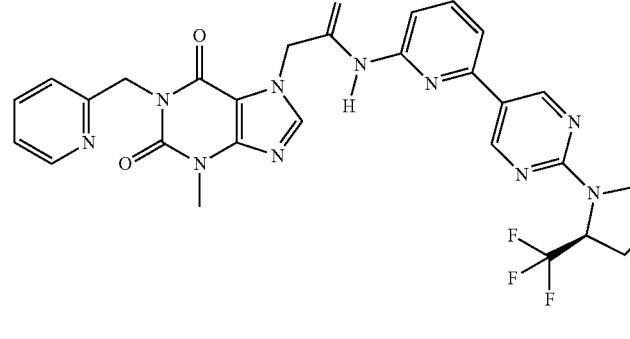 |
| 190 | 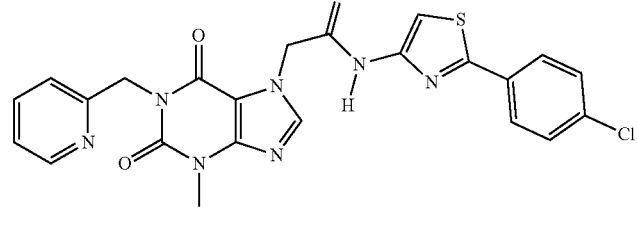 |
| 191 | 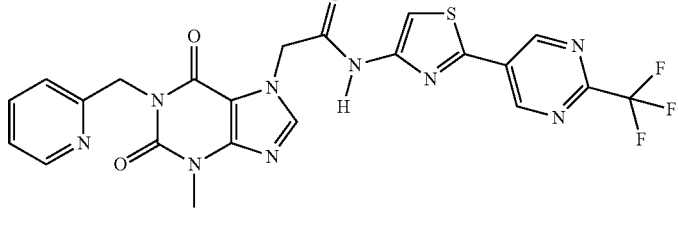 |
| 192 | 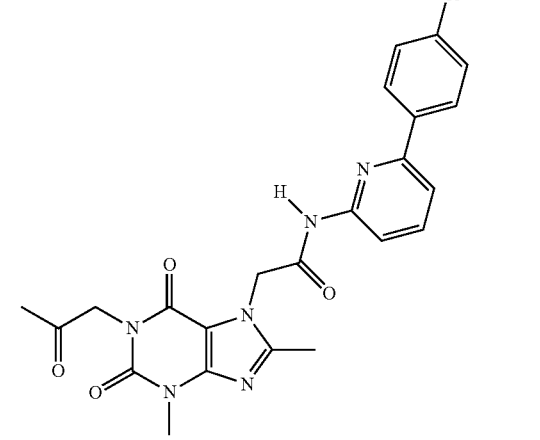 |

TABLE 1-continued

| Compound # | Structure |
|---|---|
| 193 | 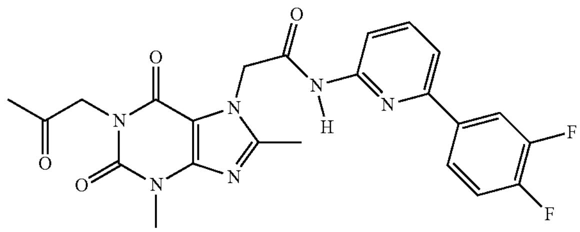 [SMILES: CC(=O)Cn1c(=O)c2c(nc(C)n2CC(=O)Nc2cccc(-c3ccc(F)c(F)c3)n2)n(C)c1=O] |
| 194 | 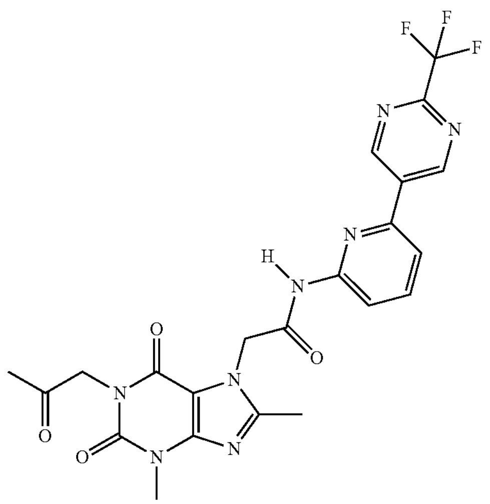 [SMILES: CC(=O)Cn1c(=O)c2c(nc(C)n2CC(=O)Nc2cccc(-c3cnc(C(F)(F)F)nc3)n2)n(C)c1=O] |
| 195 | 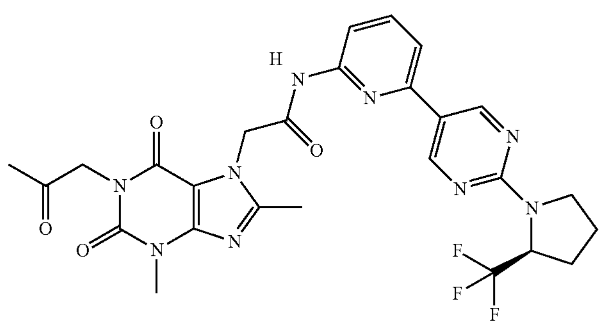 |
| 196 | 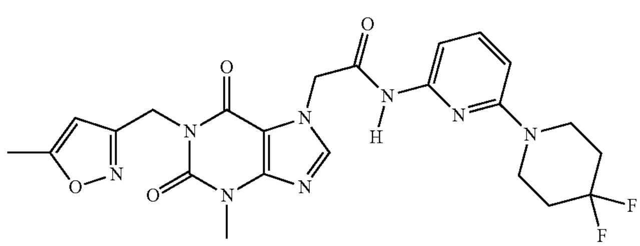 [SMILES: Cc1cc(Cn2c(=O)c3c(ncn3CC(=O)Nc3cccc(N4CCC(F)(F)CC4)n3)n(C)c2=O)no1] |
| 197 | 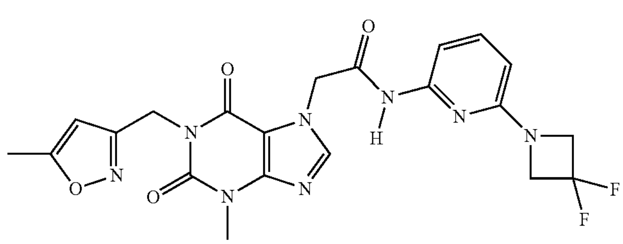 [SMILES: Cc1cc(Cn2c(=O)c3c(ncn3CC(=O)Nc3cccc(N4CC(F)(F)C4)n3)n(C)c2=O)no1] |

TABLE 1-continued

| Compound # | Structure |
|---|---|
| 198 | 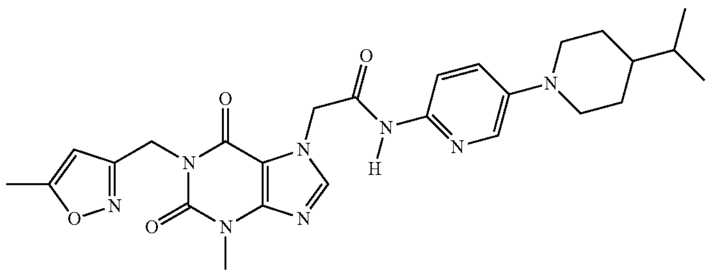 [SMILES: Cc1cc(Cn2c(=O)c3c(ncn3CC(=O)Nc3ccc(N4CCC(C(C)C)CC4)cn3)n(C)c2=O)no1] |
| 199 | 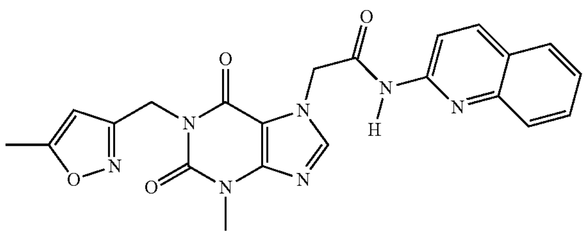 [SMILES: Cc1cc(Cn2c(=O)c3c(ncn3CC(=O)Nc3ccc4ccccc4n3)n(C)c2=O)no1] |
| 200 | 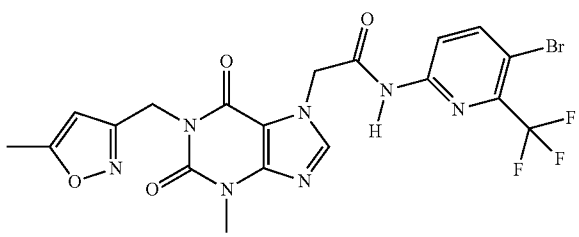 [SMILES: Cc1cc(Cn2c(=O)c3c(ncn3CC(=O)Nc3ccc(Br)c(C(F)(F)F)n3)n(C)c2=O)no1] |
| 201 | 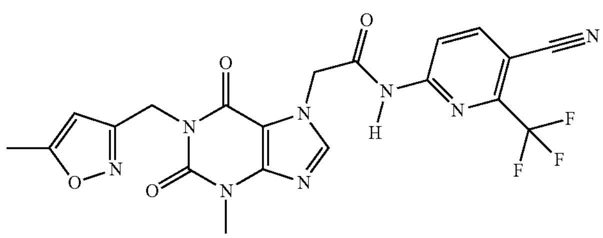 [SMILES: Cc1cc(Cn2c(=O)c3c(ncn3CC(=O)Nc3ccc(C#N)c(C(F)(F)F)n3)n(C)c2=O)no1] |
| 202 | 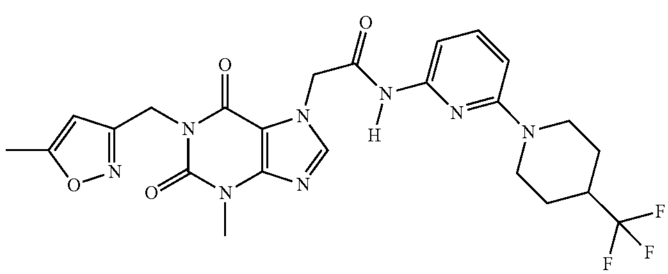 [SMILES: Cc1cc(Cn2c(=O)c3c(ncn3CC(=O)Nc3cccc(N4CCC(C(F)(F)F)CC4)n3)n(C)c2=O)no1] |
| 203 | 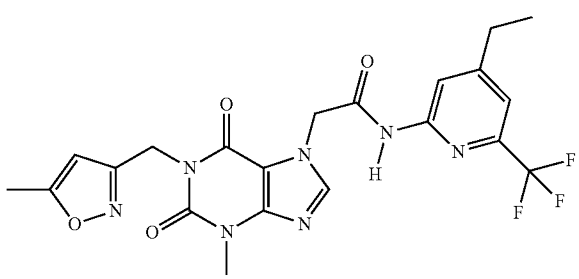 [SMILES: CCc1cc(NC(=O)Cn2cnc3c2c(=O)n(Cc2cc(C)on2)c(=O)n3C)nc(C(F)(F)F)c1] |

TABLE 1-continued
| Compound # | Structure |
|---|---|
| 204 | 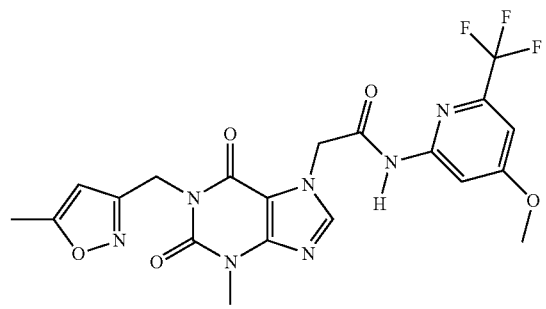 [SMILES: COc1cc(NC(=O)Cn2cnc3c2c(=O)n(Cc2cc(C)on2)c(=O)n3C)nc(C(F)(F)F)c1] |
| 211 | 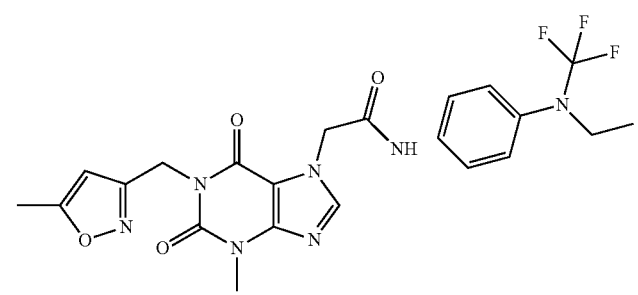 |
| 212 | 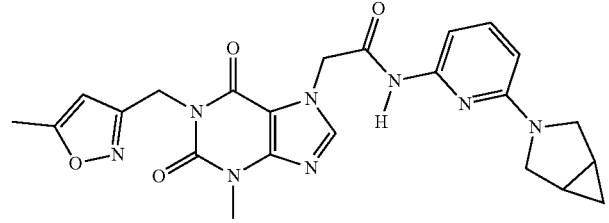 [SMILES: Cc1cc(Cn2c(=O)c3c(ncn3CC(=O)Nc3cccc(N4CC5CC5C4)n3)n(C)c2=O)no1] |
| 213 | 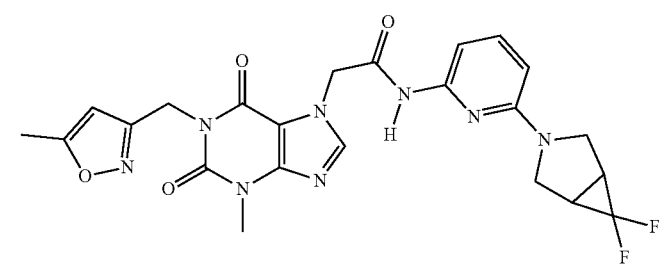 [SMILES: Cc1cc(Cn2c(=O)c3c(ncn3CC(=O)Nc3cccc(N4CC5C(C4)C5(F)F)n3)n(C)c2=O)no1] |
| 214 | 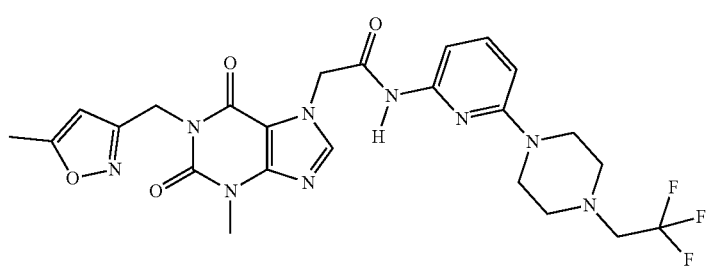 [SMILES: Cc1cc(Cn2c(=O)c3c(ncn3CC(=O)Nc3cccc(N4CCN(CC(F)(F)F)CC4)n3)n(C)c2=O)no1] |

TABLE 1-continued
| Compound # | Structure |
|---|---|
| 215 | 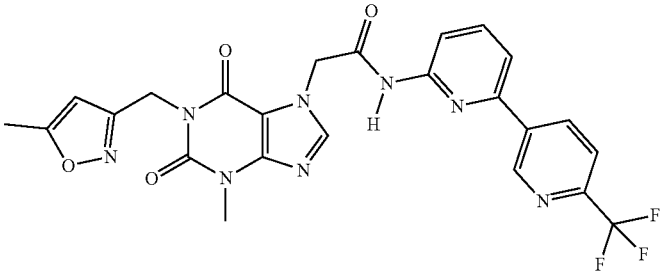 [SMILES: Cc1cc(Cn2c(=O)c3c(ncn3CC(=O)Nc3cccc(-c4ccc(C(F)(F)F)nc4)n3)n(C)c2=O)no1] |
| 216 | 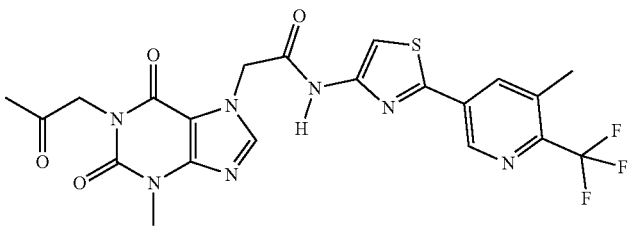 [SMILES: CC(=O)Cn1c(=O)c2c(ncn2CC(=O)Nc2csc(-c3cnc(C(F)(F)F)c(C)c3)n2)n(C)c1=O] |
| 217 | 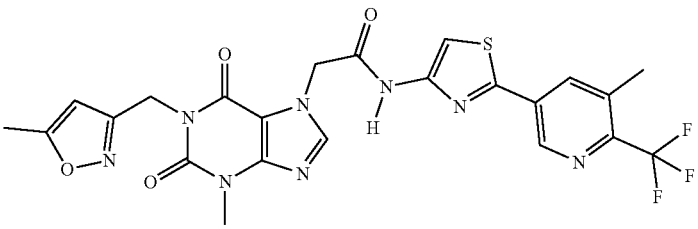 [SMILES: Cc1cc(Cn2c(=O)c3c(ncn3CC(=O)Nc3csc(-c4cnc(C(F)(F)F)c(C)c4)n3)n(C)c2=O)no1] |
| 218 | 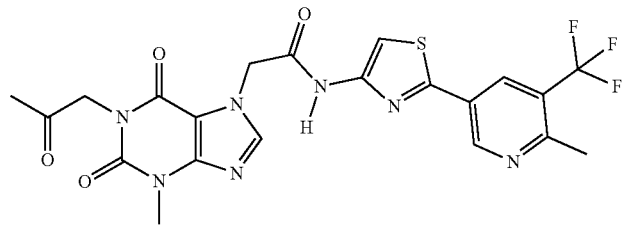 [SMILES: CC(=O)Cn1c(=O)c2c(ncn2CC(=O)Nc2csc(-c3cnc(C)c(C(F)(F)F)c3)n2)n(C)c1=O] |
| 219 | 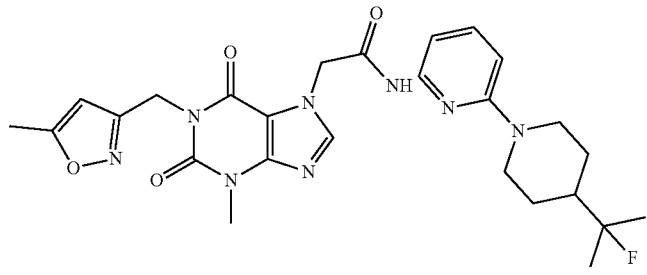 |
| 220 | 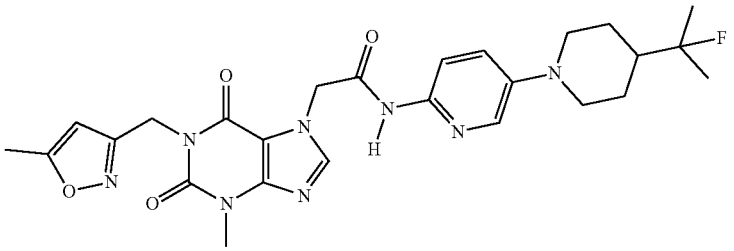 [SMILES: Cc1cc(Cn2c(=O)c3c(ncn3CC(=O)Nc3ccc(N4CCC(C(C)(C)F)CC4)cn3)n(C)c2=O)no1] |

TABLE 1-continued

| Compound # | Structure |
| --- | --- |
| 221 | 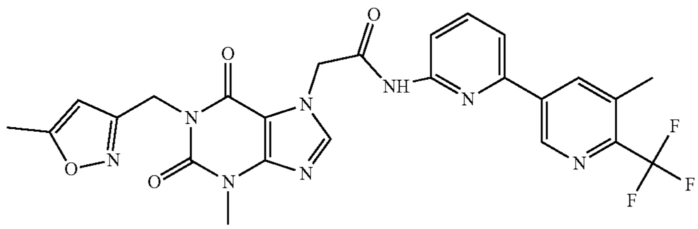 [SMILES: Cc1cc(Cn2c(=O)c3c(ncn3CC(=O)Nc3cccc(-c4cnc(C(F)(F)F)c(C)c4)n3)n(C)c2=O)no1] |
| 222 | 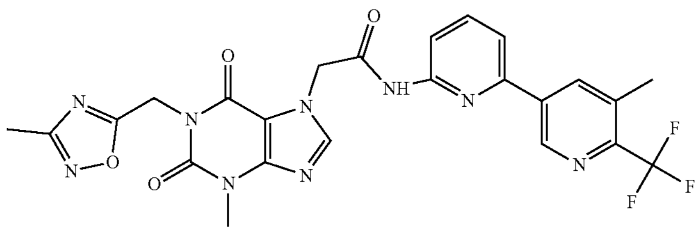 [SMILES: Cc1noc(Cn2c(=O)c3c(ncn3CC(=O)Nc3cccc(-c4cnc(C(F)(F)F)c(C)c4)n3)n(C)c2=O)n1] |
| 223 | 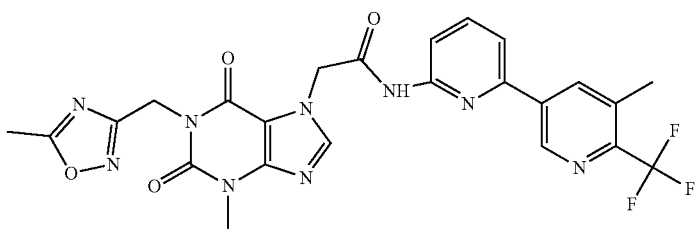 [SMILES: Cc1nc(Cn2c(=O)c3c(ncn3CC(=O)Nc3cccc(-c4cnc(C(F)(F)F)c(C)c4)n3)n(C)c2=O)no1] |
| 224 | 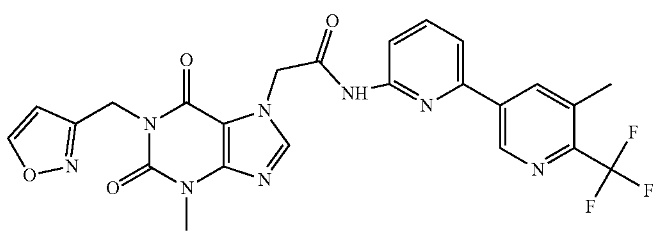 [SMILES: Cc1cc(-c2cccc(NC(=O)Cn3cnc4c3c(=O)n(Cc3ccon3)c(=O)n4C)n2)cnc1C(F)(F)F] |
| 225 | 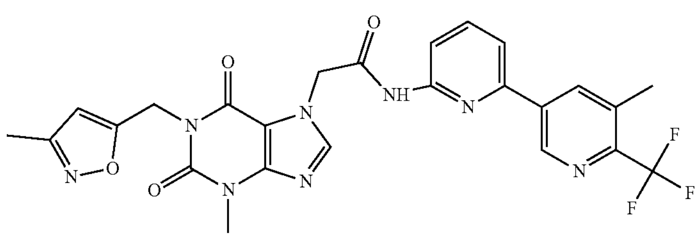 [SMILES: Cc1cc(Cn2c(=O)c3c(ncn3CC(=O)Nc3cccc(-c4cnc(C(F)(F)F)c(C)c4)n3)n(C)c2=O)on1] |
| 226 | 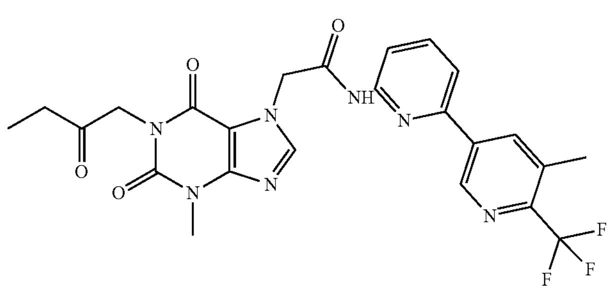 |

TABLE 1-continued

| Compound # | Structure |
|---|---|
| 227 | 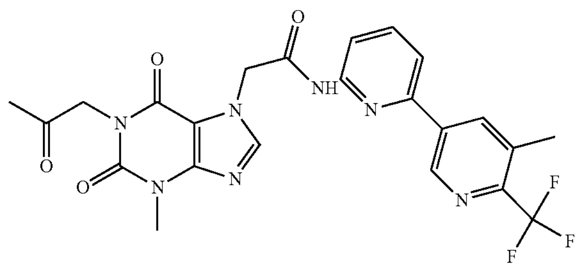 |
| 228 | 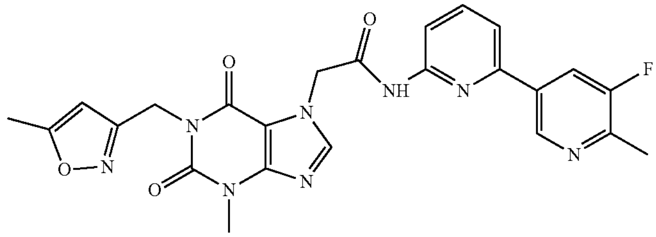 |
| 229 | 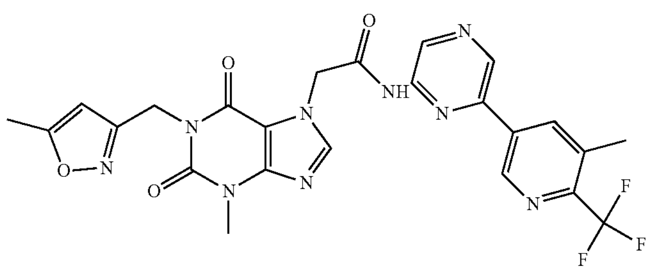 |
| 230 | 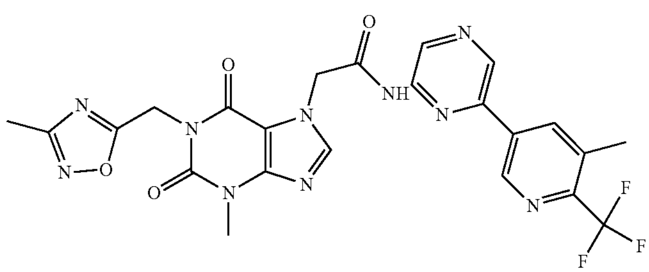 |
| 231 | 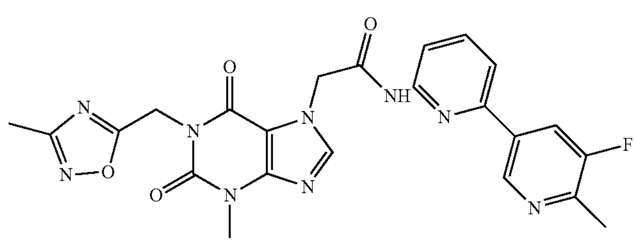 |
| 232 | 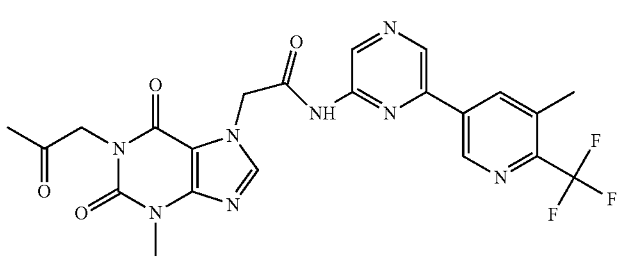 [SMILES: CC(=O)Cn1c(=O)c2c(ncn2CC(=O)Nc2cncc(-c3cnc(C(F)(F)F)c(C)c3)n2)n(C)c1=O] |

TABLE 1-continued

| Compound # | Structure |
|---|---|
| 233 | 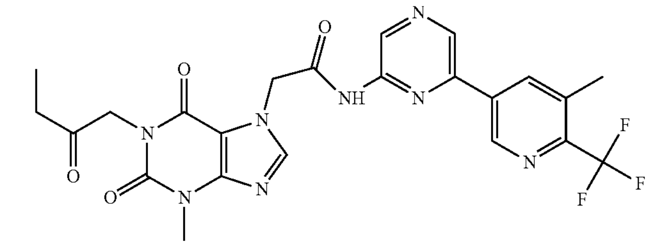 [SMILES: CCC(=O)Cn1c(=O)c2c(ncn2CC(=O)Nc2cncc(-c3cnc(C(F)(F)F)c(C)c3)n2)n(C)c1=O] |
| 234 | 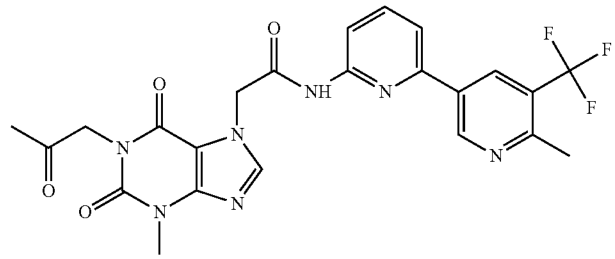 [SMILES: CC(=O)Cn1c(=O)c2c(ncn2CC(=O)Nc2cccc(-c3cnc(C)c(C(F)(F)F)c3)n2)n(C)c1=O] |
| 235 | 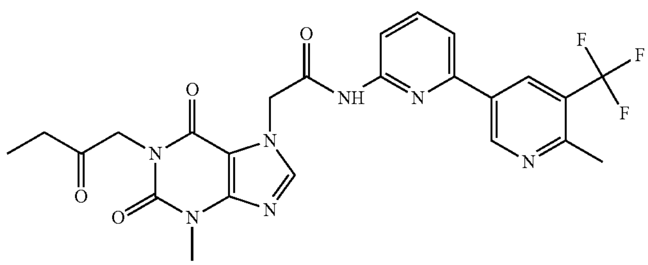 [SMILES: CCC(=O)Cn1c(=O)c2c(ncn2CC(=O)Nc2cccc(-c3cnc(C)c(C(F)(F)F)c3)n2)n(C)c1=O] |
| 236 | 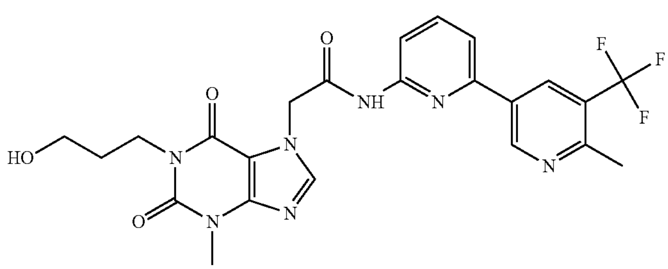 [SMILES: Cc1ncc(-c2cccc(NC(=O)Cn3cnc4c3c(=O)n(CCCO)c(=O)n4C)n2)cc1C(F)(F)F] |
| 237 | 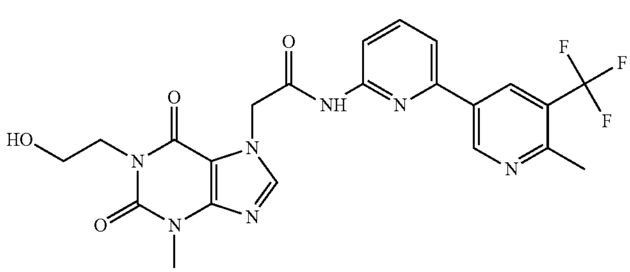 [SMILES: Cc1ncc(-c2cccc(NC(=O)Cn3cnc4c3c(=O)n(CCO)c(=O)n4C)n2)cc1C(F)(F)F] |
| 238 | 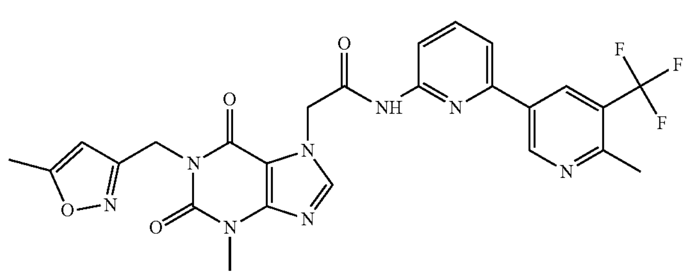 [SMILES: Cc1cc(Cn2c(=O)c3c(ncn3CC(=O)Nc3cccc(-c4cnc(C)c(C(F)(F)F)c4)n3)n(C)c2=O)no1] |

TABLE 1-continued
| Compound # | Structure |
|---|---|
| 239 | 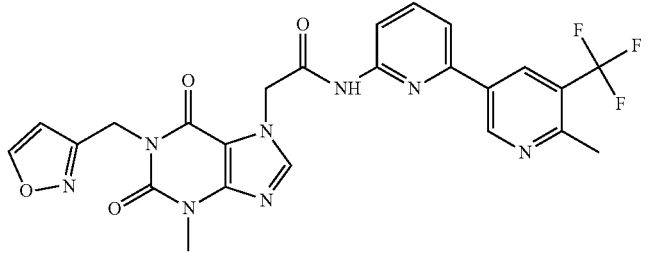 [SMILES: Cc1ncc(-c2cccc(NC(=O)Cn3cnc4c3c(=O)n(Cc3ccon3)c(=O)n4C)n2)cc1C(F)(F)F] |
| 240 | 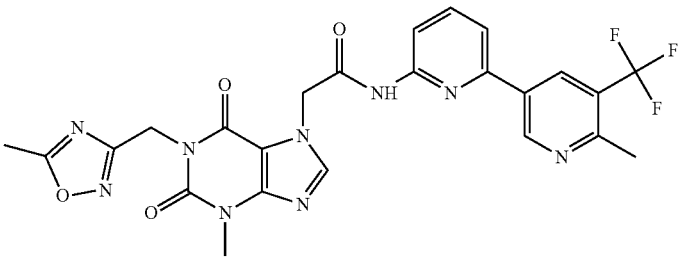 [SMILES: Cc1nc(Cn2c(=O)c3c(ncn3CC(=O)Nc3cccc(-c4cnc(C)c(C(F)(F)F)c4)n3)n(C)c2=O)no1] |
| 241 | 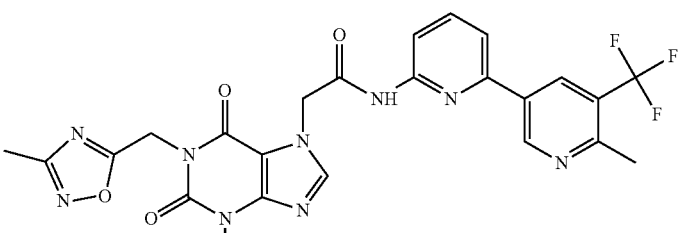 |
| 242 | 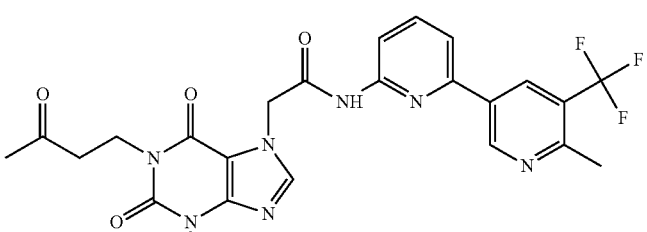 |
| 243 | 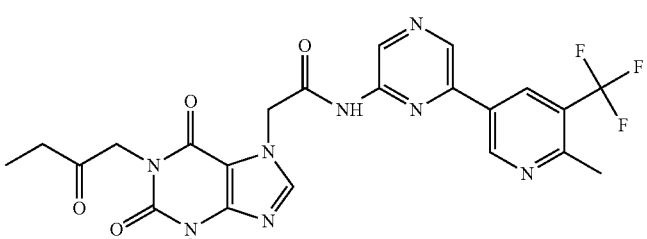 |

TABLE 1-continued

| Compound # | Structure |
|---|---|
| 245 | 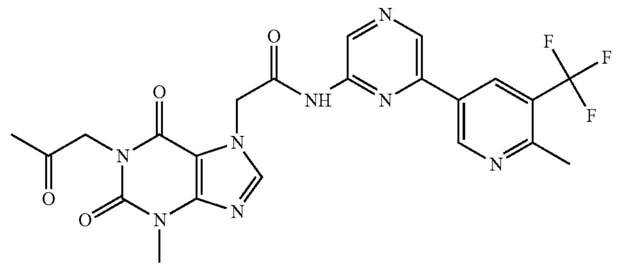 [SMILES: CC(=O)Cn1c(=O)c2c(ncn2CC(=O)Nc2cncc(-c3cnc(C)c(C(F)(F)F)c3)n2)n(C)c1=O] |
| 246 | 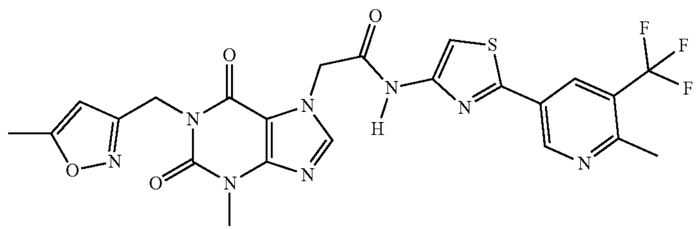 [SMILES: Cc1cc(Cn2c(=O)c3c(ncn3CC(=O)Nc3csc(-c4cnc(C)c(C(F)(F)F)c4)n3)n(C)c2=O)no1] |
| 247 | 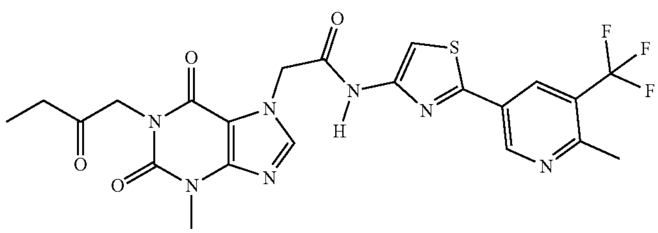 [SMILES: CCC(=O)Cn1c(=O)c2c(ncn2CC(=O)Nc2csc(-c3cnc(C)c(C(F)(F)F)c3)n2)n(C)c1=O] |
| 248 | 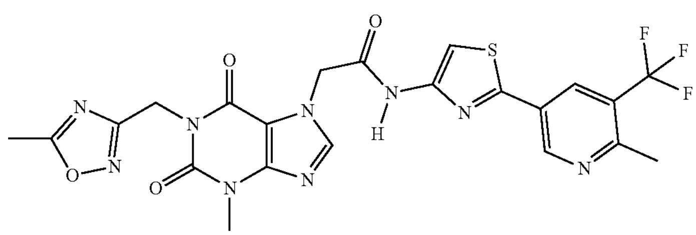 [SMILES: Cc1nc(Cn2c(=O)c3c(ncn3CC(=O)Nc3csc(-c4cnc(C)c(C(F)(F)F)c4)n3)n(C)c2=O)no1] |
| 249 | 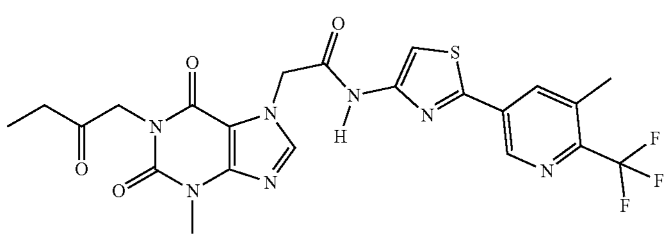 [SMILES: CCC(=O)Cn1c(=O)c2c(ncn2CC(=O)Nc2csc(-c3cnc(C(F)(F)F)c(C)c3)n2)n(C)c1=O] |
| 250 | 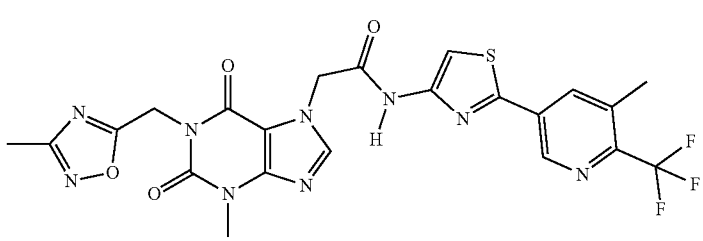 [SMILES: Cc1noc(Cn2c(=O)c3c(ncn3CC(=O)Nc3csc(-c4cnc(C(F)(F)F)c(C)c4)n3)n(C)c2=O)n1] |

TABLE 1-continued

| Compound # | Structure |
|---|---|
| 251 | 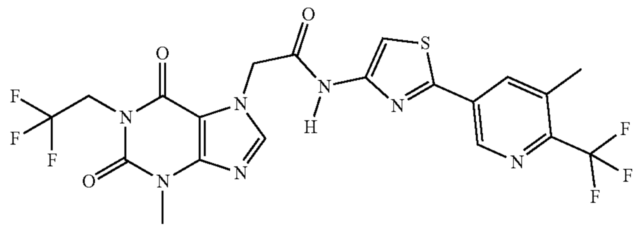 [SMILES: Cc1cc(-c2nc(NC(=O)Cn3cnc4c3c(=O)n(CC(F)(F)F)c(=O)n4C)cs2)cnc1C(F)(F)F] |
| 252 | 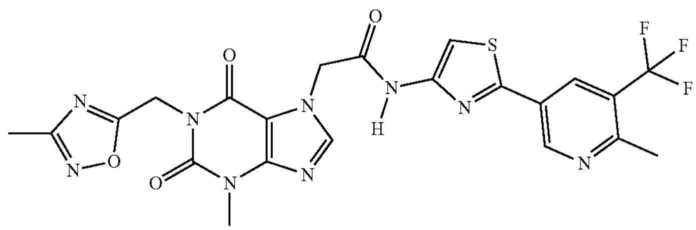 [SMILES: Cc1noc(Cn2c(=O)c3c(ncn3CC(=O)Nc3csc(-c4cnc(C)c(C(F)(F)F)c4)n3)n(C)c2=O)n1] |
| 253 | 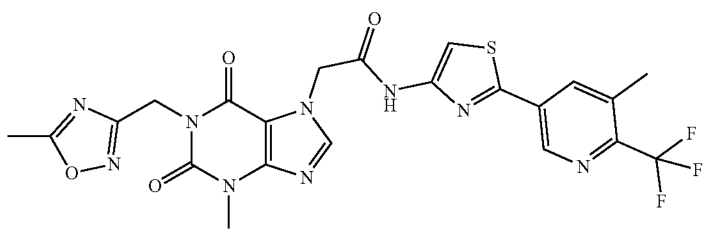 [SMILES: Cc1nc(Cn2c(=O)c3c(ncn3CC(=O)Nc3csc(-c4cnc(C(F)(F)F)c(C)c4)n3)n(C)c2=O)no1] |
| 254 | 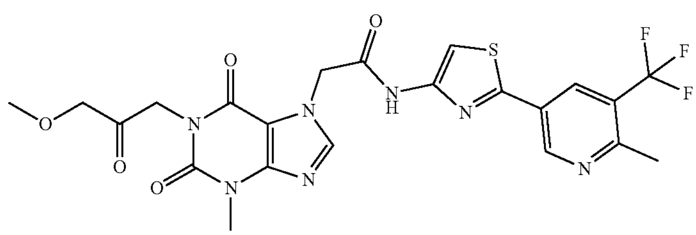 [SMILES: COCC(=O)Cn1c(=O)c2c(ncn2CC(=O)Nc2csc(-c3cnc(C)c(C(F)(F)F)c3)n2)n(C)c1=O] |
| 255 | 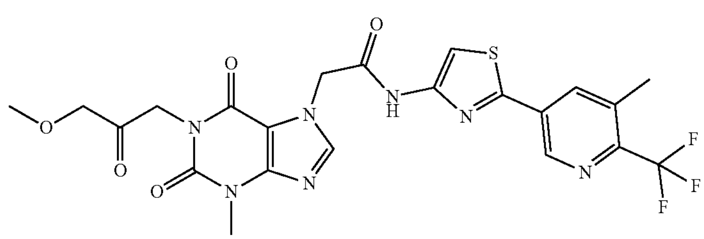 [SMILES: COCC(=O)Cn1c(=O)c2c(ncn2CC(=O)Nc2csc(-c3cnc(C(F)(F)F)c(C)c3)n2)n(C)c1=O] |
| 256 | 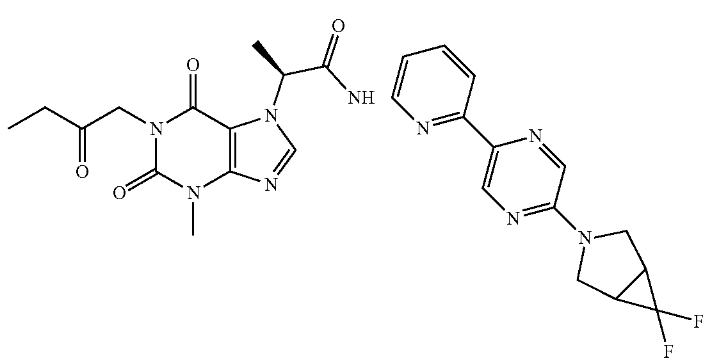 |

TABLE 1-continued
| Compound # | Structure |
|---|---|
| 257 | 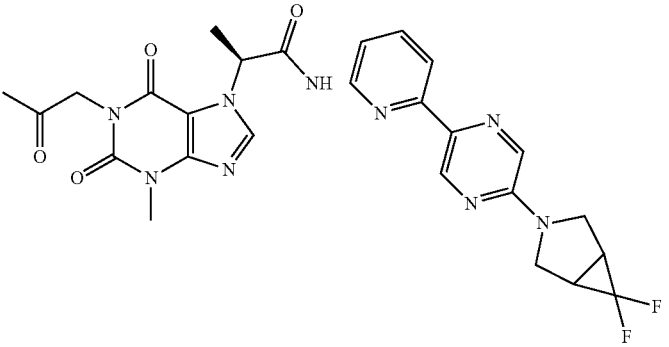 |
| 258 | 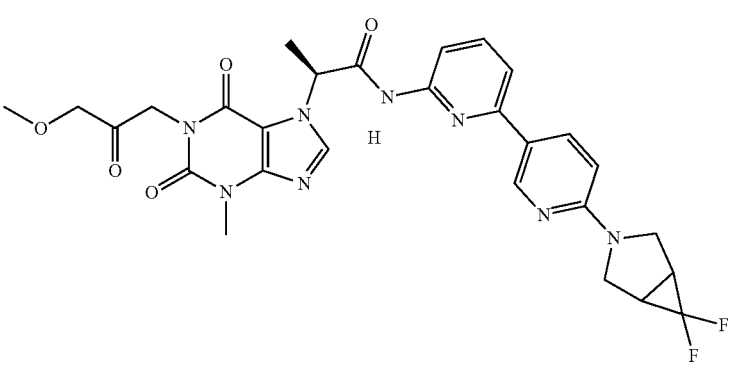 |
| 259 | 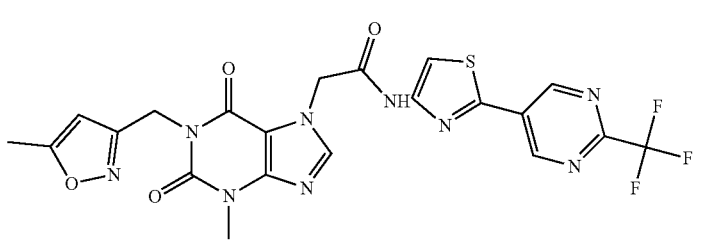 |
| 260 | 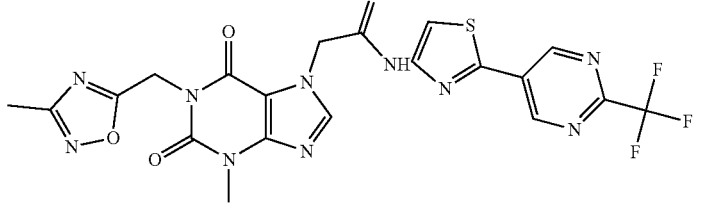 |
| 261 | 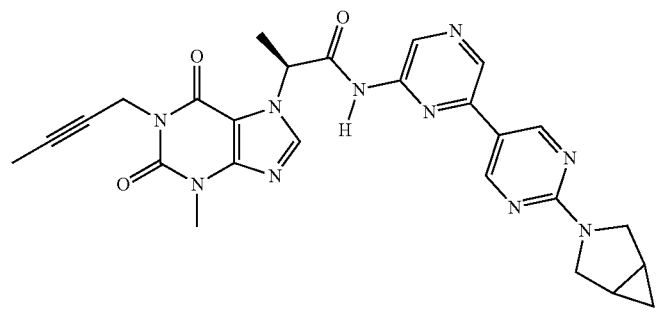 [SMILES: CC#CCn1c(=O)c2c(ncn2[C@@H](C)C(=O)Nc2cncc(-c3cnc(N4CC5CC5C4)nc3)n2)n(C)c1=O] |

TABLE 1-continued

| Compound # | Structure |
|---|---|
| 262 | 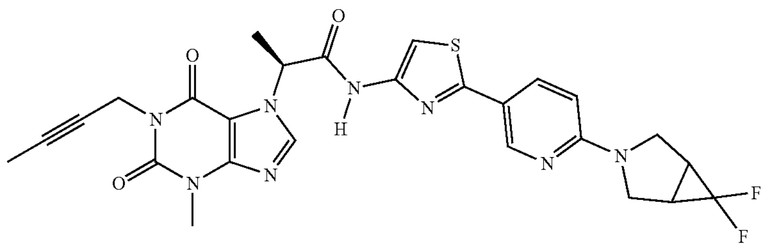 [SMILES: CC#CCn1c(=O)c2c(ncn2[C@@H](C)C(=O)Nc2csc(-c3ccc(N4CC5C(C4)C5(F)F)nc3)n2)n(C)c1=O] |
| 263 | 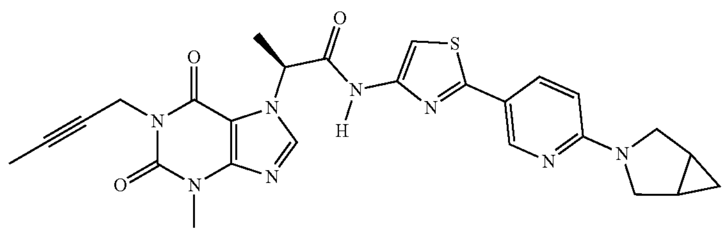 [SMILES: CC#CCn1c(=O)c2c(ncn2[C@@H](C)C(=O)Nc2csc(-c3ccc(N4CC5CC5C4)nc3)n2)n(C)c1=O] |
| 264 | 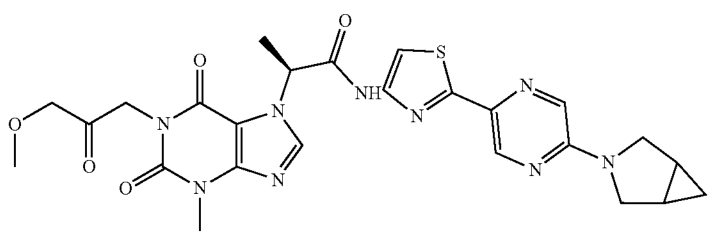 |
| 265 | 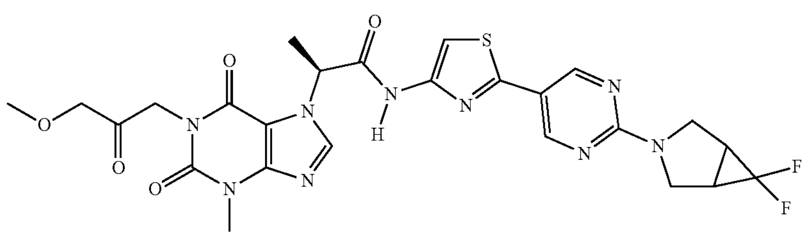 [SMILES: COCC(=O)Cn1c(=O)c2c(ncn2[C@@H](C)C(=O)Nc2csc(-c3cnc(N4CC5C(C4)C5(F)F)nc3)n2)n(C)c1=O] |
| 266 | 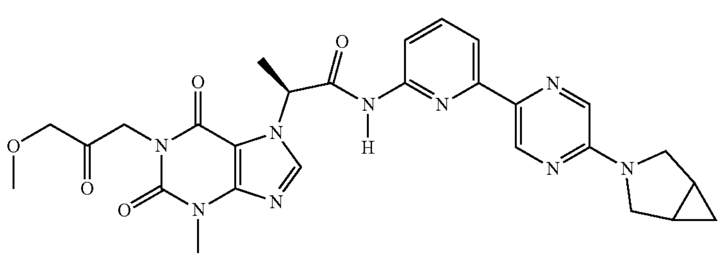 [SMILES: COCC(=O)Cn1c(=O)c2c(ncn2[C@@H](C)C(=O)Nc2cccc(-c3cnc(N4CC5CC5C4)cn3)n2)n(C)c1=O] |
| 267 | 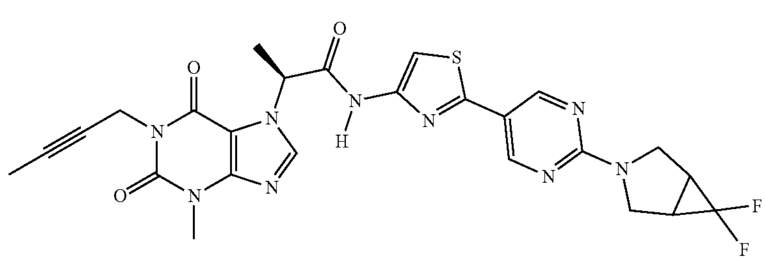 [SMILES: CC#CCn1c(=O)c2c(ncn2[C@@H](C)C(=O)Nc2csc(-c3cnc(N4CC5C(C4)C5(F)F)nc3)n2)n(C)c1=O] |

TABLE 1-continued

| Compound # | Structure |
|---|---|
| 268 | 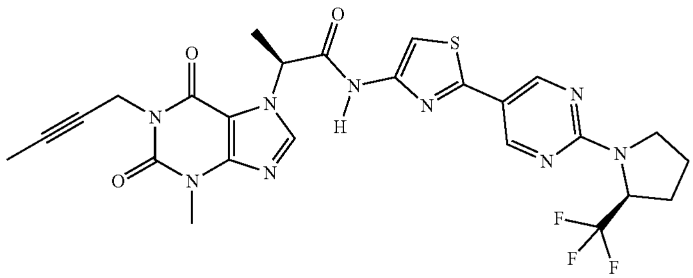 [SMILES: CC#CCn1c(=O)c2c(ncn2[C@@H](C)C(=O)Nc2csc(-c3cnc(N4CCC[C@H]4C(F)(F)F)nc3)n2)n(C)c1=O] |
| 269 | 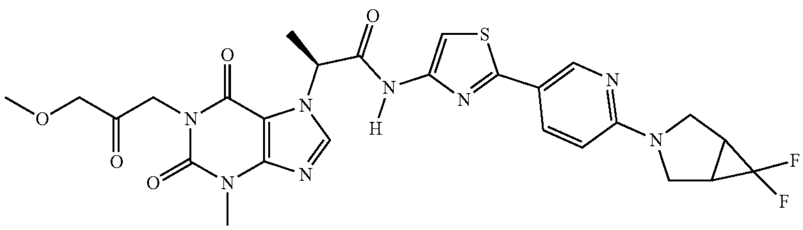 [SMILES: COCC(=O)Cn1c(=O)c2c(ncn2[C@@H](C)C(=O)Nc2csc(-c3ccc(N4CC5C(C4)C5(F)F)nc3)n2)n(C)c1=O] |
| 270 | 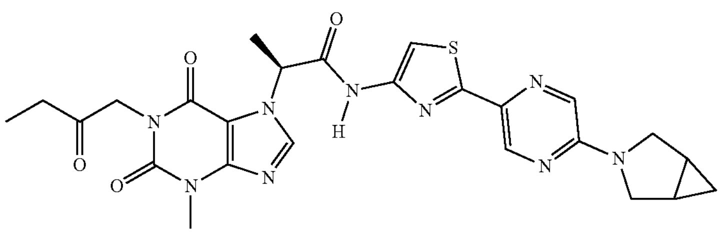 [SMILES: CCC(=O)Cn1c(=O)c2c(ncn2[C@@H](C)C(=O)Nc2csc(-c3cnc(N4CC5CC5C4)cn3)n2)n(C)c1=O] |
| 271 | 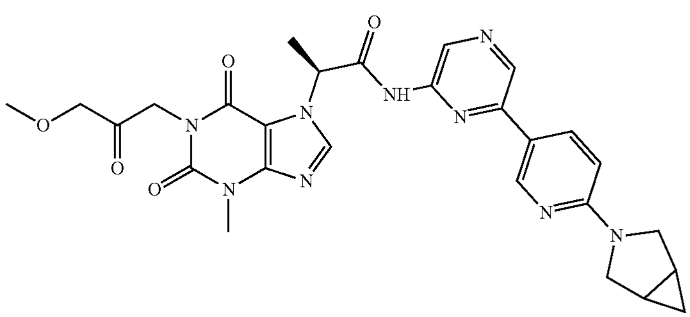 [SMILES: COCC(=O)Cn1c(=O)c2c(ncn2[C@@H](C)C(=O)Nc2cncc(-c3ccc(N4CC5CC5C4)nc3)n2)n(C)c1=O] |
| 272 | 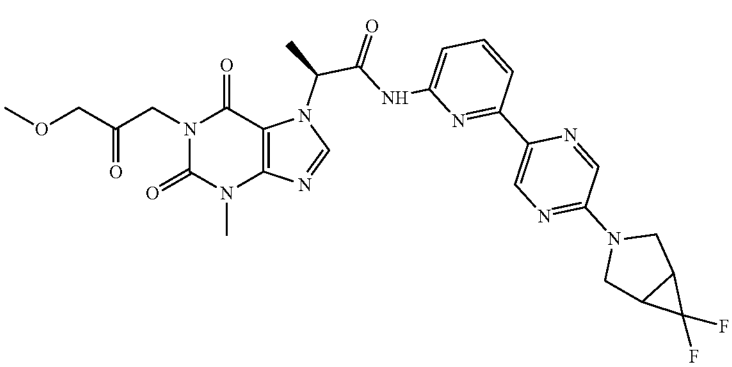 [SMILES: COCC(=O)Cn1c(=O)c2c(ncn2[C@@H](C)C(=O)Nc2cccc(-c3cnc(N4CC5C(C4)C5(F)F)cn3)n2)n(C)c1=O] |

This disclosure is not limited in its application to the details of the methods and compositions described herein. Also, the phraseology and terminology used herein is for the purpose of description and should not be regarded as limiting.

Chemical Definitions

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, propyl, butyl, and pentyl.

For compounds of the invention in which a variable appears more than once, each variable can be a different moiety selected from the Markush group defining the variable. For example, where a structure is described having two R groups that are simultaneously present on the same compound; the two R groups can represent different moieties selected from the Markush group defined for R.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

In case a compound of the present invention is depicted in form of a chemical name and as a formula in case of any discrepancy the formula shall prevail.

An asterisk may be used in sub-formulas to indicate the bond which is connected to the core molecule as defined.

As used herein, "alkyl," by itself or as part of another substituent, means, unless otherwise stated, a straight or branched chain, and can have a number of carbon atoms optionally designated (i.e., $C_1$-$C_6$ means one to six carbons). Examples of saturated hydrocarbon groups include, but are not limited to, groups such as methyl, ethyl, n-propyl, isopropyl, n-butyl, t-butyl, isobutyl, sec-butyl, n-pentyl, isopentyl, homologs and isomers of, for example, n-pentyl, n-hexyl, and the like.

As used herein, "alkenyl" can be a straight or branched hydrocarbon chain, containing at least one double bond, and having from two to six carbon atoms (i.e. $C_2$-$C_6$ alkenyl). Examples of alkenyl groups, include, but are not limited to, groups such as ethenyl (i.e., vinyl), prop-1-enyl (i.e., allyl), but-1-enyl, pent-1-enyl, penta-1,4-dienyl, and the like.

As used herein, "alkoxy" can be a straight chain or branched alkoxy group (e.g. $C_1$-$C_6$ alkyl-O—) having from one to six carbon atoms (i.e., $C_1$-$C_6$ alkoxy). Examples of alkoxy groups, include, but are not limited to, groups such as methoxy, ethoxy, propyloxy, isopropyloxy, butyloxy, isobutyloxy, tert-butyloxy, pentyloxy, or hexyloxy, and the like.

As used herein, "alkynyl" can be a straight or branched hydrocarbon chain, containing at least one triple bond, having from two to six carbon atoms (i.e. $C_2$-$C_6$ alkynyl). Examples of alkynyl groups, include, but are not limited to, groups such as ethynyl, propynyl, butynyl, pentynyl, hexynyl, and the like.

As used herein, "amide" or "amido" refers to a chemical moiety with the formula —C(O)NR$^a$— or —NR$^a$C(O)— wherein R$^a$ is H or $C_1$-$C_6$ alkyl.

As used herein, "amino" or "amine" refers to a —NH$_2$ radical group.

As used herein, "aryl" refers to a polyunsaturated, aromatic, hydrocarbon moiety which can be a single ring or multiple rings (e.g., 1 to 2 rings) which are fused together or linked covalently, having from six to twelve carbon atoms (i.e. $C_6$-$C_{12}$ aryl). Non-limiting examples of aryl groups include phenyl, 1-naphthyl, 2-naphthyl, and 4-biphenyl and the like.

As used herein, "arylalkyl" refers to an (aryl)alkyl-radical wherein aryl and alkyl moieties are as disclosed herein.

As used herein, "aryloxy" refers to —O-(aryl), wherein the aryl moiety is as defined herein.

As used herein, "arylalkoxy" refers to —O-(arylalkyl), wherein the arylalkyl moiety is as defined herein.

As used herein, "cyano" refers to a —CN radical.

As used herein, "cycloalkyl" refers to a monocyclic or polycyclic radical that contains only carbon and hydrogen, and may be saturated, or partially unsaturated. Cycloalkyl groups include groups having from 3 to 10 ring atoms (i.e. $C_3$-$C_{10}$ cycloalkyl). Examples of cycloalkyl groups include, but are not limited to, groups such as cyclopropyl, cyclobutyl, cyclopentyl, cyclopentenyl, cyclohexyl, cyclohexenyl, cycloseptyl, cyclooctyl, cyclononyl, cyclodecyl, norbornyl, and the like.

As used herein, "halo" or "halogen," independently or as part of another substituent, mean, unless otherwise stated, a fluorine, chlorine, bromine, or iodine atom. The term "halide" by itself or as part of another substituent, refers to a fluoride, chloride, bromide, or iodide atom.

As used herein, "haloalkyl" and "haloalkoxy" can include alkyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine (e.g., —$C_1$-$C_6$ alkyl-$CF_3$, alkyl-$C_2F$). Non-limiting examples of haloalkyl include trifluoroethyl, trifluoropropyl, trifluoromethyl, fluoromethyl, diflurormethyl, and fluroisopropyl.

As used herein, "heteroaryl" refers to a 5- to 14-membered aromatic radical (e.g., $C_2$-$C_{13}$ heteroaryl) that includes one or more ring heteroatoms selected from nitrogen, oxygen and sulfur, and which may be a monocyclic or bicyclic ring system. The polycyclic heteroaryl group may be fused or non-fused. The heteroatom(s) in the heteroaryl radical is optionally oxidized. One or more nitrogen atoms, if present, are optionally quaternized. The heteroaryl is attached to the rest of the molecule through any atom of the ring(s)The term "heteroaryl" is intended to include all the possible isomeric forms. Examples of heteroaryl groups include without limitation, pyridyl, pyrimidinyl, pyrazinyl, pyridazinyl, triazinyl, furyl (furanyl), quinolyl, isoquinolyl, thienyl, imidazolyl, thiazolyl, indolyl, pyrryl, oxazolyl, oxadiazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like.

As used herein, "heterocyclyl" can be a stable 3- to 18-membered non-aromatic mono, di, or tricyclic ring radical that comprises two to twelve carbon atoms and from one to six heteroatoms selected from nitrogen, oxygen and sulfur. Examples of heterocycloalkyl groups include, but are not limited to, groups such as dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, azetidinyl, azabicyclohexyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, and the like.

As used herein, "heteroarylalkyl" refers to refers to an (heteroaryl)alkyl-radical wherein the heteroaryl and alkyl moieties are as disclosed herein.

As used herein, "heteraryloxy" refers to —O-(heteroaryl), wherein the heteroaryl moiety is as defined herein.

As used herein, "heterocycloalkyl" refers to an (heterocyclyl)alkyl-moiety and can be a stable 3- to 18-membered non-aromatic ring moiety that comprises two to twelve carbon atoms and from one to six heteroatoms selected from nitrogen, oxygen and sulfur. Examples of heterocycloalkyl groups include, but are not limited to, groups such as dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, and the like covalently bonded to one or more alkyl moieties as defined herein.

As used herein, "hydroxy" or "hydroxyl" refers to —OH.

As used herein, "nitro" refers to —$NO_2$.

As used herein, "keto" refers to —C=O.

Many of the terms given above may be used repeatedly in the definition of a formula or group and in each case have one of the meanings given above, independently of one another.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds (e.g., alkyl, alkenyl, alkynyl, cycloalkyl, heterocycloalkyl, aryl, or heteroaryl, any of which may itself be further substituted), as well as halogen, carbonyl (e.g., aldehyde, ketone, ester, carboxyl, or formyl), thiocarbonyl (e.g., thioester, thiocarboxylate, or thioformate), amino, —N($R^b$)($R^c$), wherein each $R^b$ and $R^c$ is independently H or $C_1$-$C_6$ alkyl, cyano, nitro, —$SO_2$N($R^b$)($R^c$), —$SOR^d$, and S(O)$_2R^d$, wherein each $R^b$, $R^c$, and $R^d$ is independently H or $C_1$-$C_6$ alkyl. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations. The abbreviations contained in said list, and all abbreviations utilized by organic chemists of ordinary skill in the art are hereby incorporated by reference.

Contemplated equivalents of the compounds described above include compounds which otherwise correspond thereto, and which have the same general properties thereof (e.g., the ability to inhibit TRPA1 activity), wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

Definitions

As used herein, the articles "a" and "an" refer to one or to more than one (e.g., to at least one) of the grammatical object of the article.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

As used herein, an amount of a compound or combination effective to treat a disorder (e.g., a disorder as described herein), "therapeutically effective amount", "effective amount" or "effective course" refers to an amount of the compound or combination which is effective, upon single or multiple dose administration(s) to a subject, in treating a subject, or in curing, alleviating, relieving or improving a subject with a disorder (e.g., a disorder as described herein) beyond that expected in the absence of such treatment.

As set out above, certain embodiments of the present compounds may contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds disclosed herein. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (see, for example, Berge et al. (1977) "Pharmaceutical Salts", *J. Pharm. Sci.* 66:1-19.)

In other cases, the compounds disclosed herein may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds disclosed herein. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

The term, "treat" or "treatment," as used herein, refers to the application or administration of a compound, alone or in combination with, an additional agent to a subject, e.g., a subject who has a disorder (e.g., a disorder as described herein), a symptom of a disorder, or a predisposition toward a disorder, with the purpose to cure, heal, alleviate, relieve, alter, remedy, ameliorate, improve or affect the disorder.

As used herein, the term "subject" is intended to include human and non-human animals. Exemplary human subjects include a human subject having a disorder, e.g., a disorder described herein. The term "non-human animals" of the invention includes all vertebrates, e.g., non-mammals (such as chickens, amphibians, reptiles) and mammals, such as non-human primates, domesticated and/or agriculturally useful animals, e.g., sheep, dog, cat, cow, pig, etc.

The terms "antagonist" and "inhibitor" are used interchangeably to refer to an agent that decreases or suppresses a biological activity, such as to repress an activity of an ion channel, such as TRPA1. TRPA1 inhibitors include inhibitors having any combination of the structural and/or functional properties disclosed herein.

An "effective amount" of, e.g., a TRPA1 antagonist, with respect to the subject methods of inhibition or treatment, refers to an amount of the antagonist in a preparation which, when applied as part of a desired dosage regimen brings about a desired clinical or functional result. Without being bound by theory, an effective amount of a TRPA1 antagonist for use in the methods of the present invention, includes an amount of a TRPA1 antagonist effective to decrease one or more in vitro or in vivo functions of a TRPA1 channel. Exemplary functions include, but are not limited to, membrane polarization (e.g., an antagonist may prevent depolarization of a cell), ion flux, ion concentration in a cell, outward current, and inward current. Compounds that antagonize TRPA1 function include compounds that antagonize an in vitro or in vivo functional activity of TRPA1. When a particular functional activity is only readily observable in an in vitro assay, the ability of a compound to inhibit TRPA1 function in that in vitro assay serves as a reasonable proxy for the activity of that compound. In certain embodiments, an effective amount is an amount sufficient to inhibit a TRPA1-mediated current and/or the amount sufficient to inhibit TRPA1 mediated ion flux.

The term "hydrate" as used herein, refers to a compound formed by the union of water with the parent compound.

The term "preventing," when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "solvate" as used herein, refers to a compound formed by solvation (e.g., a compound formed by the combination of solvent molecules with molecules or ions of the solute).

The terms "TRPA1", "TRPA1 protein", and "TRPA1 channel" are used interchangeably throughout the application. These terms refer to an ion channel (e.g., a polypeptide) comprising the amino acid sequence set forth in SEQ ID NO: 1, SEQ ID NO:3, or SEQ ID NO: 5 of WO 2007/073505, or an equivalent polypeptide, or a functional bioactive fragment thereof. In certain embodiments, the term refers to a polypeptide comprising, consisting of, or consisting essentially of, the amino acid sequence set forth in SEQ ID NO: 1, SEQ ID NO:3, or SEQ ID NO: 5. TRPA1 includes polypeptides that retain a function of TRPA1 and comprise (i) all or a portion of the amino acid sequence set forth in SEQ ID NO: 1, SEQ ID NO:3 or SEQ ID NO: 5; (ii) the amino acid sequence set forth in SEQ ID NO: 1, SEQ ID NO:3 or SEQ ID NO: 5 with 1 to about 2, 3, 5, 7, 10, 15, 20, 30, 50, 75 or more conservative amino acid substitutions; (iii) an amino acid sequence that is at least 70%, 75%, 80%, 90%, 95%, 96%, 97%, 98%, or 99% identical to SEQ ID NO: 1, SEQ ID NO:3 or SEQ ID NO: 5; and (iv) functional fragments thereof. Polypeptides of the invention also include homologs, e.g., orthologs and paralogs, of SEQ ID NO: 1, SEQ ID NO: 3 or SEQ ID NO: 5.

In some embodiments the methods include treating inflammatory disease in a subject, the method comprising administering an effective amount of a compound of Formula (I), or a pharmaceutically acceptable salt thereof.

In some embodiments the methods include treating neuropathy in a subject, the method comprising administering an effective amount of a compound of Formula (I), or a pharmaceutically acceptable salt thereof. In some embodiments, the neuropathy is from diabetes, chemical injury, chemotherapy, and or trauma.

In some embodiments the methods include treating a dermatogological disorder in a subject, the method comprising administering an effective amount of a compound of Formula (I), or a pharmaceutically acceptable salt thereof. Exemplary dermatogological disorders include atopic dermatitis, acute pruritus, psoriasis, hives, eczema, dyshidrotic eczema, mouth ulcers, and diaper rash.

In some embodiments the methods include treating a respiratory condition in a subject, the method comprising administering an effective amount of a compound of Formula (I), or a pharmaceutically acceptable salt thereof.

Exemplary respiratory conditions include obstructive diseases such as chronic obstructive pulmonary disease. Additional exemplary respiratory conditions include asthma and cough.

Another aspect of the invention features a pharmaceutical preparation suitable for use in a human patient, or for veterinary use, comprising an effective amount of a compound of Formula (I) (or a salt thereof, or a solvate, hydrate, oxidative metabolite or prodrug of the compound or its salt), and one or more pharmaceutically acceptable excipients. The invention further contemplates the use of compounds of Formula (I) in the manufacture of a medicament or pharmaceutical preparation to treat or reduce the symptoms of any of the diseases or conditions provided in the specification. The compounds of of Formula (I) for use in treating a particular disease or condition can be formulated for administration via a route appropriate for the particular disease or condition.

Compounds of Formula (I) can be administered alone or in combination with another therapeutic agent. For instance, the compounds of Formula (I) can be administered conjointly with one or more of an anti-inflammatory agent, anti-acne agent, anti-wrinkle agent, anti- scarring agent, anti-psoriatic agent, anti-proliferative agent, anti-fungal agent, anti-viral agent, anti-septic agent, anti-migraine agent, keratolytic agent, or a hair growth inhibitor. Compounds of Formula (I) can be administered topically, orally, transdermally, rectally, vaginally, parentally, intranasally, intrapulmonary, intraocularly, intravenously, intramuscularly, intraarterially, intrathecally, intracapsularly, intraorbitally, intracardiacly, intradermally, intraperitoneally, transtracheally, subcutaneously, subcuticularly, intraarticularly, subcapsularly, subarachnoidly, intraspinally, intrasternally, sublingually, or by inhalation.

In some embodiments, compounds of Formula (I) can be administered topically.

In some embodiments, compounds of Formula (I) can be administered orally.

In some embodiments, compounds of Formula (I) can be administered parentally.

Compounds of Formula (I) include molecules having an aqueous solubility suitable for oral or parenteral (e.g., intravenous) administration leading to or resulting in the treatment of a disorder described herein, for example the treatment of pain. In some embodiments, the compound is formulated into a composition suitable for oral administration. The potency in inhibiting the TRPA1 ion channel of compounds of Formula (I) described herein was measured using the method of Example 1. Table 2 discloses the TRPA1 inhibition in vitro potency of exemplary compounds (measured by the method of Example 1).

Preferred compounds of Formula (I) include compounds that inhibit the TRPA1 ion channel with a $IC_{50}$ value obtained by the method of Example 1 of less than about 100 nM (preferably, less than about 75 nM, more preferably less than about 25 nM).

Compounds of Formula (I) can inhibit the TRPA1 ion channel. In some embodiments, a compound of Formula (I) can be administered as part of an oral or parenteral (e.g., intravenous) pharmaceutical composition to treat a disorder described herein (e.g., pain) in a therapeutically effective manner.

Certain compounds disclosed herein may exist in particular geometric or stereoisomeric forms. The present invention contemplates all such compounds, including cis- and trans-isomers, R- and S-enantiomers, diastereomers, (d)-isomers, (l)-isomers, the racemic mixtures thereof, and other mixtures thereof, as falling within the scope of the invention. For example, if one chiral center is present in a molecule, the invention includes racemic mixtures, enantiomerically enriched mixtures, and substantially enantiomerically or diastereomerically pure compounds. The composition can contain, e.g., more than 50%, more than 60%, more than 70%, more than 80%, more than 90%, more than 95%, or more than 99% of a single enantiomer or diastereomer. Additional asymmetric carbon atoms may be present in a substituent such as an alkyl group. All such isomers, as well as mixtures thereof, are intended to be included in this invention.

The "enantiomeric excess" or "% enantiomeric excess" of a composition can be calculated using the equation shown below. In the example shown below a composition contains 90% of one enantiomer, e.g., the S enantiomer, and 10% of the other enantiomer, i.e., the R enantiomer.

$$ee=(90-10)/100=80\%.$$

Thus, a composition containing 90% of one enantiomer and 10% of the other enantiomer is said to have an enantiomeric excess of 80%.

The "diastereomeric excess" or "% diastereomeric excess" of a composition can be calculated using the equation shown below. In the example shown below a composition contains 90% of one diastereomer, and 10% of another enantiomer.

$$ee=(90-10)/100=80\%.$$

Thus, a composition containing 90% of one diastereomer and 10% of the other diastereomer is said to have an diastereomeric excess of 80%.

In addition, compounds of Formula (I) can include one or more isotopes of the atoms present in Formula (I). For example, compounds of Formula (I) can include: those in which H (or hydrogen) is replaced with any isotopic form of hydrogen including $^1H$, $^2H$ or D (Deuterium), and $^3H$ (Tritium); those in which C is replaced with any isotopic form of carbon including $^{12}C$, $^{13}C$, and $^{14}C$; those in which O is replaced with any isotopic form of oxygen including $^{16}O$, $^{17}O$ and $^{18}O$; those in which N is replaced with any isotopic form of nitrogen including $^{13}N$, $^{14}N$ and $^{15}N$; those in which P is replaced with any isotopic form of phosphorous including $^{31}P$ and $^{32}P$; those in which S is replaced with any isotopic form of sulfur including $^{32}S$ and $^{35}S$; those in which F is replaced with any isotopic form of fluorine including $^{19}F$ and $^{18}F$; and the like. In an embodiment, compounds represented by Formula (I) comprise isomers of the atoms therein in their naturally occurring abundance.

Certain compounds disclosed herein can exist in unsolvated forms as well as solvated forms, including hydrated forms. In general, the solvated forms are equivalent to unsolvated forms and are encompassed within the scope of the present invention. Certain compounds disclosed herein may exist in multiple crystalline or amorphous forms. In general, all physical forms are equivalent for the uses contemplated by the present invention and are intended to be within the scope of the present invention.

Pharmaceutical Compositions

Pharmaceutical compositions containing compounds described herein such as a compound of Formula (I) or pharmaceutically acceptable salt thereof can be used to treat or ameliorate a disorder described herein, for example, a disorder responsive to the inhibition of the TRPA1 ion channel in subjects (e.g., humans and animals).

The amount and concentration of compounds of Formula (I) in the pharmaceutical compositions, as well as the quantity of the pharmaceutical composition administered to a subject, can be selected based on clinically relevant factors, such as medically relevant characteristics of the subject (e.g., age, weight, gender, other medical conditions, and the like), the solubility of compounds in the pharmaceutical compositions, the potency and activity of the compounds, and the manner of administration of the pharmaceutical compositions. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

While it is possible for a compound disclosed herein to be administered alone, it is preferable to administer the compound as a pharmaceutical formulation, where the compound is combined with one or more pharmaceutically acceptable diluents, excipients or carriers. The compounds disclosed herein may be formulated for administration in any convenient way for use in human or veterinary medicine. In certain embodiments, the compound included in the pharmaceutical preparation may be active itself, or may be a prodrug, e.g., capable of being converted to an active compound in a physiological setting.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Examples of pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) cyclodextrins such as Captisol®; and (22) other non-toxic compatible substances employed in pharmaceutical formulations.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Solid dosage forms (e.g., capsules, tablets, pills, dragees, powders, granules and the like) can include one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents.

Liquid dosage forms can include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

The tablets, and other solid dosage forms of the pharmaceutical compositions disclosed herein, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The formulations disclosed herein can be delivered via a device. Exemplary devices include, but are not limited to, a catheter, wire, stent, or other intraluminal device. Further exemplary delivery devices also include a patch, bandage, mouthguard, or dental apparatus. Transdermal patches have the added advantage of providing controlled delivery of a compound disclosed herein to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, drops, solutions and the like, are also contemplated as being within the scope of this invention.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

When the compounds disclosed herein are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The formulations can be administered topically, orally, transdermally, rectally, vaginally, parenterally, intranasally, intrapulmonary, intraocularly, intravenously, intramuscularly, intraarterially, intrathecally, intracapsularly, intraorbitally, intracardiacly, intradermally, intraperitoneally, transtracheally, subcutaneously, subcuticularly, intraarticularly, subcapsularly, subarachnoidly, intraspinally, intrasternally or by inhalation.

One specific embodiment is an antitussive composition for peroral administration comprising an agent that inhibits both a TRPA1-mediated current with an $IC_{50}$ of 1 micromolar or less, and an orally-acceptable pharmaceutical carrier in the form of an aqueous-based liquid, or solid dissolvable in the mouth, selected from the group consisting of syrup, elixer, suspension, spray, lozenge, chewable lozenge, powder, and chewable tablet. Such antitussive compositions can include one or more additional agents for treating cough, allergy or asthma symptom selected from the group consisting of: antihistamines, 5-lipoxygenase inhibitors, leukotriene inhibitors, H3 inhibitors, β-adrenergic receptor agonists, xanthine derivatives, α-adrenergic receptor agonists, mast cell stabilizers, expectorants, and NK1, NK2 and NK3 tachykinin receptor antagonists.

Still another embodiment is a metered dose aerosol dispenser containing an aerosol pharmaceutical composition for pulmonary or nasal delivery comprising an agent that inhibits a TRPA1-mediated current with an $IC_{50}$ of 1 micromolar or less. For instance, it can be a metered dose inhaler, a dry powder inhaler or an air-jet nebulizer.

Dosages

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound disclosed herein employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous, intracerebroventricular, intrathecal and subcutaneous doses of the compounds of this invention for a patient will range from about 0.0001 to about 100 mg per kilogram of body weight per day. For example, the dose can be 1-50, 1-25, or 5-10 mg/kg.

If desired, the effective daily dose of the active compound may be administered as two, three, four, five, six or more sub-doses administered separately at appropriate intervals throughout the day, optionally, in unit dosage forms.

Methods of Treatment

The compounds described herein can be used to treat or prevent a disorder described herein. For example, compounds with TRPA1 inhibitory activity are provided herein for the prevention, treatment, or alleviating symptoms of a disease or condition associated with TRPA1. Compounds of Formula (I), or pharmaceutical compositions containing one or more compounds of Formula (I), can be administered to treat disorders, conditions, or diseases described herein such as those treatable by the inhibition of TRPA1. For example, the pharmaceutical compositions comprising compounds of Formula (I), or pharmaceutically acceptable salts thereof, are useful as a perioperative analgesic, for example in the management of mild to moderate acute post-operative pain and management of moderate to severe acute pain as an adjunct to opioid analgesics. The pharmaceutical compositions comprising a therapeutically-effective dose of compounds of Formula (I), can be administered to a patient for treatment of pain in a clinically safe and effective manner, including one or more separate administrations of the pharmaceutical compositions comprising compounds of Formula (I). Additional exemplary methods include the treatment of peripheral diabetic neuropathy (PDN) and chemotherapy induced peripheral neuropathy (CIPN). For example, a pharmaceutical composition comprising a therapeutically effective dose of compounds of Formula (I), or pharmaceutically acceptable salts thereof can be administered (e.g., intravenously) to a subject in need thereof multiple times per day (e.g., BID) over a course of treatment of one or more days to treat pain in the subject. Pharmaceutical compositions comprising compounds of Formula (I) can also be used to treat or ameliorate respiratory conditions, such as obstructive diseases, e.g., chronic obstructive pulmonary disease (COPD), asthma (e.g., cold induced asthma, exercise-induced asthma, allergy-induced asthma, and occupational asthma), and cough.

Those of skill in the treatment of diseases linked to the mediation of the TRPA1 receptor will be able to determine the therapeutically effective amount of a compound of Formula (I) from the test results presented hereinafter. In general, a suitable daily dose of a compound of the invention will be that amount of the compound that is the lowest dose able to produce a therapeutic effect. Such an effective dose will generally depend upon various factors. Generally, oral, sublingual, rectal, intravenous, topical, transdermal, inhaled and intracerebroventricular doses of the compounds of this invention for a patient will range from about 0.0001 to about 100 mg per kilogram of body weight per day. For example, the dose can be 1-50, 1-25, or 5-10 mg/kg. It is contemplated, for instance, that a therapeutically effective dose will be from about 0.001 mg/kg to about 50 mg/kg per kg of body weight, more preferably from about 0.01 mg/kg to about 10 mg/kg per kg of body weight of the patient to be treated. It may be appropriate to administer the therapeutically effective dose in the form of two or more sub-doses at appropriate intervals throughout the day. Said sub-doses may be formulated as unit dosage forms, for example each containing from about 0.1 mg to about 1000 mg, more particularly from about 1 to about 500 mg, of the active ingredient per unit dosage form.

The exact dosage and frequency of administration depends on the particular compound of formula (I) used, the particular condition being treated, the severity of the condition being treated, the age, weight and general physical condition of the particular patient as well as the other medication the patient may be taking, as is well known to those skilled in the art.

Furthermore, said "therapeutically effective amount" may be lowered or increased depending on the response of the treated patient and/or depending on the evaluation of the physician prescribing the compounds of the instant invention. The effective daily amount ranges mentioned hereinabove are therefore only guidelines. A physician or veterinarian having ordinary skill in the art can readily determine and prescribe the effective amount of the pharmaceutical composition required.

Exemplary disorders suitable for treatment with a compound or composition described herein are provided below.
Pain The compounds of Formula (I) that are useful in the modulation of TRPA1 can be used in the formulation of analgesic pharmaceuticals suitable for the treatment and/or prophylaxis of pain in mammals, especially in humans. Endogenous activators of TRPA1 are produced during many pathological conditions including tissue injury, inflammation, and metabolic stress. Compounds and pharmaceutical compositions of the present invention can be administered to treat pain resulting from activation of TRPA1 including neuropathic pain. Relevant neuropathic pain conditions include, but are not limited to, painful diabetic neuropathy, chemotherapy - induced peripheral neuropathy, lower back pain, trigeminal neuralgia, post-herpetic neuralgia, sciatica, and complex regional pain syndrome Compositions and methods provided herein may also be used in connection with treatment of in the treatment of inflammation and inflammatory pain. Such disorders include rheumatoid arthritis, osteoarthritis, temperomandibular disorder. In some embodiments, the compositions and methods provided herein may be used to treat headache pain, e.g., migraine.

Disclosed compounds also may be useful in the treatment of visceral pain and inflammation. Relevant diseases include pancreatitis, inflammatory bowel disease, colitis, Crohn's disease, endometriosis, pelvic pain, and angina.

Additional exemplary pain indications for which compounds disclosed herein can be used include temperomandibular disorder, cancer pain (resulting either from the underlying disease or from the treatments), burn pain, oral pain, oral pain due to cancer treatment, crush and injury induced pain, incisional pain, bone pain, sickle cell disease pain, fibromyalgia and musculoskeletal pain. TRPA1 has been show to play a role in cancer related pain (See, e.g., Trevisan et al., Cancer Res Mar. 11, 2013.); postoperative pain (See, e.g., Wei et al, Anasthesiology, V 117, No. 1 (2012); pathological pain (See, e.g., Chen et al, Pain (2011).); and pain related to chemical injury (See, e.g., Macpherson et al, The Journal of Neuroscience, Oct. 17, 2007 27(42):11412-11415).

Hyperalgesia (e.g., mechanical hyperalegsia, cold hyperalegsia) or increased sensitivity to pain (e.g., acute, chronic). Multiple Chemical Sensitivity is a disorder linked to chemical exposure with multi-organ symptoms including respiratory symptoms and headache.

Allodynia (e.g., cutaneous allodynia, e.g., cephalic, extracephalic) is a pain due to a stimulus which does not normally provoke pain, e.g., temperature or physical stimuli, and differs from hyperalgesia, which generally refers to an extreme, exaggerated reaction to a stimulus which is normally painful.
Migraine The compounds of Formula (I) that are useful in the modulation of TRPA1 can be used in the formulation of pharmaceuticals suitable for the treatment and/or prophylaxis of migraine in mammals, especially in humans. Exposure to TRPA1 activators has been shown to trigger migraine in susceptible populations. Such activators include but are not limited to umbellulone, nitroglycerin, cigarette smoke, and formaldehyde. Accordingly, TRPA1 antagonists of the invention represent a significant possible therapeutic for the treatment of both chronic and acute migraine.
Inflammatory Diseases and Disorders Compositions and methods provided herein may also be used in connection with treatment of inflammatory diseases.

These diseases include but are not limited to asthma, chronic obstructive pulmonary disease, rheumatoid arthritis, osteoarthritis, inflammatory bowel disease, glomerulonephritis, neuroinflammatory diseases such as multiple sclerosis, and disorders of the immune system. TRPA1 has been show to play a role in pancreatic pain and inflammation (See, e.g., Schwartz et al., Gastroenterology. 2011 April; 140(4): 1283-1291.).

Peripheral neuropathy, for example diabetic neuropathy, is a particular condition that involves both a neuronal and an inflammatory component. Without being bound by a mechanistic theory, the TRPA1 antagonists of the invention may be useful in treating peripheral neuropathies including, but not limited to, diabetic neuropathy. In addition to their use in the treatment of peripheral neuropathies (e.g., reducing inflammation), the subject inhibitors may also be useful in reducing the pain associated with peripheral neuropathy. TRPA1 has been show to play a role in neuropathy and neuropathic pain (See, e.g., Wei et al, Anesthesiology 2009; 111:147-54; and Koivisto et al., Pharmacological Research 2011.).

Neurogenic inflammation often occurs when neuronal hyperexcitability leads to the release of peptides that trigger inflammation. These peptides include substance P and CGRP. Blocking TRPA1 would reduce neuronal activity and thus could block neurogenic inflammation. For example, neurogenic inflammation in the respiratory tract, can result in asthma and allergic rhinitis symptoms, and neurogenic inflammation in the dura may also mediate migraine pain.

Pancreatitis

Pancreatitis is an inflammation of the pancreas. The pancreas is a large gland behind the stomach and close to the duodenum. Normally, digestive enzymes do not become active until they reach the small intestine, where they begin digesting food. But if these enzymes become active inside the pancreas, they start "digesting" the pancreas itself. TRPA1 has been show to play a role in pancreatic pain and inflammation (See, e.g., Schwartz et al., Gastroenterology. 2011 April; 140(4): 1283-1291.).

Acute pancreatitis is usually, although not exclusively, caused by gallstones or by alcohol abuse. Acute pancreatitis usually begins with pain in the upper abdomen that may last for a few days. The pain may be severe and may become constant. The pain may be isolated to the abdomen or it may reach to the back and other areas. Sometimes, and for some patients, the pain is sudden and intense. Other times, or for other patients, the pain begins as a mild pain that worsens after eating. Someone with acute pancreatitis often looks and feels very sick. Other symptoms may include swollen and tender abdomen, nausea, vomiting, fever, and rapid pulse. Severe cases of acute pancreatitis may cause dehydration and low blood pressure, and may even lead to organ failure, internal bleeding, or death.

During acute pancreatitis attacks, the blood levels of amylase and lipase are often increased by at least 3-fold. Changes may also occur in blood levels of glucose, calcium, magnesium, sodium, potassium, and bicarbonate.

The current treatment depends on the severity of the attack. Treatment, in general, is designed to support vital bodily functions, manage pain, and prevent complications. Although acute pancreatitis typically resolved in a few days, pain management during an attack is often required. The compounds disclosed herein can be used to relieve the pain associated with acute pancreatitis.

Chronic pancreatitis may develop if injury to the pancreas continues. Chronic pancreatitis occurs when digestive enzymes attack and destroy the pancreas and nearby tissues, causing scarring and pain. Chronic pancreatitis may be caused by alcoholism, or by blocked, damaged, or narrowed pancreatic ducts. Additionally, hereditary factors appear to influence the disease, and in certain cases, there is no identifiable cause (so called idiopathic pancreatitis).

Most people with chronic pancreatitis have abdominal pain. The pain may get worse when eating or drinking, spread to the back, or become constant and disabling. Other symptoms include nausea, vomiting, weight loss, and fatty stools.

Relieving pain is the first step in treating chronic pancreatitis. Once the pain has been managed, a high carbohydrate and low fat dietary plan is put in place. Pancreatic enzymes may be used to help compensate for decrease enzyme production from the injured pancreas. Sometimes insulin or other drugs are needed to control blood glucose.

Although pain is typically managed using drug therapy, surgery may be necessary to relieve pain. Surgery may be necessary to drain an enlarged pancreatic duct or even to 10 removing a portion of a seriously injured pancreas.

Pain is frequently present with chronic pancreatitis. For example, pain is present for approximately 75% of patients with alcoholic chronic pancreatitis, 50% of patients with lateonset idiopathic chronic pancreatitis, and 100% of patients with early-onset idiopathic chronic pancreatitis (Di-Magno, 1999, Gastroenterology 116(5): 1252-1257).

A minority of patients with pain have readily identifiable lesions which are relatively easy to treat surgically or endoscopically. In other patients, pain is often thought to result from a variety of causes, including elevated intrapancreatic pressure, ischemia, and fibrosis. Without being bound by theory, however, these phenomena are not likely the underlying cause of the pain. Rather, pain may result from a background of neuronal sensitization induced by damage to the perineurium and subsequent exposure of the nerves to mediators and products of inflammation.

Given the importance of effective pain management in patients with chronic pancreatitis, additional therapies for treating painful symptoms are important and useful. The compounds disclosed herein can be used to manage the pain associated with chronic pancreatitis; they can be used alone or as part of an overall therapeutic treatment plan to manage patients with chronic pancreatitis. For example, the compounds can be administered with pancreatic enzymes and/or insulin as part of a therapeutic regimen designed to manage patients with chronic pancreatitis.

Cancer treatments are not only painful, but they may even be toxic to healthy tissue. Some chemotherapeutic agents can cause painful neuropathy. Accordingly, the compounds disclosed herein could represent a significant possible therapeutic for the treatment of the pain and/or inflammation associated with cancer treatments that cause neuropathy.

A major function of prostaglandins is to protect the gastric mucosa. Included in this function is the modulation of intracellular calcium level in human gastric cells which plays a critical role in cell proliferation. Consequently, inhibition of prostaglandins by nonsteroidal anti-inflammatory drugs (NSAIDs) can inhibit calcium influx in gastric cells (Kokoska et al. (1998) Surgery (St Louis) 124 (2):429-437). The NSAIDs that relieve inflammation most effectively also produce the greatest gastrointestinal damage (Canadian Family Physician, 5 Jan. 1998, p. 101). Thus, the ability to independently modulate calcium channels in specific cell types may help to alleviate such side effect of anti-inflammatory therapy. Additionally or alternatively, administration of TRPA1 inhibitory compounds disclosed herein may be used in combination with NSAIDs, thus promoting pain relief using reduced dosage of NSAIDs.

TRPA1 may mediate ongoing nociception in chronic pancreatitis; and may be involved in transforming acute into chronic inflammation and hyperalgesia in pancreatitis. TRPA1 may also mediate irritation and burning in the e.g., nasal and oral mucosa and respiratory lining.

Neuropathy

Because TRPA1 overactivity can lead to a toxic calcium overload, TRPA1 antagonists also have utility in the prevention of neuropathy associated with diabetes, chemical injury, chemotherapy, medicines such as statins, HIV/AIDS, Fabry's disease, vitamin deficiency, inherited polyneuropathy such as Marie-Charcot Tooth disease, and trauma. Peripheral neurodegenerative diseases such as Amyotrophic Lateral Sclerosis may also be amenable to treatment with a TRPA1 antagonist.

Pulmonary Disease and Cough

Compositions and methods provided herein may also be used in connection with the treatment of pulmonary diseases, including, but not limited to, asthma (including exercise-induced asthma, atopic asthma, allergic asthma), Chronic Obstructive Pulmonary disease (COPD, emphysema,) cystic fibrosis, bronchiectasis, bronchiolitis, allergic bronchopulmonary aspergillosis, bronchiolitis obliterans (popcorn worker lung), diseases due to chemical exposure including exposures to diacetyl, formaldehyde, and other irritants. These conditions also include tuberculosis, restrictive lung disease including asbestosis, radiation fibrosis, hypersensitivity pneumonitis, infant respiratory distress syndrome, idiopathic pulmonary fibrosis, idiopathic interstial pneumonia sarcoidosis, eosinophilic pneumonia, lymphangioleiomyomatosis, pulmonary Langerhan's cell histiocytosis, and pulmonary alveolar proteinosis; respiratory tract infections including upper respiratory tract infections (e.g., common cold, sinusitis, tonsillitis, pharyngitis and laryngitis) and lower respiratory tract infections (e.g., pneumonia); respiratory tumors whether malignant (e.g., small cell lung cancer, non-small cell lung cancer, adenocarcinoma, squamous cell carcinoma, large cell undifferentiated carcinoma, carcinoid, mesothelioma, metastatic cancer of the lung, metastatic germ cell cancer, metastatic renal cell carcinoma) or benign (e.g., pulmonary hamartoma, congenital malformations such as pulmonary sequestration and congenital cystic adenomatoid malformation (CCAM)); pleural cavity diseases (e.g., empyema and mesothelioma); and pulmonary vascular diseases, e.g, pulmonary embolism such as thromboembolism, and air embolism (iatrogenic), pulmonary arterial hypertension, pulmonary edema, pulmonary hemorrhage, inflammation and damage to capillaries in the lung resulting in blood leaking into the alveoli. Other conditions that may be treated include disorders that affect breathing mechanics (e.g., obstructive sleep apnea, central sleep apnea, Guillan-Barre syndrome, and myasthenia gravis).

The present compounds can also be useful for treating, reducing, or preventing cough (with or without the production of sputum), cough associated with asthma, cough associated with influenza, coughing blood (haemoptysis), cough of unknown etiology, and cough due to chemical exposures.

Dermatogoloical Disorders

A number of agents that cause itch activate TRPA1 directly or via activation of receptors which couple to TRPA1 downstream. Compositions and methods provided herein may also be used in connection with the treatment of itch. Indications include, but are not limited to, conditions triggered by exposure to exogenous chemicals such as contact dermatitis, poison ivy, itch due to cancer including lymphomas, itch caused by medications such as chloroquine, itch due to reactive drug metabolites or itch due to dry skin.

Additional exemplary indications include atopic dermatitis, psoriasis, hives, eczema, dyshidrotic eczema, mouth ulcers, diaper rash.

Itch

Itch, or acute pruritus, while serving an important protective function by e.g., warning against harmful agents in the environment, it can also be a debilitating condition that e.g., accompanies numerous skin, systemic and nervous system disorders. Some forms of itch are mediated by histamine signaling as such are susceptible to treatment with e.g., antihistamines. However, most pathophysiological itch conditions are insensitive to antihistamine treatment. Compounds and pharmaceutical compositions of the present invention can be administered to treat itch.

Atopic dermatitis (AD) is a chronic itch and inflammatory disorder of the skin. Patients with severe AD can develop asthma and allergic rhinitis, also known as atopic march. Skin rash and pruritus may be associated with atopic disease. Chronic itch, e.g., in AD and psoriasis; includes pathophysiological hallmarks such as robust scratching, extensive epidermal hyperplasia from e.g., eczema, kidney failure, cirrhosis, nervous system disorders, some cancers.

Allergic contact dermatitis is a common skin disease associated with inflammation and persistent pruritus.

Methods as disclosed herein may inhibit skin edema, keratinocyte hyperplasia, nerve growth, leukocyte infiltration, and antihistamine-resistant scratching behavior. Methods as disclosed herein may inhibit allergic response to e.g., exogenous stimulants, e.g., haptens, oxazolone, urushiol (e.g., from poison ivy).

Disease and Injury Models

Compounds that antagonize TRPA1 function may be useful in the prophylaxis and treatment of any of the foregoing injuries, diseases, disorders, or conditions. In addition to in vitro assays of the activity of these compounds, their efficacy can be readily tested in one or more animal models. There are numerous animal models for studying pain. The various models use various agents or procedures to simulate pain resulting from injuries, diseases, or other conditions (Blackburn-Munro (2004) Trends in Pharmacological Sciences 25: 299-305 (see, for example, Tables 1, 3, or 4)). Behavioral characteristics of challenged animals can then be observed. Compounds or procedures that may reduce pain in the animals can be readily tested by observing behavioral characteristics of challenged animals in the presence versus the absence of the test compound(s) or procedure.

Exemplary behavioral tests used to study chronic pain include tests of spontaneous pain, allodynia, and hyperalgesia. To assess spontaneous pain, posture, gait, nocifensive signs (e.g., paw licking, excessive grooming, excessive exploratory behavior, guarding of the injured body part, and self-mutilation) can be observed. To measure evoked pain, behavioral responses can be examined following exposure to heat (e.g., thermal injury model).

Exemplary animal models of pain include, but are not limited to, the models described in the Trevisan model, and the Koivisto references including Streptozotocin induced painful diabetic neuropathy, bortezomib induced peripheral neuropathy and oxaliplatin induced peripheral neuropathy; the Chung model, the spared nerve injury model, the carageenan induced hyperalgesia model, the complete Freund's adjuvant induced hyperalgesia model, the thermal injury model, the formalin model and the Bennett Model.

In the Trevisan reference, chemotherapy-induced peripheral neuropathy model involves the induction if a CIPN phenotype in mice by treatment with bortezomib or oxaliplatin (Trevisan et al, Cancer research 73, 3120-3131, 2013). Treatment of an animal with an inhibitor of TRPA1 can be evaluated using any of a variety of nociceptive tests such as the Von Frey hair test, the hot plate test, cold simulation, chemical hyperalgesia, or the rotarod test.

The model of peripheral diabetic neuropathy (PDN) in the Koivisto reference involves induction of diabetes mellitus (DM) in rats with streptozotocin, and assessing axon reflex induced by intraplantar injection of a TRPA1 agonist. (Pharmacological Research 2011) Treatment with a compound that inhibits TRPA1 can be evaluated for the reduction in DM-induced attenuation of the cutaneous axon reflex.

The Chung model of neuropathic pain (without inflammation) involves ligating one or more spinal nerves (Chung et al. (2004) Methods Mol Med 99: 35-45; Kim and Chung (1992) Pain 50: 355-363). Ligation of the spinal nerves results in a variety of behavioral changes in the animals including heat hyperalgesia, cold allodynia, and ongoing pain. Compounds that antagonize TRPA1 can be administered to ligated animals to assess whether they diminish these ligation-induced behavioral changes in comparison to that observed in the absence of compound.

Carageenan induced hyperalgesia and complete Freund's adjuvant (CFA) induced hyperalgesia are models of inflammatory pain (Walker et al. (2003) Journal of Pharmacol Exp Ther 304: 56-62; McGaraughty et al. (2003) Br J Pharmacol 140: 1381-1388; Honore et al. (2005) J Pharmacol Exp Ther). Compounds that antagonize TRPA1 can be administered to carrageenan or CFA challenged animals to assess whether they diminish cold, mechanical or heat hypersensitivity in comparison to that observed in the absence of compound. In addition, the ability of compounds that antagonize TRPA1 function to diminish cold and/or mechanical hypersensitivity can also be assessed in these models. Typically, the carrageenan induced hyperalgesia model is believed to mimic acute inflammatory pain and the CFA model is believed to mimic chronic pain and chronic inflammatory pain.

Exemplary models of inflammatory pain include the rat model of intraplantar bradykinin injection. Briefly, the baseline thermal sensitivity of the animals is assessed on a Hargreave's apparatus. TRPA1 blockers are then administered systemically. Bradykinin is subsequently injected into the paw and a hyperalgesia is allowed to develop. Thermal escape latency is then measured at multiple time points over the next few hours (Chuang et al., 2001; Vale et al., 2004).

Inflammation is often an important contributing factor to pain. As such, it is useful to identify compounds that act as anti-inflammatories. Many compounds that reduce neural activity also prevent neurogenic inflammation. To measure inflammation directly, the volume of a rat paw can be assessed using a plethysmometer. After baseline measurement is taken, carrageenan can be injected into the paw and the volume can be monitored over the course of hours in animals that have been treated with vehicle or drug. Drugs that reduce the paw swelling are considered to be anti-inflammatory.

Migraines are associated with significant pain and inability to complete normal tasks. Several models of migraine exist including the rat neurogenic inflammation model, (see Buzzi et al (1990) Br J Pharmacol; 99:202-206), and the Burstein Model (see Strassman et al., (1996) Nature 384: 560-564).

The Bennett model uses prolonged ischemia of the paw to mirror chronic pain (Xanthos et al. (2004) J Pain 5: S1). This provides an animal model for chronic pain including post-operative pain, complex regional pain syndrome, and reflex sympathetic dystrophy. Prolonged ischemia induces behavioral changes in the animals including hyperalgesia to mechanical stimuli, sensitivity to cold, pain behaviors (e.g., paw shaking, licking, and/or favoring), and hyperpathia. Compounds that antagonize TRPA1 can be administered to challenged animals to assess whether they diminish any or all of these behaviors in comparison to that observed in the absence of compound. Similar experiments can be conducted in a thermal injury or UV-burn model which can be used to mimic post-operative pain.

Additional models of neuropathic pain include central pain models based on spinal cord injury. Chronic pain is generated by inducing a spinal cord injury, for example, by dropping a weight on a surgically exposed area of spinal cord (e.g., weight-drop model). Spinal cord injury can additionally be induced by crushing or compressing the spinal cord, by delivering neurotoxin, using photochemicals, or by hemisecting the spinal cord.

Additional models of neuropathic pain include peripheral nerve injury models. Exemplary models include, but are not limited to, the neuroma model, the Bennett model, the Seltzer model, the Chung model (ligation at either L5 or L5/L6), the sciatic cryoneurolysis model, the inferior caudal trunk resection model, and the sciatic inflammatory neuritis model. Id.

Exemplary models of neuropathic pain associated with particular diseases are also available. Diabetes and shingles are two diseases often accompanied by neuropathic pain. Even following an acute shingles episodes, some patients continue to suffer from postherpetic neuralgia and experience persistent pain lasting years. Neuropathic pain caused by shingles and/or postherpetic neuralgia can be studied in the postherpetic neuralgia model (PHN). Diabetic neuropathy can be studied in diabetic mouse models, as well as chemically induced models of diabetic neuropathy.

As outlined above, cancer pain may have any of a number of causes, and numerous animal models exist to examine cancer pain related to, for example, chemotherapeutics or tumor infiltration. Exemplary models of toxin-related cancer pain include the vincristine-induced peripheral neuropathy model, the taxol-induced peripheral neuropathy model, and the cisplatin-induced peripheral neuropathy model. An exemplary model of cancer pain caused by tumor infiltration is the cancer invasion pain model (CIP).

Primary and metastatic bone cancers are associated with tremendous pain. Several models of bone cancer pain exist including the mouse femur bone cancer pain model (FBC), the mouse calcaneus bone cancer pain model (CBC), and the rat tibia bone cancer model (TBC). Id.

An additional model of pain is the formalin model. Like the carrageenan and CFA models, the formalin model involves injection of an irritant intradermally or intraperitoneally into an animal. Injection of formalin, a 37-40% percent solution of formaldehyde, is the most commonly used agent for intradermal paw injection (the formalin test). Injection of a 0.5 to 15 percent solution of formalin (usually about 3.5%) into the dorsal or plantar surface of the fore- or hindpaw produces a biphasic painful response of increasing and decreasing intensity for about 60 minutes after the injection. Typical responses include the paw being lifted, licked, nibbled, or shaken. These responses are considered nociceptive. The initial phase of the response (also known as the Early Phase), which lasts 3 to 5 minutes, is probably due to direct chemical stimulation of nociceptors. This is followed by 10 to 15 minutes during which animals display little behavior suggestive of nociception. The second phase of this response (also known as the Late Phase) starts about 15 to 20 minutes after the formalin injection and lasts 20 to 40 minutes, initially rising with both number and frequency of nociceptive behaviors, reaching a peak, then falling off. The intensities of these nociceptive behaviors are dependent on the concentration of formalin used. The second phase involves a period of sensitization during which inflammatory phenomena occur. The two phases of responsiveness to formalin injection makes the formalin model an appropriate model for studying nociceptive and acute inflammatory pain. It may also model, in some respects, neuropathic pain.

In addition to any of the foregoing models of chronic pain, compounds that antagonize TRPA1 function can be tested in one or more models of acute pain. Valenzano et al. (2005) Neuropharmacology 48: 658-672. Regardless of whether compounds are tested in models of chronic pain, acute pain, or both, these studies are typically (though not exclusively) conducted, for example, in mice, rats, or guinea pigs. Additionally, compounds can be tested in various cell lines that provide in vitro assays of pain.

Many individuals seeking treatment for pain suffer from visceral pain. Animal models of visceral pain include the rat model of inflammatory uterine pain (Wesselmann et al., (1997) Pain 73:309-317), injection of mustard oil into the gastrointestinal tract to mimic irritable bowel syndrome (Kimball et al., (2005) Am J Physiol Gastrointest Liver Physiol, 288(6):G1266-73), injection of mustard oil into the bladder to mimic overactive bladder or bladder cystitis (Riazimand (2004), BJU 94: 158-163). The effectiveness of a TRPA1 compound can be assessed by a decrease in writhing, gastrointestinal inflammation or bladder excitability.

For testing the efficacy of TRPA1 antagonists for the treatment of cough, experiments using the conscious guinea pig model of cough can be readily conducted (Tanaka and Maruyama (2003) Journal Pharmacol Sci 93: 465-470; McLeod et al. (2001) Br J Pharmacol 132: 1175- 1178). Briefly, guinea pigs serve as a useful animal model for cough because, unlike other rodents such as mice and rats, guinea pigs actually cough. Furthermore, guinea pig coughing appears to mimic human coughing in terms of the posture, behavior, and appearance of the coughing animal.

To induce cough, conscious guinea pigs are exposed to an inducing agent such as citric acid or capsaicin. The response of the animal is measured by counting the number of coughs. The effectiveness of a cough suppressing agent, for example a compound that inhibits TRPA1, can be measured by administering the agent and assessing the ability of the agent to decrease the number of coughs elicited by exposure to citric acid, capsaicin, or other similar cough-inducing agent. In this way, TRPA1 inhibitors for use in the treatment of cough can be readily evaluated and identified.

Additional models of cough may also include the unconscious guinea pig model (Rouget et al. (2004) Br J Pharmacol 141:1077-1083). Either of the foregoing models can be adapted for use with other animals capable of coughing. Exemplary additional animals capable of coughing include cats and dogs.

Compounds of the invention may be tested in multiple models of asthma. One example is the murine ovalbumin model of asthma (Caceres AI et al., Proc Natl Acad Sci U S A. 2009 June 2; 106(22):9099-104; Epub 2009 May 19). In this model, ovalbumin is injected into the intraperitoneal cavity several times over 2 weeks. Sometime in the third week, animals are challenged with intranasal ovalbumin an airway hyperresponsiveness, inflammation and inflammatory cytokine production may be measured. Compounds are dosed during the challenge phase of the model. TRPA1 knock-out mice may be substituted into the above models as reported by Caceres et al.

An example of a large animal model of asthma the conscious allergic sheep model as described in Abraham, W.M. et al. may be used to assess effects of compounds on the antigen-induced late stage response of asthma (Abraham WM., Am J Respir Crit Care Med. 2000 August; 162(2 Pt 1):603-11). Briefly, baseline airway responsiveness is measured by plethysmograph in conscious sheep prior to a nebulized administration of Ascaris suum extract to induce asthma. After baseline readings are captured, animals are challenged with a nebulized dose of Ascaris suum. Antigen sensitivity is determined by decrease in pulmonary flow resistance from baseline. Once animals demonstrate antigen-sensitivity, test compounds may be administered and additional pulmonary flow resistance readings captured to assess changes airway responsiveness. Models in the horse and beagle dog are sometimes also used.

Additional models may include the Brown Norway rat model and the C57BL/6J mouse model of asthma as described in Raemdonck et al. (Raemdonck K et al., Thorax. 2012 January; 67(1):19-25; Epub 2011 Aug 13). Briefly Brown Norway rats and C57BL/6J mice may be sensitized and challenged with aerosol delivered ovalbumin. Once sensitivity is confirmed by a decrease in lung function as measured by whole body plethysmograph readings, compounds of the invention may be administered. Visual and audible signs of respiratory distress including wheezing may also be present.

Dermatitis

Multiple mouse models of dermatological disease currently exist. For example, Liu et al. describe multiple oxazolone and urushiol-induced contact dermatis models (Liu B et al., FASEB J. 2013 September; 27(9):3549-63; Epub 2013 May 30). Briefly, Trpa1 knock-out mice receive topical administrations of oxazolone or urushiol to induce dermatitis and itch responses. Epidermis thickness may also be measured by taking ear punches and measurements of challenged areas compared with untreated ears. In vivo treatment compounds may be determined by administering compounds to the animals prior to or after ozazolone or urushiol treatments. Scratching behaviors are recorded by video cameras positioned above observation chambers. Observers blind to treatment groups record the time animals spend scratching over the course of thirty minutes.

An alternative mouse model of dry-skin evoking itch involves administration of acetone, ether, and water to the mouse as reported by Wilson et al. (Wilson SR et al., J Neurosci. 2013 May 29;33(22):9283-94) In this model, the area to be treated is shaved and mice receive topical administration of acetone and ether twice daily on the area to be observed, e.g. cheek or caudal back. In vivo efficacy of treatment compounds may be determined by administering compounds to the animals prior to or after acetone and ether administration. Scratching behavior is recorded by camera for a period of 20 minutes and quantified by observers blind to treatment groups.

In addition, pruritus may be induced by direct injection of an agent that causes itch. Examples of these agents may be found in Akayimo and Carstens, 2013. Some examples are: chloroquine (Wilson et al., 2011), bile acids, TSLP (Wilson et al., 2013), and IL-31 (Cevikbas et al., 2014). Typically scratching bouts in a defined period are recorded by an observed blinded to treatment group.

Numerous rodent models of incontinence exist. These include models of incontinence induced by nerve damage, urethral impingement and inflammation. Models of urethral impingement include the rat bladder outflow obstruction model. (Pandita, RK, and Andersson KE. Effects of intravesical administration of the K+ channel opener, Z.D6169, in conscious rats with and without bladder outflow obstruction. J Urol 162: 943-948, 1999). Inflammatory models include injection of mustard oil into the bladder.

To test the effectiveness of a TRPA1 inhibitor compound in treating incontinence, varying concentrations of compound (e.g., low, medium, and high concentration) can be administered to rats following surgical partial bladder outlet obstruction (BOO). Efficacy of the varying doses of TRPA1 inhibitory compound can be compared to controls administered excipients alone (sham control). Efficacy can further be compared to rats administered a positive control, such as atropine. Atropine is expected to decrease bladder overactivity following partial bladder outlet obstruction in the BOO model. Note that when testing compounds in the BOO model, compounds can be administered directly to the bladder or urethra (e.g., by catheter) or compounds can be administered systemically (e.g., orally, intraveneously, intraperitoneally, etc).

Several rat models of pancreatitic pain have recently been described (Lu, 2003, Anesthesiology 98(3): 734-740; Winston et al., 2003, Journal of Pain 4(6): 329-337). Lu et al. induced pancreatitis by systemic delivery of dibutylin dichloride in rats. Rats showed an increase in withdrawal events after von Frey filament stimulation of the abdomen and decreased withdrawal latency after thermal stimulation during a period of 7 days. The pain state induced in these animals was also characterized by increased levels of substance P in spinal cords (Lu, et al., 2003). To test the efficacy of a TRPA1 inhibitor in this model, a TRPA1 inhibitor can be administered following or concurrently with delivery of dibutylin dichloride. Control animals can be administered a carrier or a known pain reliever. Indicia of pain can be measured. Efficacy of a TRPA1 inhibitor can be evaluated by comparing the indicia of pain observed in animals receiving a TRPA1 inhibitor to that of animals that did not receive a TRPA1 inhibitor. Additionally, efficacy of a TRPA1 inhibitor can be compared to that of known pain medicaments.

The efficacy of von Frey filament testing as a means to measure nociceptive behavior was also shown by inducing pancreatitis by systemic L-arginine administration (Winston et al, 2003). The efficacy of a TRPA1 inhibitor can similarly be tested following pancreatitis induced by systemic L-arginine administration.

Lu et al. also described direct behavioral assays for pancreatic pain using acute noxious stimulation of the pancreas via an indwelling ductal cannula in awake and freely moving rats. These assays included cage crossing, rearing, and hind limb extension in response to intrapancreatic bradykinin infusion. Intrathecal administration of either D-APV (NMDA receptor antagonist) or morphine alone partially reduced visceral pain behaviors in this model. Combinations of both reduced pain behaviors to baseline. The efficacy of a TRPA1 inhibitor can similarly be tested in this system.

Any of the foregoing animal models may be used to evaluate the efficacy of a TRPA1 inhibitor in treating pain associated with pancreatitis. The efficacy can be compared to a no treatment or placebo control. Additionally or alternatively, efficacy can be evaluated in comparison to one or more known pain relieving medicaments.

EXAMPLES

In Vitro Characterization of Exemplary Compounds of the Invention

Example 1

Method for Measuring Inhibition of the TRPA1 Ion Channel

Compounds of Formula (I) inhibit the TRPA1 channel, as shown by measuring the in vitro inhibition of human TRPA1, provided in data tables shown in Table 2, using the procedure outlined in del Camino et al., *The Journal of Neuroscience*, 30(45):15165-15174 (Nov. 10, 2010), incorporated herein by reference and summarized below. Data for TRPA1 inhibition was obtained by this method for the indicated compounds of Formula (I), with the relevant data included in Table 2 below. All currents were recorded in whole-cell configuration using EPC-9 and EPC-10 amplifiers and Patchmaster software (HEKA) or similar. Patch pipettes had a resistance of 1.5-3 M_ and up to 75% of the series resistance was compensated. The standard pipette solution consisted of 140mM CsAsp, 10 mM EGTA, 10 mM HEPES, 2.27 mM, 20 $MgCl_2$, 1.91 mM $CaCl_2$, and up to 0.3 mM $Na_2GTP$, with pH adjusted to 7.2 with CsOH. In addition, a solution containing 145 mM CsCl, 10 mM HEPES, 10 mM EGTA, and up to 0.3 mM $Na_2GTP$ and 1 mM $MgCl_2$ (pH 7.2 adjusted with CsOH) can be used. The standard bath solution contained 150 mM NaCl, 10 mM HEPES, 10 mM glucose, 4.5 mM KCl, 1 mM EGTA, 3 mM $MgCl_2$, with pH adjusted to 7.4 with NaOH. In some instances, 2 mM $CaCl_2$ was added in place of EGTA and the concentration of $MgCl_2$ was reduced to 1 mM.

Data were collected either by continuous recordings at −60 mV or by applying voltage ramps from a holding potential of −40 mV every 4 s. Continuous recordings were collected at 400 Hz and digitally filtered off-line at 10 Hz for presentation. Voltage ramps were applied from −100 mV or −80 mV to +100 mV or +80 mV over the course of 400 ms, and data were collected at 10 kHz and filtered at 2.9 kHz. Inward and outward currents were analyzed from the ramps at −80 and 80 mV, respectively. Liquid junction potential correction was not used.

Solutions were switched using a gravity-fed continuous focal perfusion system. To achieve rapid temperature changes, two temperature control, and perfusion systems were employed simultaneously. For temperatures greater than or equal to 22° C., a Warner Instruments bipolar temperature controller (TC-344B) and inline heater (SHM-8) were used. For temperatures below 22° C. a Warner Instruments temperature controller (CL-100) and thermal cooling module (TCM-1) were used. Temperatures were confirmed using a thermistor (Warner Instruments, TA-29), with temperatures at the recorded cell estimated to be within +/−2° C. of those reported.

Table 2 shows data obtained from the in vitro assay described above. The antagonist effects of compounds of Formula (I) against human TRPA1 ("hTRPA1") in a whole cell patch configuration were evaluated using the in vitro assay described above. The current activation tested was 10 μM AITC, and the tested concentrations ranged from 320 μM to 3.2 μM.

TABLE 2

Antagonist effects of Compounds of Formula (I) against human TRPA1

| Compound # | hTRPA1 IC50 (nM) | Compound # | hTRPA1 IC50 (nM) | Compound # | hTRPA1 IC50 (nM) |
|---|---|---|---|---|---|
| 1 | 28 | 29 | 1 | 57 | 2 |
| 2 | 21 | 30 | 3 | 58 | 2 |
| 3 | 49 | 31 | 16 | 59 | 45 |
| 4 | 25 | 32 | 3 | 60 | 7 |
| 5 | 39 | 33 | 1 | 61 | 8 |
| 6 | 39 | 34 | 1 | 62 | 5 |
| 7 | 5 | 35 | 6 | 63 | 2 |
| 8 | 44 | 36 | 2 | 64 | 2 |
| 9 | 59 | 37 | 3 | 65 | 8 |
| 10 | 24 | 38 | 3 | 66 | 2 |
| 11 | 5 | 39 | 3 | 67 | 7 |
| 12 | 7 | 40 | 8 | 68 | 5 |
| 13 | 8 | 41 | 12 | 69 | 7 |
| 14 | 1 | 42 | 4 | 70 | 5 |
| 15 | 4 | 43 | 8 | 71 | 44 |
| 16 | 2 | 44 | 14 | 72 | 95 |
| 17 | 8 | 45 | 4 | 73 | 93 |
| 18 | 1 | 46 | 22 | 74 | 6 |
| 19 | 1 | 47 | 4 | 75 | 3 |
| 20 | 2 | 48 | 7 | 76 | 10 |
| 21 | 19 | 49 | 7 | 77 | 2 |
| 22 | 203 | 50 | 4 | 78 | 86 |
| 23 | 5 | 51 | >3200 | 79 | 3 |
| 24 | 10 | 52 | 23 | 80 | 1 |
| 25 | 4 | 53 | 14 | 81 | 10 |
| 26 | 1 | 54 | 7 | 82 | 5 |
| 27 | 2 | 55 | 5 | 83 | 2 |
| 28 | 1 | 56 | 3 | 84 | 4 |

| Compound # | hTRPA1 IC50 (nM) | Compound # | hTRPA1 IC50 (nM) | Compound # | hTRPA1 IC50 (nM) |
|---|---|---|---|---|---|
| 85 | 3 | 117 | 18 | 150 | 4 |
| 86 | 267 | 118 | 17 | 151 | 16 |
| 87 | 258 | 119 | 28 | 152 | 7 |
| 88 | 894 | 120 | 26 | 153 | 2 |
| 89 | 11 | 121 | 1 | 154 | >3200 |
| 90 | 3 | 122 | 1 | 155 | 5 |
| 91 | 2 | 123 | 2 | 156 | 3 |
| 92 | 33 | 124 | 1 | 157 | 1 |
| 93 | >3200 | 125 | 1 | 158 | 6 |
| 94 | 3 | 126 | 1 | 159 | 6 |
| 95 | 9 | 127 | 25 | 160 | 20 |
| 96 | 2 | 128 | 4 | 161 | 219 |
| 97 | 5 | 129 | 2 | 162 | 22 |
| 98 | 3 | 130 | 8 | 163 | 2 |
| 99 | 1 | 131 | 6 | 164 | 21 |
| 100 | 8 | 132 | 9 | 165 | 7 |
| 101 | 12 | 133 | 9 | 166 | 6 |
| 102 | 30 | 134 | 3 | 167 | 4 |
| 103 | 370 | 135 | 4 | 168 | 12 |
| 104 | 15 | 136 | 3 | 169 | 10 |
| 105 | 6 | 137 | 13 | 170 | 27 |
| 106 | 639 | 139 | 11 | 171 | 23 |
| 107 | 1 | 140 | 32 | 172 | 2 |
| 108 | 1 | 141 | 80 | 173 | 6 |
| 109 | 8 | 142 | 7 | 174 | 24 |
| 110 | 1 | 143 | 20 | 175 | 54 |
| 111 | 3 | 144 | 6 | 176 | 10 |
| 112 | 1 | 145 | 2 | 177 | 42 |
| 113 | 2 | 146 | 3 | 178 | 14 |
| 114 | 2 | 147 | 6 | 181 | 19 |
| 115 | 1 | | | 182 | 42 |
| 116 | >3200 | 149 | 2 | 183 | 3 |

| Compound # | hTRPA1 IC50 (nM) | Compound # | hTRPA1 IC50 (nM) | Compound # | hTRPA1 IC50 (nM) |
|---|---|---|---|---|---|
| 184 | 310 | 222 | 5 | 255 | 13 |
| 185 | 45 | 223 | 25 | 256 | 5 |
| 186 | 74 | 224 | 19 | 257 | 11 |
| 187 | 74 | 225 | 49 | 258 | 7 |
| 188 | 33 | 226 | 8 | 259 | 17 |
| 189 | 2 | 227 | 22 | 260 | 17 |
| 190 | 17 | 228 | 17 | 261 | 5 |
| 191 | 51 | 229 | 9 | 262 | 1 |
| 192 | 33 | 230 | 14 | 263 | 4 |
| 193 | 45 | 231 | 16 | 264 | 31 |
| 194 | 62 | 232 | 56 | 265 | 3 |
| 195 | 3 | 233 | 10 | 266 | 7 |
| 196 | 122 | 234 | 4 | 267 | 2 |
| 197 | 294 | 235 | 2 | 268 | 1 |
| 198 | 11 | 236 | 711 | 269 | 4 |
| 199 | 404 | 237 | 236 | 270 | 3 |
| 200 | 34 | 238 | 4 | 271 | 5 |
| 201 | 309 | 239 | 3 | 272 | 7 |
| 202 | 26 | 240 | 7 | | |
| 203 | 1610 | 241 | 1 | | |
| 204 | 3250 | 242 | 290 | | |
| 211 | >1000 | 243 | 6 | | |
| 212 | 62 | 245 | 8 | | |
| 213 | 141 | 246 | 1 | | |
| 214 | 92 | 247 | 2 | | |
| 215 | 25 | 248 | 4 | | |
| 216 | 16 | 249 | 6 | | |
| 217 | 3 | 250 | 6 | | |
| 218 | 4 | 251 | 219 | | |
| 219 | 23 | 252 | 1 | | |
| 220 | 72 | 253 | 20 | | |
| 221 | 5 | 254 | 14 | | |

In Vivo Efficacy of Exemplary Compounds of the Invention

Example 2

Formalin Model

Exemplary compounds of the invention were tested in the formalin-induced pain test reported by Dubuisson et al., Pain 1977 December; 4(2):161-74 (incorporated herein by reference in its entirety). Briefly, dilute formalin (50 µL of 3% formalin) was injected into the plantar surface of the hind paw of a rat. The animal was promptly returned to an observation arena (standard Plexiglass rat cage), at which point a trained observer recorded the time the animal exhibited pain behaviors (flinching, licking, biting of the injected paw/leg) in two distinct phases. The individual responsible for counting the pain behaviors in a particular study was blinded to the treatment groups.

The initial phase (Phase I: 0-5 min) is thought to have a significant component that is dependent upon direct activation of afferent fibers by formalin and functional TRPA1 (McNamara et al., 2007).

Investigators studied oral administration of compounds of the invention at the doses presented in Table 3 on pain behaviors in the formalin model in the rat. Compounds were formulated as solutions in water with various solvents and excipients including dimethyl sulfoxide (DMSO), polyethylene glycol (15)-hydroxystearate (Solutol, Sigma-Aldrich), caprylocaproyl macrogol-8 glyceride (Labrasol®, Sigma-Aldrich), polysorbate-80 (Tween®-80, Sigma-Aldrich), and polyoxyl 35 castor oil (Cremophor®EL, BASF Corp.); or suspensions in methylcellulose as indicated in Table 3. Animals were dosed orally with the vehicle, or compounds of the invention one hour prior to intraplantar formalin. Table 3 shows the duration of pain behaviors observed in the first two minutes or the duration of pain behaviors during the entire study period; five minutes. A decrease over Vehicle indicates a positive result. P values, when indicated, indicate significance compared Vehicle. Results without p values did not achieve statistical significance.

Oral administration of the compounds of the invention reduced the nociceptive responses in Phase 1 of the formalin model as seen from the data presented in Table 3.

TABLE 3

| | Duration (0-2 Minutes) Average (Seconds) | p value | Duration (0-5 Minutes) Average (Seconds) | p value | n |
|---|---|---|---|---|---|
| Study A | | | | | |
| Compound 7 formulated as solution in 4% DMSO, 10% Solutol, 86% water | | | | | |
| Vehicle PO: 4% DMSO, 10% Solutol, 86% water | 81.88 | | 194.50 | | 8 |
| Compound 7 @ 1 mpk PO | 82.38 | | 200.38 | | 8 |
| Compound 7 @ 3 mpk PO | 78.25 | | 173.75 | | 8 |
| Compound 7 @ 10 mpk PO | 67.00 | | 170.50 | | 8 |
| Study B | | | | | |
| Compound 15 formulated as solution in 8% DMSO; 92% Labrasol | | | | | |
| Vehicle PO: 8% DMSO; 92% Labrasol | 97.75 | | 222.50 | | 8 |
| Compound 15 @ 30 mpk PO | 76.00 | | 190.20 | | 5 |
| Study C | | | | | |
| Compound 18 formulated as solution in 4% DMSO; 5% Tween-80; 20% Cremophor EL; 71% water | | | | | |
| Vehicle, PO : 4% DMSO; 5% Tween-80; 20% Cremophor EL; 71% water | 91.6 | | 207.0 | | 8 |
| Compound 18 @ 1 mg/kg, PO | 78.0 | | 183.3 | | 8 |
| Compound 18 @ 3 mg/kg, PO | 58.0 | | 157.1 | | 8 |
| Compound 18 @ 10 mg/kg, PO | 35.3 | <0.01 | 181.6 | | 8 |
| Study D | | | | | |
| Compound 25 formulated as solution in 4% DMSO; 5% Tween-80; 20% Cremophor EL; 71% water | | | | | |
| Vehicle, PO: 4% DMSO; 5% Tween-80; 20% Cremophor EL; 71% water | 97.4 | | 228.4 | | 8 |
| Compound 25 @ 1 mg/kg, PO | 87.8 | | 190.1 | | 8 |
| Compound 25 @ 3 mg/kg, PO | 22.8 | <0.01 | 98.3 | <0.01 | 8 |
| Compound 25 @ 10 mg/kg, PO | 29.1 | <0.01 | 146.0 | | 8 |
| Study E | | | | | |
| Compounds formulated as solution in 4% DMSO; 5% Tween-80; 20% Cremophor EL; 71% water | | | | | |
| Vehicle, PO: 4% DMSO; 5% Tween-80; 20% Cremophor EL; 71% water | 103.4 | | 226.0 | | 8 |
| Compound 144 @ 10 mg/kg, PO | 64.6 | | 181.3 | | 8 |
| Compound 34 @ 10 mg/kg, PO | 34.9 | <0.01 | 154.6 | | 8 |
| Compound 155 @ 10 mg/kg, PO | 59.4 | <0.05 | 182.5 | | 8 |
| Compound 149 @ 30 mg/kg, PO | 41.9 | <0.01 | 153.0 | | 8 |
| Study F | | | | | |
| Compound 74 formulated as solution in 4% DMSO; 5% Tween-80; 20% Cremophor EL; 71% water | | | | | |
| Vehicle, PO: 4% DMSO; 5% Tween-80; 20% Cremophor EL; 71% water | 103.6 | | 186.9 | | 8 |
| Compound 74 @ 1 mg/kg, PO | 94.8 | | 169.0 | | 8 |
| Compound 74 @ 3 mg/kg, PO | 78.3 | | 172.9 | | 8 |
| Compound 74 @ 10 mg/kg, PO | 62.3 | <0.01 | 152.6 | | 8 |

TABLE 3-continued

| | Duration (0-2 Minutes) Average (Seconds) | p value | Duration (0-5 Minutes) Average (Seconds) | p value | n |
|---|---|---|---|---|---|
| Study G | | | | | |
| *Compound 97 formulated as solution in 4% DMSO; 5% Tween-80; 20% Cremophor EL; 71% water* | | | | | |
| Vehicle, PO: 4% DMSO; 5% Tween-80; 20% Cremophor EL; 71% water | 102.9 | | 213.7 | | 7 |
| Compound 97@ 1 mg/kg, PO | 69.3 | <0.05 | 162.4 | | 8 |
| Compound 97@ 3 mg/kg, PO | 78.5 | | 175.3 | | 8 |
| Compound 97@ 10 mg/kg, PO | 56.8 | <0.01 | 185.4 | | 8 |
| Study H | | | | | |
| *Compound 105 formulated as solution in 4% DMSO; 5% Tween-80; 20% Cremophor EL; 71% water* | | | | | |
| Vehicle, PO: 4% DMSO; 5% Tween-80; 20% Cremophor EL; 71% water | 98.5 | | 183.9 | | 8 |
| Compound 105@ 1 mg/kg, PO | 97.9 | | 162.6 | | 8 |
| Compound 105@ 3 mg/kg, PO | 86.0 | | 154.0 | | 8 |
| Compound 105@ 10 mg/kg, PO | 70.1 | <0.05 | 137.3 | <0.01 | 8 |
| Study I | | | | | |
| *Compound 160 formulated as solution in 4% DMSO; 5% Tween-80; 20% Cremophor EL; 71% water* | | | | | |
| Vehicle, PO: 4% DMSO; 5% Tween-80; 20% Cremophor EL; 71% water | 91.0 | | 192.1 | | 8 |
| Compound 160@ 1 mg/kg, PO | 68.6 | | 167.3 | | 8 |
| Compound 160@ 3 mg/kg, PO | 78.1 | | 232.0 | | 8 |
| Compound 160@ 10 mg/kg, PO | 42.5 | <0.01 | 150.4 | | 8 |
| Study J | | | | | |
| *Compound 135 formulated as solution in 4% DMSO; 5% Tween-80; 20% Cremophor EL; 71% water* | | | | | |
| Vehicle, PO: 4% DMSO; 5% Tween-80; 20% Cremophor EL; 71% water | 91.4 | | 184.9 | | 8 |
| Compound 135@ 1 mg/kg, PO | 91.1 | | 153.3 | | 7 |
| Compound 135@ 3 mg/kg, PO | 80.3 | | 120.3 | <0.01 | 7 |
| Compound 135@ 10 mg/kg, PO | 74.3 | | 139.0 | <0.05 | 7 |
| Study K | | | | | |
| *Compound 61 formulated as solution in 4% DMSO; 5% Tween-80; 20% Cremophor EL; 71% water* | | | | | |
| Vehicle, PO: 4% DMSO; 5% Tween-80; 20% Cremophor EL; 71% water | 86.9 | | 177.9 | | 8 |
| Compound 61@ 1 mg/kg, PO | 89.4 | | 149.3 | | 7 |
| Compound 61@ 3 mg/kg, PO | 90.3 | | 152.3 | | 8 |
| Compound 61@ 10 mg/kg, PO | 52.8 | <0.01 | 120.0 | <0.01 | 8 |
| Study L: 406 | | | | | |
| *Compound 79 formulated as suspension in 0.5% methylcellulose* | | | | | |
| Vehicle, PO: 0.5% methylcellulose | 95.1 | | 184.1 | | 8 |
| Compound 79: '180 1 mg/kg, PO | 86.1 | | 169.8 | | 8 |
| Compound 79: '180 3 mg/kg, PO | 86.5 | | 151.1 | | 8 |
| Compound 79: '180 10 mg/kg, PO | 77.3 | | 142.5 | <0.05 | 8 |
| Study M | | | | | |
| *Compound 104 formulated as solution in 4% DMSO; 5% Tween-80; 20% Cremophor EL; 71% water* | | | | | |
| Vehicle, PO: 4% DMSO; 5% Tween-80; 20% Cremophor EL; 71% water | 104.3 | | 176.9 | | 8 |
| Compound 104@ 1 mg/kg, PO | 98.5 | | 167.9 | | 8 |
| Compound 104@ 3 mg/kg, PO | 70.9 | <0.01 | 140.0 | | 7 |
| Compound 104@ 10 mg/kg, PO | 56.6 | <0.01 | 128.9 | <0.01 | 8 |

TABLE 3-continued

|  | Duration (0-2 Minutes) Average (Seconds) | p value | Duration (0-5 Minutes) Average (Seconds) | p value | n |
|---|---|---|---|---|---|
| Study N |  |  |  |  |  |
| Compound 172 formulated as solution in 4% DMSO; 5% Tween-80; 20% Cremophor EL; 71% water |  |  |  |  |  |
| Vehicle, PO: 4% DMSO; 5% Tween-80; 20% Cremophor EL; 71% water | 92.0 |  | 187.9 |  | 8 |
| Compound 172 @ 1 mg/kg, PO | 88.6 |  | 151.0 |  | 8 |
| Compound 172 @ 3 mg/kg, PO | 91.1 |  | 149.0 |  | 8 |
| Compound 172 @ 10 mg/kg, PO | 83.1 |  | 151.6 |  | 8 |
| Study O |  |  |  |  |  |
| Compound 61 formulated as solution in 4% DMSO; 5% Tween-80; 20% Cremophor EL; 71% water |  |  |  |  |  |
| Vehicle, PO: 4% DMSO; 5% Tween-80; 20% Cremophor EL; 71% water | 92.3 |  | 160.3 |  | 8 |
| Compound 253 @ 1 mg/kg, PO | 79.3 |  | 126.4 | <0.05 | 8 |
| Compound 253 @ 3 mg/kg, PO | 78.8 |  | 119.6 | <0.01 | 8 |
| Compound 253 @ 10 mg/kg, PO | 76.4 |  | 116.0 | <0.01 | 8 |
| Study P |  |  |  |  |  |
| Compounds formulated as solution in 8% DMSO and 92% Labrasol |  |  |  |  |  |
| Vehicle, PO: 8% DMSO and 92% Labrasol | 76.0 |  | 194.0 |  | 8 |
| Compound 153 @ 30 mg/kg, PO | 31.9 | <0.05 | 173.1 |  | 7 |
| Compound 14 @ 30 mg/kg, PO | 34.3 | <0.05 | 123.4 |  | 7 |
| Study Q |  |  |  |  |  |
| Compound 153 formulated as solution in 8% DMSO and 92% Labrasol |  |  |  |  |  |
| Vehicle, PO: 8% DMSO and 92% Labrasol | 100.3 |  | 231.1 |  | 8 |
| Compound 153 @ 1 mg/kg, PO | 84.5 |  | 172.5 |  | 8 |
| Compound 153 @ 3 mg/kg, PO | 86.4 |  | 198.8 |  | 8 |
| Compound 153 @ 10 mg/kg, PO | 87.9 |  | 214.6 |  | 8 |
| Study R |  |  |  |  |  |
| Compounds formulated as solution in 8% DMSO and 92% Labrasol |  |  |  |  |  |
| Vehicle, PO: 8% DMSO and 92% Labrasol | 98.6 |  | 227.9 |  | 9 |
| Compound 153 @ 30 mg/kg, PO | 52.8 | <0.01 | 173.4 |  | 8 |
| Compound 14 @ 30 mg/kg, PO | 39.6 | <0.01 | 160.6 | <0.05 | 8 |
| Study S |  |  |  |  |  |
| Compound 153 formulated as solution in 4% DMSO; 5% Tween-80; 25% Cremophor EL; 66% water |  |  |  |  |  |
| Vehicle, PO: 4% DMSO; 5% Tween-80; 25% Cremophor EL; 66% water | 83.5 |  | 199.9 |  | 8 |
| Compound 153 @ 1 mg/kg, PO | 71.4 |  | 164.6 |  | 8 |
| Compound 153 @ 3 mg/kg, PO | 81.5 |  | 216.9 |  | 8 |
| Compound 153 @ 10 mg/kg, PO | 50.1 |  | 160.3 |  | 8 |
| Study T |  |  |  |  |  |
| Compound 21 formulated as solution in 4% DMSO; 5% Tween-80; 20% Cremophor EL; 71% water |  |  |  |  |  |
| Vehicle, PO: 4% DMSO; 5% Tween-80; 20% Cremophor EL; 71% water | 97.8 |  | 196.9 |  | 8 |
| Compound 21 @ 1 mg/kg, PO | 99.6 |  | 206.9 |  | 8 |
| Compound 21 @ 3 mg/kg, PO | 97.5 |  | 186.9 |  | 8 |
| Compound 21 @ 10 mg/kg, PO | 71.8 | <0.05 | 116.5 | <0.01 | 8 |

TABLE 3-continued

| | Duration (0-2 Minutes) Average (Seconds) | p value | Duration (0-5 Minutes) Average (Seconds) | p value | n |
|---|---|---|---|---|---|
| Study U | | | | | |
| Compound 21 formulated as suspension in 0.5% methylcellulose | | | | | |
| Vehicle, PO: 0.5% methylcellulose | 88.3 | | 200.8 | | 8 |
| Compound 21 @ 1 mg/kg, PO | 80.5 | | 202.5 | | 8 |
| Compound 21 @ 3 mg/kg, PO | 86.5 | | 190.1 | | 8 |
| Compound 21 @ 10 mg/kg, PO | 78.0 | | 202.8 | | 8 |
| Study V | | | | | |
| Compound 21 formulated as suspension in 0.5% methylcellulose | | | | | |
| Vehicle, PO: 0.5% methylcellulose | 100.1 | | 192.3 | | 8 |
| Compound 21 @ 10 mg/kg, PO | 92.3 | | 163.1 | | 8 |
| Compound 21 @ 30 mg/kg, PO | 100.5 | | 165.4 | | 8 |

Example 3

Effect on Cold Hypersensitivity

Embodiments of the invention may be efficacious in the treatment of inflammatory pain. Compounds of the invention were tested by the CFA-induced pain test method. Compounds were formulated as solutions in water with various solvents and excipients including dimethyl sulfoxide (DMSO), polyethylene glycol (15)-hydroxystearate (Solutol®, Sigma-Aldrich), caprylocaproyl macrogol-8 glyceride (Labrasol®, Sigma-Aldrich), polysorbate-80 (Tween®-80, Sigma-Aldrich), and polyoxyl 35 castor oil (Cremophor® EL, BASF Corp.); or suspensions in methylcellulose as indicated in Table 3 for oral delivery.

Briefly, the hind paw was sensitized to cold temperature (allodynic) by administering 0.1 mL of Complete Freund's Adjuvant (CFA) to the right hind paw. Three days later, the time taken for the animal to lift its CFA-injected paw was recorded compared to its un-injected normal left hind paw. Animals were placed on the surface of the cold plate (1° C.) and the operator stopped testing at the instant when the animal displayed discomfort by flinching or lifting its paw from the plate (paw withdrawal latency, or PWL). To avoid tissue damage the maximum cut-off time was 5 minutes. Animals that were allodynic (average PWL to the first three pain behaviors <150 seconds for the CFA-injected hind paw: ~>50% difference between the normal and CFA-injected paw) were included in the study and subsequently randomized across treatment groups. The following day, the animals were dosed orally under blinded conditions. Following the 1-2 hour pre-treatment time, the post-dose PWL readings were again taken. The efficacy of the drug treatment was assessed by comparing the PWL in the drug treatment animals to those animals that receive the vehicle. P values, when indicated, indicate significance compared Vehicle. Results without p values did not achieve statistical significance.

Compounds of the invention were tested at the doses presented in Table 4 below.

TABLE 4

| | Average PWL Post-CFA | Average PWL Post-Treatment | PWL Change (s) | P Value | n |
|---|---|---|---|---|---|
| Study AA | | | | | |
| Compound 18 formulated as solution in 4% DMSO; 5% Tween-80; 20% Cremophor EL; and 71% water | | | | | |
| Vehicle, PO: 4% DMSO; 5% Tween-80; 20% Cremophor EL; and 71% water | 96.5 | 128.3 | 31.7 | | 10 |
| Compound 18 @ 1 mg/kg, PO | 97.1 | 246.8 | 149.7 | <0.01 | 11 |
| Compound 18 @ 3 mg/kg, PO | 97.0 | 233.5 | 136.4 | <0.01 | 11 |
| Compound 18 @ 10 mg/kg, PO | 97.0 | 256.1 | 159.1 | <0.01 | 11 |
| Study BB | | | | | |
| Compound 25 formulated as solution in 4% DMSO; 5% Tween-80; 20% Cremophor EL; and 71% water | | | | | |
| Vehicle, PO: 4% DMSO; 5% Tween-80; 20% Cremophor EL; and 71% water | 103.0 | 99.5 | −3.5 | | 10 |
| Compound 25 @ 0.3 mg/kg, PO | 105.0 | 170.2 | 65.2 | <0.05 | 10 |
| Compound 25 @ 1 mg/kg, PO | 105.1 | 224.8 | 119.7 | <0.01 | 10 |
| Compound 25 @ 3 mg/kg, PO | 105.1 | 259.9 | 154.9 | <0.01 | 10 |

TABLE 4-continued

| | Average PWL Post-CFA | Average PWL Post-Treatment | PWL Change (s) | P Value | n |
|---|---|---|---|---|---|
| Study CC | | | | | |
| Compound 34 formulated as solution in 4% DMSO; 5% Tween-80; 20% Cremophor EL; and 71% water | | | | | |
| Vehicle, PO: 4% DMSO; 5% Tween-80; 20% Cremophor EL; and 71% water | 103.9 | 105.3 | 1.4 | | 10 |
| Compound 34@ 0.3 mg/kg, PO | 104.9 | 185.6 | 80.7 | | 9 |
| Compound 34@ 1 mg/kg, PO | 98.0 | 205.4 | 107.4 | <0.05 | 10 |
| Compound 34@ 3 mg/kg, PO | 103.6 | 272.6 | 169.0 | <0.01 | 10 |
| Study DD | | | | | |
| Compound 74 formulated as solution in 4% DMSO; 5% Tween-80; 20% Cremophor EL; and 71% water | | | | | |
| Vehicle, PO: 4% DMSO; 5% Tween-80; 20% Cremophor EL; and 71% water | 90.1 | 89.2 | −0.9 | | 10 |
| Compound 74@ 0.3 mg/kg, PO | 91.1 | 160.9 | 69.9 | <0.05 | 10 |
| Compound 74@ 1 mg/kg, PO | 90.4 | 271.3 | 181.0 | <0.01 | 10 |
| Compound 74@ 3 mg/kg, PO | 90.9 | 273.2 | 182.3 | <0.01 | 10 |
| Study EE | | | | | |
| Compound 97 formulated as solution in 4% DMSO; 5% Tween-80; 20% Cremophor EL; and 71% water | | | | | |
| Vehicle, PO: 4% DMSO; 5% Tween-80; 20% Cremophor EL; and 71% water | 111.9 | 108.7 | −3.2 | | 9 |
| Compound 97@ 0.3 mg/kg, PO | 117.3 | 194.7 | 77.3 | <0.05 | 10 |
| Compound 97@ 1 mg/kg, PO | 112.9 | 262.7 | 149.8 | <0.01 | 10 |
| Compound 97@ 3 mg/kg, PO | 103.5 | 260.8 | 157.3 | <0.01 | 8 |
| Study FF | | | | | |
| Compound 105 formulated as solution in 4% DMSO; 5% Tween-80; 20% Cremophor EL; and 71% water | | | | | |
| Vehicle, PO: 4% DMSO; 5% Tween-80; 20% Cremophor EL; and 71% water | 102.3 | 126.1 | 23.8 | | 10 |
| Compound 105@ 0.3 mg/kg, PO | 102.4 | 137.3 | 34.9 | | 10 |
| Compound 105@ 1 mg/kg, PO | 102.3 | 215.2 | 112.8 | <0.01 | 10 |
| Compound 105@ 3 mg/kg, PO | 102.7 | 226.3 | 123.6 | <0.01 | 10 |
| Study GG | | | | | |
| Compound 160 formulated as solution in 4% DMSO; 5% Tween-80; 20% Cremophor EL; and 71% water | | | | | |
| Vehicle, PO: 4% DMSO; 5% Tween-80; 20% Cremophor EL; and 71% water | 107.6 | 105.5 | −2.1 | | 10 |
| Compound 160@ 0.3 mg/kg, PO | 108.2 | 173.0 | 64.7 | <0.05 | 10 |
| Compound 160@ 1 mg/kg, PO | 108.1 | 269.6 | 161.5 | <0.01 | 10 |
| Compound 160@ 3 mg/kg, PO | 107.5 | 253.6 | 146.2 | <0.01 | 10 |
| Study HH: | | | | | |
| Compound 61 formulated as solution in 4% DMSO; 5% Tween-80; 20% Cremophor EL; and 71% water | | | | | |
| Vehicle, PO: 4% DMSO; 5% Tween-80; 20% Cremophor EL; and 71% water | 96.0 | 99.2 | 3.3 | | 10 |
| Compound 61@ 0.3 mg/kg, PO | 96.2 | 157.1 | 60.9 | | 10 |
| Compound 61@ 1 mg/kg, PO | 96.0 | 235.4 | 139.4 | <0.01 | 10 |
| Compound 61@ 3 mg/kg, PO | 95.8 | 278.5 | 182.7 | <0.01 | 10 |
| Study II | | | | | |
| Compound 79 formulated as a suspension in 0.5% methylcellulose | | | | | |
| Vehicle, PO: 0.5% methylcellulose | 101.8 | 122.0 | 20.2 | | 10 |
| Compound 79@ 1 mg/kg, PO | 102.2 | 140.2 | 38.0 | | 10 |
| Compound 79@ 3 mg/kg, PO | 102.2 | 201.8 | 99.6 | <0.05 | 10 |
| Compound 79@ 10 mg/kg, PO | 102.3 | 231.5 | 129.3 | <0.01 | 10 |

TABLE 4-continued

| | Average PWL Post-CFA | Average PWL Post-Treatment | PWL Change (s) | P Value | n |
|---|---|---|---|---|---|
| Study JJ | | | | | |
| Compound 104 formulated as solution in 4% DMSO; 5% Tween-80; 20% Cremophor EL and 71% water | | | | | |
| Vehicle, PO: 4% DMSO; 5% Tween-80; 20% Cremophor EL; and 71% water | 104.1 | 108.6 | 4.5 | | 10 |
| Compound 104@ 0.3 mg/kg, PO | 105.1 | 190.0 | 84.9 | <0.01 | 10 |
| Compound 104@ 1 mg/kg, PO | 104.2 | 295.1 | 190.9 | <0.01 | 10 |
| Compound 104@ 3 mg/kg, PO | 104.9 | 281.7 | 176.8 | <0.01 | 10 |
| Study KK | | | | | |
| Compound 14 formulated as solution in 4% DMSO; 5% Tween-80; 25% Cremophor EL; and 66% water | | | | | |
| Vehicle, PO: 4% DMSO; 5% Tween-80; 25% Cremophor EL; and 66% water | 90.8 | 109.7 | 19.2 | | 10 |
| Compound 14@ 1 mg/kg, PO | 90.3 | 194.8 | 104.2 | <0.01 | 10 |
| Compound 14@ 3 mg/kg, PO | 92.3 | 180.0 | 87.6 | <0.01 | 10 |
| Compound 14@ 10 mg/kg, PO | 90.9 | 237.4 | 146.3 | <0.01 | 10 |
| Study LL | | | | | |
| Compound 153 formulated as solution in 4% DMSO; 5% Tween-80; 25% Cremophor EL; and 66% water | | | | | |
| Vehicle, PO: 4% DMSO; 5% Tween-80; 25% Cremophor EL; and 66% water | 92.6 | 101.7 | 9.1 | | 9 |
| Compound 153@ 1 mg/kg, PO | 92.5 | 178.1 | 85.6 | <0.01 | 10 |
| Compound 153@ 3 mg/kg, PO | 92.8 | 223.6 | 130.8 | <0.01 | 10 |
| Compound 153@ 10 mg/kg, PO | 92.7 | 247.1 | 154.3 | <0.01 | 10 |
| Study MM | | | | | |
| Compound 21 formulated as solution in 4% DMSO; 5% Tween-80; 20% Cremophor EL; and 71% water | | | | | |
| Vehicle, PO: 4% DMSO; 5% Tween-80; 20% Cremophor EL; and 71% water | 110.4 | 96.5 | −13.9 | | 10 |
| Compound 21@ 0.3 mg/kg, PO | 109.6 | 159.2 | 49.6 | | 10 |
| Compound 21@ 1 mg/kg, PO | 114.3 | 208.5 | 94.2 | <0.01 | 10 |
| Compound 21@ 3 mg/kg, PO | 110.1 | 258.9 | 148.8 | <0.01 | 10 |
| Study NN | | | | | |
| Compound 21 formulated as a suspension in 0.5% methylcellulose | | | | | |
| Vehicle, PO: 0.5% methylcellulose | 95.3 | 93.5 | −1.7 | | 11 |
| Compound 21@ 0.3 mg/kg, PO | 94.5 | 106.4 | 11.9 | | 11 |
| Compound 21@ 1 mg/kg, PO | 95.4 | 155.2 | 59.8 | <0.01 | 10 |
| Compound 21@ 3 mg/kg, PO | 94.3 | 236.7 | 142.4 | <0.01 | 10 |

In summary, these studies suggest that compounds of the invention have the potential to be efficacious in the treatment of inflammatory pain following oral administration.

Example 4

General Experimental Procedures

General Procedures

All reactions were run under an inert atmosphere, generally nitrogen. All non-aqueous reactions were run using solvents. All reactions were stirred either with a magnetic stir bar or with overhead mechanical stirring. All saturated extraction solutions are assumed to be aqueous (saturated NH$_4$Cl for example). Drying organic solutions with a drying agent implies that the drying agent was removed from the organic solution by filtration. Chromatography refers to column chromatography on silica gel. Preparative thin layer chromatography (TLC) was run plates. Concentration of reaction mixtures implies concentration under reduced pressure and the use of a rotary evaporation instrument. Drying of final products implies drying under high vacuum conditions. Sonication implies the use of an ultrasonic bath. All $^1$H-NMR data were obtained at 400 MHz. Mass spectra were obtained in positive ion mode and are reported as the protonated species MH$^+$. LCMS were performed on a SHIMADZU LCMS-2010EV instrument (Chromolith SdeedROP, RP-18e column. 50×4.6 mm. mobile phase: Solvent A: CH$_3$CN/H$_2$O/HCOOH=10/90/0.05. Solvent B: CH$_3$CN/H$_2$O/HCOOH=90/10/0.05. 0.8 min@10% B. 2.7 min gradient (10-95% B), then 0.8 min@95% B. Flow rate: 3 mL/min. temperature: 40° C.). Preparative HPLC was performed either on a SHIMADZU LC-8A instrument. (Column: YMC Pack ODS-A (150*30 mm 10 um)) or LC-6AD (column: Shim=Pack PREP-ODS-H (250*20mm, 10 um)) with UV detection which was controlled by LC solution Chemstation software, with H₂O (0.1% HCOOH) and MeOH (CH₃CN) as mobile phase at the indicated flow rate. Chiral HPLC was performed using a CHIRALPAK IB column (150*4.6 mm, 5 um) with the mobile phase comprised of hexanes/EtOH (65/35, 0.8 mL/min, 25 minute run time) at 30° C., using a 15 uL sample injection volume (1 mg/mL in MeOH) and UV detector set at 220/254 nm.

Abbreviations
DCM dichloromethane
DIC N,N'-diisopropylcarbodiimide
DMAP 4-dimethylaminopyridine
DMF N,N-dimethylformamide
EDC 1-ethyl-3-(3-dimethylaminopropyl)carbodiimide
EA ethyl acetate
Ether diethyl ether
h hours
HOAc acetic acid
HOAT 1-hydroxy-7-azabenzotriazole
LAH lithium aluminum hydride
MeOH methanol
min minutes
n-BuLi "butyllithium
Pd/C palladium on activated carbon, generally 10% palladium load
PE petroleum ether
RT room temperature
S. aq. Saturated aqueous
TBAI tetrabutylammonium iodide
TEA triethylamine
TFA trifluoroacetic acid
TLC thin layer chromatography
THF tetrahydrofuran
Preparations Preparation 1 (S)-methyl 2-(3-methyl-2,6-dioxo-2,3-dihydro-1H-purin-7(6H)-yl)propanoate

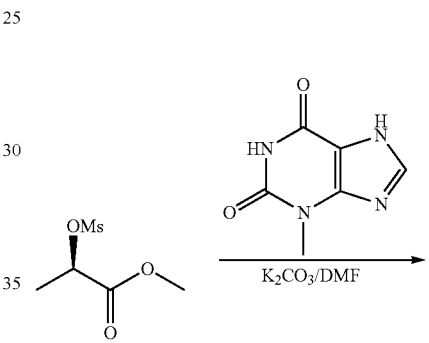

Step 1 (R)-methyl 2-(methylsulfonyloxy)propanoate

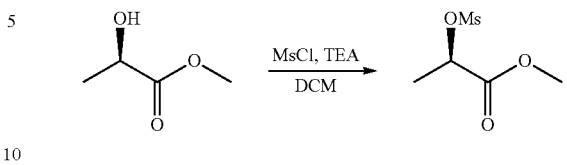

A solution of (R)-methyl 2-hydroxypropanoate (30 g, 0.28 mol) and TEA (80 mL, 0.56 mol) in DCM (300 mL) was chilled to 0° C. and methanesulfonyl chloride (33.6 mL, 0.42 mol) was added dropwise at 0° C. over 1 h. The mixture was stirred at 10-20° C. for 1.5 h. The reaction mixture was quenched with ice-water (100 mL). The organic layer was separated, washed with water (2×50 mL) and brine, dried over Na₂SO₄ and concentrated to afford the crude product (R)-methyl 2-(methylsulfonyloxy)propanoate (50 g, 95.2%) as brick red oil which was used without purification.

Step 2 (S)-methyl 2-(3-methyl-2,6-dioxo-2,3-dihydro-1H-purin-7(6H)-yl)propanoate

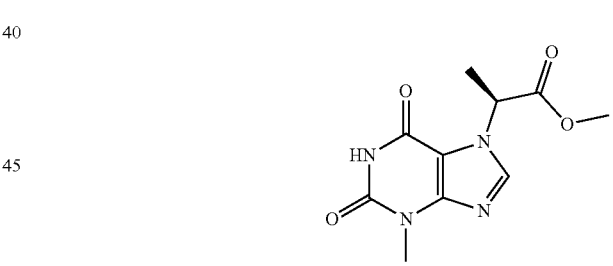

To a mixture of 3-methyl-xanthine (5.858 g, 35.3 mmol) and (R)-methyl 2-(methylsulfonyloxy)propanoate (6.417 g, 35.3 mmol) in DMF (100 mL) was added potassium carbonate (7.298 g, 53 mmol). The reaction mixture was stirred at 50° C. for 20 h. The reaction mixture was poured into water (10 mL) and extracted with EA (2×10 mL). LCMS showed product in the aqueous phase, so the aqueous phase was acidified to pH 0 and extracted with DCM. Combined organic layers were dried over Na₂SO₄ and concentrated. The residue was purified by chromatography (eluted with MeOH/DCM 0-3%) to afford (S)-methyl 2-(3-methyl-2,6-dioxo-2,3-dihydro-1H-purin-7(6H)-yl)propanoate (4.5843 g, 52% yield) as a white solid. MH⁺253.

Preparation 2 (S)-2-(2-(2-(trifluoromethyl)pyrrolidin-1-yl)pyrimidin-5-yl)pyrimidin-4-amine

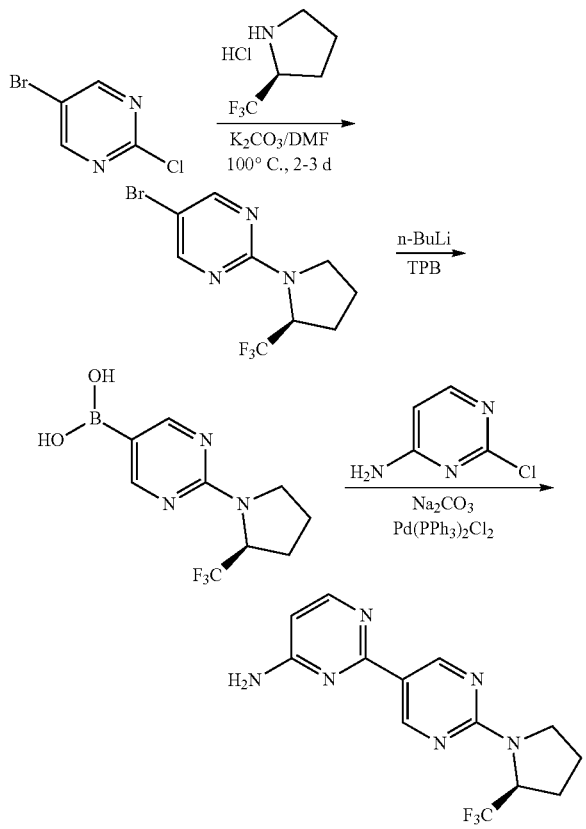

Step 1 (S)-5-bromo-2-(2-(trifluoromethyl)pyrrolidin-1-yl)pyrimidine

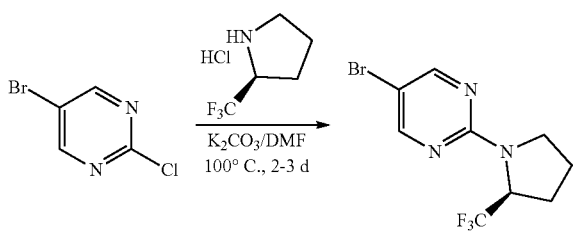 [SMILES: Clc1ncc(Br)cn1 ; Cl ; FC(F)(F)[C@@H]1CCCN1 ; FC(F)(F)[C@@H]1CCCN1c1ncc(Br)cn1]

A mixture of (S)-2-(trifluoromethyl)pyrrolidine hydrochloride (40 g, 0.23 mol), POTASSIUM CARBONATE (94.6 g, 0.68 mol) and 5-bromo-2-chloropyrimidine (48 g, 0.25 mol) in DMF (200 mL) was stirred at 100° C. for 24 hr, then $N_1,N_2$-dimethylethane-1,2-diamine (4 mL) was added and the reaction was stirred for another 2 h to consume unreacted 5-bromo-2-chloropyrimidine. The reaction was quenched with water (400 mL), and extracted with EA (3×500 mL). The combined organic phase was washed with 10% aqueous LiCl, dried over $Na_2SO_4$ and concentrated. The residue was purified by chromatography eluting with PE:EA (50:1) to afford (S)-5-bromo-2-(2-(trifluoromethyl) pyrrolidin-1-yl) pyrimidine (50 g, 74%) as a white solid. $^1$H NMR (DMSO-$d_6$) δ 8.54 (s, 2H), 4.90-4.94 (m, 2H), 3.56-3.58 (m, 2H), 2.02-2.16 (m, 4H). MH$^+$296.

Step 2 (S)-2-(2-(trifluoromethyl)pyrrolidin-1-yl)pyrimidin-5-ylboronic acid

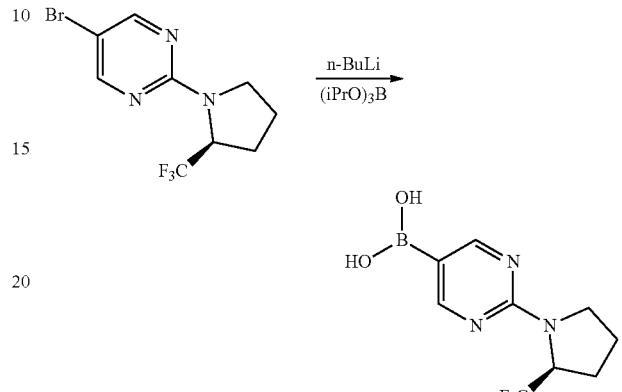

A solution of (S)-5-bromo-2-(2-(trifluoromethyl)pyrrolidin-1-yl)pyrimidine (50 g, 0.17 mol) and triisopropyl borate (44.4 g, 0.23 mol) in THF (400 mL) was cooled to −78° C. and n-BuLi (105 mL, 2.4 M in hexane) was added dropwise. The reaction was stirred 2 h at −78° C. The reaction was quenched with water (150 mL) and allowed to warm to RT. The reaction was concentrated to leave the aqueous phase. The aqueous phase was extracted with ether (2×50 mL) to remove impurities (product in aqueous layer). The pH was adjusted to 5 with 6 N HCl and then it was extracted with EA (3×100 mL). The combined organic phase was dried over $Na_2SO_4$ and concentrated to afford (S)-2-(2-(trifluoromethyl)pyrrolidin-1-yl) pyrimidin-5-ylboronic acid (45 g, quantitative yield) as an off-white solid. MH$^+$262.

Step 3 (S)-2-(2-(2-(trifluoromethyl)pyrrolidin-1-yl)pyrimidin-5-yl)pyrimidin-4-amine

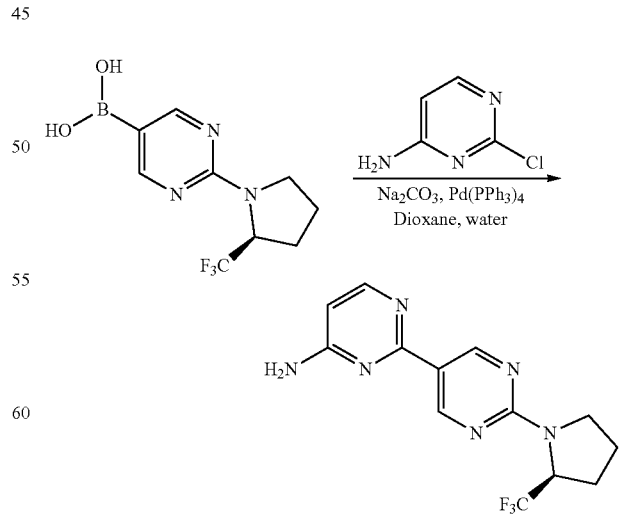

To a mixture of (S)-2-(2-(trifluoromethyl)pyrrolidin-1-yl)pyrimidin-5-ylboronic acid (9.5 g, 36.4 mmol), 2-chloropyrimidin-4-amine (4.3 g, 33.1 mmol) and Na$_2$CO$_3$ (7.0 g, 66.2 mmol) in dioxane (105 mL) and water (35 mL) was added Pd(PPh$_3$)$_4$ (3.8 mg, 3.31 mmol). The mixture was degassed with nitrogen and then stirred at 110° C. for 3 h. The reaction was cooled and filtered through Celite. The filtrate was partitioned with EA (300 mL) and water (150 mL). The organic phase was washed with brine (100 mL), dried over Na$_2$SO$_4$ and concentrated. The residue was purified by chromatography eluting with DCM/MeOH (100:1 to 80:1 to 70:1) to give (S)-2-(2-(2-(trifluoromethyl)pyrrolidin-1-yl)pyrimidin-5-yl)pyrimidin-4-amine (8 g, 78%) as a white solid. $^1$H-NMR (CDCl$_3$) δ 9.16 (s, 2H), 8.13-8.14 (d, J=10 Hz, 1H), 6.97 (s, 2H), 6.34-6.35 (d, J=6 Hz, 1H), 5.09-5.13 (m, 1H), 3.67-3.72 (m, 2H), 2.06-2.21 (m, 4H). MH$^+$311.

Preparation 3 (R)-2-(2-(2-(trifluoromethyl)pyrrolidin-1-yl)pyrimidin-5-yl)pyrimidin-4-amine

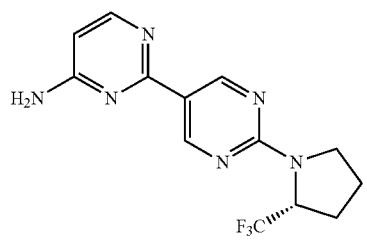 [SMILES: Nc1ccnc(-c2cnc(N3CCC[C@@H]3C(F)(F)F)nc2)n1]

The title compound was prepared using the method of preparation 2. MH$^+$311

Preparation 4 3-azabicyclo[3.1.0]hexane hydrochloride

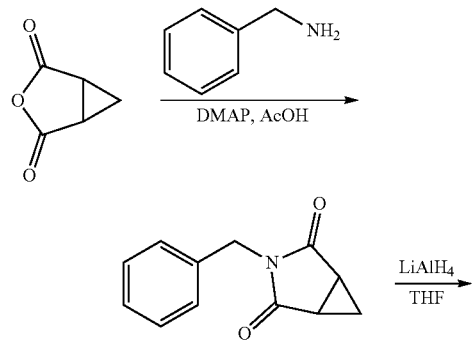

Step 1 3-benzyl-3-azabicyclo[3.1.0]hexane-2,4-dione

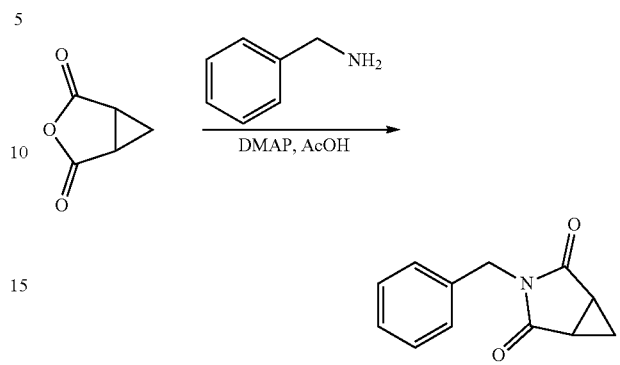

To a mixture of 3-oxabicyclo[3.1.0]hexane-2,4-dione (2.3 g, 20.5 mmol) in AcOH (30 mL) was added DMAP (150 mg) and benzylamine (2.2 mL, 20.5 mmol). The mixture was stirred at 100° C. for 40 h; then it was cooled to RT. The reaction was concentrated and the residue was dissolved in EA. The organic phase was washed with water and brine, dried over Na$_2$SO$_4$ and concentrated. The residue was purified via chromatography eluting with PE:EA (8:1 to 5:1) to afford 3-benzyl-3-azabicyclo[3.1.0]hexane-2,4-dione (3.7 g, 89.6%) as a white solid. MH$^+$202.

Step 2 3-benzyl-3-azabicyclo[3.1.0]hexane

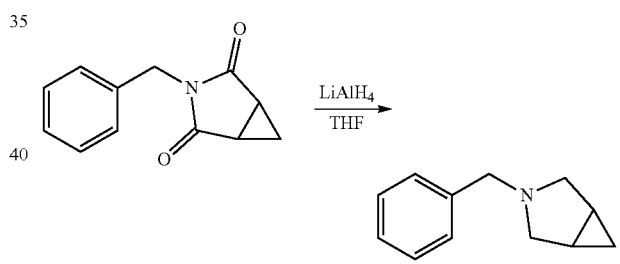

To a solution of 3-benzyl-3-azabicyclo[3.1.0]hexane-2,4-dione (2.0 g, 10.0 mmol) in THF (30 mL) was added LAH (1.5 g, 40.0 mmol). The reaction mixture was heated at reflux 4 h and then it was cooled to 0° C. The cold reaction mixture was carefully quenched with saturated NH$_4$Cl and then it was filtered. The filtrate was concentrated to afford the title compound (1.5 g, 86.7%) as clear oil. MH$^+$174.

Step 3 3-azabicyclo[3.1.0]hexane hydrochloride

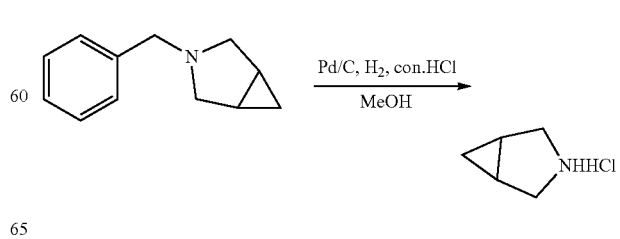

A mixture of 3-benzyl-3-azabicyclo[3.1.0]hexane (1.3 g, 7.5 mmol), 10% Pd/C (130 mg) and conc. HCl (0.63 mL, 7.5 mmol) in MeOH (20 mL) was stirred at RT under an of hydrogen (balloon) for 18 h. The reaction was filtered through Celite and the filtrate was concentrated to give the title compound (850 mg, 95%) as a white solid. MH+84

Preparation 5 2'-(3-azabicyclo[3.1.0]hexan-3-yl)-[2,5'-bipyrimidin]-4-amine

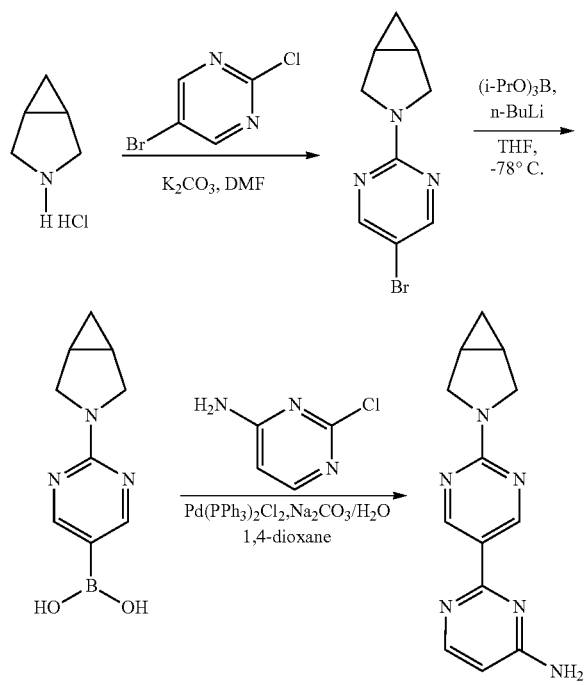

Step 1 3-(5-bromopyrimidin-2-yl)-3-azabicyclo[3.1.0]hexane

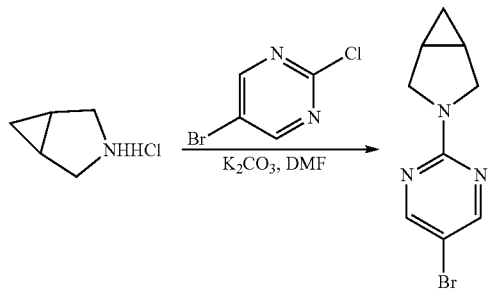

A sealed tube was charged with 5-bromo-2-chloropyrimidine (671.7 mg, 3.5 mmol), 3-azabicyclo[3.1.0]hexane hydrochloride (416.7 mg, 3.5 mmol), potassium carbonate (967.5 mg, 7.0 mmol) and DMF (4 mL). The tube was sealed and stirred at 130° C. for 2 h. The reaction was cooled to RT and poured into cold water (4 mL). The solid that formed was collected and dried to give 3-(5-bromopyrimidin-2-yl)-3-azabicyclo[3.1.0]hexane (480 mg, 57.4%) as a white solid. MH+240.

Step 2 (2-(3-azabicyclo[3.1.0]hexan-3-yl)pyrimidin-5-yl)boronic acid

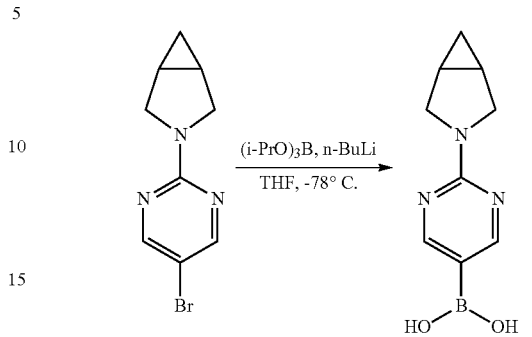

To a solution of 3-(5-bromopyrimidin-2-yl)-3-azabicyclo[3.1.0]hexane (480 mg, 2.0 mmol) and triisopropyl borate (0.7 mL, 3.0 mmol) in THF (6 mL) was added n-BuLi (1.1 mL, 2.4 M in hexane, 2.6 mmol) dropwise at −78° C. The reaction was stirred at −78° C. for 2 h and then it was quenched with water and warmed to RT. The reaction was concentrated and the aqueous residue was extracted with ether (2×20 mL). The aqueous layer was separated, adjusted to pH 6 with 1N HCl and extracted with EA (3×20 mL). The combined organic phase was washed with brine, dried over $Na_2SO_4$, and concentrated to give the title product (200 mg, 48.5%) as a white solid. MH+206.

Step 3 2'-(3-azabicyclo[3.1.0]hexan-3-yl)-[2,5'-bipyrimidin]-4-amine

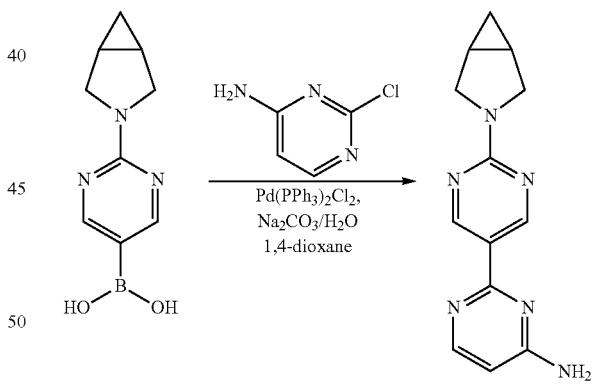

A mixture of (2-(3-azabicyclo[3.1.0]hexan-3-yl)pyrimidin-5-yl)boronic acid (150.0 mg, 1.2 mmol), 2-chloropyrimidin-4-amine (237.9 mg, 1.2 mmol), Pd(PPh$_3$)$_2$Cl$_2$ (86.0 mg, 0.1 mmol) and Na$_2$CO$_3$ (245.9 mg, 2.3 mmol) in 1,4-dioxane (5 mL) and water (1 mL) was degassed with nitrogen and stirred at 80° C. overnight. The reaction was cooled to RT and poured into EA. The organic phase was separated, washed with water and brine, dried over Na$_2$SO$_4$ and concentrated. The residue was dissolved in ether. An insoluble residue was removed by filtration and the filtrate was concentrated to give 2'-(3-azabicyclo[3.1.0]hexan-3-yl)[2,5'-bipyrimidin]-4-amine (100 mg, 33.8%) as a white solid. MH+255.

Preparation 6 3-methyl-1-((5-methylisoxazol-3-yl)methyl)-1H-purine-2,6(3H,7H)-dione

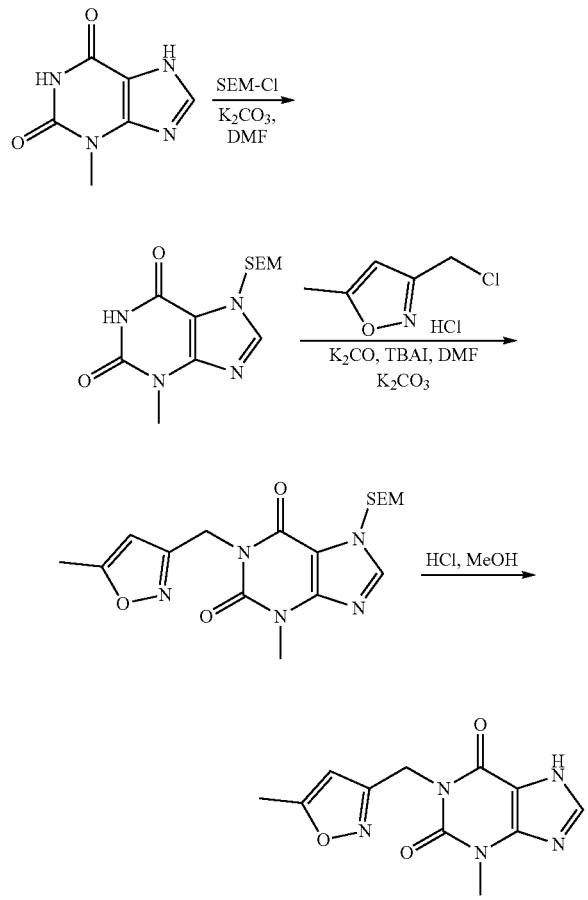

Step 1 3-methyl-7-((2-(trimethylsilyl)ethoxy)methyl)-1H- purine-2,6(3H,7H)-dione

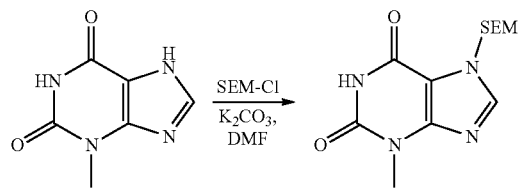 [SMILES: Cn1c(=O)[nH]c(=O)c2[nH]cnc21 ; "SEM-Cl" ; Cn1c(=O)[nH]c(=O)c2c1ncn2COCC[Si](C)(C)C]

To a stirred solution of 3-methyl-1H-purine-2,6(3H,7H)-dione (5 g, 30.10 mmol) and potassium carbonate (6.24 g, 45.14 mmol) in DMF (50 mL) at 0° C. was added (2-(chloromethoxy)ethyl)trimethylsilane (5.33 mL, 30.1 mml). After the addition, the mixture was warmed to RT and stirred overnight. The reaction mixture was diluted with DCM, and washed with s. aq. LiCl. The organic layer was separated, dried over Na2SO4, and concentrated to afford 3-methyl-7-((2-(trimethylsilyl)ethoxy)methyl)-1H-purine-2,6(3H,7H)-dione (3.78 g, 42.4% yield) as yellow solid. Retention time (LC-MS): 1.160 min. MH$^+$297.

Step 2 3-methyl-1-((5-methylisoxazol-3-yl)methyl)-7-((2-(trimethylsilyl) ethoxy)methyl)-1H-purine-2,6 (3H,7H)-dione

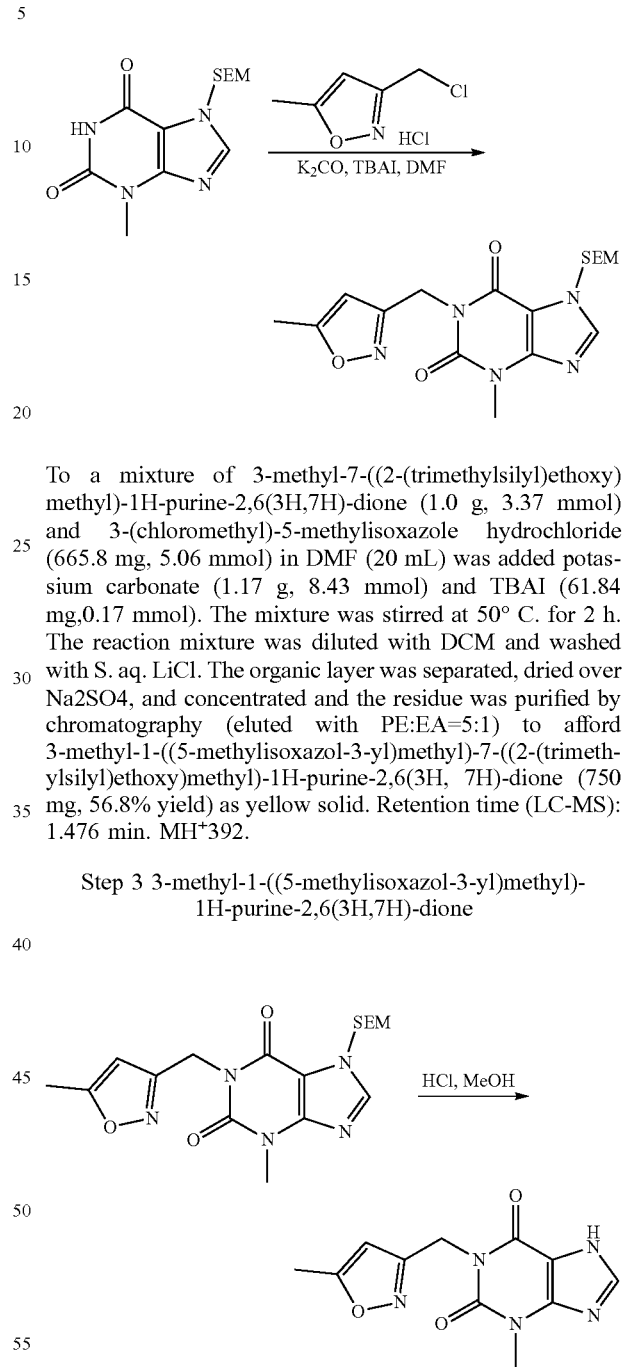

To a mixture of 3-methyl-7-((2-(trimethylsilyl)ethoxy)methyl)-1H-purine-2,6(3H,7H)-dione (1.0 g, 3.37 mmol) and 3-(chloromethyl)-5-methylisoxazole hydrochloride (665.8 mg, 5.06 mmol) in DMF (20 mL) was added potassium carbonate (1.17 g, 8.43 mmol) and TBAI (61.84 mg, 0.17 mmol). The mixture was stirred at 50° C. for 2 h. The reaction mixture was diluted with DCM and washed with S. aq. LiCl. The organic layer was separated, dried over Na2SO4, and concentrated and the residue was purified by chromatography (eluted with PE:EA=5:1) to afford 3-methyl-1-((5-methylisoxazol-3-yl)methyl)-7-((2-(trimethylsilyl)ethoxy)methyl)-1H-purine-2,6(3H, 7H)-dione (750 mg, 56.8% yield) as yellow solid. Retention time (LC-MS): 1.476 min. MH$^+$392.

Step 3 3-methyl-1-((5-methylisoxazol-3-yl)methyl)-1H-purine-2,6(3H,7H)-dione

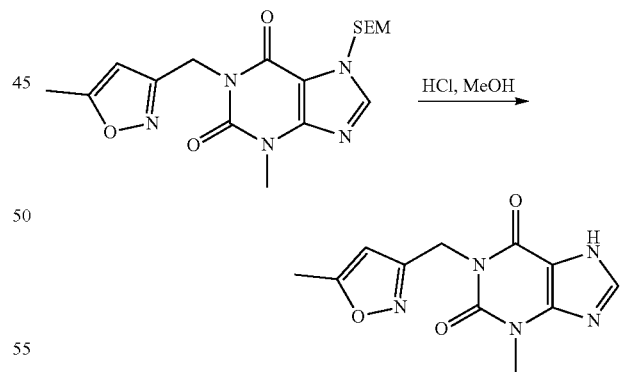

To a stirred solution of 3-methyl-1-((5-methylisoxazol-3-yl)methyl)- 7-((2-(trimethylsilypethoxy)methyl)-1H-purine-2, 6(3H,7H)-dione (750 mg, 1.92 mmol) in EtOH (5 mL) was added conc. HCl (1 mL). After the addition, the mixture was heated to reflux for 2 h and then cooled to RT. The mixture was concentrated to dryness to give a crude product of 3-methyl-1-((5-methylisoxazol-3-yl)methyl)-1H-purine-2,6 (3H,7H)-dione (415 mg, 82.9% yield) as yellow solid which was used in the next step without any further purification. Retention time (LC-MS): 0.544 min. MH$^+$262.

Preparation 7 (S)-methyl 2-(3-methyl-2,6-dioxo-1-(pyridin-2-ylmethyl)-1,2,3,6-tetra-hydropurin-7-yl)propanoate

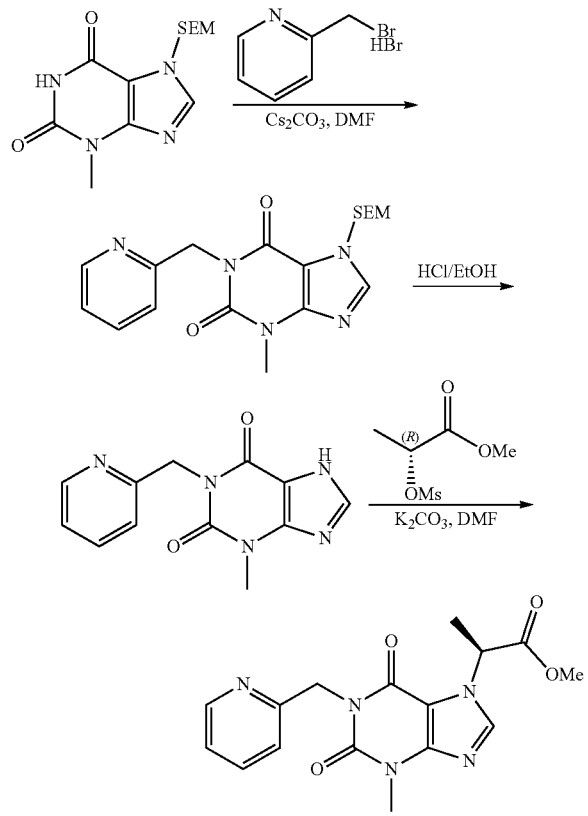

Step 1 3-methyl-1-(pyridin-2-ylmethyl)-7-((2-(trimethylsilyl)ethoxy)methyl)-1H-purine-2,6(3H,7H)-dione

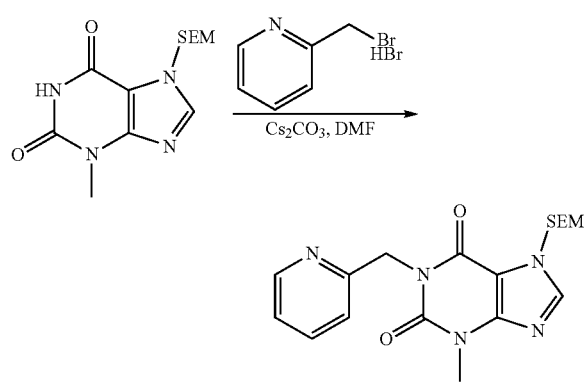

To a solution of 3-methyl-7-((2-(trimethylsilyl)ethoxy)methyl)-1H-purine-2,6(3H,7H)-dione (500 mg, 1.69 mmol) in DMF (10 mL) were added cesium carbonate (1.1 g, 3.37 mmol), 2-(bromomethyl)pyridine (509 mg, 2.02 mmol) and tetrabutyl ammonium iodide (62 mg, 0.17 mmol). After the addition, the mixture was stirred at 100° C. for 2 h and cooled to RT. The mixture was diluted with EA and washed with S. aq. LiCl. The organic layer was separated, dried over Na2SO4, and concentrated and the residue was purified by chromatography to afford 3-methyl-1-(pyridin-2-ylmethyl)-7-((2-(trimethylsilyl)ethoxy)methyl)-1H- purine-2,6(3H, 7H)-dione (370 mg, 56.4% yield) as a white solid. Retention time (LC-MS): 1.373 min. MH⁺388

Step 2 3-methyl-1-(pyridin-2-ylmethyl)-1H-purine-2,6(3H,7H)-dione

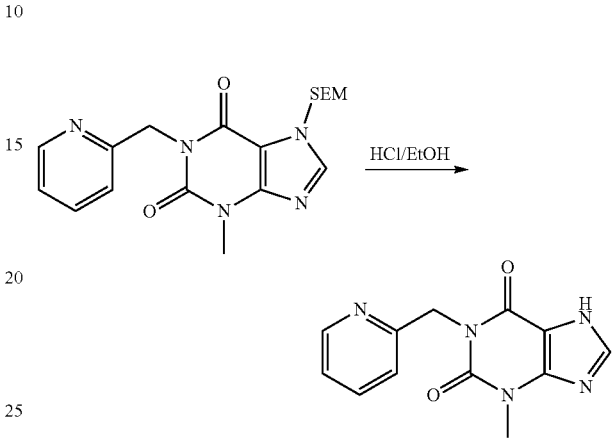

To a stirred solution of 3-methyl-1-(pyridin-2-ylmethyl)-7-((2-(trimethylsilyl)ethoxy)methyl)-1H-purine-2,6(3H,7H)-dione (370 mg, 0.95 mmol) in EtOH (8 mL) was added conc. HCl (4 mL). After the addition, the mixture was heated to reflux for 2 h and cooled to RT. The solvent was removed under vacuum, then the residue was adjusted pH to 7 with aqueous Na₂CO₃ and filtered. The filter cake dried under vacuum to afford 3-methyl-1-(pyridin-2-ylmethyl)-1H-purine-2,6 (3H,7H)-dione (170 mg, 69.1% yield) as an off-white solid. Retention time (LC-MS): 0.452 min. MH⁺258

Step 3 (S)-methyl 2-(3-methyl-2,6-dioxo-1-(pyridin-2-ylmethyl)-1,2,3,6-tetra-hydropurin-7-yl)propanoate

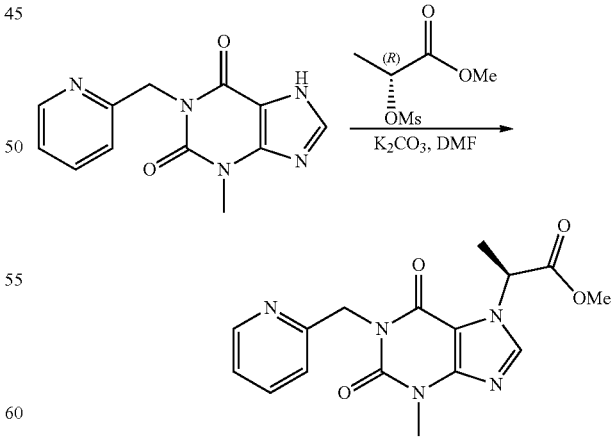

To a mixture of 3-methyl-1-(pyridin-2-ylmethyl)-1H-purine-2,6(3H,7H)-dione (100 mg, 0.39 mmol) and potassium carbonate (53 mg, 0.39 mmol) in DMF (2 mL) was added (R)-methyl 2-(methylsulfonyloxy)propanoate (142 mg, 0.78 mmol). After the addition, the mixture was stirred at RT for 3 h. The mixture was cooled to 0° C., diluted with water (4 mL) and extracted with EA (3×2 mL). The combined organic layers were dried over Na$_2$SO$_4$ and filtered. The filtrate was concentrated under reduced pressure and the residue was purified by chromatography (eluted with DCM/MeOH=40/1) to afford (S)-methyl 2-(3-methyl-2,6-dioxo-1-(pyridin-2-ylmethyl)-1,2,3,6-tetrahydropurin-7-yl)propanoate (50 mg, 37.5% yield) as a white solid. Retention time (LC-MS): 0.348 min. MH$^+$344

Preparation 8 6'-(trifluoromethyl)-[2,3'-bipyridin]-6-amine

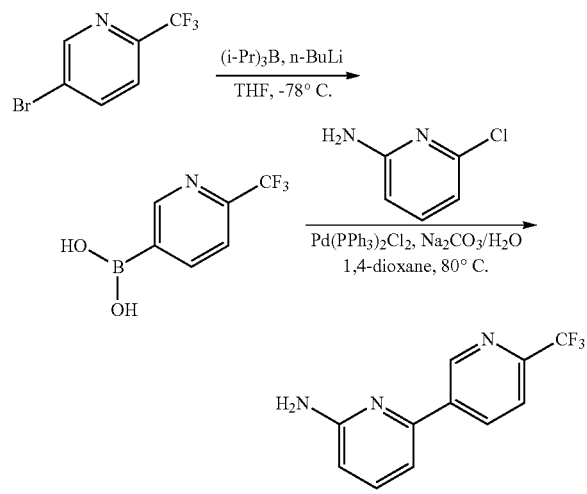

Step 1 (2-(3-azabicyclo[3.1.0]hexan-3-yl)pyrimidin-5-yl)boronic

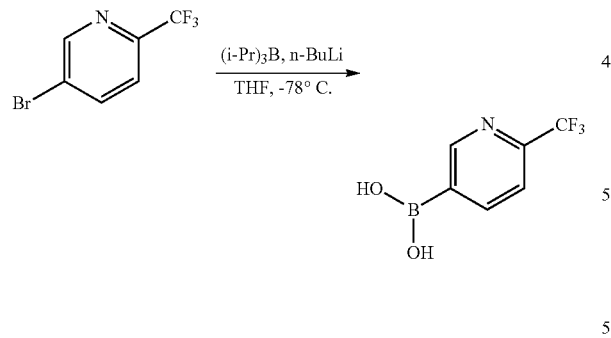

To a solution of 5-bromo-2-(trifluoromethyl)pyridine (1.6 g, 7.2 mmol) and ($^i$PrO)$_3$B (2.5 mL, 10.8 mmol) in THF (6 mL) was added dropwise n-BuLi (4.5 mL, 2.4 M in hexane, 10.8 mmol) at −78° C. The reaction mixture was stirred at the same temperature for 2 h and quenched with water. The solvent was removed under reduced pressure and the residue was extracted with Ether (2×60 mL). The aqueous layer was separated, adjusted to pH 6 with 1N HCl and extracted with EA (3×60 mL). Combined organic layers were washed with brine, dried over Na$_2$SO$_4$, and concentrated to give the title product (1.3 g, 95.7% yield) as a white solid.

Step 2 6'-(trifluoromethyl)-[2,3'-bipyridin]-6-amine

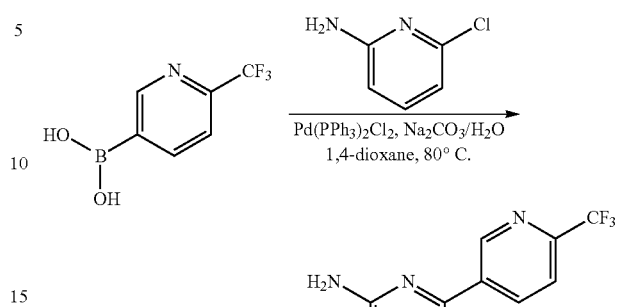

A mixture of (6-(trifluoromethyl)pyridin-3-yl)boronic acid (382.1 mg, 2.0 mmol), 6-chloropyridin-2-amine (343.9 mg, 2.0 mmol), Pd(PPh$_3$)$_2$Cl$_2$ (140.4 mg, 0.2 mmol) and Na$_2$CO$_3$ (424.0 mg, 4.0 mmol) in 1,4-dioxane (10 mL) and H$_2$O (2 mL) was degassed and stirred at 80° C. under N$_2$ overnight. The reaction mixture was cooled down and poured into EA. The organic phase was separated, washed with water and brine, dried over Na$_2$SO$_4$ and filtered. The filtrate was concentrated under reduced pressure and the residue was triturated with Ether. The mixture was filtered and the filtrate was concentrated to give the title compound (190 mg, 39.7% yield) as a white solid. Retention time (LC-MS): 0.42 min. MH$^+$255.

Preparation 9 6-(2-(trifluoromethyl)pyrimidin-5-yl)pyrazin-2-amine

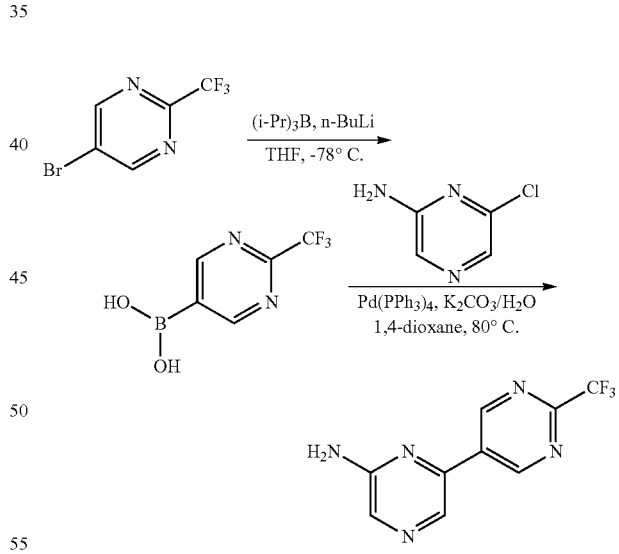

Step 1 (2-(trifluoromethyl)pyrimidin-5-yl)boronic acid

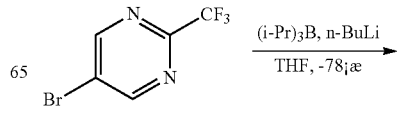

-continued

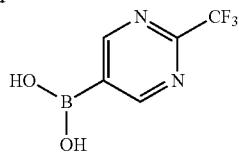

To a solution of 5-bromo-2-(trifluoromethyl)pyrimidine (700.6 mg, 3.1 mmol) and(ⁱPrO)₃B (1.1 mL, 4.7 mmol) in THF (10 mL) was added dropwise n-BuLi (1.7 mL , 2.4M in hexane, 4.0 mmol) at −78° C. The mixture was stirred at the same temperature for 2 h and quenched with water. The solvent was removed under reduced pressure and the residue was extracted with Ether (2×40 mL). The aqueous layer was separated, then adjusted to pH 6 with 1N HCl and extracted with EA (3×40 mL). Combined organic layers were washed with brine, dried over Na2SO4, and concentrated to give the title product (400 mg, 67.2% yield) as a white solid. Retention time (LC-MS): 0.66 min. MH⁺193

Step 2 6-(2-(trifluoromethyl)pyrimidin-5-yl)pyrazin-2-amine

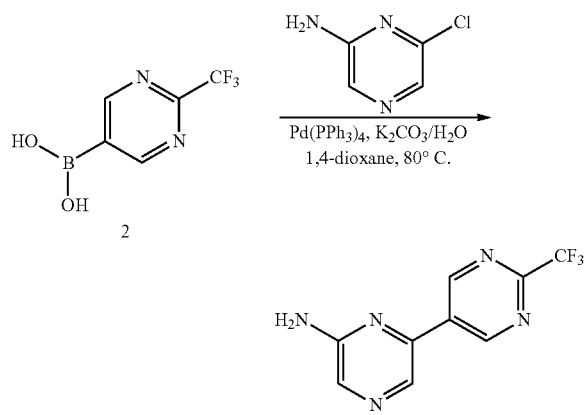

A mixture of (2-(trifluoromethyl)pyrimidin-5-yl)boronic acid (420.0 mg, 2.2 mmol), 6-chloropyrazin-2-amine (378.3 mg, 2.2 mmol), Pd(PPh₃)₄ (252.7 mg, 0.2 mmol) and potassium carbonate (604.6 mg, 4.4 mmol) in 1,4-dioxane (5 mL) and H₂O (1 mL) was degassed and stirred at 90° C. under N₂ overnight. The reaction mixture was cooled down and poured into EA. The organic phase was separated, washed with water and brine, dried over Na₂SO₄ and filtered. The filtrate was concentrated under reduced pressure and the residue was dissolved in Ether. The mixture was filtered and the filtrate was concentrated to give the title product (200 mg, 52.6% yield) as a white solid.

Preparation 10 (S)-2-(3-methyl-2,6-dioxo-1-(2-oxo-propyl)-2,3-dihydro-1H-purin-7(6H)- yl)propanoic acid -continued

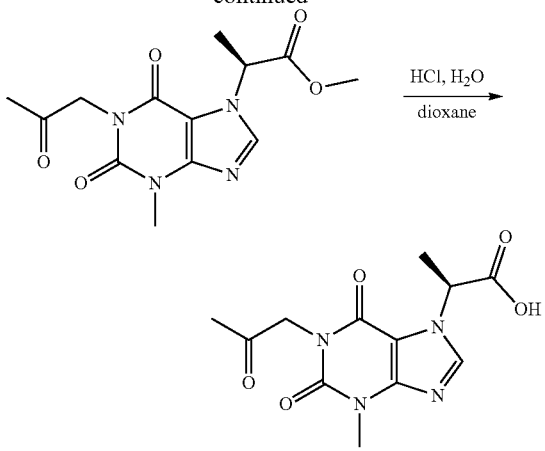

Step 1 (S)-methyl 2-(3-methyl-2,6-dioxo-1-(2-oxopropyl)-2,3-dihydro-1H-purin-7(6H)-yl)propanoate

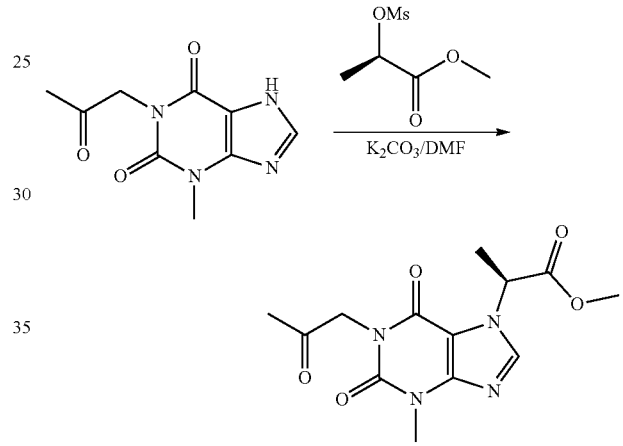

To a mixture of 3-methyl-1-(2-oxopropyl)-1H-purine-2,6 (3H,7H)-dione (4.3 g, 19.35 mmol) and (R)-methyl 2-(methylsulfonyloxy)propanoate (6.5 g, 38.70 mmol) in DMF (30 mL) was added potassium carbonate (2.67 g, 19.35 mmol). The reaction mixture was stirred at r.t. for 3 h. The reaction mixture was poured into water (50 mL) and extracted with EA (2×50 mL). Combined organic layers were dried over Na₂SO₄ and filtered. The filtrate was concentrated under reduced pressure and the residue was purified by chromatography (eluted with PE:EA=2:1) to afford 3-methyl-1-(2-oxopropyl)-1H-purine-2,6 (3H,7H)-dione (850 mg, 14.3% yield) as yellow solid. Retention time (LC-MS): 0.556 min. MH⁺309.

Step 2 (S)-2-(3-methyl-2,6-dioxo-1-(2-oxopropyl)-2, 3-dihydro-1H-purin-7(6H)-yl)propanoic acid

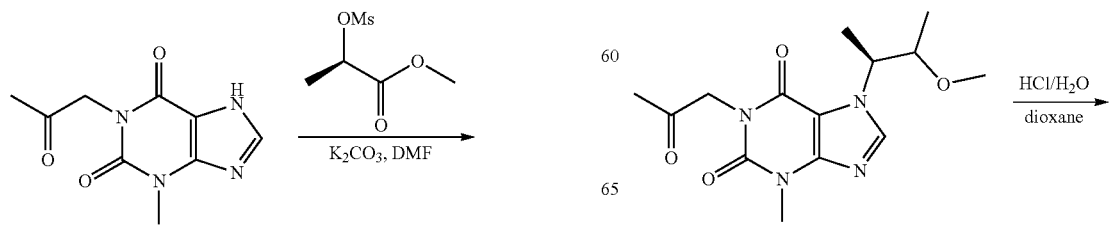

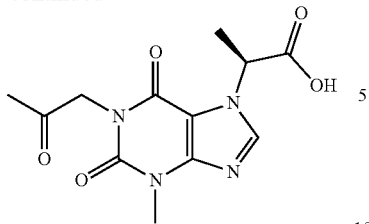

A mixture of (S)-methyl 2-(3-methyl-2,6-dioxo-1-(2-oxo-propyl)-2,3-dihydro-1H- purin-7(6H)-yl)propanoate (850 mg, 2.74 mmol) and HCl (1M, 2.5 mL) in dioxane (5 mL) was stirred at 110° C. for 2 h. The reaction mixture was poured into water (50 mL) and extracted with EA (2×50 mL). The combined organic layers were dried over Na$_2$SO$_4$ and filtered. The filtrate was concentrated under reduced pressure and the residue was purified by chromatography (DCM:MeOH=20:1) to afford (S)-2-(3-methyl-2,6-dioxo-1-(2-oxopropyl)-2,3-dihydro-1H-purin-7(6H)-yl)propanoic acid (540 mg, 67.0% yield) as yellow oil. Retention time (LC-MS): 0.424 min. MH$^+$295.

Preparation 11 (S)-2-(2-(2-(trifluoromethyl)pyrrolidin-1-yl)pyrimidin-5-yl)thiazol-4-amine

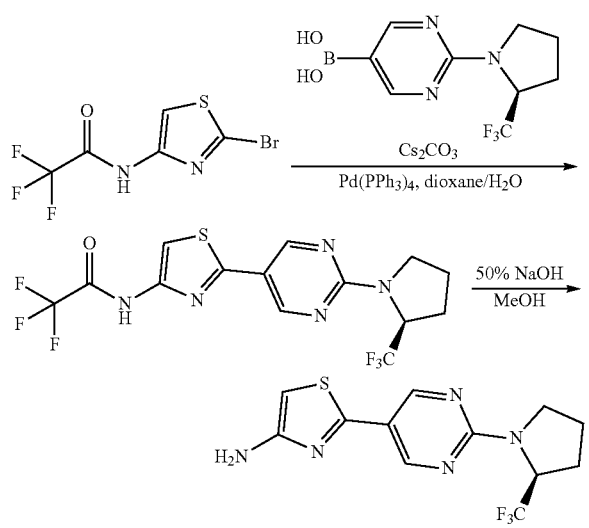

Step 1 (S)-2,2,2-trifluoro-N-(2-(2-(2-(trifluoromethyl)pyrrolidin-1-yl)pyrimidin-5-yl)thiazol-4-yl)acetamide A mixture of (S)-2-(2-(trifluoromethyl)pyrrolidin-1-yl)pyrimidin-5-ylboronic acid (573 mg, 2.19 mmol), N-(2-bromothiazol-4-yl)-2,2,2-trifluoroacetamide (500 mg, 1.82 mmol), Pd(PPh$_3$)$_4$ (105 mg, 0.09 mmol) and Cs$_2$CO$_3$ (1.8 g, 5.46 mmol) in 1,4-dioxane (10 mL) and H$_2$O (2 mL) was degassed and stirred at 110° C. under N$_2$ for 3 h. The reaction mixture was cooled down and poured into EA. The organic phase was separated, washed with water and brine, dried over Na$_2$SO$_4$ and filtered. The filtrate was concentrated under reduced pressure and the residue was purified via chromatography (eluted with PE:EA=10:1) to give (S)-2,2,2-trifluoro-N-(2-(2-(2-(trifluoromethyl)pyrrolidin-1-yl)pyrimidin -5-yl)thiazol-4-yl)acetamide (247 mg, 32.9% yield) as yellow solid. Retention time (LC-MS): 1.822 min. MH$^+$412.

Step 2 (S)-2-(2-(2-(trifluoromethyl)pyrrolidin-1-yl)pyrimidin-5-yl)thiazol-4-amine

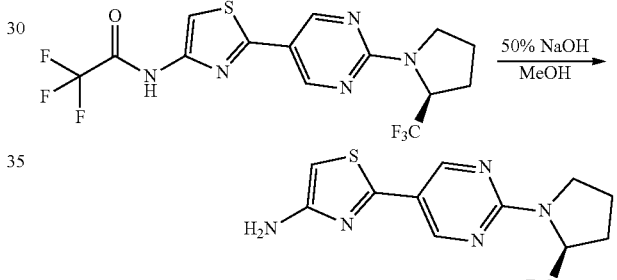

To a stirred solution of (S)-2,2,2-trifluoro-N-(2-(2-(2-(trifluoromethyl)pyrrolidin -1-yl)pyrimidin-5-yl)thiazol-4-yl)acetamide (200 mg, 0.48 mmol) in MeOH (4 mL) was added 50% NaOH (2 mL). After addition, the mixture was heated to reflux for 2 hr, cooled to r.t., and concentrated under reduced pressure. The residue was diluted with water (4 mL) and extracted with DCM (3×2 mL). Combined organic layers were dried over Na$_2$SO$_4$ and filtered. The filtrate was concentrated under reduced pressure to afford (S)-2-(2-(2-(trifluoromethyl)pyrrolidin-1-yl)pyrimidin -5-yl)thiazol-4-amine (110 mg, 71.9% yield) as yellow solid. Retention time (LC-MS): 0.785 min. MH$^+$316.

Preparation 12 2-(3-methyl-2,6-dioxo-2,3,6,7-tetrahydro-1H-purin-1-yl)acetonitrile

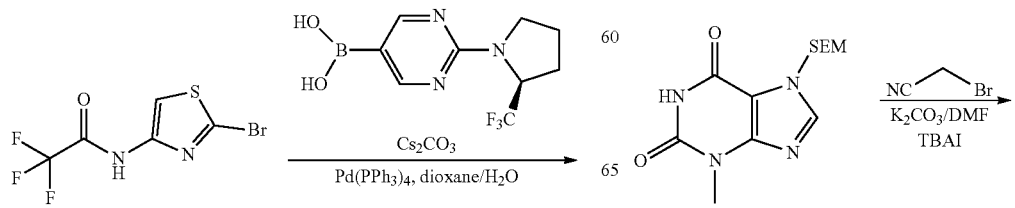

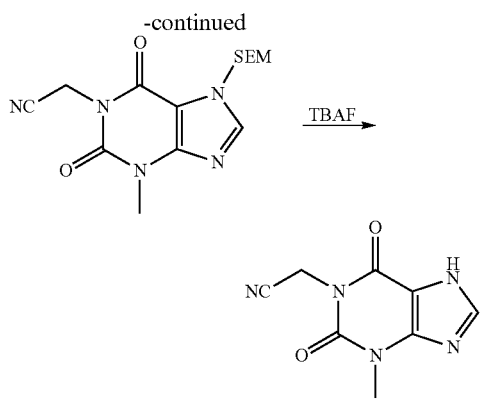

Step 1 2-(3-methyl-2,6-dioxo-7-((2-(trimethylsilyl)ethoxy)methyl)-2,3,6,7-tetrahydro-1H-purin-1-yl)acetonitrile

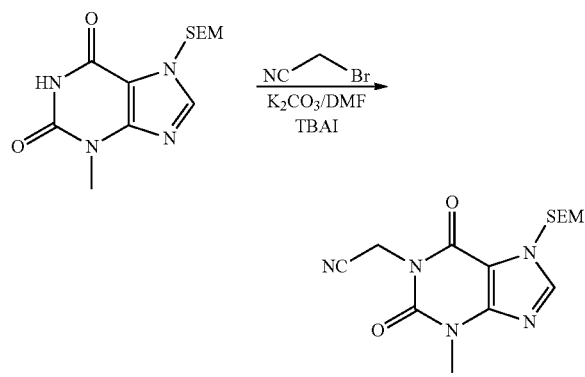

To a solution of 3-methyl-7-(2-trimethylsilanyl-ethoxymethyl)-3,7-dihydro-purine-2,6-dione (450 mg, 1.52 mmol) in DMF (7 mL) was added potassium carbonate (420 mg, 3.04 mmol), TBAI (56 mg, 0.15 mmol) followed by dropwise addition of 2-bromoacetonitrile (0.13 mL, 1.82 mmol). The reaction mixture was stirred at 50° C. under N₂ overnight. The reaction mixture was quenched by water (30 mL), and then extracted with EA (3×5 mL). The combined organic layers were washed with saturated aqueous LiCl solution (15 mL) and brine (15 mL), dried over Na₂SO₄ and filtered. The filtrate was concentrated to give a residue, which was purified with column chromatography (eluted with DCM: MeOH=70:1) to afford 2-(3-methyl-2,6-dioxo-7-((2-(trimethylsilyl)ethoxy)methyl)-2,3,6,7-tetrahydro-1H-purin-1-yl)acetonitrile (490 mg, 80% yield) as a brown oil. Retention time (LC-MS): 1.486 min. MH⁺336.

Step 2 2-(3-methyl-2,6-dioxo-2,3,6,7-tetrahydro-1H-purin-1-yl)acetonitrile

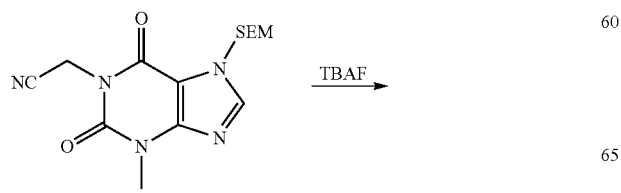

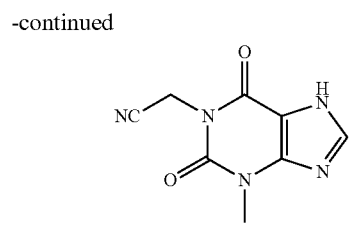

To a solution of 2-(3-methyl-2,6-dioxo-7-((2-(trimethylsilyl)ethoxy)methyl)-2,3,6,7-tetrahydro-1H-purin-1-yl)acetonitrile (400 mg, 1.19 mmol) in THF (10 mL) was added TBAF (933 mg, 3.57 mmol), then the mixture was stirred at 75° C. overnight. The mixture was cooled to RT and concentrated. The residue was diluted with water and extracted with chloroform/isopropanol (3:1) (3×5 mL). Then the organic layers were dried over Na₂SO₄ and filtered. The filtrate was concentrated and the residue was purified with column chromatography (eluted with DCM: MeOH=70:1) to afford 2-(3-methyl-2,6-dioxo-2,3,6,7-tetrahydro-1H-purin-1-yl)acetonitrile (210 mg yield 86%) as a brown solid. Retention time (LC-MS): 0.372min. MH⁺206.

Preparation 13 2-chloro-N-(6-(2-(trifluoromethyl)pyrimidin-5-yl)pyridin-2-yl)propanamide

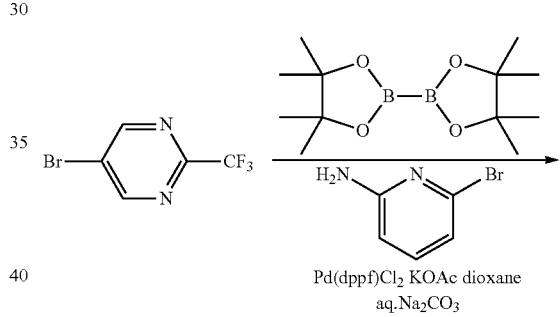

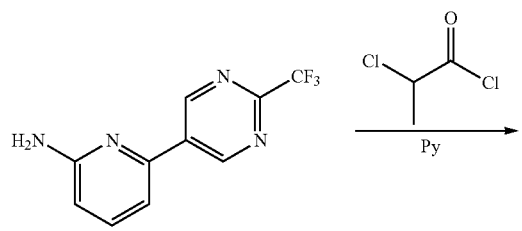

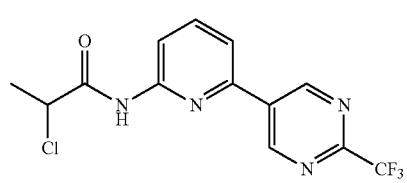

Step 1 6-(2-(trifluoromethyl)pyrimidin-5-yl)pyridin-2-amine

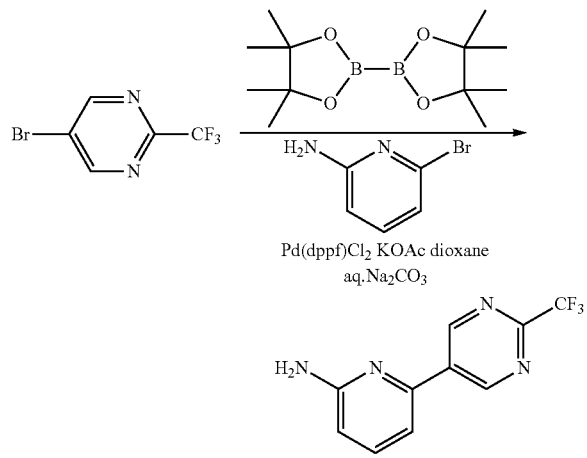

A mixture of 5-bromo-2-(trifluoromethyl)pyrimidine (1 g, 4.42 mmol), 4,4,5,5-tetramethyl-2-(4,4,5,5-tetramethyl-1,3,2-dioxaborolan-2-yl)-1,3,2-dioxaborolane (1.35 g, 5.31 mmol), KOAc (1.30 g, 13.27 mmol) in a dioxane (10 mL) was added Pd(dppf)Cl$_2$ (161.8 mg, 0.22 mmol). After the mixture was degassed and purged with N$_2$ for three times, it was stirred at 100° C. for 2 hrs under N$_2$ atmosphere. The mixture was cooled to RT 6-bromopyridin-2-amine (633.5 mg, 3.68 mmol), aqueous Na$_2$CO$_3$ solution (5 mL, 2 M) and Pd(dppf)C12 (161.8 mg 0.22 mmol) were added to the above mixture under N$_2$ atmosphere. The mixture was stirred at 100° C. under N$_2$ for 2 hrs. The reaction mixture was extracted with DCM (2×10 mL). Combined organic layers were washed with brine, dried over Na2SO4, and concentrated and the residue was purified with column chromatography (eluted with PE:EA=5:1) to afford 6-(2-(trifluoromethyl)pyrimidin-5-yl)pyridin-2-amine (670 mg, 64% yield) as a white solid. Retention time (LC-MS): 1.029 min. MH$^+$241.

Step 2 2-chloro-N-(6-(2-(trifluoromethyl)pyrimidin-5-yl)pyridin-2-yl)propanamide

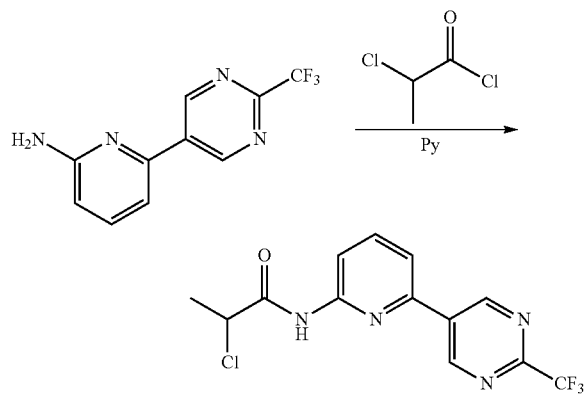

To a mixture of 6-(2-(trifluoromethyl)pyrimidin-5-yl)pyridin-2-amine (100 mg, 0.42 mmol) in pyridine (2 mL) was added 3-chloro-butan-2-one (0.06 mL, 0.63 mmol) at 0° C. Then the mixture was stirred at RT for 2 hrs. The reaction mixture was quenched by water (20 mL), and then extracted with EA (3×5 mL). The combined organic layers were washed by the saturated aqueous LiCl and brine, dried over Na$_2$SO$_4$ and filtered. The filtrate was concentrated and the residue was purified with column chromatography (eluted with PE:EA=3:1) to afford 2-chloro-N-(6-(2-(trifluoromethyl)pyrimidin-5-yl)pyridin-2-yl)propanamide (80 mg, 58% yield) as a white solid. Retention time (LC-MS): 1.560 min. MH$^+$331.

Preparation 14 (S)-methyl 2-(1-(cyanomethyl)-3-methyl-2,6-dioxo-2,3-dihydro-1H-purin-7(6H)-yl)propanoate

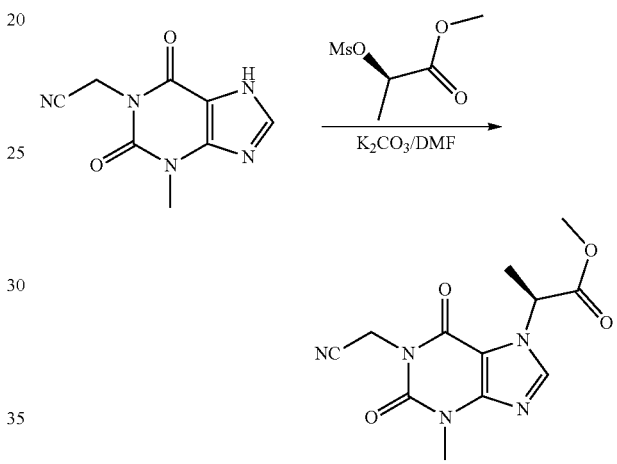

To solution of 2-(3-methyl-2,6-dioxo-2,3,6,7-tetrahydro-1H-purin-1-yl)acetonitrile (300 mg, 1.46 mmol) in DMF (7 mL) was added (R)-methyl 2-(methylsulfonyloxy)propanoate (533 mg, 2.93 mmol), and potassium carbonate(202 mg 1.46 mmol). The reaction mixture was stirred at 50° C. under N$_2$ overnight. The reaction mixture was quenched by water (50 mL), and then extracted with EA (3×10 mL). The combined organic layers were washed by the saturated aqueous LiCl and brine, dried over Na$_2$SO$_4$ and filtered. The filtrate was concentrated and the residue was purified with column chromatography (eluted with DCM:MeOH=100:1) to afford (S)-methyl 2-(1-(cyanomethyl)-3-methyl-2,6-dioxo-2,3-dihydro-1H-purin-7(6H)-yl)propanoate (250 mg, 59% yield) as a brown oil. Retention time (LC-MS): 0.622 min. MH$^+$292.

Preparation 15 2'-(6,6-difluoro-3-azabicyclo[3.1.0]hexan-3-yl)-[2,5'-bipyrimidin]-4-amine

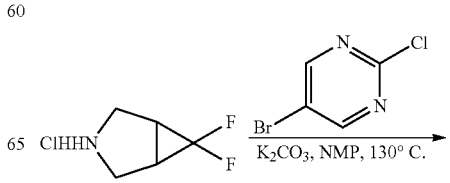

-continued

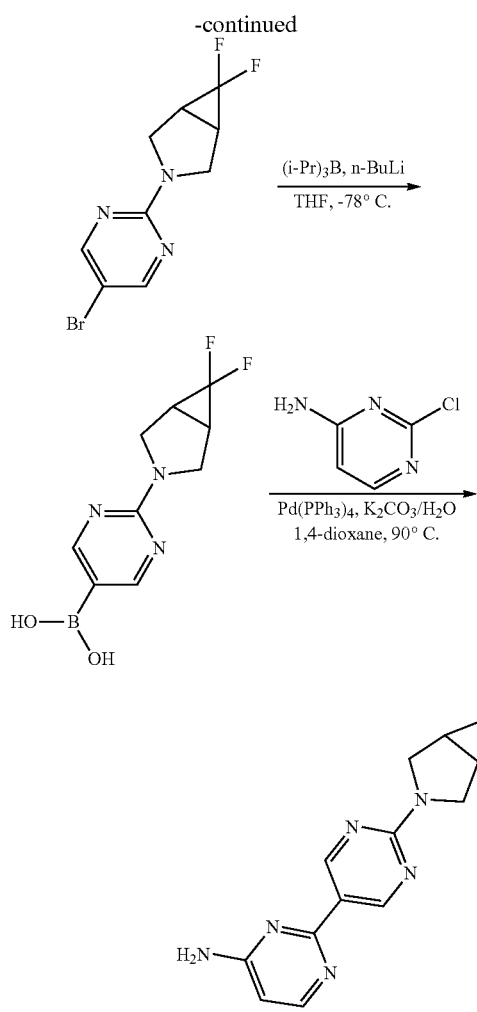

Step 1 3-(5-bromopyrimidin-2-yl)-6,6-difluoro-3-azabicyclo[3.1.0]hexane

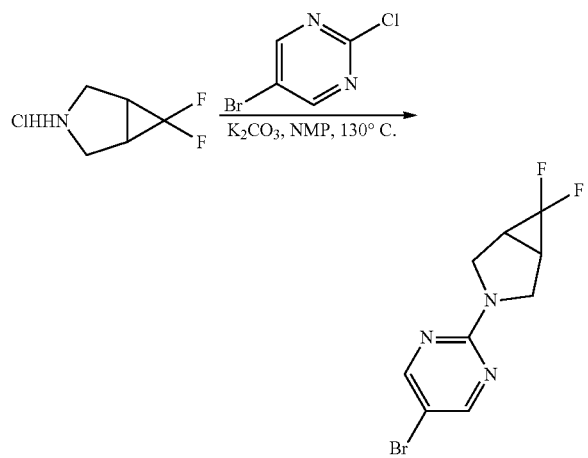

A sealed tube was charged with 5-bromo-2-chloropyrimidine (748.5 mg, 3.9 mmol), 6,6-difluoro-3-azabicyclo[3.1.0]hexane hydrochloride (604.6 mg, 3.9 mmol), potassium carbonate (1.1 g, 7.8 mmol) and NMP (3 mL). After the mixture was stirred at 130° C. for 3 hrs, it was poured into water (4 mL). The solid was collected by filtration and dried under vacuum to give the title product (1.0 g, 93.2% yield) as a white solid. Retention time (LC-MS): 1.65 min. MH$^+$276.

Step 2 (2-(6,6-difluoro-3-azabicyclo[3.1.0]hexan-3-yl)pyrimidin-5-yl)boronic acid

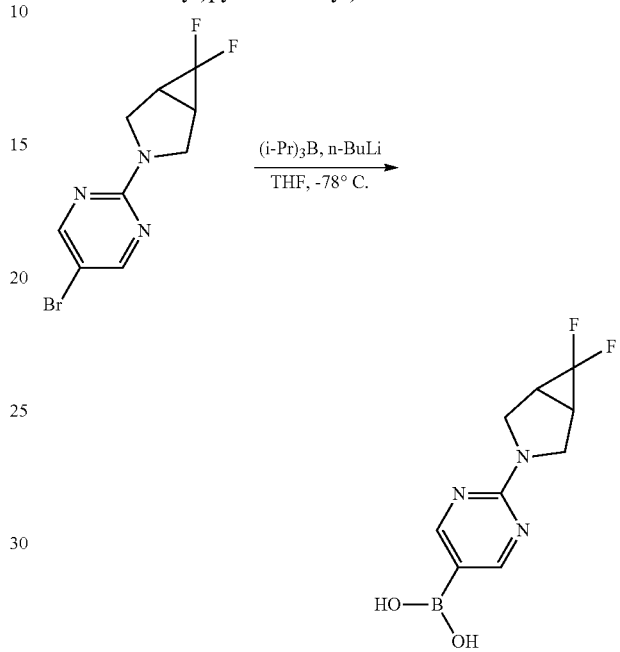

To a solution of 3-(5-bromopyrimidin-2-yl)-6,6-difluoro-3-azabicyclo[3.1.0]hexane (1.1 g, 4.1 mmol) and (i-PrO)$_3$B (1.4 mL, 6.2 mmol) in THF (20 mL) was added n-BuLi (3.9 mL, 1.6 M in hexane, 6.2 mmol) dropwise at −78° C. After the mixture was stirred at −78° C. for 2 hrs, it was quenched with water. The solvent was removed under reduced pressure and the aqueous layer was washed with Ether (2×50 mL). The aqueous layer was then adjusted to pH 6 with 1N HCl and extracted with EA (3×50 mL). The combined organic layers were washed with brine, dried over Na2SO4, and concentrated to give 2-(6,6-difluoro-3-azabicyclo[3.1.0]hexan-3-yl)pyrimidin-5-yl)boronic acid (700 mg, 72.6% yield) as a white solid.

Step 3 2'-(6,6-difluoro-3-azabicyclo[3.1.0]hexan-3-yl)-[2,5'-bipyrimidin]-4-amine

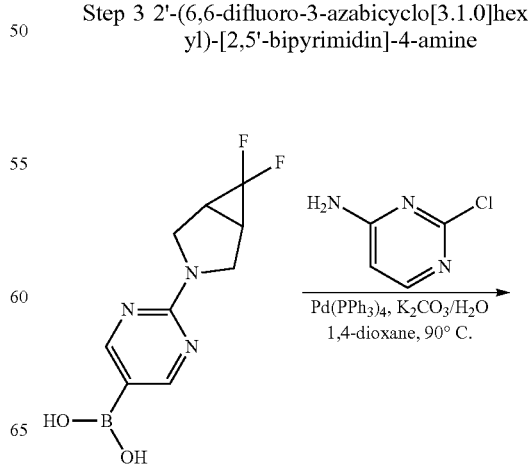

-continued

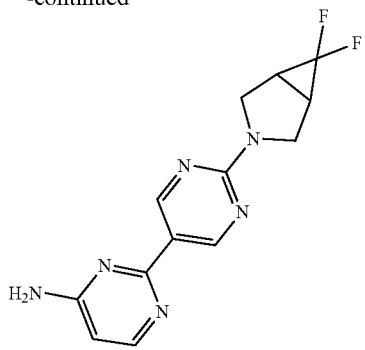

A mixture of (2-(6,6-difluoro-3-azabicyclo[3.1.0]hexan-3-yl)pyrimidin-5-yl)boronic acid (241.0 mg, 1.0 mmol), 2-chloropyrimidin-4-amine (129.0 mg, 1.0 mmol), Pd(PPh₃)₄ (57.8 mg, 0.05 mmol) and potassium carbonate (276.4 mg, 2.0 mmol) in 1,4-dioxane (5 mL) and H₂O (1 mL) was degassed and purged with N₂ for three times and stirred at 90° C. under N₂ for 3 hrs. The reaction mixture was cooled down and poured into EA. The organic phase was separated, washed with water and brine, dried over Na₂SO₄ and filtered. The filtrate was concentrated under reduced pressure and the residue was purified with column chromatography (eluted with DCM: MeOH=50:1) to afford 2'-(6,6-difluoro-3-azabicyclo[3.1.0]hexan-3-yl)-[2,5'-bipyrimidin]-4-amine (210 mg, 72.3% yield) as a white solid. Retention time (LC-MS): 0.37 min. MH⁺291.

Preparation 16 6-(2-(6,6-difluoro-3-azabicyclo[3.1.0]hexan-3-yl)pyrimidin-5-yl)pyrazin-2-amine

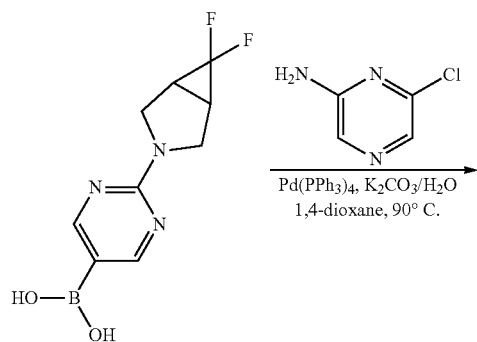

A mixture of (2-(6,6-difluoro-3-azabicyclo[3.1.0]hexan-3-yl)pyrimidin-5-yl)boronic acid (192.9 mg, 0.8 mmol), 6-chloropyrazin-2-amine (103.2 mg, 0.8 mmol), Pd(PPh₃)₄ (46.2 mg, 0.04 mmol) and potassium carbonate (221.1 mg, 1.6 mmol) in 1,4-dioxane (5 mL) and H₂O (1 mL) was degassed and stirred at 90° C. under N₂ for 3 hrs. The reaction mixture was cooled down and diluted with EA. The organic phase was separated, washed with water and brine, dried over Na₂SO₄ and filtered. The filtrate was concentrated under reduced pressure and the residue was purified with column chromatography (eluted with DCM:MeOH=50:1) to afford 6-(2-(6,6-difluoro-3-azabicyclo[3.1.0]hexan-3-yl)pyrimidin-5-yl)pyrazin-2-amine (180 mg, 77.5% yield) as a white solid. Retention time (LC-MS): 0.37 min. MH⁺291.

Preparation 17 (S)-methyl 2-(3-methyl-1-((5-methylisoxazol-3-yl)methyl)-2,6-dioxo-2,3-dihydro-1H-purin-7(6H)-yl)propanoate

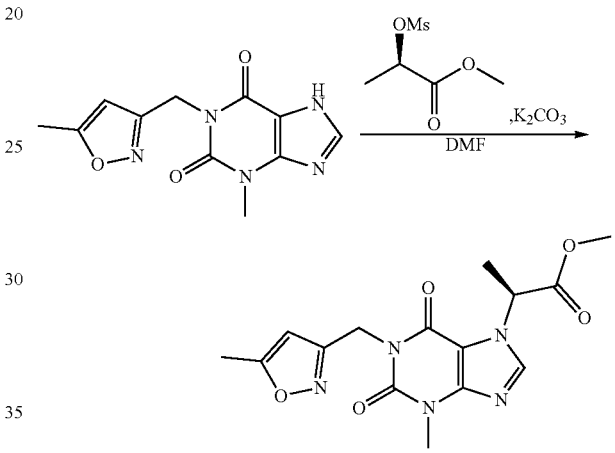

To a solution of 3-methyl-1-((5-methylisoxazol-3-yl)methyl)-1H-purine-2,6(3H,7H)-dione (600 mg, 2.30 mmol) and potassium carbonate (836.78 mg, 4.60 mmol). The mixture was stirred at 50° C. overnight. The mixture was diluted with EA, washed with water, brine, dried over Na₂SO₄ and filtered. The filtrate was evaporated to give the crude product. The crude product was purified with column chromatography (PE:EA=4:1 to 1:3) to give the (S)-methyl 2-(3-methyl-1-((5-methylisoxazol-3-yl)methyl)-2,6-dioxo-2,3-dihydro-1H-purin-7(6H)-yl)propanoate (640 mg, 80.2% yield) as a white solid. Retention time (LC-MS): 0.735 min. MH⁺347.

Preparation 18 6-(2-(6,6-difluoro-3-azabicyclo[3.1.0]hexan-3-yl)pyrimidin-5-yl)pyridin-2-amine

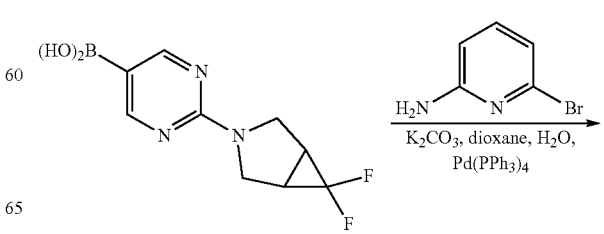

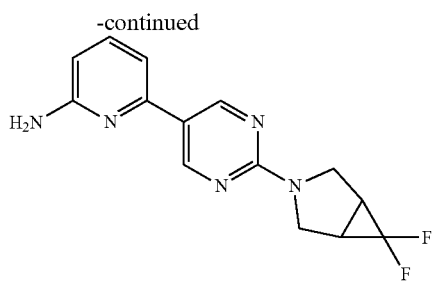

A mixture of 2-(6,6-difluoro-3-azabicyclo[3.1.0]hexan-3-yl)pyrimidin-5-ylboronic acid (200 mg, 0.83 mmol), 6-bromopyridin-2-amine (128 mg, 1.0 mmol), Pd(PPh$_3$)$_4$ (57.8 mg, 0.05 mmol) and potassium carbonate(229 mg, 1.66 mmol) in 1,4-dioxane (5 mL) and H$_2$O (1 mL) was degassed and stirred at 90° C. under N$_2$ for 3 hrs. The reaction mixture was cooled to RT and poured into EA. The organic phase was separated, washed with water and brine, dried over Na$_2$SO$_4$ and filtered. The filtrate was concentrated under reduced pressure and the residue was purified with column chromatography (eluted with DCM:MeOH=50:1) to afford 6-(2-(6,6- difluoro-3-azabicyclo[3.1.0]hexan-3-yl)pyrimidin-5-yl)pyridin-2-amine (180 mg, 75.0% yield) as a white solid. Retention time (LC-MS): 0.499 min. MH$^+$290.

The procedure set forth above was used to produce the following compounds using the appropriate starting materials.

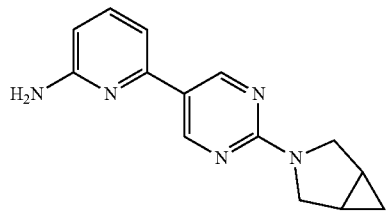 [SMILES: Nc1cccc(-c2cnc(N3CC4CC4C3)nc2)n1]

Retention time (LC-MS): 0.723 min. MH$^+$254.

Preparation 19 (R)-2-(2-(2-(trifluoromethyl)pyrrolidin-1-yl)pyrimidin-5-yl)thiazol-4-amine

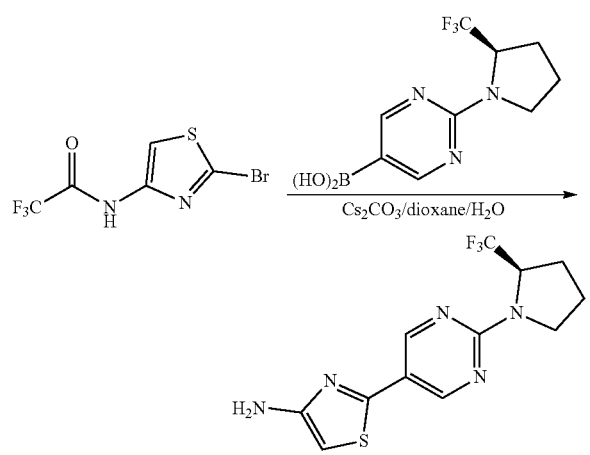

A mixture of N-(2-bromothiazol-4-yl)-2,2,2-trifluoroacetamide (200 mg, 0.73 mmol), (R)-2-(2-(trifluoromethyl)pyrrolidin-1-yl)pyrimidin-5-ylboronic acid (228 mg, 0.87 mmol), Pd(PPh$_3$)$_4$ (57.8 mg, 0.05 mmol) and Cs$_2$CO$_3$ (710 mg, 2.18 mmol) in 1,4-dioxane (5 mL) and H$_2$O (1 mL) was degassed and stirred at 110° C. under N$_2$ for 3 hrs. The reaction mixture was cooled down and poured into EA. The organic phase was separated, washed with water and brine, dried over Na$_2$SO$_4$ and filtered. The filtrate was concentrated under reduced pressure and the residue was purified with column chromatography (eluted with DCM:MeOH=10:1) to afford (R)-2-(2-(2-(trifluoromethyl)pyrrolidin-1-yl)pyrimidin-5-yl)thiazol-4-amine (55 mg, 24.0% yield) as a white solid. Retention time (LC-MS): 1.417 min. MH$^+$316.

Preparation 20 N-(2'-(3-azabicyclo[3.1.0]hexan-3-yl)-2,5'-bipyrimidin-4-yl)-2-chloropropanamide (3, ZY-000461-133)

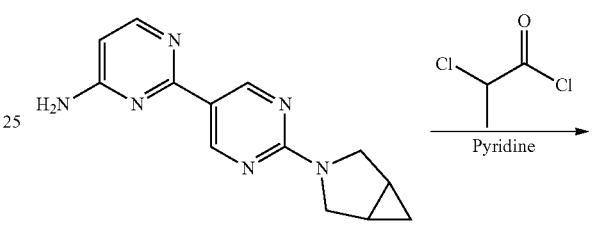

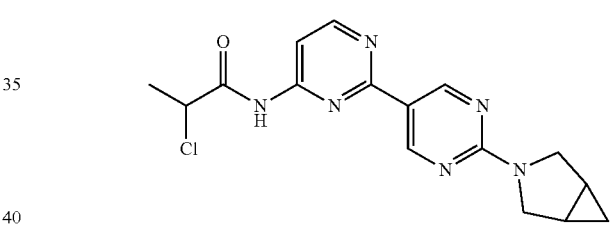

To a solution of 2'-(3-azabicyclo[3.1.0]hexan-3-yl)-2,5'-bipyrimidin-4-amine (100 mg, 0.39 mmol) in pyridine (3 mL) was added drop-wise 2-chloropropanoyl chloride (0.56 mL, 0.59 mmol) at 0° C. After the mixture was stirred at RT for 1 h and it was poured into EA. The organic layer was separated, washed with water and brine, dried over Na$_2$SO$_4$, and concentrated to give the title product (120 mg, 88.5% yield) as a yellow solid. Retention time (LC-MS): 1.571 min. MH$^+$345.

Preparation 21 6-(2-(6,6-difluoro-3-azabicyclo[3.1.0]hexan-3-yl)pyrimidin-5-yl)pyridin-2-amine

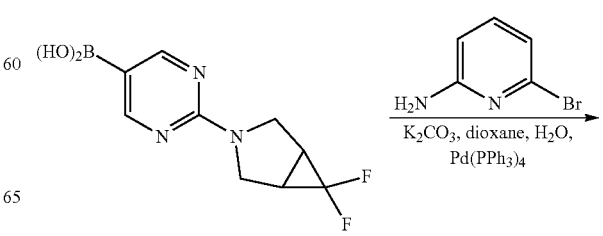

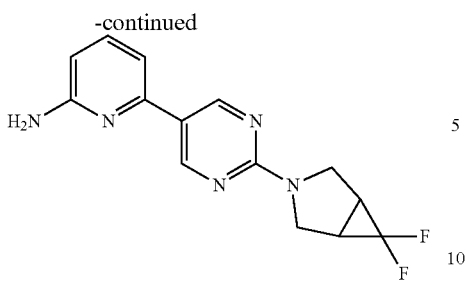

A mixture of 2-(6,6-difluoro-3-azabicyclo[3.1.0]hexan-3-yl)pyrimidin-5-ylboronic acid (200 mg, 0.83 mmol), 6-bromopyridin-2-amine (128 mg, 1.0 mmol), Pd(PPh$_3$)$_4$ (57.8 mg, 0.05 mmol) and potassium carbonate (229 mg, 1.66 mmol) in 1,4-dioxane (5 mL) and H$_2$O (1 mL) was degassed and stirred at 90° C. under N$_2$ for 3 hrs. The reaction mixture was cooled to RT and poured into EA. The organic phase was separated, washed with water and brine, dried over Na$_2$SO$_4$ and filtered. The filtrate was concentrated under reduced pressure and the residue was purified with column chromatography (eluted with DCM:MeOH=50:1) to afford 6-(2-(6,6-difluoro-3-azabicyclo[3.1.0]hexan-3-yl)pyrimidin-5-yl)pyridin-2-amine (180 mg, 75.0% yield) as a white solid. Retention time (LC-MS): 0.499 min. MH$^+$290.

The procedure set forth above was used to produce the following compounds using the appropriate starting materials.

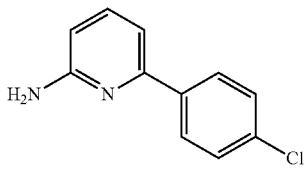 [SMILES: Nc1cccc(-c2ccc(Cl)cc2)n1]

Retention time (LC-MS): 0.449 min. MH$^+$205.

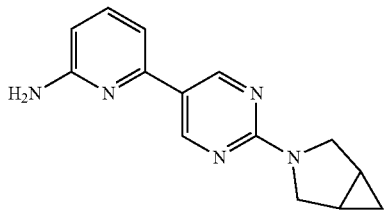 [SMILES: Nc1cccc(-c2cnc(N3CC4CC4C3)nc2)n1]

Retention time (LC-MS): 0.723 min. MH$^+$254.

Preparation 22
6-(3,4-dichlorophenyl)pyridin-2-amine.

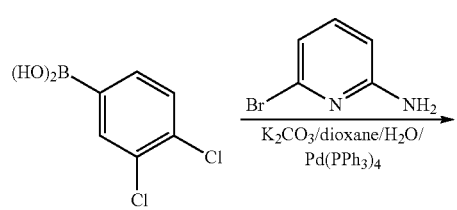

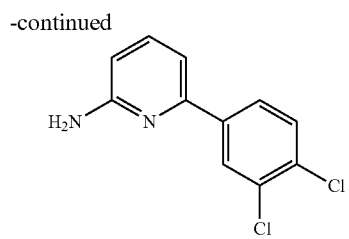

To a mixture of 3,4-dichlorophenylboronic acid (200 mg, 1.05 mmol), 6-bromopyridin-2-amine (218 mg, 1.26 mmol) in 1,4-dioxane (5 mL) and H$_2$O (1 mL) was added potassium carbonate290 mg, 2.10 mmol). After the mixture was degassed with N$_2$ for 3 times, Pd(PPh$_3$)$_4$ (57.8 mg, 0.05 mmol) was added under N$_2$ and the mixture was stirred at 100° C. for 3 hrs. The reaction mixture was cooled down and poured into EA. The organic phase was separated, washed with water and brine, dried over Na$_2$SO$_4$ and filtered. The filtrate was concentrated under reduced pressure and the residue was purified by chromatography (eluted with DCM:MeOH=50:1) to afford 6-(3,4-dichlorophenyl)pyridin-2-amine (200 mg, 79.8% yield) as a white solid. Retention time (LC-MS): Retention 1.546 min. MH$^+$240.

Preparation 23
2-(3,4-dichlorophenyl)thiazol-4-amine

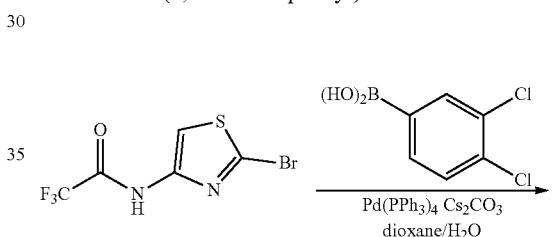

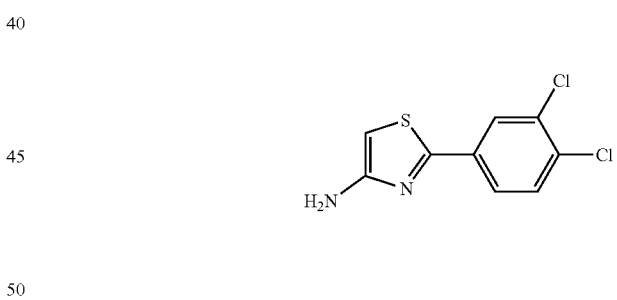

To a mixture of 3,4-dichlorophenylboronic acid (600 mg, 2.18 mmol), N-(2-bromothiazol-4-yl)-2,2,2-trifluoroacetamide (416 mg, 2.18 mmol) in 1,4-dioxane (15 mL) and H$_2$O (3 mL) was added Cs$_2$CO$_3$ (2.13g, 6.54 mmol) and the mixture was degassed with N$_2$ for three times. Pd(PPh$_3$)$_4$ (75 mg, 0.06 mmol) was added and the reaction mixture was stirred at 100° C. under N$_2$ overnight. The mixture was cooled down and poured into EA. The organic phase was separated, washed with water and brine, dried over Na$_2$SO$_4$ and filtered. The filtrate was concentrated under reduced pressure. The filtrate was concentrated and the residue was purified by chromatography (eluted with DCM:MeOH=100:1) to afford 2-(3,4-dichlorophenyl)thiazol-4-amine (200 mg, 26.88% yield) as a yellow solid. Retention time (LC-MS): 1.651 min. MH$^+$245.

Preparation 24 N-(2'-(3-azabicyclo[3.1.0]hexan-3-yl)-2,5'-bipyrimidin-4-yl)-2-chloropropanamide

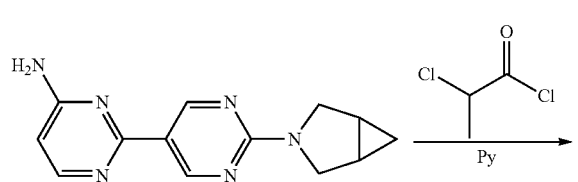

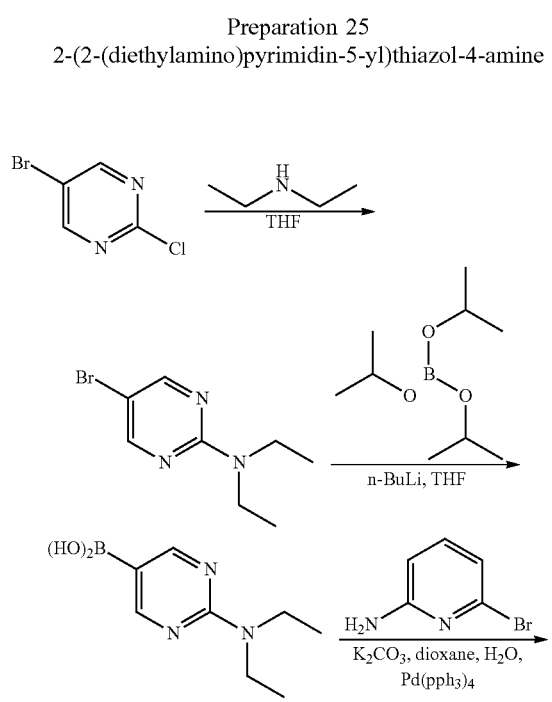

To a solution of 2'-(3-azabicyclo[3.1.0]hexan-3-yl)-2,5'-bipyrimidin-4-amine (80 mg, 0.31 mmol) in pyridine (2 mL) was added drop-wise 2-chloropropanoyl chloride (0.04 mL, 0.45 mmol) at 0° C. The mixture was stirred at RT for 2 hrs and poured into EA. The organic layer was separated, washed with water and brine, dried over $Na_2SO_4$ and filtered. The filtrate was concentrated and the residue was purified by chromatography (eluted with DCM:MeOH=70:1) to afford N-(2'-(3-azabicyclo[3.1.0]hexan-3-yl)-2,5'-bipyrimidin-4-yl)-2-chloropropanamide (130 mg, 120% yield) as a white solid. Retention time (LC-MS): 1.525 min. $MH^+345$.

Preparation 25
2-(2-(diethylamino)pyrimidin-5-yl)thiazol-4-amine

-continued

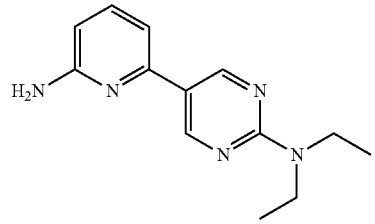

Step 1 5-bromo-N,N-diethylpyrimidin-2-amine

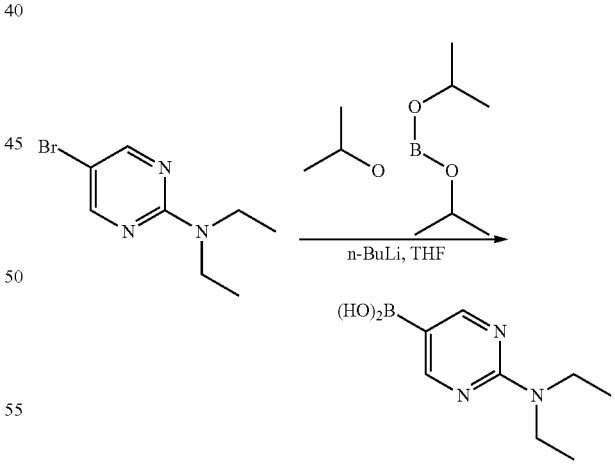

A solution of 5-bromo-2-chloropyrimidine (1.0 g, 5.17 mmol) and diethylamine (2.13 mL, 20.68 mmol) in THF (5 mL) was stirred at 80° C. for 3 hrs. The mixture was cooled and concentrated to dryness to give the crude product, which was purified by chromatography (eluted with PE:EA=100:1) to give 5-bromo-N,N-diethylpyrimidin-2-amine (1.14 g, 95.8% yield) as a yellow solid. Retention time (LC-MS): 1.827 min. $MH^+231$.

Step 2 2-(diethylamino)pyrimidin-5-ylboronic acid

To a solution of 5-bromo-N,N-diethylpyrimidin-2-amine (1.14 g, 4.95 mmol) and triisopropyl borate (2.29 mL, 9.91 mmol) in THF (20 mL) was added drop-wise n-BuLi (5.95 mL, 1M in THF, 5.95 mmol) at −78° C. and the mixture was stirred at this temperature for 3 hrs. The mixture was poured into ice-water (15 mL) and washed with Ether (5 mL ×2). The aqueous layer was adjusted to pH 5 with diluted aq.HCl and the mixture was extracted with EA (20 mL×2). The combined organic layer was separated, washed with water and brine, dried over Na₂SO₄, and filtered. The filtrate was concentrated and under reduced pressure to give 2-(diethylamino)pyrimidin-5-ylboronic acid (450 mg, 65.3% yield) as a white solid. Retention time (LC-MS): 0.398 min. MH⁺196. Step 3 2-(2-(diethylamino)pyrimidin-5-yl)thiazol-4-amine

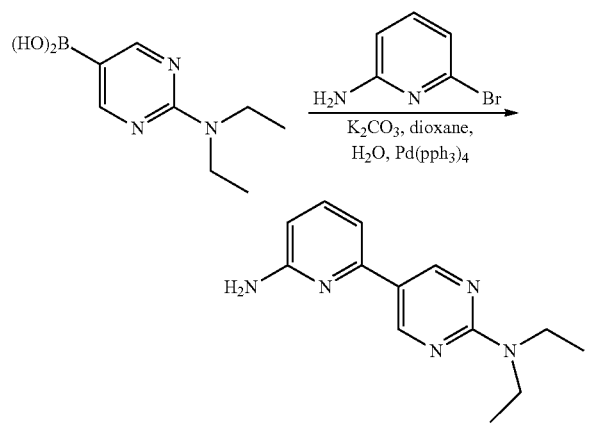

To a mixture of 2-(diethylamino)pyrimidin-5-ylboronic acid (100 mg, 0.51 mmol), 6-bromopyridin-2-amine (106 mg, 0.62 mmol) in 1,4-dioxane (5 mL) and H₂O (1 mL) was added potassium carbonate (142 mg, 1.03 mmol). After the mixture was degassed with N₂ for 3 times, Pd(PPh₃)₄ (57.8 mg, 0.05 mmol) was added under N₂ and the mixture was stirred at 100° C. for 3 hrs. The reaction mixture was cooled down and poured into EA. The organic phase was separated, washed with water and brine, dried over Na₂SO₄ and filtered. The filtrate was concentrated under reduced pressure and the residue was purified by chromatography (eluted with DCM:MeOH=100:1) to afford 5-(6-aminopyridin-2-yl)-N,N-diethylpyrimidin-2-amine (100 mg, 80.2% yield) as a white solid. Retention time (LC-MS): Retention 0.399 min. MH⁺244.

Preparation 26 (R)-2-(6-(2-(trifluoromethyl)pyrrolidin-1-yl)pyridin-3-yl)thiazol-4-amine.

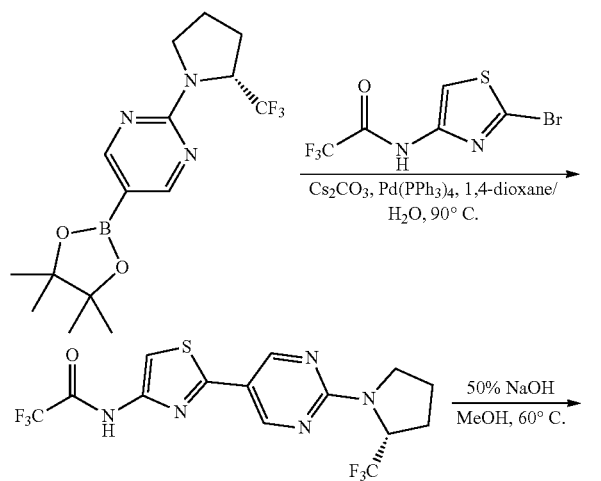

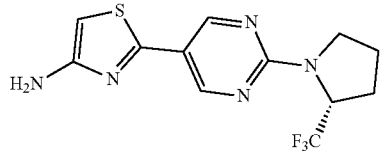

Step 1 (R)-2,2,2-trifluoro-N-(2-(2-(2-(trifluoromethyl)pyrrolidin-1-yl)pyrimidin-5-yl)thiazol-4-yl)acetamide

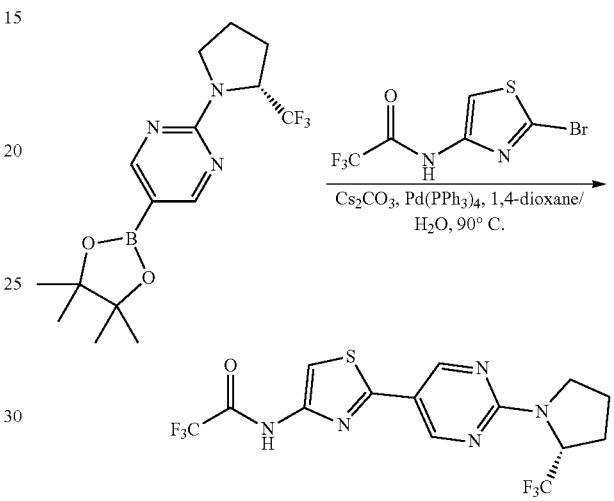

To a mixture of (R)-5-(4,4,5,5-tetramethyl-1,3,2-dioxaborolan-2-yl)-2-(2-(trifluoromethyl)pyrrolidin-1-yl)pyrimidine (246.5 mg, 0.9 mmol), N-(2-bromothiazol-4-yl)-2,2,2-trifluoroacetamide (309.0 mg, 0.9 mmol) in 1,4-dioxane (5 mL) and H₂O (1 mL) was added Cs₂CO₃ (880.2 mg, 2.7 mmol). After the mixture was degassed with N₂ for 3 times, Pd(PPh₃)₄ (52.0 mg, 0.05 mmol) was added under N₂ and the mixture was stirred at 100° C. for 4 hrs. The reaction mixture was cooled down and poured into EA. The organic phase was separated, washed with water and brine, dried over Na₂SO₄ and filtered. The filtrate was concentrated under reduced pressure and the residue was purified by chromatography (eluted with PE:EA=10:1) to afford the title product (140 mg, 37.8% yield) as a white solid. Retention time (LC-MS): Retention 1.769 min. MH⁺411.

Step 2 (R)-2-(6-(2-(trifluoromethyl)pyrrolidin-1-yl)pyridin-3-yl)thiazol-4-amine

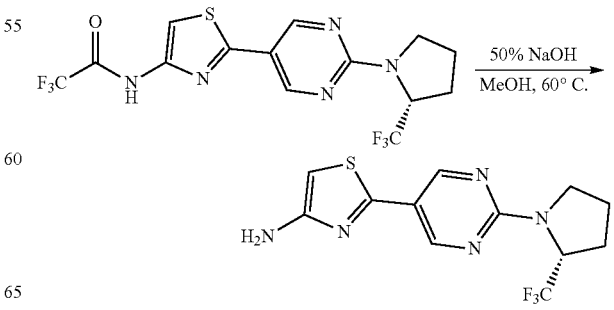

A mixture of (R)-2,2,2-trifluoro-N-(2-(2-(2-(trifluoromethyl)pyrrolidin-1-yl)pyrimidin-5-yl)thiazol-4-yl)acetamide (140.0 mg, 0.34 mmol) in MeOH (5 mL) and 50% NaOH (1 mL) was stirred at 60° C. overnight. The solvent was removed. The residue was purified by column chromatography (eluted with PE:EA=1:1) to afford the title product (70 mg, 65.2% yield) as a white solid. Retention time (LC-MS): 1.426 min. MH$^+$316.

Preparation 27 2-(2-(trifluoromethyl)pyrimidin-5-yl)thiazol-4-amine

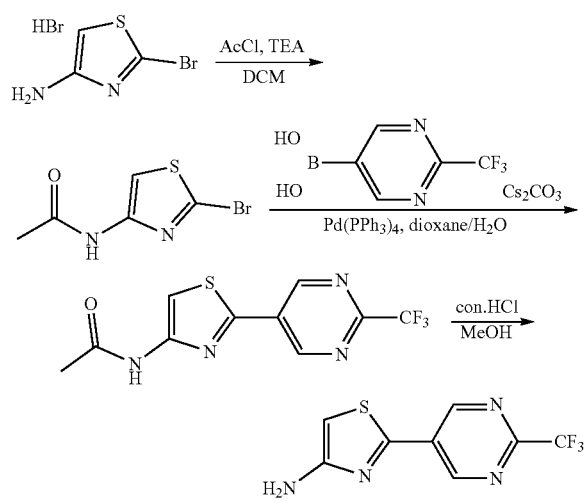

Step 1 N-(2-bromothiazol-4-yl)acetamide (ZSL-000466-082).

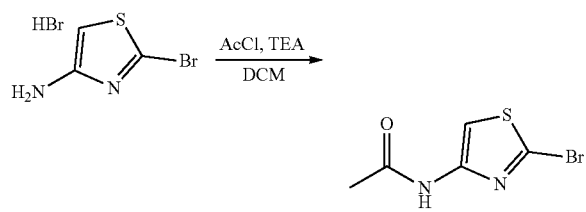

To a suspension of 2-bromothiazol-4-amine hydrogen bromide (1 g, 3.87 mmol) in DCM (5 mL) was added dropwise TEA (2.1 mL, 15.48 mmol) at 0° C. After the addition, the reaction mixture was stirred at r.t for 15 min. then acetyl chloride (450 mg, 5.81 mmol) was added. The reaction mixture was stirred at r.t overnight. The reaction mixture was quenched with water (10 mL). The mixture was neutralized with saturated aq. NaHCO$_3$ solution and extracted with EA. Combined organic layers were washed with water and brine, dried over Na$_2$SO$_4$ and filtered. The filtrate was concentrated under reduced pressure and the residue was purified by chromatography (eluted with PE:EA=10:1 to 3:1) to afford N-(2-bromothiazol-4-yl)acetamide (250 mg, 29.4% yield) as a white solid. Retention time (LC-MS): 1.930 min. MH$^+$221.

Step 2 N-(2-(2-(trifluoromethyl)pyrimidin-5-yl)thiazol-4-yl)

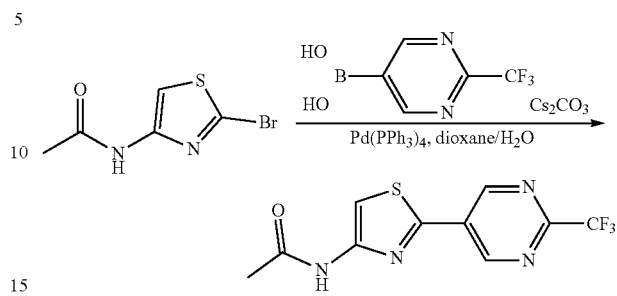

To a mixture of 2-(trifluoromethyl)pyrimidin-5-ylboronic acid (173 mg, 0.90 mmol), N-(2-bromothiazol-4-yl)acetamide (200 mg, 0.90 mmol) in 1,4-dioxane (4 mL) and H$_2$O (0.8 mL) was added Cs$_2$CO$_3$ (880 mg, 2.70 mmol). The mixture was degassed with N$_2$ for three times. Pd(PPh$_3$)$_4$ (52 mg, 0.045 mmol) was added and the reaction mixture was stirred at 100° C. under N$_2$ overnight. The mixture was cooled down and poured into EA. The organic phase was separated, washed with water and brine, dried over Na$_2$SO$_4$ and filtered. The filtrate was concentrated under reduced pressure. The residue was purified by chromatography (eluted with DCM:MeOH=100:1) to afford N-(2-(2-(trifluoromethyl)pyrimidin-5-yl)thiazol-4-yl)acetamide (90 mg, 34.6% yield) as a white solid. Retention time (LC-MS): 1.663 min. MH$^+$289.

Step 3 2-(2-(trifluoromethyl)pyrimidin-5-yl)thiazol-4-amine

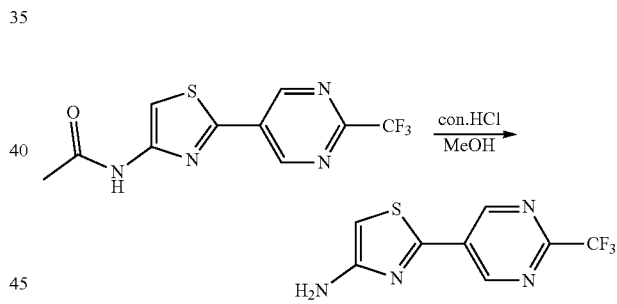

To a solution of N-(2-(2-(trifluoromethyl)pyrimidin-5-yl)thiazol-4-yl)acetamide (3, 90 mg, 0.31 mmol) in MeOH (2 mL) was added con.HCl (0.4 mL). The reaction mixture was heated to reflux for 2 hrs. The solvent was removed under reduced pressure to afford the product 2-(2-(trifluoromethyl)pyrimidin-5-yl)thiazol-4-amine (77 mg, 99.1% yield) as a yellow solid without further purification. Retention time (LC-MS): 0.758 min. MH$^+$247.

Preparation 28 2-(6-(3-azabicyclo[3.1.0]hexan-3-yl)pyridin-3-yl)thiazol-4-amine

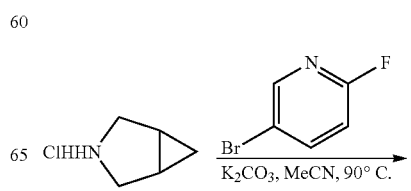

-continued

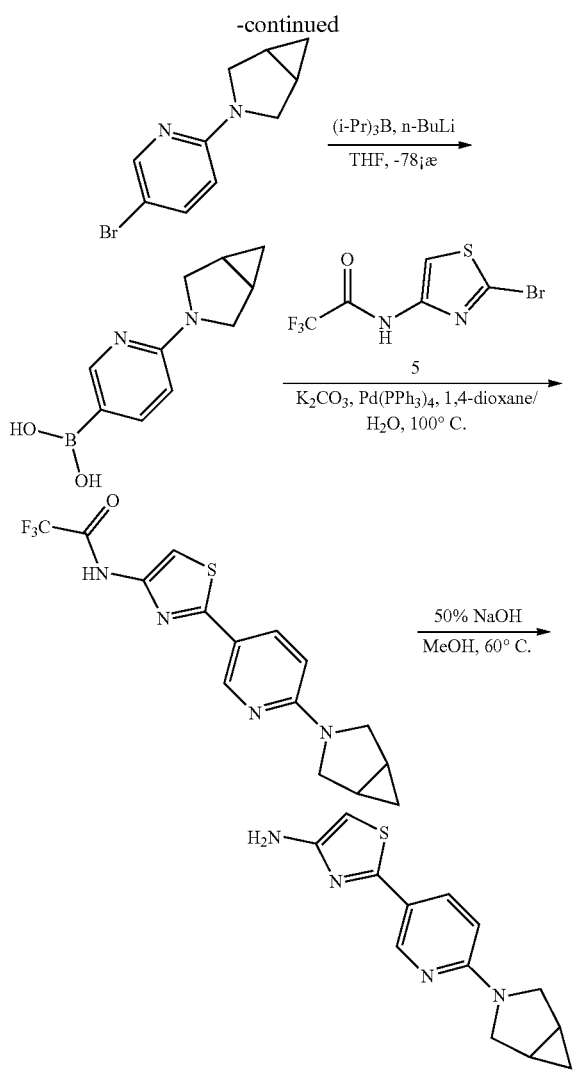

Step 1 3-(5-bromopyridin-2-yl)-3-azabicyclo [3.1.0] hexane

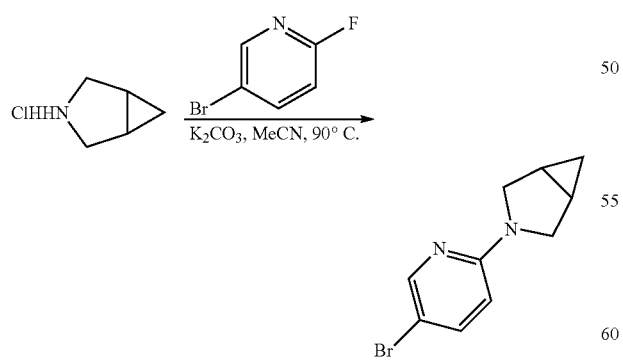

In a microwave reaction tube containing 3-azabicyclo[3.1.0]hexane hydrochloride (892.9 mg, 7.5 mmol) and 5-bromo-2-fluoropyridine (1.3 g, 7.5 mmol) was added MeCN (4 mL) and potassium carbonate (2.1 g, 15.0 mmol). The mixture was heated in a Biotage Microwave Initiator device at 90° C. for 45 min. The mixture was poured into EA. The organic phase was washed with water and brine, dried over Na₂SO₄ and filtered. The filtrate was concentrated under reduced pressure. The crude product was purified by chromatography (eluted with PE:EA=8:1) to afford 3-(5-bromopyridin-2-yl)-3-azabicyclo[3.1.0]hexane (550 mg, 30.8% yield) as a white solid. Retention time (LC-MS): 1.295 min. MH⁺239.

Step 2 (6-(3-azabicyclo [3.1.0] hexan-3-yl)pyridin-3-yl)boronic acid

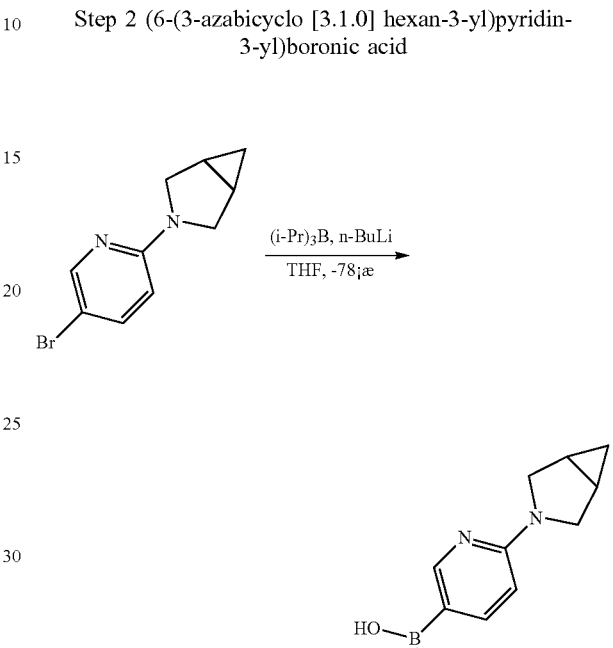

To a solution of 3-(5-bromopyridin-2-yl)-3-azabicyclo [3.1.0]hexane (119.0 mg, 0.5 mmol) and (ⁱPrO)₃B (0.17 mL, 0.75 mmol) in THF (4 mL) was added n-BuLi (0.47 mL, 1.6 M in hexane, 0.75 mmol) dropwise at −78° C. The mixture was stirred at the same temperature for 2 h. The reaction was quenched with water. The solvent was removed under reduced pressure and the aqueous layer was extracted with Ether (2×5 mL). The aqueous layer was then adjusted to pH 6 with 1N HCl and extracted with EA (3×10 mL). Combined organic layers were washed with brine, dried over Na₂SO₄, and concentrated to give the title product (80 mg, 78.4% yield) as a white solid. Retention time (LC-MS): 0.384 min. MH⁺205.

Step 3 N-(2-(6-(3-azabicyclo[3.1.0]hexan-3-yl)pyridin-3-yl)thiazol-4-yl)-2,2,2-trifluoroacetamide

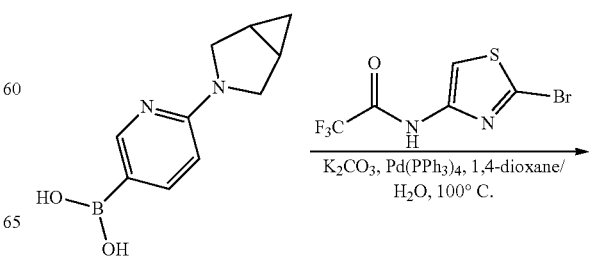

-continued

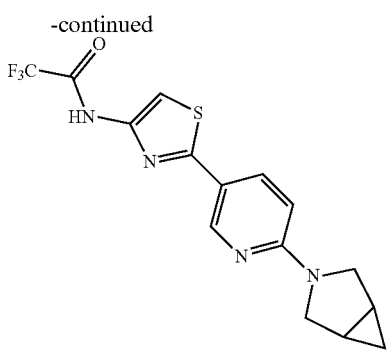

To a mixture of (6-(3-azabicyclo[3.1.0]hexan-3-yl)pyridin-3-yl)boronic acid (80.0 mg, 0.4 mmol), N-(2-bromothiazol-4-yl)-2,2,2-trifluoroacetamide (107.4 mg, 0.4 mmol) in 1,4-dioxane (5 mL) and H₂O (1 mL) was added Cs₂CO₃ (260.6 mg, 0.8 mmol). After the mixture was degassed with N₂ for 3 times, Pd(PPh₃)₄ (23.0 mg, 0.02 mmol) was added under N₂ and the mixture was stirred at 100° C. for 4 hrs. The reaction mixture was cooled down and poured into EA. The organic phase was separated, washed with water and brine, dried over Na₂SO₄ and filtered. The filtrate was concentrated under reduced pressure and the residue was purified by chromatography (eluted with PE/EA=10:1) to afford the title product (50 mg, 36.0% yield) as a white solid. Retention time (LC-MS): 1.978 min. MH⁺355.

Step 4 2-(6-(3-azabicyclo[3.1.0]hexan-3-yl)pyridin-3-yl)thiazol-4-amine

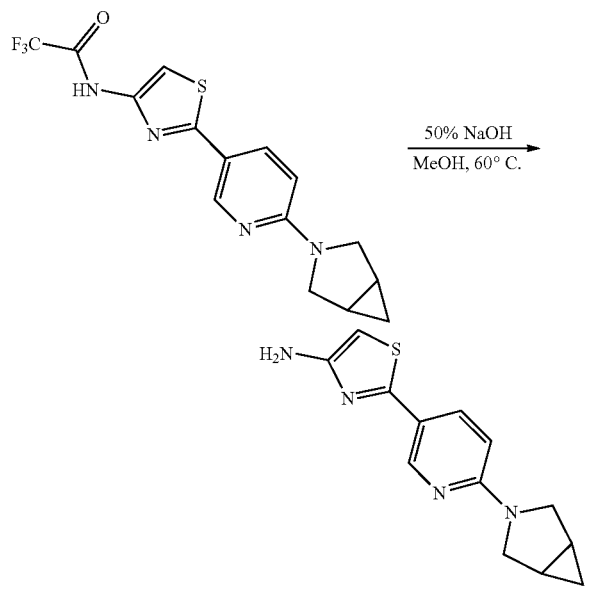

A mixture of N-(2-(6-(3-azabicyclo[3.1.0]hexan-3-yl)pyridin-3-yl)thiazol-4-yl)-2,2,2-trifluoroacetamide (50.0 mg, 0.14 mmol) in MeOH (2 mL) and 50% NaOH (0.3 mL) was stirred at 60° C. overnight. The solvent was removed. The residue was purified by column chromatography (eluted with PE:EA=1:1) to afford the title product (30 mg, 82.0% yield) as a white solid. Retention time (LC-MS): 0.629 min. MH⁺259.

Preparation 29 6'-(3-azabicyclo[3.1.0]hexan-3-yl)-2,3'-bipyridin-6-amine

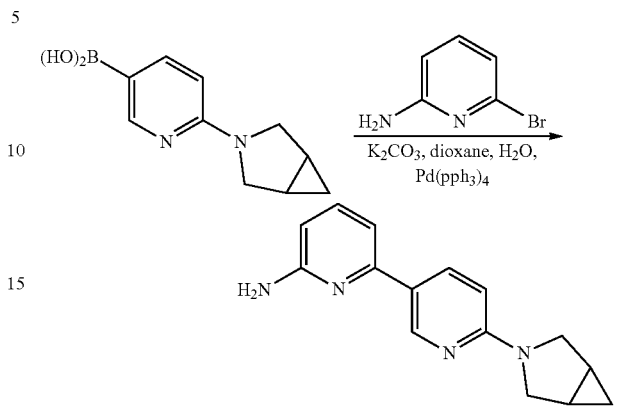

To a mixture of 6-(3-azabicyclo[3.1.0]hexan-3-yl)pyridin-3-ylboronic acid (300 mg, 1.47 mmol) and 6-bromopyridin-2-amine (305 mg, 1.76 mmol) in 1,4-dioxane (5 mL) and H₂O (1 mL) was added potassium carbonate (610 mg, 4.41 mmol). After the mixture was degassed with N₂ for 3 times, Pd(PPh₃)₄ (80.9 mg, 0.07 mmol) was added under N₂ and the mixture was stirred at 100° C. for 3 hrs. The reaction mixture was cooled down and poured into EA. The organic phase was separated, washed with water and brine, dried over Na₂SO₄ and filtered. The filtrate was concentrated under reduced pressure and the residue was purified by chromatography (eluted with DCM:MeOH=50:1) to afford 6'-(3-azabicyclo[3.1.0]hexan-3-yl)-2,3'-bipyridin-6-amine (200 mg, 54.0% yield) as a white solid. Retention time (LC-MS): Retention 0.445 min. MH⁺253.

Preparation 30
2-(2-(diethylamino)pyrimidin-5-yl)thiazol-4-amine

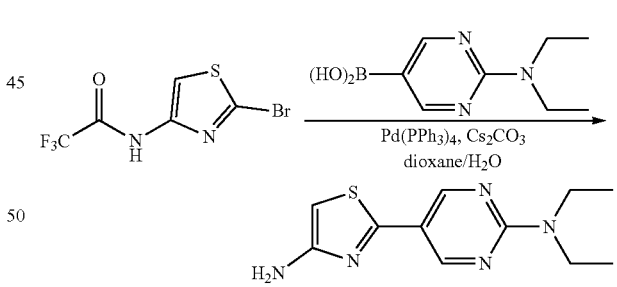

A mixture of 2-(diethylamino)pyrimidin-5-ylboronic acid (600 mg, 3.08 mmol), N-(2-bromothiazol-4-yl)-2,2,2-trifluoroacetamide (864 mg, 3.08 mmol), Pd(PPh₃)₄ (75 mg, 0.06 mmol) and Cs₂CO₃ (3.01g, 9.23 mmol) in 1,4-dioxane (15 mL) and H₂O (3 mL) was degassed and stirred at 110° C. under N₂ overnight. The reaction mixture was cooled down and poured into EA. The organic phase was separated, washed with water and brine, dried over Na₂SO₄ and filtered. The filtrate was concentrated under reduced pressure and the residue was purified by chromatography (eluted with DCM:MeOH=80:1) to afford 2-(2-(diethylamino)pyrimidin-5-yl)thiazol-4-amine (245 mg, yield 31.94%) as a brown solid. Retention time (LC-MS): 1.310 min. MH⁺250.

Preparation 31 (R)-6-(2-(2-(trifluoromethyl)pyrrolidin-1-yl)pyrimidin-5-yl)pyridin-2-amine

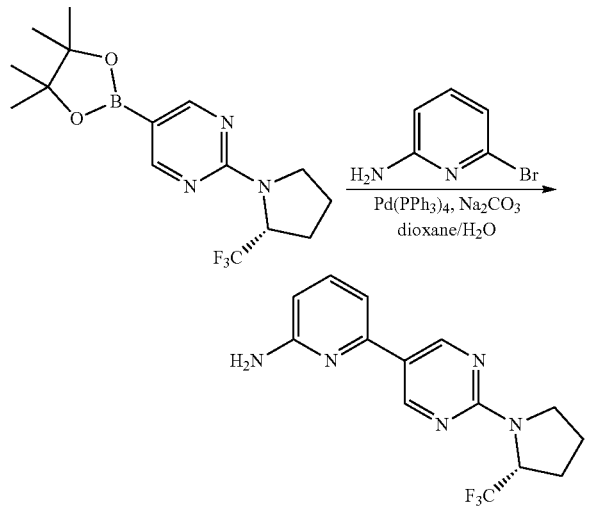

A mixture of (R)-5-(4,4,5,5-tetramethyl-1,3,2-dioxaborolan-2-yl)-2-(2-(trifluoromethyl)pyrrolidin-1-yl)pyrimidine (129 mg, 0.375 mmol), 6-bromopyridin-2-amine (65 mg, 0.375 mmol), Pd(PPh₃)₄ (6 mg, 0.003 mmol) and Na₂CO₃ (119 mg, 1.13 mmol) in 1,4-dioxane (5 mL) and H₂O (1 mL) was degassed and stirred at 110° C. under N₂ overnight. The reaction mixture was cooled down and poured into EA. The organic phase was separated, washed with water and brine, dried over Na₂SO₄ and filtered. The filtrate was concentrated under reduced pressure and the residue was purified by chromatography (eluted with DCM:MeOH=50:1) to afford (R)-6-(2-(2-(trifluoromethyl)pyrrolidin-1-yl)pyrimidin-5-yl)pyridin-2-amine (70 mg, yield 60.24%) as a yellow solid. Retention time (LC-MS): 0.536 min. MH⁺310.

Preparation 32 (R)-6-(2-(2-(trifluoromethyl)pyrrolidin-1-yl)pyrimidin-5-yl)pyrazin-2-amine

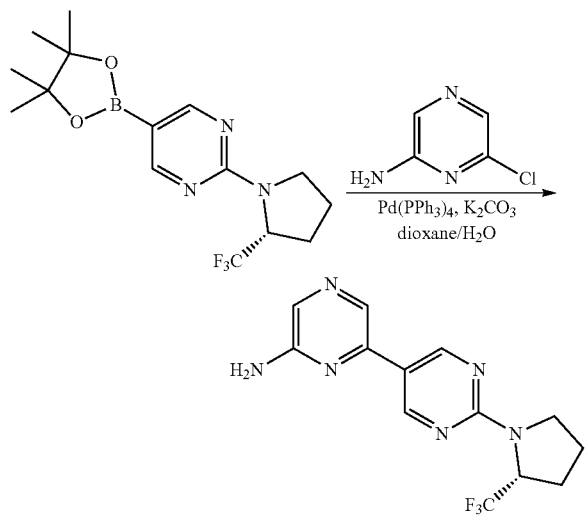

A mixture of (R)-5-(4,4,5,5-tetramethyl-1,3,2-dioxaborolan-2-yl)-2-(2-(trifluoromethyl)pyrrolidin-1-yl)pyrimidine (132 mg, 0.385 mmol), 6-chloropyrazin-2-amine (50 mg, 0.385 mmol), Pd(PPh₃)₄ (6 mg, 0.003 mmol) and potassium carbonate (132 mg, 0.9 mmol) in 1,4-dioxane (5 mL) and H₂O (1 mL) was degassed and stirred at 110° C. under N₂ overnight. The reaction mixture was cooled down and poured into EA. The organic phase was separated, washed with water and brine, dried over Na₂SO₄ and filtered. The filtrate was concentrated under reduced pressure and the residue was purified by chromatography (eluted with DCM/MeOH=50:1) to afford (R)-6-(2-(2-(trifluoromethyl)pyrrolidin-1-yl)pyrimidin-5-yl)pyrazin-2-amine (70 mg, yield 60%) as a yellow solid. Retention time (LC-MS): 1.198 min. MH⁺311.

Preparation 33 6-(6-(3-azabicyclo[3.1.0]hexan-3-yl)pyridin-3-yl)pyrazin-2-amine

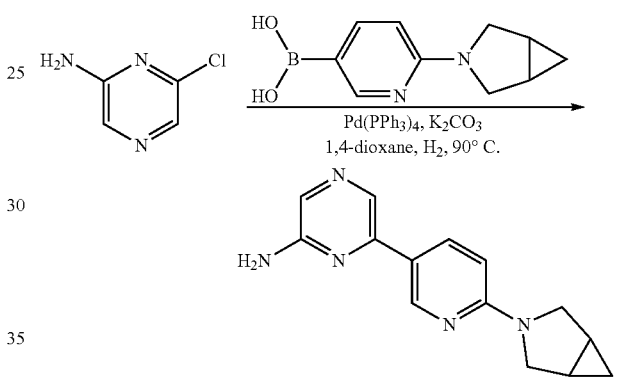

To a mixture of (6-(3-azabicyclo[3.1.0]hexan-3-yl)pyridin-3-yl)boronic acid (163.2 mg, 0.8 mmol), 6-chloropyrazin-2-amine (103.2 mg, 0.8 mmol) in 1,4-dioxane (5 mL) and H₂O (1 mL) was added potassium carbonate (221.1 mg, 1.6 mmol). After the mixture was degassed with N₂ for 3 times, Pd(PPh₃)₄ (46.2 mg, 0.04 mmol) was added under N₂ and the mixture was stirred at 100° C. for 2 hrs. The reaction mixture was cooled down and poured into EA. The organic phase was separated, washed with water and brine, dried over Na₂SO₄ and filtered. The filtrate was concentrated under reduced pressure and the residue was purified by chromatography (eluted with PE:EA=1:1) to afford the title product (140 mg, 69.2% yield) as a white solid. Retention time (LC-MS): 0.353 min. MH⁺254.

Preparation 34 (S)-6-(2-(2-(trifluoromethyl)pyrrolidin-1-yl)pyrimidin-5-yl)pyridin-2-amine

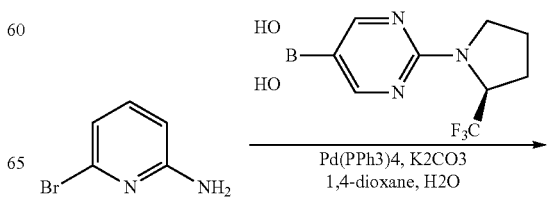

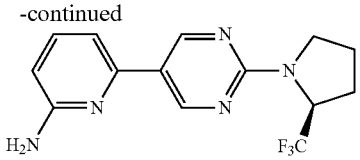

To a mixture of (S)-2-(2-(trifluoromethyl)pyrrolidin-1-yl)pyrimidin-5-ylboronic acid (731 mg, 2.79 mmol), 6-bromopyridin-2-amine (400 mg, 2.32 mmol) in 1,4-dioxane (8 mL) and H$_2$O (1.6 mL) was added potassium carbonate(641 mg, 4.65 mmol). After the mixture was degassed with N$_2$ for three times, Pd(PPh$_3$)$_4$ (133 mg, 0.12 mmol) was added under N$_2$ and the mixture was stirred at 100° C. for 3 hrs. The reaction mixture was cooled down and poured into EA. The organic phase was separated, washed with water and brine, dried over Na$_2$SO$_4$ and filtered. The filtrate was concentrated under reduced pressure and the residue was purified by chromatography (eluted with PE:EA=3:1) to afford (S)-6-(2-(2-(trifluoromethyl)pyrrolidin-1-yl)pyrimidin-5-yl)pyridin-2-amine (550 mg, 76.6% yield) as a white solid. Retention time (LC-MS): Retention 1.556 min. MH$^+$310.

Preparation 35 2-(6-(3-azabicyclo[3.1.0]hexan-3-yl)pyridin-3-yl)pyrimidin-4-amine

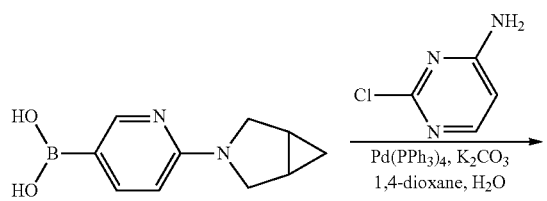

To a mixture of 6-(3-azabicyclo[3.1.0]hexan-3-yl)pyridin-3-ylboronic acid (400 mg, 1.96 mmol), potassium carbonate (542.00 mg, 3.92 mmol) and 2-chloropyrimidine (254.90 mg, 1.96 mmol) in 1,4-dioxane (15 mL) and H$_2$O (3 mL) was added Pd(PPh$_3$)$_4$ (226.47 mg, 0.20 mmol). The reaction mixture was stirred at 100° C. under N$_2$ for 2 h. The mixture was cooled and filtered through Celite, and the filtrate was extracted with EA (3×50 mL). The combined organic layers were dried over Na$_2$SO$_4$ and filtered. The filtrate was concentrated under reduced pressure and the residue was purified with column chromatography (PE:EA=20:1 to =1:1) to afford 2-(6-3-azabicyclo[3.1.0]hexan-3-yl)pyridin-3-yl)pyrimidin-4-amine (150 mg, 30.2% yield) as a yellow solid. Retention time (LC-MS): 0.449 min. MH$^+$254.

Preparation 36 ((R)-2'-(2-(trifluoromethyl)pyrrolidin-1-yl)-2,5'-bipyrimidin-4-amine

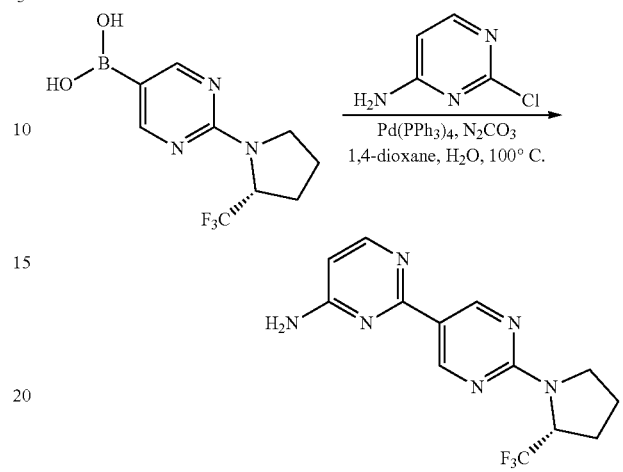

To a mixture of (R)-2-(2-(trifluoromethyl)pyrrolidin-1-yl)pyrimidin-5-ylboronic acid (200 mg, 0.766 mmol), 2-chloropyrimidin-4-amine (88 mg, 0.689 mmol) in 1,4-dioxane (2.3 mL) and H$_2$O (0.75 mL) was added Na$_2$CO$_3$ (162 mg, 1.52 mmol). After the mixture was degassed with N$_2$ for 3 times, Pd(PPh$_3$)$_4$ (28 mg, 0.029 mmol) was added under N$_2$ and the mixture was stirred at 100° C. for 3 hrs. The reaction mixture was cooled down and poured into EA. The organic phase was separated, washed with water and brine, dried over Na$_2$SO$_4$ and filtered. The filtrate was concentrated under reduced pressure and the residue was purified with column chromatography (eluted with PE: acetone =4:1) to afford (R)-2'-(2-(trifluoromethyl)pyrrolidin-1-yl)-2,5'-bipyrimidin-4-amine (200 mg,84% yield) as a white solid. Retention time (LC-MS): Retention 0.361min. MH$^+$311.

Preparation 37 (R)-2-(2-(2-(trifluoromethyl)pyrrolidin-1-yl)pyrimidin-5-yl)thiazol-4-amine

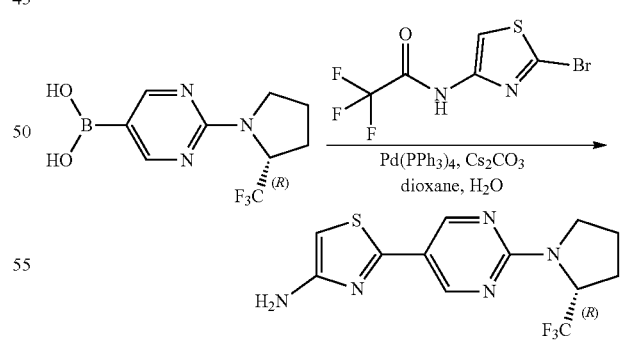

To a mixture of (R)-2-(2-(trifluoromethyl)pyrrolidin-1-yl)pyrimidin-5-ylboronic acid (229 mg, 0.87 mmol), N-(2-bromothiazol-4-yl)-2,2,2-trifluoroacetamide (200 mg, 0.73 mmol) in 1,4-dioxane (4 mL) and H$_2$O (0.8 mL) was added Cs$_2$CO$_3$ (731 mg, 2.19 mmol). After the mixture was degassed with N$_2$ for three times, Pd(PPh$_3$)$_4$ (42 mg, 0.04 mmol) was added and the reaction mixture was stirred at 100° C. under N$_2$ overnight. The mixture was cooled down and poured into EA. The organic phase was separated, washed with water and brine, dried over Na$_2$SO$_4$ and filtered. The filtrate was concentrated under reduced pressure. The filtrate was concentrated and the residue was purified with column chromatography (eluted with DCM: MeOH=100:1) to afford (R)-2-(2-(2-(trifluoromethyl)pyrrolidin-1-yl)pyrimidin-5-yl)thiazol-4-amine (60 mg, 26.02% yield) as a yellow solid. Retention time (LC-MS): 1.651 min. MH$^+$316.

Preparation 38 (S)-2-(3-methyl-2,6-dioxo-2,3-dihydro-1H-purin-7(6H)-yl)-N-(6-(2-(trifluoromethyl)pyrimidin-5-yl)pyridin-2-yl)propanamide

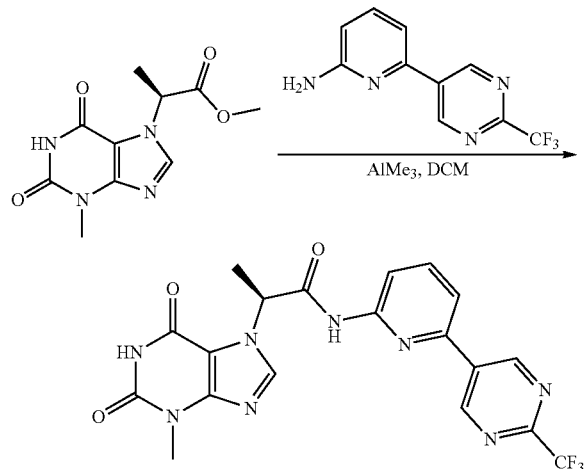

To a solution of 6-(2-(trifluoromethyl)pyrimidin-5-yl)pyridin-2-amine (200 mg, 0.83 mmol) in DCM (5 mL) was added drop-wise trimethylaluminum (2.90 mL, 1M in n-hexane, 2.90 mmol) at 0 oC. After the addition, the mixture was warmed to RT and stirred for 0.5 h. Then a solution of (S)-methyl 2-(3-methyl-2,6-dioxo-2,3-dihydro-1H-purin-7(6H)-yl)propanoate (210 mg, 0.83 mmol) in DCM (2 mL) was added drop-wise and the reaction mixture was stirred at 30° C. overnight. The reaction was quenched by addition of several drops of MeOH. The mixture was concentrated under reduced pressure and the residue was purified by chromatography (PE/EA=1:2) to afford a crude product, which was further purified via preparative HPLC to afford (S)-2-(3-methyl-2,6-dioxo-2,3-dihydro-1H-purin-7(6H)-yl)-N-(6-(2-(trifluoromethyl)pyrimidin-5-yl)pyridin-2-yl)propanamide (250 mg, 55.1% yield) as a white solid. Retention time (LC-MS): 0.573 min. MH$^+$461.

Preparation 39 Oxetan-3-ylmethyl methanesulfonate

To a solution of oxetan-3-ylMeOH (300 mg, 3.40 mmol) and TEA (0.95 mL, 6.80 mmol) in DCM (4 mL) was added dropwise methanesulfonyl chloride (0.4 mL, 5.11 mmol) at 0° C. over 10 min. After the addition, the mixture was stirred at 10° C. to 20° C. for 1.5 h. TLC (PE/EA=3/1, Rf (TM)=0.6, Rf (SM)=0.5, developed by potassium permanganate) showed the starting material was completely consumed. The reaction was quenched by addition of ice-water (5 mL). The organic layer was separated, washed with water (2×3 mL) and brine, dried over Na$_2$SO$_4$ and filtered. The filtrate was concentrated to afford the crude product oxetan-3-ylmethyl methanesulfonate (500 mg, 88.3% yield) as a brick red oil which was used directly in the next step without further purification.

Preparation 40 N-(2-(4-(trifluoromethyl)phenyl)thiazol-4-yl)

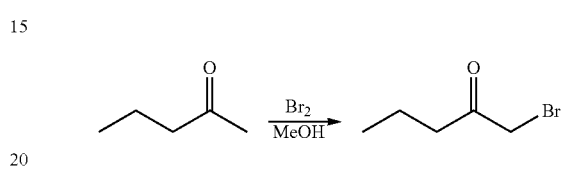

To a solution of pentan-2-one (4 g, 46.5 mmol) in MeOH (45 mL) cooled to -30° C. under a nitrogen atmosphere, Br$_2$ (2.32 mL, 46.5 mmol) was added drop-wise. The reaction mixture was allowed to warm to RT and stirred for 2 hrs, then concentrated in vacuo, diluted with ether and washed with aqueous saturated NaHCO$_3$ solution followed by brine. The organic layer was dried over Na$_2$SO$_4$, filtered and concentrated under reduced pressure. The residue was purified by chromatography (eluted with PE:EA=100:1) to afford 1-bromopentan-2-one (5 g, 65.79% yield) as a brown oil.

Preparation 41 2-(2-(6,6-difluoro-3-azabicyclo[3.1.0]hexan-3-yl)pyrimidin-5-yl)thiazol-4-amine

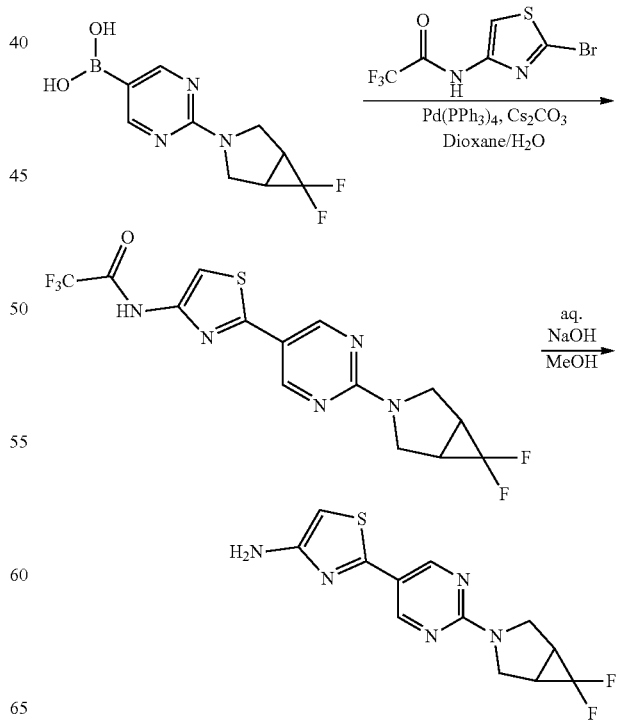

Step 1 N-(2-(2-(6,6-difluoro-3-azabicyclo[3.1.0]
hexan-3-yl)pyrimidin-5-yl)thiazol-4-yl)-2,2,2-trif-
luoroacetamide

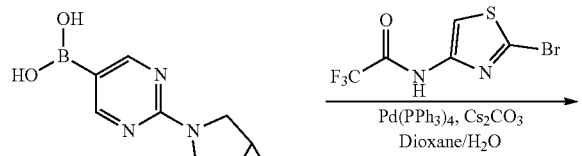

To a solution of 2-(6,6-difluoro-3-azabicyclo[3.1.0]hexan-3-yl)pyrimidin-5-ylboronic acid (300 mg, 1.24 mmol), Cs₂CO₃ (811.17 mg, 2.49 mmol) and N-(2-bromothiazol-4-yl)-2,2,2-trifluoroacetamide (376.62 mg, 1.37 mmol) in 1,4-dioxane (10 mL) and H₂O (1.24 mL) was added Pd(PPh₃)₄ (143.78 mg, 0.12 mmol). After degassed three times under N₂, the reaction mixture was stirred at 110° C. under N₂ for 2 hrs. The mixture was cooled and filtered through Celite, and the filtrate was extracted with EA (3×50 mL). Combined organic layers were dried over Na₂SO₄ and filtered. The filtrate was concentrated under reduced pressure and the residue was purified by chromatography (PE/EA=10 :1 to=1 :1) to afford N-(2-(2-(6,6-difluoro-3-azabicyclo[3.1.0]hexan-3-yl)pyrimidin-5-yl)thiazol-4-yl)-2,2,2-trifluoroacetamide (240 mg, 65.1% yield) as a yellow solid. Retention time (LC-MS): 1.402 min. MH⁺392.

Step 2 2-(2-(6,6-difluoro-3-azabicyclo[3.1.0]hexan-
3-yl)pyrimidin-5-yl)thiazol-4-amine

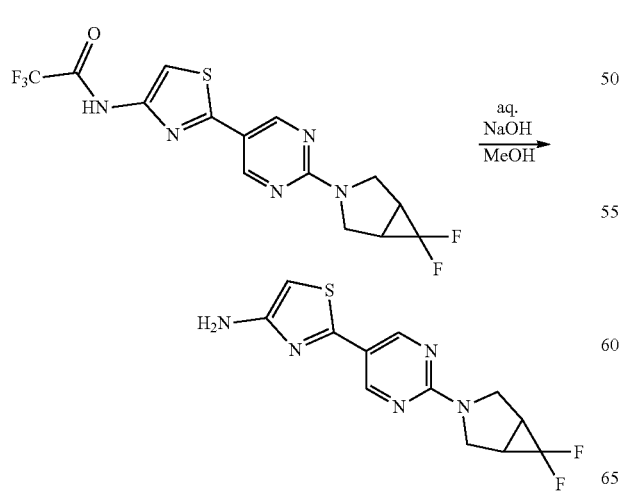

To a solution of N-(2-(2-(6,6-difluoro-3-azabicyclo[3.1.0] hexan-3-yl)pyrimidin-5-yl)thiazol-4-yl)-2,2,2-trifluoroacetamide (240 mg, 0.61 mmol) in MeOH (10 mL) was added NaOH (2 mL, 50% wt) at RT. The reaction mixture was stirred at 80° C. overnight. The mixture was concentrated to dryness and ethanol (4 mL) was added. The slurry was filtered. The solids were washed with water (10 mL ×4) and dried under vacuum to afford 2-(2-(6,6-difluoro-3-azabicyclo[3.1.0]hexan-3-yl)pyrimidin-5-yl)thiazol-4-amine (140 mg, 77.3% yield) as a gray solid. Retention time (LC-MS): 0.856 min. MH⁺296.

Preparation 42 (S)-methyl 2-(1-(3-methoxy-2-oxo-
propyl)-3-methyl-2,6-dioxo-2,3-dihydro-1H-purin-7
(6H)-yl)propanoate

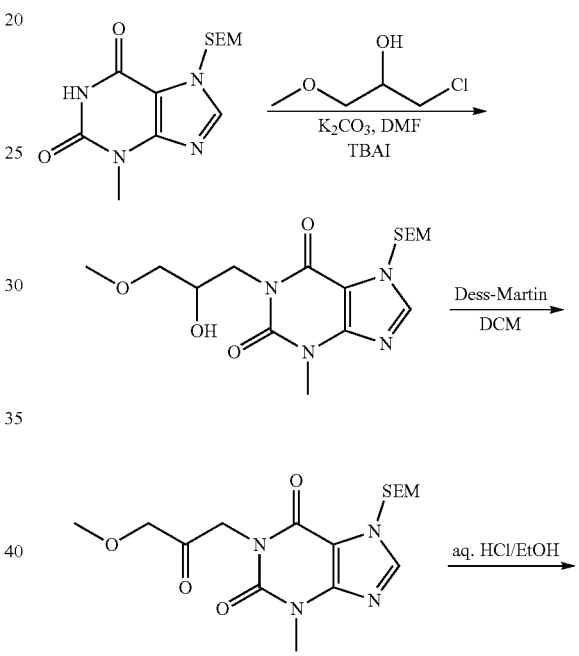

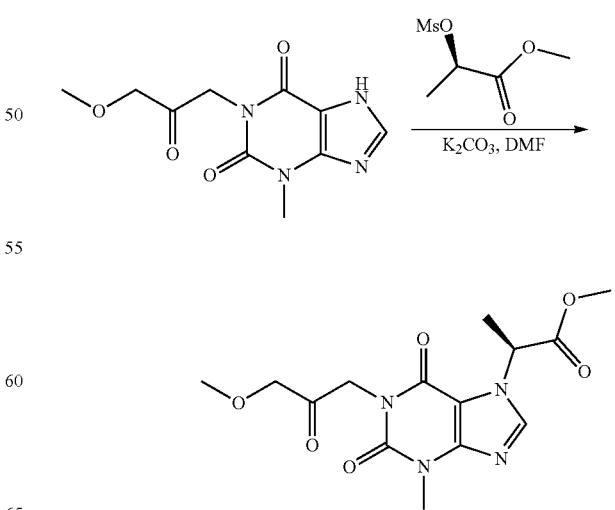

Step 1 1-(2-hydroxy-3-methoxypropyl)-3-methyl-7-((2-(trimethylsilyl)ethoxy)methyl)-1H-purine-2,6(3H,7H)-dione

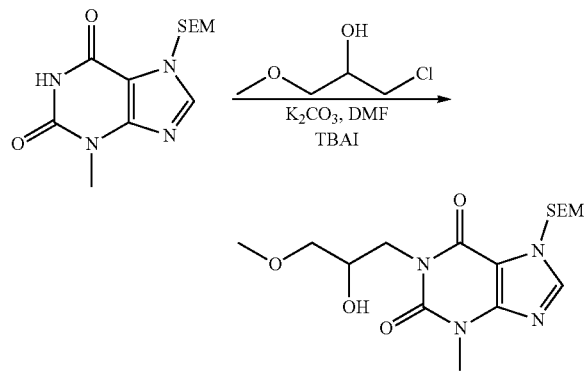

To a solution of 3-methyl-7-((2-(trimethylsilyl)ethoxy)methyl)-1H-purine-2,6(3H,7H)-dione (500 mg, 1.689 mmol) in DMF (10 mL) was added 1-chloro-3-methoxy-propan-2-ol (252 mg, 2.02 mmol) followed by potassium carbonate(466 mg 3.37 mmol) and TBAI (59 mg 0.16 mmol). The mixture was stirred at RT under $N_2$ overnight. The reaction mixture was quenched by water (20 mL), and then extracted with EA (3×10 mL). The combined organic layers were washed by the saturated aqueous lithium chloride solution (15 mL) and brine (15 mL), dried over $Na_2SO_4$ and filtered. The filtrate was concentrated and the residue was purified by chromatography (eluted with DCM:MeOH=80:1) to afford 1-(2-hydroxy-3-methoxypropyl)-3-methyl-7-((2-(trimethylsilypethoxy)methyl)-1H-purine-2,6(3H,7H)-dione (420 mg, 64.75% yield) as a white solid. Retention time (LC-MS): 1.005 min. MH$^+$385.

Step 2 1-(3-methoxy-2-oxopropyl)-3-methyl-7-((2-(trimethylsilyl)ethoxy)methyl)-1H-purine-2,6(3H,7H)-dione

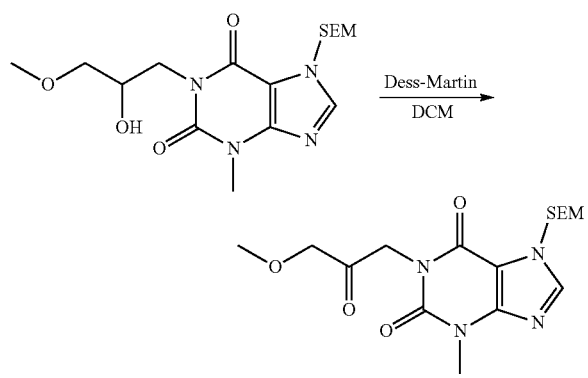

To mixture of 1-(2-hydroxy-3-methoxypropyl)-3-methyl-7-((2-(trimethylsilyl)ethoxy)methyl)-1H-purine-2,6(3H,7H)-dione (350 mg, 0.91 mmol) in DCM (10 mL) was added Dess-Martin periodinane (578 mg, 1.365 mmol) in portions at 0° C. The mixture was stirred at RT overnight. The reaction mixture was quenched by water (8 mL), and then extracted with DCM (3×10 mL). Combined organic layers were washed by the saturated aqueous lithium chloride solution (15 mL) and brine (15 mL), dried over $Na_2SO_4$ and filtered. The filtrate was concentrated and the residue was purified by chromatography (eluted with DCM:MeOH=100:1) to afford 1-(3-methoxy-2-oxopropyl)-3-methyl-7-((2-(trimethylsilyl)ethoxy)methyl)-1H-purine-2,6(3H,7H)-dione (340 mg, 97.65% yield) as a white solid. Retention time (LC-MS): 1.127 min. MH$^+$383.

Step 3 1-(3-methoxy-2-oxopropyl)-3-methyl-1H-purine-2,6(3H,7H)-dione

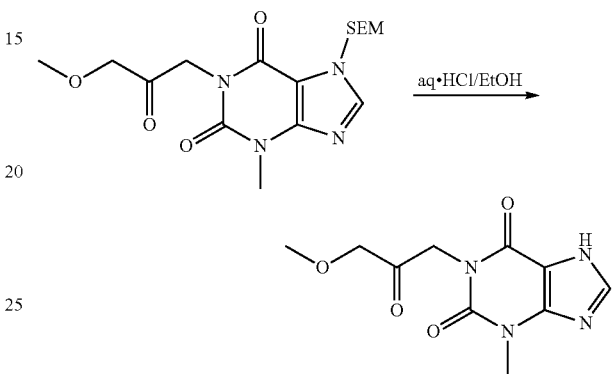

To a solution of 1-(3-methoxy-2-oxopropyl)-3-methyl-7-((2-(trimethylsilyl)ethoxy)methyl)-1H-purine-2,6(3H,7H)-dione (340 mg, 0.88 mmol) in EtOH (6 mL) was added concentrated hydrochloride acid (3 mL), and the mixture was stirred at 90° C. for 2 hrs. The mixture was concentrated to dryness and the residue was dissolved in water (10 mL) and extracted with chloroform/iso-propanol (2/1, 15 mL ×2). The combined organic layers were concentrated to dryness to give crude product, which was purified by chromatography (eluted with DCM:MeOH=20:1) to afford 1-(3-methoxy-2-oxopropyl)-3-methyl-1H-purine-2,6(3H,7H)-dione (140 mg, 62.44% yield) as a yellow solid. Retention time (LC-MS): 0.326 min. MH$^+$253.

Step 4 (S)-methyl 2-(1-(3-methoxy-2-oxopropyl)-3-methyl-2,6-dioxo-2,3-dihydro-1H-purin-7(6H)-yl)propanoate

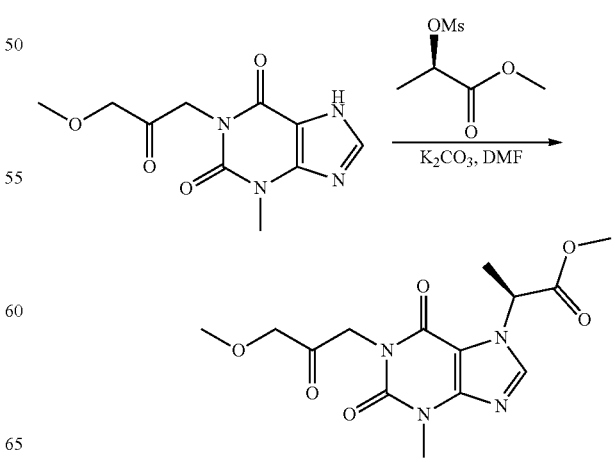

To a solution of 1-(3-methoxy-2-oxopropyl)-3-methyl-1H-purine-2,6(3H,7H)-dione (140 mg, 0.555 mmol) in DMF (10 mL) was added (R)-methyl 2-((methylsulfonyl)oxy)propanoate (202 mg, 1.11 mmol) and potassium carbonate (76.7 mg 0.555). The mixture was stirred at 50° C. overnight. The reaction mixture was quenched by water (10 mL), and then extracted with EA (3×10 mL). The combined organic layers were washed by the saturated aqueous lithium chloride solution (10 mL) and brine (10 mL), dried over Na$_2$SO$_4$ and filtered. The filtrate was concentrated and the residue was purified by chromatography (eluted with DCM:MeOH=100: 1) to afford (S)-methyl 2-(1-(3-methoxy-2-oxopropyl)-3-methyl-2,6-dioxo-2,3-dihydro-1H-purin-7(6H)-yl)propanoate (140 mg, 74.55% yield) as a yellow oil. Retention time (LC-MS): 0.417 min. MH$^+$339.

Preparation 43 6-(2-(6,6-difluoro-3-azabicyclo[3.1.0]hexan-3-yl)pyrimidin-5-yl)pyrazin-2-amine

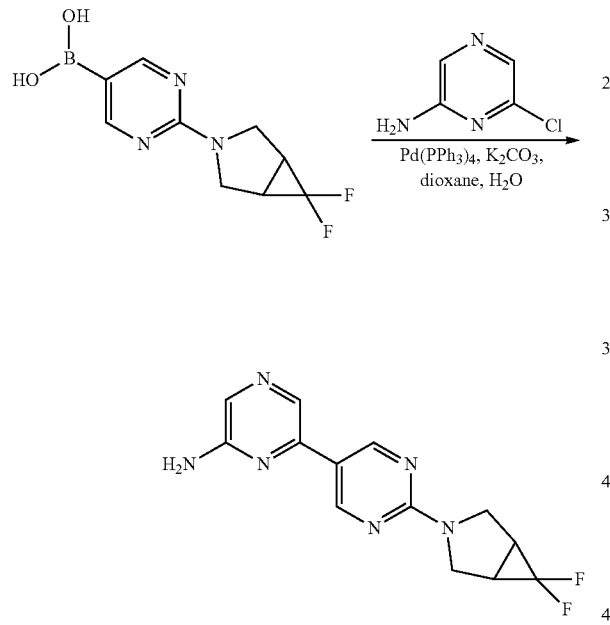

To a mixture of 2-(6,6-difluoro-3-azabicyclo[3.1.0]hexan-3-yl)pyrimidin-5-ylboronic acid (250 mg, 1.04 mmol), 6-chloropyrazin-2-amine (160 mg, 1.24 mmol) in 1,4-dioxane (5 mL) and H$_2$O (1 mL) was added potassium carbonate (287 mg, 2.07 mmol). After the mixture was degassed with N$_2$ for 3 times, Pd(PPh$_3$)$_4$ (25 mg, 0.02 mmol) was added under N$_2$ and the mixture was stirred at 100° C. for 3 hrs. The reaction mixture was cooled down and poured into EA. The organic phase was separated, washed with water and brine, dried over Na$_2$SO$_4$ and filtered. The filtrate was concentrated under reduced pressure and the residue was purified by chromatography (eluted with DCM:MeOH=50:1) to afford 6-(2-(6,6-difluoro-3-azabicyclo[3.1.0]hexan-3-yl)pyrimidin-5-yl)pyrazin-2-amine (160 mg, 53.1% yield) as a yellow solid. Retention time (LC-MS): Retention 0.623 min. MH$^+$290.

Preparation 44 2'-(6,6-difluoro-3-azabicyclo[3.1.0]hexan-3-yl)-[2,5'-bipyrimidin]-4-amine

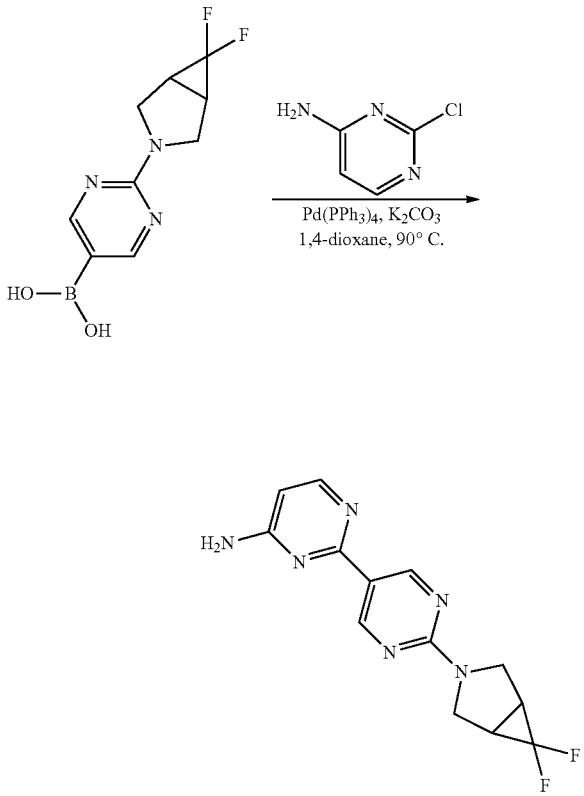

To a mixture of (2-(6,6-difluoro-3-azabicyclo[3.1.0]hexan-3-yl)pyrimidin-5-yl)boronic acid (250.0 mg, 1.0 mmol), 2-chloropyrimidin-4-amine (133.8 mg, 1.0 mmol) in 1,4-dioxane (6 mL) and H$_2$O (1.5 mL) was added potassium carbonate(286.6 mg, 2.1 mmol). After the mixture was degassed with N$_2$ for 3 times, Pd(PPh$_3$)$_4$ (59.9 mg, 0.05 mmol) was added under N$_2$ and the mixture was stirred at 90° C. overnight. The reaction mixture was cooled down and poured into EA. The organic phase was separated, washed with water and brine, dried over Na$_2$SO$_4$ and filtered. The filtrate was concentrated under reduced pressure and the residue was purified by chromatography (eluted with PE:acetone=2:1) to afford the title product (210 mg, 69.8% yield) as a white solid. Retention time (LC-MS): 0.422 min. MH$^+$291.

Preparation 45 6'-(6,6-difluoro-3-azabicyclo[3.1.0]hexan-3-yl)-[2,3'-bipyridin]-6-amine

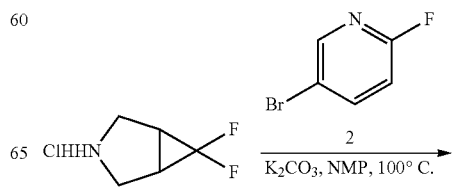

-continued

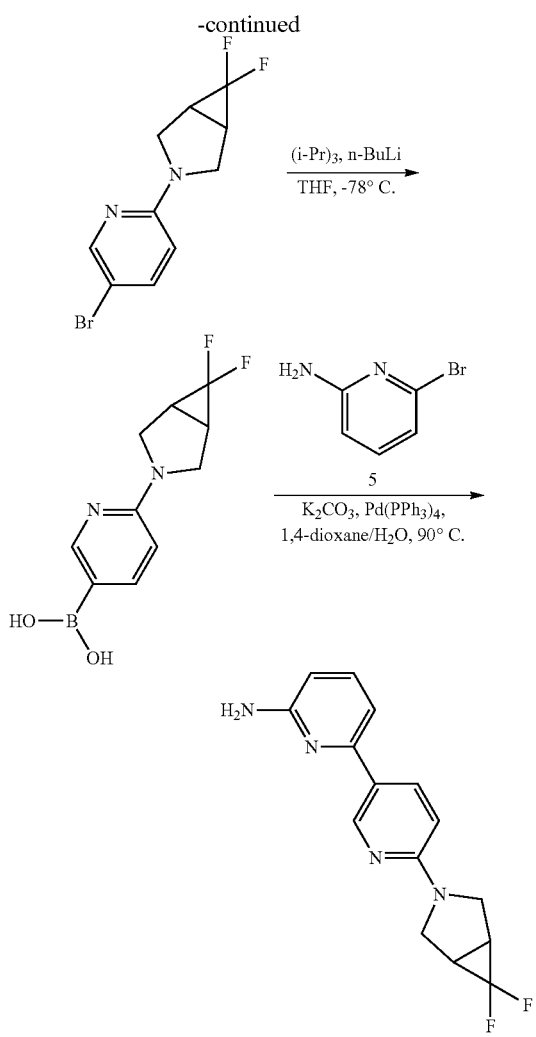

Step 1 3-(5-bromopyridin-2-yl)-6,6-difluoro-3-azabicyclo[3.1.0]hexane

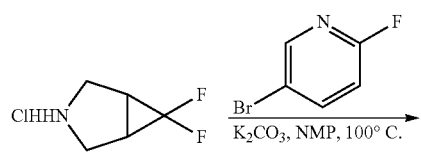

A sealed tube was charged with 6,6-difluoro-3-azabicyclo[3.1.0]hexane hydrochloride (620 mg, 4.0 mmol), 5-bromo-2-fluoropyridine (835.2 g, 4.8 mmol), NMP (5 mL) and potassium carbonate (1.38 g, 10.0 mmol). The mixture was stirred at 100° C. overnight. The mixture was poured into EA. The organic phase was washed with water and brine, dried over $Na_2SO_4$ and filtered. The filtrate was concentrated under reduced pressure. The crude product was purified by chromatography (eluted with PE:EA=10:1) to afford 3-(5-bromopyridin-2-yl)-6,6-difluoro-3-azabicyclo[3.1.0]hexane (680 mg, 62.0% yield) as a white solid. Retention time (LC-MS): 1.249 min. $MH^+$275.

Step 2 (6-(6,6-difluoro-3-azabicyclo[3.1.0]hexan-3-yl)pyridin-3-yl)boronic acid

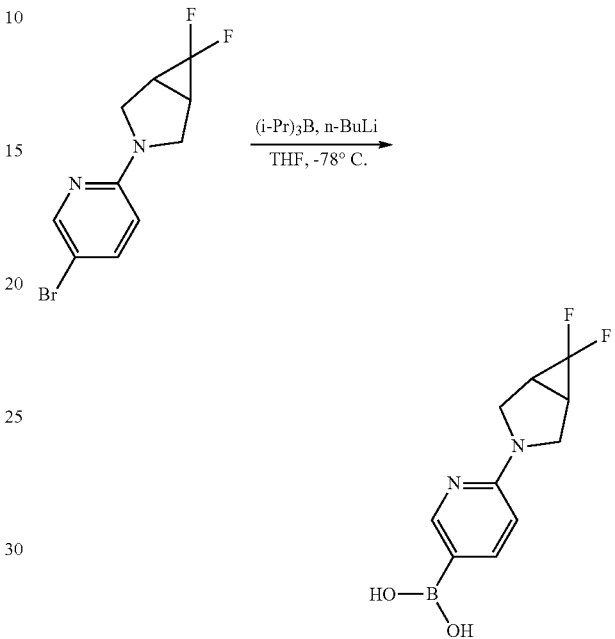

To a solution of 3-(5-bromopyridin-2-yl)-6,6-difluoro-3-azabicyclo[3.1.0]hexane (900.0 mg, 3.3 mmol) and ($^i$PrO)$_3$B (1.14 mL, 4.9 mmol) in THF (10 mL) was added n-BuLi (2.67 mL, 1.6 M in hexane, 6.6 mmol) drop-wise at −78° C. The mixture was stirred at the same temperature for 1 h. The reaction was quenched with water. The solvent was removed under reduced pressure and the aqueous layer was extracted with Ether (2×5 mL). The aqueous layer was then adjusted to pH 8 with 1N HCl and extracted with EA (3×30 mL). Combined organic layers were washed with brine, dried over $Na_2SO_4$, and concentrated to give the title product (780 mg, 98.9% yield) as a white solid. Retention time (LC-MS): 0.347 min. $MH^+$241.

Step 3 6'-(6,6-difluoro-3-azabicyclo[3.1.0]hexan-3-yl)-[2,3'-bipyridin]-6-amine

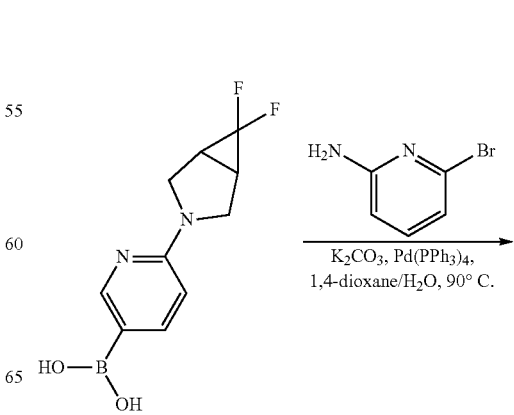

-continued

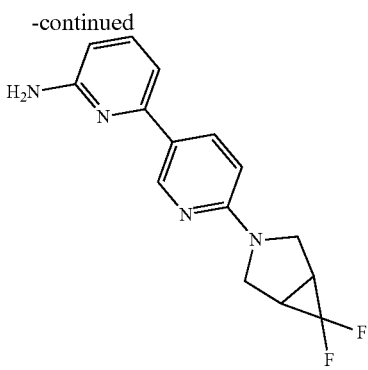

To a mixture of (6-(6,6-difluoro-3-azabicyclo[3.1.0]hexan-3-yl)pyridin-3-yl)boronic acid (300.0 mg, 1.25 mmol), 6-bromopyridin-2-amine (215.0 mg, 1.25 mmol) in 1,4-dioxane (5 mL) and H$_2$O (1 mL) was added potassium carbonate (345.5 mg, 2.5 mmol). After the mixture was degassed with N$_2$ for 3 times, Pd(PPh$_3$)$_4$ (72.2 mg, 0.06 mmol) was added under N$_2$ and the mixture was stirred at 90° C. for 2 hrs. The reaction mixture was cooled down and poured into EA. The organic phase was separated, washed with water and brine, dried over Na$_2$SO$_4$ and filtered. The filtrate was concentrated under reduced pressure and the residue was purified by chromatography (eluted with PE:EA=1:1) to afford the title product (280 mg, 77.8% yield) as a white solid. Retention time (LC-MS): 0.321 min. MH$^+$289.

Preparation 46 2-(6-(6,6-difluoro-3-azabicyclo[3.1.0]hexan-3-yl)pyridin-3-yl)pyrimidin-4-amine

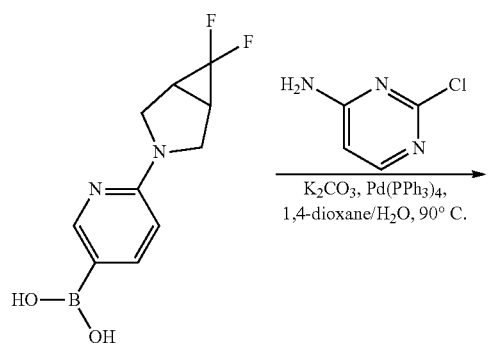

To a mixture of (6-(6,6-difluoro-3-azabicyclo[3.1.0]hexan-3-yl)pyridin-3-yl)boronic acid (240.0 mg, 1.0 mmol), 2-chloropyrimidin-4-amine (129.0 mg, 1.0 mmol) in 1,4-dioxane (5 mL) and H$_2$O (1 mL) was added potassium carbonate (276.4 mg, 2.0 mmol). After the mixture was degassed with N$_2$ for 3 times, Pd(PPh$_3$)$_4$ (57.8 mg, 0.05 mmol) was added under N$_2$ and the mixture was stirred at 90° C. for 3 hrs. The reaction mixture was cooled down and poured into EA. The organic phase was separated, washed with water and brine, dried over Na$_2$SO$_4$ and filtered. The filtrate was concentrated under reduced pressure and the residue was purified by chromatography (eluted with PE:EA=1:1) to afford the title product (140 mg, 58.1% yield) as a white solid. Retention time (LC-MS): 0.365 min. MH$^+$290.

Preparation 47 (S)-2-(3-methyl-2,6-dioxo-2,3-dihydro-1H-purin-7(6H)-yl)-N-(6-(2-(trifluoromethyl)pyrimidin-5-yl)pyridin-2-yl)propanamide

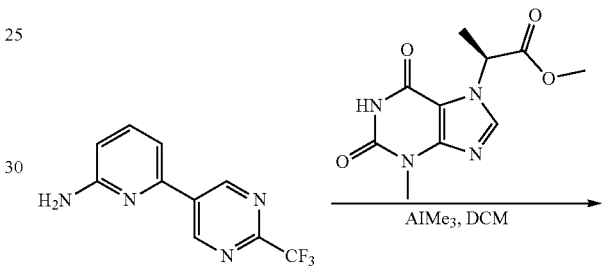

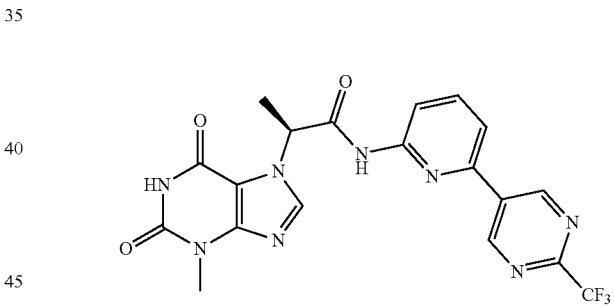

To a mixture of 6-(2-(trifluoromethyl)pyrimidin-5-yl)pyridin-2-amine (200 mg, 0.83 mmol) in DCM (10 mL) was added trimethylaluminium (3.32 mL, 3.32 mmol) at 0° C. The mixture was stirred at 0° C. for 30 min, followed by (S)-methyl 2-(3-methyl-2,6-dioxo-2,3-dihydro-1H-purin-7(6H)-yl)propanoate (210 mg, 0.83 mmol) was added. The final mixture was stirred at 30° C. overnight. The mixture was concentrated under reduced pressure directly and the residue was purified by chromatography (DCM:MeOH=20:1) to afford (S)-2-(3-methyl-2,6-dioxo-2,3-dihydro-1H-purin-7(6H)-yl)-N-(6-(2-(trifluoromethyl)pyrimidin-5-yl)pyridin-2-yl)propanamide (150 mg, 39% yield, ee: 99%) as a white solid. Retention time (LC-MS): 1.796min. MH$^+$460. 1H NMR (400 MHz, DMSO) δ 11.25 (s, 1H), 9.68 (s, 2H), 8.33 (s, 1H), 8.18-7.87 (m, 3H), 5.78 (d, J=10.4 Hz, 1H), 3.39 (s, 3H), 1.86 (d, J=7.3 Hz, 3H), 1.24 (s, 1H).

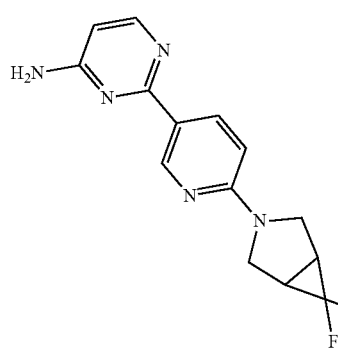

Preparation 48 (2S)-N-(2-(2-(3-azabicyclo[3.1.0]hexan-3-yl)pyrimidin-5-yl)thiazol-4-yl)-2-(3-methyl-2,6-dioxo-2,3-dihydro-1H-purin-7(6H)-yl)propanamide

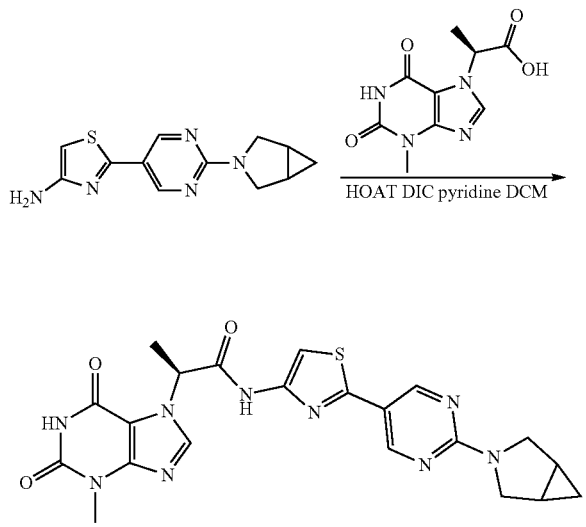

To a solution of (S)-2-(3-methyl-2,6-dioxo-2,3-dihydro-1H-purin-7(6H)-yl)propanoic acid (275 mg, 1.16 mmol) and 2-(2-(3-azabicyclo[3.1.0]hexan-3-yl)pyrimidin-5-yl)thiazol-4-amine (300 mg, 1.16 mmol) in DCM (20 mL) was added HOAt (157 mg, 1.16 mmol) at RT. The reaction mixture was cooled under ice-water bath to 0° C., and pyridine (0.19 mL, 2.31 mmol) was added drop-wise followed by drop-wise addition of DIC (0.27 mL, 1.74 mmol) under $N_2$ protection. The ice-water bath was removed after the addition and the mixture was stirred at 30° C. overnight. The reaction mixture was washed with water (20 mL). The DCM layer was separated, and the aqueous layer was extracted with DCM (20 mL ×2). The combined organic layers were dried over $Na_2SO_4$, filtered, concentrated under reduced pressure directly and the residue was purified by chromatography (DCM:MeOH=20:1) to afford (2S)-N-(2-(2-(3-azabicyclo[3.1.0]hexan-3-yl)pyrimidin-5-yl)thiazol-4-yl)-2-(3-methyl-2,6-dioxo-2,3-dihydro-1H-purin-7(6H)-yl)propanamide (500 mg, 90% yield, ee >98%) as a white solid. Retention time (LC-MS): 4.217 min. MEt 479.

Preparation 49 6-(2-(6,6-difluoro-3-azabicyclo[3.1.0]hexan-3-yl)pyrimidin-5-yl)pyrazin-2-amine

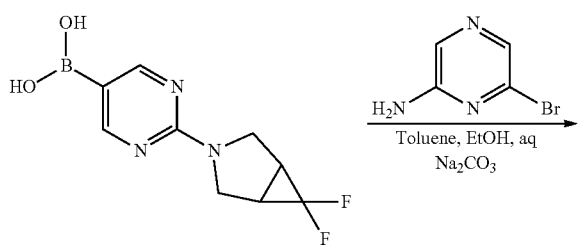

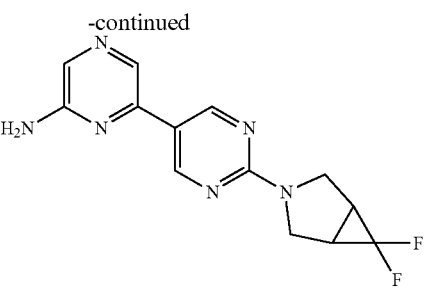

mixture of 2-(6,6-difluoro-3-azabicyclo[3.1.0]hexan-3-yl)pyrimidin-5-ylboronic acid (300 mg, 1.5 mmol) and 6-bromopyrazin-2-amine (238 mg, 1.37 mmol) in toluene/ethanol (4 mL/2 mL) was added aqueous $Na_2CO_3$ solution (1 mL, 2M) and the mixture was degassed under $N_2$ for three times. To the above mixture, 6-tetrakis(triphenylphosphine)palladium (30 mg, 0.04 mmol) were added under $N_2$ and the reaction mixture was stirred at 100° C. under $N_2$ for 2 h. The mixture was diluted with DCM, washed with brine, dried over $Na_2SO_4$, concentrated and purified by chromatography (eluted with PE:EA=2:1) to give 6-(2-(6,6-difluoro-3-azabicyclo[3.1.0]hexan-3-yl)pyrimidin-5-yl)pyrazin-2-amine (210 mg, 58.1% yield) as a white solid. Retention time (LC-MS): 1.359 min. $MH^+291$.

Preparation 50 6-(6-(6,6-difluoro-3-azabicyclo[3.1.0]hexan-3-yl)pyridin-3-yl)pyrazin-2-amine

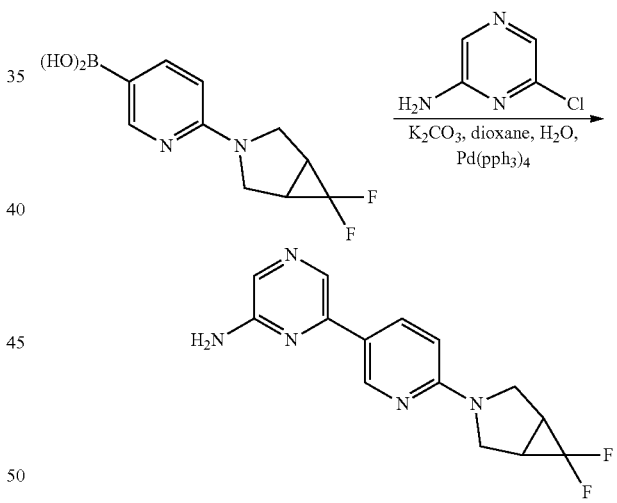

To a mixture of 6-(6,6-difluoro-3-azabicyclo[3.1.0]hexan-3-yl)pyridin-3-ylboronic acid (220 mg, 0.9 mmol), 6-chloropyrazin-2-amine (190 mg, 1.1 mmol) in 1,4-dioxane (5 mL) and $H_2O$ (1 mL) was added potassium carbonate (380 mg, 2.8 mmol). After the mixture was degassed with $N_2$ for three times, $Pd(PPh_3)_4$ (23.0 mg, 0.02 mmol) was added under $N_2$ and the mixture was stirred at 100° C. for 4 hrs. The reaction mixture was cooled down and diluted EA (15 mL). The mixture was washed with water and brine, dried over $Na_2SO_4$ and filtered. The filtrate was concentrated under reduced pressure and the residue was purified by chromatography (eluted with PE:EA=5:1) to afford 6-(6-(6,6-difluoro-3-azabicyclo[3.1.0]hexan-3-yl)pyridin-3-yl)pyrazin-2-amine (160 mg, 60.3% yield) as a light yellow solid. Retention time (LC-MS): 0.509 min. $MH^+290$.

Preparation 51 6-(5-(trifluoromethyl)-1,2,4-oxadiazol-3-yl)pyridin-2-amine

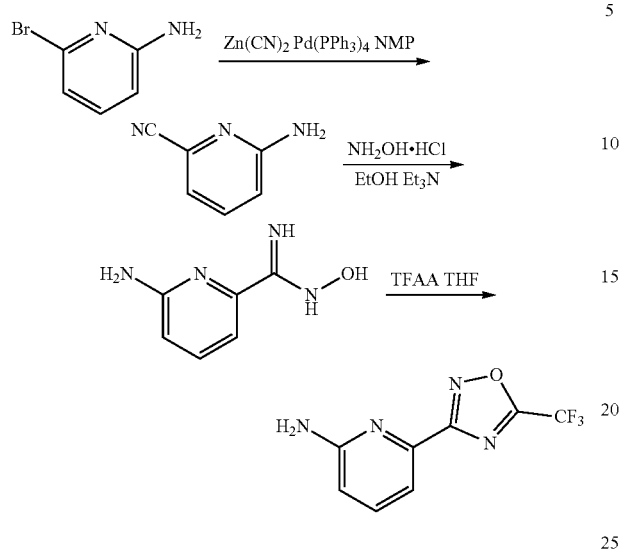

Step 1 6-aminopicolinonitrile

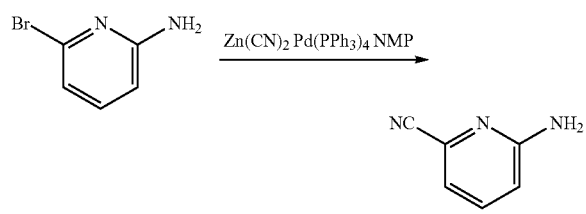

In a microwave reaction tube containing 6-bromopyridin-2-amine (1 g, 5.8 mmol), Zn(CN)$_2$ (1.4 g, 11.6 mmol) and NMP (10 mL) was added Pd(PPh$_3$)$_4$ (0.67 g, 0.58 mmol). The mixture was heated in a Biotage Microwave Initiator device at 150° C. for 30 min. The mixture was poured into EA. The organic phase was washed with water and brine, dried over Na$_2$SO$_4$ and filtered. The filtrate was concentrated under reduced pressure. The crude product was purified by chromatography (eluted with PE:EA=5:1) to afford 6-aminopicolinonitrile (600 mg, 86.96% yield) as a white solid. Retention time (LC-MS): 0.378 min. MH$^+$120.

Step 2 6-amino-N-hydroxypicolinimidamide

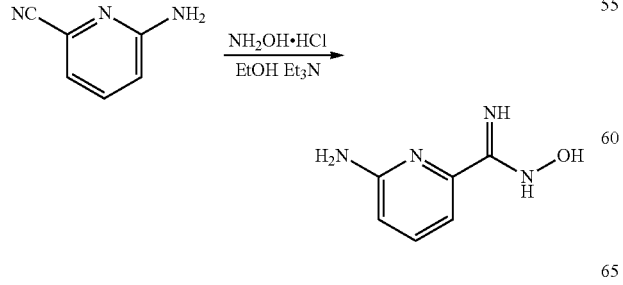

To a solution of 6-aminopicolinonitrile (600 mg, 5.1 mmol) in ethanol (6 mL) and water (3 mL) was added hydroxylamine hydrochloride (711 mg, 10.2 mmol) and sodium carbonate (1.6 g, 15.3 mmol) and the mixture was stirred at 85° C. for 1 h. The mixture was concentrated under reduced pressure, the residue was washed with water and extracted with chloroform/isopropanol (3:1). The organic layer was dried over Na$_2$SO$_4$, and evaporated to afford 6-amino-N-hydroxypicolinimidamide (500 mg, 72.67% yield) as a yellow solid. Retention time (LC-MS): 0.348 min. MH$^+$153.

Step 3 6-(5-(trifluoromethyl)-1,2,4-oxadiazol-3-yl)pyridin-2-amine

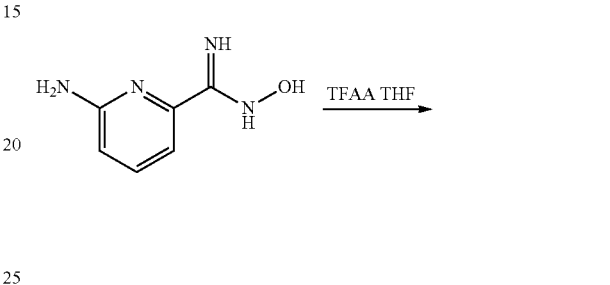

To a solution of 6-amino-N-hydroxypicolinimidamide (250 mg, 1.85 mmol)in in THF (5 mL) was added drop-wise trifluoroacetic anhydride (0.05 mL, 3.70 mmol) at 0° C. and the mixture was heated at 60° C. overnight. The reaction mixture was concentrated, diluted with water, extracted with EA (3×10 mL). The organic layers were washed with brine, dried over sodium sulfate and concentrated. The crude product obtained was purified by chromatography (eluted with PE:EA=5:1) to afford 6-(5-(trifluoromethyl)-1,2,4-oxadiazol-3-yl)pyridin-2-amine (80 mg, 18.82% yield) as a white solid. Retention time (LC-MS): 0.953 min. MH$^+$231.

Preparation 52 2-(6-(6,6-difluoro-3-azabicyclo[3.1.0]hexan-3-yl)pyridin-3-yl)thiazol-4-amine

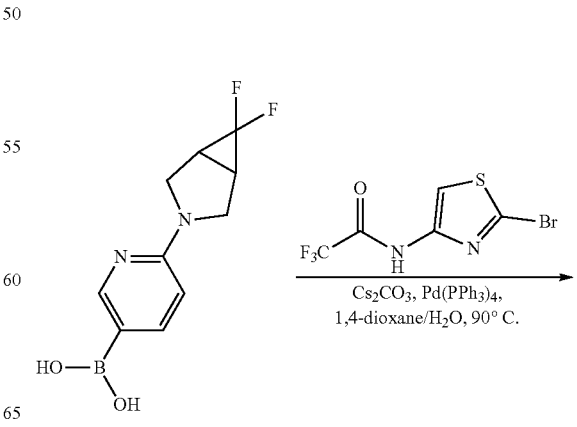

-continued

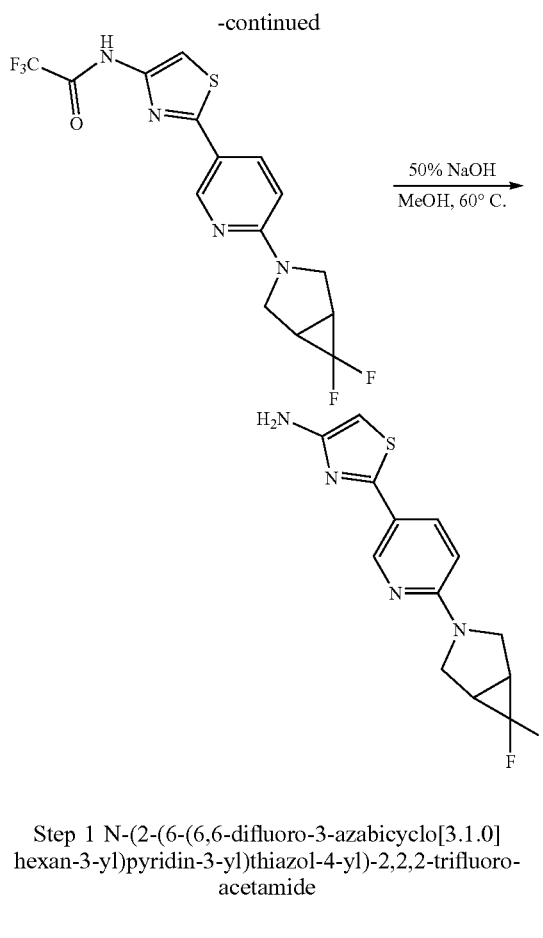

Step 1 N-(2-(6-(6,6-difluoro-3-azabicyclo[3.1.0]
hexan-3-yl)pyridin-3-yl)thiazol-4-yl)-2,2,2-trifluoro-
acetamide

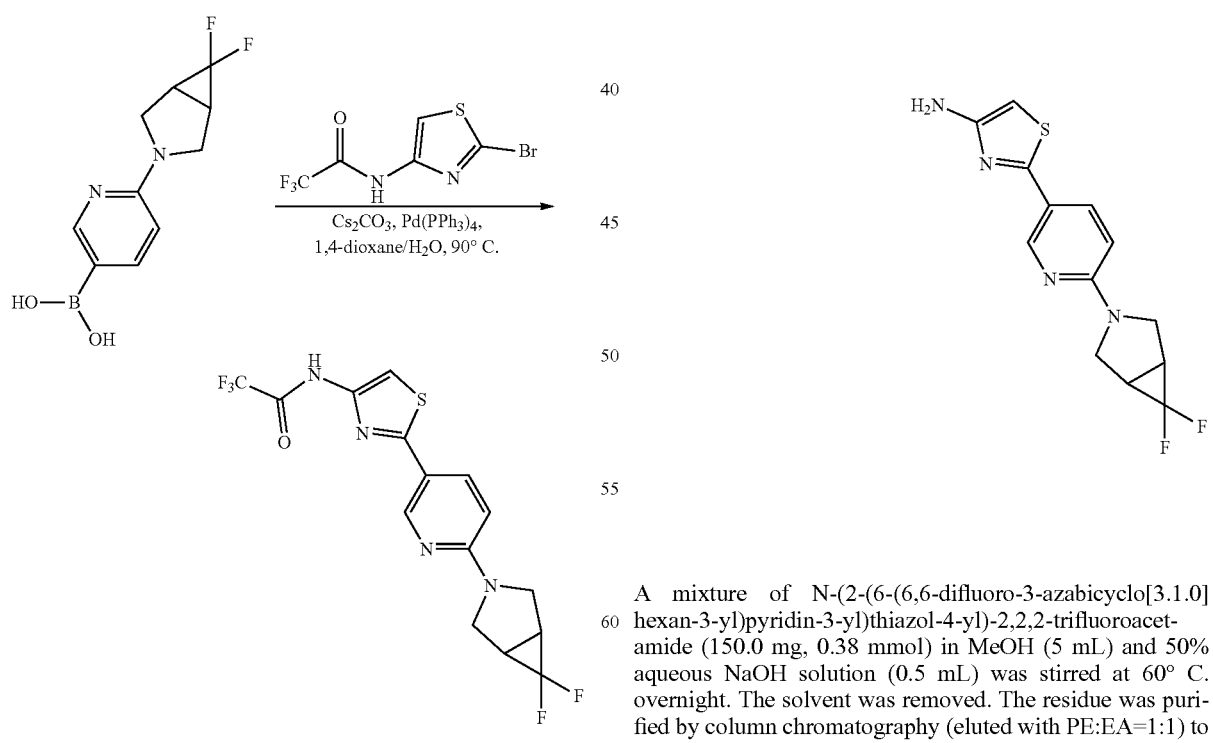

To a mixture of (6-(6,6-difluoro-3-azabicyclo[3.1.0]hexan-3-yl)pyridin-3-yl)boronic acid (240.0 mg, 1.0 mmol), N-(2-bromothiazol-4-yl)-2,2,2-trifluoroacetamide (273.9 mg, 1.0 mmol) in 1,4-dioxane (8 mL) and H₂O (2 mL) was added Cs₂CO₃ (978.0 mg, 3.0 mmol). After the mixture was degassed with N₂ for 3 times, Pd(PPh₃)₄ (57.8 mg, 0.05 mmol) was added under N₂ and the mixture was stirred at 90° C. for 2 hrs. The reaction mixture was cooled down and poured into EA. The organic phase was separated, washed with water and brine, dried over Na₂SO₄ and filtered. The filtrate was concentrated under reduced pressure and the residue was purified by chromatography (eluted with PE:EA=10:1) to afford N-(2-(6-(6,6-difluoro-3-azabicyclo[3.1.0]hexan-3-yl)pyridin-3-yl)thiazol-4-yl)-2,2,2-trifluoro-acetamide (150 mg, 46.1% yield) as a white solid. Retention time (LC-MS): 1.447 min. MH⁺391.

Step 2 2-(6-(6,6-difluoro-3-azabicyclo[3.1.0]hexan-3-yl)pyridin-3-yl)thiazol-4-amine

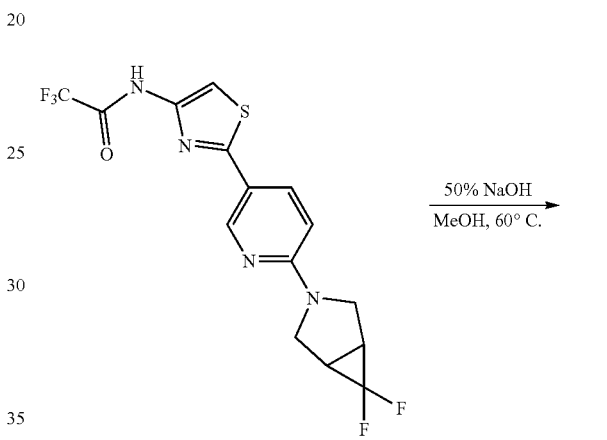

A mixture of N-(2-(6-(6,6-difluoro-3-azabicyclo[3.1.0]hexan-3-yl)pyridin-3-yl)thiazol-4-yl)-2,2,2-trifluoroacet-amide (150.0 mg, 0.38 mmol) in MeOH (5 mL) and 50% aqueous NaOH solution (0.5 mL) was stirred at 60° C. overnight. The solvent was removed. The residue was purified by column chromatography (eluted with PE:EA=1:1) to afford 2-(6-(6,6-difluoro-3-azabicyclo[3.1.0]hexan-3-yl)pyridin-3-yl)thiazol-4-amine (100 mg, 88.4% yield) as light yellow solid. Retention time (LC-MS): 0.844 min. MH⁺295.

Preparation 53 2-(5-methyl-6-(trifluoromethyl)pyridin-3-yl)thiazol-4-amine

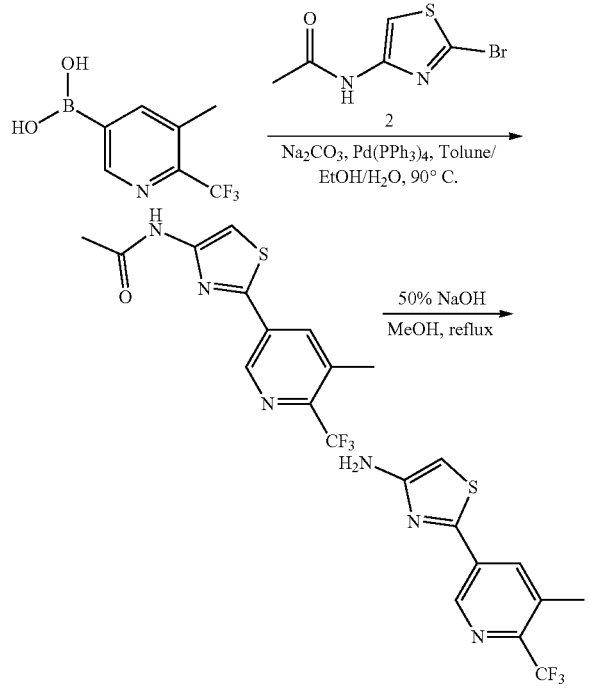

Step 1 N-(2-(5-methyl-6-(trifluoromethyl)pyridin-3-yl)thiazol-4-yl)

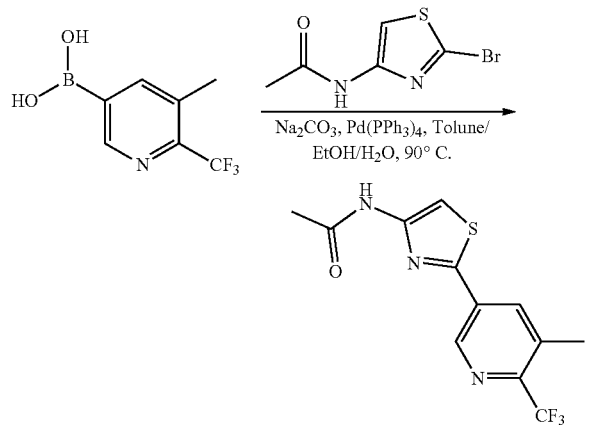

To a mixture of (5-methyl-6-(trifluoromethyl)pyridin-3-yl) boronic acid (451.0 mg, 2.2 mmol), N-(2-bromothiazol-4-yl)acetamide (483.8 mg, 2.2 mmol) in 1,4-dioxane (12 mL) and H₂O (3 mL) was added Cs₂CO₃ (1.8 g, 5.5 mmol). After the mixture was degassed with N₂ for 3 times, Pd(PPh₃)₄ (127.1 mg, 0.11 mmol) was added under N₂ and the mixture was stirred at 90° C. for 3 hrs. The reaction mixture was cooled down and poured into EA. The organic phase was separated, washed with water and brine, dried over Na₂SO₄ and filtered. The filtrate was concentrated under reduced pressure and the residue was purified by chromatography (eluted with PE:EA=3:1) to afford the title product (500 mg, 75.7% yield) as light yellow solid. Retention time (LC-MS): 1.331 min. MH⁺302.

Step 2 2-(5-methyl-6-(trifluoromethyl)pyridin-3-yl)thiazol-4-amine

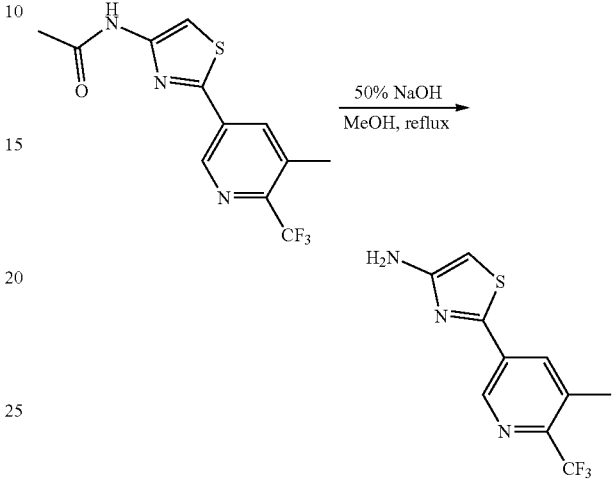

A mixture of N-(2-(5-methyl-6-(trifluoromethyl)pyridin-3-yl)thiazol-4-yl)acetamide (500.0 mg, 1.7 mmol) in MeOH (10 mL) and 50% NaOH (0.8 mL) was stirred at 85° C. overnight. The solvent was removed. The residue was purified by column chromatography (eluted with PE:EA=1:1) to afford the title product (360 mg, 83.6% yield) as a white solid. Retention time (LC-MS): 1.243 min. MH⁺260.

Preparation 54 2-(5-methyl-6-(trifluoromethyl)pyridin-3-yl)pyrimidin-4-amine

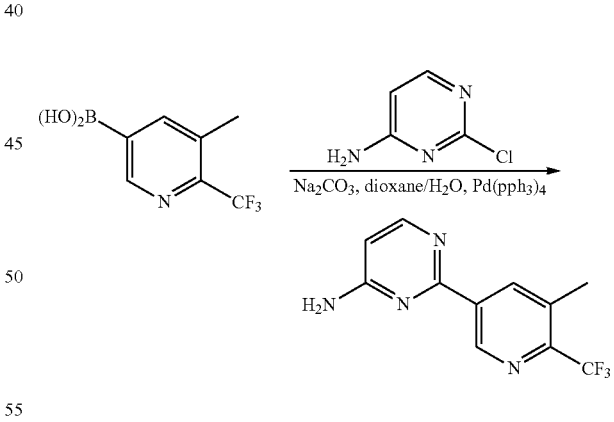

To a mixture of 5-methyl-6-(trifluoromethyl)pyridin-3-ylboronic acid (50 mg, 0.24 mmol), 2-chloropyrimidin-4-amine (35 mg, 0.27 mmol) in 1,4-dioxane (5 mL) and H₂O (1 mL) was added Na₂CO₃ (78 mg, 0.73 mmol). After the mixture was degassed with N₂ for 3 times, Pd(PPh₃)₄ (5.0 mg, 0.01 mmol) was added under N₂ and the mixture was stirred at 100° C. overnight. The reaction mixture was cooled down and poured into EA. The organic phase was separated, washed with water and brine, dried over Na₂SO₄ and filtered. The filtrate was concentrated under reduced pressure and the residue was purified by chromatography (eluted with PE:EA=5:1) to afford 2-(5-methyl-6-(trifluoromethyl)pyridin-3-yl)pyrimidin-4-amine (58 mg, 93.5% yield) as light yellow solid. Retention time (LC-MS): 0.522 min. MH⁺255.

Preparation 55 5'-(3-azabicyclo[3.1.0]hexan-3-yl)-2,2'-bipyrazin-6-amine

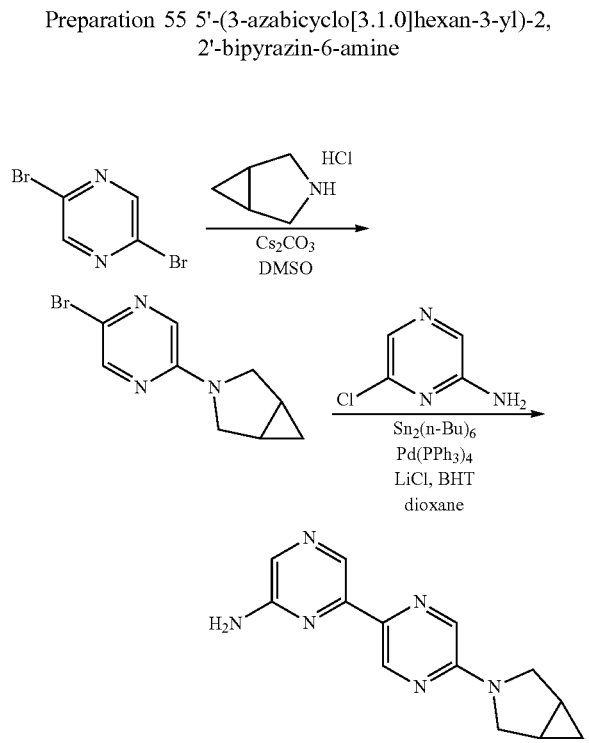

Step 1 3-(5-bromopyrazin-2-yl)-3-azabicyclo[3.1.0]hexane

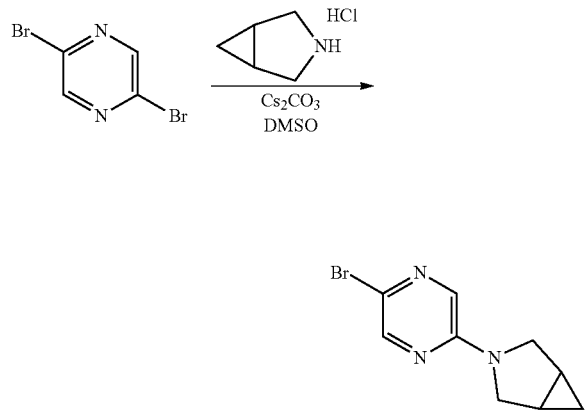

To a solution of 2,5-dibromopyrazine (1 g, 4.2 mmol) in DMSO (20 mL) was added 3-azabicyclo[3.1.0]hexane hydrochloride (0.6 g, 5.04 mmol) followed by $Cs_2CO_3$ and the mixture was stirred at 100° C. in an sealed tube for 2 hrs. The mixture was cooled and diluted with EA (50 mL) and washed with water, brine successively, dried and concentrated to give crude product, which was purified by chromatography (PE/EA=5:1) to give 3-(5-bromopyrazin-2-yl)-3-azabicyclo[3.1.0]hexane (560 mg, 55.5% yield) as yellow solid. Retention time (LC-MS): 1.468 min. MH⁺240.

Step 2 5'-(3-azabicyclo[3.1.0]hexan-3-yl)-2,2'-bipyrazin-6-amine

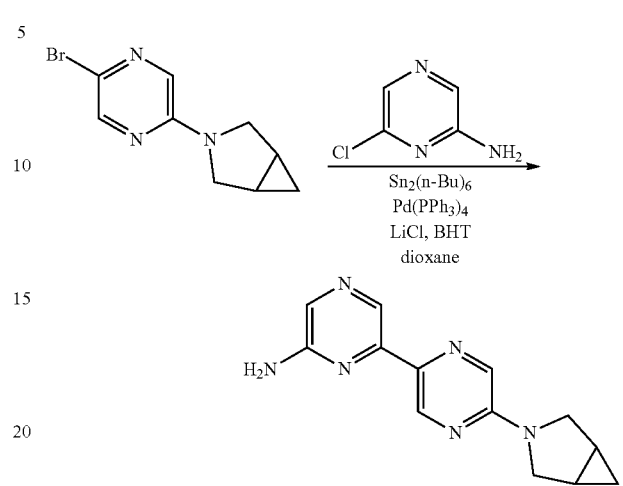

A mixture of 3-(5-bromopyrazin-2-yl)-3-azabicyclo[3.1.0] hexane (400 mg, 1.66 mmol), 6-chloropyrazin-2-amine (1.08 g, 8.33 mmol), LiCl (84.35 mg, 1.99 mmol) and 2,6-di-tert-butyl-4-methylphenol (36.6 mg, 0.166 mmol) in 1,4-dioxane (25 mL) was degassed under $N_2$ for three times and terakis(triphenylphosphine)palladium (153 mg, 0.133 mmol) was added under $N_2$ atmosphere. The mixture was degassed again and Hexa-n-butyldizinn (1.15 g, 1.99 mmol) was added, the reaction mixture was stirred under $N_2$ at 110° C. overnight. The mixture was concentrated to dryness and the crude product was purified column chromatography (DCM/MeOH=50:1 to 20:1) to give 5'-(3-azabicyclo[3.1.0] hexan-3-yl)-2,2'-bipyrazin-6-amine (140 mg. 33.2% yield) as brown solid. Retention time (LC-MS): 1.023 min. MH⁺255.

Preparation 56 6-(5-(3-azabicyclo[3.1.0]hexan-3-yl)pyrazin-2-yl)pyridin-2-amine

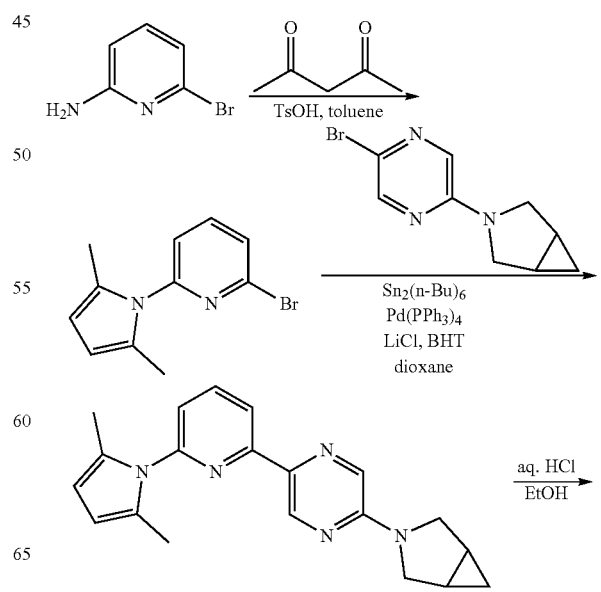

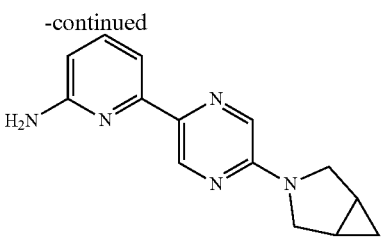

Step 1
2-bromo-6-(2,5-dimethyl-1H-pyrrol-1-yl)pyridine

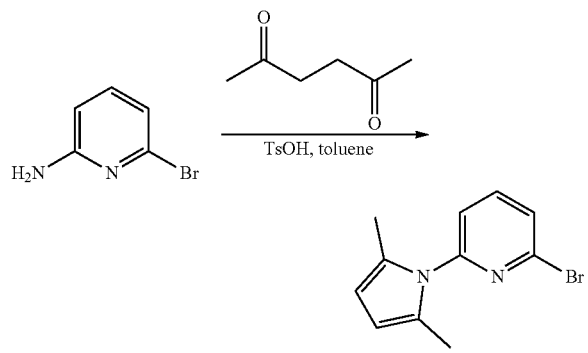

To a mixture of 6-bromopyridin-2-amine (5 g, 28.7 mmol) and acetonylacetone (4.1 mL, 34.7 mmol) in toluene (30 mL) was added p-toluenesulfonic acid (50 mg, 0.28 mmol) and the mixture was heated in a Dean-Stark apparatus for 2 hrs. The mixture was cooled to r.t. and diluted with EA (50 mL), washed with saturated aq.NaHCO$_3$, brine successively, dried and concentrated to give crude product, which was purified by chromatography (PE/EA=20:1) to give 2-bromo-6-(2,5-dimethyl-1H-pyrrol-1-yl)pyridine (6.8 g, 94.1% yield) as yellow solid. Retention time (LC-MS): 1.575 min. MH$^+$251.

Step 2 3-(5-(6-(2,5-dimethyl-1H-pyrrol-1-yl)pyridin-2-yl)pyrazin-2-yl)-3-azabicyclo[3.1.0]hexane

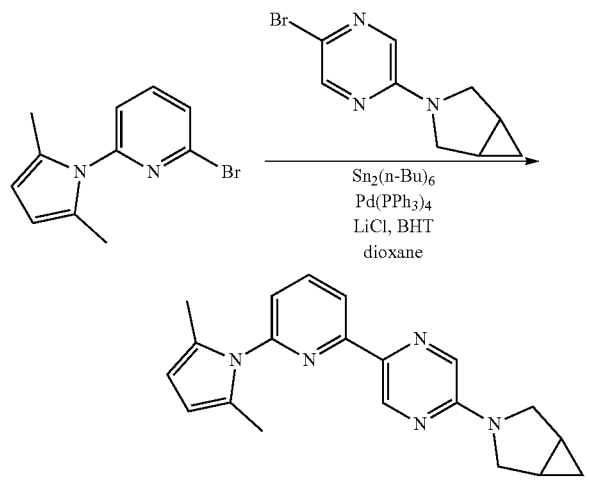

A mixture of 3-(5-bromopyrazin-2-yl)-3-azabicyclo[3.1.0]hexane (240 mg, 1 mmol), 2-bromo-6-(2,5-dimethyl-1H-pyrrol-1-yl)pyridine (250 mg, 1 mmol), LiCl (42.2 mg, 1 mmol) and 2,6-di-tert-butyl-4-methylphenol (50 mg, 0.227 mmol) in 1,4-dioxane (10 mL) was degassed under N$_2$ for three times and terakis(triphenylphosphine)palladium (92.4 mg, 0.08 mmol) was added under N$_2$ atmosphere. The mixture was degassed again and Hexa-n-butyldizinn (696 mg, 1.2 mmol) was added, the reaction mixture was stirred under N$_2$ at 110° C. overnight. The mixture was concentrated to dryness and the crude product was purified column chromatography (DCM/MeOH=80:1 to 50:1) to give 3-(5-(6-(2,5-dimethyl-1H-pyrrol-1-yl)pyridin-2-yl)pyrazin-2-yl)-3-azabicyclo[3.1.0]hexane (130 mg, 39.2% yield) as brown solid. Retention time (LC-MS): 1.905 min. MH$^+$332.

Step 3 6-(5-(3-azabicyclo[3.1.0]hexan-3-yl)pyrazin-2-yl)pyridin-2-amine

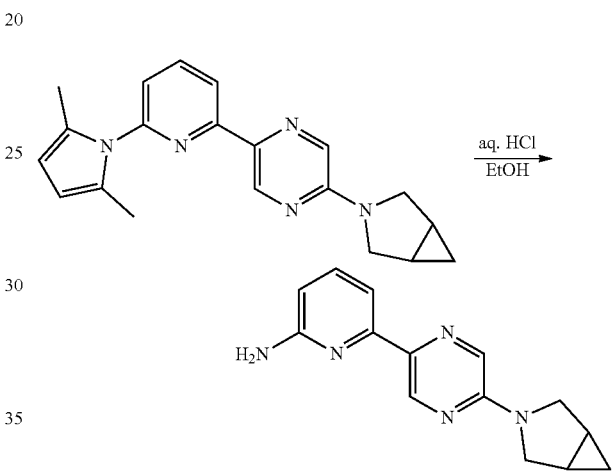

To a solution of 3-(5-(6-(2,5-dimethyl-1H-pyrrol-1-yl)pyridin-2-yl)pyrazin-2-yl)-3-azabicyclo[3.1.0]hexane (130 mg, 0.392 mmol) in EtOH (5 mL) was added concentrated aq.HCl (1 mL) and the mixture was heated to reflux for 2 hrs. The mixture was concentrated to dryness and dissolved in DCM (10 mL), washed with saturated aq.NaHCO$_3$, brine successively, dried and concentrated to give crude product, which was purified column chromatography (DCM/MeOH=20:1) to give 6-(5-(3-azabicyclo[3.1.0]hexan-3-yl)pyrazin-2-yl)pyridin-2-amine (56 mg, 59.4 yield) as dark brown solid. Retention time (LC-MS): 0.890 min. MH$^+$254.

Preparation 57
2-(5-chloro-6-methylpyridin-3-yl)thiazol-4-amine

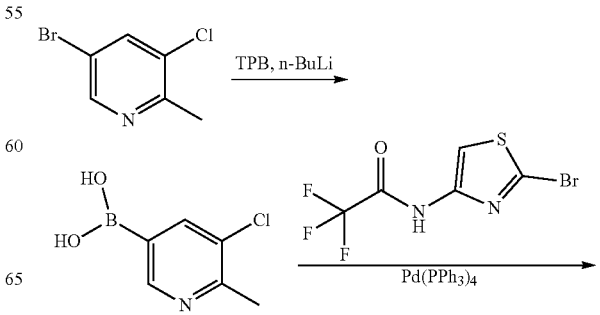

-continued

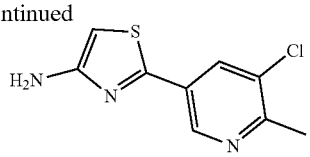

Step 1 5-chloro-6-methylpyridin-3-ylboronicacid

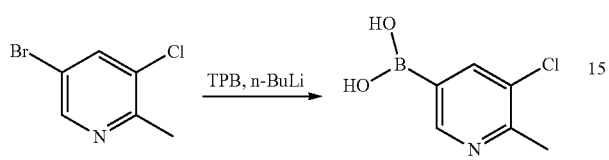

To a solution of 5-bromo-3-chloro-2-methylpyridine (1.03 g, 5 mmol) and (i-PrO)₃B (2.24 mL, 10 mmol) in THF (10 mL) was added n-BuLi (3.75 mL, 1.6 M in hexane, 6 mmol) drop-wise at −78° C. After the mixture was stirred at −78° C. for 1 hr, it was quenched with water. The solvent was removed under reduced pressure and the aqueous layer was washed with Ether (2×10 mL). The aqueous layer was then adjusted to pH-8 with 1N aqueous HCl solution and extracted with EA (3×50 mL). The combined organic layers were dried over Na₂SO₄, and concentrated to give 5-chloro-6-methylpyridin-3-ylboronic acid (650 mg, 76% yield) as a white solid. Retention time (LC-MS): Retention 0.458 min. MH⁺172

Step 2
2-(5-chloro-6-methylpyridin-3-yl)thiazol-4-amine

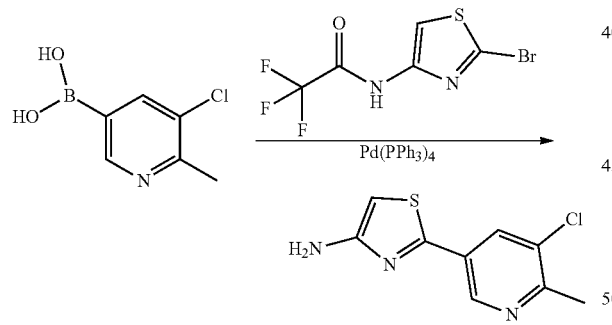

To a mixture of 5-chloro-6-methylpyridin-3-ylboronic acid (600 mg, 3.5 mmol), N-(2-bromothiazol-4-yl)-2,2,2-trifluoroacetamide (1.06 g, 3.85 mmol) in EtOH (18 mL), H₂O (9 mL) and toluene (36 mL) was added Na₂CO₃ (1.16 g, 10.5 mmol). After the mixture was degassed with N₂ for 3 times, Pd(PPh₃)₄ (203 mg, 1.75 mmol) was added under N₂ and the mixture was stirred at 90° C. overnight. The reaction mixture was cooled down and poured into EA. The organic phase was separated, washed with water and brine, dried over Na₂SO₄ and filtered. The filtrate was concentrated under reduced pressure and the residue was purified by chromatography (eluted with PE:Acetone=10:1) to afford 2-(5-chloro-6-methylpyridin-3-yl)thiazol-4-amine (120 mg, 15% yield) as yellow solid. Retention time (LC-MS): Retention 1.225 min. MH⁺226.

Preparation 58
2-(5-fluoro-6-methylpyridin-3-yl)thiazol-4-amine

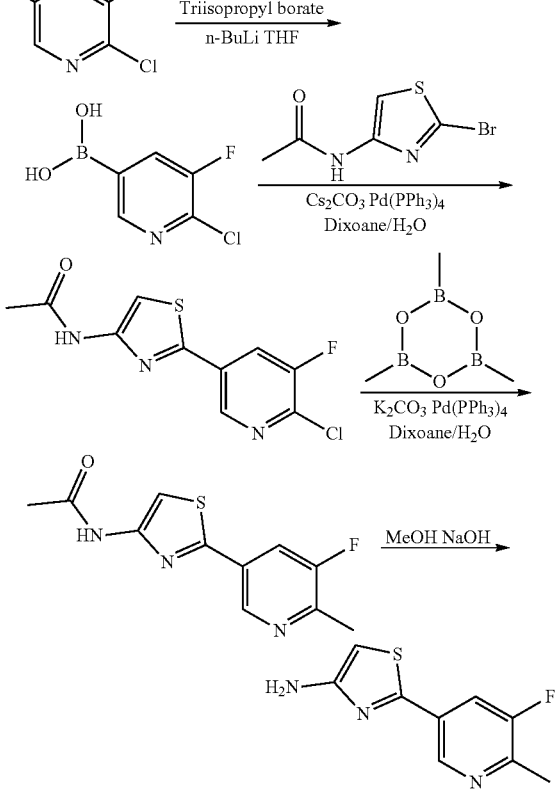

Step 1 (6-chloro-5-fluoropyridin-3-yl)boronic acid

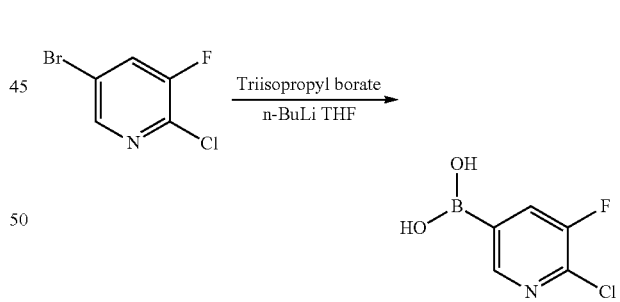

To a solution of 5-bromo-2-chloro-3-fluoropyridine (1 g, 4.78 mmol) and triisopropyl borate (2.2 mL, 9.56 mmol) in THF (10 mL) was added drop-wise n-butyllithium (3.6 mL, 1.6 M , 5.95 mmol) at −78° C. and stirred for 3 hrs. Then the mixture was poured into H₂O and THF was evaporated. The H₂O layer was adjusted to pH 14 with NaOH(1 M) and extracted with Ether. Then the H₂O layer was adjusted to pH 5 with HCl (6 M) and extracted with EA. The organic layer was separated, washed with water and brine, dried over Na2SO4, and concentrated to give (6-chloro-5-fluoropyridin-3-yl)boronic acid (600 mg, 71.8% yield) as a white solid. Retention time (LC-MS): 0.635 min. MH⁺178.

Step 2 N-(2-(6-chloro-5-fluoropyridin-3-yl)thiazol-4-yl)acetamide

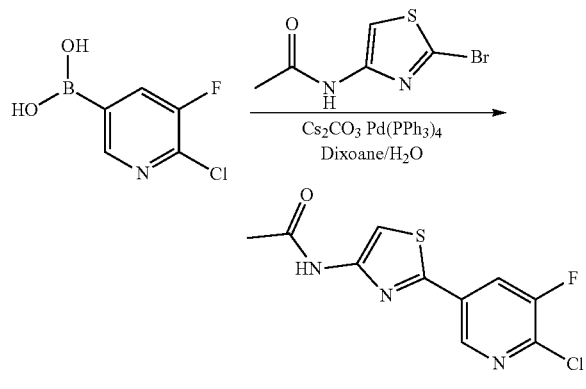

To a solution of N-(2-bromothiazol-4-yl)acetamide (750 mg, 3.41 mmol) (6-chloro-5-fluoropyridin-3-yl)boronic acid (600 mg, 3.41 mmol) in 1,4-dioxane (10 mL) and H$_2$O (2.5 mL) was added Cs$_2$CO$_3$ (2.2 g, 6.80 mmol) and the mixture was degassed with N$_2$ for three times Pd(PPh$_3$)$_4$ (345 mg, 0.34 mmol) was added and the reaction mixture was stirred at 100° C. under N$_2$ overnight. The mixture was cooled down and poured into EA. The organic phase was separated, washed with water and brine, dried over Na$_2$SO$_4$ and filtered. The filtrate was concentrated under reduced pressure. The filtrate was concentrated and the residue was purified by chromatography (eluted with PE:EA=8:1) to afford N-(2-(6-chloro-5-fluoropyridin-3-yl)thiazol-4-yl)acetamide (800 mg, 86.6% yield) as yellow solid. Retention time (LC-MS): 1.194 min. MH$^+$272.

Step 3 N-(2-(5-fluoro-6-methylpyridin-3-yl)thiazol-4-yl)acetamide

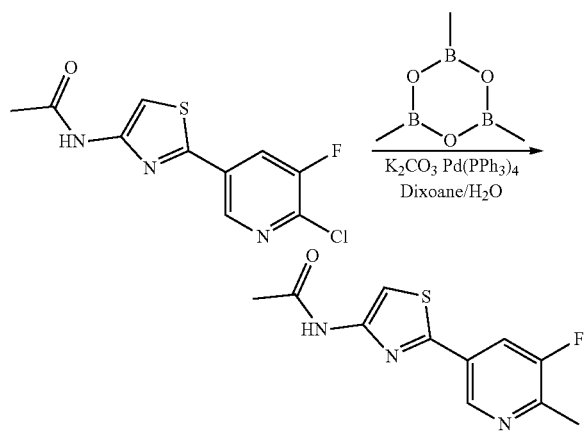

To a solution of N-(2-(6-chloro-5-fluoropyridin-3-yl)thiazol-4-yl)acetamide (700 mg, 2.58 mmol), trimethylboroxine (0.40 mL, 2.84 mmol) in 1,4-dioxane (10 mL) and H$_2$O (1 mL) was added potassium carbonate (712 mg, 5.16 mmol) and the mixture was degassed with N$_2$ for three times Pd(PPh$_3$)$_4$ (300 mg, 0.26 mmol) was added and the reaction mixture was stirred at 100° C. under N$_2$ for 4 hrs. The mixture was cooled down and poured into EA. The organic phase was separated, washed with water and brine, dried over Na$_2$SO$_4$ and filtered. The filtrate was concentrated under reduced pressure. The filtrate was concentrated and the residue was purified by chromatography (eluted with PE:EA=3:1) to afford N-(2-(5-fluoro-6-methylpyridin-3-yl)thiazol-4-yl)acetamide (370 mg, 57.18% yield) as a white solid. Retention time (LC-MS): 1.252 min. MH$^+$252.

Step 4 2-(5-fluoro-6-methylpyridin-3-yl)thiazol-4-amine

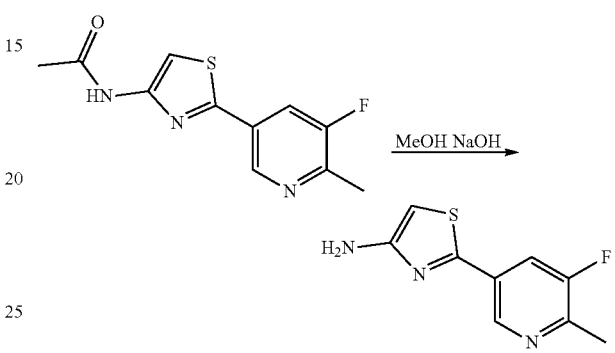

To a solution of N-(2-(5-fluoro-6-methylpyridin-3-yl)thiazol-4-yl)acetamide (370 mg, 1.47 mmol) in MeOH (10 mL) was added 50% NaOH (2 mL). The mixture was stirred at 80° C. for 2 hrs. The reaction mixture was concentrated and extracted with DCM. The organic phase was separated, washed with brine, dried over Na$_2$SO$_4$ and filtered. The filtrate was concentrated under reduced pressure to afford 2-(5-fluoro-6-methylpyridin-3-yl)thiazol-4-amine (40 mg, yield 58.82%) as a yellow solid. Retention time (LC-MS): 1.068 min. MH$^+$210.

Preparation 59 (S)-methyl 3-(6-aminopyridin-2-yl)-1,2,4-oxadiazol-5(2H)-one

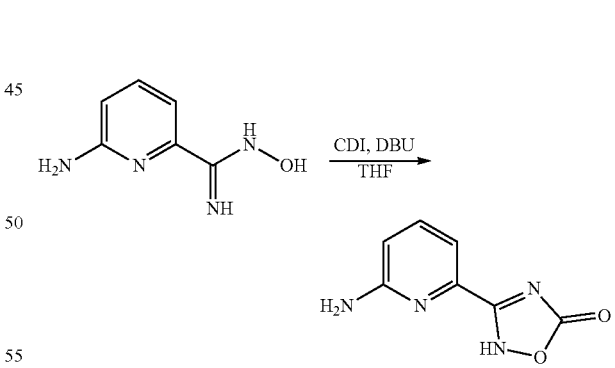

To a solution of 6-amino-N-hydroxypicolinimidamide (300 mg, 1.97 mmol) in THF (10 mL) was added CDI (447.60 mg, 2.76 mmol) at RT. The reaction was stirred at RT for 2 h, then the mixture was cooled to 0° C. and DBU (0.41 mL, 2.76 mmol) was added. After the reaction was stirred at RT overnight and water was added. The solid was filtered off and washed with aq.HCl (0.5M), the aqueous was extracted with EA (3×50 mL). Combined organic layers were dried over Na$_2$SO$_4$ and filtered. The filtrate was concentrated under reduced pressure to afford 3-(6-aminopyridin-2-yl)-1, 2,4-oxadiazol-5(2H)-one (300 mg, 85.4% yield) as a a yellow solid. Retention time (LC-MS): 0.694 min. MH+179.

Preparation 60 6'-methyl-5'-(trifluoromethyl)-[2,3'-bipyridin]-6-amine

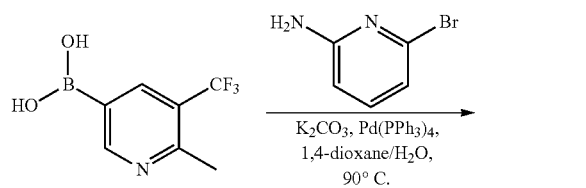

To a mixture of (6-methyl-5-(trifluoromethyl)pyridin-3-yl)boronic acid (205.0 mg, 1.0 mmol), 6-bromopyridin-2-amine (172.0 mg, 1.0 mmol) in 1,4-dioxane (4 mL) and H₂O (1 mL) was added potassium carbonate (276.4 mg, 2.0 mmol). After the mixture was degassed with N₂ for 3 times, Pd(PPh₃)₄ (57.8 mg, 0.05 mmol) was added under N₂ and the mixture was stirred at 90° C. for 2 hrs. The reaction mixture was cooled down and diluted with EA, washed with water and brine, dried over Na₂SO₄ and filtered. The filtrate was concentrated under reduced pressure and the residue was purified by chromatography (eluted with PE:EA=1:1) to afford 6'-methyl-5'-(trifluoromethyl)-[2,3'-bipyridin]-6-amine (180 mg, 71.1% yield) as a white solid. Retention time (LC-MS): 0.499 min. MH+254.

Preparation 61 2-(6-methyl-5-(trifluoromethyl)pyridin-3-yl)thiazol-4-amine

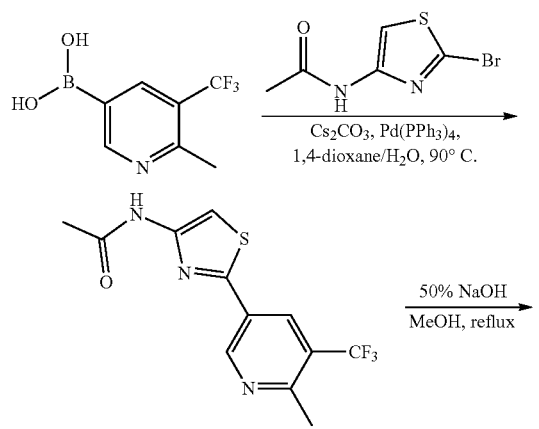

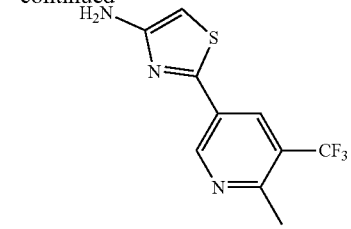

Step 1 N-(2-(6-methyl-5-(trifluoromethyl)pyridin-3-yl)thiazol-4-yl)acetamide

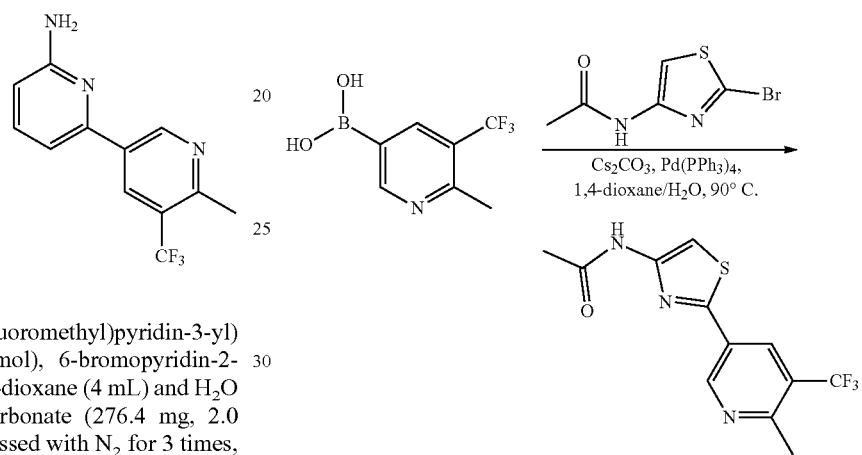

To a mixture of (6-methyl-5-(trifluoromethyl)pyridin-3-yl)boronic acid (451.0 mg, 2.2 mmol), N-(2-bromothiazol-4-yl)acetamide (483.8 mg, 2.2 mmol) in 1,4-dioxane (4 mL) and H₂O (1 mL) was added Cs₂CO₃ (1.79 g, 5.5 mmol). After the mixture was degassed with N₂ for 3 times, Pd(PPh₃)₄ (127.1 mg, 0.11 mmol) was added under N₂ and the mixture was stirred at 100° C. for 2 hrs. The reaction mixture was cooled down and poured into EA. The organic phase was separated, washed with water and brine, dried over Na₂SO₄ and filtered. The filtrate was concentrated under reduced pressure and the residue was purified by chromatography (eluted with PE:EA=4:1) to afford N-(2-(6-methyl-5-(trifluoromethyl)pyridin-3-yl)thiazol-4-yl)acetamide (550 mg, 83.0% yield) as a white solid. Retention time (LC-MS): 1.458 min. MH+302.

Step 2 2-(6-methyl-5-(trifluoromethyl)pyridin-3-yl)thiazol-4-amine

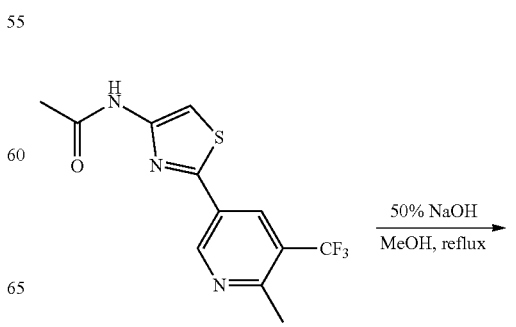

-continued

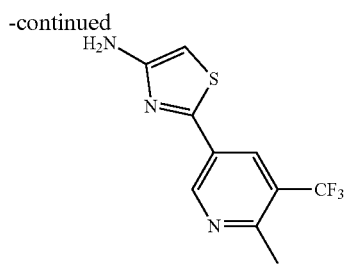

A mixture of N-(2-(6-methyl-5-(trifluoromethyl)pyridin-3-yl)thiazol-4-yl)acetamide (550.0 mg, 1.8 mmol) in MeOH (8 mL) and 50% aqueous NaOH solution (1.0 mL) was stirred at 80° C. for 4 hrs. The solvent was removed. The residue was purified by column chromatography (eluted with PE:EA=1:1) to afford 2-(6-methyl-5-(trifluoromethyl)pyridin-3-yl)thiazol-4-amine (420 mg, 88.4% yield) as a white solid. Retention time (LC-MS): 1.343 min. MH$^+$260.

Preparation 62 (S)-2-(1-(3-methoxy-2-oxopropyl)-3-methyl-2,6-dioxo-2,3-dihydro-1H-purin-7(6H)-yl)propanoic acid

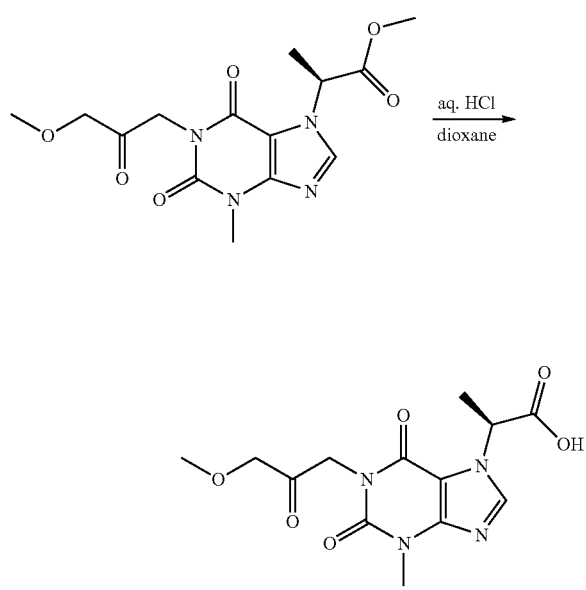

To a solution of (S)-methyl 2-(1-(3-methoxy-2-oxopropyl)-3-methyl-2,6-dioxo-2,3-dihydro-1H-purin-7(6H)-yl)propanoate (300 mg, 0.887 mmol) in dioxane (5 mL) was added concentrated aq.HCl (6 M, 5 mL) and the mixture was heated to reflux for 2 hrs. The mixture was concentrated to dryness and dissolved in DCM (10 mL), washed with saturated aq.NaHCO$_3$, brine successively, dried and concentrated to give crude product, which was purified column chromatography (PE/EA=1:2) to give (S)-2-(1-(3-methoxy-2-oxopropyl)-3-methyl-2,6-dioxo-2,3-dihydro-1H-purin-7(6H)-yl)propanoic acid (260 mg, 93% yield) as a yellow solid. Retention time (LC-MS): 0.385 min, MH$^+$324.

Preparation 63 (S)-2-(3-methyl-2,6-dioxo-2,3-dihydro-1H -purin-7(6H)-yl)-N-(2-(5-methyl-6-(trifluoromethyl)pyridin-3-yl)thiazol-4-yl)propanamide

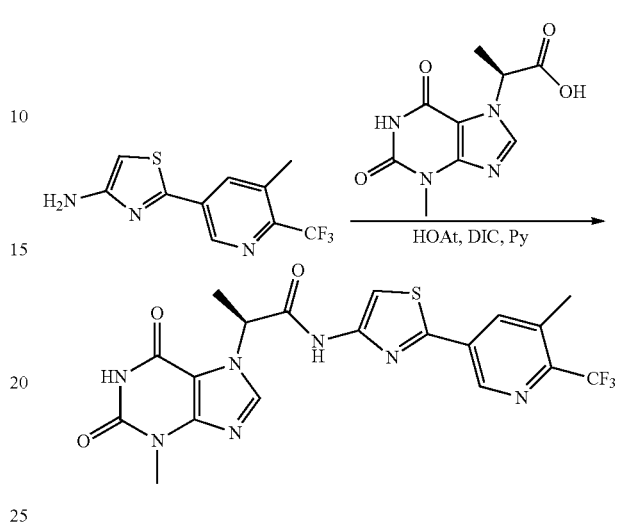

To a solution of (S)-2-(3-methyl-2,6-dioxo-2,3-dihydro-1H-purin-7(6H)-yl)propanoic acid (73 mg, 0.308 mmol) and 2-(5-methyl-6-(trifluoromethyl)pyridin-3-yl)thiazol-4-amine (80 mg, 0.308 mmol) in DCM (2 mL) was added HOAt (42 mg, 0.308 mmol) at RT. The reaction mixture was cooled under ice-water bath to 0° C., and pyridine (0.07 mL, 0.925 mmol) was added drop-wise followed by drop-wise addition of DIC (0.07 mL, 0.462 mmol) under N$_2$ protection. The ice-water bath was removed after the addition and the mixture was stirred at 30° C. overnight. The reaction mixture was washed with water (2 mL). The organic layer was separated, and the aqueous layer was extracted with DCM (2 mL ×2). The combined organic layers were dried over Na$_2$SO$_4$, filtered and concentrated to dryness to give crude product, which was purified by chromatography (DCM: MeOH=20:1) to afford (S)-2-(3-methyl-2,6-dioxo-2,3-dihydro-1H-purin-7(6H)-yl)-N-(2-(5-methyl-6-(trifluoromethyl)pyridin-3-yl)thiazol-4-yl)propanamide (130 mg, 91% yield) as a white solid. Retention time (LC-MS): 3.042 min, MR$^+$465.

Preparation 64 6-(6-methyl-5-(trifluoromethyl)pyridin-3-yl)pyrazin-2-amine

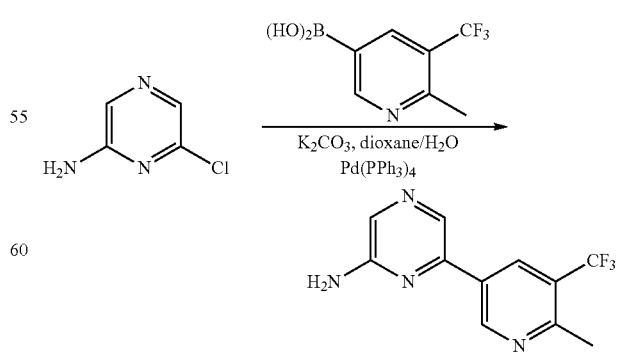

To a mixture of 6-methyl-5-(trifluoromethyl)pyridin-3-ylboronic acid (200.0 mg, 1.0 mmol), 6-chloropyrazin-2-amine (130.0 mg, 1.0 mmol) in 1,4-dioxane (8 mL) and H₂O (2 mL) was added potassium carbonate (346.0 mg, 2.5 mmol). After the mixture was degassed with N₂ for 3 times, Pd(PPh₃)₄ (11.5 mg, 0.01 mmol) was added under N₂ and the mixture was stirred at 100° C. for 3 hrs. The reaction mixture was cooled down and poured into EA. The organic phase was separated, washed with water and brine, dried over Na₂SO₄ and filtered. The filtrate was concentrated under reduced pressure and the residue was purified by chromatography (eluted with PE:EA=5:1) to afford 6-(6-methyl-5-(trifluoromethyl)pyridin-3-yl)pyrazin-2-amine (178 mg, 69.78% yield) as a yellow solid. Retention time (LC-MS): 1.058 min. MH⁺255.

Preparation 65 6-(6-methyl-5-(trifluoromethyl)pyridin-3-yl)pyrazin-2-amine

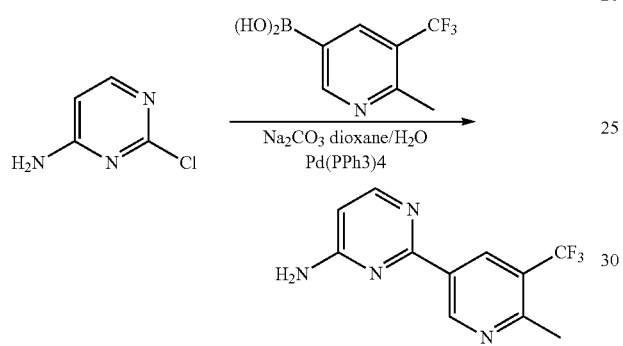

To a mixture of 6-methyl-5-(trifluoromethyl)pyridin-3-ylboronic acid (359.0 mg, 1.93 mmol), 2-chloropyrimidin-4-amine (250.0 mg, 1.93 mmol) in 1,4-dioxane (8 mL) and H₂O (2 mL) was added Na₂CO₃ (465.0 mg, 4.4 mmol). After the mixture was degassed with N₂ for 3 times, Pd(PPh₃)₄ (21.5 mg, 0.019 mmol) was added under N₂ and the mixture was stirred at 100° C. for 3 hrs. The reaction mixture was cooled down and poured into EA. The organic phase was separated, washed with water and brine, dried over Na₂SO₄ and filtered. The filtrate was concentrated under reduced pressure and the residue was purified by chromatography (eluted with PE:EA=5:1) to afford 2-(6-methyl-5-(trifluoromethyl)pyridin-3-yl)pyrimidin-4-amine (330 mg, 73.99% yield) as a yellow solid. Retention time (LC-MS): 0.812 min. MH⁺255.

Preparation 66 2-(8-((tert-butyldimethylsilyloxy)methyl)-3-methyl-2,6-dioxo-1-(2-oxobutyl)-2,3-dihydro-1H-purin-7(6H)-yl)-N-(6'-(trifluoromethyl)-2,3'-bipyridin-6-yl)propanamide

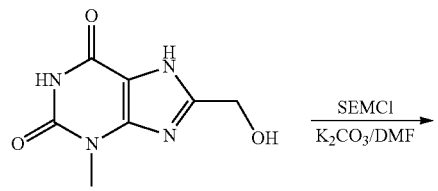

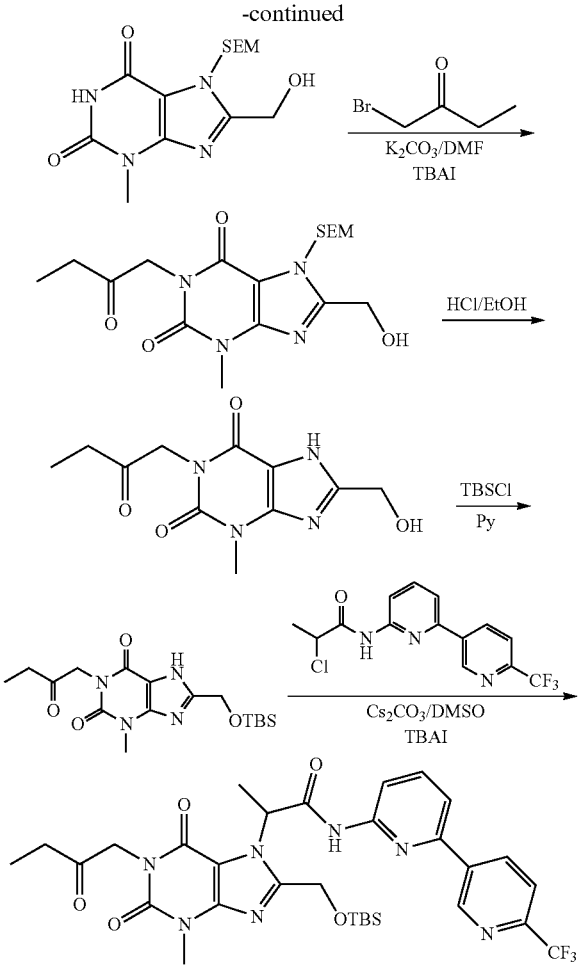

Step 1 8-(hydroxymethyl)-3-methyl-7-((2-(trimethylsilyl)ethoxy)methyl)-1H-purine-2,6(3H,7H)-dione

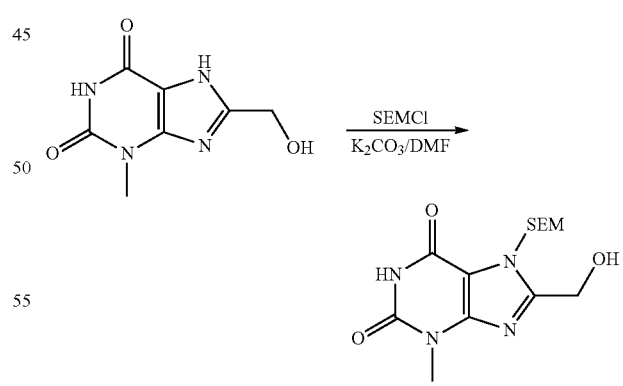

To a mixture of 8-(hydroxymethyl)-3-methyl-1H-purine-2,6(3H,7H)-dione (2.0 g, 10.2 mmol), potassium carbonate (4.23 g, 30.59 mmol) in DMF (40 mL) was added 2-(trimethylsilyl)ethoxymethyl chloride (1.8 mL, 10.2 mmol) dropwise at 0° C. The mixture was stirred at 0° C. for 10 min and RT overnight. The reaction mixture was quenched by water (20 mL), and then extracted with EA (3×20 mL). The combined organic layers were washed with saturated aqueous LiCl solution (15 mL) and brine (15 mL), dried over Na$_2$SO$_4$ and filtered. The filtrate was concentrated to get 8-(hydroxymethyl)-3-methyl-7-((2-(trimethylsilyl)ethoxy)methyl)-1H-purine-2,6(3H,7H)-dione (1.6 g, yield 48%) as a yellow solid. Retention time (LC-MS): 1.210 min. MH$^+$327.

Step 2 8-(hydroxymethyl)-3-methyl-1-(2-oxobutyl)-7-((2-(trimethylsilyl)ethoxy)methyl)-1H-purine-2,6(3H,7H)-dione

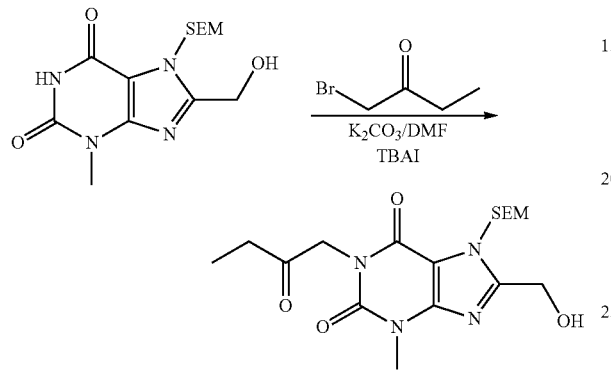

To a solution of 8-(hydroxymethyl)-3-methyl-7-((2-(trimethylsilyl)ethoxy)methyl)-1H-purine-2,6(3H,7H)-dione (300 mg, 0.919 mmol) in DMF (300 mL) was added potassium carbonate (254 mg 1.84 mmol), TBAI (30 mg 0.081 mmol) followed by dropwise addition of 1-bromobutan-2-one (166 mg, 1.1 mmol), the mixture was stirred at RT for 2 hrs. The reaction mixture was quenched by water (20 mL), and then extracted with EA (3×5 mL). The combined organic layers were washed with saturated aqueous LiCl solution (15 mL) and brine (15 mL), dried over Na$_2$SO$_4$ and filtered. The filtrate was concentrated to give a residue, which was purified with column chromatography (eluted with DCM:MeOH=40:1) to afford 8-(hydroxymethyl)-3-methyl-1-(2-oxobutyl)-7-((2-(trimethylsilyl)ethoxy)methyl)-1H-purine-2,6(3H,7H)-dione (350 mg, yield 96%) as a brown solid. Retention time (LC-MS): 1.477 min. MH$^+$396.

Step 3 8-(hydroxymethyl)-3-methyl-1-(2-oxobutyl)-1H-purine-2,6(3H,7H)-dione

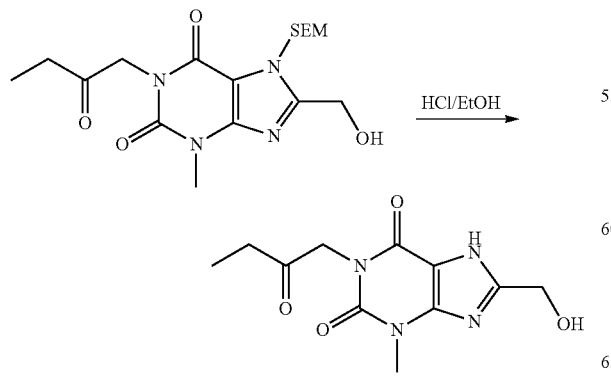

To a solution of 8-(hydroxymethyl)-3-methyl-1-(2-oxobutyl)-7-((2-(trimethylsilyl)ethoxy)methyl)-1H-purine-2,6(3H,7H)-dione (300 mg, 2.3 mmol) in EtOH (5 mL) was added conc. hydrochloride acid (2 mL) and the mixture was stirred at 90° C. for 2 hrs. The mixture was cooled to RT and concentrated to one third volume. The mixture was neutralized with 1N aqueous NaOH solution at 0° C. and extracted with EA (3×5 mL). The combined organic layers were dried over Na$_2$SO$_4$ and concentrated to afford 8-(hydroxymethyl)-3-methyl-1-(2-oxopropyl)-1H-purine-2,6(3H,7H)-dione (160 mg, 79% yield) as a white solid. Retention time (LC-MS): 0.384 min. MH$^+$267.

Step 4 8-((tert-butyldimethylsilyloxy)methyl)-3-methyl-1-(2-oxobutyl)-1H-purine-2,6(3H,7H)-dione

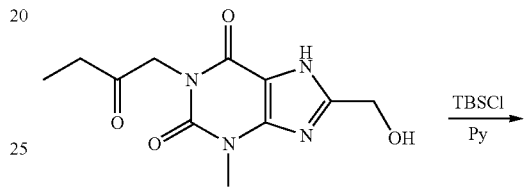

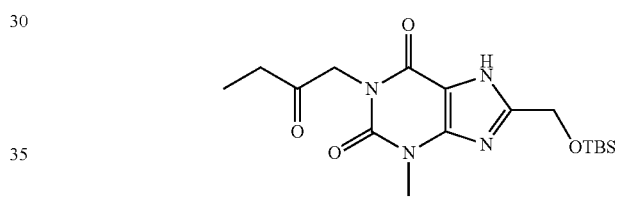

To mixture of 8-(hydroxymethyl)-3-methyl-1-(2-oxobutyl)-1H-purine-2,6(3H,7H)-dione (100 mg, 0.375 mmol) in pyridine (3 mL) was added TBSCl (339 mg, 2.25 mmol) in portions. The mixture was stirred at RT overnight. The reaction mixture was quenched by water (8 mL), and then extracted with EA (3×10 mL). The combined organic layers were washed saturated aqueous LiCl solution (5 mL) and brine (5 mL), dried over Na$_2$SO$_4$ and filtered. The filtrate was concentrated to get 8-((tert-butyldimethylsilyloxy)methyl)-3-methyl-1-(2-oxobutyl)-1H-purine-2,6(3H,7H)-dione (140 mg, 97% yield) as a brown solid. Retention time (LC-MS): 1.577 min. MH$^+$381.

Step 5 2-(8-((tert-butyldimethylsilyloxy)methyl)-3-methyl-2,6-dioxo-1-(2-oxobutyl)-2,3-dihydro-1H-purin-7(6H)-yl)-N-(6'-(trifluoromethyl)-2,3'-bipyridin-6-yl)propanamide

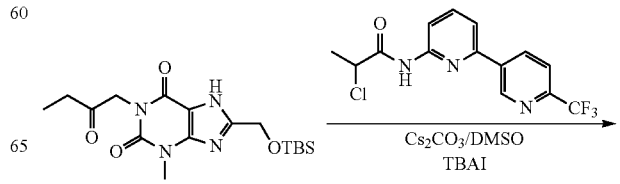

-continued

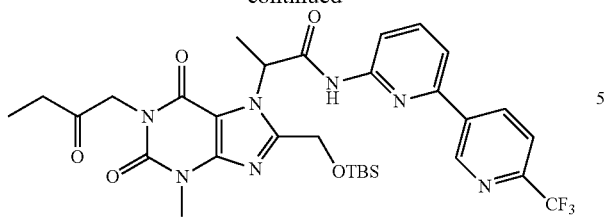

To a mixture of 8-((tert-butyldimethylsilyloxy)methyl)-3-methyl-1-(2-oxobutyl)-1H-purine-2,6(3H,7H)-dione (60 mg, 0.157 mmol), 2-chloro-N-(6'-(trifluoromethyl)-2,3'-bipyridin-6-yl)propanamide (52 mg, 0.157 mmol) in DMSO (2 mL) was added $Cs_2CO_3$ (92 mg, 0.394 mmol) and TBAI (6 mg 0.02 mmol) and the mixture was stirred at 50° C. under $N_2$ for 6 hrs. The reaction mixture was quenched by water (10 mL), and then extracted with EA (3×8 mL). The combined organic layers were washed with saturated aqueous LiCl solution (5 mL) and brine (5 mL), dried over $Na_2SO_4$ and filtered. The filtrate was concentrated to give a crude product, which was purified with column chromatography (eluted with DCM:MeOH=30:1) to afford 2-(8-((tert-butyldimethylsilyloxy)methyl)-3-methyl-2,6-dioxo-1-(2-oxobutyl)-2,3-dihydro-1H-purin-7(6H)-yl)-N-(6'-(trifluoromethyl)-2,3'-bipyridin-6-yl)propanamide (12 mg, 11% yield) as a white solid. Retention time (LC-MS): 2.042min. $MH^+$674.

Preparation 67
6-(5-chloro-6-methylpyridin-3-yl)pyrazin-2-amine

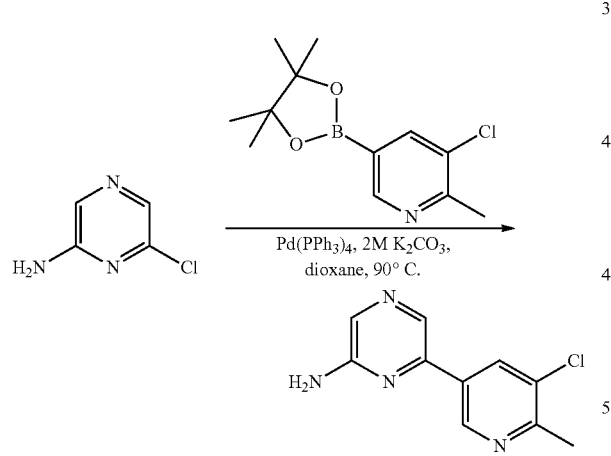

To a solution of 6-chloropyrazin-2-amine (413 mg, 2.96 mmol) in dioxane (12 mL) in a sealed tube was added 3-chloro-2-methyl-5-(4,4,5,5-tetramethyl-1,3,2-dioxaborolan-2-yl)pyridine (750 mg, 2.96 mmol) and aq. potassium carbonate (2M, 4.44 mL, 8.88 mmol). The reaction was degassed with argon for 5 min and $Pd(PPh_3)_4$ (171 mg, 0.148 mmol) was added. The reaction was heated at 90° C. for 18 h, cooled to RT, diluted with water (100 mL) and extracted with EA (3×75 mL). The combined organic layers were dried with $MgSO_4$ and concentrated to a residue which was purified by chromatography eluted with EA/Hep (20:80 to 100:0) to give 6-(5-chloro-6-methylpyridin-3-yl)pyrazin-2-amine (346 mg, 53% yield) as a pale yellow solid. LCMS: $MH^+$221 and $T_R$=2.162 min.

Preparation 68 6'-methyl-5'-(trifluoromethyl)-[2,3'-bipyridin]-6-amine

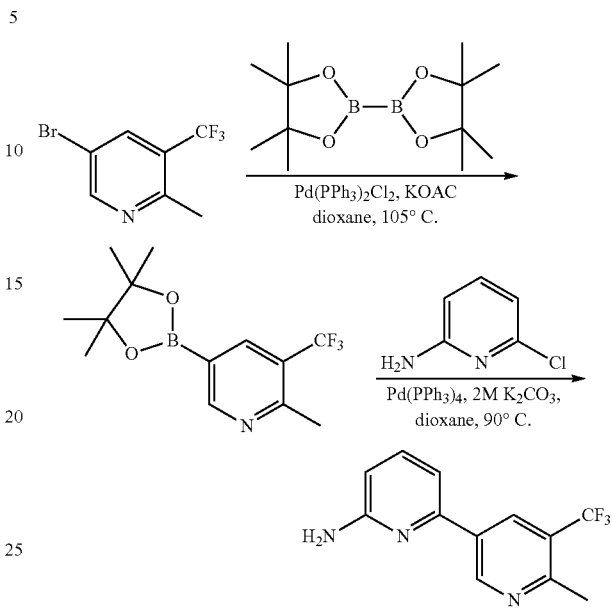

Step 1 2-methyl-5-(4,4,5,5-tetramethyl-1,3,2-dioxaborolan-2-yl)-3-(trifluoromethyl)pyridine

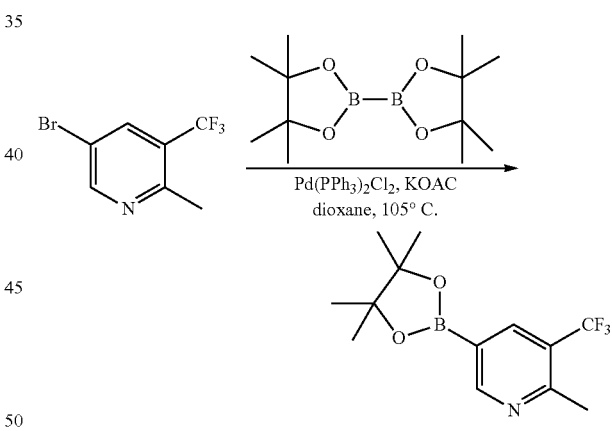

To a solution of 5-bromo-2-methyl-3-(trifluoromethyl)pyridine (1.0 g, 4.17 mmol) in dioxane (20 mL) in a sealed tube was added 4,4,4',5,5,5'5'-octamethyl-2-2'-bi(1,3,2-dioxaborolane) (1.59 g, 6.25 mmol) and KOAc (819 mg, 8.34 mmol). The reaction was degassed with argon for 5 minutes then Pd(PPH3)2C12 (0.0147 mg, 0.021 mmol) was added. The reaction was heated at 105° C. for 18 h, cooled to RT, diluted with water (100 mL) and extracted with EA (3×75 mL). The combined organic layer were dried with $MgSO_4$ and concentrated to a residue which was purified by chromatography eluted with EA/HEP (5:95 to 30:70) to give 2-methyl-5-(4,4,5,5-tetramethyl-1,3,2-dioxaborolan-2-yl)-3-(trifluoromethyl)pyridine (1.2 g, 100% yield) as a white solid. LCMS: $MH^+$206 (converts to boronic acid on LCMS) and TR =1.804 min.

Step 2 6'-methyl-5'-(trifluoromethyl)-[2,3'bipyridin]-6-amine

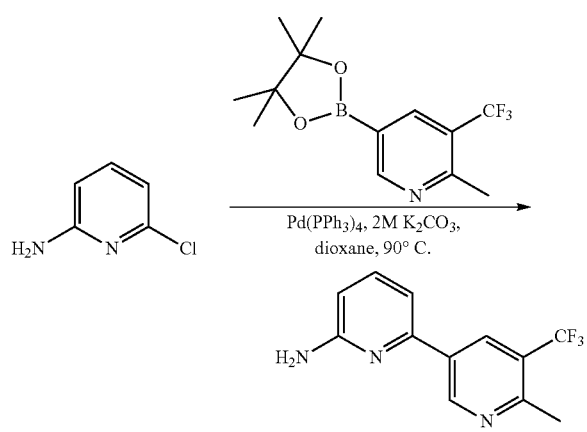

To a solution of 6-chloropyridin-2-amine (723 mg, 4.18 mmol) in dioxane (18 mL) in a sealed tube was added 2-methyl-5-(4,4,5,5-tetramethyl-1,3,2-dioxaborolan-2-yl)-3-(trifluoromethyl)pyridine (1.20 g, 4.18 mmol) and aq. potassium carbonate (2M, 6.27 mL, 12.54 mmol). The reaction was degassed with argon for 5 min then Pd(PPh$_3$)$_4$ (242 mg, 0.209 mmol) was added. The reaction was heated at 90° C. for 4 h, cooled to RT, diluted with water (100 mL) and extracted with EA (3×75 mL). The combined organic layers were dried with MgSO$_4$ and concentrated to a residue which was purified by chromatography eluted with EA/Hep (5:95 to 30:70) to give 6'-methyl-5'-(trifluoromethyl)-[2,3'-bipyridin]-6-amine (1.02 g, 96% yield) as a pale yellow solid. LCMS: MH$^+$254 and R$_t$=1.814 min.

Preparation 69 6-(6-methyl-5-(trifluoromethyl)pyridin-3-yl)pyrazin-2-amine

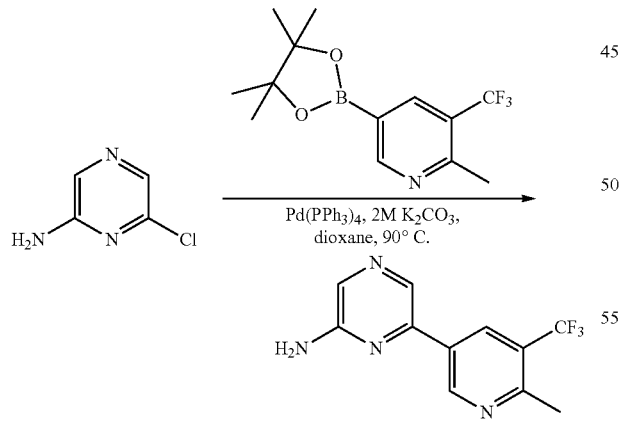

To a solution of 6-chloropyrazin-2-amine (465 mg, 3.59 mmol) in dioxane (15 mL) in a sealed tube was added 2-methyl-5-(4,4,5,5-tetramethyl-1,3,2-dioxaborolan-2-yl)-3-(trifluoromethyl)pyridine (1.03 g, 3.59 mmol) and aq. potassium carbonate (2M, 5.39 mL, 12.54 mmol). The reaction was degassed with argon for 5 min, Pd(PPh$_3$)$_4$ (207 mg, 0.180 mmol) was added and then heated at 90° C. for 4 h. The reaction was cooled to RT, diluted with water (100 mL) and extracted with EA (3×75 mL). The combined organic layers were dried with MgSO$_4$ and concentrated to a residue which was purified by chromatography eluted with EA/Hep (10:90 to 30:70) to give 6-(6-methyl-5-(trifluoromethyl)pyridin-3-yl)pyrazin-2-amine (707 mg, 96% yield) as a pale yellow solid. LCMS: MH$^+$255 and R$_t$=2.507 min.

Preparation 70 6-(5-(3-azabicyclo[3.1.0]hexan-3-yl)pyrazin-2-yl)pyridin-2-amine

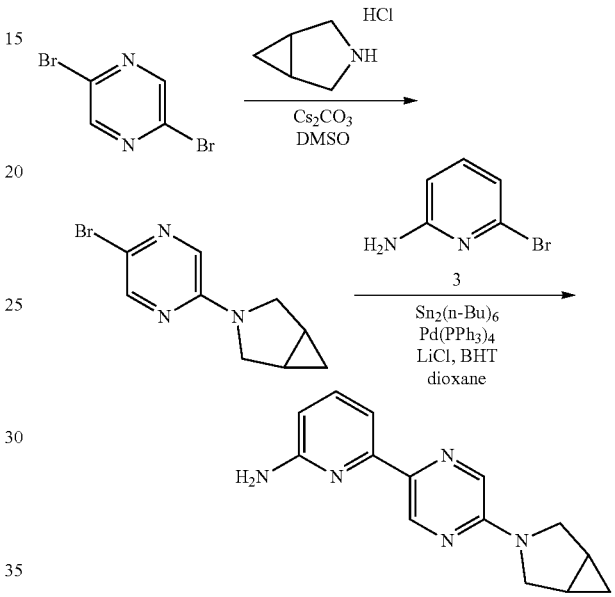

Step 1 3-(5-bromopyrazin-2-yl)-3-azabicyclo [3.1.0] hexane

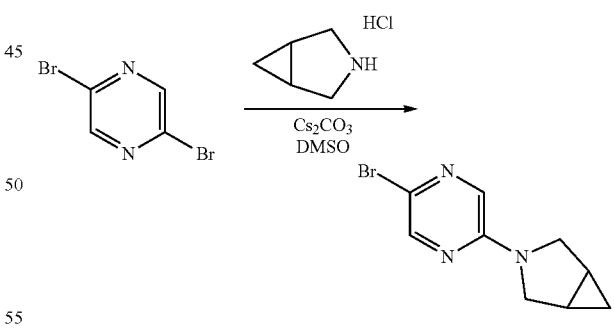

To a solution of 2,5-dibromopyrazine (4.65 g, 19.57 mmol) in DMSO (100 mL) was added 3-azabicyclo[3.1.0]hexane hydrochloride (1.8 g, 15.05 mmol) followed by Cs$_2$CO$_3$ (12.26 g, 37.63 mmol) and the mixture was stirred at 100° C. in a sealed tube for 4 hrs. The mixture was cooled and diluted with EA (150 mL) and washed with water, brine successively, dried and concentrated to give a crude product, which was purified by chromatography (PE/EA=5:1) to give 3-(5-bromopyrazin-2-yl)-3-azabicyclo[3.1.0]hexane (3.3 g, 91.32% yield) as a yellow solid. Retention time (LC-MS): 1.468 min. MH$^+$240.

Step 2 6-(5-(3-azabicyclo[3.1.0]hexan-3-yl)pyrazin-2-yl)pyridin-2-amine

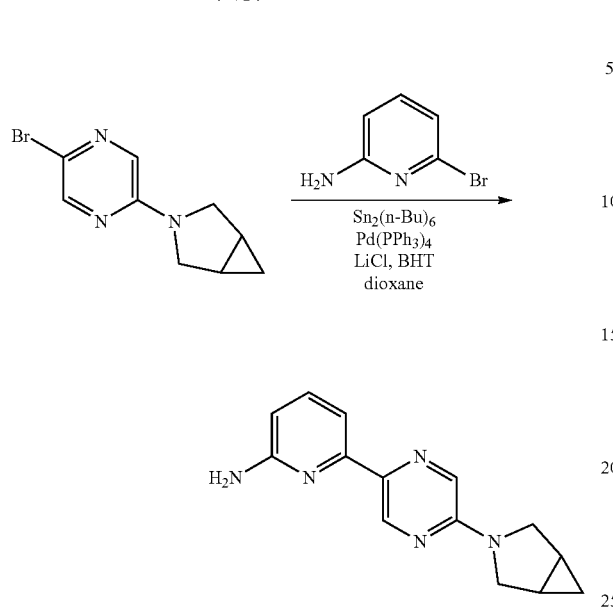

A mixture of 3-(5-bromopyrazin-2-yl)-3-azabicyclo[3.1.0]hexane (1.3 g, 5.4 mmol), 6-bromopyridin-2-amine (1.12 g, 6.5 mmol), LiCl (229 mg, 5.4 mmol) and 2,6-di-tert-butyl-4-methylphenol (220 mg, 1 mmol) in 1,4-dioxane (30 mL) was degassed with $N_2$ for three times and terakis(triphenylphosphine)palladium (499 mg, 0.43 mmol) was added under $N_2$ atmosphere. The mixture was degassed again and hexan-n-butylditin (6.26 g, 10.8 mmol) was added, the reaction mixture was stirred under $N_2$ at 110° C. for 40 hrs. The mixture was diluted with EA (200 mL) and washed with aq. KF solution, brine successively, dried and concentrated to dryness and the crude product was purified with column chromatography (DCM/MeOH=60:1 to 30:1) to give 6-(5-(3-azabicyclo[3.1.0]hexan-3-yl)pyrazin-2-yl)pyridin-2-amine (750 mg. 54.8% yield) as brown solid. Retention time (LC-MS): 0.456 min. MH$^+$254.

Preparation 71 5'-(3-azabicyclo[3.1.0]hexan-3-yl)-2,2'-bipyrazin-6-amine

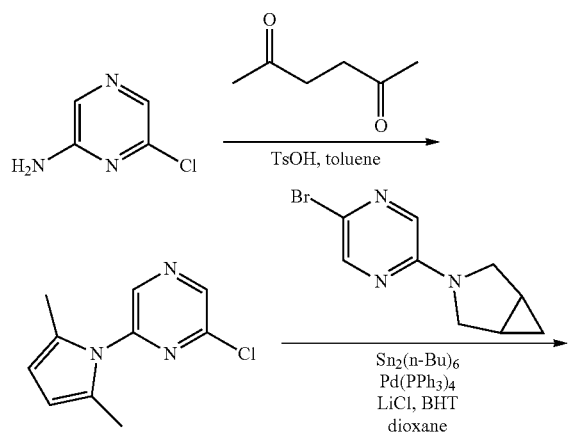

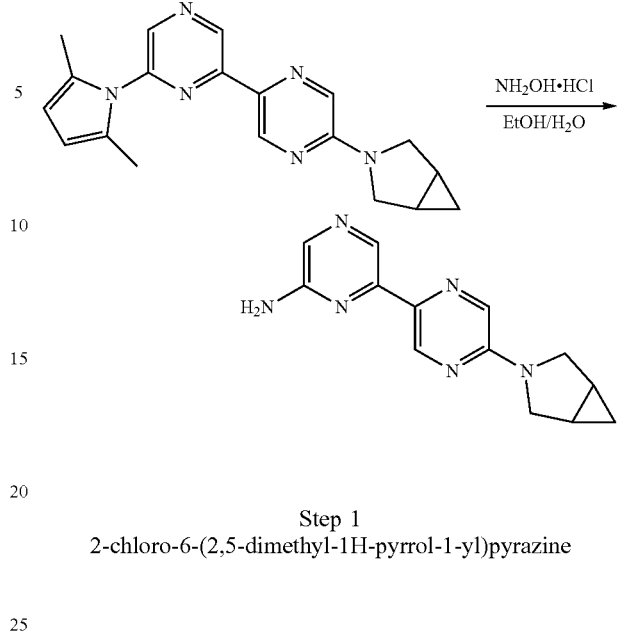

Step 1 2-chloro-6-(2,5-dimethyl-1H-pyrrol-1-yl)pyrazine

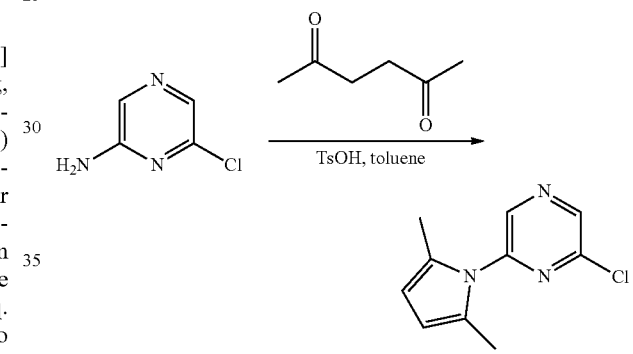

To a mixture of 6-chloropyrazin-2-amine (5 g, 38.6 mmol) and acetonylacetone (6.6 g, 57.9 mmol) in toluene (50 mL) was added p-toluenesulfonic acid (100 mg, 0.56 mmol) and the mixture was heated in a Dean-Stark apparatus for 2 hrs. The mixture was cooled to r.t. and diluted with EA (50 mL), washed with saturated aq.NaHCO$_3$, brine successively, dried and concentrated to give a crude product, which was purified by chromatography (PE/EA=20:1) to give 2-chloro-6-(2,5-dimethyl-1H-pyrrol-1-yl)pyrazine (6.1 g, 77.3% yield) as a yellow solid. Retention time (LC-MS): 1.503 min. MH$^+$208.

Step 2 3-(6'-(2,5-dimethyl-1H-pyrrol-1-yl)-2,2'-bipyrazin-5-yl)-3-azabicyclo[3.1.0]hexane

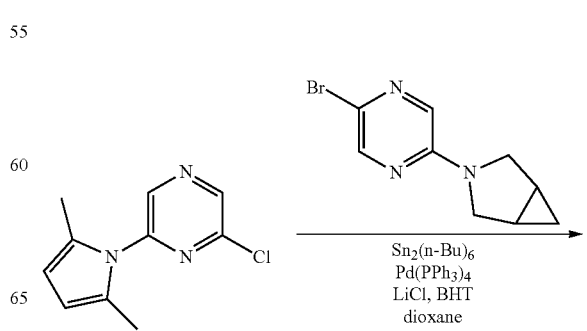

237

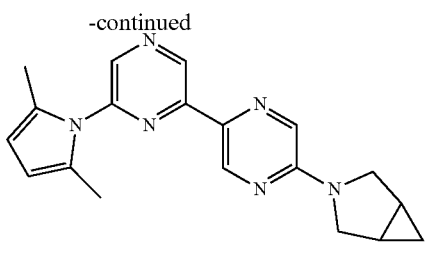

238

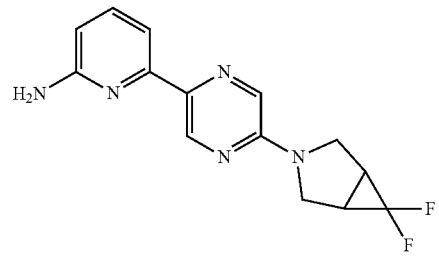 [SMILES: Nc1cccc(-c2cnc(N3CC4C(C3)C4(F)F)cn2)n1]

Retention time (LC-MS): 0.521 min. MH⁺290.

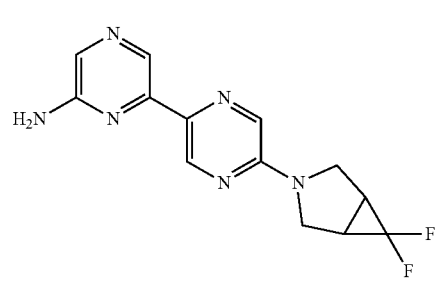 [SMILES: Nc1cncc(-c2cnc(N3CC4C(C3)C4(F)F)cn2)n1]

Retention time (LC-MS): 0.652 min. MH⁺291.

A mixture of 3-(5-bromopyrazin-2-yl)-3-azabicyclo[3.1.0]hexane (2.6 g, 10.8 mmol), 2-chloro-6-(2,5-dimethyl-1H-pyrrol-1-yl)pyrazine (2.6 g, 12.52 mmol), LiCl (530 mg, 12.52 mmol) and 2,6-di-tert-butyl-4-methylphenol (220 mg, 1 mmol) in 1,4-dioxane (60 mL) was degassed with N$_2$ for three times and terakis(triphenylphosphine)palladium (1.1 g, 1 mmol) was added under N$_2$ atmosphere. The mixture was degassed again and hexa-n-butylditin (14.5 g, 25.64 mmol) was added, the reaction mixture was stirred under N$_2$ at 110° C. for 40 hrs. The mixture was diluted with EA (200 mL) and washed with aq. KF solution, brine successively, dried and concentrated to dryness to give a crude product, which was purified by chromatography (PE/EA=5:1 to 1:1) to give 5'-(3-azabicyclo[3.1.0]hexan-3-yl)-2,2'-bipyrazin-6-amine (1.4 g. 33.6% yield) as a pale yellow solid. Retention time (LC-MS): 1.964 min. MH⁺333.

Step 3  5'-(3-azabicyclo[3.1.0]hexan-3-yl)-2,2'-bi-pyrazin-6-amine

Preparation 72  2-(5-(3-azabicyclo[3.1.0]hexan-3-yl)pyrazin-2-yl)thiazol-4-amine

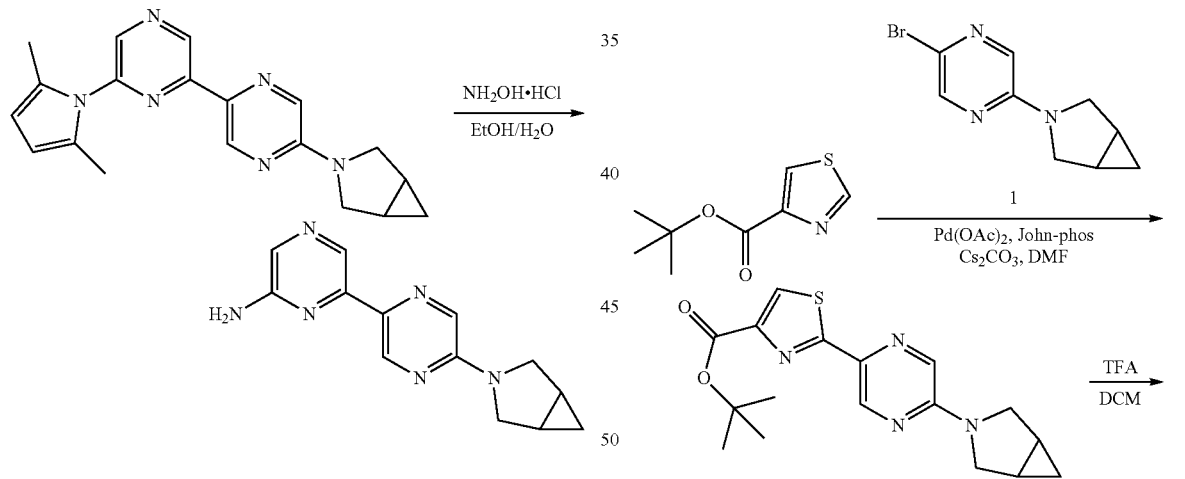

To a solution of 5'-(3-azabicyclo[3.1.0]hexan-3-yl)-2,2'-bipyrazin-6-amine (850 mg, 2.56 mmol) in EtOH/H$_2$O (20 mL/5 mL) was added hydroxylamine hydrochloride (1.77 g, 25.57 mmol) and the mixture was heated to reflux for 40 hrs. The mixture was concentrated to one third volume and basified by adding 2 N aq. NaOH solution at 0° C. The mixture was extracted with DCM twice and then combined organic layers were washed with brine, dried and concentrated to give a crude product, which was purified by chromatography (DCM/MeOH=60:1 to 30:1) to give 5'-(3-azabicyclo[3.1.0]hexan-3-yl)-2,2'-bipyrazin-6-amine (410 mg, 21.0 mg, 63% yield) as brown solid. Retention time (LC-MS): 0.832 min. MH⁺255.

The procedure set forth above was used to produce the following compounds using the appropriate starting materials.

-continued

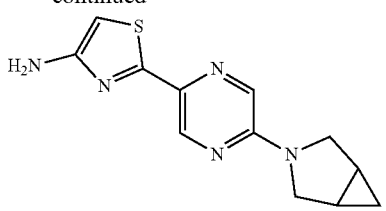

Step 1 tert-butyl 2-(5-(3-azabicyclo[3.1.0]hexan-3-yl)pyrazin-2-yl)thiazole-4-carboxylate

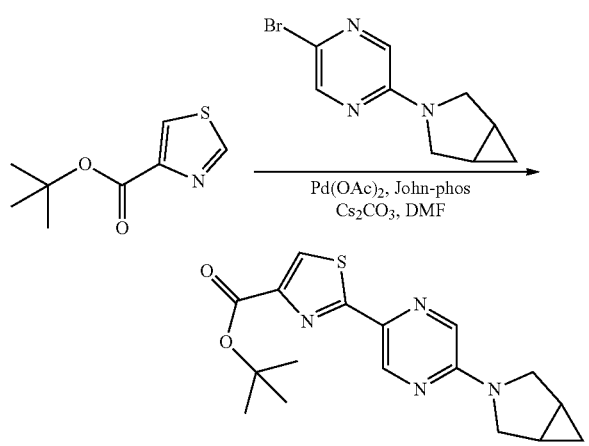

To a mixture of tert-butyl thiazole-4-carboxylate (928 mg, 5.02 mmol), 3-(5-bromopyrazin-2-yl)-3-azabicyclo[3.1.0]hexane (1 g, 4.18 mmol) in DMF (20 mL) was added Cs₂CO₃ (2.7 g, 8.36 mmol). After the mixture was degassed with N₂ for three times, Pd(OAc)₂ (94 mg, 0.42 mmol) and John-phos (146 mg, 0.42 mmol) were added under N₂ and the mixture was stirred at 100° C. overnight. The reaction mixture was cooled down and poured into EA. The organic phase was separated, washed with water and brine, dried over Na₂SO₄ and filtered. The filtrate was concentrated under reduced pressure and the residue was purified by chromatography (eluted with PE:EA=4:1) to afford tert-butyl 2-(5-(3-azabicyclo[3.1.0]hexan-3-yl)pyrazin-2-yl)thiazole-4-carboxylate (800 mg, 55.5% yield) as yellow solid. Retention time (LC-MS): 1.347 min. MH⁺345.

Step 2 2-(5-(3-azabicyclo[3.1.0]hexan-3-yl)pyrazin-2-yl)thiazole-4-carboxylic acid

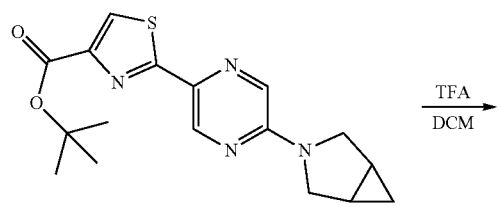

-continued

To a solution of tert-butyl 2-(5-(3-azabicyclo[3.1.0]hexan-3-yl)pyrazin-2-yl)thiazole-4-carboxylate (800 mg, 2.31 mmol) in DCM (10 mL) was added TFA (2 mL) at 0° C. After the addition, the mixture was stirred at RT overnight. The mixture was concentrated to dryness. The crude was washed with ether to give 2-(5-(3-azabicyclo[3.1.0]hexan-3-yl)pyrazin-2-yl)thiazole-4-carboxylic acid (500 mg, 74.9% yield) as a white solid. Retention time (LC-MS): 0.790 min. MH⁺289.

Step 3 Tert-butyl 2-(5-(3-azabicyclo[3.1.0]hexan-3-yl)pyrazin-2-yl)thiazol-4-ylcarbamate

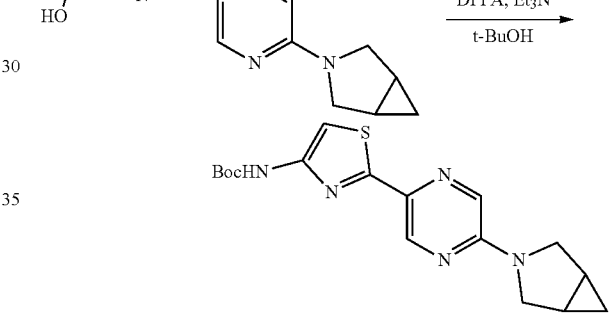

Diphenylphosphonic azide (0.45 mL, 2.12 mmol) was added drop-wise to a mixture of 2-(5-(3-azabicyclo[3.1.0]hexan-3-yl)pyrazin-2-yl)thiazole-4-carboxylic acid (500 mg, 1.73 mmol) and Et₃N (0.35 mL, 2.60 mmol) in t-BuOH (10 mL). The mixture was heated to 80° C. overnight. The reaction mixture was quenched with water and extracted with EA (2×5 mL). The combined organic layers were dried over Na₂SO₄ and filtered. The filtrate was concentrated and the residue was purified by chromatography (eluted with PE:EA=10:1) to afford tert-butyl (2-(5-(3-azabicyclo[3.1.0]hexan-3-yl)pyrazin-2-yl)thiazol-4-yl)carbamate (5, 130 mg, 20.8% yield) as a white solid. Retention time (LC-MS): 1.543 min. MH⁺360.

Step 4 2-(5-(3-azabicyclo[3.1.0]hexan-3-yl)pyrazin-2-yl)thiazol-4-amine

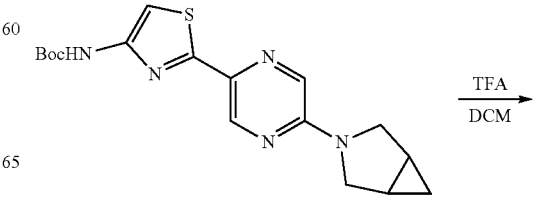

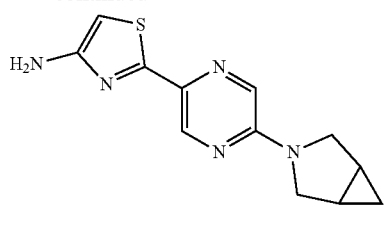

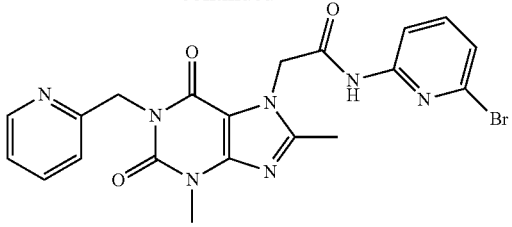

To a solution of tert-butyl (2-(5-(3-azabicyclo[3.1.0]hexan-3-yl)pyrazin-2-yl)thiazol-4-yl)carbamate (130 mg, 0.36 mmol) in DCM (4 mL) was added TFA (2 mL) at 0° C. After the addition, the mixture was stirred at RT for 2 hrs. The reaction mixture was diluted with DCM and quenched with sat. potassium carbonate. The organic layer was separated, dried over $Na_2SO_4$ and filtered. The filtrate was concentrated under reduced pressure to give 2-(5-(3-azabicyclo[3.1.0]hexan-3-yl)pyrazin-2-yl)thiazol-4-amine (80 mg, 85.2% yield) as yellow solid. Retention time (LC-MS): 0.790 min. $MH^+260$.

Preparation 73 N-(6-bromopyridin-2-yl)-2-(3,8-dimethyl-2,6-dioxo-1-(pyridin-2-ylmethyl)-2,3-dihydro-1H-purin-7(6H)-yl)acetamide

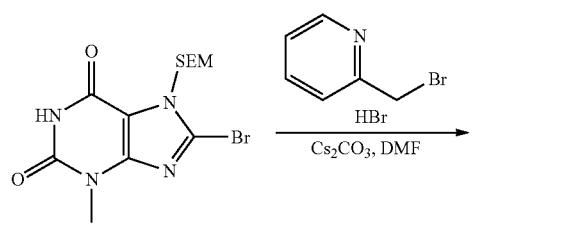

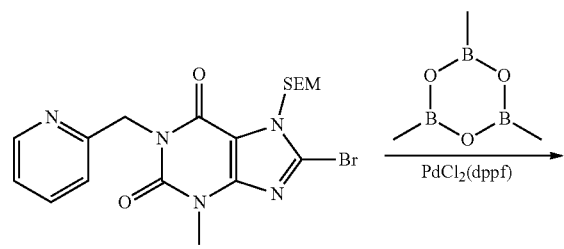

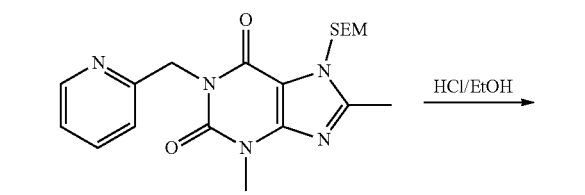

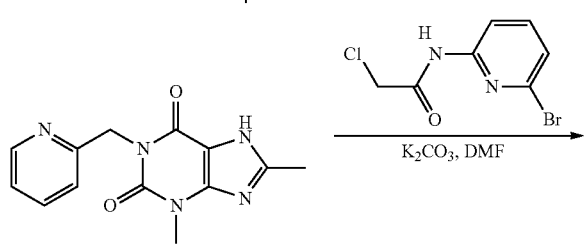

Step 1 8-bromo-3-methyl-1-(pyridin-2-ylmethyl)-7-((2-(trimethylsilyl)ethoxy)methyl)-1H-purine-2,6(3H,7H)-dione To a mixture of 8-bromo-3-methyl-7-((2-(trim ethyl silyl)ethoxy)methyl)-1H-purine-2,6(3H,7H)-dione (2.9 g, 9.78 mmol) and 2-(bromomethyl)pyridine hydrobromide (3.0 g, 11.74 mmol) in DMF (50 mL) was added cesium carbonate (6.5 g, 19.57 mmol) and TBAI (142.7 mg,0.39 mmol). The reaction mixture was stirred at 100° C. for 2 h. The mixture was cooled down to RT and diluted with DCM. The resulting solution was washed with S. aq. LiCl, dried over $Na_2SO_4$, and concentrated and the residue was purified by chromatography (eluted with PE:EA=5:1) to afford 8-bromo-3-methyl-1-(pyridin-2-ylmethyl)-7-((2-(trimethyl silyl) ethoxy)methyl)-1H-purine-2,6(3H,7H)-dione (2.5 g, 66.0% yield) as yellow oil. Retention time (LC-MS): 1.534 min. $MH^+468$.

Step 2 3,8-dimethyl-1-(pyridin-2-ylmethyl)-7-((2-(trimethylsilyl)ethoxy)methyl)-1H-purine-2,6(3H,7H)-dione

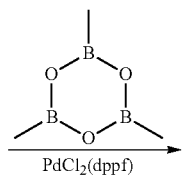

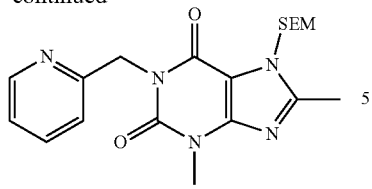

To a mixture of 8-bromo-3-methyl-1-(pyridin-2-ylmethyl)-7-((2-(trimethyl silyl)ethoxy)methyl)-1H-purine-2,6(3H,7H)-dione (2, 1 g, 2.14 mmol), 2,4,6-trimethyl-1,3,5,2,4,6-trioxatriborinane (404 mg, 3.22 mmol) and potassium carbonate (593 mg, 4.29 mmol) in dioxane (50 mL) was added Pd(dppf)Cl$_2$ (80 mg, 0.11 mmol) after degassed three times under N$_2$ atmosphere. The mixture was then heated to 110° C. for 2 h. The reaction mixture was cooled and filtered through Celite. The filtrate was extracted with EA (3×200 mL). Combined organic layers were dried over Na$_2$SO$_4$ and filtered. The filtrate was concentrated under reduced pressure and the residue was purified by chromatography (eluted with PE/EA=1/1) to afford 3,8-dimethyl-1-(pyridin-2-ylmethyl)-7-((2-(trimethylsilyl)ethoxy)methyl)-1H-purine-2,6(3H,7H)-dione (800 mg, 93.1% yield) as a white solid. Retention time (LC-MS): 1.232 min. MH$^+$403.

Step 3 3,8-dimethyl-1-(pyridin-2-ylmethyl)-1H-purine-2,6(3H,7H)-dione

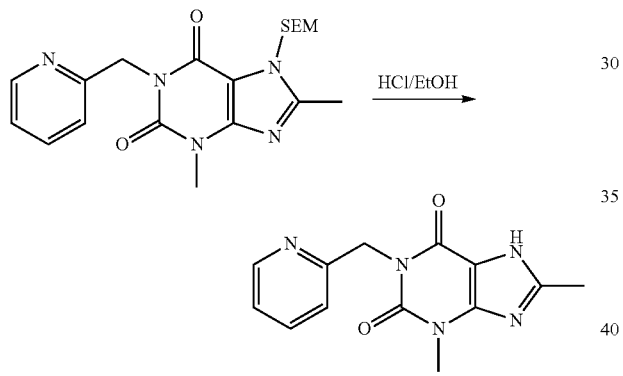

To a stirred solution of 3,8-dimethyl-1-(pyridin-2-ylmethyl)-7-((2-(trimethylsilyl)ethoxy)methyl)-1H-purine-2,6(3H,7H)-dione (800 mg, 1.99 mmol) in EtOH (5 mL) was added conc. HCl (1 mL). After the addition, the mixture was heated to reflux for 2 h and then cooled to RT. The mixture was concentrated to dryness to give crud 3,8-dimethyl-1-(pyridin-2-ylmethyl)-1H-purine-2,6(3H,7H)-dione (490 mg, 98.0% yield) as an off-white solid which was used directly without any further purification. Retention time (LC-MS): 0.386 min. MH$^+$272.

Step 4 N-(6-bromopyridin-2-yl)-2-(3,8-dimethyl-2,6-dioxo-1-(pyridin-2-ylmethyl)-2,3-dihydro-1H-purin-7(6H)-yl)acetamide

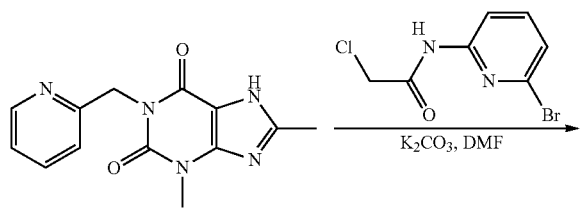

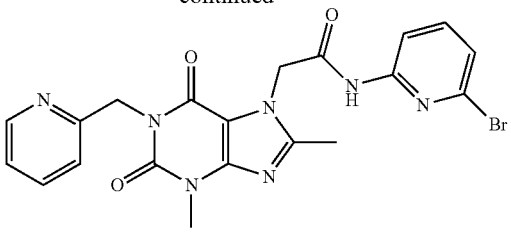

A mixture of 3,8-dimethyl-1-(pyridin-2-ylmethyl)-1H-purine-2,6(3H,7H)-dione (490 mg, 1.81 mmol), TBAI (68 mg, 0.018 mmol), N-(6-bromopyridin-2-yl)-2-chloroacetamide (541 mg, 2.17 mmol) and potassium carbonate (499 mg, 3.61 mmol) in DMF (5 mL) was stirred at 50° C. for 2 h. The reaction mixture was quenched by water (40 mL), and then extracted with EA (3×50 mL). Combined organic layers were dried over Na$_2$SO$_4$ and filtered. The filtrate was concentrated and the residue was purified by chromatography (eluted with DCM:MeOH=60:1) to afford N-(6-bromopyridin-2-yl)-2-(3,8-dimethyl-2,6-dioxo-1-(pyridin-2-ylmethyl)-2,3-dihydro-1H-purin-7(6H)-yl)acetamide (740 mg, 84.6% yield) as a white solid. Retention time (LC-MS): 1.081 min. MH$^+$486.

Preparation 74 N-(6-bromopyridin-2-yl)-2-(8-(hydroxymethyl)-3-methyl-2,6-dioxo-1-(2-oxopropyl)-2,3-dihydro-1H-purin-7(6H)-yl)acetamide

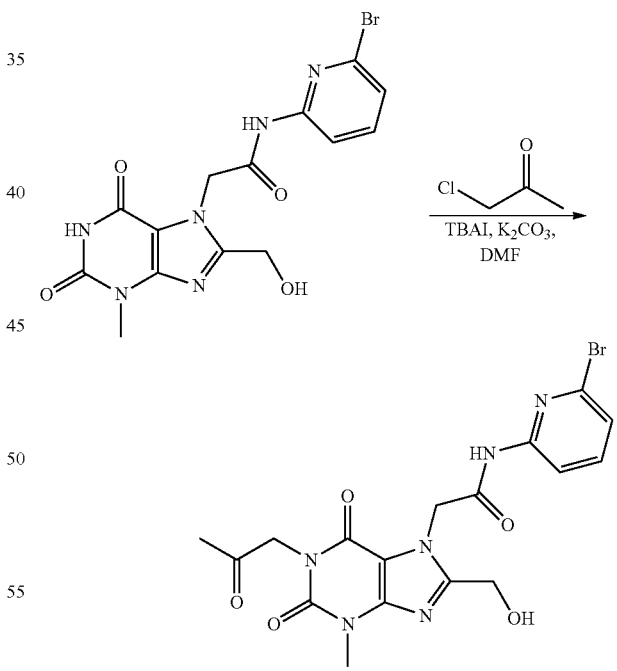

A mixture of N-[6-(3,4-Difluoro-phenyl)-pyridin-2-yl]-2-[8-hydroxymethyl-3-methyl-2,6-dimethylene-1-(2-oxo-propyl)-1,2,3 ,6-tetrahydro-purin-7-yl]-acetamide (370 mg, 0.94 mmol), potassium carbonate (260 mg, 1.88 mmol), TBAI (58 mg, 0.09 mmol) in DMF (2 ml) was stirred at 50° C. under N$_2$ overnight. The reaction mixture was quenched by water (10 mL), and then extracted with EA (3×5 mL). Combined organic layers were dried over Na$_2$SO$_4$ and filtered. The filtrate was concentrated and the residue was purified by chromatography (eluted with DCM:MeOH=15:1) to afford N-(6-bromopyridin-2-yl)-2-(8-(hydroxymethyl)-3-methyl-2,6-dioxo-1-(2-oxopropyl)-2,3-dihydro-1H-purin-7(6H)-yl)acetamide (136 mg, 32% yield) as a yellow solid. Retention time (LC-MS): 0.815 min. MH$^+$465.

Preparation 75 N-(6-bromopyridin-2-yl)-2-(3-methyl-2,6-dioxo-1-(2-oxopropyl)-1,2,3,6-tetrahydropurin-7-yl)acetamide

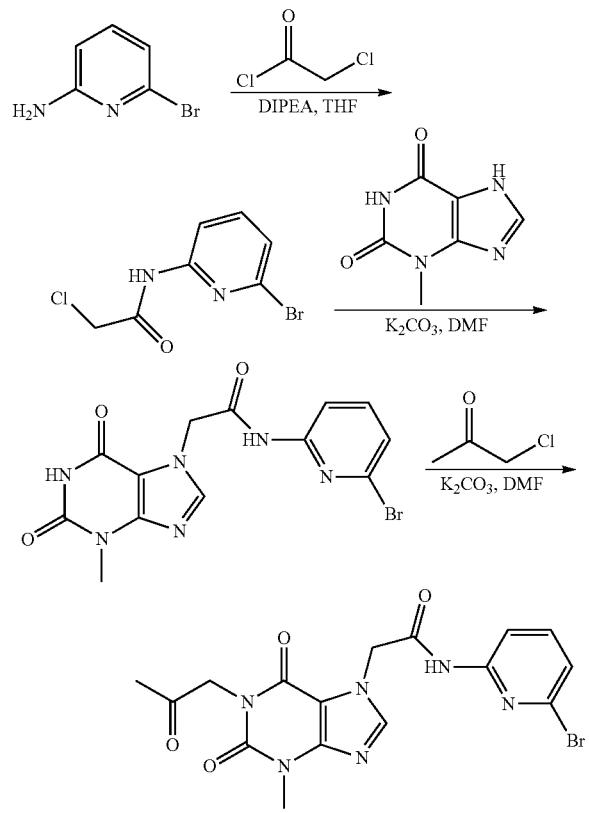

Step 1 N-(6-bromopyridin-2-yl)-2-chloroacetamide

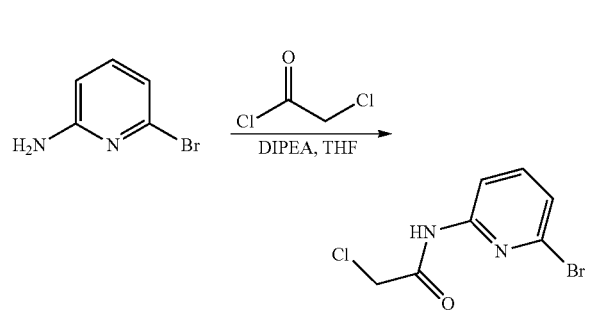

To a solution of 6-bromopyridin-2-amine (5 g, 28.90 mmol) and TEA (10.0 ml, 43.35 mmol) in DCM (50 mL) was added dropwise 2-chloroacetyl chloride (3.45 mL, 72.25 mmol) at RT under N$_2$ atmosphere. After addition, the mixture was stirred at RT overnight. The reaction was quenched by addition of water, and the reaction mixture was extracted with DCM (2×50 mL). Combined organic layers were dried over Na$_2$SO$_4$ and filtered. The filtrate was concentrated under reduced pressure and the residue was purified by chromatography (eluted with PE:EA=20:1) to afford N-(6-bromopyridin-2-yl)-2-chloroacetamide (3.0 g, 41.6% yield) as a white solid. Retention time (LC-MS): 1.276 min. MH$^+$251.

Step 2 N-(6-bromopyridin-2-yl)-2-(3-methyl-2,6-dioxo-1,2,3,6-tetrahydro-purin-7-yl)acetamide

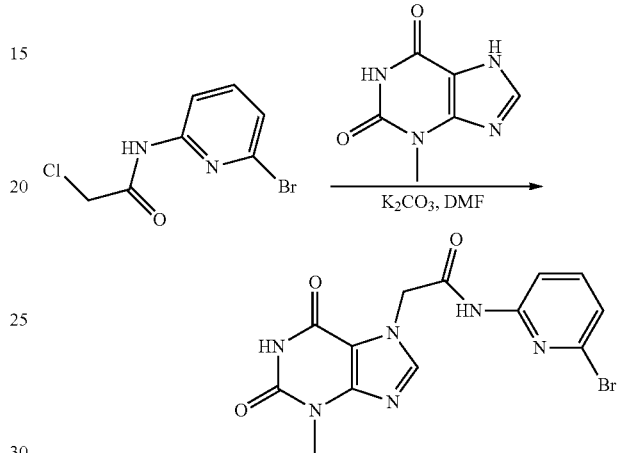

To a mixture of N-(6-bromopyridin-2-yl)-2-chloroacetamide (3.0 g, 12.04 mmol) and 3-methyl-1H-purine-2,6(3H,7H)-dione (2.2 g, 13.24 mmol) in DMF (60 mL) was added potassium carbonate (2.16 g, 15.65 mmol). The reaction mixture was stirred at RT overnight. The mixture was poured into water (200 mL) and filtered. The solid was collected and dried under vacuum to give N-(6-bromopyridin-2-yl)-2-(3-methyl-2,6-dioxo-1,2,3,6-tetrahydropurin-7-yl)acetamide (4.2 g, 83.7% yield) as a white solid. Retention time (LC-MS): 0.658 min. MH$^+$379.

Step 3 N-(6-bromopyridin-2-yl)-2-(3-methyl-2,6-dioxo-1-(2-oxopropyl)-1,2,3,6-tetrahydropurin-7-yl)acetamide

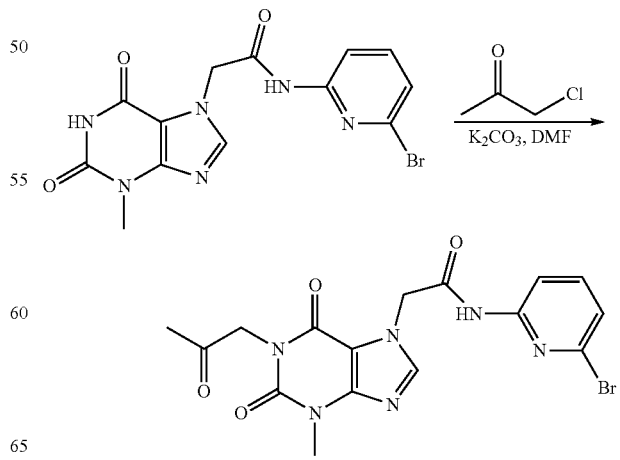

A mixture of N-(6-bromopyridin-2-yl)-2-(3-methyl-2,6-dioxo-1,2,3,6-tetrahydropurin-7-yl)acetamide (5, 1.5 g, 3.96 mmol), 1-chloropropan-2-one (0.47 mL, 5.93 mmol), potassium carbonate (1.37 g, 9.89 mmol) and a catalytic amount of TBAI in N, N-dimethyl formamide (50 mL) was stirred at 50° C. for 2 h. The reaction mixture was poured into water and filtered. The solid was washed with water twice, collected, dried under vacuum and then re-crystallized from ethanol to give N-(6-bromopyridin-2-yl)-2-(3-methyl-2,6-dioxo-1-(2-oxopropyl)-1,2,3,6-tetrahydropurin-7-yl)acetamide (835 mg, 48.5% yield) as a white solid. Retention time (LC-MS): 1.100 min. MH+435.

Preparation 76 N-(6-bromopyridin-2-yl)-2-(3-methyl-2,6-dioxo-1-(pyridin-2-ylmethyl)-2,3-dihydro-1H-purin-7(6H)-yl)acetamide

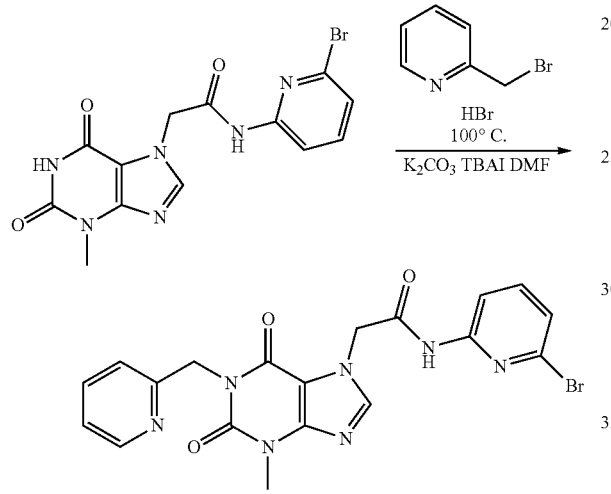

To a solution of N-(6-bromopyridin-2-yl)-2-(3-methyl-2,6-dioxo-2,3-dihydro-1H-purin-7(6H)-yl)acetamide (1.5 g, 3.97 mmol) in DMF (15 mL) were added potassium carbonate (1.6 g, 12 mmol), 2-(bromomethyl)pyridine (1.2 g, 4.76 mmol) and tetrabutyl ammonium iodide (30 mg, 0.081 mmol). After the addition, the mixture was stirred at 100° C. for 2 h and cooled to RT. The mixture was diluted with EA and washed with S. aqueous LiCl. The organic layer was separated, dried over Na2SO4, and concentrated and the residue was purified by chromatography to afford N-(6-bromopyridin-2-yl)-2-(3-methyl-2,6-dioxo-1-(pyridin-2-ylmethyl)-2,3-dihydro-1H-purin-7(6H)-yl)acetamide (450 mg, 24.2% yield) as grey solid. Retention time (LC-MS): 0.473 min. MH+470.

Preparation 77 N-(2-bromothiazol-4-yl)-2-(3-methyl-2,6-dioxo-1-(pyridin-2-ylmethyl)-2,3-dihydro-1H-purin-7(6H)-yl)acetamid

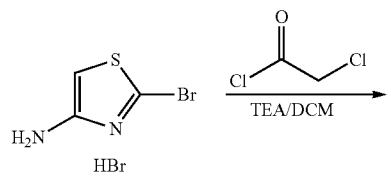

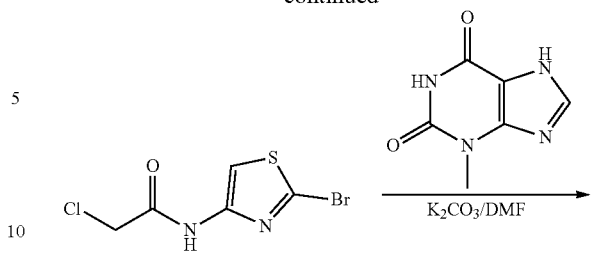

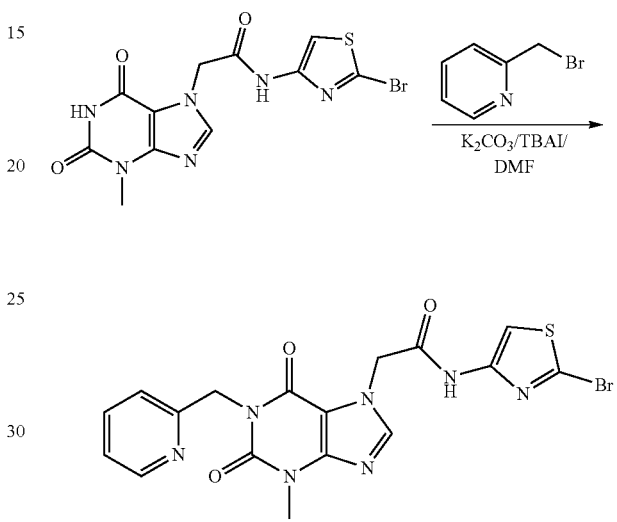

Step 1 N-(2-bromothiazol-4-yl)-2-chloroacetamide

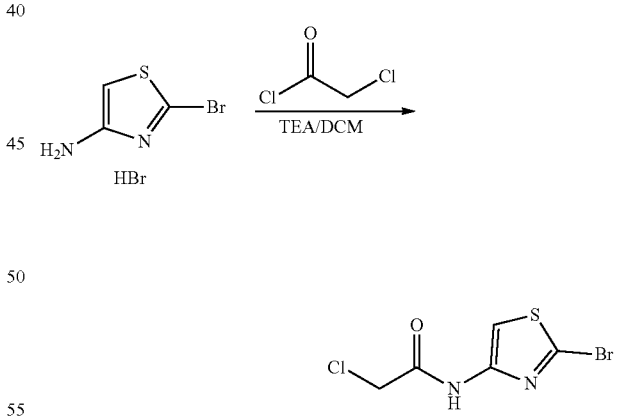

To a solution of 2-bromothiazol-4-amine hydrobromide (1 g, 3.85 mol) in methylene chloride (10 mL) was added slowly TEA (1.5 g, 15.4 mol) at 0° C. The solution was stirred for 15 min at the same temperature and then 2-chloroacetyl chloride (651 mg, 5.77 mmol) was added. The mixture was stirred overnight at RT. The solvent was removed under reduced pressure and the residue was purified via chromatography (eluted with PE:EA=2:1) to afford N-(2-bromothiazol-4-yl)-2-chloroacetamide (650 mg, 66.1% yield) as light yellow oil.

249

Step 2 N-(2-bromothiazol-4-yl)-2-(3-methyl-2,6-dioxo-1-(pyridin-2-ylmethyl)-2,3-dihydro-1H-purin-7(6H)-yl)acetamide

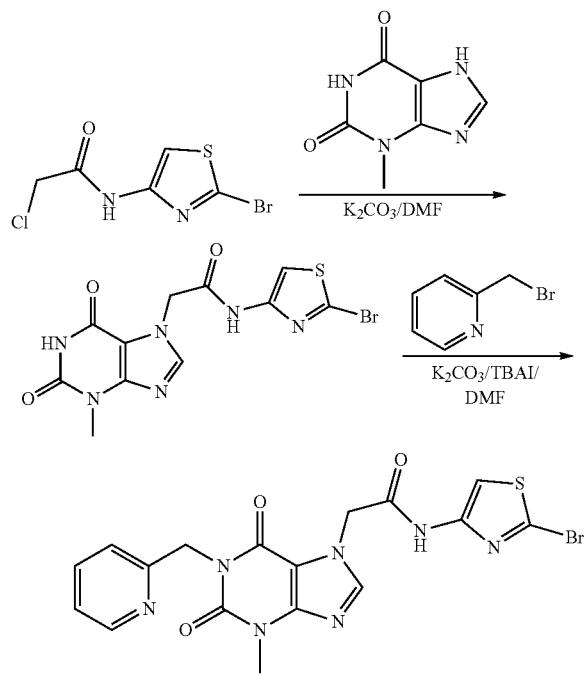

To a mixture of 3-methyl-7-((2-(trimethylsilyl)ethoxy)methyl)-1H-purine-2,6(3H,7H)-dione (250 mg, 1.50 mmol), N-(2-bromothiazol-4-yl)-2-chloroacetamide (346 mg, 1.35 mmol) in DMF (10 mL) was added potassium carbonate (250 mg, 1.81 mmol), and the mixture was stirred at RT for 2 h. Then 2-(bromomethyl)pyridine (400 mg, 2.25 mmol), potassium carbonate (200 mg, 3.76 mmol) and TBAI (10 mg) were added into the mixture. The mixture was stirred at 100° C. for 2 h and cooled to RT. The mixture was extracted with DCM (3×10 mL). Combined organic layers were washed with S. aqueous ammonium chloride, dried over Na₂SO₄, and filtered. The filtrate was concentrated and the residue was purified by chromatography (eluted with DCM:MeOH=20:1) to give N-(2-bromothiazol-4-yl)-2-(3-methyl-2,6-dioxo-1-(pyridin-2-ylmethyl)-2,3-dihydro-1H-purin-7(6H)-yl)acetamide (270 mg, 54.0% yield) as brown oil. Retention time (LC-MS): 1.874 min. MH⁺477.

Preparation 78 N-(6-bromopyridin-2-yl)-2-(3,8-dimethyl-2,6-dioxo-1-(2-oxopropyl)-1,2,3,6-tetrahydropurin-7-yl)acetamide

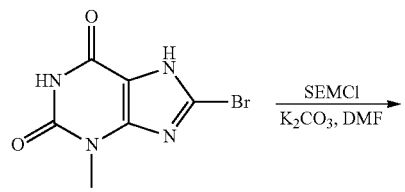

250

-continued

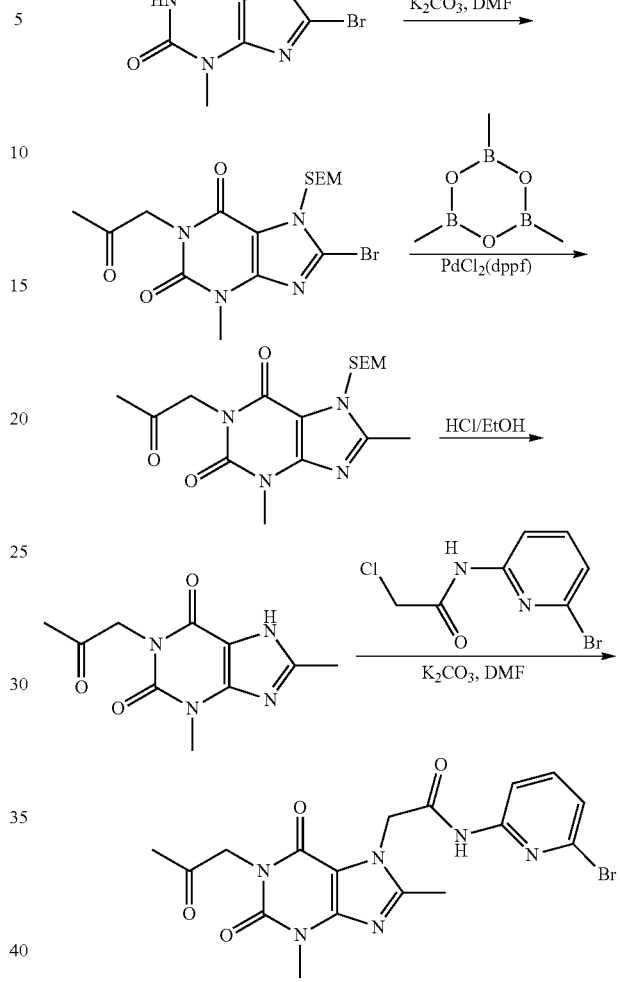

Step 1 8-bromo-3-methyl-7-((2-(trimethylsilyl)ethoxy)methyl)-1H-purine-2,6(3H,7H)-dione

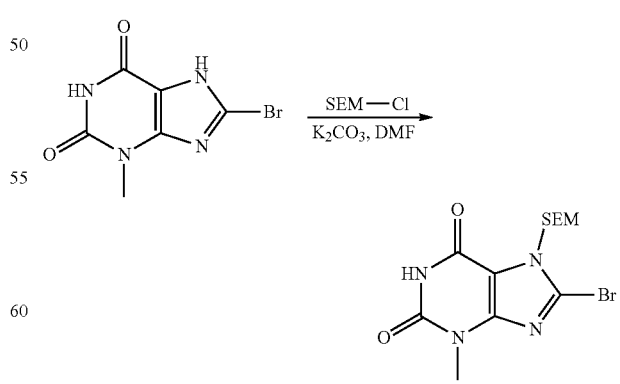

To a mixture of 8-bromo-3-methyl-1H-purine-2,6(3H,7H)-dione (3 g, 0.012 mol) and potassium carbonate (3.4 g, 0.024 mol) in DMF (30 mL) was added SEM-Cl (2.45 g, 0.014 mol) at 0° C. After the addition, the mixture was stirred at RT for 2 h. The mixture was then diluted with EA and washed with water, 10% aqueous LiCl successively, dried and concentrated to give crude product, which was washed with EtOH to afford 8-bromo-3-methyl-7-((2-(trimethylsilyl)ethoxy)methyl)-1H-purine-2,6(3H,7H)-dione (3.5 g, 74% yield) as a white solid. Retention time (LC-MS): 1.364. MH$^+$-CO 347.

Step 2 8-bromo-3-methyl-1-(2-oxopropyl)-7-((2-(trimethylsilyl)ethoxy)methyl)-1H-purine-2,6(3H,7H)-dione

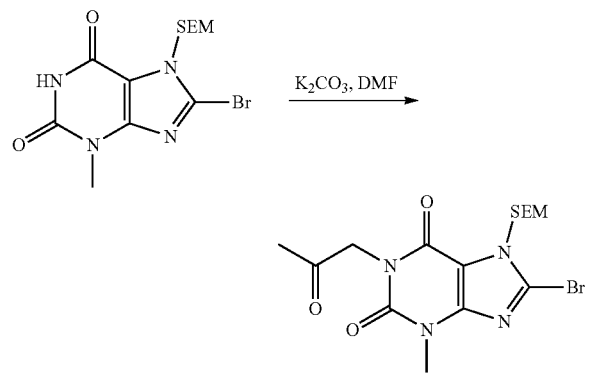

To a mixture of 8-bromo-3-methyl-7-((2-(trimethyl silyl)ethoxy)methyl)-1H-purine-2,6(3H,7H)-dione (1.5 g, 4.01 mmol), TBAI (148 mg, 0.4 mmol) and potassium carbonate (3.4 g, 0.024 mol) in DMF (30 mL) was added 1-chloropropan-2-one (422 mg, 4-81 mmol) at 0° C. After the addition, the mixture was stirred at 50° C. for 2 h. The mixture was cooled to RT, diluted with water (60 mL) and filtered. The filter cake was washed with EtOH and dried under vacuum to afford 8-bromo-3-methyl-1-(2-oxopropyl)-7-((2-(trimethylsilyl)ethoxy)methyl)-1H-purine-2,6(3H,7H)-dione (1.6 g, 93% yield) as a white solid. Retention time (LC-MS): 1.639 min. (MH$^+$-CO) 403.

Step 3 3,8-dimethyl-1-(2-oxopropyl)-7-((2-(trimethylsilyl)ethoxy)methyl)-1H-purine-2,6(3H,7H)-dione

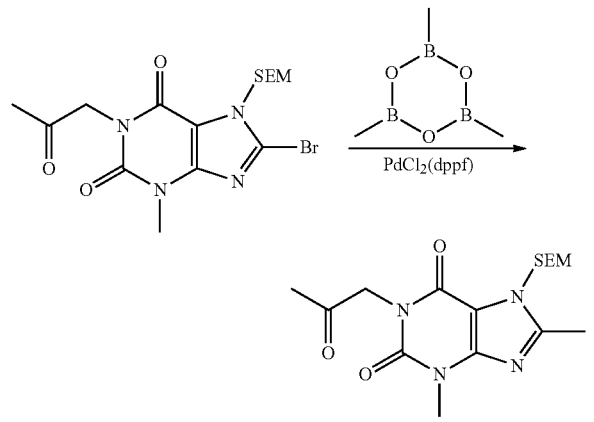

To a mixture of 8-bromo-3-methyl-1-(2-oxopropyl)-7-((2-(trimethylsilyl)ethoxy)methyl)-1H-purine-2,6(3H,7H)-dione (1.5 g, 3.48 mmol), 2,4,6-trimethyl-1,3,5,2,4,6-trioxatriborinane (526 mg, 4.17 mmol) and potassium carbonate (960 mg, 6.96 mmol) in dioxane (400 mL) was added Pd(dppf)Cl$_2$ (254 mg, 0.348 mmol) after degassed three times under N$_2$ atmosphere, then the mixture was heated to 110° C. for 2 h. The mixture was cooled and filtered through Celite. The filtrate was extracted with EA (3×500 mL). Combined organic layers were dried over Na$_2$SO$_4$ and filtered. The filtrate was concentrated under reduced pressure and the residue was purified by chromatography (eluted with PE/EA=1/1) to afford 3,8-dimethyl-1-(2-oxopropyl)-7-((2-(trimethylsilyl)ethoxy)methyl)-1H-purine-2,6(3H,7H)-dione (650 mg, 50.2% yield) as a white solid. Retention time (LC-MS): 1.454 min. MH$^+$339.

Step 4 3,8-dimethyl-1-(2-oxopropyl)-1H-purine-2,6(3H,7H)-dione

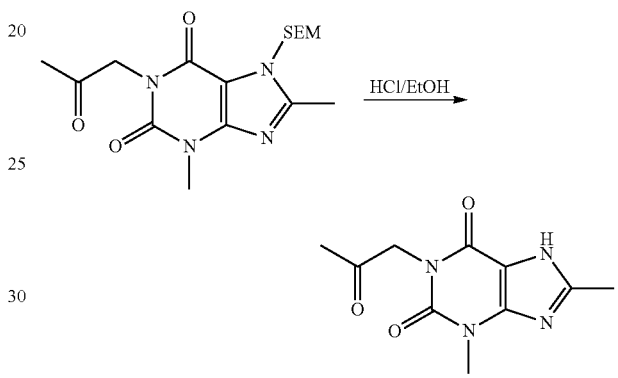

To a stirred solution of 3,8-dimethyl-1-(2-oxopropyl)-7-((2-(trimethylsilyl)ethoxy)methyl)-1H-purine-2,6(3H,7H)-dione (650 mg, 1.77 mmol) in EtOH (15 mL) was added conc. HCl (3 mL). After the addition, the mixture was heated to reflux for 2 h and cooled to RT. The mixture was concentrated to dryness to give 3,8-dimethyl-1-(2-oxopropyl)-1H-purine-2,6(3H,7H)-dione (410 mg, 85% yield) as an off-white solid. Retention time (LC-MS): 0.405 min. MH$^+$237.

Step 5 N-(6-bromopyridin-2-yl)-2-(3,8-dimethyl-2,6-dioxo-1-(2-oxopropyl)-1,2,3,6-tetrahydropurin-7-yl)acetamide

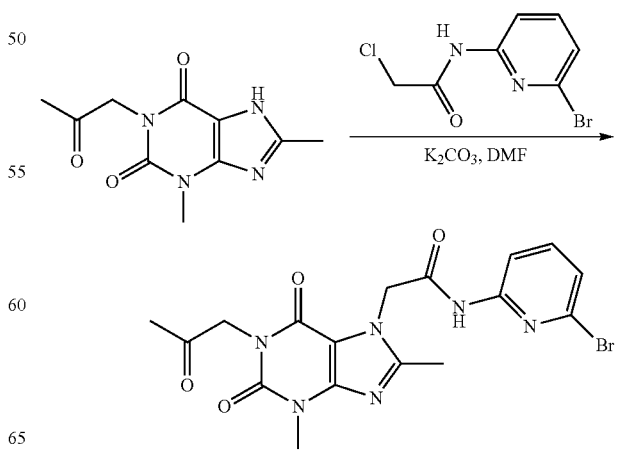

A mixture of 3,8-dimethyl-1-(2-oxopropyl)-1H-purine-2,6 (3H,7H)-dione (410 mg, 1.73 mmol), TBAI (64 mg, 0.017 mmol), N-(6-bromopyridin-2-yl)-2-chloroacetamide (514 mg, 2.07 mmol) and potassium carbonate (477 mg, 3.46 mmol) in DMF (8 mL) was stirred at 50° C. for 2 h. The reaction mixture was quenched by water (60 mL), and then extracted with EA. Combined organic layers were dried over Na$_2$SO$_4$ and filtered. The filtrate was concentrated and the residue was purified by chromatography (eluted with DCM/MeOH=80/1) to afford N-(6-bromopyridin-2-yl)-2-(3,8-dimethyl-2,6-dioxo-1-(2-oxopropyl)-1,2,3,6-tetrahydropurin-7-yl)acetamide (550 mg, 65.1% yield) as a white solid. Retention time (LC-MS): 1.024 min. MH$^+$449.

Preparation 79 3-methyl-1-((5-methylisoxazol-3-yl)methyl)-1H-purine-2,6(3H,7H)-dione

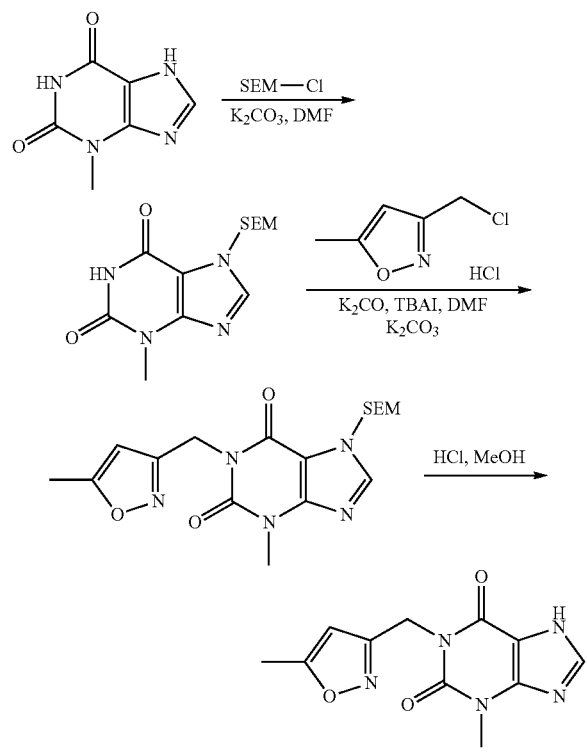

Step 1 3-methyl-7-((2-(trimethylsilyl)ethoxy)methyl)-1H- purine-2,6(3H,7H)-dione

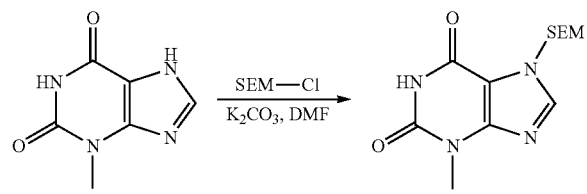

To a stirred solution of 3-methyl-1H-purine-2,6(3H,7H)-dione (5 g, 30.10 mmol) and potassium carbonate (6.24 g, 45.14 mmol) in DMF (5 mL) at 0° C. was added (2-(chloromethoxy)ethyl)trimethylsilane (5.33 mL, 30.10 mmol). After the addition, the mixture was warmed to RT and stirred over night. The reaction mixture was diluted with DCM, and washed with s. aq. LiCl. The organic layer was separated, dried over Na2SO4, and concentrated to afford 3-methyl-7-((2-(trimethylsilyl)ethoxy)methyl)-1H-purine-2,6(3H,7H)-dione (3.78 g, 42.4% yield) as yellow solid. Retention time (LC-MS): 1.160 min. MH$^+$297.

Step 2 3-methyl-1-((5-methylisoxazol-3-yl)methyl)-7-((2-(trimethylsilyl) ethoxy)methyl)-1H-purine-2,6 (3H,7H)-dione

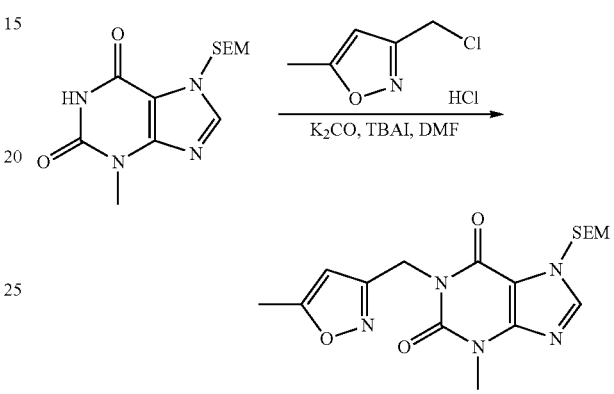

To a mixture of 3-methyl-7-((2-(trimethylsilyl)ethoxy) methyl)-1H-purine -2,6(3H,7H)-dione (1.0 g, 3.37 mmol) and 3-(chloromethyl)-5-methylisoxazole hydrochloride (665.80 mg, 5.06 mmol) in DMF (20 mL) was added potassium carbonate (1.17 g, 8.43 mmol) and TBAI (61.84 mg, 0.17 mmol). The mixture was stirred at 50° C. for 2 h. The reaction mixture was diluted with DCM and washed with S. aq. LiCl. The organic layer was separated, dried over Na2SO4, and concentrated and the residue was purified by chromatography (eluted with PE:EA=5:1) to afford 3-methyl-1-((5-methylisoxazol-3-yl)methyl)-7-((2-(trimethylsilyl)ethoxy)methyl)-1H-purine-2,6(3H, 7H)-dione (750 mg, 56.8% yield) as yellow solid. Retention time (LC-MS): 1.476 min. MH$^+$392.

Step 3 3-methyl-1-((5-methylisoxazol-3-yl)methyl)-1H-purine-2,6(3H,7H)-dione

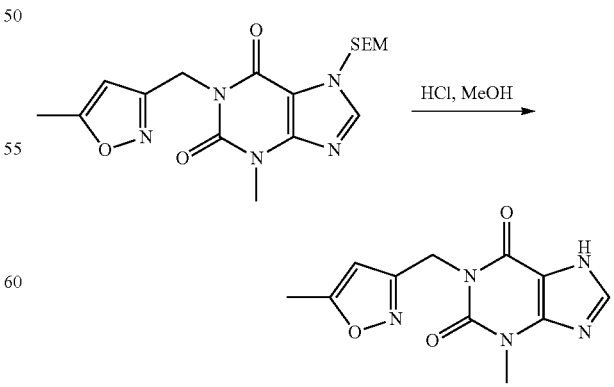

To a stirred solution of 3-methyl-1-((5-methylisoxazol-3-yl)methyl)- 7-((2-(trimethylsilyl)ethoxy)methyl)-1H-purine-2, 6(3H,7H)-dione (750 mg, 1.92 mmol) in EtOH (5 mL) was added conc. HCl (1 mL). After the addition, the mixture was heated to reflux for 2 h and then cooled to RT. The mixture was concentrated to dryness to give a crude product of 3-methyl-1-((5-methylisoxazol-3-yl)methyl)-1H-purine-2,6 (3H,7H)-dione (415 mg, 82.9% yield) as yellow solid which was used in the next step without any further purification. Retention time (LC-MS): 0.544 min. MH$^+$262.

Preparation 80 N-(5-bromo-6-(trifluoromethyl)pyridin-2-yl)-2-chloroacetamide

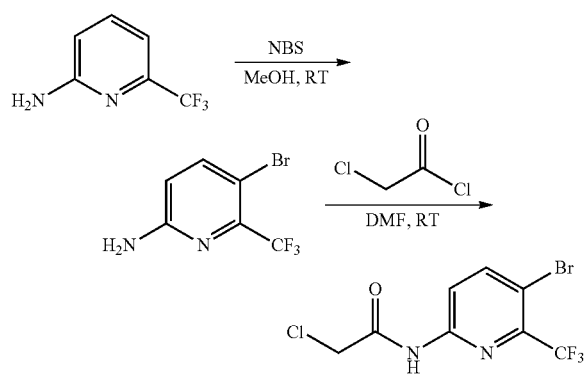

Step 1 5-bromo-6-(trifluoromethyl)pyridin-2-amine

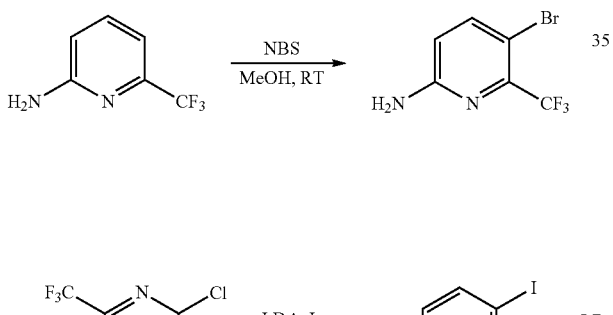

To a mixture of 6-(trifluoromethyl)pyridin-2-amine (600 mg, 3.7 mmol) in MeOH (10 mL) was added NBS (659 mg, 3.7 mmol) in portions at 0° C. The reaction mixture was stirred at r.t. overnight. The reaction mixture was concentrated under reduced pressure and the residue was purified by chromatography (eluted with PE:EA=4:1) to afford the title compound (650 mg, 73.1% yield) as a white solid. Retention time (LC-MS): 1.33 min. MH$^+$241.

Step 2 N-(5-bromo-6-(trifluoromethyl)pyridin-2-yl)-2-chloroacetamide

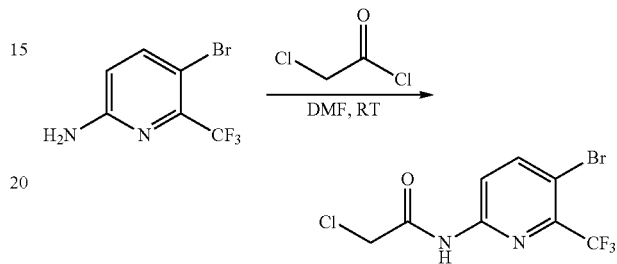

To a solution of 5-bromo-6-(trifluoromethyl)pyridin-2-amine (72 mg, 0.3 mmol) in DMF (2 mL) was added dropwise 2-chloroacetyl chloride (0.05 mL, 0.6 mmol) at 0° C. The reaction mixture was stirred at r.t. for 2 h and poured into EA. The mixture was washed with water and brine, dried over Na2SO4, and concentrated to give the title compound (85 mg, 89.7% yield) as yellow solid. Retention time (LC-MS): 1.64 min. MH$^+$319.

Preparation 81 N-(3,4-dimethoxybenzyl)-N-(4-ethyl-6-(trifluoromethyl)pyridin-2-yl)-2-(1-(isoxazol-3-ylmethyl)-3-methyl-2,6-dioxo-2,3-dihydro-1H-purin-7(6H)-yl)acetamide

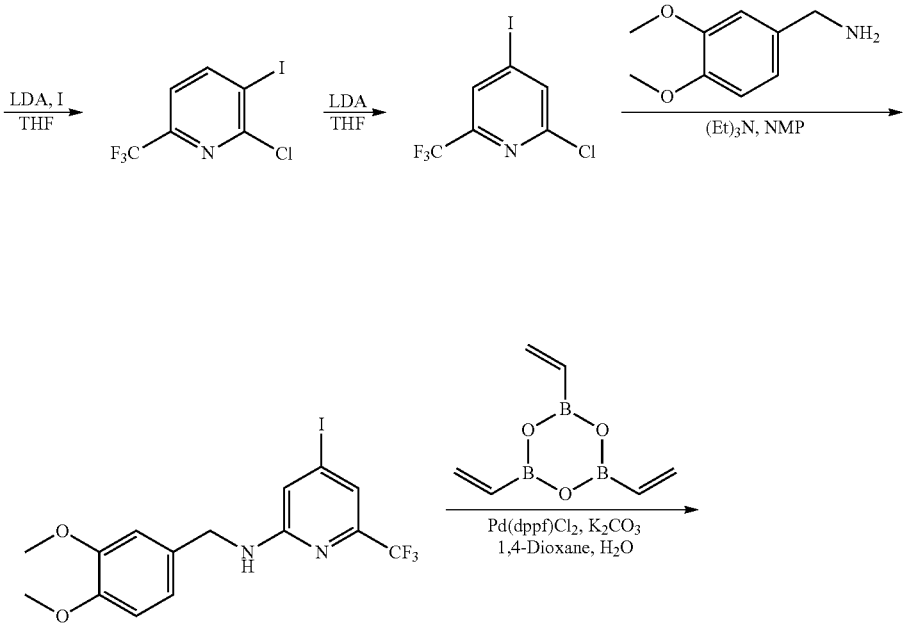

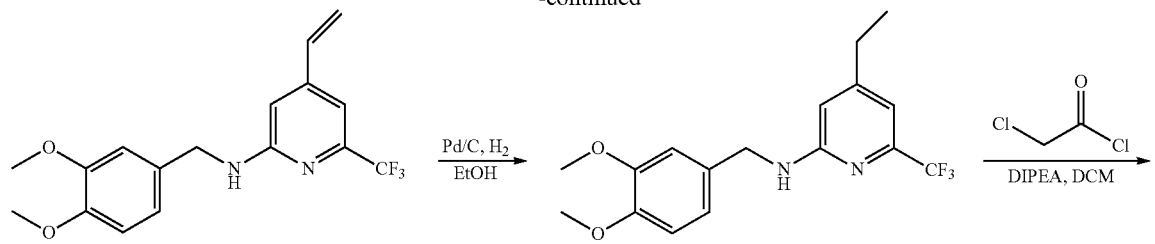

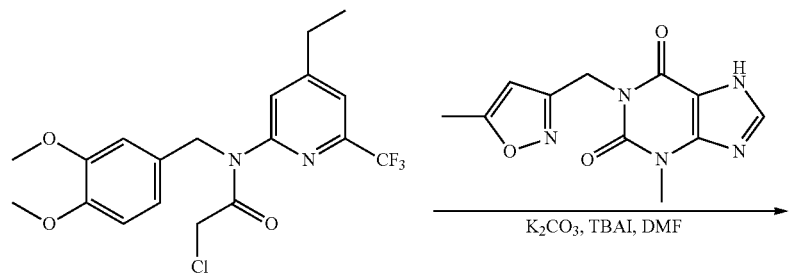

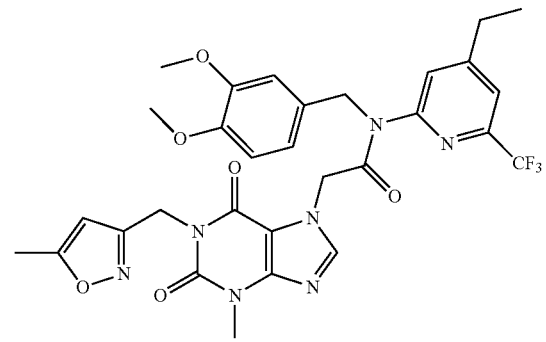

Step 1 2-chloro-3-iodo-6-(trifluoromethyl)pyridine

To a solution of 2-chloro-6-(trifluoromethyl)pyridine (10.0 g, 55.25 mmol) in THF (200 mL) was added dropwise LDA (30.39 mL, 2 M) at −78° C. via funnel under $N_2$ atmosphere. The reaction mixture was stirred at that temperature for 1 hr, followed by dropwise addition of $I_2$ (16.84 g, 66.30 mmol). The mixture was stirred at that temperature for 1 hr, then warmed to r.t. and stirred for another 2 h. The reaction mixture was quenched with water (40 mL), and concentrated under reduced pressure. The aqueous layer was separated, and extracted with EA (2×100 mL). Combined organic layers were washed with water and brine, dried over $Na_2SO_4$ and filtered. The filtrate was concentrated and the residue was purified by column chromatography (eluted with PE) to give the 2-chloro-3-iodo-6-(trifluoromethyl)pyridine (14.3 g, 84% yield) as a white solid. $^1$HNMR (400 MHz, DMSO-$d_6$) δ 8.64 (d, J=8.0 Hz, 1H), 7.61 (d, J=8.0 Hz, 1H).

Step 2 2-chloro-4-iodo-6-(trifluoromethyl)pyridine

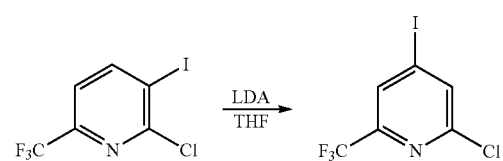 [SMILES: FC(F)(F)c1ccc(I)c(Cl)n1 ; "LDA" ; FC(F)(F)c1cc(I)cc(Cl)n1 ; "THF"]

To a mixture of 2-chloro-3-iodo-6-(trifluoromethyl)pyridine (3.07 g, 10.0 mmol) in THF (35 mL) was added dropwise LDA (5.5 mL, 2M) at −78° C. via syringe under $N_2$ atmosphere. The reaction mixture was stirred at that temperature for 1 h. The reaction mixture was quenched with aqueous HCl (15 mL, 1 M) at −78° C. and stirred for 0.5 h. The mixture was warmed to r.t., stirred for another 0.5 hr, and then concentrated under reduced pressure. The aqueous layer was separated and extracted with EA (2×100 mL). Combined organic layers were washed with water and brine, dried over $Na_2SO_4$ and filtered. The filtrate was concentrated and the residue was purified by column chromatography (eluted with PE) to give the 2-chloro-4-iodo-6-(trifluoromethyl)pyridine (2.5 g, 81% yield) as a white solid. $^1$HNMR (400 MHz, DMSO-$d_6$) δ 8.39 (s, 1H), 8.34 (s, 1H).

Step 3 N-(3,4-dimethoxybenzyl)-4-iodo-6-(trifluoromethyl)pyridin-2-amine

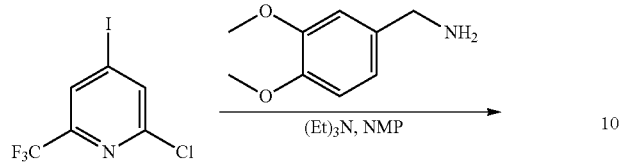

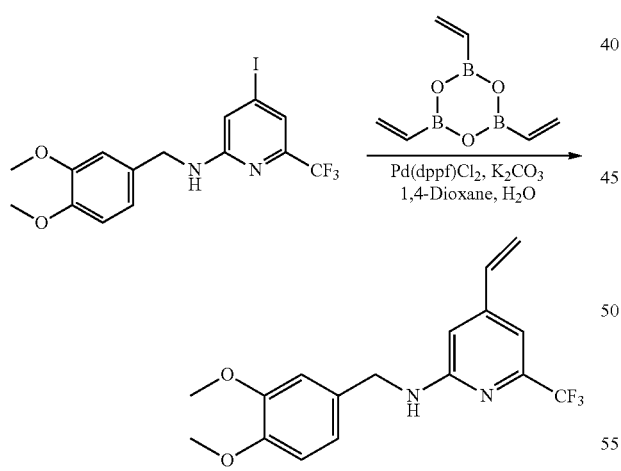

To a solution of 2-chloro-4-iodo-6-(trifluoromethyl)pyridine (1.0 g, 3.26 mmol) in NMP (5 mL) was added (3,4-dimethoxyphenyl)methanamine (2.45 mL, 16.29 mmol) and Et$_3$N (2.26 mL, 16.29 mmol). The mixture was heated in a microwave at 100° C. for 20 min. The reaction mixture was diluted with EA, washed with water and brine, dried over Na$_2$SO$_4$ and filtered. The filtrate was concentrated under reduced pressure and the residue was purified by column chromatography (eluted with PE:EA=15:1 to 10:1) to give the N-(3,4-dimethoxybenzyl)-4-iodo-6-(trifluoromethyl)pyridin-2-amine(400 mg, 28% yield) as a white solid. Retention time (LC-MS): 1.923 min. MH$^+$439.

Step 4 N-(3,4-dimethoxybenzyl)-6-(trifluoromethyl)-4-vinylpyridin-2-amine

To a solution of N-(3,4-dimethoxybenzyl)-4-iodo-6-(trifluoromethyl)pyridin-2-amine (320 mg, 0.73 mmol), potassium carbonate (201.64 mg, 1.46 mmol) and 2,4,6-trivinyl-1,3,5,2,4,6-trioxatriborinane (141.65 mg, 0.88 mmol) in 1,4-dioxane (5 mL) and H$_2$O (1 mL) was added Pd(dppf)Cl$_2$ (53.46 mg, 0.073 mmol) after degassed three times under N$_2$ atmosphere. The reaction mixture was stirred at 80° C. under N$_2$ overnight. The reaction mixture was cooled and filtered through Celite. The filtrate was extracted with EA (3×50 mL). Combined organic layers were dried over Na$_2$SO$_4$ and filtered. The filtrate was concentrated under reduced pressure and the residue was purified by chromatography (eluted with DCM:MeOH=100:1 to 80:1) to afford N-(3,4-dimethoxybenzyl)-6-(trifluoromethyl)-4-vinylpyridin-2-amine (210 mg, 85% yield) as a white solid. Retention time (LC-MS): 1.776 min. MH$^+$339.

Step 5 N-(3,4-dimethoxybenzyl)-4-ethyl-6-(trifluoromethyl)pyridin-2-amine

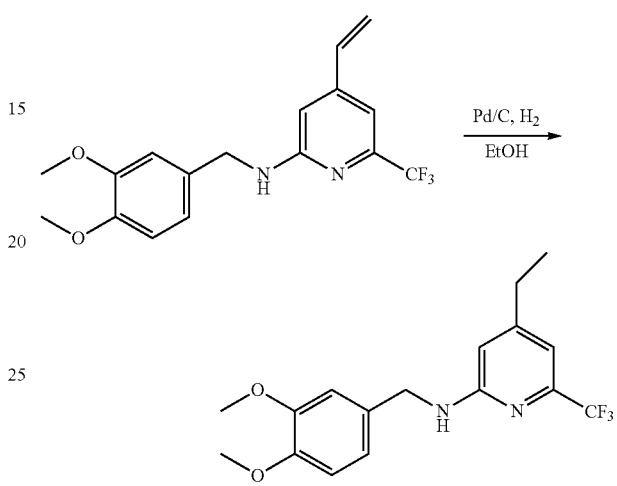

To a solution of N-(3,4-dimethoxybenzyl)-6-(trifluoromethyl)-4-vinylpyridin-2-amine (210 mg, 0.62 mmol) in ethanol (5 mL) was added Pd/C (50 mg) after degassed three times under H2 atmosphere. The reaction mixture was stirred at r.t. under H2 for 1.5 h. The reaction mixture was filtered through Celite. The filtrate was concentrated under reduced pressure and the residue was purified by chromatography (PE:EA=10:1 to3:1) to afford N-(3,4-dimethoxybenzyl)-6-(trifluoromethyl)-4-vinylpyridin-2-amine (210 mg, 99% yield) as a white solid. Retention time (LC-MS): 1.786 min. MH$^+$341.

Step 6 2-chloro-N-(3,4-dimethoxybenzyl)-N-(4-ethyl-6-(trifluoromethyl)pyridine-2-yl)acetamide

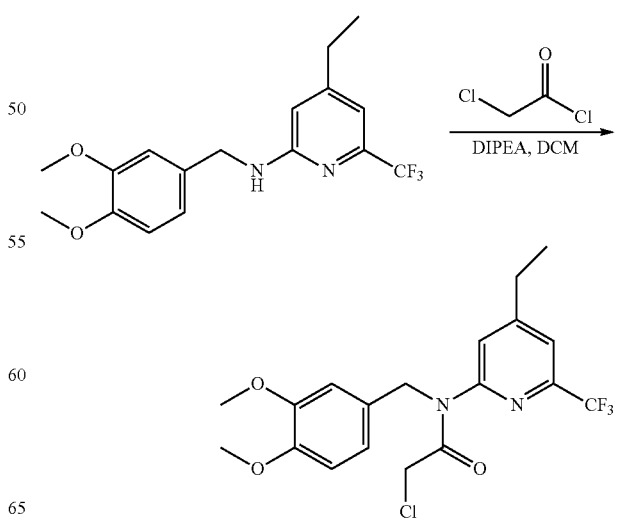

To a solution of N-(3,4-dimethoxybenzyl)-4-ethyl-6-(trifluoromethyl)pyridin-2-amine (50 mg, 0.15 mmol) and DIPEA (0.05 mL, 0.29 mmol) in DCM (5 mL) was added dropwise 2-chloroacetyl chloride (0.02 mL, 0.22 mmol) at 0° C. The reaction mixture was warmed to r.t. and stirred for 5 h. The reaction mixture was quenched with water (10 mL). The mixture was neutralized with S. aq. NaHCO$_3$ and extracted with EA. Combined organic layers were washed with water and brine, dried over Na$_2$SO$_4$ and filtered. The filtrate was concentrated under reduced pressure and the residue was purified by chromatography (eluted with PE:EA=10:1 to 3:1) to afford 2-chloro-N-(3,4-dimethoxybenzyl)-N-(4-ethyl- 6-(trifluoromethyl)pyridin-2-yl)acetamide (50 mg, 81% yield) as a white solid. Retention time (LC-MS): 1.730 min. MH$^+$417.

Step 7 N-(3,4-dimethoxybenzyl)-N-(4-ethyl-6-(trifluoromethyl)pyridin-2-yl)-2-(1-(isoxazol-3-ylmethyl)-3-methyl-2,6-dioxo-2,3-dihydro-1H-purin-7(6H)-yl)acetamide

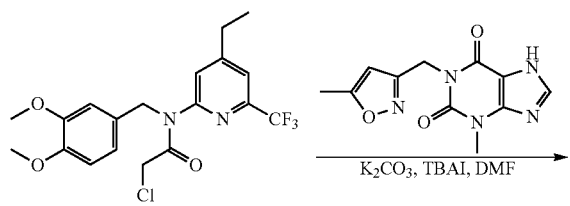

A mixture of 2-chloro-N-(3,4-dimethoxybenzyl)-N-(4-ethyl-6-(trifluoromethyl) pyridin-2-yl)acetamide (50 mg, 0.12 mmol), potassium carbonate (33.17 mg, 0.24 mmol), 3-methyl-1-((5-methylisoxazol-3-yl)methyl)-1H-purine-2,6 (3H,7H)-dione (25.96 mg, 0.192 mmol) and TBAI (4.44 mg, 0.012 mmol) in DMF (5 mL) was stirred at 50° C. for 2 h. The reaction mixture was diluted with EA, washed with water, brine, dried over Na$_2$SO$_4$ and filtered. The filtrate was purified by chromatography (eluted with DCM: MeOH=100:1 to 50:1) to afford N-(3,4-dimethoxybenzyl)-N-(4-ethyl-6-(trifluoromethyl)pyridin-2-yl)-2-(1-(isoxazol-3-ylmethyl)-3-methyl-2,6-dioxo-2,3-dihydro-1H-purin-7 (6H)-yl)acetamide (50 mg, 64% yield) as yellow solid. Retention time (LC-MS): 1.703 min. MH$^+$642.

Preparation 82
6-(4,4-difluoropiperidin-1-yl)pyridin-2-amine

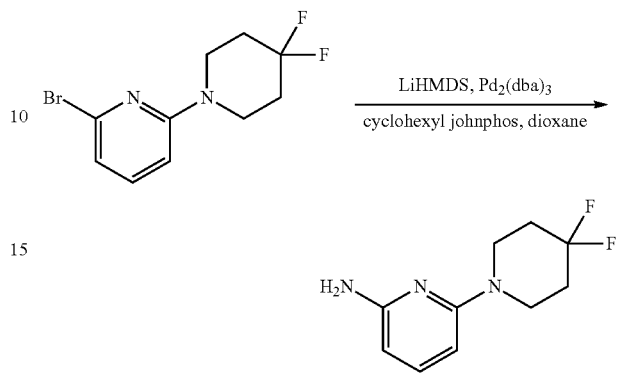

To a mixture of 2-bromo-6-(4,4-difluoropiperidin-1-yl)pyridine (400 mg, 1.44 mmol), Pd$_2$(dba)$_3$ (53 mg, 57.74 μmol) and biphenyl-2-yldicyclohexylphosphine (41 mg, 115.48 μmol) in dioxane (5 mL) was added LiHMDS (483 mg, 2.89 mmol) after degassed three times under N$_2$ atmosphere. The mixture was then heated to 60° C. for 2 h. The reaction mixture was concentrated under reduced pressure and the residue was purified by chromatography (eluted with DCM: MeOH=50:1) to afford 6-(4,4-difluoropiperidin-1-yl)pyridin-2-amine (165 mg, 53.6% yield) as a white solid. Retention time (LC-MS): 0.527 min. MH$^+$214.

Preparation 83 N-(6-(4-chlorophenyl)pyridin-2-yl)-2-(8-(hydroxymethyl)-3-methyl-2,6-dioxo-2,3-dihydro-1H-purin-7(6H)-yl)acetamide

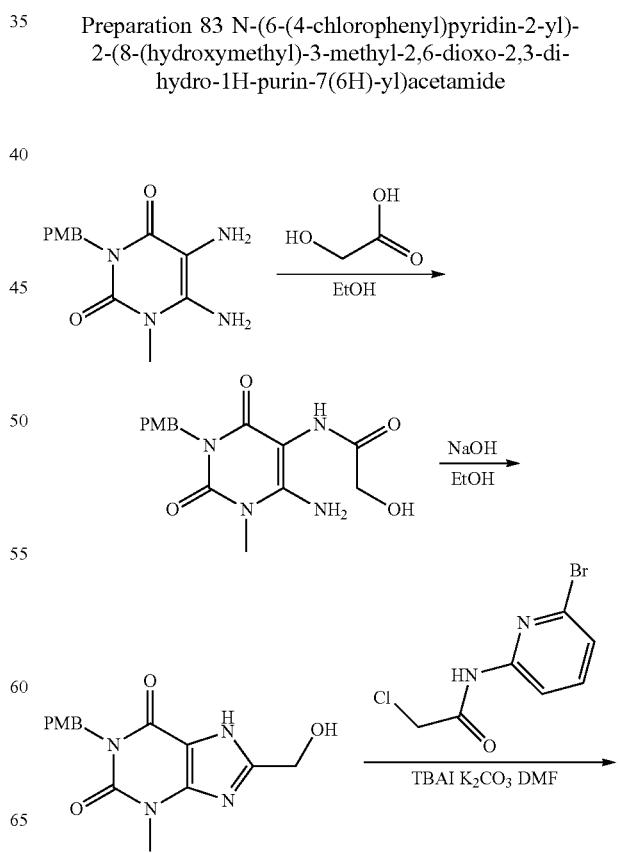

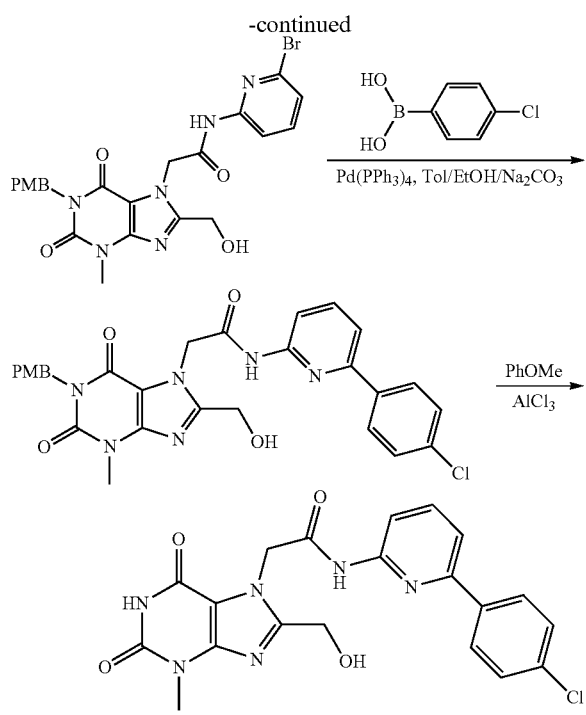

Step 1 8-(hydroxymethyl)-1-(4-methoxybenzyl)-3-methyl-1H-purine-2,6(3H,7H)-dione

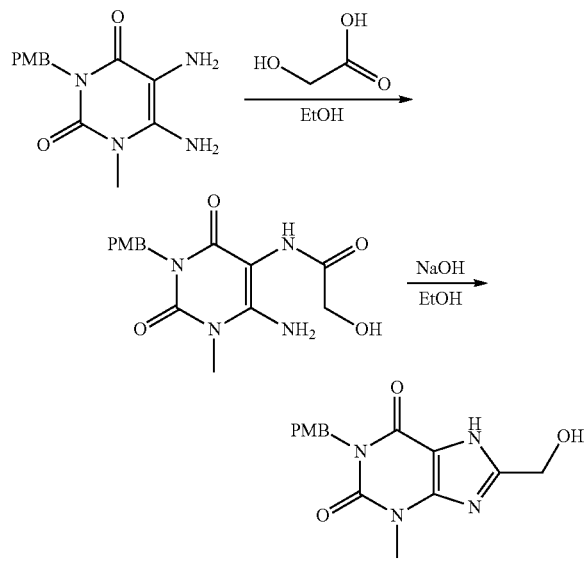

A mixture of 5,6-diamino-3-(4-methoxybenzyl)-1-methyl-pyrimidine-2,4(1H,3H)-dione (2 g, 7.2 mmol) and 2-hydroxyHOAc (1.104 g, 18.1 mmol) was heated to 100° C. under stiring. The mixture was melted and solidified. EtOH (10 mL) was then added in and the reaction mixture was stirred at 100° C. for another 2 h till completion. NaOH (2M, 20 mL) was added to a stirred solution of the above mixture in EtOH (10 mL). The mixture was heated at 80° C. for 3 hr, then cooled to 0° C. and neutralized with acetic acid. The reaction mixture was pooled into water (10 mL), and then extracted with EA (3×5 mL). Combined organic layers were dried over $Na_2SO_4$ and filtered. The filtrate was concentrated under reduced pressure to afford 8-(hydroxymethyl)-1-(4-methoxybenzyl)-3-methyl-1H-purine-2,6(3H,7H)-dione (800 mg 42% yield) as orange solid. Retention time (LC-MS): 0.643 min. $MH^+317$.

Step 2 N-(6-bromopyridin-2-yl)-2-(8-(hydroxymethyl)-1-(4-methoxybenzyl)-3-methyl-2,6-dioxo-2,3-dihydro-1H-purin-7(6H)-yl)acetamide

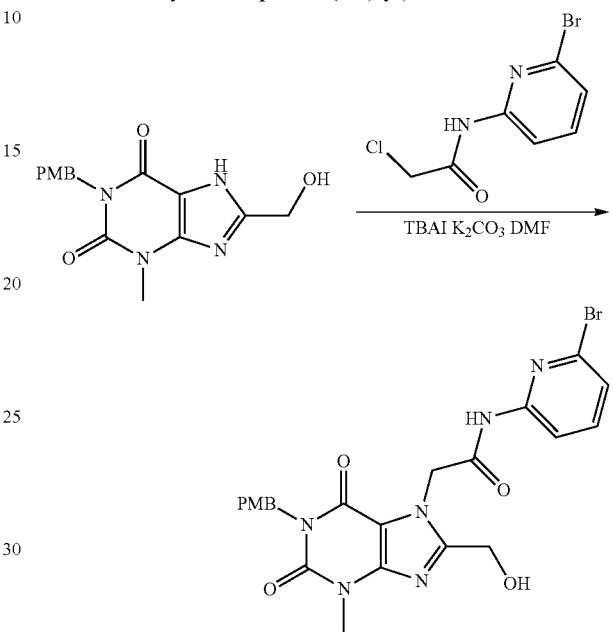

A mixture of 8-(hydroxymethyl)-1-(4-methoxybenzyl)-3-methyl-1H-purine-2,6(3H,7H)-dione (650 mg, 2.05 mmol), N-(6-bromopyridin-2-yl)-2-chloroacetamide (612 mg, 2.46 mmol), potassium carbonate (568 mg 4.11 mmol), TBAI (76 mg 0.21 mmol) and DMF (20 mL) was stirred at 50° C. under $N_2$ for 2 h. The reaction mixture was quenched by water (20 mL), and then extracted with EA (3×5 mL). Combined organic layers were washed with S. aq. LiCl (15 mL) and S. aq. NaCl (15 mL), dried over $Na_2SO_4$ and filtered. The filtrate was concentrated and the residue was purified by chromatography (eluted with DCM:MeOH=50:1) to afford N-(6-bromopyridin-2-yl)-2-(8-(hydroxymethyl)-1-(4-methoxybenzyl)-3-methyl-2,6-dioxo-2,3-dihydro-1H-purin-7(6H)-yl)acetamide (670 mg 61% yield) as a yellow solid. Retention time (LC-MS): 1.329 min. $MH^+529$.

Step 3 N-(6-(4-chlorophenyl)pyridin-2-yl)-2-(8-(hydroxymethyl)-1-(4-methoxy benzyl)-3-methyl-2,6-dioxo-2,3-dihydro-1H-purin-7(6H)-yl)

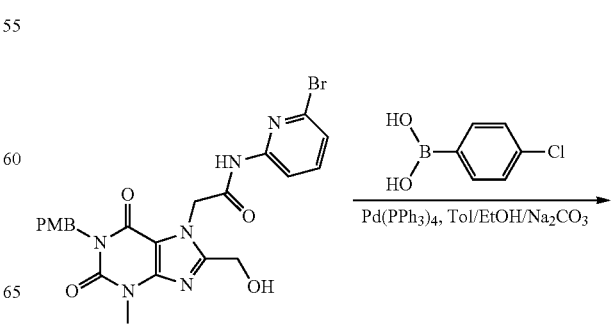

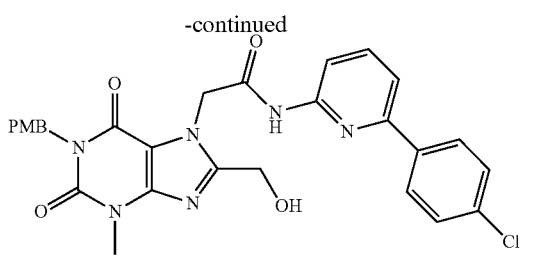

To a mixture of N-(6-bromopyridin-2-yl)-2-(8-(hydroxymethyl)-1-(4-methoxybenzyl)-3-methyl-2,6-dioxo-2,3-dihydro-1H-purin-7(6H,8H,9H)-yl)acetamide (200 mg, 0.38 mmol) and 4-chlorophenylboronic acid (118 mg, 0.14 mmol) in toluene/EtOH/2N aq. Na$_2$CO$_3$ (6 mL/3 mL/1.5 mL) was added Pd(PPh$_3$)$_4$ (44 mg, 0.04 mmol) after degassed three times under N$_2$ atmosphere. The mixture was then heated to 100° C. for 2 h. The reaction mixture was cooled to r.t. and filtered. The filtrate was extracted with EA (3×5 mL). Combined organic layers were dried over Na$_2$SO$_4$ and filtered. The filtrate was concentrated and the residue was purified by chromatography (eluted with DCM:MeOH=50:1) to afford N-(6-(4-chlorophenyl)pyridin-2-yl)-2-(8-(hydroxymethyl)-1-(4-methoxybenzyl)-3-methyl-2,6-dioxo-2,3-dihydro-1H-purin-7(6H)-yl)acetamide (150 mg 57% yield) as brown solid. Retention time (LC-MS): 1.579 min. MH$^+$561.

Step 4 N-(6-(4-chlorophenyl)pyridin-2-yl)-2-(8-(hydroxymethyl)-3-methyl-2,6-dioxo-2,3-dihydro-1H-purin-7(6H)-yl)acetamide

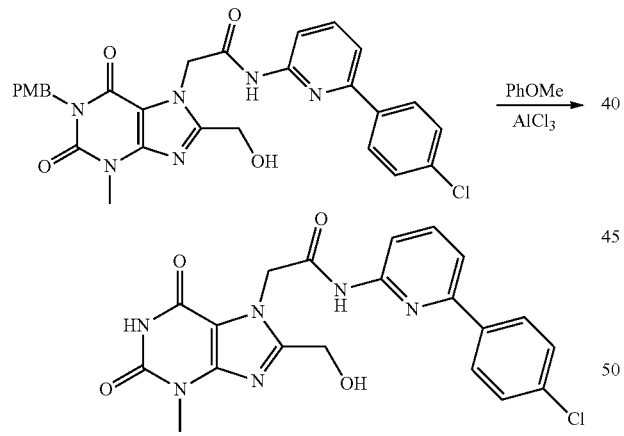

To a mixture of N-(6-(4-chlorophenyl)pyridin-2-yl)-2-(8-(hydroxymethyl)-1-(4-methoxybenzyl)-3-methyl-2,6-dioxo-2,3-dihydro-1H-purin-7(6H)-yl)acetamide (120 mg, 0.303 mmol) in PhOMe (10 mL) was added AlCl$_3$ (162 mg, 1.212 mmol) at 0° C. The mixture was stirred at 0° C. for 10 min and at r.t. overnight. The reaction mixture was quenched by conc. HCl (10 mL), and then extracted with EA (3×5 mL). Combined organic layers were washed with the S.aq. NaCl (15 mL), dried over Na$_2$SO$_4$ and filtered. The filtrate was concentrated under reduced pressure and the residue was purified by chromatography (eluted with DCM:MeOH=50:1) to afford N-(6-(4-chlorophenyl)pyridin-2-yl)-2-(8-(hydroxy methyl)-3-methyl-2,6-dioxo-2,3-dihydro-1H-purin-7(6H)-yl)acetamide (60 mg 51% yield) as a yellow solid. Retention time (LC-MS): 1.382 min. MH$^+$441.

Preparation 83 N-(6-Bromo-pyridin-2-yl)-2-(8-hydroxymethyl-3-methyl-2,6-dioxo-1-pyridin-2-ylmethyl-1,2,3,6-tetrahydro-purin-7-yl)-acetamide

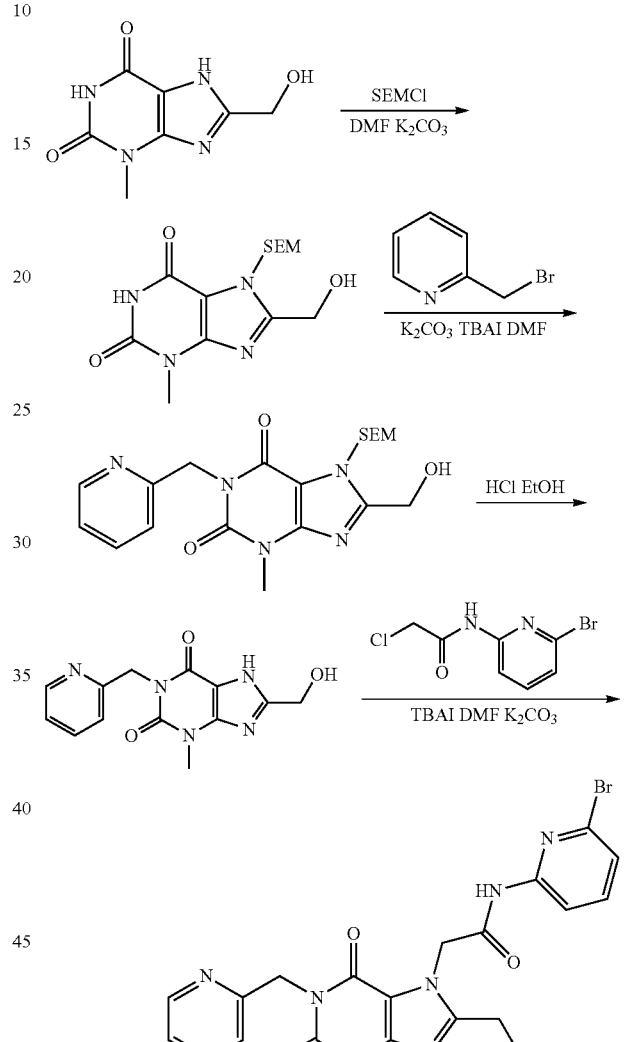

Step 1 8-Hydroxymethyl-3-methyl-7-(2-trimethylsilanyl-ethoxymethyl)-3,7-dihydro-purine-2,6-dione

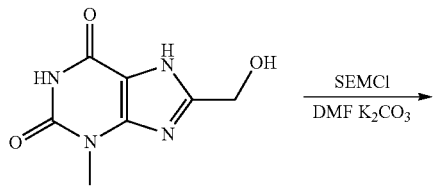

-continued

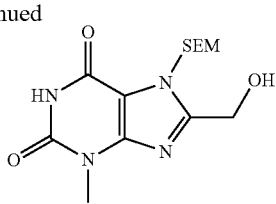

To mixture of 8-hydroxymethyl-3-methyl-3,7-dihydro-purine-2,6-dione (500 mg, 2.5 mmol), potassium carbonate (706 mg, 5 mmol) in DMF(5 mL) was added SEMCl (0.5 mL, 3.0 mmol) at 0° C. The mixture was stirred at 0° C. for 10 min and at r.t. overnight. The reaction mixture was quenched with water (20 mL), and then extracted with EA (3×5 mL). Combined organic layers were washed with S. aq. LiCl (15 mL) and brine (15 mL), dried over $Na_2SO_4$ and filtered. The filtrate was concentrated under reduced pressure to give 8-Hydroxymethyl-3-methyl-7-(2-trimethylsilanyl- ethoxymethyl)-3,7-dihydro-purine-2,6-dione (380 mg, yield 38%) as a white solid. Retention time (LC-MS): 1.165 min. $MH^+$327.

Step 2 8-Hydroxymethyl-3-methyl-1-pyridin-2-ylm-ethyl-7-(2-trimethylsilanyl-ethoxymethyl)-3,7-di-hydro-purine-2,6-dione

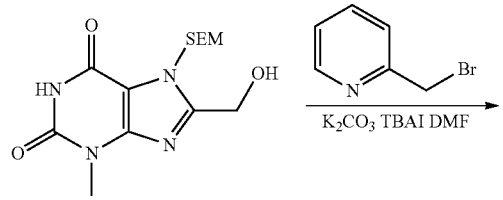

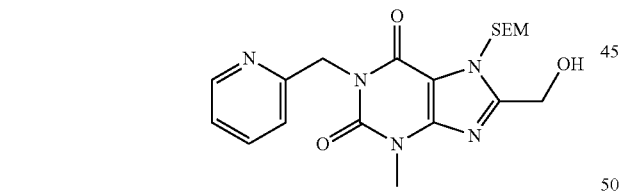

A mixture of 8-hydroxymethyl-3-methyl-7-(2-trimethylsilanyl-ethoxymethyl)-3,7-dihydro-purine-2,6-dione (380 mg, 0.96 mmol), 2-bromomethyl-pyridine (292 mg, 1.15 mmol), $Cs_2CO_3$ (629 mg 1.92 mmol), TBAI (89 mg 0.10 mmol) and DMF (5 mL) was stirred at 100° C. under $N_2$ for 2 h. The reaction mixture was quenched with water (20 mL), and then extracted with EA (3×5 mL). Combined organic layers were washed with s. aq. LiCl (15 mL) and brine (15 mL), dried over $Na_2SO_4$ and filtered. The filtrate was concentrated under reduced pressure and the residue was purified by chromatography (eluted with DCM:MeOH=50:1) to afford 8-Hydroxymethyl-3-methyl-1-pyridin -2-ylmethyl-7-(2-trimethylsilanyl-ethoxymethyl)-3,7-dihydro-purine-2,6-dione (300 mg, yield 62%) as a white solid. Retention time (LC-MS): 1.059 min. $MH^+$418.

Step 3 8-Hydroxymethyl-3-methyl-1-pyridin-2-ylm-ethyl-3,7-dihydro-purine -2,6-dione

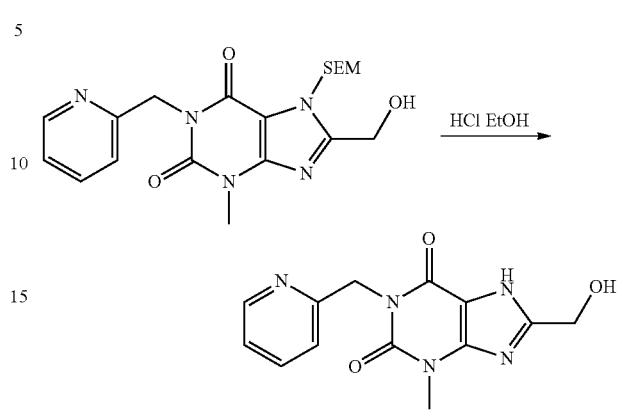

A mixture of 8-hydroxymethyl-3-methyl-1-pyridin-2-ylmethyl-7-(2-trimethylsilanyl-ethoxymethyl)-3,7-dihydro-purine-2,6-dione (300 mg, 0.72 mmol) in 12 N aq. HCl/EtOH (3 mL/6 mL) was stirred at 90° C. for 2 h. The mixture was cooled to r.t. and concentrated. The residue was neutralized with 1N aq. NaOH at 0° C. and concentrated to afford 8-hydroxymethyl-3-methyl-1-pyridin-2-ylmethyl-3,7-dihydro-purine-2,6-dione (200 mg yield 97%) as a white solid. Retention time (LC-MS): 0.366min. $MH^+$288.

Step 4 N-(6-Bromo-pyridin-2-yl)-2-(8-hydroxym-ethyl-3-methyl-2,6-dioxo-1-pyridin-2-ylmethyl-1,2,3,6-tetrahydro-purin-7-yl)-acetamide

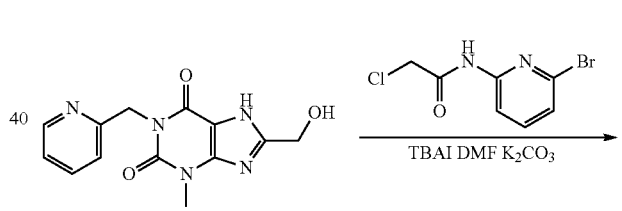

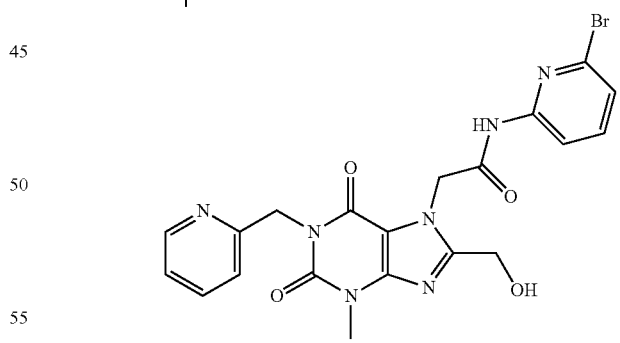

A mixture of 8-hydroxymethyl-3-methyl-1-pyridin-2-ylm-ethyl-3,7-dihydro- purine-2,6-dione (200 mg, 0.70 mmol), N-(6-bromopyridin-2-yl)-2-chloroacetamide (208 mg, 0.84 mmol), potassium carbonate (192 mg 1.40 mmol), TBAI (26 mg 0.07 mmol) and DMF (3 mL) was stirred at 50° C. under $N_2$ for 2 h. The reaction mixture was quenched with water (20 mL), and then extracted with EA (3×5 mL). Combined organic layers were washed by the S. aq. LiCl (15 mL) and brine (15 mL). Then the organic layers were dried over $Na_2SO_4$ and filtered. The filtrate was concentrated and the residue was purified by chromatography (eluted with DCM: MeOH=30:1) to afford N-(6-bromo-pyridin-2-yl)-2-(8-hydroxymethyl-3-methyl-2,6-dioxo-1-pyridin-2-ylmethyl-1,2,3,6-tetrahydro-purin-7-yl)-acetamide (300 mg, yield 87%) as a yellow solid. Retention time (LC-MS): 0.803 min. MH+500.

Preparation 84
N1-ethyl-N1-(trifluoromethyl)benzene-1,4-diamine

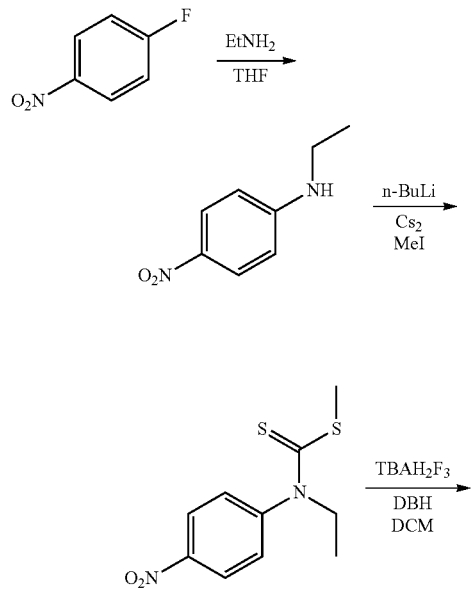

Step 1 N-ethyl-4-nitroaniline

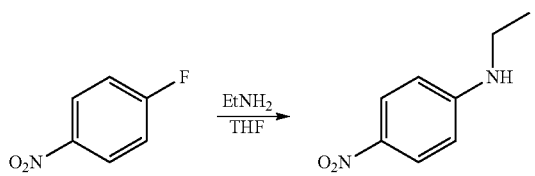

A solution of 1-fluoro-4-nitrobenzene (2 g, 14.17 mmol) in EtNH$_2$/THF solution (30 mL, 2 mmol/L) was stirred at 50° C. in a sealed tube for 16 h. The mixture was concentrated to dryness to give crude product which was purified by chromatography (eluted with PE:EA=5:1) to afford N-ethyl-4-nitroaniline (1.7 g, 72.2% yield) as yellow solid. Retention time (LC-MS): 1.347 min. MH+167.

Step 2 Methyl ethyl(4-nitrophenyl)carbamodithioate

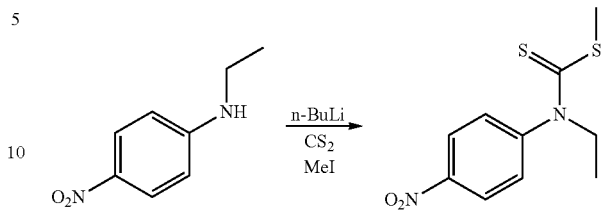

To a solution of N-ethyl-4-nitroaniline (1 g, 6.01 mmol) in THF (30 mL) was added dropwise n-BuLi (3 mL, 7.2 mmol) at −10° C. After addition, the mixture was stirred at 0° C. for 1 h. Carbon disulphide (0.91 g, 12.03 mmol) was added dropwise to the above mixture and the reaction mixture was stirred at r.t. for 16 h. Iodomethane (1.7 g, 12.03 mmol) was added to the mixture at 0° C. and the mixture was stirred at r.t. for 5 h. The mixture was quenched with saturated aqueous sodium bicarbonate (50 mL) and extracted with EA (3×50 mL). Combined organic layer were dried over Na$_2$SO$_4$ and concentrated under reduced pressure. The residue was purified by chromatography (eluted with PE:EA=3:1) to give methyl ethyl(4-nitrophenyl)carbamodithioate (350 mg, 22.72% yield) as yellow syrup. $^1$H-NMR (400 MHz, CDCl$_3$) δ 8.33-8.35 (d, J=6.8 Hz, 2H), 7.43-7.45 (d, J=7.2 Hz, 2H), 4.32-4.36 (q, 2H), 2.52 (s, 3H), 1.26-1.30 (t, 3H).

Step 3 N-ethyl-4-nitro-N-(trifluoromethyl)aniline

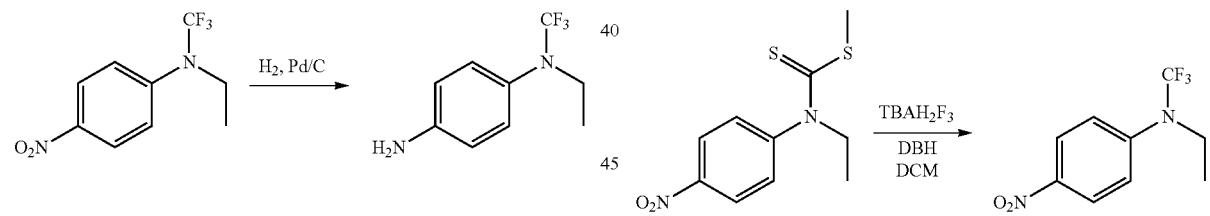

To a solution of methyl ethyl(4-nitrophenyl)carbamodithioate (250 mg, 0.975 mmol) in DCM (10 mL) was added tetrabutylammonium dihydrogentrifluoride (1.47 g, 4.875 mmol). The mixture was stirred at RT for 10 min, followed by addition of 1,3-dibromo-5,5-dimethylhydantoin (1.11 g, 3.9 mmol) in one portion. The reaction mixture was stirred at r.t. for 3 hr, then poured into a mixture of aqueous NaHCO$_3$/NaHSO$_3$/NaOH solution (10 mL, 1M:1M:1M) and extracted with EA (3×10 mL). Combined organic layer were washed with brine, dried over Na$_2$SO$_4$ and concentrated under reduced pressure. The residue was purified by chromatography (eluted with PE:EA=3:1) to give N-ethyl-4-nitro-N-(trifluoromethyl)aniline (140 mg, 61.7% yield) as yellow solid. $^1$H-NMR (400 MHz, CDCl$_3$) δ 8.28-8.30 (d, J=8.8 Hz, 2H), 7.43-7.45 (br, 2H), 3.80-3.86 (q, 2H), 2.52 (s, 3H), 1.25-1.31 (t, 3H).

Step 4
N1-ethyl-N1-(trifluoromethyl)benzene-1,4-diamine

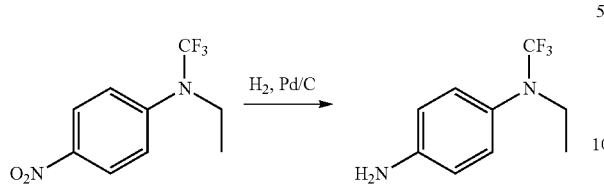

To a solution of N-ethyl-4-nitro-N-(trifluoromethyl)aniline (140 mg, 0.598 mmol) in MeOH (3 mL) was added Pd/C (30 mg, 10%) under $N_2$ atmosphere. The mixture was degassed under $N_2$ for three times and stirred under H2 balloon at r.t. for 16 h. The mixture was filtered and the filtrate was concentrated to give N1-ethyl-N1-(trifluoromethyl)benzene-1,4-diamine (110 mg, 90% yield) as yellow oil, which was directly used to the next reaction without purification. Retention time (LC-MS): 0.602 min.

Preparation 85 N-(6-(3-azabicyclo [3.1.0] hexan-3-yl)pyridin-2-yl)-2-chloroacetamide

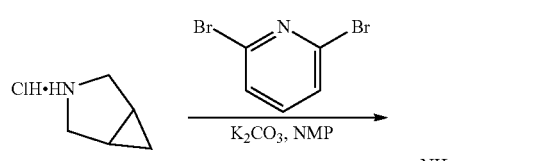

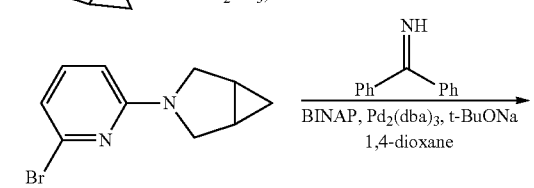

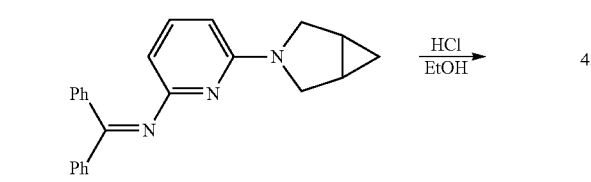

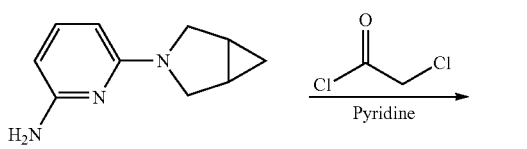

Step 1 3-(6-bromopyridin-2-yl)-3-azabicyclo[3.1.0]hexane

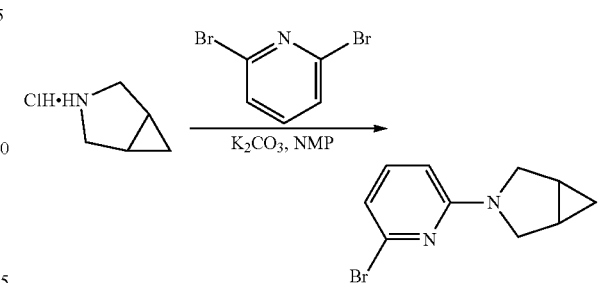

To a solution of 3-azabicyclo[3.1.0]hexane hydrochloride (300 mg, 2.51 mmol) in NMP (3 mL) was added 2,6-dibromopyridine (594.53 mg, 12.51 mmol) and POTASSIUM CARBONATE (693.42 mg, 5.02 mmol).The mixture was heated in a sealed tube at 130° C. for 6 hrs. The mixture was diluted with EA and water, and the organic layer was washed with brine, dried over $Na_2SO_4$ and filtered. The filtrate was evaporated and the crude product obtained was purified with column chromatography (PE:EA=100:1) to give 3-(6-bromopyridin-2-yl)-3-azabicyclo[3.1.0]hexane (500 mg, 83.7% yield) as a white solid. Retention time (LC-MS): 1.798 min, $MH^+238$.

Step 2 6-(3-azabicyclo[3.1.0]hexan-3-yl)-N-(diphenylmethylene)pyridin-2-amine

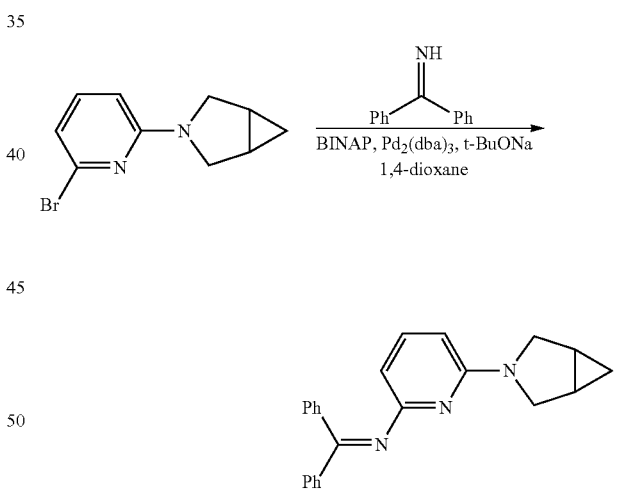

To a solution of 3-(6-bromopyridin-2-yl)-3-azabicyclo [3.1.0]hexane (350 mg, 1.47 mmol), diphenylmethanimine (0.5 mL, 2.94 mmol), BINAP (91.62 mg, 0.15 mmol) and t-BuONa (282.65 mg,2.49 mmol) in 1,4-dioxane (10 mL) was added $Pd_2$(dba) 3 (134.71 mg, 0.15 mmol). After the mixture was degassed and purged with $N_2$ three times, it was stirred at 100° C. under $N_2$ for 1 h and. The mixture was cooled, filtered through Celite and the solids were washed with EA. The filtrate was concentrated under reduced pressure to afford 6-(3-azabicyclo[3.1.0]hexan-3-yl)-N-(diphenylmethylene)pyridin-2-amine (350 mg, 70.1% yield) as a brown oil, which was used for next step without purification. Retention time (LC-MS): 1.541 min. $MH^+339$.

Step 3 6-(3-azabicyclo[3.1.0]hexan-3-yl)pyridin-2-amine

To a solution of 6-(3-azabicyclo[3.1.0]hexan-3-yl)-N-(diphenylmethylene)pyridin-2-amine (400 mg, 1.18 mmol) in EtOH (20 mL) was added aqueous HCl (2 mL, 12 M). The mixture was stirred at RT for 30 min. The mixture was neutralized with saturated aqueous NaHCO₃ to pH=7-8 and extracted with EA (3×50 mL). The combined organic layers were washed with water and brine, dried over Na₂SO₄ and filtered. The filtrate was evaporated to give the crude product, which was purified with column chromatography (PE:EA=50:1 to 10:1) to give the 6-(3-azabicyclo[3.1.0]hexan-3-yl)pyridin-2-amine (160 mg, 77.4% yield) as a brown oil. Retention time (LC-MS): 0.364 min. MH$^+$175.

Step 4 N-(6-(3-azabicyclo [3.1.0] hexan-3-yl)pyridin-2-yl)-2-chloroacetamide To a solution of 6-(3-azabicyclo[3.1.0]hexan-3-yl)pyridin-2-amine (50 mg, 0.15 mmol) in pyridine (5 mL) was added dropwise 2-chloroacetyl chloride (0.05 mL, 0.57 mmol) at 0° C. After addition, the mixture was warmed to RT and stirred for 3 hrs. The reaction mixture was diluted with water (10 mL) and EA (15 mL). The organic layer was washed with brine, dried over Na₂SO₄ and filtered. The filtrate was concentrated under reduced pressure and the residue was purified with column chromatography (PE:EA=20:1 to 5:1) to afford N-(6-(3-azabicyclo[3.1.0]hexan-3-yl)pyridin-2-yl)-2-chloroacetamide (30 mg, 46.1% yield) as a white solid. Retention time (LC-MS): 1.229 min. MH$^+$252.

Preparation 86 2-chloro-N-(6-(6,6-difluoro-3-azabicyclo [3.1.0] hexan-3-yl)pyridine-2-yl)acetamide

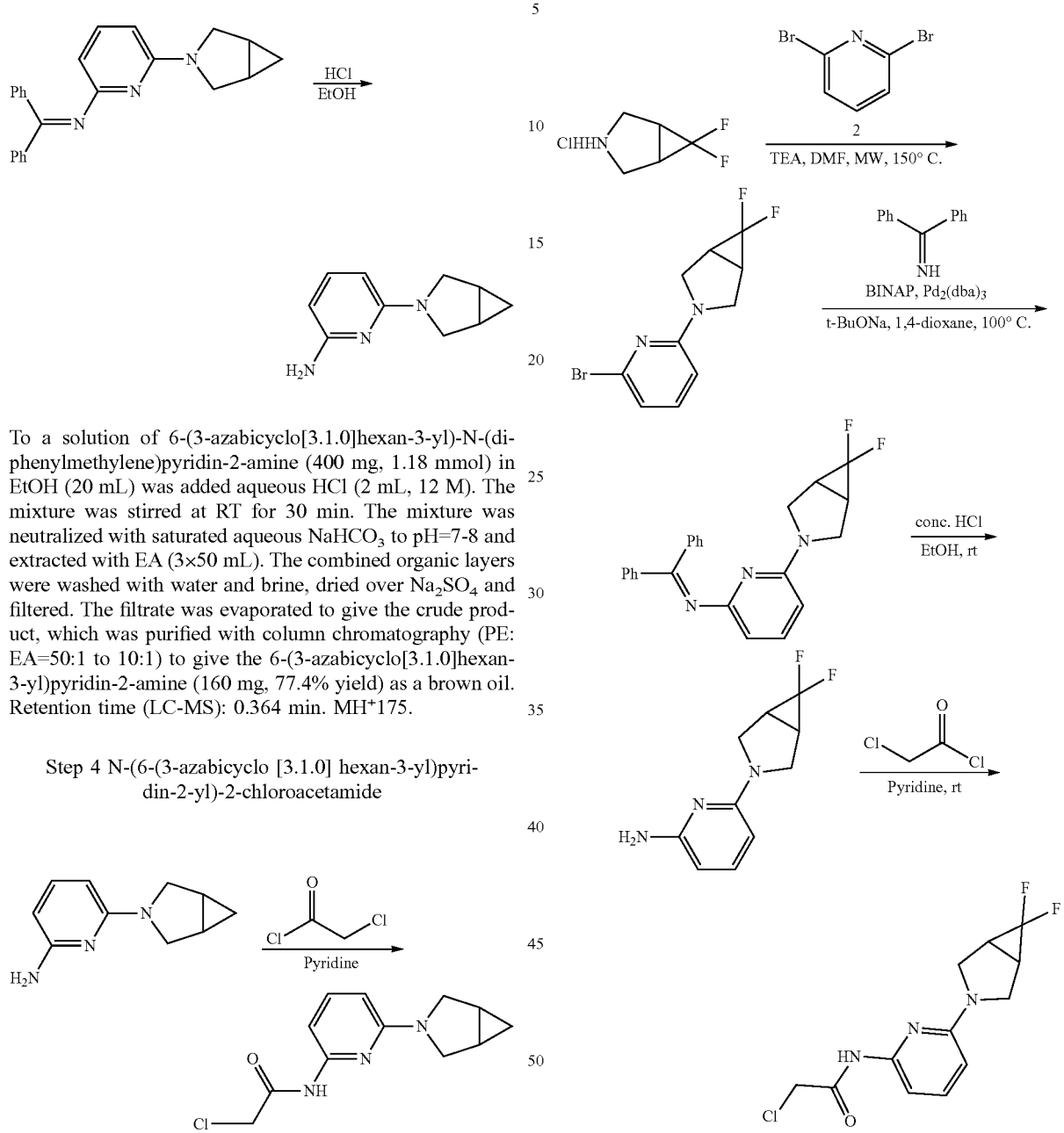

Step 1 3-(6-bromopyridin-2-yl)-6,6-difluoro-3-azabicyclo[3.1.0]hexane

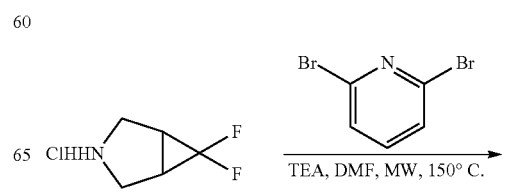

-continued

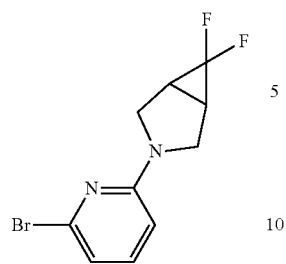

In a microwave reaction tube containing 6,6-difluoro-3-azabicyclo[3.1.0]hexane hydrochloride (1, 190.0 mg, 1.2 mmol), 2,6-dibromopyridine(287.8 mg, 1.2 mmol) was added NMP (4 mL) and TEA (248.0 mg, 2.5 mmol). The mixture was heated in a Biotage Microwave Initiator device at 150° C. for 45 min. The mixture was poured into EA. The organic phase was washed with water and brine, dried over $Na_2SO_4$ and filtered. The filtrate was concentrated under reduced pressure. The crude product was purified by chromatography (eluted with PE:EA=8:1) to afford 3-(6-bromopyridin-2-yl)-6,6-difluoro-3-azabicyclo[3.1.0]hexane (300 mg, 89.3% yield) as a white solid. Retention time (LC-MS): 1.70 min. $MH^+275$.

Step 2 6-(6,6-difluoro-3-azabicyclo[3.1.0]hexan-3-yl)-N-(diphenylmethylene-)pyridin-2-amine

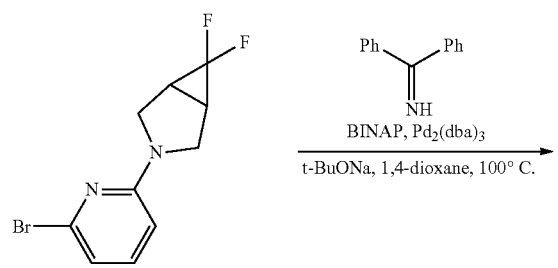

A solution of 3-(6-bromopyridin-2-yl)-6,6-difluoro-3-azabicyclo[3.1.0]hexane (320 mg, 1.2 mmol), diphenylmethanimine (0.4 mL, 2.3 mmol), BINAP (72.7 mg, 0.1 mmol), $Pd_2(dba)_3$ (107.0 mg, 0.1 mmol) and t-BuONa (224.5 mg, 2.3 mmol) in 1,4-dioxane (6 mL) was degassed with $N_2$ and stirred at 100° C. under nitrogen for 1 h. LCMS showed the starting materials was consumed. The mixture was extracted with EA. The organic layer was washed with brine, dried over $Na_2SO_4$ and concentrated to give 6-(6,6-difluoro-3-azabicyclo[3.1.0]hexan-3-yl)-N-(diphenylmethylene) 188yridine-2-amine (350 mg, 85.2% yield) as a yellow solid. Retention time (LC-MS): 1.83 min. $MH^+376$.

Step 3 6-(6,6-difluoro-3-azabicyclo[3.1.0]hexan-3-yl)pyridine-2-amine

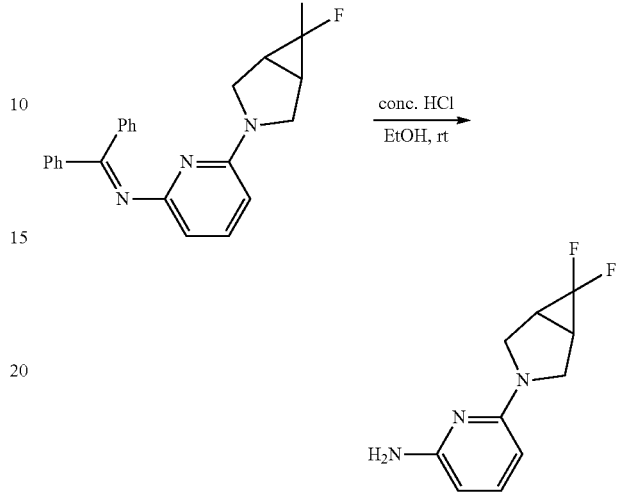

To a solution of 6-(6,6-difluoro-3-azabicyclo[3.1.0]hexan-3-yl)-N-(diphenylmethylene)pyridine-2-amine(350 mg, 1.0 mmol) in EtOH (5 mL) was added conc. hydrochloride acid (12 M, 1 mL). The mixture was stirred at RT for 1 h. Then mixture was neutralized with 1M aq.$NaHCO_3$ solution. The mixture was extracted with EA, washed with brine, dried over $Na_2SO_4$ and concentrated. The residue was purified by chromatography (eluted with PE:EA=4:1) to afford 6-(6,6-difluoro-3-azabicyclo[3.1.0]hexan-3-yl)pyridine-2-amine (300 mg, 89.3% yield) as a white solid. Retention time (LC-MS): 0.35 min. $MH^+212$.

Step 4 2-chloro-N-(6-(6,6-difluoro-3-azabicyclo[3.1.0]hexan-3-yl)pyridine-2-yl)acetamide

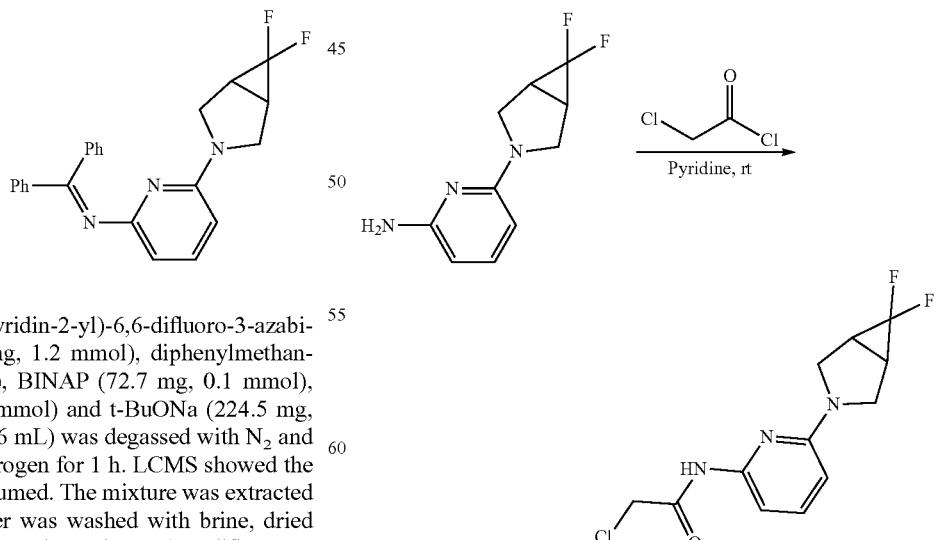

To a solution of 6-(6,6-difluoro-3-azabicyclo[3.1.0]hexan-3-yl)pyridine-2-amine (160.0 mg, 0.8 mmol) in pyridine (3 mL) was added dropwise 2-chloroacetyl chloride (0.09 mL, 1.1 mmol) at 0° C. The mixture was stirred at RT for 1 hr and poured into EA. The organic layer was separated, washed with water and brine, dried over Na$_2$SO$_4$, and concentrated to give 2-chloro-N-(6-(6,6-difluoro-3-azabicyclo[3.1.0]hexan-3-yl)pyridine-2-yl)acetamide (200 mg, 91.9% yield) as a yellow solid. Retention time (LC-MS): 1.47 min. MH$^+$288.

Preparation 87 2-chloro-N-(6-(4-(2,2,2-trifluoroethyl)piperazin-1-yl)pyridin-2-yl)acetamide

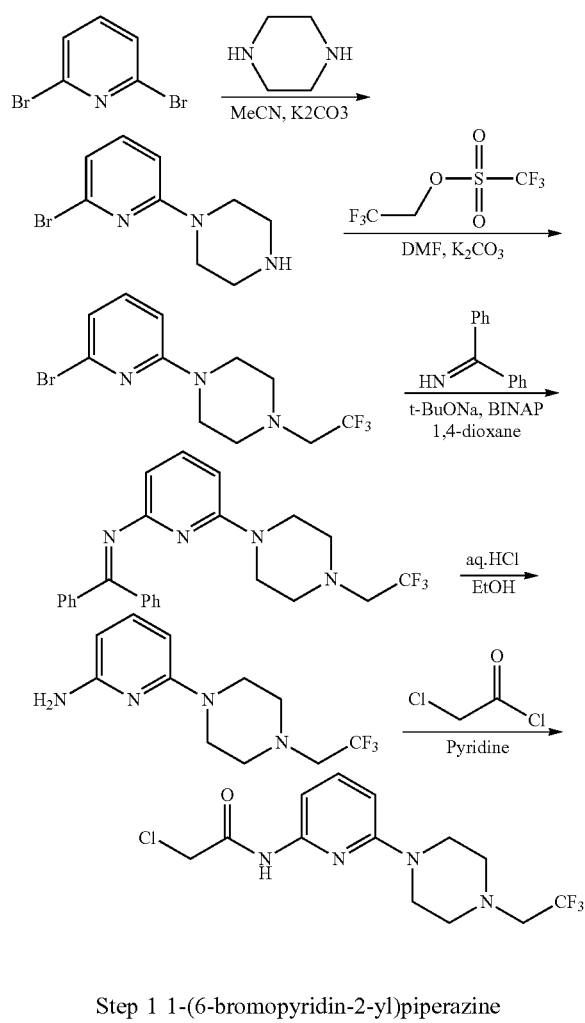

Step 1 1-(6-bromopyridin-2-yl)piperazine

To a solution of 2,6-dibromopyridine (1.0 g, 4.22 mmol) in MeCN (20 mL) was added piperazine (1.09 g, 12.66 mmol) and potassium carbonate (583.44 mg, 4.22 mmol).The mixture was stirred at 85° C. overnight. The mixture was concentrated and diluted with EA, washed with water, brine, dried over Na$_2$SO$_4$ and filtered. The filtrate was evaporated to give the crude product. The crude product was purified by column chromatography (DCM/MeOH=100:1 to 50:1) to give the product. MeOH/HCl (5 mL) was added and concentrated to give 1-(6-bromopyridin-2-yl)piperazine hydrochloride (1.03 g, 87.5% yield) as a white solid. Retention time (LC-MS): 0.369 min. MH$^+$242.

Step 2 1-(6-bromopyridin-2-yl)-4-(2,2,2-trifluoroethyl)piperazine

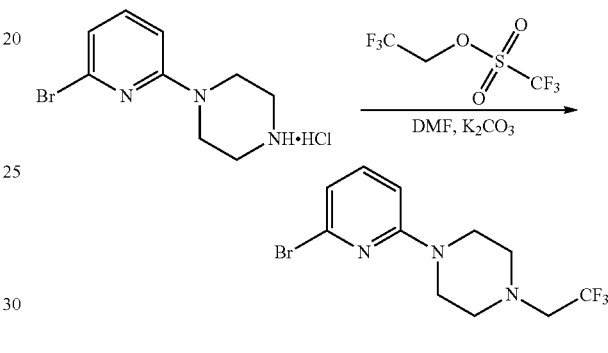

To a mixture of 1-(6-bromopyridin-2-yl)piperazine hydrochloride (300 mg, 1.08 mmol) in DMF (10 mL) was added 2,2,2-trifluoroethyl trifluoromethanesulfonate (0.31 mL, 2.15 mmol) and potassium carbonate (446.51 mg, 3.23 mmol). The mixture was stirred at 70° C. for 3h. The mixture was diluted with EA, washed with water, brine, dried over Na$_2$SO$_4$ and filtered. The filtrate was evaporated to give the crude product. The crude product was purified by column chromatography (PE/EA=10:1 to 1:2) to give 1-(6-bromopyridin-2-yl)-4-(2,2,2-trifluoroethyl)piperazine (320 mg, 91.7% yield) as a brown oil. Retention time (LC-MS): 1.826 min. MH$^+$325.

Step 3 N-(diphenylmethylene)-6-(4-(2,2,2-trifluoroethyl)piperazin-1-yl)pyridin-2-amine

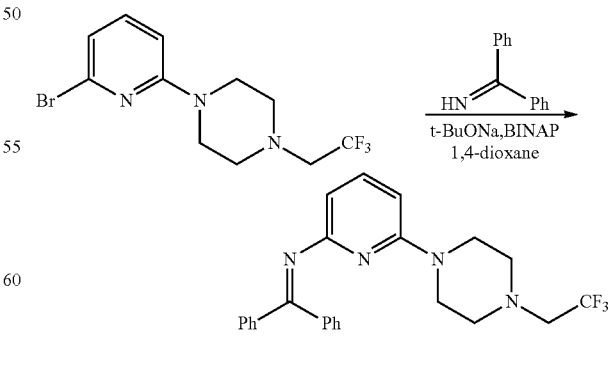

To a solution of 1-(6-bromopyridin-2-yl)-4-(2,2,2-trifluoroethyl)piperazine (200 mg, 0.62 mmol), diphenylmethanimine (0.21 mL, 1.23 mmol), BINAP (38.46 mg, 0.062 mmol) and t-BuONa (118.64 mg, 1.23 mmol) in 1,4-dioxane (15 mL) was added Pd$_2$(dba)$_3$ (56.54 mg, 0.062 mmol) under N$_2$ atmosphere. The reaction mixture was stirred at 130° C. under N$_2$ for 2h. The mixture was cooled and filtered through Celite, and the filtrate was extracted with EA (3×50 mL). The combined organic layers were dried over Na$_2$SO$_4$ and filtered. The filtrate was concentrated under reduced pressure and the residue was used to next step without purification to afford N-(diphenylmethylene)-6-(4-(2,2,2-trifluoroethyl)piperazin-1-yl)pyridin-2-amine (200 mg, 76.4% yield) as a brown oil. Retention time (LC-MS): 1.951 min. MH$^+$425.

Step 4 6-(4-(2,2,2-trifluoroethyl)piperazin-1-yl)pyridin-2-amine

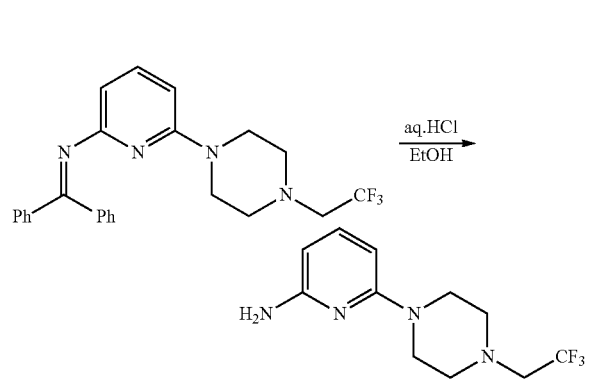

To a solution of N-(diphenylmethylene)-6-(4-(2,2,2-trifluoroethyl)piperazin-1-yl)pyridin-2-amine (200 mg, 0.47 mmol) in EtOH (10 mL) was added HC (1 mL, 12 M). After stirred at rt for 3h, the mixture was nuetralized with aq.NaHCO$_3$ to pH 7-8 and evaporated. The mixture was extracted with EA (3×50 mL), washed with water, brine, dried over Na$_2$SO$_4$ and filtered. The filtrate was evaporated to give the crude product. The crude product was purified by column chromatography (PE/EA=10:1 to 1:1) to give 6-(4-(2,2,2-trifluoroethyl)piperazin-1-yl)pyridin-2-amine (100 mg, 81.5% yield) as a brown oil. Retention time (LC-MS): 0.493 min. MH$^+$261.

Step 5 2-chloro-N-(6-(4-(2,2,2-trifluoroethyl)piperazin-1-yl)pyridin-2-yl)acetamide

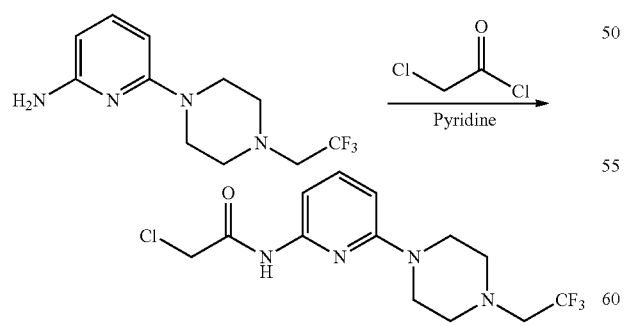

To a solution of 6-(4-(2,2,2-trifluoroethyl)piperazin-1-yl)pyridin-2-amine (100 mg, 0.38 mmol) in pyridine (3 mL) was added dropwise 2-chloroacetyl chloride (0.06 mL, 0.77 mmol) at 0° C. After addition, the mixture was warmed to RT and stirred for 3h. The reaction mixture was quenched with water (10 mL). The mixture was neutralized with saturated aqueous NH$_4$Cl and extracted with EA. The organic layer was washed with water, brine, dried over Na$_2$SO$_4$ and filtered. The filtrate was concentrated under reduced pressure and the residue was purified by chromatography (PE/EA=20:1 to 8:1) to afford 2-chloro-N-(6-(4-(2,2,2-trifluoroethyl)piperazin-1-yl)pyridin-2-yl)acetamide (15 mg, 11.5% yield) as a brown solid. Retention time (LC-MS): 1.510 min. MH$^+$337.

Preparation 88 2-chloro-N-(6'-(trifluoromethyl)-2,3'-bipyridin-6-yl)acetamide

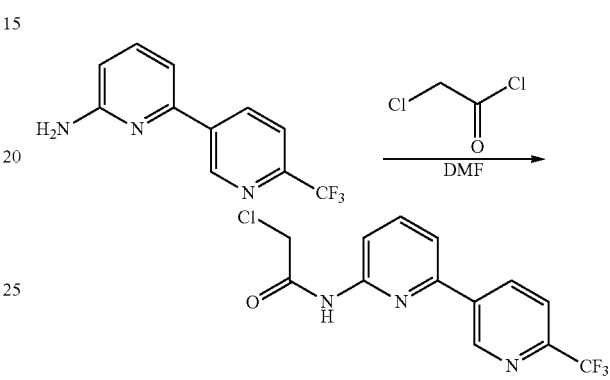

To a mixture of 6'-(trifluoromethyl)-2,3'-bipyridin-6-amine (60 mg, 0.25 mmol) and DMF (3 mL) was added dropwise 2-chloroacetyl chloride (34.1 mg, 0.301 mmol) at 0° C. The mixture was stirred at RT overnight and poured into EA. The organic phase was separated, washed with water and brine, dried over Na$_2$SO$_4$, and concentrated and the residue was purified by chromatography to give 2-chloro-N-(6'-(trifluoromethyl)-2,3'-bipyridin-6-yl)acetamide. (75 mg, 94.7% yield) as a white solid. Retention time (LC-MS): 1.440 min. MH$^+$316.

Preparation 89 2-chloro-N-(2-(5-methyl-6-(trifluoromethyl)pyridin-3-yl)thiazol-4-yl)acetamide

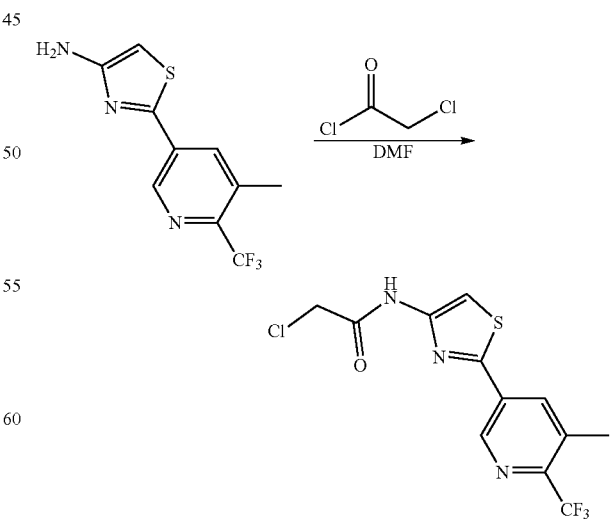

To a solution of 2-(5-methyl-6-(trifluoromethyl)pyridin-3-yl)thiazol-4-amine (60 mg, 0.23 mmol) in DMF (2 mL) was added 2-chloroacetyl chloride (0.04 mL, 0.46 mmol) at 0° C. After the addition, the mixture was stirred at RT for 1 h. The reaction mixture was quenched by water (10 mL) and diluted with EA (15 mL). The organic layer was separated, washed with saturated aq.NH$_4$Cl (10 mL) and brine (10 mL), dried over Na$_2$SO$_4$ and filtered. The filtrate was concentrated and the residue was purified by chromatography (eluted with PE:EA=15:1) to afford 2-chloro-N-(2-(5-methyl-6-(trifluoromethyl)pyridin-3-yl)thiazol-4-yl)acetamide (70 mg, 90.1% yield) as a white solid. Retention time (LC-MS): 1.519 min. MH$^+$336.

Preparation 90 2-chloro-N-(2-(6-methyl-5-(trifluoromethyl)pyridin-3-yl)thiazol-4-yl)acetamide

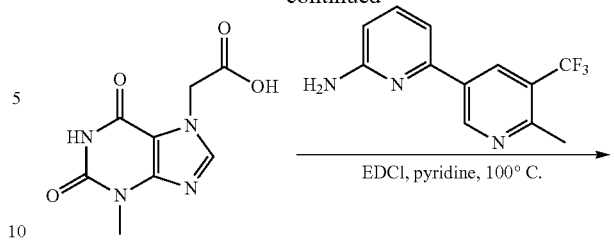

To a solution of 2-(6-methyl-5-(trifluoromethyl)pyridin-3-yl)thiazol-4-amine (170 mg, 0.656 mmol) in DMF (5 mL) was added 2-chloroacetyl chloride (105 mg, 925.74 mmol) drop-wise at 0° C. The mixture was stirred at RT for 1 h. The mixture was diluted with EA and washed with water and brine, dried over Na$_2$SO$_4$ and filtered. The filtrate was concentrated under reduced pressure. The filtrate was concentrated and the residue was purified by chromatography (PE/EA=5:1) to afford 2-chloro-N-(2-(6-methyl-5-(trifluoromethyl)pyridin-3-yl)thiazol-4-yl)acetamide (200 mg, 91% yield) as a yellow solid. Retention time (LC-MS): 1.494 min. MH$^+$335.

Preparation 91 2-(3-methyl-2,6-dioxo-2,3-dihydro-1H-purin-7(6H)-yl)-N-(6'-methyl-5'-(trifluoromethyl-[2,3'-bipyridin]-6-yl)acetamide

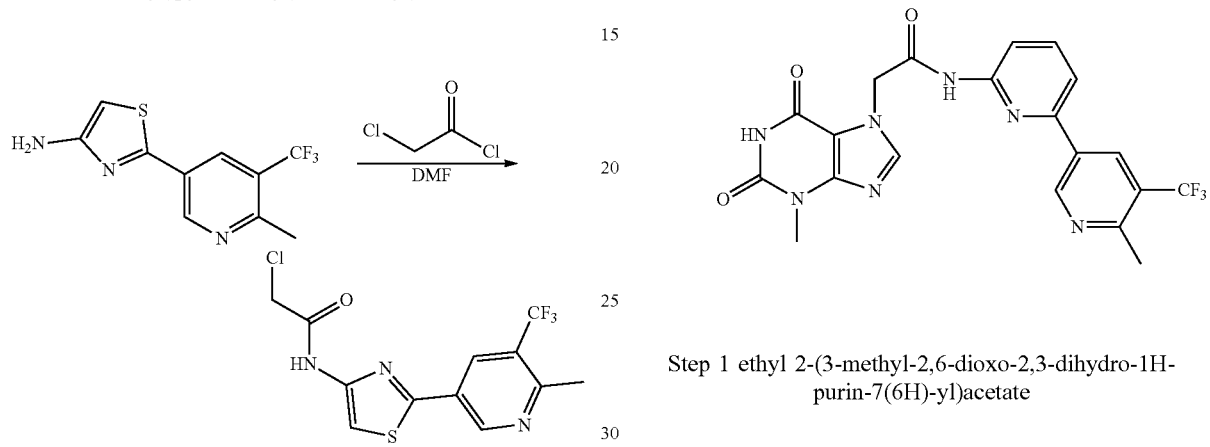

Step 1 ethyl 2-(3-methyl-2,6-dioxo-2,3-dihydro-1H-purin-7(6H)-yl)acetate

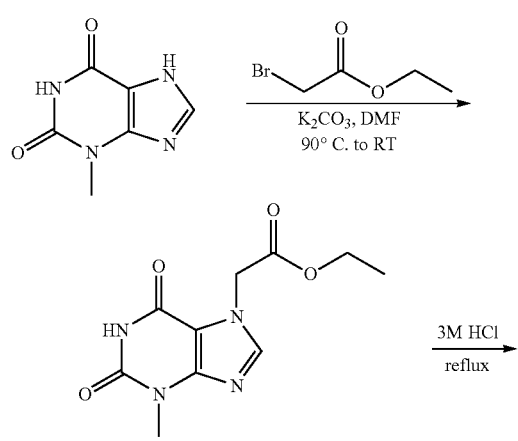

To a suspension of 3-methyl-1H-purine-2,6(3H,7H)-dione (10 g, 60.19 mmol) in DMF (160 mL) was added potassium carbonate (16.64 g, 120.38 mmol). The reaction was stirred by a mechanical stirrer, heated at 90° C. for 3 h, cooled to RT then ethyl 2-bromoacetate (6.66 mL, 60.19 mmol) dissolved in DMF (40 mL) was added drop wise over 1 h. The heterogeneous white reaction was rapidly stirred for 18 h, cooled in an ice bath, water (240 ml) was added, stirred for 15 min then filtered the insoluble solid. The solid was washed with water (100 ml) and MeOH (4×50 mL) then dried to give ethyl 2-(3-methyl-2,6-dioxo-2,3-dihydro-1H-purin-7(6H)-yl)acetate (8.30 g, 55% yield) as a white solid. LCMS: MH$^+$253 and R$_f$=1.454 min.

Step 2 2-(3-methyl-2,6-dioxo-2,3-dihydro-1H-purin-7(6H)-yl)acetic acid

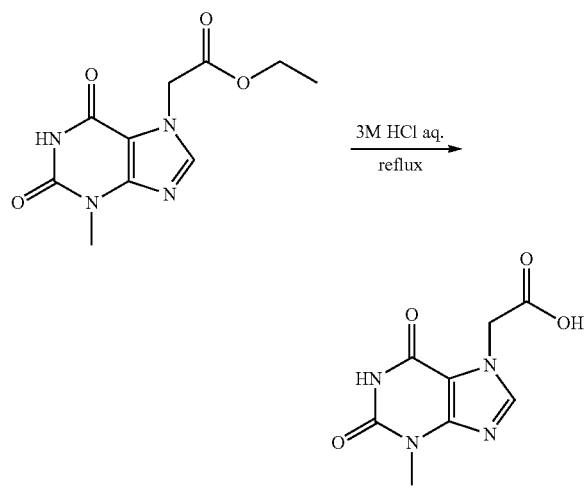

Ethyl 2-(3-methyl-2,6-dioxo-2,3-dihydro-1H-purin-7(6H)-yl)acetate (8.20 g, 32.51 mmol) was slurried in aq. HCl (3M, 162.6 mL, 487.66 mmol). The reaction was heated at reflux for 30 min, cooled to RT and filtered the insoluble solid. The solid was washed with water (2×20 mL), MeOH (2×20 mL) and Ether (50 mL) then azeotroped with toluene (2×25 mL) and dried to give 2-(3-methyl-2,6-dioxo-2,3-dihydro-1H-purin-7(6H)-yl)acetic acid (7.29 g, 100% yield) as a white solid. LCMS: MH$^+$225 and R$_t$=0.40 min.

Step 3 2-(3-methyl-2,6-dioxo-2,3-dihydro-1H-purin-7(6H)-yl)-N-(6'-methyl-5'-(trifluoromethyl)-[2,3-bipyridin]-6-yl)acetamide

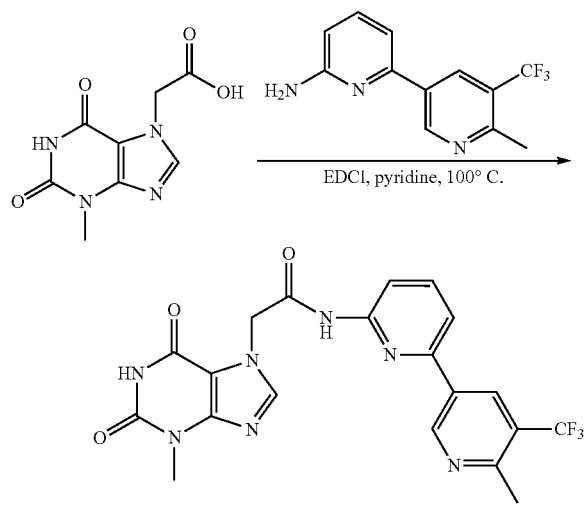

2-(3-methyl-2,6-dioxo-2,3-dihydro-1H-purin-7(6H)-yl)acetic acid (0.531 g, 2.37 mmol), 6'-methyl-5'-(trifluoromethyl)-[2,3'-bipyridin]-6-amine (0.40 g, 1.58 mmol) and EDCI (1.21 g, 6.32 mmol) were combined in pyridine (24 mL). The reaction was heated at 100° C. for 18 h, cooled to RT and EA (100 mL) was added. The insoluble solid was filtered off, washed with water (2×15 mL), EA (30 mL) and dried to give 2-(3-methyl-2,6-dioxo-2,3-dihydro-1H-purin-7(6H)-yl)-N-(6'-methyl-5'-(trifluoromethyl)-[2,3-bipyridin]-6-yl)acetamide (0.72g, 100% yield) as a tan solid. LCMS MH$^+$460 and R$_t$=2.615. Used without further purification.

Preparation 92 2-(3-methyl-2,6-dioxo-2,3-dihydro-1H-purin-7(6H)-yl)-N-6-(6-methyl-5-(trifluoromethyl) pyridin-3-yl)pyrazin-2-yl)acetamide

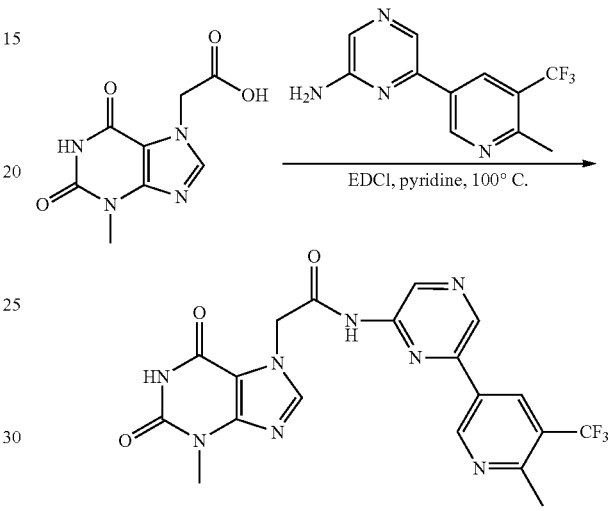

2-(3-methyl-2,6-dioxo-2,3-dihydro-1H-purin-7(6H)-yl)acetic acid (0.661 g, 2.95 mmol), 6-(6-methyl-5-(trifluoromethyl)pyridin-3-yl)pyrazin-2-amine (0.50 g, 1.58 mmol) and EDCI (1.51 g, 7.88 mmol) were combined in pyridine (30 mL). The reaction was heated at 100° C. for 18 h, cooled to RT and aq. NH$_4$Cl (100 mL) was added. The mixture was stirred for 20 min an insoluble solid formed and was filtered off. The solid was washed with EA (2×20 mL), dried to give 2-(3-methyl-2,6-dioxo-2,3-dihydro-1H-purin-7(6H)-yl)-N-6-(6-methyl-5-(trifluoromethyl)pyridin-3-yl)pyrazin-2-yl)acetamide (494 mg, 54.4% yield) as a tan solid. LCMS MH$^+$461 and R$_t$=2.341. Used without further purification.

Preparation 93 3-methyl-1-(2-oxopropyl)-8-(pyridine-4-yl)-1H-purine-2,6(3H,7H)-dione

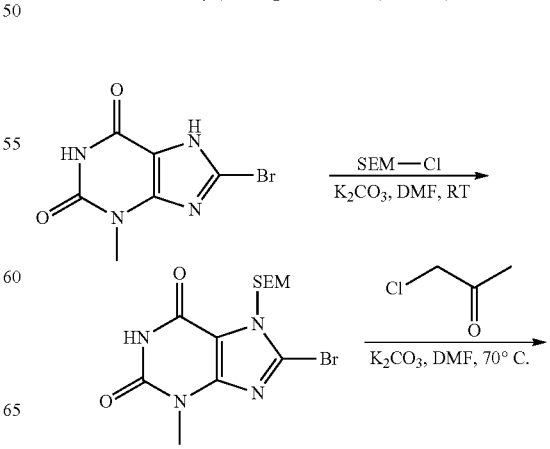

285

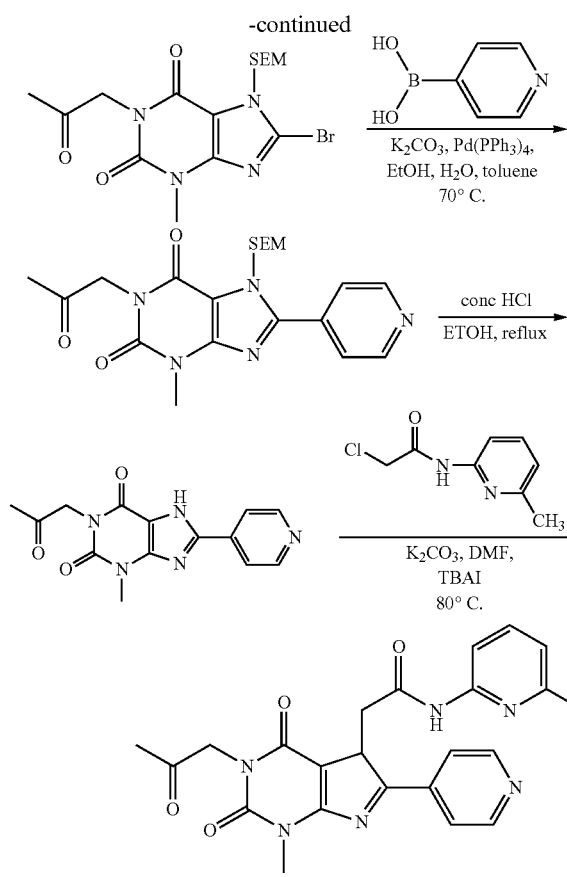

Step 1 8-Bromo-3-methyl-7-((2-trimethylsilyl)ethoxy)methyl-1H-purine-2,6(3H,7H)-dione

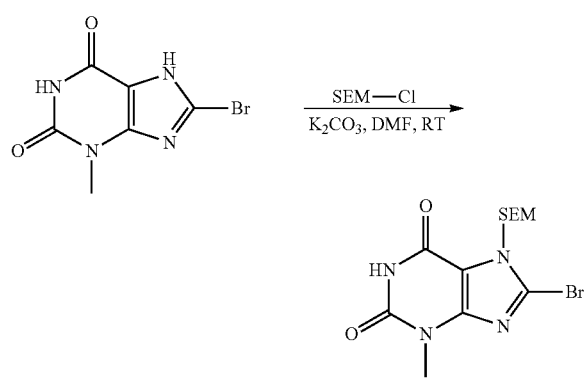

8-bromo-3-methyl-1H-purine-2,6(3H,7H)-dione (5 g, 20.41 mmol) and postassium carbonate (8.46 g, 61.23 mmol) were combined in DMF (50 mL), cooled to 0° C. and 2-(trimethylsilyl)ethoxymethyl chloride (3.61 mL, 20.41 mmol) was added drop wise. The reaction was stirred at RT for 3 h, diluted with water (300 mL) and extracted with EA (3×100 mL). Pooled organic layers were washed with aq. 1N LiCl (2×150 mL), dried with MgSO₄ and concentrated to give 8-bromo-3-methyl-7-((2-trimethylsilyl)ethoxy)methyl-1H-purine-2,6(3H,7H)-dione (7.0 g, 91.3% yield) as a white solid. Used without further purification.

286

Step 2 8-Bromo-3-methyl-1-(2-oxopropyl)-7-((2-(trimethylsilyl)ethoxy)methyl)-1H-purine-2,6(3H,7H)-dione

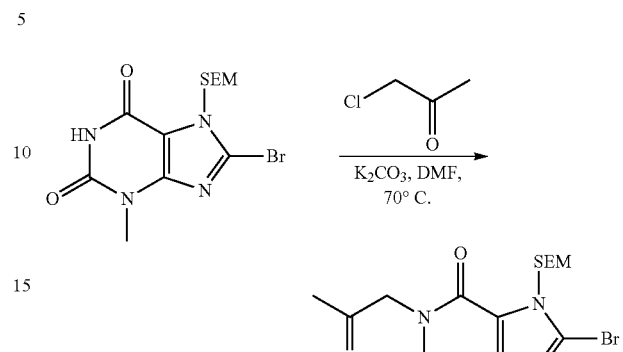

8-bromo-3-methyl-7-((2-trimethylsilyl)ethoxy)methyl-1H-purine-2,6(3H,7H)-dione (2.0 g, 5.33 mmol), postassium carbonate (1.47 g, 10.66 mmol) and 1-chloropropane (0.64 mL, 7.99 mmol) were combined in DMF (20 mL). The reaction was heated at 70° C. for 3 h, cooled to RT, diluted with water (100 mL) and extracted with EA (3×75 mL). Combined organic layers were washed with aq. 1N LiCl (2×100 mL), dried with MgSO₄ and concentrated to a residue which was purified by chromatography eluted with EA/Hep (10:90 to 25:75) to give 8-bromo-3-methyl-1-(2-oxopropyl)-7-((2-(trimethylsilyl)ethoxy)methyl)-1H-purine-2,6(3H,7H)-dione (1.48 g, 64.35 yield) as a white solid.

Step 3 3-Methyl-1-(2-oxopropyl)-8-(pyridine-4-yl)-7-((2-(trimethylsilyl)ethoxy)-methyl)-1H-purine-2,6(3H,7H)-dione

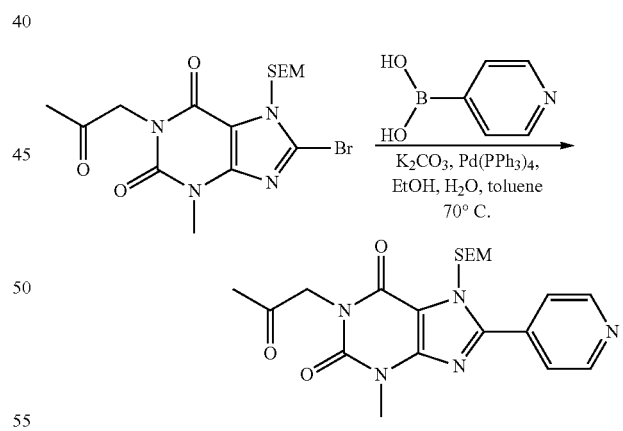

8-bromo-3-methyl-1-(2-(trim ethyl silyl)ethoxy)methyl)-1H-purine-2,6(3H, 7H)-dione (250 mg, 0.580 mmol), postassium carbonate (192 mg, 1.392 mmol) and pyridine-4-ylboronic acid (71 mg, 0.580 mmol) were combined in EtOH (4 mL), water (0.6 mL) and toluene (0.6 mL). The mixture was degassed with Argon then Pd(Ph3)4 (67 mg, 0.058 mmol) was added. The reaction was heated at 70° C. for 18 h then concentrated to a residue which was purified by chromatography eluted with EA/Hep (20:80 to 100:0) to give 3-methyl-1-(2-oxopropyl)-8-(pyridine-4-yl)-7-((2-(trimethylsilyl)ethoxy)methyl)-1H-purine-2,6(3H, 7H)-dione (210 mg, 84.3% yield) as a white solid. $^1$H NMR (CDCl$_3$) δ: 8.84 (d, J=8 Hz), 8.43 (d, J=8 Hz, 2H), 5.95 (s, 2H), 4.88 (s, 2H), 3.89 (t, J=12 Hz, 2H), 3.62 (s, 2H), 2.30 (s, 3H), 1.01 (t, J=8 Hz, 2H), 0.01 (s, 9H). LCMS MH$^+$430 and R$_t$=3.178 min.

Step 4 3-Methyl-1-(2-oxopropyl)-8-(pyridine-4-yl)-1H-purine-2,6(3H,7H)-dione

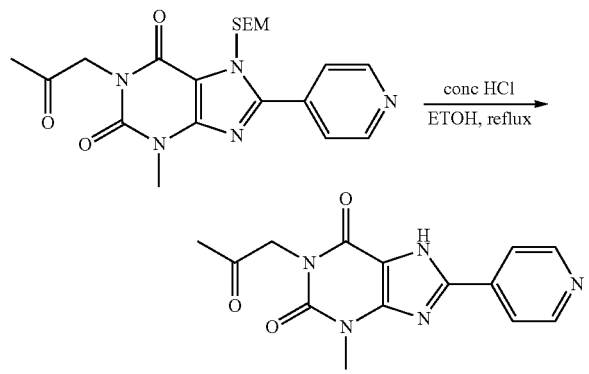

3-methyl-1-(2-oxopropyl)-8-(pyridine-4-yl)-7-((2-(trimethyl silyl)ethoxy)methyl)-1H-purine-2,6(3H,7H)-dione (210 mg, 0.489 mmol) was dissolved in EtOH (5 mL) and concentrated HCl (1 mL). The reaction was heated at reflux for 1 h, cooled to RT and filtered the insoluble solid. The solid was washed with EtOH (2×5 mL) and dried to give 3-methyl-1-(2-oxopropyl)-8-(pyridine-4-yl)-1H-purine-2,6 (3H,7H)-dione (82 mg, 56.2% yield) as a yellow solid. $^1$H NMR (DMSO-d6) δ: 8.88 D, J=8 Hz, 2H), 8.33 (d, J=8 Hz, 2H), 4.79 (s, 2H), 3.52 (s, 3H), 2.22 (s, 3H). LCMS: MH$^+$300 and R$_t$=1.414 min.

Preparation 94 (S)-methyl 2-(3-methyl-2,6-dioxo-1-(2,2,2-trifluoroethyl)-2,3-dihydro-1H-purin-7(6H)-yl)propanoate

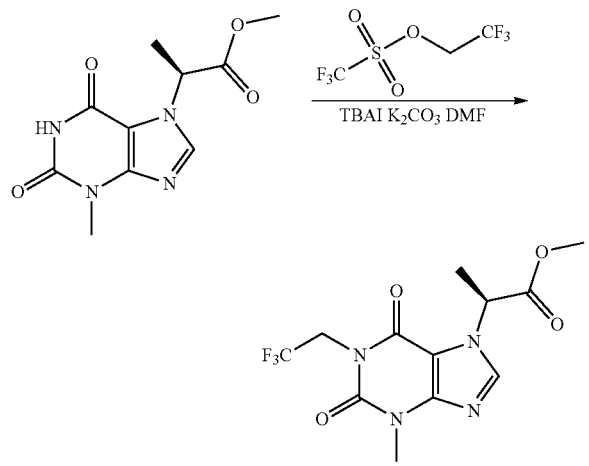

A mixture of (S)-methyl 2-(3-methyl-2,6-dioxo-2,3-dihydro-1H-purin-7(6H)-yl)propanoate (200 mg, 0.792 mmol), 2,2,2-trifluoroethyl trifluoromethanesulfonate (184 mg, 0.792 mmol), potassium carbonate (109 mg, 0.792 mmol) and a catalytic amount of TBAI in N, N-dimethyl formamide (5 mL) was stirred at 50° C. for 2 hrs. The mixture was cooled down and poured into EA. The organic phase was separated, washed with water and brine, dried over Na$_2$SO$_4$ and filtered. The filtrate was concentrated under reduced pressure. The filtrate was concentrated and the residue was purified by chromatography (PE/EA=1:1) to afford (S)-methyl 2-(3-methyl-2,6-dioxo-1-(2,2,2-trifluoroethyl)-2,3-dihydro-1H-purin-7(6H)-yl)propanoate (250 mg, 94% yield) as a white solid. Retention time (LC-MS): 0.905 min. MH$^+$334.

Preparation 95 2-(3-methyl-2,6-dioxo-2,3-dihydro-1H-purin-7(6H)-yl)-N-(2-(6-methyl-5-(trifluoromethyl)pyridin-3-yl)thiazol-4-yl)acetamide

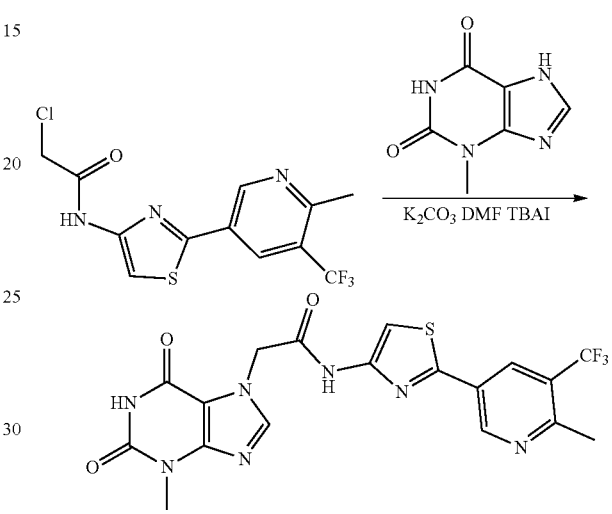

A mixture of 2-chloro-N-(2-(6-methyl-5-(trifluoromethyl)pyridin-3-yl)thiazol-4-yl)acetamide (120 mg, 0.302 mmol), 3-methyl-1H-purine-2,6(3H,7H)-dione (60 mg, 0.302 mmol), potassium carbonate (42.5 mg, 0.302 mmol) and a catalytic amount of TBAI in N, N-dimethylformamide (10 mL) was stirred at 50° C. for 2 hrs. The mixture was cooled down and poured into EA. The organic phase was separated, washed with water and brine, dried over Na$_2$SO$_4$ and filtered. The filtrate was concentrated under reduced pressure. The filtrate was concentrated and the residue was purified by chromatography (DCM/MeOH=20:1) to afford 2-(3-methyl-2,6-dioxo-2,3-dihydro-1H-purin-7(6H)-yl)-N-(2-(6-methyl-5-(trifluoromethyl)pyridin-3-yl)thiazol-4-yl)acetamide (140 mg, 83% yield) as a white solid. R$_t$ (LC-MS): 1.340 min. MH$^+$465.

Preparation 96 (2S)-N-(6-(2-(6,6-difluoro-3-azabicyclo[3.1.0]hexan-3-yl)pyrimidin-5-yl)pyrazin-2-yl)-2-(3-methyl-2,6-dioxo-2,3-dihydro-1H-purin-7(6H)-yl)propanamide

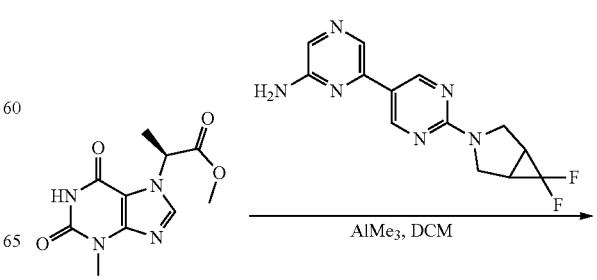

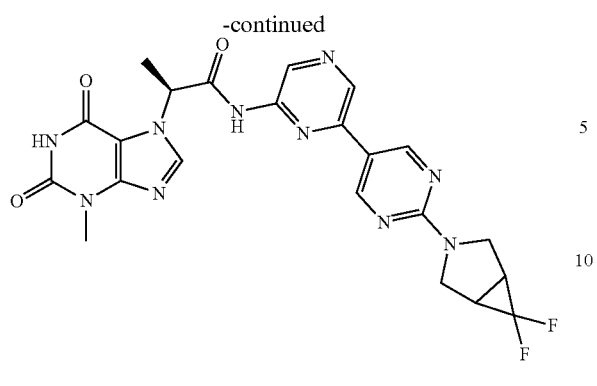

To a solution of (2S)-N-(6-(2-(6,6-difluoro-3-azabicyclo[3.1.0]hexan-3-yl)pyrimidin-5-yl)pyrazin-2-yl)-2-(3-methyl-2,6-dioxo-2,3-dihydro-1H-purin-7(6H)-yl)propanamide (115.1 mg, 0.40 mmol) in DCM (2 mL) was added drop-wise trimethylaluminum (1.60 mL, 1.60 mmol) at 0° C. After the addition, the mixture was warmed to RT and stirred for 0.5 h. Then a solution of (S)-methyl 2-(3-methyl-2,6-dioxo-2,3-dihydro-1H-purin-7(6H)-yl)propanoate (100.0 mg, 0.40 mmol) in DCM (2 mL) was added drop-wise and the reaction mixture was stirred at 30° C. overnight. The reaction was quenched by addition of several drops of MeOH. The mixture was concentrated under reduced pressure and the residue was purified by chromatography (DCM:MeOH=100:1) to afford a crude product, which was further purified via preparative TLC (DCM:MeOH=20:1) to give (2S)-N-(6-(2-(6,6-difluoro-3-azabicyclo[3.1.0]hexan-3-yl)pyrimidin-5-yl)pyrazin-2-yl)-2-(3-methyl-2,6-dioxo-2,3-dihydro-1H-purin-7(6H)-yl)propanamide (6 mg, 3.0% yield) as a white solid. $R_f$ (LC-MS): 1.274 min. LC-MS: m/z: 511. $^1$H NMR (400 MHz, DMSO) δ 11.34 (s, 1H), 11.17 (s, 1H), 9.13 (s, 1H), 9.07 (s, 2H), 8.93 (s, 1H), 8.32 (s, 1H), 5.81 (s, 1H), 4.00 (d, J=12.2 Hz, 2H), 3.86 (d, J=11.0 Hz, 2H), 3.38 (s, 3H), 2.72 (d, J=11.2 Hz, 2H), 1.86 (d, J=7.3 Hz, 3H).

Preparation 97 (S)-2-(3-methyl-1-((5-methyl-1,2,4-oxadiazol-3-yl)methyl)-2,6-dioxo-2,3-dihydro-1H-purin-7(6H)-yl)-N-(6'-methyl-5'-(trifluoromethyl)-2,3'-bipyridin-6-yl)propanamide

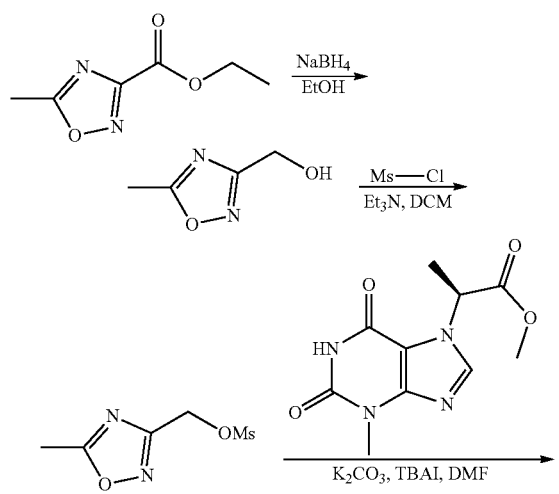

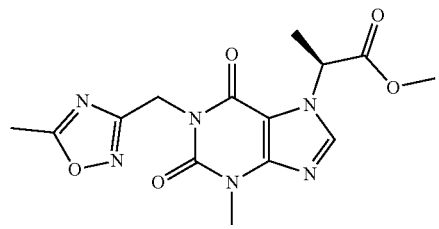

Step 1 (5-methyl-1,2,4-oxadiazol-3-yl)MeOH

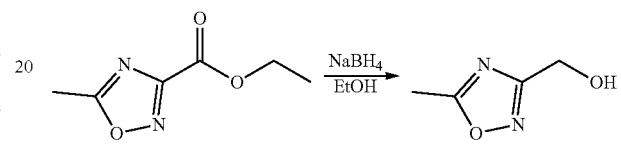

To a solution of ethyl 5-methyl-1,2,4-oxadiazole-3-carboxylate (2.0 g, 12.8 mmol) in EtOH (20 mL) was added NaBH$_4$ (0.97 g, 25.6 mmol) at RT. The reaction was stirred at RT for overnight. The reaction mixture was concentrated under reduced pressure and the residue was purified by chromatography (DCM/MeOH=100:1 to 40:1) to give (5-methyl-1,2,4-oxadiazol-3-yl)MeOH (500 mg, 34.2% yield) as a colorless oil. Retention time (LC-MS): 0.385 min. $^{MH+}$115.

Step 2 (5-methyl-1,2,4-oxadiazol-3-yl)methyl methanesulfonate

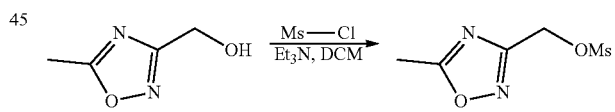

To a solution of (5-methyl-1,2,4-oxadiazol-3-yl)MeOH (100.0 mg, 0.88 mmol) and TEA (0.14 mL, 0.96 mmol) in DCM (3 mL) was cooled under ice-water bath to 0° C., followed by drop-wise addition of methanesulfonyl chloride (0.08 mL, 0.96 mmol). The ice-water bath was removed after the addition and the mixture was stirred at RT overnight. The reaction mixture was washed with water (5 mL). The organic layer was separated, dried over Na$_2$SO$_4$ and filtered. The filtrate was concentrated under reduced pressure and the residue was purified by chromatography (DCM/MeOH=50:1) to give (5-methyl-1,2,4-oxadiazol-3-yl)methyl methanesulfonate (100 mg, 86.08% yield) as a colorless oil. Retention time (LC-MS): 0.324 min. $^{MH+}$193.

Step 3 (S)-methyl 2-(3-methyl-1-((5-methyl-1,2,4-oxadiazol-3-yl)methyl)-2,6-dioxo-2,3-dihydro-1H-purin-7(6H)-yl)propanoate

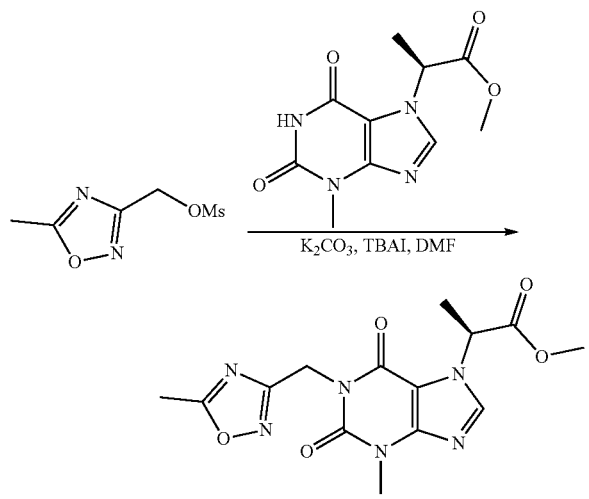

A mixture of (5-methyl-1,2,4-oxadiazol-3-yl)methyl methanesulfonate (100.0 mg, 0.52 mmol), (S)-methyl 2-(3-methyl-2,6-dioxo-2,3-dihydro-1H-purin-7(6H)-yl)propanoate (130.0 mg, 0.52 mmol), potassium carbonate (143.0 mg, 1.03 mmol) and a catalytic amount of TBAI in N, N-dimethylformamide (1 mL) was stirred at 50° C. overnight. The mixture was diluted with EA and washed with water, brine successively, dried and concentrated to give crude product, which was purified by chromatography (DCM/MeOH=50:1) to give (S)-methyl 2-(3-methyl-1-((5-methyl-1,2,4-oxadiazol-3-yl)methyl)-2,6-dioxo-2,3-dihydro-1H-purin-7(6H)-yl)propanoate (150 mg, 63.7% yield) as a colorless oil. Retention time (LC-MS): 0.537 min. LC-MS: m/z: 349.

Preparation 98 (2-(3-methyl-2,6-dioxo-2,3-dihydro-1H-purin-7(6H)-yl)-N-(2-(5-methyl-6-(trifluoromethyl)pyridin-3-yl)thiazol-4-yl)acetamide

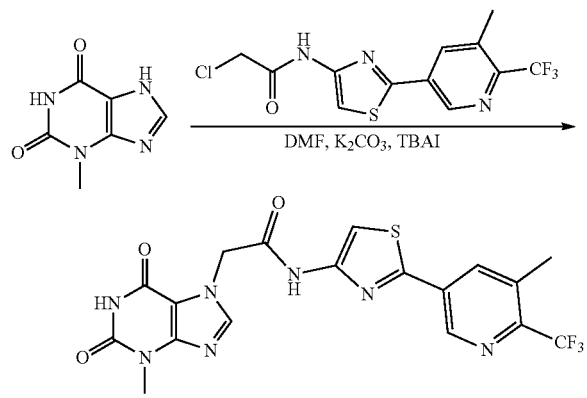

To a solution of 2-chloro-N-(2-(5-methyl-6-(trifluoromethyl)pyridin-3-yl)thiazol-4-yl)acetamide (130 mg, 0.39 mmol) and 3-methyl-1H-purine-2,6(3H,7H)-dione (64.33 mg, 0.39 mmol) in DMF (5 mL) was added TBAI (14.30 mg, 0.039 mmol) and POTASSIUM CARBONATE (107.03 mg, 0.77 mmol) under N₂ protection. The mixture was stirred at 50° C. for 2 hrs. The reaction was quenched by water (15 mL) and extracted with EA (2×15 mL). The combined organic layer was washed with saturated brine (2×15 mL), dried over Na₂SO₄ and filtered. The filtrate was concentrated. The crude product was purified by chromatography (DCM:MeOH=100:1 to 40:1) to afford 2-(3-methyl-2,6-dioxo-2,3-dihydro-1H-purin-7(6H)-yl)-N-(2-(5-methyl-6-(trifluoromethyl)pyridin-3-yl)thiazol-4-yl) acetamide (70 mg, 38.9% yield) as a yellow solid. Retention time (LC-MS): 1.156 min. MH⁺466.

Preparation 99 6-(5-(6,6-difluoro-3-azabicyclo[3.1.0]hexan-3-yl)pyrazin-2-yl)pyridin-2-amine

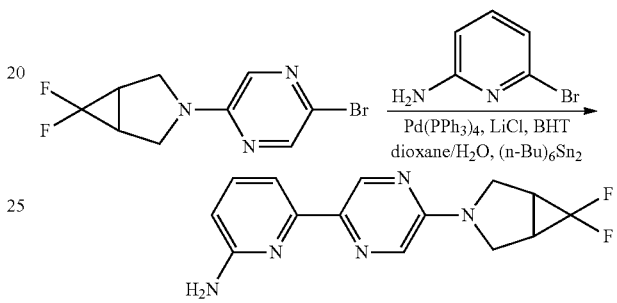

A mixture of 3-(5-bromopyrazin-2-yl)-6,6-difluoro-3-azabicyclo[3.1.0]hexane (500 mg, 1.81 mmol), 6-bromopyridin-2-amine (374 mg, 2.17 mmol), LiCl (76.0 mg, 1.81 mmol) and 2,6-di-tert-butyl-4-methylphenol (39.6 mg, 0.18 mmol) in 1,4-dioxane (10 mL) was degassed withr N₂ for three times and terakis(triphenylphosphine)palladium (104 mg, 0.09 mmol) was added under N₂ atmosphere. The mixture was degassed again and hexa-n-butylditin (2.09 g, 3.62 mmol) was added, the reaction mixture was stirred under N₂ at 110° C. over two nights. The mixture was concentrated to dryness and the crude product was purified column chromatography (DCM/MeOH=50:1 to 20:1) to give 6-(5-(6,6-difluoro-3-azabicyclo[3.1.0]hexan-3-yl)pyrazin-2-yl)pyridin-2-amine (140 mg, 26.7% yield) as a yellow solid. Retention time (LC-MS): 1.038 min. MH⁺290.

Preparation 100 2'-(3-azabicyclo[3.1.0]hexan-3-yl)-2,5'-bipyrimidin-4-amine

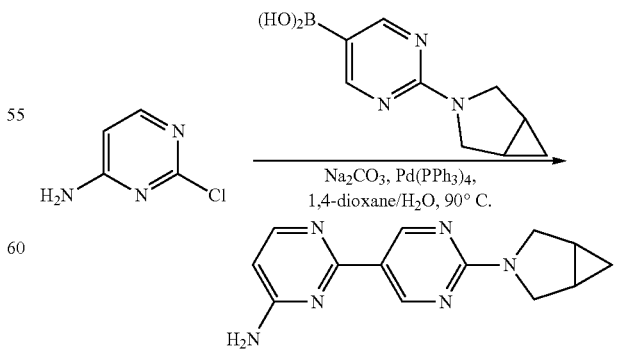

To a mixture of 2-chloropyrimidin-4-amine (100.0 mg, 0.772 mmol), 2-(3-azabicyclo[3.1.0]hexan-3-yl)pyrimidin- 5-ylboronic acid (158.0 mg, 0.772 mmol) in 1,4-dioxane (5 mL) and H₂O (1 mL) was added Na₂CO₃ (204.5 mg, 1.93 mmol). After the mixture was degassed with N₂ for 3 times, Pd(PPh₃)₄ (11.5 mg, 0.01 mmol) was added under N₂ and the mixture was stirred at 90° C. for 2 hrs. The reaction mixture was cooled down and diluted with EA, washed with water and brine, dried over Na₂SO₄ and filtered. The filtrate was concentrated under reduced pressure and the residue was purified by chromatography (eluted with PE:EA=1:1) to afford 2'-(3-azabicyclo[3.1.0]hexan-3-yl)-2,5'-bipyrimidin-4-amine (124 mg, 63.17% yield) as a yellow solid. Retention time (LC-MS): 0.573 min. MH⁺255.

Preparation 101 6-(2-(3-azabicyclo[3.1.0]hexan-3-yl)pyrimidin-5-yl)pyrazin-2-amine

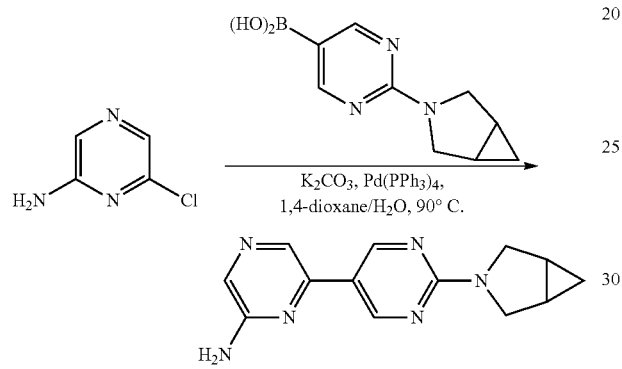

To a mixture of 6-chloropyrazin-2-amine (100.0 mg, 0.772 mmol), 2-(3-azabicyclo[3.1.0]hexan-3-yl)pyrimidin-5-ylboronic acid (158.0 mg, 0.772 mmol) in 1,4-dioxane (5 mL) and H₂O (1 mL) was added potassium carbonate (266.0 mg, 1.93 mmol). After the mixture was degassed with N₂ for 3 times, Pd(PPh₃)₄ (11.5 mg, 0.01 mmol) was added under N₂ and the mixture was stirred at 90° C. for 2 hrs. The reaction mixture was cooled down and diluted with EA, washed with water and brine, dried over Na₂SO₄ and filtered. The filtrate was concentrated under reduced pressure and the residue was purified by chromatography (eluted with PE:EA=1:1) to afford 6-(2-(3-azabicyclo[3.1.0]hexan-3-yl)pyrimidin-5-yl)pyrazin-2-amine (160 mg, 81.51% yield) as a yellow solid. Retention time (LC-MS): 1.071 min. MH⁺255.

Preparation 102 (S)-2-(3-methyl-2,6-dioxo-1-(2-oxobutyl)-2,3-dihydro-1H-purin-7(6H)-yl)propanoic acid

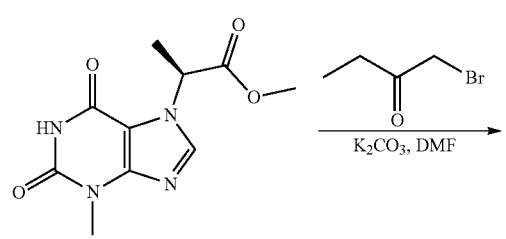

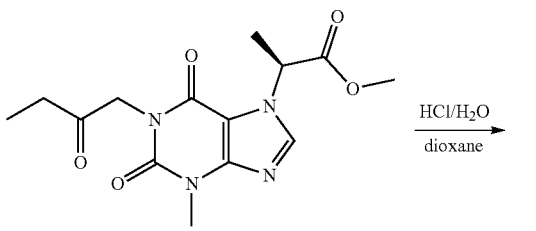

Step 1 (S)-methyl 2-(3-methyl-2,6-dioxo-1-(2-oxobutyl)-2,3-dihydro-1H-purin-7(6H)-yl)propanoate

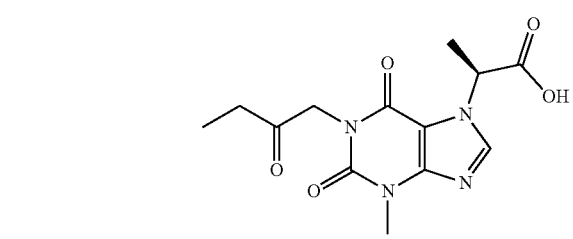

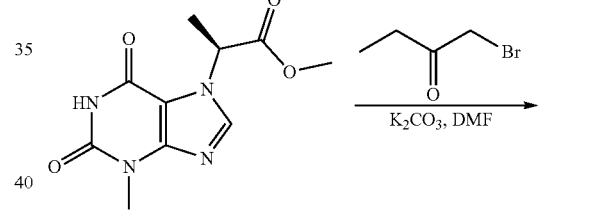

A mixture of 1-bromobutan-2-one (407 mg, 2.69 mmol), (S)-methyl 2-(3-methyl-2,6-dioxo-2,3-dihydro-1H-purin-7(6H)-yl)propanoate (523 mg, 2.07 mmol) and potassium carbonate (429 mg, 3.11 mmol) in DMF (15 mL) was stirred at rt overnight. The mixture was diluted with EA and washed with water and brine successively, dried, and concentrated, and the resulting residue was purified by chromatography (EA:heptane 0-100%) to give (S)-methyl 2-(3-methyl-2,6-dioxo-1-(2-oxobutyl)-2,3-dihydro-1H-purin-7(6H)-yl)propanoate (449 mg, 67% yield) as a colorless oil. MH+323.

Step 2 (S)-2-(3-methyl-2,6-dioxo-1-(2-oxobutyl)-2,3-dihydro-1H-purin-7(6H)-yl)propanoic acid

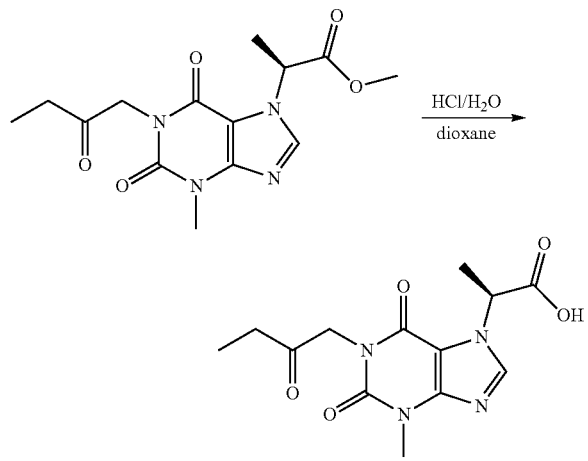

A mixture of (S)-methyl 2-(3-methyl-2,6-dioxo-1-(2-oxobutyl)-2,3-dihydro-1H-purin-7(6H)-yl)propanoate (390 mg, 1.21 mmol) and HCl (1M, 2.5 mL) in dioxane (5 mL) was stirred at 110 °C. for 2 h. The reaction mixture was poured into water (50 mL) and extracted with EA (2×50 mL). The combined organic layers were dried over $Na_2SO_4$ and filtered. The filtrate was concentrated under reduced pressure and the residue was purified by chromatography (DCM:MeOH=20:1) to afford (S)-2-(3-methyl-2,6-dioxo-1-(2-oxobutyl)-2,3-dihydro-1H-purin-7(6H)-yl)propanoic acid (224 mg, 60% yield) as a yellow oil. $MH^+$309.

Compound 1. (2S)-2-(3-methyl-2,6-dioxo-1-(pyridin-2-ylmethyl)-1,2,3,6-tetrahydro purin-7-yl)-N-(6-(6-(trifluoromethyl)pyridin-3-yl)pyridin-2-yl)propanamide

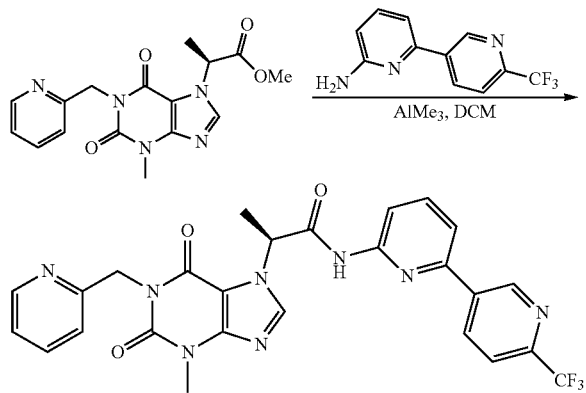

To a solution of (S)-methyl 6-(6-(trifluoromethyl)pyridin-3-yl)pyridin-2-amine (20 mg, 0.084 mmol) in DCM (1 mL) was added dropwise trimethylaluminium (0.06 mL, 2.0 M) at 0° C. via syringe under $N_2$ atmosphere. After the addition, the mixture was stirred at RT for 20 min, then a solution of (S)-methyl 2-(3-methyl-2,6-dioxo-1-(pyridin-2-ylmethyl)-1,2,3,6-tetrahydropurin-7-yl)propanoate (28 mg, 0.084 mmol) in dry DCM was added. The reaction solution was stirred for 3 hr, and then quenched with water (5 mL). The reaction mixture was extracted with DCM (3×3 mL). Combined organic layers were dried over $Na_2SO_4$ and filtered. The filtrate concentrated under reduced pressure and the residue was purified by pre-TLC to afford (2S)-2-(3-methyl-2,6-dioxo-1-(pyridin-2-ylmethyl)-1,2,3,6-tetrahydropurin-7-yl)-N-(6-(6-(trifluoromethyl)pyridin-3-yl)pyridin-2-yl) propanami de (20 mg, 43.4% yield) as a white solid. 1H-NMR (400 MHz, DMSO-$d_6$) δ 11.17 (s, 1H), 9.40 (s, 1H), 8.68 (t, J=1.2 Hz, 1H), 8.38 (s, 2H), 8.02 (d, J=8.4 Hz, 2H), 7.95 (t, J=7.6 Hz, 1H), 7.88 (d, J=7.6 Hz, 1H), 7.68 (t, J=6.4 Hz, 1H), 7.18 (s, 1H), 5.80 (d, J=5.6 Hz, 1H), 5.11 (s, 2H), 3.57 (s, 3H), 1.85 (d, J=7.6 Hz, 3H). Retention time (LC-MS): 1.441 min. $MH^+$551.

Compound 2. (S)-2-(3-methyl-2,6-dioxo-1-(2-oxopropyl)-2,3-dihy dro-1H-purin-7(6H)-yl)-N-(6'-(trifluoromethyl)-[2,3'-bipyridin]-6-yl)propanamide

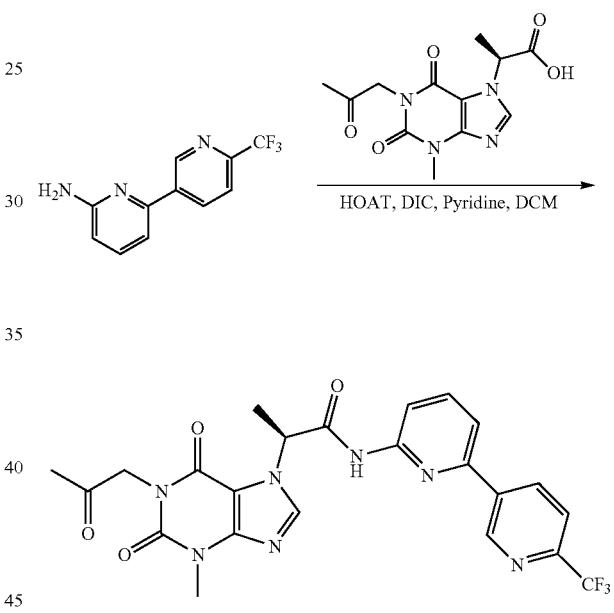

To a solution of 6'-(trifluoromethyl)-[2,3'-bipyridin]-6-amine (59.8 mg, 0.25 mmol) and (S)-2-(3-methyl-2,6-dioxo-1-(2-oxopropyl)-2,3-dihydro-1H-purin-7(6H)-yl)propanoic acid (73.5 mg, 0.25 mmol) in DCM (3 mL) was added HOAt (40.8 mg, 0.3 mmol) at r.t. The reaction mixture was cooled under ice-water bath to 0° C., followed by slow dropwise addition of pyridine (39.5 mg, 0.5 mmol) and DIC (47.2 mg, 0.4 mmol) under $N_2$ protection. The ice-water bath was removed after the addition and the mixture was stirred at r.t. for 18 h. The reaction mixture was washed with water (5 mL), and S. aq. $NH_4Cl$ (5 mL). The organic layer was separated, dried over $Na_2SO_4$ and filtered. The filtrate was concentrated under reduced pressure and the residue was purified via prep-TLC (eluted with PE:EA=1:1) to afford the title product (80 mg, 62.1% yield) as a white solid. $^1$HNMR (400 MHz, DMSO-$d_6$) δ 11.20 (s, 1H), 9.45 (s, 1H), 8.71 (d, J=8.1 Hz, 1H), 8.39 (s, 1H), 8.07 (t, J=8.1 Hz, 2H), 7.98 (t, J=7.9 Hz, 1H), 7.92 (d, J=7.7 Hz, 1H), 5.79 (s, 1H), 4.70 (d, J=2.5 Hz, 2H), 3.46 (s, 3H), 2.16 (s, 3H), 1.88 (d, J=7.3 Hz, 3H). Retention time (LC-MS): 2.28 min. $MH^+$516.

Compound 3. (S)-2-(3-methyl-2,6-dioxo-1-(2-oxo-propyl)-2,3-dihydro-1H-purin-7(6H)-yl)-N-(6-(6-(trifluoromethyl)pyridin-3-yl)pyrazin-2-yl)propanamide

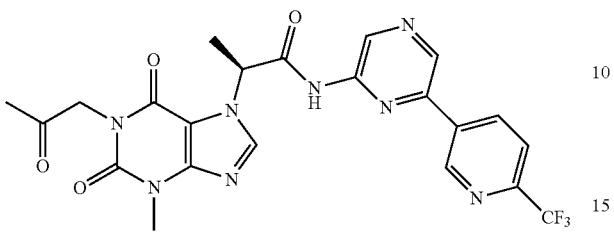

This compound was prepared using the method described for compound 2 with appropriate starting materials. $^1$HNMR (400 Hz, DMSO-$d_6$) δ 11.57 (s, 1H), 9.48 (s, 1H), 9.30 (s, 1H), 9.18 (s, 1H), 8.76 (d, J=8.0 Hz, 1H), 8.42 (s, 1H), 8.14 (d, J=8.3 Hz, 1H), 5.80 (d, J=6.9 Hz, 1H), 4.78-4.59 (m, 2H), 3.47 (s, 3H), 2.16 (s, 3H), 1.91 (d, J=7.2 Hz, 3H). Retention time (LC-MS): 2.055 min. MH$^+$517.1.

Compound 4. (S)-2-(3-methyl-2,6-dioxo-1-(2-oxo-propyl)-2,3-dihydro-1H-purin-7(6H)-yl)-N-(6-(2-(trifluoromethyl)pyrimidin-5-yl)pyridin-2-yl)propanamide

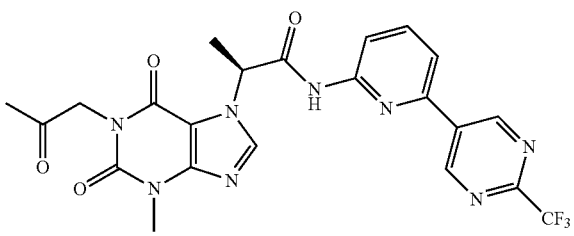 [SMILES: CC(=O)Cn1c(=O)c2c(ncn2[C@@H](C)C(=O)Nc2cccc(-c3cnc(C(F)(F)F)nc3)n2)n(C)c1=O]

This example was prepared using the similar method described in Example 2 with appropriate starting materials. $^1$HNMR (400 MHz, DMSO-$d_6$) δ 10.70 (s, 1H), 9.66 (s, 1H), 8.40 (s, 1H), 8.10-8.12 (d, J=7.6 Hz, 1H), 7.98-8.01 (m, 2H), 5.78-5.79 (m, 1H), 4.70 (s, 2H), 3.64 (s, 3H), 2.16 (s, 3H), 1.87-1.89 (d, J=7.2 Hz, 3H). Retention time (LC-MS): 2.217 min. MH$^+$517.1.

Compound 5. (S)-2-(3-methyl-2,6-dioxo-1-(pyridin-2-ylmethyl)-2,3-dihydro-1H-purin-7(6H)-yl)-N-(6-(2-(trifluoromethyl)pyrimidin-5-yl)pyridin-2-yl)propanamide

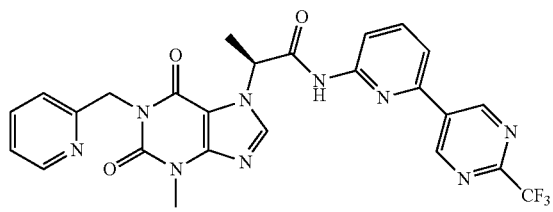 [SMILES: C[C@@H](C(=O)Nc1cccc(-c2cnc(C(F)(F)F)nc2)n1)n1cnc2c1c(=O)n(Cc1ccccn1)c(=O)n2C]

This compound was prepared using the method described for Compound 2 with appropriate starting materials. $^1$H NMR (400 Hz, DMSO-$d_6$) δ 11.26 (s, 1H), 9.65 (s, 2H), 8.40 (d, J=7.1 Hz, 2H), 8.10 (d, J=7.8 Hz, 1H), 8.06-7.94 (m, 2H), 7.69 (td, J=7.7, 1.7 Hz, 1H), 7.25-7.16 (m, 2H), 5.90-5.73 (m, 1H), 5.20-5.07 (m, 2H), 3.48 (s, 3H), 1.88 (d, J=7.3 Hz, 3H). Retention time (LC-MS): 2.128 min. MH$^+$552.

Compound 6. (S)-2-(3-methyl-2,6-dioxo-1-(2-oxo-propyl)-2,3-dihydro-1H-purin-7(6H)-yl)-N-(6-(2-(trifluoromethyl)pyrimidin-5-yl)pyrazin-2-yl)propanamide

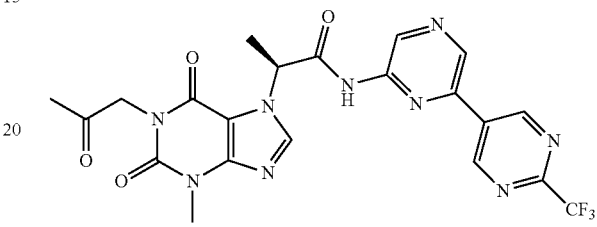

This compound was prepared using the method described for Compound 2 with appropriate starting materials. 1H NMR (400 MHz, DMSO-$d_6$) δ 11.64 (s, 1H), 9.71 (s, 2H), 9.35 (s, 1H), 9.23 (s, 1H), 8.42 (s, 1H), 5.80 (d, J=7.2 Hz, 1H), 4.70 (s, 2H), 3.47 (s, 3H), 2.16 (s, 3H), 1.90 (d, J=7.3 Hz, 3H). Retention time (LC-MS): 2.21 min. MH$^+$518.

Compound 7. (S)-2-(3-methyl-1-((5-methylisoxazol-3-yl)methyl)-2,6-dioxo-2,3-dihydro-1H-purin-7(6H)-yl)-N-(6'-(trifluoromethyl)-[2,3'-bipyridin]-6-yl)propanamide

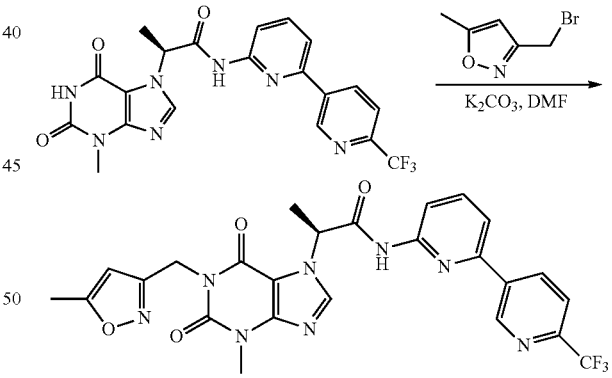

To a solution of (S)-2-(3-methyl-2,6-dioxo-2,3-dihydro-1H-purin-7(6H)-yl)-N-(6'-(trifluoromethyl)-[2,3'-bipyridin]-6-yl)propanamide (27 mg, 0.059 mmol) and potassium carbonate (8.1 mg, 0.059 mmol) in DMF (1 mL) was added 3-(bromomethyl)-5-methylisoxazole (10 mg, 0.059 mmol). The mixture was stirred at rt overnight. The mixture was diluted with EA and washed with water, saturated aqueous NH$_4$Cl solution and brine, dried over Na$_2$SO$_4$, and evaporated. The residue was purified by silica gel column chromatography (0-2% MeOH/DCM) to give the product (S)-2-(3-methyl-1-((5-methylisoxazol-3-yl)methyl)-2,6-dioxo-2,3-dihydro-1H-purin-7(6H)-yl)-N-(6'-(trifluoromethyl)-[2,3'-bipyridin]-6-yl)propanamide (30.1 mg, 92% yield) as a white solid. ¹H NMR (400 MHz, DMSO-D6) δ 11.20 (s, 1H), 9.94 (d, J=1.5 Hz, 1H), 8.69 (m, 1H), 8.39 (s, 1H), 7.90-8.24 (m, 4H), 6.07 (s, 1H), 5.81 (m, 1H), 5.02 (m, 2H), 3.46 (s, 3H), 2.29 (m, 3H), 1.87 (m, 3H). MH⁺555.

Compound 8. (S)-2-(3-methyl-2,6-dioxo-1-(pyridin-2-ylmethyl)-2,3-dihydro-1H-purin-7(6H)-yl)-N-(6-(2-(trifluoromethyl)pyrimidin-5-yl)pyrazin-2-yl)propanamide

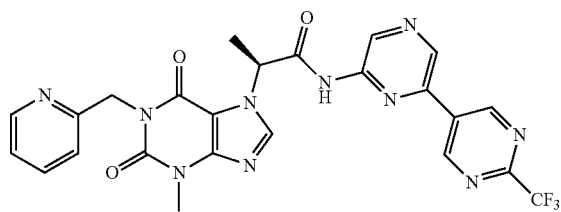 [SMILES: C[C@@H](C(=O)Nc1cncc(-c2cnc(C(F)(F)F)nc2)n1)n1cnc2c1c(=O)n(Cc1ccccn1)c(=O)n2C]

This compound was prepared using the method described for compound 2 with appropriate starting materials. ¹H NMR (400 MHz, DMSO-d₆) δ 11.63 (s, 1H), 9.68 (s, 2H), 9.34 (s, 1H), 9.22 (s, 1H), 8.46-8.37 (m, 2H), 7.69 (t, J=6.9 Hz, 1H), 7.21 (t, J=8.4 Hz, 2H), 5.84 (d, J=7.0 Hz, 1H), 5.13 (s, 2H), 3.48 (s, 3H), 1.90 (d, J=7.3 Hz, 3H). Retention time (LC-MS):1.92 min. MH⁺553.

Compound 9. (2S)-2-(3-methyl-2,6-dioxo-1-(pyridin-2-ylmethyl)-1,2,3,6-tetrahydropurin-7-yl)-N-(6-(6-(trifluoromethyl)pyridin-3-yl)pyrazin-2-yl)propanamide

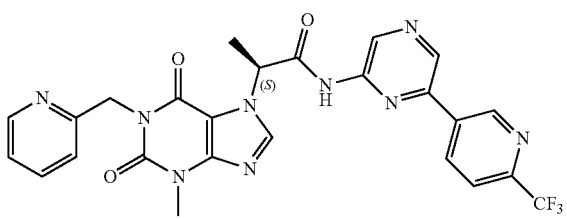

This compound was prepared using the method described for compound 2 with appropriate starting materials. ¹H-NMR (400 MHz, DMSO-d₆) δ 11.09 (s, 1H), 8.12 (s, 1H), 7.94-7.95 (d, J=1.6 Hz, 1H), 7.87-7.91 (t, J=14.6 Hz, 1H), 7.72-7.74 (d, J=8.0 Hz, 1H), 7.58-7.60 (d, J=8.4 Hz, 1H), 5.30 (s, 2H), 4.49 (s, 2H), 3.42 (s, 3H), 2.50 (s, 3H), 2.17 (s, 3H). Retention time (LC-MS): 1.211 min. MH⁺552.

Compound 10. 2-(1-(cyanomethyl)-3-methyl-2,6-dioxo-2,3-dihydro-1H-purin-7(6H)-yl)-N-(6-(2-(trifluoromethyl)pyrimidin-5-yl)pyridin-2-yl)propanamide

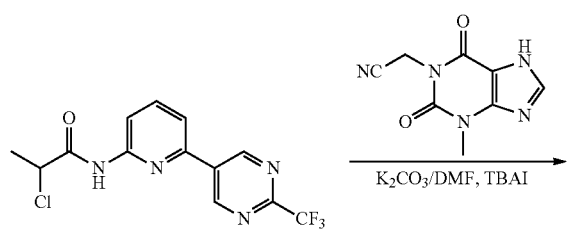

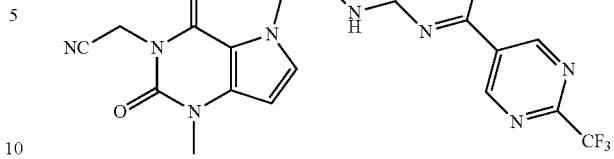

To a solution of 2-(3-methyl-2,6-dioxo-2,3,6,7-tetrahydro-1H-purin-1-yl)acetonitrile (42 mg, 0.20 mmol) in DMF (1 mL) was added 2-chloro-N-(6-(2-(trifluoromethyl)pyrimidin-5-yl)pyridin-2-yl)propanamide (7, 80 mg, 0.24 mmol), followed by potassium carbonate (56 mg, 0.40 mmol) and TBAI (8 mg, 0.02 mmol). The mixture was stirred at 50° C. under N₂ overnight. The reaction mixture was quenched by water (20 mL), and then extracted with EA (3×5 mL). The combined organic layers were washed with saturated aqueous LiCl solution and brine, dried over Na₂SO₄ and filtered. The filtrate was concentrated to dryness and purified with preparative HPLC to afford 2-(1-(cyanomethyl)-3-methyl-2,6-dioxo-2,3-dihydro-1H-purin-7(6H)-yl)-N-(6-(2-(trifluoromethyl)pyrimidin-5-yl)pyridin-2-yl)propanamide (6.1 mg, 5% yield) as a white solid. ¹H NMR (400 MHz, DMSO-D6) δ 11.33 (s, 1H), 9.68 (s, 2H), 8.45 (s, 1H), 8.12 (d, J=7.0 Hz, 1H), 8.02 (q, J=7.7 Hz, 2H), 5.81 (s, 1H), 4.85 (s, 2H), 3.49 (s, 3H), 1.89 (d, J=7.2 Hz, 3H). Retention time (LC-MS): 2.289 min. MH⁺500.

Compound 11. (2S)-N-(6-(2-(3-azabicyclo[3.1.0]hexan-3-yl)pyrimidin-5-yl)pyridin-2-yl)-2-(1-(cyanomethyl)-3-methyl-2,6-dioxo-2,3-dihydro-1H-purin-7(6H)-yl)propanamide

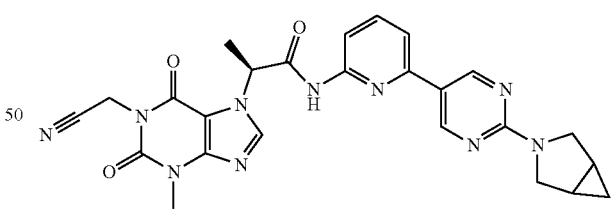

This compound was prepared using the method described for compound 1 with appropriate starting materials. ¹H NMR (400 MHz, DMSO-D6) δ 11.05 (s, 1H), 9.00 (s, 2H), 8.43 (s, 1H), 7.83 (dd, J=18.9, 11.2 Hz, 2H), 7.61 (d, J=8.2 Hz, 1H), 5.76 (s, 1H), 4.84 (s, 2H), 3.85 (d, J=11.2 Hz, 2H), 3.55 (d, J=11.2 Hz, 2H), 3.49 (s, 3H), 1.87 (d, J=7.3 Hz, 3H), 1.70 (s, 2H), 0.78 (s, 1H), 0.18 (s, 1H).Retention time (LC-MS): 3.161min. MH⁺513.

Compound 12. (2S)-N-(6-(2-(3-azabicyclo[3.1.0]hexan-3-yl)pyrimidin-5-yl)pyrazin-2-yl)-2-(1-(cyanomethyl)-3-methyl-2,6-dioxo-2,3-dihydro-1H-purin-7(6H)-yl)propanamide

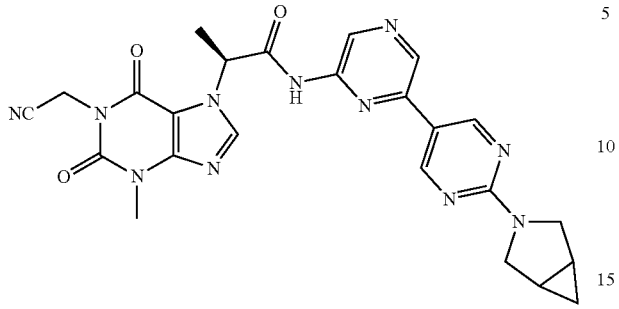

This compound was prepared using the method described for compound 1 with appropriate starting materials. $^1$H NMR (400 MHz, DMSO-D6) δ 11.40 (s, 1H), 9.11 (s, 1H), 9.04 (s, 2H), 8.91 (s, 1H), 8.44 (s, 1H), 5.82 (s, 1H), 4.84 (s, 2H), 3.86 (d, J=11.4 Hz, 2H), 3.56 (d, J=11.5 Hz, 2H), 3.49 (s, 3H), 1.89 (d, J=7.2 Hz, 3H), 1.70 (s, 2H), 0.78 (d, J=4.6 Hz, 1H), 0.17 (d, J=4.3 Hz, 1H). Retention time (LC-MS): 2.074 min. MH+514.

Compound 13. (2S)-N-(6-(2-(3-azabicyclo[3.1.0]hexan-3-yl)pyrimidin-5-yl)pyrazin-2-yl)-2-(3-methyl-2,6-dioxo-1-(2-oxobutyl)-2,3-dihydro-1H-purin-7(6H)-yl)propanamide

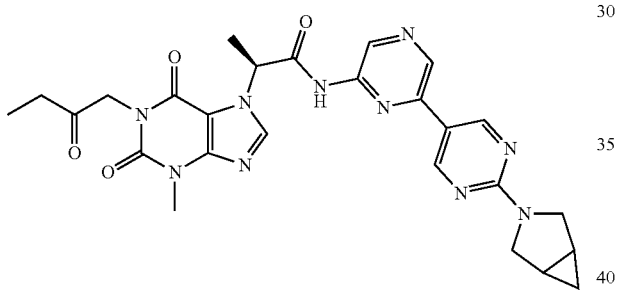

This cCompound was prepared using the method described-for Compound 2 with appropriate starting materials. $^1$H NMR (400 MHz, DMSO-D6) δ 11.33 (s, 1H), 9.09 (s, 1H), 9.02 (s, 2H), 8.90 (s, 1H), 8.40 (s, 1H), 5.80 (s, 1H), 4.69 (d, J=2.1 Hz, 2H), 3.85 (d, J=11.4 Hz, 2H), 3.56 (d, J=10.9 Hz, 2H), 3.46 (s, 3H), 2.54 (d, J=7.3 Hz, 2H), 1.88 (d, J=7.3 Hz, 3H), 1.73-1.67 (m, 2H), 0.93 (t, J=7.3 Hz, 3H), 0.77 (d, J=4.7 Hz, 1H), 0.16 (d, J=4.3 Hz, 1H). Retention time (LC-MS): 2.24min. MH+545.

Compound 14. ((2S)-N-(2-(2-(3-azabicyclo[3.1.0]hexan-3-yl)pyrimid in-5-yl)thiazol-4-yl)-2-(3-methyl-2,6-dioxo-1-(2-oxobutyl)-2,3-dihydro-1H-purin-7(6H)-yl)propanamide

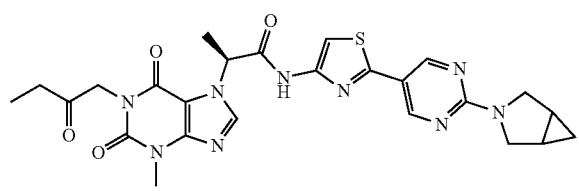 [SMILES: CCC(=O)Cn1c(=O)c2c(ncn2[C@@H](C)C(=O)Nc2csc(-c3cnc(N4CC5CC5C4)nc3)n2)n(C)c1=O]

This compound was prepared using the method described for compound 1 with appropriate starting materials and was purified with preparative TLC. $^1$H NMR (400 MHz, DMSO-D6) δ 11.58 (s, 1H), 8.80 (s, 2H), 8.37 (s, 1H), 7.46 (s, 1H), 5.70 (d, J=7.3 Hz, 1H), 4.69 (d, J=2.4 Hz, 2H), 3.83 (d, J=11.4 Hz, 2H), 3.55 (d, J=11.3 Hz, 2H), 3.45 (s, 3H), 2.57-2.51 (m, 2H), 1.83 (d, J=7.3 Hz, 3H), 1.73-1.67 (m, 2H), 0.94 (t, J=7.3 Hz, 3H), 0.77 (d, J=4.8 Hz, 1H), 0.16 (d, J=4.2 Hz, 1H). Retention time (LC-MS): 2.41min. MH+550.

Compound 15. (S)-2-(3-methyl-1-((5-methylisoxazol-3-yl)methyl)-2,6-dioxo-2,3-dihydro-1H-purin-7(6H)-yl)-N-(6-(2-(trifluoromethyl)pyrimidin-5-yl)pyridin-2-yl)propanamide

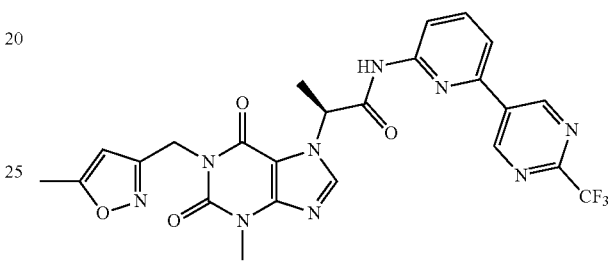

This compound was prepared using the method described for compound 1 with appropriate starting materials. 1H NMR (400 MHz, DMSO-D6) δ 11.28 (s, 1H), 9.67 (s, 2H), 8.41 (s, 1H), 8.12 (d, J=7.6 Hz, 1H), 8.07-7.80 (m, 2H), 6.09 (s, 1H), 5.83 (d, J=6.7 Hz, 1H), 5.02 (s, 2H), 3.48 (s, 3H), 2.30 (s, 3H), 1.88 (d, J=7.3 Hz, 3H). Retention time (LC-MS): 2.523 min. MH+555.

Compound 16. (S)-2-(3-methyl-2,6-dioxo-1-(2-oxopropyl)-2,3-dihydro-1H-purin-7(6H)-yl)-N-(2-(2-((S)-2-(trifluoromethyl)pyrrolidin-1-yl)pyrimidin-5-yl)thiazol-4-yl)propanamide

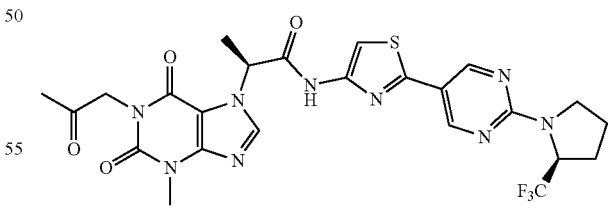

This compound was prepared using the method described for Compound 1 with appropriate starting materials. $^1$H NMR (400 MHz, DMSO-D6) δ 11.64 (s, 1H), 8.94 (s, 2H), 8.41 (d, J=14.0 Hz, 1H), 7.54 (s, 1H), 5.71 (q, J=7.2 Hz, 1H), 5.10 (p, J=7.8 Hz, 1H), 4.76-4.63 (m, 2H), 3.78-3.62 (m, 2H), 3.46 (s, 3H), 2.21 (d, J=9.0 Hz, 1H), 2.17 (s, 4H), 2.09 (d, J=14.0 Hz, 2H), 1.84 (d, J=7.3 Hz, 3H). Retention time (LC-MS): 2.570 min. MH+592.

Compound 17. N-(2'-(3-azabicyclo[3.1.0]hexan-3-yl)-2,5'-bipyrimidin-4-yl)-2-(3-methyl-2,6-dioxo-1-(2-oxobutyl)-2,3-dihydro-1H-purin-7(6H)-yl)propanamide

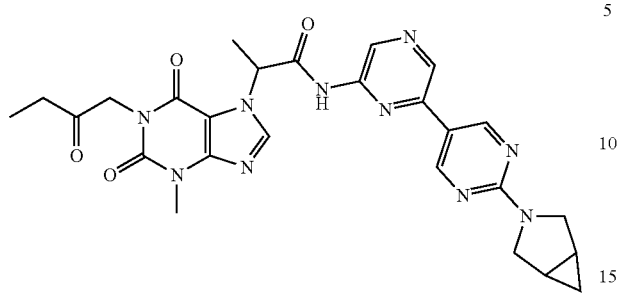

This compound was prepared using the method described for compound 10 with appropriate starting materials and was purified with preparative TLC. $^1$H NMR (400 MHz, DMSO-D6) δ 11.41 (s, 1H), 9.15 (s, 2H), 8.67 (d, J=6 Hz, 2H), 8.40 (s, 1H), 7.79 (d, J=5.6 Hz, 1H), 5.78 (d, J=7.2 Hz, 1H), 4.69 (d, J=2.4 Hz, 2H), 3.86 (d, J=11.2 Hz, 2H), 3.57 (d, J=11.2 Hz, 2H), 3.33 (s, 3H), 2.55-2.49 (m, 2H), 1.87 (d, J=7.2 Hz, 3H), 1.70 (t, J=3.6 Hz, 2H), 0.93 (t, J=7.2 Hz, 3H), 0.77 (d, J=4.8 Hz, 1H), 0.17 (q, J=4.0 Hz, 1H). Retention time (LC-MS): 2.246 min. MH$^+$545.

Compound 18. (S)-2-(3-methyl-2,6-dioxo-1-(2-oxobutyl)-2,3-dihydro-1H-purin-7(6H)-yl)-N-(2-(2-((S)-2-(trifluoromethyl)pyrrolidin-1-yl)pyrimidin-5-yl)thiazol-4-yl)propanamide

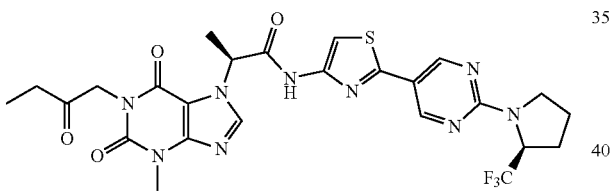

This compound was prepared using the method described for compound 2 with appropriate starting materials. $^1$H NMR (400 MHz, DMSO-D6) δ 11.65 (s, 1H), 8.94 (s, 2H), 8.41 (d, J=11.7 Hz, 1H), 7.54 (s, 1H), 5.72 (d, J=7.3 Hz, 1H), 5.21-5.00 (m, 1H), 4.69 (d, J=2.4 Hz, 2H), 3.71 (t, J=6.6 Hz, 2H), 3.46 (s, 3H), 2.58-2.52 (m, 2H), 2.28-2.01 (m, 4H), 1.84 (d, J=7.3 Hz, 3H), 0.94 (t, J=7.3 Hz, 3H). Retention time (LC-MS): 2.675 min. MH$^+$605.

Compound 19. (S)-N-(2-(3,4-dichlorophenyl)thiazol-4-yl)-2-(3-methyl-2,6-dioxo-1-(2-oxobutyl)-2,3-dihydro-1H-purin-7(6H)-yl)propanamide

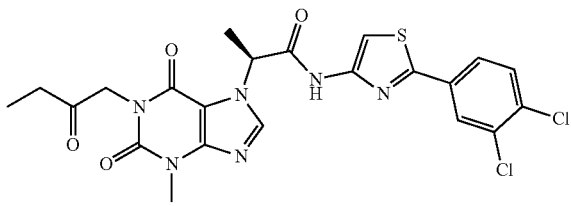 [SMILES: CCC(=O)Cn1c(=O)c2c(ncn2[C@@H](C)C(=O)Nc2csc(-c3ccc(Cl)c(Cl)c3)n2)n(C)c1=O]

This compound was prepared using the method described for compound 2 with appropriate starting materials. $^1$H NMR (400 MHz, DMSO-D6) δ 11.65 (s, 1H), 8.39 (s, 1H), 8.13 (d, J=1.9 Hz, 1H), 7.89 (dd, J=8.4, 2.0 Hz, 1H), 7.79 (d, J=8.4 Hz, 1H), 7.66 (s, 1H), 5.71 (q, J=7.3 Hz, 1H), 4.78-4.60 (m, 2H), 3.46 (s, 3H), 2.59-2.52 (m, 2H), 1.85 (d, J=7.3 Hz, 3H), 0.94 (t, J=7.3 Hz, 3H). Retention time (LC-MS): 2.869 min. MH$^+$534.

Compound 20. (S)-N-(2-(3,4-dichlorophenyl)thiazol-4-yl)-2-(3-methyl-2,6-dioxo-1-(2-oxopropyl)-2,3-dihydro-1H-purin-7(6H)-yl)propanamide

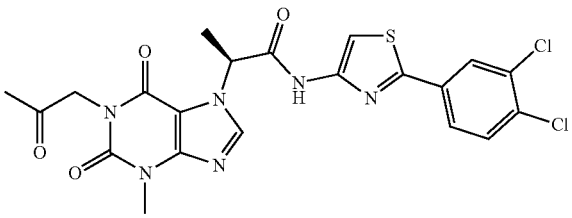 [SMILES: CC(=O)Cn1c(=O)c2c(ncn2[C@@H](C)C(=O)Nc2csc(-c3ccc(Cl)c(Cl)c3)n2)n(C)c1=O]

This compound was prepared using the method described for compound 2 with appropriate starting materials. $^1$H NMR (400 MHz, DMSO-D6) δ 11.65 (s, 1H), 8.39 (s, 1H), 8.13 (d, J=2.1 Hz, 1H), 7.89 (dd, J=8.4, 2.1 Hz, 1H), 7.79 (d, J=8.4 Hz, 1H), 7.66 (s, 1H), 5.71 (q, J=7.2 Hz, 1H), 4.70 (d, J=1.3 Hz, 2H), 3.46 (s, 3H), 2.17 (s, 3H), 1.85 (d, J=7.3 Hz, 3H). Retention time (LC-MS): 2.750 min. MH$^+$521.

Compound 21. Preparation of (S)-2-(3-methyl-1-((5-methylisoxazol-3-yl)methyl)-2,6-dioxo-2,3-dihydro-1H-purin-7(6H)-yl)-N-(6-(2-(trifluoromethyl)pyrimidin-5-yl)pyrazin-2-yl)propanamide

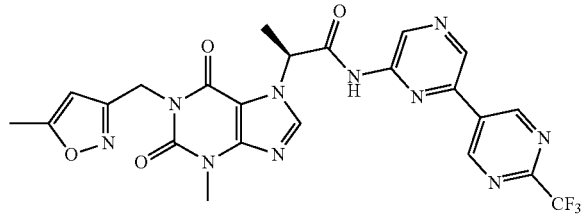 [SMILES: Cc1cc(Cn2c(=O)c3c(ncn3[C@@H](C)C(=O)Nc3cncc(-c4cnc(C(F)(F)F)nc4)n3)n(C)c2=O)no1]

This compound was prepared using the method described for compound 1 with appropriate starting materials. $^1$H NMR (400 MHz, DMSO-D6) δ 11.65 (s, 1H), 9.70 (s, 2H), 9.35 (s, 1H), 9.23 (s, 1H), 8.43 (s, 1H), 6.09 (s, 1H), 5.84 (d, J=7.0 Hz, 1H), 5.02 (s, 2H), 3.48 (s, 3H), 2.32 (d, J=12.0 Hz, 3H), 1.90 (d, J=7.3 Hz, 3H). Retention time (LC-MS): 2.241 min. MH$^+$557.

Compound 22. (S)-2-(1-(cyanomethyl)-3-methyl-2,6-dioxo-2,3-dihydro-1H-purin-7(6H)-yl)-N-(6-(2-(trifluoromethyl)pyrimidin-5-yl)pyrazin-2-yl)propanamide

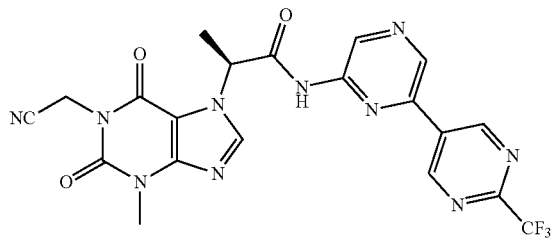 [SMILES: C[C@@H](C(=O)Nc1cncc(-c2cnc(C(F)(F)F)nc2)n1)n1cnc2c1c(=O)n(CC#N)c(=O)n2C]

This compound was prepared using the method described for compound 2 with appropriate starting materials. ¹H NMR (400 MHz, DMSO-D6) δ 11.76 (s, 1H), 9.78 (s, 2H), 9.42 (s, 1H), 9.29 (s, 1H), 8.52 (s, 1H), 5.89 (d, J=7.1 Hz, 1H), 4.91 (s, 2H), 3.55 (s, 3H), 1.98 (d,J=7.3 Hz, 3H). Retention time (LC-MS): 2.091 min. MH⁺501.

Compound 23. (S)-2-(1,3-dimethyl-2,6-dioxo-2,3-dihydro-1H-purin-7(6H)-yl)-N-(6-(4-(trifluoromethyl)phenyl)pyridin-2-yl)propanamide

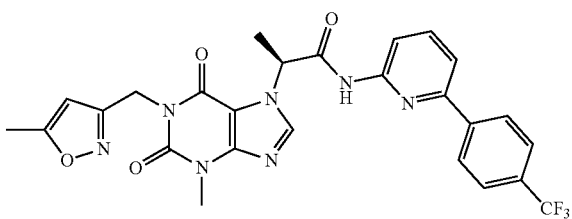

This compound was prepared using the method described for compound 2 with appropriate starting materials. ¹H NMR (400 MHz, DMSO-D6) δ 11.18 (s, 1H), 11.18 (s, 1H), 8.41 (s, 1H), 8.41 (s, 1H), 8.32 (d, J=8.3 Hz, 2H), 8.32 (d, J=8.3 Hz, 2H), 8.01 (s, 1H), 8.01 (s, 1H), 7.94 (t, J=7.9 Hz, 1H), 7.99-7.79 (m, 4H), 7.89 (d, J=8.3 Hz, 2H), 7.83 (d, J=7.6 Hz, 1H), 6.09 (s, 1H), 6.09 (s, 1H), 5.82 (s, 1H), 5.82 (s, 1H), 5.02 (s, 2H), 5.02 (s, 2H), 3.47 (s, 3H), 3.47 (s, 3H), 3.34 (s, 33H), 2.54-2.46 (m, 27H), 2.30 (s, 3H), 2.30 (s, 3H), 1.87 (d, J=7.3 Hz, 3H), 1.87 (d, J=7.3 Hz, 3H), -0.00 (s, 6H). Retention time (LC-MS): 2.718 min. MH⁺554.

Compound 24. N-(2'-(3-azabicyclo[3.1.0]hexan-3-yl)-2,5'-bipyrimidin-4-yl)-2-(1-(cyanomethyl)-3-methyl-2,6-dioxo-2,3-dihydro-1H-purin-7(6H)-yl)propanamide

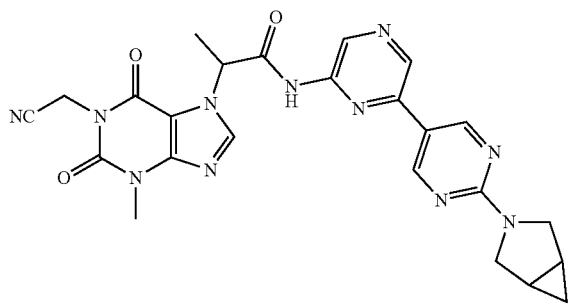 [SMILES: CC(C(=O)Nc1cncc(-c2cnc(N3CC4CC4C3)nc2)n1)n1cnc2c1c(=O)n(CC#N)c(=O)n2C]

This compound was prepared using the method described for compound 10 with appropriate starting materials. ¹H NMR (400 MHz, DMSO-D6) δ 11.46 (s, 1H), 9.14 (s, 2H), 8.66 (d, J=5.7 Hz, 1H), 8.41 (s, 1H), 7.78 (d, J=5.6 Hz, 1H), 5.77 (s, 1H), 4.82 (s, 2H), 3.85 (d, J=11.5 Hz, 2H), 3.56 (d, J=11.3 Hz, 2H), 3.46 (s, 3H), 1.86 (d, J=7.3 Hz, 3H), 1.68 (s, 2H), 0.76 (s, 1H), 0.16 (d, J=4.2 Hz, 1H). Retention time (LC-MS): 2.147 min. MH⁺514.

Compound 25. (2S)-N-(6-(2-(6,6-difluoro-3-azabicyclo 13.1.01hexan-3-yl)pyrimidin-5-yl)pyridin-2-yl)-2-(3-methyl-2,6-dioxo-1-(2-oxopropyl)-2,3-dihydro-1H-purin-7(6H)-yl)propanamide

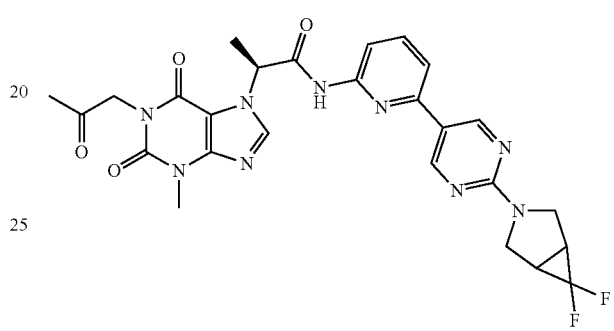

This compound was prepared using the method described for compound 2 with appropriate starting materials. ¹H NMR (400 MHz, DMSO-D6) δ 11.02 (s, 1H), 9.03 (s, 2H), 8.40 (s, 1H), 7.89 (d, J=7.7 Hz, 1H), 7.83 (t, J=7.9 Hz, 1H), 7.63 (d, J=8.0 Hz, 1H), 5.79 (s, 1H), 4.75-4.64 (m, 2H), 3.99 (d, J=11.9 Hz, 2H), 3.84 (d, J=10.5 Hz, 2H), 3.46 (s, 3H), 2.70 (d, J=10.8 Hz, 2H), 2.16 (s, 3H), 1.86 (d, J=7.3 Hz, 3H). Retention time (LC-MS): 2.311 min. MH⁺566.

Compound 26. (2S)-N-(6-(2-(6,6-difluoro-3-azabicyclo[3.1.0]hexan-3-yl)pyrimidin-5-yl)pyridin-2-yl)-2-(3-methyl-2,6-dioxo-1-(2-oxobutyl)-2,3-dihydro-1H-purin-7(6H)-yl)propanamide

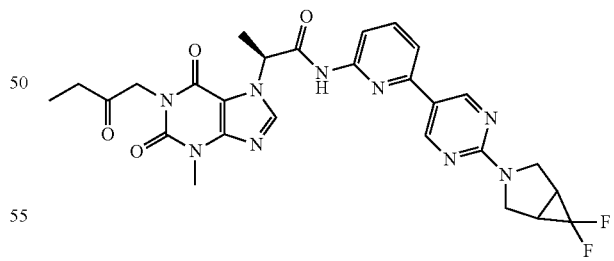

This compound was prepared using the method described for compound 2 with appropriate starting materials. ¹H NMR (400 MHz, DMSO-D6) δ 11.02 (s, 1H), 9.03 (s, 2H), 8.40 (s, 1H), 7.89 (d, J=8.4 Hz, 1H), 7.83 (t, J=7.9 Hz, 1H), 7.63 (d, J=7.6 Hz, 1H), 5.79 (s, 1H), 4.79-4.62 (m, 2H), 3.99 (d, J=11.9 Hz, 2H), 3.84 (d, J=10.7 Hz, 2H), 3.46 (s, 3H), 2.71 (d, J=11.2 Hz, 2H), 2.61-2.51 (m, 2H), 1.86 (d, J=7.2 Hz, 3H), 0.93 (t, J=7.2 Hz, 3H). Retention time (LC-MS): 2.364 min. MH⁺580.

Compound 27. (S)-N-(6-(2-(diethylamino)pyrimidin-5-yl)pyridin-2-yl)-2-(3-methyl-1-((5-methylisoxazol-3-yl)methyl)-2,6-dioxo-2,3-dihydro-1H-purin-7(6H)-yl)propanamide

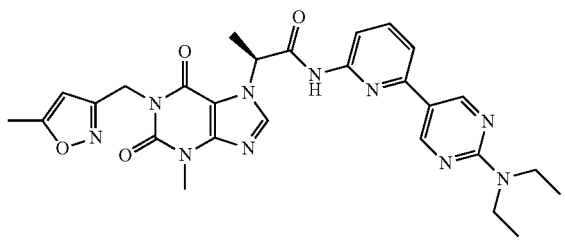 [SMILES: CCN(CC)c1ncc(-c2cccc(NC(=O)[C@H](C)n3cnc4c3c(=O)n(Cc3cc(C)on3)c(=O)n4C)n2)cn1]

This compound was prepared using the method described for compound 1 with appropriate starting materials. ¹H NMR (400 MHz, DMSO-D6) δ 10.99 (s, 1H), 8.97 (s, 2H), 8.37 (s, 1H), 7.85 (d, J=7.4 Hz, 1H), 7.79 (t, J=7.9 Hz, 1H), 7.58 (d, J=7.9 Hz, 1H), 6.06 (s, 1H), 5.77 (d, J=25.7 Hz, 1H), 5.00 (s, 2H), 3.63 (q, J=7.0 Hz, 4H), 3.45 (s, 3H), 2.28 (s, 3H), 1.84 (d, J=7.3 Hz, 3H), 1.13 (t, J=7.0 Hz, 6H). Retention time (LC-MS): 2.563 min. MH⁺559.

Compound 28. (S)-2-(1-(cyanomethyl)-3-methyl-2,6-dioxo-2,3-dihydro-1H-purin-7(6H)-yl)-N-(2-(2-((S)-2-(trifluoromethyl)pyrrolidin-1-yl)pyrimidin-5-yl)thiazol-4-yl)propanamide

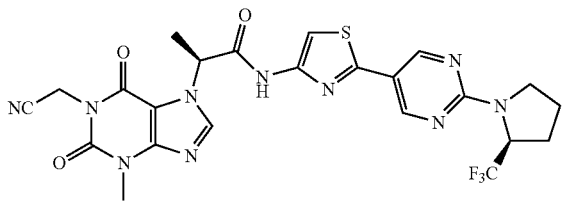 [SMILES: C[C@@H](C(=O)Nc1csc(-c2cnc(N3CCC[C@H]3C(F)(F)F)nc2)n1)n1cnc2c1c(=O)n(CC#N)c(=O)n2C]

This compound was prepared using the method described for compound 2 with appropriate starting materials and was purified via preparative HPLC, 19.7% yield as a light yellow solid. ¹H NMR (400 MHz, DMSO-D6) δ 11.73 (s, 1H), 8.98 (s, 2H), 8.46 (s, 1H), 7.58 (s, 1H), 5.76 (q, J=7.4 Hz, 1H), 5.19-5.08 (m, 1H), 4.88 (s, 2H), 3.73 (dd, J=12.3, 6.6 Hz, 2H), 3.51 (s, 3H), 2.30-2.09 (m, 4H), 1.89 (d, J=7.3 Hz, 3H). Retention time (LC-MS): 2.607 min. MH⁺575.

Compound 29. (S)-2-(1-(cyanomethyl)-3-methyl-2,6-dioxo-2,3-dihydro-1H-purin-7(6H)-yl)-N-(2-(3,4-dichlorophenyl)thiazol-4-yl)propanamide

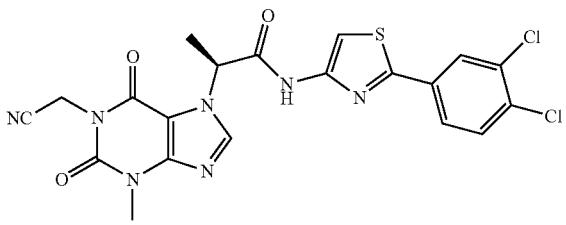 [SMILES: C[C@@H](C(=O)Nc1csc(-c2ccc(Cl)c(Cl)c2)n1)n1cnc2c1c(=O)n(CC#N)c(=O)n2C]

This compound was prepared using the method described for compound 2 with appropriate starting materials and was purified via preparative HPLC to provide a yellow solid (10.5% yield). ¹H NMR (400 MHz, DMSO-D6) δ 11.71 (s, 1H), 8.43 (s, 1H), 8.14 (d, J=2.0 Hz, 1H), 7.90 (dd, J=8.4, 2.1 Hz, 1H), 7.80 (d, J=8.4 Hz, 1H), 7.67 (s, 1H), 5.73 (q, J=7.3 Hz, 1H), 4.85 (s, 2H), 3.49 (s, 3H), 1.86 (d, J=7.3 Hz, 3H). Retention time (LC-MS): 2.819 min. MH⁺504.

Compound 30. (2S)-2-(1-(cyanomethyl)-3-methyl-2,6-dioxo-2,3-dihydro-1H-purin-7(6H)-yl)-N-(6-(2-(6,6-difluoro-3-azabicyclo[3.1.0]hexan-3-yl)pyrimidin-5-yl)pyridin-2-yl)propanamide

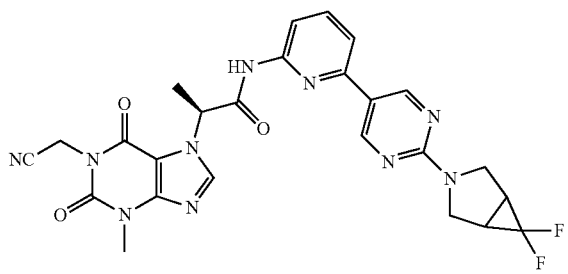 [SMILES: C[C@@H](C(=O)Nc1cccc(-c2cnc(N3CC4C(C3)C4(F)F)nc2)n1)n1cnc2c1c(=O)n(CC#N)c(=O)n2C]

This compound was prepared using the method described for compound 2 with appropriate starting materials to provide a white solid (14% yield). ¹H NMR (400 MHz, DMSO-D6) δ 11.08 (s, 1H), 9.04 (s, 2H), 8.43 (s, 1H), 7.90 (d, J=7.9 Hz, 1H), 7.83 (t, J=7.9 Hz, 1H), 7.64 (d, J=7.9 Hz, 1H), 5.81 (s, 1H), 4.84 (s, 2H), 3.99 (d, J=11.9 Hz, 2H), 3.85 (d, J=10.5 Hz, 2H), 3.48 (s, 3H), 2.70 (d, J=10.6 Hz, 2H), 1.87 (d, J=7.3 Hz, 3H). Retention time (LC-MS): 2.309 min. MH⁺549.

Compound 31. (S)-2-(3-methyl-2,6-dioxo-1-(2-oxopropyl)-2,3-dihydro-1H-purin-7(6H)-yl)-N-(2-(2-(trifluoromethyl)pyrimidin-5-yl)thiazol-4-yl)propanamide

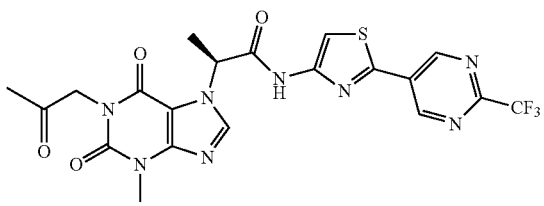 [SMILES: CC(=O)Cn1c(=O)c2c(ncn2[C@@H](C)C(=O)Nc2csc(-c3cnc(C(F)(F)F)nc3)n2)n(C)c1=O]

Thisc was prepared using the method described for compound 2 with appropriate starting materials and purified via preparative HPLC to provide a yellow solid (23.5% yield). ¹H NMR (400 MHz, DMSO-D6) δ 11.84 (s, 1H), 9.53 (s, 2H), 8.40 (s, 1H), 7.86 (s, 1H), 5.72 (d, J=7.4 Hz, 1H), 4.70 (s, 2H), 3.46 (s, 3H), 2.17 (s, 3H), 1.86 (d, J=7.3 Hz, 3H). Retention time (LC-MS): 2.286 min. MH⁺523.

Compound 32. (S)-2-(3-methyl-1-((5-methylisoxazol-3-yl)methyl)-2,6-dioxo-2,3-dihydro-1H-purin-7(6H)-yl)-N-(2-(2-(trifluoromethyl)pyrimidin-5-yl)thiazol-4-yl)propanamide

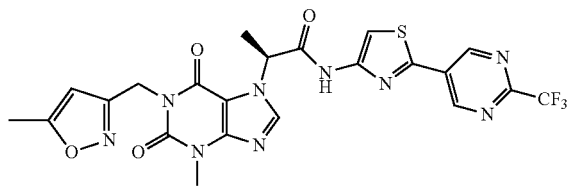 [SMILES: Cc1cc(Cn2c(=O)c3c(ncn3[C@@H](C)C(=O)Nc3csc(-c4cnc(C(F)(F)F)nc4)n3)n(C)c2=O)no1]

This compound was prepared using the method described for compound 1 with appropriate starting materials to provide a white solid (29.8% yield). ¹H NMR (400 MHz, DMSO-D6) δ 11.86 (s, 1H), 9.53 (s, 2H), 8.41 (s, 1H), 7.87 (s, 1H), 6.09 (s, 1H), 5.75-5.77 (m, 1H), 5.02 (s, 2H), 3.47 (s, 3H), 2.31 (s, 3H), 1.86 (d, J=7.2 Hz, 3H). Retention time (LC-MS): 2.241 min. MH⁺562.

Compound 33. (2S)-N-(2-(6-(3-azabicyclo[3.1.0]hexan-3-yl)pyridin-3-yl)thiazol-4-yl)-2-(1-(cyanomethyl)-3-methyl-2,6-dioxo-2,3-dihydro-1H-purin-7(6H)-yl)propanamide

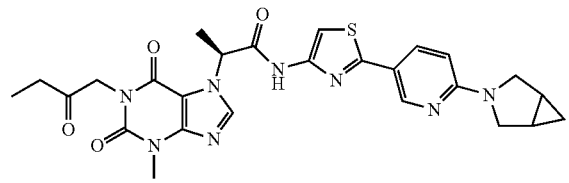 [SMILES: CCC(=O)Cn1c(=O)c2c(ncn2[C@@H](C)C(=O)Nc2csc(-c3ccc(N4CC5CC5C4)nc3)n2)n(C)c1=O]

This compound was prepared using the method described for compound 2 with appropriate starting materials to provide a white solid (5.5% yield). ¹H NMR (400 MHz, DMSO-D6) δ 11.54 (s, 1H), 8.61 (d, J=2.4 Hz, 1H), 8.38 (s, 1H), 7.92 (dd, J=8.8, 2.5 Hz, 1H), 7.40 (s, 1H), 6.56 (d, J=8.7 Hz, 1H), 5.70 (d, J=7.4 Hz, 1H), 4.70 (d, J=2.6 Hz, 2H), 3.70 (d, J=10.4 Hz, 2H), 3.46 (s, 3H), 2.05-1.95 (m, 2H), 1.84 (d, J=7.3 Hz, 3H), 1.72 (s, 2H), 0.94 (t, J=7.3 Hz, 3H), 0.81 (dd, J=30.4, 5.8 Hz, 3H), 0.18 (d, J=4.1 Hz, 1H). Retention time (LC-MS): 2.045 min. MH⁺549.

Compound 34. (2S)-N-(2-(2-(3-azabicyclo[3.1.0]hexan-3-yl)pyrimidin-5-yl)thiazol-4-yl)-2-(1-(cyanomethyl)-3-methyl-2,6-dioxo-2,3-dihydro-1H-purin-7(6H)-yl)propanamide

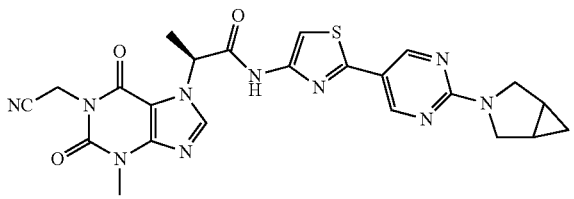 [SMILES: C[C@@H](C(=O)Nc1csc(-c2cnc(N3CC4CC4C3)nc2)n1)n1cnc2c1c(=O)n(CC#N)c(=O)n2C]

This compound was prepared using the method described for compound 1 with appropriate starting materials as a white solid. ¹H NMR (400 MHz, DMSO-D6) δ 11.67 (s, 1H), 8.81 (s, 2H), 8.42 (s, 1H), 7.47 (s, 1H), 5.72 (d, J=7.2 Hz, 1H), 4.84 (s, 2H), 3.84 (d, J=11.4 Hz, 2H), 3.55 (d, J=11.0 Hz, 2H), 3.48 (s, 3H), 1.84 (d, J=7.2 Hz, 3H), 1.70 (s, 2H), 0.77 (d, J=4.6 Hz, 1H), 0.17 (d, J=4.0 Hz, 1H). Retention time (LC-MS): 2.249 min. MH⁺519.

Compound 35. (2S)-N-(6'-(3-azabicyclo[3.1.0]hexan-3-yl)-2,3'-bipyridin-6-yl)-2-(1-(cyanomethyl)-3-methyl-2,6-dioxo-2,3-dihydro-1H-purin-7(6H)-yl)

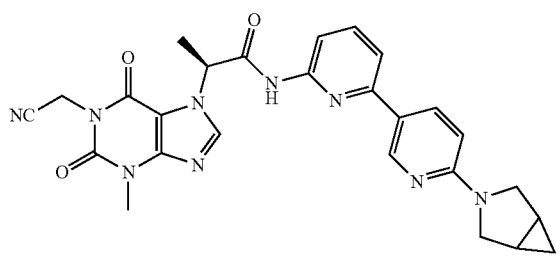 [SMILES: C[C@@H](C(=O)Nc1cccc(-c2ccc(N3CC4CC4C3)nc2)n1)n1cnc2c1c(=O)n(CC#N)c(=O)n2C]

This compound was prepared using the method described for Compound 1 with appropriate starting materials in 36.5% yield as a white solid. ¹H NMR (400 MHz, DMSO-D6) δ 11.01 (s, 1H), 8.80 (d, J=2.2 Hz, 1H), 8.43 (s, 1H), 8.18 (dd, J=8.9, 2.4 Hz, 1H), 7.83 (d, J=8.2 Hz, 1H), 7.77 (t, J=7.9 Hz, 1H), 7.58 (d, J=8.1 Hz, 1H), 6.57 (d, J=8.9 Hz, 1H), 5.81 (d, J=6.8 Hz, 1H), 4.85 (s, 2H), 3.72 (d, J=10.4 Hz, 2H), 3.49 (s, 3H), 3.44 (d, J=10.0 Hz, 2H), 1.87 (d, J=7.3 Hz, 3H), 1.74-1.68 (m, 2H), 0.76 (dd, J=12.2, 7.7 Hz, 1H), 0.24-0.17 (m, 1H). Retention time (LC-MS): 1.400 min. MH⁺512.

Compound 36. (S)-N-(2-(2-(diethylamino)pyrimidin-5-yl)thiazol-4-yl)-2-(3-methyl-1-((5-methylisoxazol-3-yl)methyl)-2,6-dioxo-2,3-dihydro-1H-purin-7(6H)-yl)propanamide

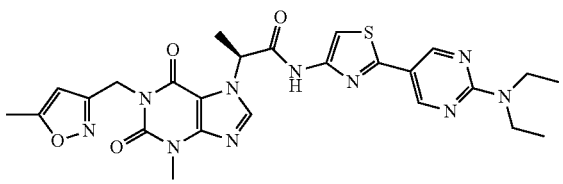 [SMILES: CCN(CC)c1ncc(-c2nc(NC(=O)[C@H](C)n3cnc4c3c(=O)n(Cc3cc(C)on3)c(=O)n4C)cs2)cn1]

This compound was prepared using the method described for Compound 1 with appropriate starting materials ¹H NMR (400 MHz, DMSO-D6) δ 11.73 (s, 1H), 8.93 (s, 2H), 8.50 (s, 1H), 7.58 (s, 1H), 6.20 (s, 1H), 5.86 (q, J=7.1 Hz, 1H), 5.13 (s, 2H), 3.76 (q, J=7.0 Hz, 4H), 3.58 (s, 3H), 2.43 (s, 3H), 1.95 (d, J=7.3 Hz, 3H), 1.27 (t, J=7.0 Hz, 6H). Retention time (LC-MS): 2.641 min. MH⁺565.

Compound 37. (2S)-N-(6'-(3-azabicyclo[3.1.0]hexan-3-yl)-2,3'-bipyridin-6-yl)-2-(3-methyl-2,6-dioxo-1-(2-oxobutyl)-2,3-dihydro-1H-purin-7(6H)-yl)propanamide

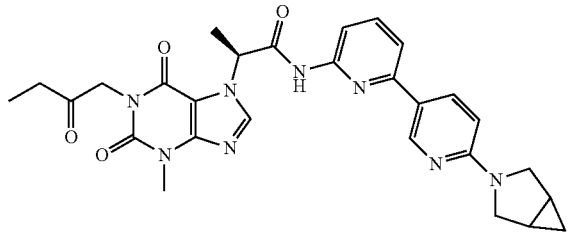 [SMILES: CCC(=O)Cn1c(=O)c2c(ncn2[C@@H](C)C(=O)Nc2cccc(-c3ccc(N4CC5CC5C4)nc3)n2)n(C)c1=O]

This compound was prepared using the method described for Compound 2 with appropriate starting materials in 44.6% yield as a white solid. $^1$H NMR (400 MHz, DMSO-D6) δ 10.96 (s, 1H), 8.79 (d, J=2.2 Hz, 1H), 8.40 (s, 1H), 8.16 (s, 1H), 7.82 (d, J=7.7 Hz, 1H), 7.77 (t, J=7.9 Hz, 1H), 7.58 (d, J=7.9 Hz, 1H), 6.56 (d, J=8.9 Hz, 1H), 5.78 (d, J=6.7 Hz, 1H), 4.77-4.62 (m, 2H), 3.71 (d, J=10.4 Hz, 2H), 3.46 (s, 3H), 3.42 (s, 2H), 2.57-2.52 (m, 2H), 2.09 (s, 1H), 1.86 (d, J=7.3 Hz, 3H), 1.74-1.67 (m, 2H), 0.93 (t, J=7.3 Hz, 3H), 0.76 (dd, J=12.2, 7.7 Hz, 1H), 0.20 (d, J=4.1 Hz, 1H). Retention time (LC-MS): 1.428 min. MH$^+$543.

Compound 38. (S)-N-(2-(2-(diethylamino)pyrimidin-5-yl)thiazol-4-yl)-2-(3-methyl-2,6-dioxo-1-(2-oxobutyl)-2,3-dihydro-1H-purin-7(6H)-yl)propanamide

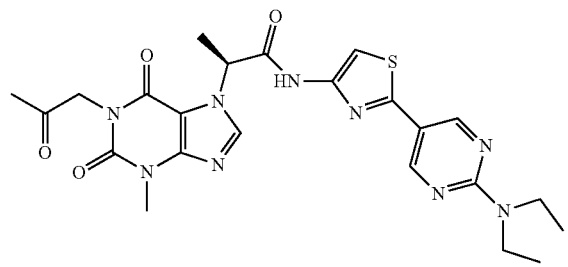 [SMILES: CCN(CC)c1ncc(-c2nc(NC(=O)[C@H](C)n3cnc4c3c(=O)n(CC(C)=O)c(=O)n4C)cs2)cn1]

This compound was prepared using the method described for compound 2 with appropriate starting materials in 28.57% yield as a white solid. $^1$H NMR (400 MHz, DMSO-D6) δ 11.60 (s, 1H), 8.82 (s, 2H), 8.39 (s, 1H), 7.46 (s, 1H), 5.71 (d, J=7.1 Hz, 1H), 4.75-4.63 (m, 2H), 3.65 (d, J=6.9 Hz, 4H), 3.46 (s, 3H), 2.53 (d, J=7.6 Hz, 2H), 1.84 (d, J=7.1 Hz, 3H), 1.15 (t, J=6.8 Hz, 6H), 0.94 (t, J=7.2 Hz, 3H). Retention time (LC-MS): 2.587 min. MH$^+$540.

Compound 39. (S)-2-(1-(cyanomethyl)-3-methyl-2,6-dioxo-2,3-dihydro-1H-purin-7(6H)-yl)-N-(6-(2-((R)-2-(trifluoromethyl)pyrrolidin-1-yl)pyrimidin-5-yl)pyridin-2-yl)propanamide

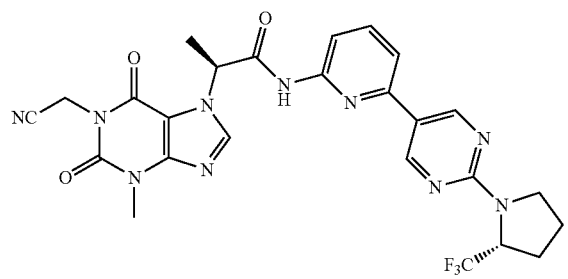 [SMILES: C[C@@H](C(=O)Nc1cccc(-c2cnc(N3CCC[C@@H]3C(F)(F)F)nc2)n1)n1cnc2c1c(=O)n(CC#N)c(=O)n2C]

This compound was prepared using the method described for compound 1 with appropriate starting materials in 10% yield as a white solid. $^1$H NMR (400 MHz, DMSO-D6) δ 11.10 (s, 1H), 9.12 (s, 2H), 8.44 (s, 1H), 7.87 (dd, J=19.5, 11.8 Hz, 2H), 7.69 (d, J=7.6 Hz, 1H), 5.82 (s, 1H), 5.15-5.06 (m, 1H), 4.85 (s, 2H), 3.72 (t, J=6.8 Hz, 2H), 3.49 (s, 3H), 2.23-2.11 (m, 2H), 2.09 (s, 2H), 1.88 (d, J=7.2 Hz, 3H). Retention time (LC-MS): 2.517 min. MH$^+$569.

Compound 40. (S)-2-(1-(cyanomethyl)-3-methyl-2,6-dioxo-2,3-dihydro-1H-purin-7(6H)-yl)-N-(6-(2-((R)-2-(trifluoromethyl)pyrrolidin-1-yl)pyrimidin-5-yl)pyrazin-2-yl)propanamide

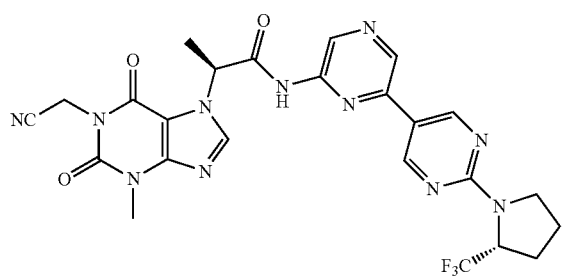 [SMILES: C[C@@H](C(=O)Nc1cncc(-c2cnc(N3CCC[C@@H]3C(F)(F)F)nc2)n1)n1cnc2c1c(=O)n(CC#N)c(=O)n2C]

This compound was prepared using the method described for compound 1 with appropriate starting materials in 12% yield as a white solid. $^1$H NMR (400 MHz, DMSO-D6) δ 11.45 (s, 1H), 9.17 (s, 1H), 9.15 (s, 2H), 8.98 (s, 1H), 8.45 (s, 1H), 5.82 (d, J=7.5 Hz, 1H), 5.18-5.08 (m, 1H), 4.85 (s, 2H), 3.72 (dd, J=13.6, 6.9 Hz, 2H), 3.49 (s, 3H), 2.18 (dd, J=32.5, 12.2 Hz, 2H), 2.08 (s, 2H), 1.90 (d, J=7.3 Hz, 3H). Retention time (LC-MS): 3.073 min. MH$^+$570.

Compound 41. (2S)-N-(6-(6-(3-azabicyclo[3.1.0]hexan-3-yl)pyridin-3-yl)pyrazin-2-yl)-2-(3-methyl-2,6-dioxo-1-(2-oxopropyl)-2,3-dihydro-1H-purin-7(6H)-yl)propanamide

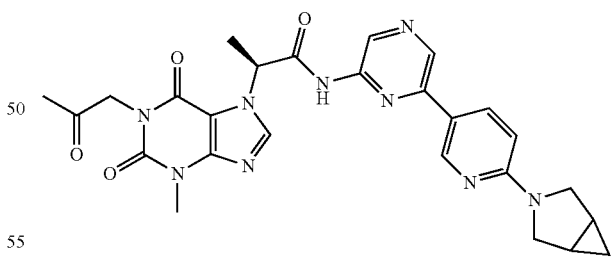

This compound was prepared using the method described for compound 2 with appropriate starting materials in 32% yield as a white solid. $^1$H NMR (400 MHz, DMSO-D6) δ 11.29 (s, 1H), 9.04 (s, 1H), 8.89 (s, 1H), 8.85 (d, J=2.3 Hz, 1H), 8.41 (s, 1H), 8.19 (dd, J=8.9, 2.4 Hz, 1H), 6.61 (d, J=9.0 Hz, 1H), 5.79 (s, 1H), 4.70 (s, 2H), 3.73 (d, J=10.4 Hz, 2H), 3.46 (s, 3H), 3.45 (s, 2H), 2.16 (s, 3H), 1.88 (d, J=7.3 Hz, 3H), 1.74-1.69 (m, 2H), 0.77 (d, J=4.6 Hz, 1H), 0.19 (d, J=4.2 Hz, 1H). Retention time (LC-MS): 2.460 min. MH$^+$530.

Compound 42. (2S)-N-(6-(6-(3-azabicyclo[3.1.0]hexan-3-yl)pyridin-3-yl)pyrazin-2-yl)-2-(3-methyl-2,6-dioxo-1-(2-oxobutyl)-2,3-dihydro-1H-purin-7(6H)-yl)propanamide

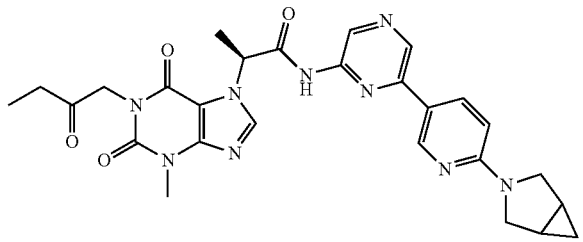 [SMILES: CCC(=O)Cn1c(=O)c2c(ncn2[C@@H](C)C(=O)Nc2cncc(-c3ccc(N4CC5CC5C4)nc3)n2)n(C)c1=O]

This compound was prepared using the method described for compound 2 with appropriate starting materials in 23.9% yield. Retention time (LC-MS): 2.581 min. MH+544. $^1$H NMR (400 MHz, DMSO-D6) δ 11.28 (s, 1H), 9.04 (s, 1H), 8.89 (s, 1H), 8.85 (d, J=2.2 Hz, 1H), 8.41 (s, 1H), 8.19 (dd, J=8.9, 2.4 Hz, 1H), 6.60 (d, J=9.0 Hz, 1H), 5.79 (d, J=6.8 Hz, 1H), 4.70 (t, J=4.1 Hz, 2H), 3.73 (d, J=10.5 Hz, 2H), 3.46 (s, 3H), 3.45 (s, 2H), 2.55 (d, J=7.3 Hz, 2H), 1.88 (d, J=7.3 Hz, 3H), 1.74-1.70 (m, 2H), 0.93 (t, J=7.3 Hz, 3H), 0.77 (dd, J=12.3, 7.8 Hz, 1H), 0.19 (d, J=4.2 Hz, 1H).

Compound 43. (2S)-N-(6-(6-(3-azabicyclo[3.1.0]hexan-3-yl)pyridin-3-yl)pyrazin-2-yl)-2-(1-(cyanomethyl)-3-methyl-2,6-dioxo-2,3-dihydro-1H-purin-7(6H)-yl)propanamide

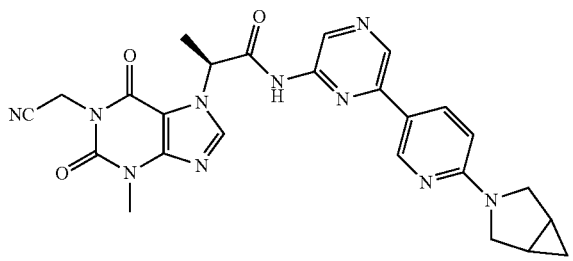 [SMILES: C[C@@H](C(=O)Nc1cncc(-c2ccc(N3CC4CC4C3)nc2)n1)n1cnc2c1c(=O)n(CC#N)c(=O)n2C]

This compound was prepared using the method described for compound 1 with appropriate starting materials in 24.7% yield as a white solid. $^1$H NMR (400 MHz, DMSO-D6) δ 11.35 (s, 1H), 9.06 (s, 1H), 8.90 (s, 1H), 8.86 (d, J=2.3 Hz, 1H), 8.45 (s, 1H), 8.20 (dd, J=8.9, 2.4 Hz, 1H), 6.61 (d, J=9.0 Hz, 1H), 5.83 (s, 1H), 4.85 (s, 2H), 3.73 (d, J=10.5 Hz, 2H), 3.49 (s, 3H), 3.45 (s, 2H), 1.89 (d, J=7.3 Hz, 3H), 1.72 (s, 2H), 0.77 (d, J=4.6 Hz, 1H), 0.20 (d, J=4.1 Hz, 1H). Retention time (LC-MS): 2.528 min. MH+513.

Compound 44. (2S)-N-(6'-(3-azabicyclo[3.1.0]hexan-3-yl)-2,3'-bipyridin-6-yl)-2-(3-methyl-2,6-dioxo-1-(2-oxopropyl)-2,3-dihydro-1H-purin-7(6H)-yl)propanamide

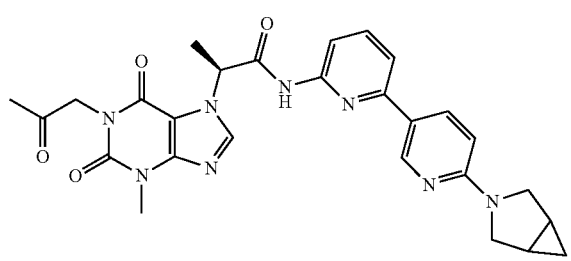 [SMILES: CC(=O)Cn1c(=O)c2c(ncn2[C@@H](C)C(=O)Nc2cccc(-c3ccc(N4CC5CC5C4)nc3)n2)n(C)c1=O]

This compound was prepared using the method described for compound 2 with appropriate starting materials in 36.5% yield as a white solid. $^1$H NMR (400 MHz, DMSO-D6) δ 10.95 (s, 1H), 8.78 (d, J=2.2 Hz, 1H), 8.39 (s, 1H), 8.17 (dd, J=8.9, 2.4 Hz, 1H), 7.82 (d, J=8.1 Hz, 1H), 7.76 (t, J=7.8 Hz, 1H), 7.57 (d, J=8.0 Hz, 1H), 6.56 (d, J=8.9 Hz, 1H), 5.77 (d, J=8.1 Hz, 1H), 4.76-4.63 (m, 2H), 3.71 (d, J=10.3 Hz, 2H), 3.45 (s, 3H), 3.41 (s, 2H), 2.16 (s, 3H), 1.86 (d, J=7.2 Hz, 3H), 1.74-1.65 (m, 2H), 0.76 (dd, J=12.3, 7.7 Hz, 1H), 0.19 (d, J=4.1 Hz, 1H). Retention time (LC-MS): 2.556 min. MH+529.

Compound 45. (S)-2-(1-(cyanomethyl)-3-methyl-2,6-dioxo-2,3-dihydro-1H-purin-7(6H)-yl)-N-(6-(2-((S)-2-(trifluoromethyl)pyrrolidin-1-yl)pyrimidin-5-yl)pyridin-2-yl)propanamide

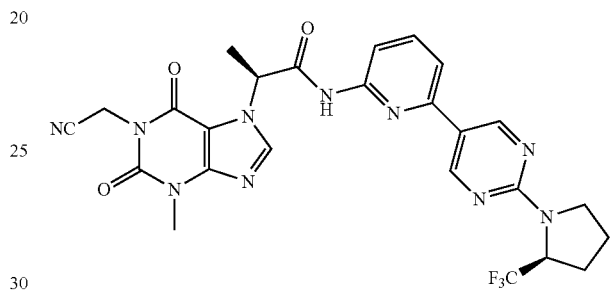

This compound was prepared using the method described for compound 1 with appropriate starting materials in 6.5% yield as a white solid. $^1$H NMR (400 MHz, DMSO-D6) δ 11.09 (s, 1H), 9.12 (s, 2H), 8.44 (s, 1H), 7.83-7.93 (m, 2H), 7.68 (d, J=7.2 Hz, 1H), 5.79-5.82 (m, 1H), 5.11 (t, J=8.8 Hz, 1H), 4.85 (s, 2H), 3.68-3.74 (m, 2H), 3.49 (s, 3H), 2.09-2.32 (m, 4H), 1.87 (d, J=7.6 Hz, 3H). Retention time (LC-MS): 2.341 min. MH+569.

Compound 46. (2S)-N-(2-(6-(3-azabicyclo[3.1.0]hexan-3-yl)pyridin-3-yl)pyrimidin-4-yl)-2-(3-methyl-2,6-dioxo-1-(2-oxopropyl)-2,3-dihydro-1H-purin-7(6H)-yl)propanamide

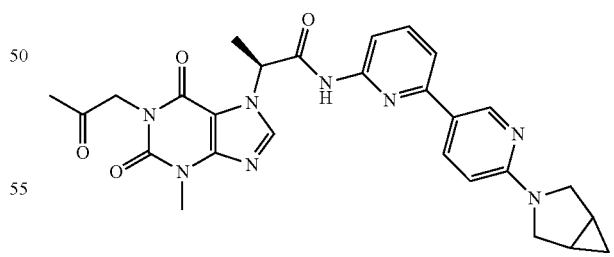

This compound was prepared using the method described for compound 2 with appropriate starting materials in 9.5% yield as a yellow solid. $^1$H NMR (400 MHz, DMSO-D6) δ 11.36 (s, 1H), 9.04 (d, J=2.2 Hz, 1H), 8.65 (d, J=5.7 Hz, 1H), 8.40 (s, 1H), 8.35 (dd, J=8.9, 2.3 Hz, 1H), 7.73 (d, J=5.6 Hz, 1H), 6.58 (d, J=9.0 Hz, 1H), 5.78 (d, J=6.9 Hz, 1H), 4.76-4.52 (m, 2H), 3.73 (d, J=10.6 Hz, 2H), 3.47 (d, J=6.1 Hz, 2H), 3.46 (s, 3H), 2.16 (s, 3H), 1.88 (d, J=7.3 Hz, 3H), 1.77-1.67 (m, 2H), 0.77 (dd, J=12.3, 7.7 Hz, 1H), 0.25-0.13 (m, 1H). Retention time (LC-MS): 2.568 min. MH+530.

Compound 47. (2S)-N-(2-(6-(3-azabicyclo[3.1.0] hexan-3-yl)pyridin-3-yl)pyrimidin-4-yl)-2-(3-methyl-2,6-dioxo-1-(2-oxobutyl)-2,3-dihydro-1H-purin-7(6H)-yl)propanamide

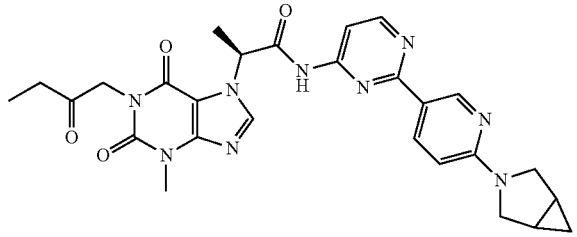 [SMILES: CCC(=O)Cn1c(=O)c2c(ncn2[C@@H](C)C(=O)Nc2ccnc(-c3ccc(N4CC5CC5C4)nc3)n2)n(C)c1=O]

This compound was prepared using the method described for compound 2 with appropriate starting materials in 13.9% yield as a yellow solid. $^1$H NMR (400 MHz, DMSO-D6) δ 11.35 (s, 1H), 9.04 (s, 1H), 8.65 (d, J=5.6 Hz, 1H), 8.40 (s, 1H), 8.35 (d, J=8.8 Hz, 1H), 7.74 (d, J=5.4 Hz, 1H), 6.58 (d, J=9.0 Hz, 1H), 5.79 (s, 1H), 4.67 (d, J=19.8 Hz, 2H), 3.73 (d, J=10.4 Hz, 2H), 3.47 (d, J=4.7 Hz, 2H), 3.42 (d, J=30.5 Hz, 3H), 1.88 (d, J=7.2 Hz, 3H), 1.72 (s, 2H), 1.24 (s, 2H), 0.94 (t, J=7.2 Hz, 3H), 0.78 (s, 1H), 0.20 (d, J=3.8 Hz, 1H). Retention time (LC-MS): 1.504 min. MH+544.

Compound 48. (S)-2-(1-(cyanomethyl)-3-methyl-2,6-dioxo-2,3-dihydro-1H-purin-7(6H)-yl)-N-(6-(2-((S)-2-(trifluoromethyl)pyrrolidin-1-yl)pyrimidin-5-yl)pyrazin-2-yl)propanamide

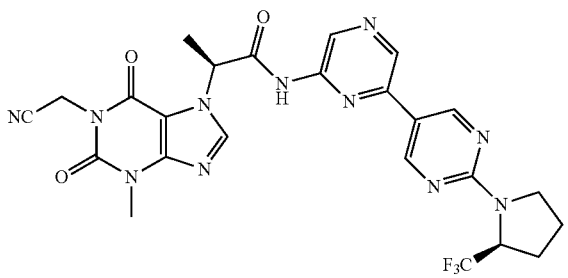 [SMILES: C[C@@H](C(=O)Nc1cncc(-c2cnc(N3CCC[C@H]3C(F)(F)F)nc2)n1)n1cnc2c1c(=O)n(CC#N)c(=O)n2C]

This compound was prepared using the method described for compound 1 with appropriate starting materials in 21.3% yield as a white solid. $^1$H NMR (400 MHz, DMSO-D6) δ 11.54 (s, 1H), 9.22 (s, 1H), 9.22 (s, 2H), 9.04 (s, 1H), 8.52 (s, 1H), 5.88 (d, J=6.8 Hz, 1H), 5.23-5.15 (m, 1H), 4.91 (s, 2H), 3.78 (d, J=6.1 Hz, 2H), 3.55 (s, 3H), 2.34-2.20 (m, 2H), 2.14 (s, 2H), 1.96 (d, J=7.2 Hz, 3H). Retention time (LC-MS): 1.939 min. MH+570.

Compound 49. (S)-2-(1-(cyanomethyl)-3-methyl-2,6-dioxo-2,3-dihydro-1H-purin-7(6H)-yl)-N-(2'-((R)-2-(trifluoromethyl)pyrrolidin-1-yl)-2,5'-bipyrimidin-4-yl)propanamide

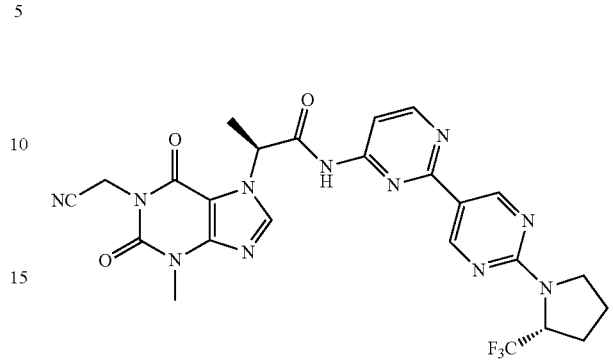

This compound was prepared using the method described for compound 1 with appropriate starting materials in 16.9% yield. $^1$H NMR (400 MHz, DMSO-D6) δ 11.53 (s, 1H), 9.26 (s,2H), 8.73 (d, J=5.6 Hz, 1H), 8.45 (s, 1H), 7.85 (d, J=5.2 Hz, 1H), 5.80 (d J=6.8 Hz, 1H), 5.17-5.13 (m,1H), 4.84 (s, 2H), 3.76-3.71 (m, 2H), 3.49 (s, 3H), 2.36-2.00 (m, 4H), 1.89 (d, J=7.6 Hz, 3H). Retention time (LC-MS): 2.016 min. MH+:570.

Compound 50. (R)-2-(2-(2-(trifluoromethyl)pyrrolidin-1-yl)pyrimidin-5-yl)thiazol-4-amine

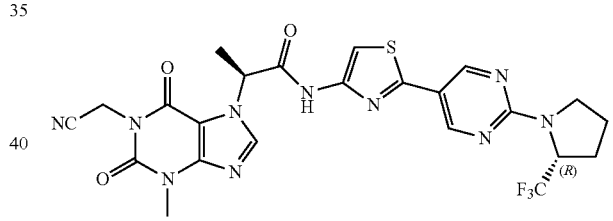

This compound was prepared using the method described for compound 1 with appropriate starting materials in 28.3% yield as a white solid. $^1$H NMR (400 MHz, DMSO-D6) δ 11.77 (s, 1H), 9.01 (s, 2H), 8.50 (s, 1H), 7.61 (s, 1H), 5.79-5.81 (m, 1H), 5.15-5.19 (m, 1H), 4.91 (s, 2H), 3.74-3.80 (m, 2H), 3.55 (s, 3H), 2.14-2.29 (m, 4H), 1.91 (d, J=7.2 Hz, 3H). Retention time (LC-MS): 2.441 min. MH+575.

Compound 51. (S)-2-(3-methyl-1-(oxetan-3-ylmethyl)-2,6-dioxo-2,3-dihydro-1H-purin-7(6H)-yl)-N-(6-(2-(trifluoromethyl)pyrimidin-5-yl)pyridin-2-yl)

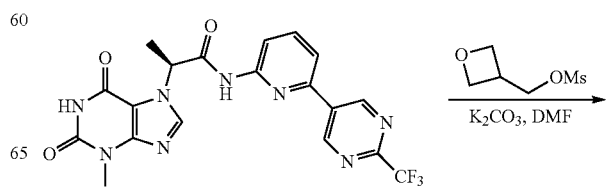

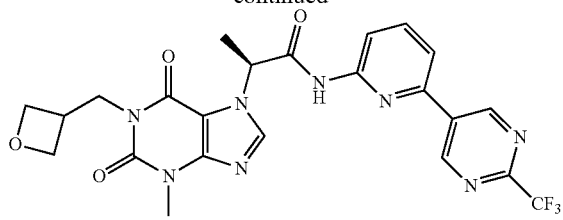

To a solution of (S)-2-(3-methyl-2,6-dioxo-2,3-dihydro-1H-purin-7(6H)-yl)-N-(6-(2-(trifluoromethyl)pyrimidin-5-yl)pyridin-2-yl)propanamide (80 mg, 0.17 mmol) and potassium carbonate (48 mg, 0.35 mmol) in DMF (2 mL) was added oxetan-3-ylmethyl methanesulfonate (69 mg, 0.42 mmol). The mixture was stirred at 50° C. overnight. The mixture was diluted with EA and washed with water, saturated aqueous NH$_4$Cl solution and brine, dried over Na$_2$SO$_4$, and evaporated. The residue was purified by preparative TLC to give the product (S)-2-(3-methyl-1-(oxetan-3-ylmethyl)-2,6-dioxo-2,3-dihydro-1H-purin-7(6H)-yl)-N-(6-(2-(trifluoromethyl)pyrimidin-5-yl)pyridin-2-yl)propanamide (20 mg, 21.7% yield) as a white solid. $^1$H NMR (400 MHz, DMSO-D6) δ 11.28 (s, 1H), 9.68 (s, 2H), 8.43 (s, 1H), 7.99-8.12 (m, 3H), 5.82-5.84 (m, 1H), 4.51-4.55 (m, 2H), 4.33-4.39 (m, 2H), 4.07-4.18 (m, 2H), 3.45 (s, 3H), 3.19-3.27 (m, 1H), 1.87 (d, J=6.8 Hz, 3H). Retention time (LC-MS): 2.656 min. MH$^+$531.

Compound 52. (S)-2-(3-methyl-2,6-dioxo-1-(2-oxopentyl)-2,3-dihydro-1H-purin-7(6H)-yl)-N-(6-(2-(trifluoromethyl)pyrimidin-5-yl)pyridin-2-yl)propanamide

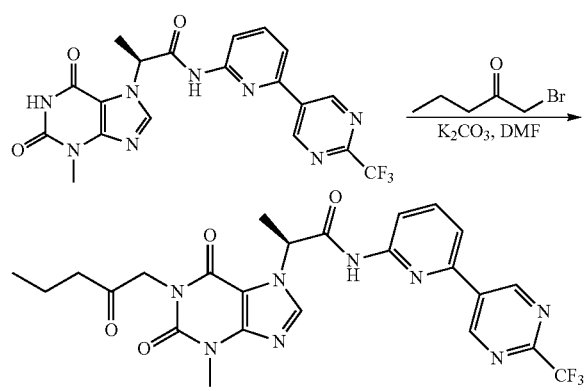

To a mixture of (S)-2-(3-methyl-2,6-dioxo-2,3-dihydro-1H-purin-7(6H)-yl)-N-(6-(2-(trifluoromethyl)pyrimidin-5-yl)pyridin-2-yl)propanamide (80 mg, 0.17 mmol) and potassium carbonate (48 mg, 0.34 mmol) in DIVIF (2 mL) was added drop-wise 1-bromopentan-2-one (68 mg, 0.42 mmol). The reaction mixture was stirred at 50° C. for 1 h and poured into EA. The organic phase was separated, washed with water and brine, dried over Na$_2$SO$_4$, and concentrated and the residue was purified by prep-HPLC to afford (S)-2-(3-methyl-2,6-dioxo-1-(2-oxopentyl)-2,3-dihydro-1H-purin-7(6H)-yl)-N-(6-(2-(trifluoromethyl)pyrimidin-5-yl)pyridin-2-yl)propanamide (25 mg, 27.17% yield) as a white solid. $^1$H NMR (400 MHz, DMSO-D6) δ 11.27 (s, 1H), 9.67 (s, 2H), 8.41 (s, 1H), 8.11 (d, J=6.7 Hz, 1H), 8.02 (q, J=7.6 Hz, 2H), 5.81 (s, 1H), 4.69 (s, 2H), 3.46 (s, 3H), 2.47 (d, J=7.2 Hz, 2H), 1.88 (d, J=7.3 Hz, 3H), 1.48 (m, 2H), 0.84 (t, J=7.4 Hz, 3H). Retention time (LC-MS): 2.181 min. MH$^+$545.

Compound 53. (2S)-N-(2-(6-(3-azabicyclo[3.1.0]hexan-3-yl)pyridin-3-yl)pyrimidin-4-yl)-2-(1-(cyanomethyl)-3-methyl-2,6-dioxo-2,3-dihydro-1H-purin-7(6H)-yl)propanamide

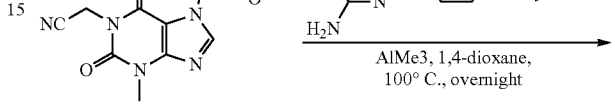

To a solution of 2-(6-(3-azabicyclo[3.1.0]hexan-3-yl)pyridin-3-yl)pyrimidin-4-amine (50 mg, 0.20 mmol) in 1,4-dioxane (3 mL) was added drop-wise trimethylaluminum (0.79 mL, 0.79 mmol) at 0° C. After the addition, the mixture was warmed to RT and stirred for 0.5 h. Then a solution of (S)-methyl 2-(1-(cyanomethyl)-3-methyl-2,6-dioxo-2,3-dihydro-1H-purin-7(6H)-yl)propanoate (57.49 mg, 0.20 mmol) in 1,4-dioxane (2 mL) was added drop-wise and the reaction mixture was stirred at 100° C. overnight. The reaction was quenched by addition of several drops of MeOH. The mixture was concentrated under reduced pressure and the residue was purified by chromatography (DCM:MeOH=100:1 to 50:1) to afford a crude product, which was further purified via preparative TLC(DCM:MeOH=15:1) to afford (2S)-N-(2-(6-(3-azabicyclo[3.1.0]hexan-3-yl)pyridin-3-yl)pyrimidin-4-yl)-2-(1-(cyanomethyl)-3-methyl-2,6-dioxo-2,3-dihydro-1H-purin-7(6H)-yl)propanamide (15 mg, 14.8% yield) as a yellow solid. 1H NMR (400 MHz, DMSO-D6) δ 11.41 (s, 1H), 9.04 (d, J=2.1 Hz, 1H), 8.64 (d, J=5.7 Hz, 1H), 8.43 (s, 1H), 8.34 (m, J=8.9, 2.3 Hz, 1H), 7.73 (d, J=5.7 Hz, 1H), 6.57 (d, J=9.0 Hz, 1H), 5.77 (d, J=17.5 Hz, 1H), 4.83 (s, 2H), 3.72 (d, J=10.8 Hz, 2H), 3.46 (d, J=10.6 Hz, 5H), 1.87 (d, J=7.3 Hz, 3H), 1.70 (s, 2H), 0.76 (d, J=4.6 Hz, 1H), 0.18 (d, J=3.9 Hz, 1H). Retention time (LC-MS): 2.282 min. MH$^+$513.

319

Compound 54. (S)-2-(1-(cyanomethyl)-3-methyl-2,6-dioxo-2,3-dihydro-1H-purin-7(6H)-yl)-N-(2'-((S)-2-(trifluoromethyl)pyrrolidin-1-yl)-2,5'-bipyrimidin-4-yl)propanamide

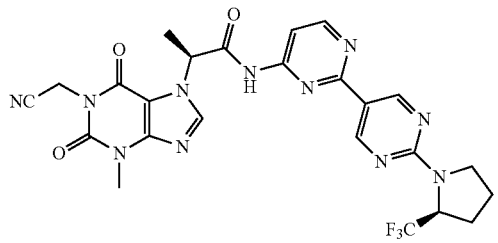 [SMILES: C[C@@H](C(=O)Nc1ccnc(-c2cnc(N3CCC[C@H]3C(F)(F)F)nc2)n1)n1cnc2c1c(=O)n(CC#N)c(=O)n2C]

This compound was prepared using the method described for compound 53 with appropriate starting materials in 5.4% yield as a yellow solid. $^1$H NMR (400 MHz, DMSO-D6) δ 11.54 (s, 1H), 9.26 (s, 2H), 8.73 (d, J=5.7 Hz, 1H), 8.45 (s, 1H), 7.85 (d, J=5.7 Hz, 1H), 5.80 (d, J=7.0 Hz, 1H), 5.23-5.08 (m, 1H), 4.84 (s, 2H), 3.80-3.64 (m, 2H), 3.49 (s, 3H), 2.25-2.01 (m, 4H), 1.89 (d, J=7.3 Hz, 3H). Retention time (LC-MS): 2.097 min. MH$^+$570.

Compound 55. (S)-2-(3-methyl-1-((5-methylisoxazol-3-yl)methyl)-2,6-dioxo-2,3-dihydro-1H-purin-7(6H)-yl)-N-(6-(5-(trifluoromethyl)pyridin-3-yl)pyrazin-2-yl)propanamide

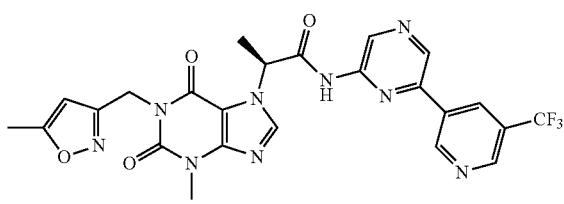 [SMILES: Cc1cc(Cn2c(=O)c3c(ncn3[C@@H](C)C(=O)Nc3cncc(-c4cncc(C(F)(F)F)c4)n3)n(C)c2=O)no1]

This compound was prepared using the method described for compound 1 with appropriate starting materials in 7.6% yield as a white solid. $^1$H NMR (400 MHz, DMSO-D6) δ 11.57 (s, 1H), 9.64 (s, 1H), 9.31 (s, 1H), 9.24 (s, 1H), 9.13 (s, 1H), 8.84 (s, 1H), 8.43 (s, 1H), 6.09 (s, 1H), 5.83 (d, J=7.1 Hz, 1H), 5.02 (s, 2H), 3.48 (s, 3H), 2.31 (s, 3H), 1.90 (d, J=7.3 Hz, 3H). Retention time (LC-MS): 1.834 min. MH$^+$556.

320

Compound 56. (2S)-N-(2-(2-(6,6-difluoro-3-azabicyclo[3.1.0]hexan-3-yl)pyrimidin-5-yl)thiazol-4-yl)-2-(3-methyl-2,6-dioxo-1-(2-oxopropyl)-2,3-dihydro-1H-purin-7(6H)-yl)propanamide

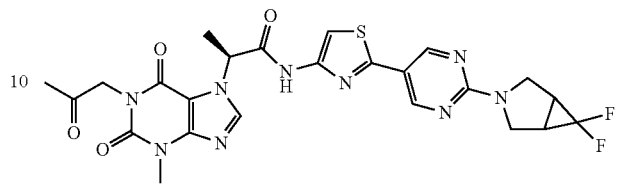

This compound was prepared using the method described for Compound 2 with appropriate starting materials in 38.7% yield as a yellow solid. $^1$H NMR (400 MHz, DMSO-d6) δ 11.62 (s, 1H), 8.85 (s, 2H), 8.39 (s, 1H), 7.49 (s, 1H), 5.70 (d, J=7.1 Hz, 1H), 4.70 (s, 2H), 3.98 (d, J=12.1 Hz, 2H), 3.85 (d, J=11.4 Hz, 2H), 3.45 (s, 3H), 2.72 (d, J=11.5 Hz, 2H), 2.17 (s, 3H), 1.84 (d, J=7.1 Hz, 3H). Retention time (LC-MS): 1.846 min. MH$^+$572.

Compound 57. (2S)-N-(2-(2-(6,6-difluoro-3-azabicyclo[3.1.0]hexan-3-yl)pyrimidin-5-yl)thiazol-4-yl)-2-(3-methyl-2,6-dioxo-1-(2-oxobutyl)-2,3-dihydro-1H-purin-7(6H)-yl)propanamide

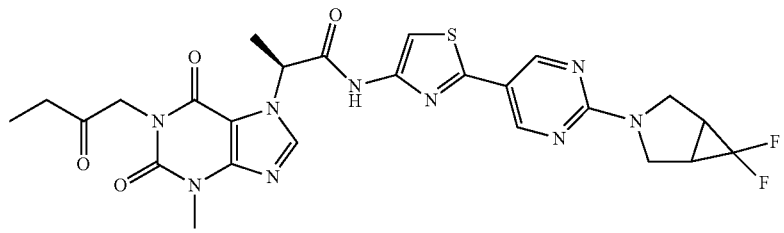 [SMILES: CCC(=O)Cn1c(=O)c2c(ncn2[C@@H](C)C(=O)Nc2csc(-c3cnc(N4CC5C(C4)C5(F)F)nc3)n2)n(C)c1=O]

This compound was prepared using the method described for Compound 2 with appropriate starting materials in 40.2% yield as a light yellow solid. $^1$H NMR (400 MHz, DMSO-d6) δ 11.62 (s, 1H), 8.85 (s, 2H), 8.39 (s, 1H), 7.49 (s, 1H), 5.80-5.64 (m, 1H), 4.78-4.60 (m, 2H), 3.98 (d, J=12.0 Hz, 2H), 3.85 (d, J=10.9 Hz, 2H), 3.45 (s, 3H), 2.72 (d, J=10.7 Hz, 2H), 2.58-2.52 (m, 2H), 1.84 (d, J=7.2 Hz, 3H), 0.94 (t, J=7.3 Hz, 3H). Retention time (LC-MS): 1.999 min. MH$^+$586.

Compound 58. (2S)-2-(1-(cyanomethyl)-3-methyl-2,6-dioxo-2,3-dihydro-1H-purin-7(6H)-yl)-N-(2-(2-(6,6-difluoro-3-azabicyclo[3.1.0]hexan-3-yl)pyrimidin-5-yl)thiazol-4-yl)propanamide

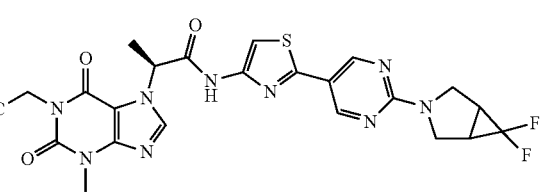

This compound was prepared using the method described for Compound 1 with appropriate starting materials in 17.7% yield as a yellow solid. $^1$H NMR (400 MHz, DMSO-d6) δ 11.68 (s, 1H), 8.87 (s, 2H), 8.43 (s, 1H), 7.51 (s, 1H), 5.73 (q, J=7.0 Hz, 1H), 4.85 (s, 2H), 3.99 (d, J=12.1 Hz, 2H), 3.86 (d, J=11.0 Hz, 2H), 3.49 (s, 3H), 2.72 (d, J=10.6 Hz, 2H), 1.85 (d, J=7.3 Hz, 3H). Retention time (LC-MS): 1.945 min. MH+555.

Compound 59. (S)-2-(1-(3-methoxy-2-oxopropyl)-3-methyl-2,6-dioxo-2,3-dihydro-1H-purin-7(6H)-yl)-N-(6-(2-(trifluoromethyl)pyrimidin-5-yl)pyridin-2-yl)propanamide

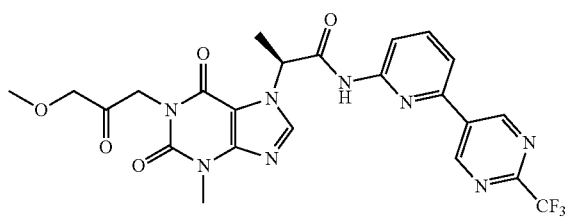 [SMILES: COCC(=O)Cn1c(=O)c2c(ncn2[C@@H](C)C(=O)Nc2cccc(-c3cnc(C(F)(F)F)nc3)n2)n(C)c1=O]

This compound was prepared using the method described for compound 1 with appropriate starting materials and purified via preparative HPLC to afford (S)-2-(1-(cyanomethyl)-3-methyl-2,6-dioxo-2,3-dihydro-1H-purin-7(6H)-yl)-N-(6-(2-((R)-2-(trifluoromethyl)pyrrolidin-1-yl)pyrimidin-5-yl)pyrazin-2-yl)propanamide in 3% yield as a white solid. $^1$H NMR (400 MHz, DMSO-D6) δ 9.62 (s, 2H), 8.31 (s, 1H), 8.18 (s, 1H), 7.95 (t, 1H), 7.88 (d, J=7.6 Hz, 1H), 7.53 (s, 1H), 5.87 (d, J=7.1 Hz, 1H), 4.92 (s, 2H), 4.22 (s, 2H), 3.60 (d, J=8.9 Hz, 3H), 3.43 (s, 3H), 1.98 (d, J=7.3 Hz, 3H). Retention time (LC-MS): 1.799 min. MH+547.

Compound 60. (2S)-2-(1-(cyanomethyl)-3-methyl-2,6-dioxo-2,3-dihydro-1H-purin-7(6H)-yl)-N-(6-(2-(6,6-difluoro-3-azabicyclo[3.1.0]hexan-3-yl)pyrimidin-5-yl)pyrazin-2-yl)propanamide

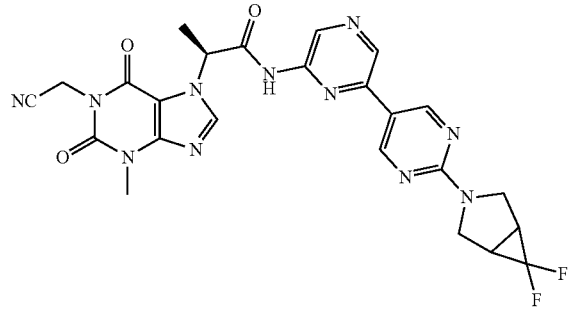 [SMILES: C[C@@H](C(=O)Nc1cncc(-c2cnc(N3CC4C(C3)C4(F)F)nc2)n1)n1cnc2c1c(=O)n(CC#N)c(=O)n2C]

This compound was prepared using the method described for compound 1 with appropriate starting materials in 27.7% yield as a white solid. $^1$H NMR (400 MHz, DMSO-D6) δ 11.39 (s, 1H), 9.14 (s, 1H), 9.08 (s, 2H), 8.93 (s, 1H), 8.45 (s, 1H), 5.83 (d, J=6.8 Hz, 1H), 4.85 (s, 2H), 4.01 (d, J=12.0 Hz, 2H), 3.87 (d, J=10.5 Hz, 2H), 3.50 (s, 3H), 2.72 (d, J=12.1 Hz, 2H), 1.90 (d, J=7.3 Hz, 3H). Retention time (LC-MS): 2.013 min. MH+550.

Compound 61. (2S)-N-(2'-(6,6-difluoro-3-azabicyclo[3.1.0]hexan-3-yl)-[2,5'-bipyrimidin]-4-yl)-2-(3-methyl-2,6-dioxo-1-(2-oxopropyl)-2,3-dihydro-1H-purin-7(6H)-yl)propanamide

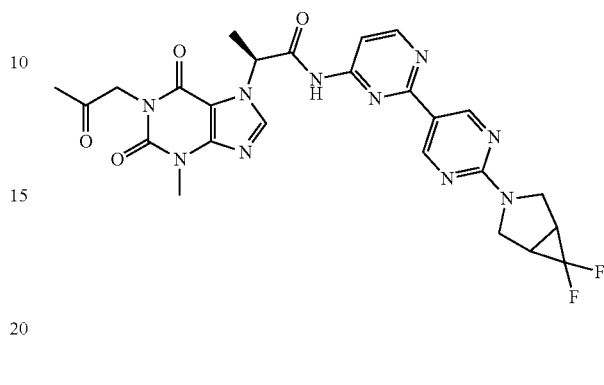

This compound was prepared using the method described for compound 2 with appropriate starting materials in 5.0% yield as a white solid. $^1$H NMR (400 MHz, DMSO-D6) δ 11.44 (s, 1H), 9.19 (s, 2H), 8.69 (d, J=5.7 Hz, 1H), 8.40 (s, 1H), 7.81 (d, J=5.7 Hz, 1H), 5.77 (d, J=7.4 Hz, 1H), 4.70 (s, 2H), 4.01 (d, J=12.1 Hz, 2H), 3.87 (d, J=11.3 Hz, 2H), 3.46 (s, 3H), 2.72 (d, J=10.9 Hz, 2H), 2.16 (s, 3H), 1.88 (d, J=7.3 Hz, 3H). Retention time (LC-MS): 1.598 min. MH+567.

Compound 62. (2S)-N-(2'-(6,6-difluoro-3-azabicyclo[3.1.0]hexan-3-yl)-[2,5'-bipyrimidin]-4-yl)-2-(3-methyl-2,6-dioxo-1-(2-oxobutyl)-2,3-dihydro-1H-purin-7(6H)-yl)propanamide

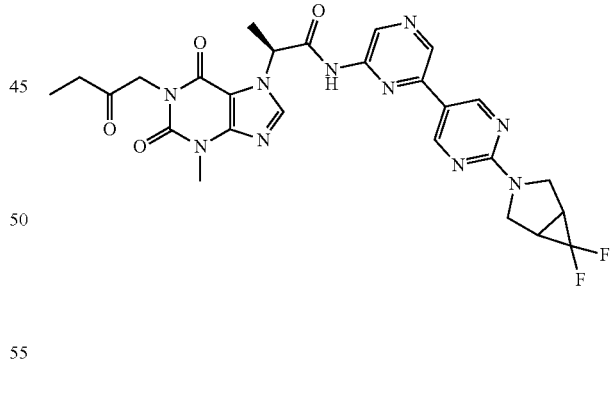

This compound was prepared using the method described for compound 2 with appropriate starting materials in 5.0% yield. $^1$H NMR (400 MHz, DMSO-D6) δ 11.41 (s, 1H), 9.19 (s, 2H), 8.69 (d, J=5.7 Hz, 1H), 8.40 (s, 1H), 7.81 (d, J=5.7 Hz, 1H), 5.78 (d, J=6.8 Hz, 1H), 4.69 (d, J=2.1 Hz, 2H), 4.01 (d, J=12.1 Hz, 2H), 3.87 (d, J=10.7 Hz, 2H), 3.46 (s, 3H), 2.72 (d, J=11.2 Hz, 2H), 2.54 (d, J=7.3 Hz, 2H), 1.87 (d, J=7.3 Hz, 3H), 0.93 (t, J=7.3 Hz, 3H). Retention time (LC-MS): 1.819 min. MH+581.

Compound 63. (2S)-N-(2-(6-(3-azabicyclo[3.1.0]hexan-3-yl)pyridin-3-yl)thiazol-4-yl)-2-(3-methyl-2,6-dioxo-1-(2-oxopropyl)-2,3-dihydro-1H-purin-7(6H)-yl)propanamide

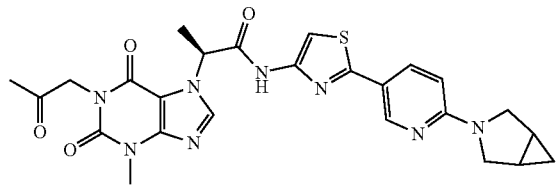 [SMILES: CC(=O)Cn1c(=O)c2c(ncn2[C@@H](C)C(=O)Nc2csc(-c3ccc(N4CC5CC5C4)nc3)n2)n(C)c1=O]

This compound was prepared using the method described for compound 2 with appropriate starting materials in 14.5% yield. $^1$H NMR (400 MHz, DMSO-D6) δ 11.54 (s, 1H), 8.61 (d, J=2.2 Hz, 1H), 8.38 (s, 1H), 7.92 (dd, J=8.8, 2.3 Hz, 1H), 7.39 (s, 1H), 6.56 (d, J=8.9 Hz, 1H), 5.70 (d, J=7.3 Hz, 1H), 4.70 (s, 2H), 3.70 (d, J=10.5 Hz, 2H), 3.45 (s, 3H), 3.44 (s, 2H), 2.17 (s, 3H), 1.84 (d, J=7.3 Hz, 3H), 1.71 (s, 2H), 0.77 (d, J=4.7 Hz, 1H), 0.18 (d, J=4.0 Hz, 1H). Retention time (LC-MS): 0.739 min. MH$^+$535.

Compound 64. (2S)-N-(2-(6-(3-azabicyclo[3.1.0]hexan-3-yl)pyridin-3-yl)thiazol-4-yl)-2-(1-(cyanomethyl)-3-methyl-2,6-dioxo-2,3-dihydro-1H-purin-7(6H)-yl)propanamide

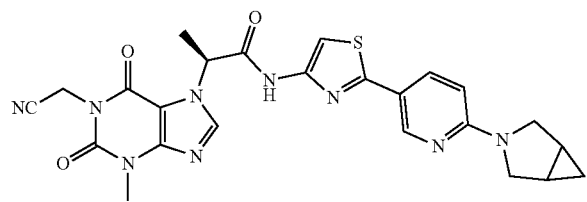 [SMILES: C[C@@H](C(=O)Nc1csc(-c2ccc(N3CC4CC4C3)nc2)n1)n1cnc2c1c(=O)n(CC#N)c(=O)n2C]

This compound was prepared using the method described for compound 1 with appropriate starting materials in 4.8% yield (ee: 92%) as a white solid. $^1$H NMR (400 MHz, DMSO-D6) δ 11.59 (s, 1H), 8.61 (d, J=2.3 Hz, 1H), 8.42 (s, 1H), 7.92 (dd, J=8.9, 2.4 Hz, 1H), 7.40 (s, 1H), 6.56 (d, J=9.0 Hz, 1H), 5.72 (d, J=7.2 Hz, 1H), 4.84 (s, 2H), 3.70 (d, J=10.1 Hz, 2H), 3.48 (s, 3H), 3.45 (d, J=10.7 Hz, 2H), 1.84 (d, J=7.3 Hz, 3H), 1.71 (s, 2H), 0.77 (d, J=4.4 Hz, 1H), 0.18 (d, J=4.2 Hz, 1H). Retention time (LC-MS): 0.853 min. MH$^+$518.

Compound 65. ((2S)-N-(6'-(6,6-difluoro-3-azabicyclo[3.1.0]hexan-3-yl)-[2,3'-bipyridin]-6-yl)-2-(3-methyl-2,6-dioxo-1-(2-oxopropyl)-2,3-dihydro-1H-purin-7(6H)-yl)propanamide

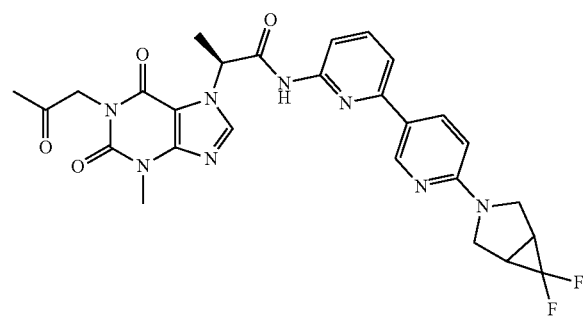 [SMILES: CC(=O)Cn1c(=O)c2c(ncn2[C@@H](C)C(=O)Nc2cccc(-c3ccc(N4CC5C(C4)C5(F)F)nc3)n2)n(C)c1=O]

This compound was prepared using the method described for compound 2 with appropriate starting materials in 17.9% yield (ee: 94%) as a white solid. $^1$H NMR (400 MHz, DMSO-D6) δ 10.96 (s, 1H), 8.82 (d, J=2.2 Hz, 1H), 8.39 (s, 1H), 8.21 (dd, J=8.9, 2.4 Hz, 1H), 7.84 (d, J=7.9 Hz, 1H), 7.78 (t, J=7.9 Hz, 1H), 7.60 (d, J=8.1 Hz, 1H), 6.60 (d, J=8.9 Hz, 1H), 5.79 (s, 1H), 4.70 (d, J=2.5 Hz, 2H), 3.86 (m, 2H), 3.76 (d, J=9.5 Hz, 2H), 3.46 (s, 3H), 2.72 (d, J=10.9 Hz, 2H), 2.16 (s, 3H), 1.86 (d, J=7.3 Hz, 3H). Retention time (LC-MS): 0.600 min. MH$^+$565.

Compound 66. (2S)-N-(2-(6-(3-azabicyclo[3.1.0]hexan-3-yl)pyridin-3-yl)thiazol-4-yl)-2-(1-(cyanomethyl)-3-methyl-2,6-dioxo-2,3-dihydro-1H-purin-7(6H)-yl)propanamide

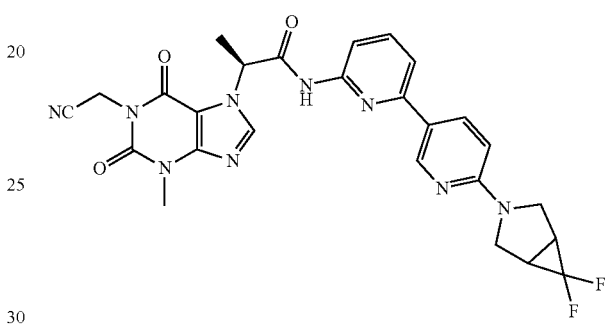

This compound was prepared using the method described for compound 1 with appropriate starting materials in 4.3% yield (ee: 99.5%). $^1$H NMR (400 MHz, DMSO-D6) δ 11.01 (s, 1H), 8.83 (d, J=2.2 Hz, 1H), 8.43 (s, 1H), 8.23 (dd, J=8.8, 2.4 Hz, 1H), 7.85 (d, J=7.1 Hz, 1H), 7.79 (t, J=7.9 Hz, 1H), 7.60 (d, J=7.9 Hz, 1H), 6.61 (d, J=8.9 Hz, 1H), 5.82 (s, 1H), 4.85 (s, 2H), 3.86 (d, J=11.0 Hz, 2H), 3.77 (d, J=9.5 Hz, 2H), 3.49 (s, 3H), 2.72 (d, J=10.5 Hz, 2H), 1.88 (d, J=7.3 Hz, 3H). Retention time (LC-MS): 2.608 min. MH$^+$545.

Compound 67. (2S)-2-(1-(cyanomethyl)-3-methyl-2,6-dioxo-2,3-dihydro-1H-purin-7(6H)-yl)-N-(2'-(6,6-difluoro-3-azabicyclo[3.1.0]hexan-3-yl)-[2,5'-bipyrimidin]-4-yl)propanamide

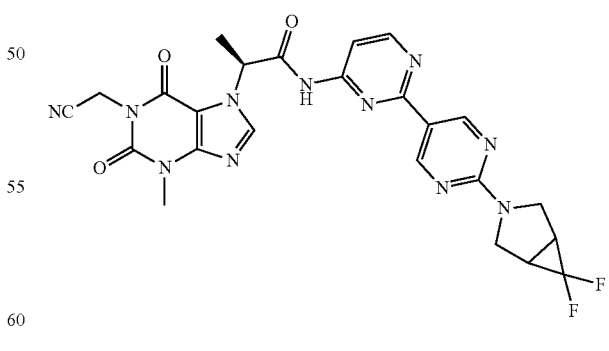

This compound was prepared using the method described for compound 53 with appropriate starting materials in 10.6% yield (ee: 61.2%). $^1$H NMR (400 MHz, DMSO-D6) δ 11.49 (s, 1H), 9.23 (d, J=20.1 Hz, 2H), 8.69 (d, J=5.7 Hz, 1H), 8.43 (s, 1H), 7.82 (d, J=5.6 Hz, 1H), 5.80 (d, J=7.5 Hz, 1H), 4.84 (s, 2H), 4.02 (d, J=12.2 Hz, 2H), 3.88 (d, J=11.2

Hz, 2H), 3.49 (s, 3H), 2.71 (d, J=11.4 Hz, 2H), 1.89 (d, J=7.2 Hz, 3H). Retention time (LC-MS): 2.082 min. MH+550.

Compound 68. (2S)-N-(6'-(6,6-difluoro-3-azabicyclo[3.1.0]hexan-3-yl)-[2,3'-bipyridin]-6-yl)-2-(3-methyl-2,6-dioxo-1-(2-oxobutyl)-2,3-dihydro-1H-purin-7(6H)-yl)propanamide

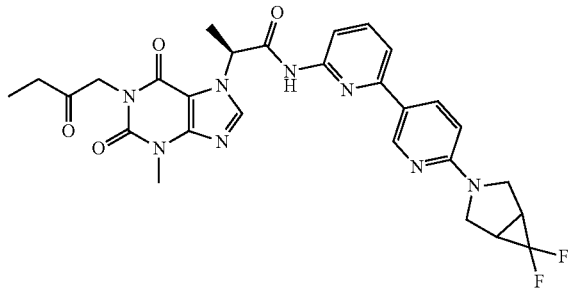 [SMILES: CCC(=O)Cn1c(=O)c2c(ncn2[C@@H](C)C(=O)Nc2cccc(-c3ccc(N4CC5C(C4)C5(F)F)nc3)n2)n(C)c1=O]

This compound was prepared using the method described for compound 2 with appropriate starting materials in 14.7% yield (ee: 98.6%). ¹H NMR (400 MHz, DMSO-D6) δ 10.97 (s, 1H), 8.82 (d, J=2.2 Hz, 1H), 8.40 (s, 1H), 8.22 (dd, J=8.8, 2.4 Hz, 1H), 7.90-7.75 (m, 2H), 7.60 (d, J=7.9 Hz, 1H), 6.61 (d, J=8.9 Hz, 1H), 5.79 (d, J=6.4 Hz, 1H), 4.70 (d, J=3.6 Hz, 2H), 3.86 (d, J=11.1 Hz, 2H), 3.76 (d, J=9.4 Hz, 2H), 3.46 (s, 3H), 2.72 (d, J=10.8 Hz, 2H), 2.55 (d, J=7.2 Hz, 2H), 1.87 (d, J=7.3 Hz, 3H), 0.94 (t, J=7.3 Hz, 3H). Retention time (LC-MS): 1.731 min. MH+579.

Compound 69. (2S)-N-(2-(6-(6,6-difluoro-3-azabicyclo[3.1.0]hexan-3-yl)pyridin-3-yl)pyrimidin-4-yl)-2-(3-methyl-2,6-dioxo-1-(2-oxopropyl)-2,3-dihydro-1H-purin-7(6H)-yl)propanamide

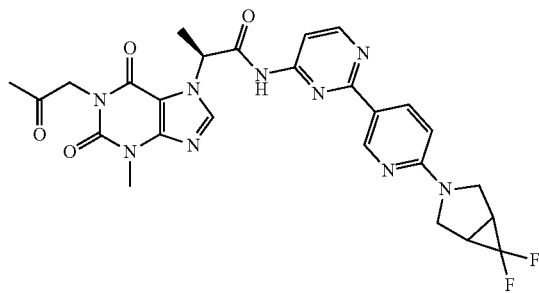 [SMILES: CC(=O)Cn1c(=O)c2c(ncn2[C@@H](C)C(=O)Nc2ccnc(-c3ccc(N4CC5C(C4)C5(F)F)nc3)n2)n(C)c1=O]

This compound was prepared using the method described for compound 2 with appropriate starting materials in 26.5% yield (ee: 86.7%). ¹H NMR (400 MHz, DMSO-D6) δ 11.42 (s, 1H), 9.02 (d, J=2.0 Hz, 1H), 8.68 (d, J=5.7 Hz, 1H), 8.44 (dd, J=9.0, 2.2 Hz, 1H), 8.40 (s, 1H), 7.78 (d, J=5.6 Hz, 1H), 6.73 (d, J=9.0 Hz, 1H), 5.77 (d, J=7.2 Hz, 1H), 4.69 (d, J=1.4 Hz, 2H), 3.91 (d, J=11.3 Hz, 2H), 3.83 (d, J=9.7 Hz, 2H), 3.46 (s, 3H), 2.76 (d, J=10.3 Hz, 2H), 2.16 (s, 3H), 1.88 (d, J=7.3 Hz, 3H). Retention time (LC-MS): 1.773 min. MH+566.

Compound 70. (2S)-N-(2-(6-(6,6-difluoro-3-azabicyclo[3.1.0]hexan-3-yl)pyridin-3-yl)pyrimidin-4-yl)-2-(3-methyl-2,6-dioxo-1-(2-oxobutyl)-2,3-dihydro-1H-purin-7(6H)-yl)propanamide

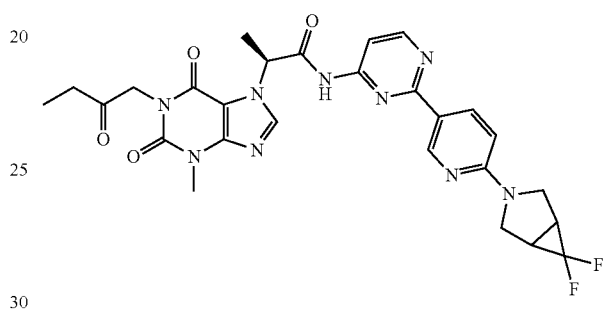

This compound was prepared using the method described for compound 2 with appropriate starting materials in 6.9% yield (ee: 85.4%). ¹H NMR (400 MHz, DMSO-D6) δ 11.42 (s, 1H), 9.02 (d, J=2.0 Hz, 1H), 8.68 (d, J=5.7 Hz, 1H), 8.45 (dd, J=9.1, 2.1 Hz, 1H), 8.41 (s, 1H), 7.78 (d, J=5.7 Hz, 1H), 6.74 (d, J=9.1 Hz, 1H), 5.78 (d, J=7.5 Hz, 1H), 4.69 (d, J=2.5 Hz, 2H), 3.91 (d, J=11.3 Hz, 2H), 3.83 (d, J=9.6 Hz, 2H), 3.46 (s, 3H), 2.77 (d, J=10.5 Hz, 2H), 2.55 (d, J=7.3 Hz, 2H), 1.88 (d, J=7.3 Hz, 3H), 0.94 (t, J=7.3 Hz, 3H). Retention time (LC-MS): 2.046 min. MH+580.

Compound 71. (2S)-N-(2-(2-(3-azabicyclo[3.1.0]hexan-3-yl)pyrimidin-5-yl)thiazol-4-yl)-2-(3-methyl-1-(2-(methylamino)-2-oxoethyl)-2,6-dioxo-2,3-dihydro-1H-purin-7(6H)-yl)propanamide

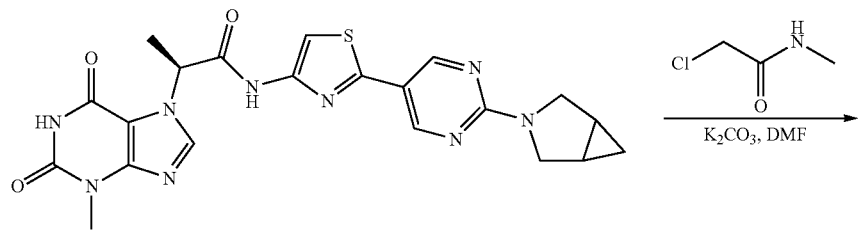

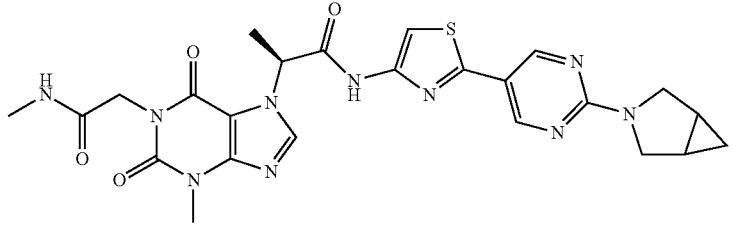

A mixture of (2S)-N-(2-(2-(3-azabicyclo[3.1.0]hexan-3-yl)pyrimidin-5-yl)thiazol-4-yl)-2-(3-methyl-2,6-dioxo-2,3-dihydro-1H-purin-7(6H)-yl)propanamide (50 mg, 0.104 mmol), 2-chloro-N-methylacetamide (11.2 mg, 0.104 mmol), potassium carbonate (14 mg, 0.104 mmol) and a catalytic amount of TBAI in N, N-dimethyl formamide (1 ml) was stirred at 50° C. for 2 hrs. The mixture was poured into water, filtered and the solid was washed with water twice, dried under vacuum and recrystallized from ethanol to give (2S)-N-(2-(2-(3-azabicyclo[3.1.0]hexan-3-yl)pyrimidin-5-yl)thiazol-4-yl)-2-(3-methyl-1-(2-(methylamino)-2-oxoethyl)-2,6-dioxo-2,3-dihydro-1H-purin-7(6H)-yl)propanamide (10.5 mg, ee: 93%) as a white solid. $^1$H NMR (400 MHz, DMSO-D6) δ 11.58 (s, 1H), 8.75 (s, 2H), 8.32 (s, 1H), 7.90 (s, 1H), 7.42 (s, 1H), 5.69 (q, J=7.6 Hz, 1H), 4.31 (d, J=4.4 Hz, 2H), 3.79 (d, J=11.6 Hz, 2H), 3.50 (d, J=11.2 Hz, 2H), 3.39 (s, 3H), 2.49 (d, J=4.8 Hz, 3H), 1.78 (d, J=7.2 Hz, 3H), 1.64 (m, 2H), 0.72 (m, 1H), 0.11 (m, 1H). Retention time (LC-MS): 1.881min. MH$^+$:551.

Compound 72. (2S)-N-(2-(2-(3-azabicyclo[3.1.0]hexan-3-yl)pyrimidin-5-yl)thiazol-4-yl)-2-(1-(2-amino-2-oxoethyl)-3-methyl-2,6-dioxo-2,3-dihydro-1H-purin-7(6H)-yl)propanamide

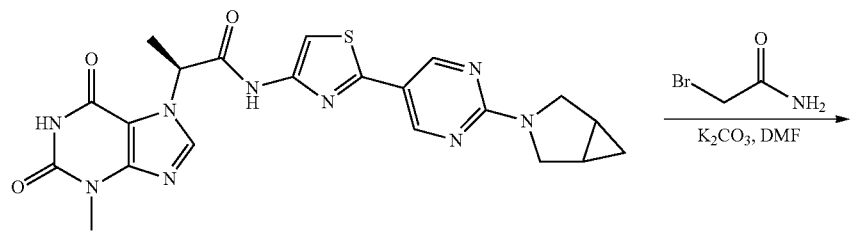

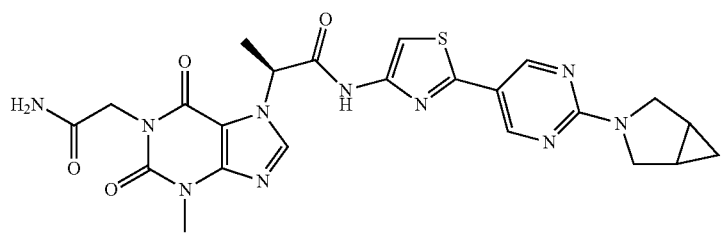

A mixture of (2S)-N-(2-(2-(3-azabicyclo[3.1.0]hexan-3-yl)pyrimidin-5-yl)thiazol-4-yl)-2-(3-methyl-2,6-dioxo-2,3-dihydro-1H-purin-7(6H)-yl)propanamide (50 mg, 0.104 mmol), 2-bromoacetamide (14 mg, 0.104 mmol), potassium carbonate (14 mg, 0.104 mmol) and a catalytic amount of TBAI in N, N-dimethyl formamide (1 ml) was stirred at 50° C. for 2 hrs. The mixture was poured into water, filtered and the solid was washed with water twice, dried under vacuum and recrystallized from ethanol to give (2S)-N-(2-(2-(3-azabicyclo[3.1.0]hexan-3-yl)pyrimidin-5-yl)thiazol-4-yl)-2-(1-(2-amino-2-oxoethyl)-3-methyl-2,6-dioxo-2,3-dihydro-1H-purin-7(6H)-yl)propanamide (23.1 mg, ee: 93%) as a white solid. 1H NMR (400 MHz, DMSO-D6) δ 11.47 (s, 1H), 8.65 (s, 2H), 8.21 (s, 1H), 7.34 (d, J=20.9 Hz, 2H), 6.91 (s, 1H), 5.58 (d, J=7.3 Hz, 1H), 4.20 (s, 2H), 3.67 (d, J=11.4 Hz, 2H), 3.39 (d, J=11.3 Hz, 2H), 3.28 (s, 3H), 1.67 (d, J=7.3 Hz, 3H), 1.59 (m, 2H), 0.61 (d, J=4.7 Hz, 1H), 0.01 (d, J=4.2 Hz, 1H). Retention time (LC-MS): 1.830min. MH$^+$536.

Compound 73. (2S)-N-(2-(2-(3-azabicyclo[3.1.0]hexan-3-yl)pyrimidin-5-yl)thiazol-4-yl)-2-(3-methyl-1-(oxetan-2-ylmethyl)-2,6-dioxo-2,3-dihydro-1H-purin-7(6H)-yl)propanamide

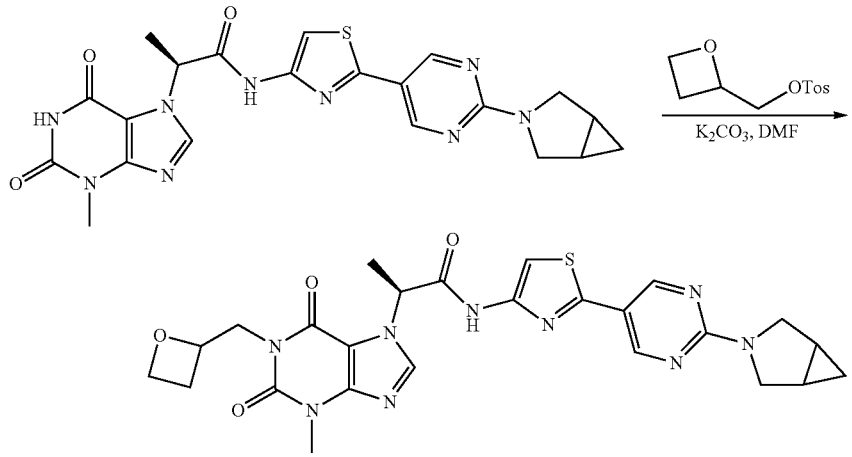

A mixture of (2S)-N-(2-(2-(3-azabicyclo[3.1.0]hexan-3-yl)pyrimidin-5-yl)thiazol-4-yl)-2-(3-methyl-2,6-dioxo-2,3-dihydro-1H-purin-7(6H)-yl)propanamide (50 mg, 0.104 mmol), oxetan-2-ylmethyl 4-methylbenzenesulfonate (25 mg, 0.104 mmol), potassium carbonate (14 mg, 0.104 mmol) and a catalytic amount of TBAI in N, N-dimethylformamide (1 ml) was stirred at 50° C. for 2 hrs. The mixture was poured into water, filtered and the solid was washed with water twice, dried under vacuum and recrystallized from ethanol to give (2S)-N-(2-(2-(3-azabicyclo[3.1.0]hexan-3-yl)pyrimidin-5-yl)thiazol-4-yl)-2-(3-methyl-1-(oxetan-2-ylmethyl)-2,6-dioxo-2,3-dihydro-1H-purin-7(6H)-yl)propanamide (3.3 mg, ee: 21.7%) as a white solid. 1H NMR (400 MHz, DMSO-D6) δ 11.61 (s, 1H), 8.81 (s, 2H), 8.34 (s, 1H), 7.46 (s, 1H), 5.73 (d, J=7.2 Hz, 1H), 4.94 (m, 1H), 4.42 (dd, J=14.2,6.7 Hz, 2H), 4.27 (m, 2H), 3.83 (d, J=11.4 Hz, 2H), 3.57 (s, 2H), 3.44 (s, 3H), 2.57 (d, J=7.7 Hz, 1H), 2.43 (d, J=10.1 Hz, 1H), 1.82 (d, J=7.2 Hz, 3H), 1.70 (s, 2H), 0.77 (d, J=4.9 Hz, 1H), 0.16 (d, J=4.3 Hz, 1H). Retention time (LC-MS): 2.347min. MH+549.

Compound 74. (2S)-N-(6-(2-(6,6-difluoro-3-azabicyclo[3.1.0]hexan-3-yl)pyrimidin-5-yl)pyrazin-2-yl)-2-(3-methyl-2,6-dioxo-1-(2-oxopropyl)-2,3-dihydro-1H-purin-7(6H)-yl)propanamide (ZY-000530-052).

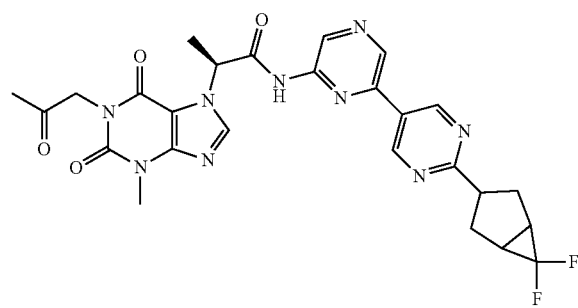 [SMILES: CC(=O)Cn1c(=O)c2c(ncn2[C@@H](C)C(=O)Nc2cncc(-c3cnc(C4CC5C(C4)C5(F)F)nc3)n2)n(C)c1=O]

This compound was prepared using the method described forcompound 2 with appropriate starting materials in 7.8% yield (ee: 59.7%) as a white solid. ¹H NMR (400 MHz, DMSO-D6) δ 11.37 (s, 1H), 9.12 (s, 1H), 9.07 (s, 2H), 8.93 (s, 1H), 8.41 (s, 1H), 5.80 (d, J=7.5 Hz, 1H), 4.76-4.64 (m, 2H), 4.01 (d, J=12.0 Hz, 2H), 3.87 (d, J=10.5 Hz, 2H), 3.47 (s, 3H), 2.72 (d, J=10.5 Hz, 2H), 2.17 (s, 3H), 1.89 (d, J=7.3 Hz, 3H). Retention time (LC-MS): 0.937 min. MH+567.

Compound 75. (2S)-N-(6-(2-(6,6-difluoro-3-azabicyclo[3.1.0]hexan-3-yl)pyrimidin-5-yl)pyrazin-2-yl)-2-(3-methyl-2,6-dioxo-1-(2-oxobutyl)-2,3-dihydro-1H-purin-7(6H)-yl)propanamide

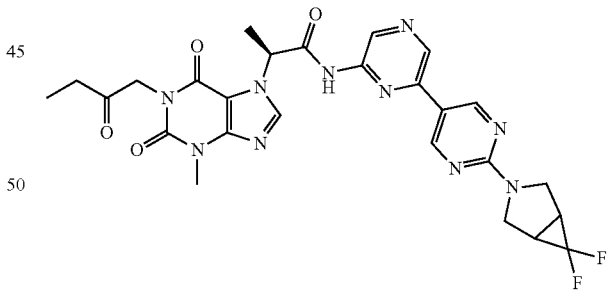

This compound was prepared using the method described for compound 2 with appropriate starting materials. ¹H NMR (400 MHz, DMSO-D6) δ 9.12 (s, 1H), 9.07 (s, 2H), 8.93 (s, 1H), 8.41 (s, 1H), 5.80 (d, J=7.4 Hz, 1H), 4.70 (d, J=2.1 Hz, 2H), 4.00 (d, J=12.1 Hz, 2H), 3.86 (d, J=10.5 Hz, 2H), 3.46 (s, 3H), 2.72 (d, J=10.7 Hz, 2H), 2.54 (d, J=3.8 Hz, 2H), 1.89 (d, J=7.3 Hz, 3H), 0.93 (t, J=7.3 Hz, 3H). Retention time (LC-MS): 2.283 min. MH+581. ee: 74.8%

Compound 76. (2S)-N-(6-(6-(6,6-difluoro-3-azabi-cyclo[3.1.0]hexan-3-yl)pyridin-3-yl)pyrazin-2-yl)-2-(3-methyl-2,6-dioxo-1-(2-oxopropyl)-2,3-dihydro-1H-purin-7(6H)-yl)propanamide

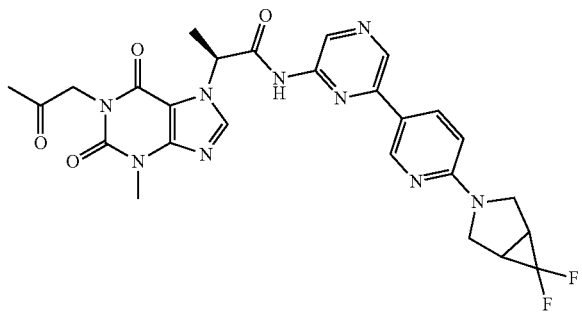 [SMILES: CC(=O)Cn1c(=O)c2c(ncn2[C@@H](C)C(=O)Nc2cncc(-c3ccc(N4CC5C(C4)C5(F)F)nc3)n2)n(C)c1=O]

This compound was prepared using the method described for compound 2 with appropriate starting materials in 7.7% yield (ee: 82.7%) as a white solid. ¹H NMR (400 MHz, DMSO-D6) δ 11.28 (s, 1H), 9.06 (s, 1H), 8.93-8.85 (m, 2H), 8.40 (s, 1H), 8.25 (dd, J=8.9, 2.4 Hz, 1H), 6.67 (d, J=9.0 Hz, 1H), 5.80 (d, J=6.9 Hz, 1H), 4.70 (s, 2H), 3.88 (d, J=11.2 Hz, 2H), 3.79 (d, J=9.2 Hz, 2H), 3.47 (s, 3H), 2.73 (d, J=9.9 Hz, 2H), 2.16 (s, 3H), 1.89 (d, J=7.3 Hz, 3H). Retention time (LC-MS): 1.466 min. MH⁺566.

Compound 77. (2S)-N-(6-(6-(6,6-difluoro-3-azabi-cyclo 13.1.01hexan-3-yl)pyridin-3-yl)pyrazin-2-yl)-2-(3-methyl-2,6-dioxo-1-(2-oxopropyl)-2,3-dihydro-1H-purin-7(6H)-yl)propanamide

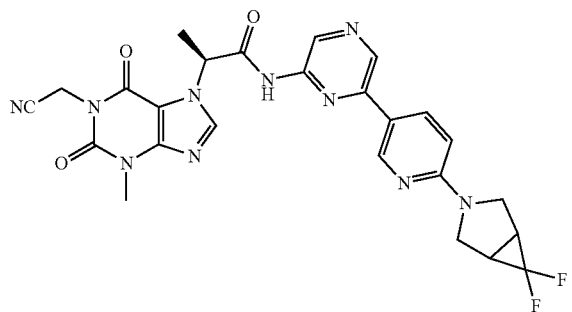 [SMILES: C[C@@H](C(=O)Nc1cncc(-c2ccc(N3CC4C(C3)C4(F)F)nc2)n1)n1cnc2c1c(=O)n(CC#N)c(=O)n2C]

This compound was prepared using the method described for compound 1 with appropriate starting materials in 17.6% yield (ee: 95.5%) as a white solid. ¹H NMR (400 MHz, DMSO-D6) δ 11.34 (s, 1H), 9.07 (s, 1H), 8.95-8.84 (m, 2H), 8.44 (s, 1H), 8.25 (dd, J=8.9, 2.4 Hz, 1H), 6.66 (d, J=8.9 Hz, 1H), 5.83 (d, J=7.1 Hz, 1H), 4.85 (s, 2H), 3.88 (d, J=11.3 Hz, 2H), 3.79 (d, J=9.6 Hz, 2H), 3.50 (s, 3H), 2.73 (d, J=10.8 Hz, 2H), 1.90 (d, J=7.3 Hz, 3H). Retention time (LC-MS): 1.558 min. MH⁺549.

Compound 78. (S)-2-(3-methyl-2,6-dioxo-1-(2-oxo-pentyl)-2,3-dihydro-1H-purin-7(6H)-yl)-N-(6-(2-(trifluoromethyl)pyrimidin-5-yl)pyridin-2-yl)pro-panamide

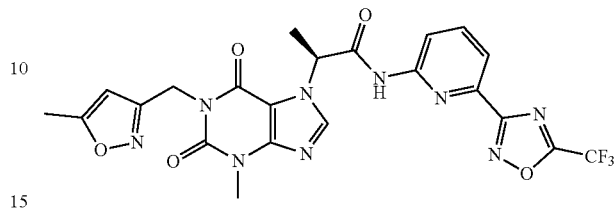

This compound was prepared using the method described for compound 2 with appropriate starting materials in 6.5% yield (ee: 69.3%) as a white solid. ¹H NMR (400 MHz, DMSO-D6) δ 11.54 (s, 1H), 8.40 (s, 1H), 8.25 (d, J=8.8 Hz, 1H), 8.12-8.02 (m, 1H), 7.92 (d, J=7.6 Hz, 1H), 6.08 (s, 1H), 5.83 (d, J=7.2 Hz, 1H), 5.02 (s, 2H), 3.47 (s, 3H), 2.31 (s, 3H), 1.87 (d, J=7.2 Hz, 3H). Retention time (LC-MS): 2.445 min. MH⁺546.

Compound 79. (2S)-N-(2-(6-(6,6-difluoro-3-azabi-cyclo[3.1.0]hexan-3-yl)pyridin-3-yl)thiazol-4-yl)-2-(3-methyl-2,6-dioxo-1-(2-oxopropyl)-2,3-dihydro-1H-purin-7(6H)-yl)propanamide

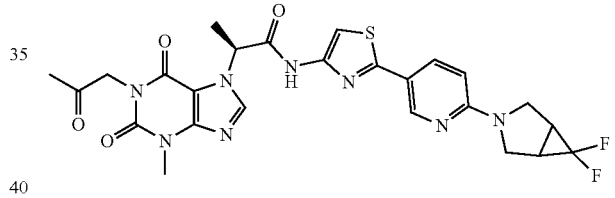

This compound was prepared using the method described for compound 2 with appropriate starting materials in 68.8% yield as a yellow solid. ¹H NMR (400 MHz, DMSO-D6) δ 11.56 (s, 1H), 8.64 (d, J=2.1 Hz, 1H), 8.39 (s, 1H), 7.97 (dd, J=8.9, 2.3 Hz, 1H), 7.42 (s, 1H), 6.61 (d, J=8.9 Hz, 1H), 5.70 (d, J=7.3 Hz, 1H), 4.70 (s, 2H), 3.85 (d, J=11.3 Hz, 2H), 3.76 (d, J=10.4 Hz, 2H), 3.46 (s, 3H), 2.73 (d, J=11.2 Hz, 2H), 2.17 (s, 3H), 1.84 (d, J=7.2 Hz, 3H). Retention time (LC-MS): 1.591 min. MH⁺571.

Compound 80. (2S)-N-(2-(6-(6,6-difluoro-3-azabi-cyclo[3.1.0]hexan-3-yl)pyridin-3-yl)thiazol-4-yl)-2-(3-methyl-2,6-dioxo-1-(2-oxobutyl)-2,3-dihydro-1H-purin-7(6H)-yl)propanamide

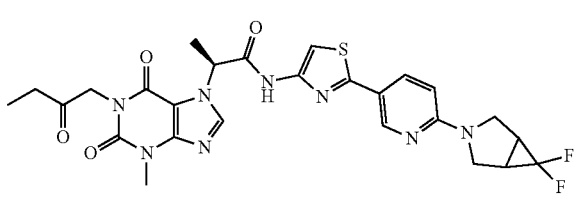 [SMILES: CCC(=O)Cn1c(=O)c2c(ncn2[C@@H](C)C(=O)Nc2csc(-c3ccc(N4CC5C(C4)C5(F)F)nc3)n2)n(C)c1=O]

This compound was prepared using the method described in Compound 2 with appropriate starting materials in 59.1% yield as yellow solid. ¹H NMR (400 MHz, DMSO-D6)δ 11.55 (s, 1H), 8.64 (d, J=2.3 Hz, 1H), 8.38 (s, 1H), 7.96 (dd, J=8.9, 2.4 Hz, 1H), 7.42 (s, 1H), 6.60 (d, J=8.9 Hz, 1H), 5.70 (d, J=7.3 Hz, 1H), 4.69 (d, J=2.4 Hz, 2H), 3.85 (d, J=11.4 Hz, 2H), 3.76 (d, J=9.6 Hz, 2H), 3.45 (s, 3H), 2.72 (d, J=10.9 Hz, 2H), 2.53 (d, J=7.4 Hz, 2H), 1.83 (d, J=7.3 Hz, 3H), 0.94 (t, J=7.3 Hz, 3H). Retention time (LC-MS): 1.813 min. MH⁺585.

Compound 81. (S)-N-(2-(5-chloro-6-methylpyridin-3-yl)thiazol-4-yl)-2-(3-methyl-2,6-dioxo-1-(2-oxo-propyl)-2,3-dihydro-1H-purin-7(6H)-yl)propanamide

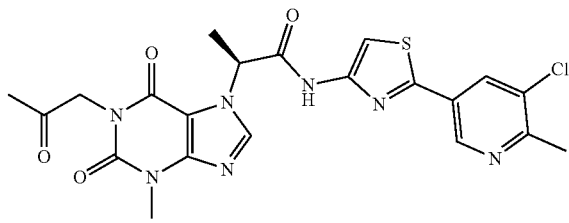 [SMILES: CC(=O)Cn1c(=O)c2c(ncn2[C@@H](C)C(=O)Nc2csc(-c3cnc(C)c(Cl)c3)n2)n(C)c1=O]

This compound was prepared using the method described for compound 2 with appropriate starting materials in 18.7% yield as light yellow solid. ¹H NMR (400 MHz, DMSO-D6) δ 11.69 (s, 1H), 8.95 (d, J=1.9 Hz, 1H), 8.40 (s, 1H), 8.30 (d, J=1.9 Hz, 1H), 7.68 (s, 1H), 5.71 (d, J=7.3 Hz, 1H), 4.70 (d, J=1.2 Hz, 2H), 3.46 (s, 3H), 2.61 (s, 3H), 2.17 (s, 3H), 1.85 (d, J=7.3 Hz, 3H). Retention time (LC-MS): 1.737 min. MH⁺502.

Compound 82. (S)-2-(3-methyl-2,6-dioxo-1-(2-oxo-propyl)-2,3-dihydro-1H-purin-7(6H)-yl)-N-(2-(5-methyl-6-(trifluoromethyl)pyridin-3-yl)thiazol-4-yl)propanamide

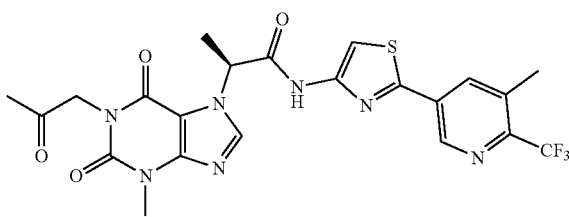 [SMILES: CC(=O)Cn1c(=O)c2c(ncn2[C@@H](C)C(=O)Nc2csc(-c3cnc(C(F)(F)F)c(C)c3)n2)n(C)c1=O]

This compound was prepared using the method described for compound 2 with appropriate starting materials in 56.2% yield as yellow solid. ¹H NMR (400 MHz, DMSO-D6)δ 11.76 (s, 1H), 9.07 (s, 1H), 8.39 (s, 2H), 7.76 (s, 1H), 5.72 (d, J=7.3 Hz, 1H), 4.70 (s, 2H), 3.46 (s, 3H), 2.55 (d, J=1.5 Hz, 3H), 2.16 (s, 3H), 1.86 (d, J=7.3 Hz, 3H). Retention time (LC-MS): 2.286

Compound 83. (S)-2-(3-methyl-2,6-dioxo-1-(2-oxobutyl)-2,3-dihydro-1H-purin-7(6H)-yl)-N-(2-(5-methyl-6-(trifluoromethyl)pyridin-3-yl)thiazol-4-yl)propanamide

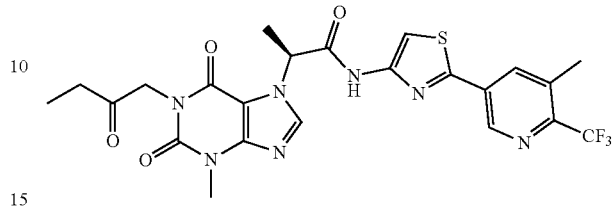

This compound was prepared using the method described for compound 2 with appropriate starting materials in 45.5% yield as light yellow solid. ¹H NMR (400 MHz, DMSO-D6)δ 11.76 (s, 1H), 9.06 (s, 1H), 8.39 (s, 2H), 7.76 (s, 1H), 5.72 (d, J=7.3 Hz, 1H), 4.69 (d, J=2.4 Hz, 2H), 3.46 (s, 3H), 2.55 (d, J=1.6 Hz, 3H), 2.53 (d, J=7.6 Hz, 2H), 1.86 (d, J=7.3 Hz, 3H), 0.94 (t, J=7.3 Hz, 3H). Retention time (LC-MS): 2.488 min. MH⁺550.

Compound 84. (2S)-N-(6-(6-(6,6-difluoro-3-azabi-cyclo[3.1.0]hexan-3-yl)pyridin-3-yl)pyrazin-2-yl)-2-(3-methyl-2,6-dioxo-1-(2-oxobutyl)-2,3-dihydro-1H-purin-7(6H)-yl)propanamide

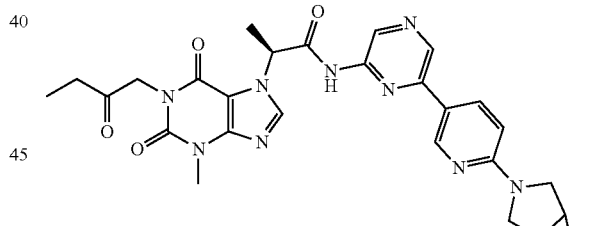

This compound was prepared using the method described for compound 2 with appropriate starting materials in 15.0% yield as a white solid. ¹H NMR (400 MHz, DMSO-D6) δ 11.31 (s, 1H), 9.06 (s, 1H), 8.93-8.86 (m, 2H), 8.41 (s, 1H), 8.24 (dd, J=8.9, 2.4 Hz, 1H), 6.65 (d, J=8.9 Hz, 1H), 5.79 (d, J=6.6 Hz, 1H), 4.70 (d, J=2.1 Hz, 2H), 3.88 (d, J=11.2 Hz, 2H), 3.78 (d, J=9.7 Hz, 2H), 3.47 (s, 3H), 2.73 (d, J=10.9 Hz, 2H), 2.58-2.52 (m, 2H), 1.89 (d, J=7.3 Hz, 3H), 0.94 (t, J=7.3 Hz, 3H). Retention time (LC-MS): 0.837 min. MH⁺580.

Compound 85. (S)-2-(3-methyl-1-((5-methylisoxazol-3-yl)methyl)-2,6-dioxo-2,3-dihydro-1H-purin-7(6H)-yl)-N-(2-(5-methyl-6-(trifluoromethyl)pyridin-3-yl)pyrimidin-4-yl)propanamide

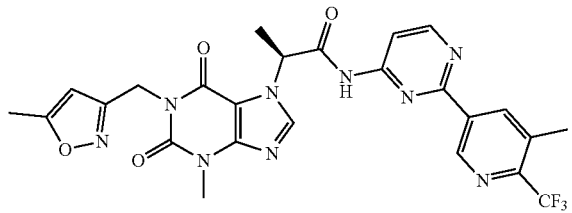

This compound was prepared using the method described for compound 2 with appropriate starting materials in 17.6% yield as a white solid. ¹H NMR (400 MHz, DMSO-D6) δ 9.39 (s, 1H), 8.86 (d, J=5.8 Hz, 1H), 8.74 (s, 1H), 8.42 (s, 1H), 8.00 (d, J=5.7 Hz, 1H), 6.08 (s, 1H), 5.82 (d, J=7.3 Hz, 1H), 5.01 (s, 2H), 3.48 (s, 3H), 2.58 (s, 3H), 2.30 (s, 3H), 1.89 (d, J=7.3 Hz, 3H). Retention time (LC-MS): 2.482 min. MH⁺570.

Compound 86. (2S)-N-(2-(2-(3-azabicyclo[3.1.0]hexan-3-yl)pyrimidin-5-yl)thiazol-4-yl)-2-(1-(2-methoxyethyl)-3-methyl-2,6-dioxo-2,3-dihydro-1H-purin-7(6H)-yl)propanamide

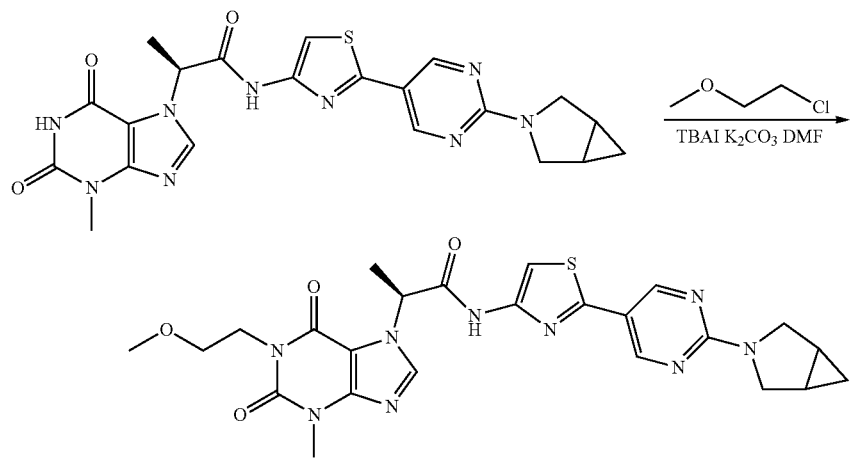

A mixture of (2S)-N-(2-(2-(3-azabicyclo[3.1.0]hexan-3-yl)pyrimidin-5-yl)thiazol-4-yl)-2-(3-methyl-2,6-dioxo-2,3-dihydro-1H-purin-7(6H)-yl)propanamide (50 mg, 0.104 mmol), 1-chloro-2-methoxyethane (14 mg, 0.104 mmol), potassium carbonate (14 mg, 0.104 mmol) and a catalytic amount of TBAI in N, N-dimethyl formamide (1 mL) was stirred at 50° C. for 2 hrs. The mixture was diluted with EA and washed with water, brine successively, dried and concentrated to give crude product, which was purified via preparative HPLC to give (2S)-N-(2-(2-(3-azabicyclo[3.1.0]hexan-3-yl)pyrimidin-5-yl)thiazol-4-yl)-2-(1-(2-methoxyethyl)-3-methyl-2,6-dioxo-2,3-dihydro-1H-purin-7(6H)-yl)propanamide (5.1 mg, 9.1% yield) as a white solid. ¹H NMR (400 MHz, DMSO-D6) δ 11.62 (s, 1H), 8.82 (s, 2H), 8.35 (s, 1H), 7.48 (s, 1H), 5.75 (m, J=7.3 Hz, 1H), 4.01 (m, J=6.0 Hz, 2H), 3.84 (m, J=11.4 Hz, 2H), 3.57 (s, 2H), 3.43 (m, 5H), 3.20 (s, 3H), 1.83 (m, J=7.3 Hz, 3H), 1.72 (m, 2H), 0.76 (m, 1H), 0.16 (m, 1H). Retention time (LC-MS): 1.897 min. MH⁺537.

Compound 87. (S)-2-(3-methyl-1-(2-(methylamino)-2-oxoethyl)-2,6-dioxo-2,3-dihydro-1H-purin-7(6H)-yl)-N-(6-(2-(trifluoromethyl)pyrimidin-5-yl)pyridin-2-yl)propanamide

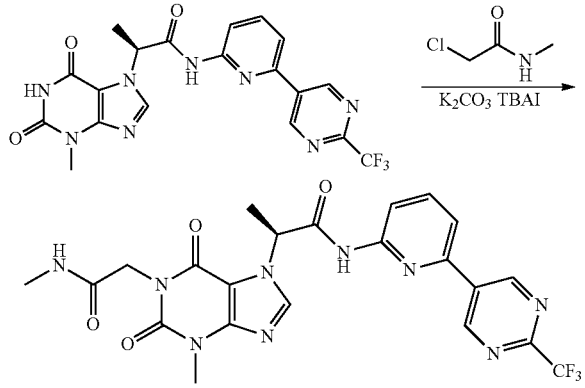

A mixture of (S)-2-(3-methyl-2,6-dioxo-2,3-dihydro-1H-purin-7(6H)-yl)-N-(6-(2-(trifluoromethyl)pyrimidin-5-yl)pyridin-2-yl)propanamide (50 mg, 0.108 mmol), 2-chloro-N-methylacetamide (12 mg, 0.108 mmol), potassium carbonate (15 mg, 0.108 mmol) and a catalytic amount of TBAI in N, N-dimethyl formamide (1 mL) was stirred at 50° C. for 2 hrs. The mixture was diluted with EA and washed with water, brine successively, dried and concentrated to give crude product, which was purified via preparative HPLC to give (S)-2-(3-methyl-1-(2-(methylamino)-2-oxoethyl)-2,6-dioxo-2,3-dihydro-1H-purin-7(6H)-yl)-N-(6-(2-(trifluoromethyl)pyrimidin-5-yl)pyridin-2-yl)propanamide (2.8 mg, 5% yield) as a white solid. ¹E1 NMR (400 MHz, DMSO-D6) δ 11.30 (s, 1H), 9.68 (s, 2H), 8.41 (s, 1H), 8.12 (m, J=6.9 Hz, 1H), 8.12 (m, 3H), 5.83 (s, 1H), 4.37 (m, J=7.5 Hz, 2H), 3.46 (s, 3H), 2.54 (m, J=4.5 Hz, 3H), 1.88 (m, J=7.3 Hz, 3H). Retention time (LC-MS): 1.383 min. MH⁺531.

Compound 88. (2S)-2-(3-methyl-1-(oxetan-2-ylmethyl)-2,6-dioxo-2,3-dihydro-1H-purin-7(6H)-yl)-N-(6-(2-(trifluoromethyl)pyrimidin-5-yl)pyridin-2-yl)propanamide

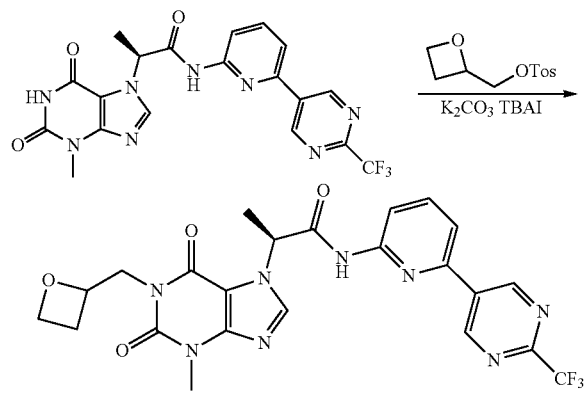

A mixture of (S)-2-(3-methyl-2,6-dioxo-2,3-dihydro-1H-purin-7(6H)-yl)-N-(6-(2-(trifluoromethyl)pyrimidin-5-yl)pyridin-2-yl)propanamide (50 mg, 0.108 mmol), oxetan-2-ylmethyl 4-methylbenzenesulfonate (26 mg, 0.108 mmol), potassium carbonate (15 mg, 0.108 mmol) and a catalytic amount of TBAI in N, N-dimethyl formamide (1 mL) was stirred at 50° C. for 2 hrs. The mixture was diluted with EA and washed with water, brine successively, dried and concentrated to give crude product, which was purified via preparative HPLC to give (2S)-2-(3-methyl-1-(oxetan-2-ylmethyl)-2,6-dioxo-2,3-dihydro-1H-purin-7(6H)-yl)-N-(6-(2-(trifluoromethyl)pyrimidin-5-yl)pyridin-2-yl)propanamide (7.2 mg, 12.6% yield) as a white solid. $^1$H NMR (400 MHz, DMSO-D6) δ 11.28 (s, 1H), 9.68 (s, 2H), 8.37 (m, J=1.2 Hz, 1H), 8.11 (m, J=7.1 Hz, 1H), 8.01 (m, J=8.2 Hz, 2H), 5.83 (s, 1H), 4.83 (m, 1H), 4.41 (m, 2H), 4.11 (m, 2H), 3.45 (s, 3H), 2.59 (m, 1H), 2.42 (m, J=8.5 Hz, 1H), 1.87 (m, J=7.3 Hz, 3H). Retention time (LC-MS): 1.841 min. MH$^+$530.

Compound 89. (S)-2-(3-methyl-1-(3-methyl-2-oxobutyl)-2,6-dioxo-2,3-dihydro-1H-purin-7(6H)-yl)-N-(6-(2-(trifluoromethyl)pyrimidin-5-yl)pyridin-2-yl)propanamide

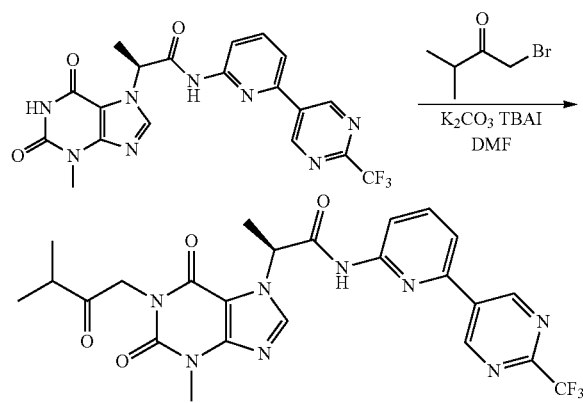

A mixture of (S)-2-(3-methyl-2,6-dioxo-2,3-dihydro-1H-purin-7(6H)-yl)-N-(6-(2-(trifluoromethyl)pyrimidin-5-yl)pyridin-2-yl)propanamide (50 mg, 0.108 mmol), 1-bromo-3-methylbutan-2-one (17 mg, 0.108 mmol), potassium carbonate (15 mg, 0.108 mmol) and a catalytic amount of TBAI in N, N-dimethyl formamide (1 ml) was stirred at 50° C. for 2 hrs. The mixture was diluted with EA and washed with water, brine successively, dried and concentrated to give crude product, which was purified via preparative HPLC to give (S)-2-(3-methyl-1-(3-methyl-2-oxobutyl)-2,6-dioxo-2,3-dihydro-1H-purin-7(6H)-yl)-N-(6-(2-(trifluoromethyl)pyrimidin-5-yl)pyridin-2-yl)propanamide (20.7 mg, 35.1% yield) as a white solid. 1H NMR (400 MHz, DMSO-D6) δ 11.28 (s, 1H), 9.68 (s, 2H), 8.42 (s, 1H), 8.12 (m, J=7.4 Hz, 1H), 7.99 (m, 2H), 5.82 (s, 1H), 4.79 (s, 2H), 3.47 (s, 3H), 2.79 (m, 1H), 1.89 (m, J=7.3 Hz, 3H), 1.05 (m, 6H). Retention time (LC-MS): 2.519 min. MH$^+$544.

Compound 90. (S)-N-(2-(5-chloro-6-methylpyridin-3-yl)thiazol-4-yl)-2-(1,3-dimethyl-2,6-dioxo-2,3-dihydro-1H-purin-7(6H)-yl)propanamide

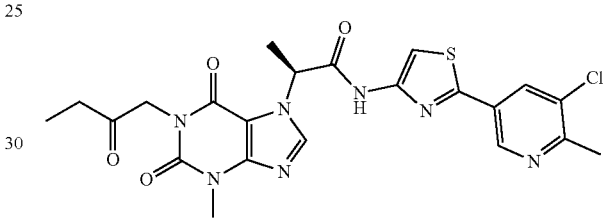

This compound was prepared using the method described for compound 2 with appropriate starting materials and purified via preparative HPLC in 50% yield as a white solid. $^1$H NMR (400 MHz, DMSO-D6) δ 11.69 (s, 1H), 8.95 (d, J=2.0 Hz, 1H), 8.34 (s, 1H), 8.29 (d, J=2.4 Hz, 1H), 7.68 (s, 1H), 5.71 (d, J=7.2 Hz, 1H), 4.69 (d, J=2.4 Hz, 2H), 2.53 (q, J=7.2 Hz,2H),3.46 (s, 3H), 2.61 (s, 3H), 1.85 (d, J=7.2 Hz, 3H), 0.94 (t, J=7.2 Hz, 3H). Retention time (LC-MS): 2.098 min. MH$^+$516.

Compound 91. (S)-N-(2-(5-chloro-6-methylpyridin-3-yl)thiazol-4-yl)-2-(1,3-dimethyl-2,6-dioxo-2,3-dihydro-1H-purin-7(6H)-yl)propanamide

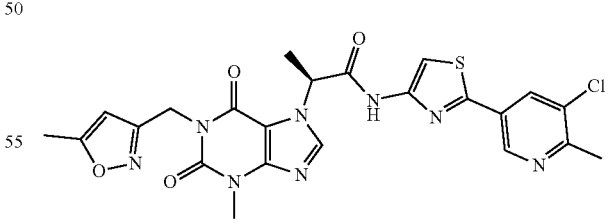

This compound was prepared using the method described for compound 2 with appropriate starting materials in 20% yield as a white solid. $^1$H-NMR (400 MHz, DMSO-D6) δ 11.72 (s, 1H), 11.72 (s, 1H), 8.95 (d, J=1.6 Hz, 1H), 8.40 (s, 1H), 8.30 (s, 1H), 7.68 (s, 1H), 6.09 (s, 1H), 5.75 (d, J=7.2 Hz, 1H), 5.02 (s, 2H), 3.55 (s, 1H), 2.61 (s, 3H), 2.31 (s, 3H), 1.85 (d, J=7.2 Hz, 3H). Retention time (LC-MS): 2.088 min. MH$^+$541.

Compound 92. (S)-N-(2-(5-fluoro-6-methylpyridin-3-yl)thiazol-4-yl)-2-(3-methyl-2,6-dioxo-1-(2-oxopropyl)-2,3-dihydro-1H-purin-7(6H)-yl)propanamide

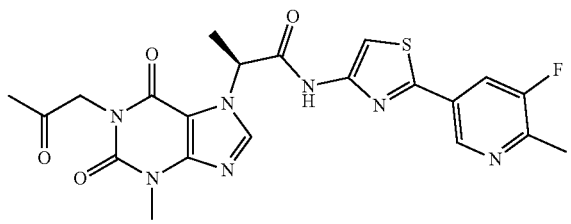 [SMILES: CC(=O)Cn1c(=O)c2c(ncn2[C@@H](C)C(=O)Nc2csc(-c3cnc(C)c(F)c3)n2)n(C)c1=O]

This compound was prepared using the method described for compound 2 with appropriate starting materials in 2.6% yield as a white solid. $^1$H NMR (400 MHz, DMSO-D6) δ 11.69 (s, 1H), 8.87 (s, 1H), 8.39 (s, 1H), 8.09 (d, J=10.4 Hz, 1H), 7.68 (s, 1H), 5.72 (d, J=7.2 Hz, 1H), 4.70 (s, 2H), 3.46 (s, 3H), 2.52 (m, 3H), 2.17 (s, 3H), 1.85 (d, J=7.2 Hz, 3H). Retention time (LC-MS): 1.544 min. MH$^+$486.

Compound 93. (S)-2-(3-methyl-1-((5-methylisoxazol-3-yl)methyl)-2,6-dioxo-2,3-dihydro-1H-purin-7(6H)-yl)-N-(6-(5-oxo-2,5-dihydro-1,2,4-oxadiazol-3-yl)pyridin-2-yl)propanamide

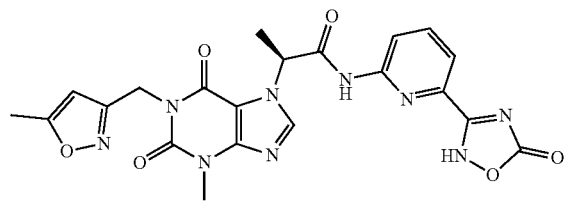 [SMILES: Cc1cc(Cn2c(=O)c3c(ncn3[C@@H](C)C(=O)Nc3cccc(-c4nc(=O)o[nH]4)n3)n(C)c2=O)no1]

This compound was prepared using the method described for compound 2 with appropriate starting materials in 7.7% yield as a white solid. 1H NMR (400 MHz, DMSO-D6) δ 11.25 (s, 1H), 8.39 (s, 1H), 8.15 (s, 1H), 8.05 (d, J=7.9 Hz, 1H), 7.91 (t, J=7.9 Hz, 1H), 7.61 (d, J=7.5 Hz, 1H), 6.08 (s, 1H), 5.82 (d, J=6.7 Hz, 1H), 5.09-4.92 (m, 2H), 3.47 (s, 3H), 2.31 (s, 3H), 1.85 (d, J=7.2 Hz, 3H). Retention time (LC-MS): 3.437 min. MH$^+$494.

Compound 94. (S)-2-(3-methyl-1-((5-methylisoxazol-3-yl)methyl)-2,6-dioxo-2,3-dihydro-1H-purin-7(6H)-yl)-N-(2-(5-methyl-6-(trifluoromethyl)pyridin-3-yl)thiazol-4-yl)propanamide

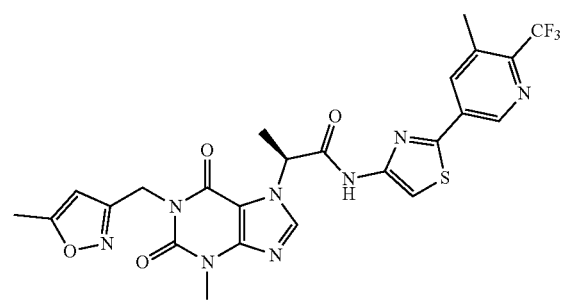 [SMILES: Cc1cc(Cn2c(=O)c3c(ncn3[C@@H](C)C(=O)Nc3csc(-c4cnc(C(F)(F)F)c(C)c4)n3)n(C)c2=O)no1]

This compound was prepared using the method described for compound 2 with appropriate starting materials in 54.1% yield as a yellow solid. 1H NMR (400 MHz, DMSO-D6) δ 11.79 (s, 1H), 9.07 (s, 1H), 8.41 (s, 2H), 7.78 (s, 1H), 6.10 (s, 1H), 5.77 (d, J=7.1 Hz, 1H), 5.03 (s, 2H), 3.48 (s, 3H), 2.56 (s, 3H), 2.32 (s, 3H), 1.87 (d, J=7.1 Hz, 3H). Retention time (LC-MS): 2.044min. MH$^+$575.

Compound 95. (S)-2-(1-(isoxazol-3-ylmethyl)-3-methyl-2,6-dioxo-2,3-dihydro-1H-purin-7(6H)-yl)-N-(6'-(trifluoromethyl)-[2,3'-bipyridin]-6-yl)propanamide

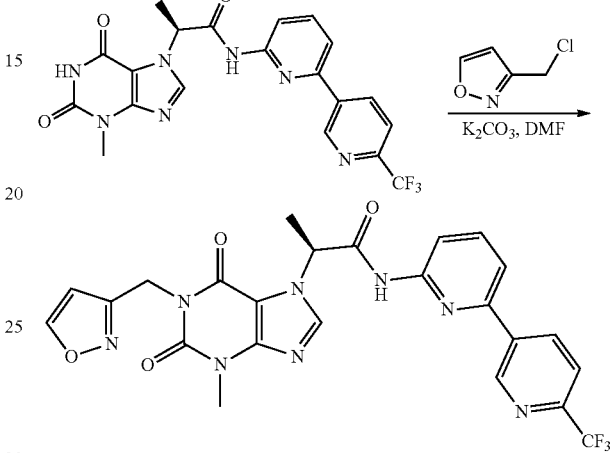

To a solution of (S)-2-(3-methyl-2,6-dioxo-2,3-dihydro-1H-purin-7(6H)-yl)-N-(6'-(trifluoromethyl)-[2,3'-bipyridin]-6-yl)propanamide (15 mg, 0.033 mmol) and POTASSIUM CARBONATE(9 mg, 0.065 mmol) in DMF (1 mL) was added 3-(chloromethyl)isoxazole (3.7 mg, 0.049 mmol). The mixture was stirred at rt overnight. The mixture was diluted with EA and washed with water, saturated aqueous NH$_4$Cl solution and brine, dried over Na$_2$SO$_4$, and evaporated. The residue was purified by silica gel column chromatography (0-2% MeOH/DCM) to give the product (S)-2-(1-(isoxazol-3-ylmethyl)-3-methyl-2,6-dioxo-2,3-dihydro-1H-purin-7(6H)-yl)-N-(6'-(trifluoromethyl)-[2,3'-bipyridin]-6-yl)propanamide (16.5 mg, 92% yield) as a white solid. $^1$H NMR (400 MHz, DMSO-D6) δ 11.20 (s, 1H), 9.43 (s, 1H), 8.78 (s, 1H), 8.68 (d, J=1.8 Hz, 1H), 8.39 (s, 1H), 7.89-8.05 (m, 4H), 6.45 (s, 1H), 5.82 (m, 1H), 5.09 (s, 2H), 3.47(s, 3H), 1.87 (d, J=7.3 Hz, 3H). MH$^+$541.

Compound 96. (S)-2-(3-methyl-1-((5-methylisoxazol-3-yl)methyl)-2,6-dioxo-2,3-dihydro-1H-purin-7(6H)-yl)-N-(6-(2-((S)-2-(trifluoromethyl)pyrrolidin-1-yl)pyrimidin-5-yl)pyrazin-2-yl)propanamide

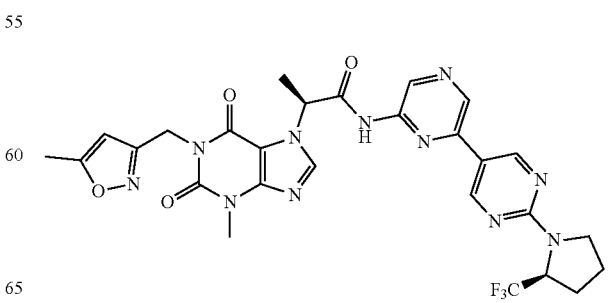

This compound was prepared using the method described for compound 1 with appropriate starting materials in 28% yield as a white solid. 1H NMR (400 MHz, DMSO-D6) δ 11.37 (s, 1H), 9.13 (m, 3H), 8.95 (s, 1H), 8.39 (s, 1H), 6.07 (s, 1H), 5.82 (d, J=7.1 Hz, 1H), 5.10 (m, 1 H), 5.01 (s, 2H), 3.70 (m, 2 H), 3.46 (s, 3H), 2.29 (s, 3H), 1.98-2.20 (m, 4H), 1.87 (d, J=7.1 Hz, 3H). MH$^+$626.

Compound 97 (S)-2-(3-methyl-2,6-dioxo-1-(2-oxo-propyl)-2,3-dihydro-1H-purin-7(6H)-yl)-N-(6'-methyl-5'-(trifluoromethyl)-[2,3'-bipyridin]-6-yl)propanamide

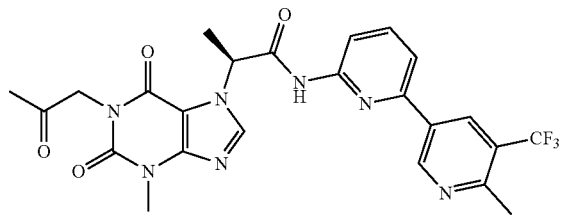 [SMILES: CC(=O)Cn1c(=O)c2c(ncn2[C@@H](C)C(=O)Nc2cccc(-c3cnc(C)c(C(F)(F)F)c3)n2)n(C)c1=O]

This compound was prepared using the method described for compound 2 with appropriate starting materials in 23.6% yield (ee: 90%) as a grey solid. $^1$H NMR (400 MHz, DMSO-d6) δ 11.14 (s, 1H), 9.41 (s, 1H), 8.70 (s, 1H), 8.39 (s, 1H), 8.02 (s, 1H), 7.98-7.90 (m, 2H), 5.79 (d, J=7.2 Hz, 1H), 4.74-4.64 (m, 2H), 3.46 (s, 3H), 2.71 (s, 3H), 2.15 (s, 3H), 1.87 (d, J=7.3 Hz, 3H). Retention time (LC-MS): 2.149 min. MH$^+$530.

Compound 98. (S)-2-(3-methyl-2,6-dioxo-1-(2-oxo-propyl)-2,3-dihydro-1H-purin-7(6H)-yl)-N-(2-(6-methyl-5-(trifluoromethyl)pyridin-3-yl)thiazol-4-yl)propanamide

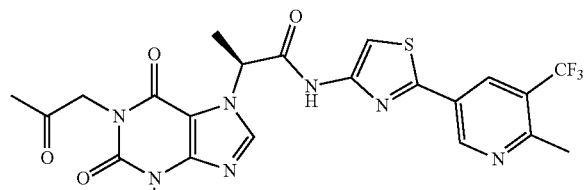

This compound was prepared using the method described for compound 2 with appropriate starting materials in 56.1% yield as a light yellow solid. $^1$H NMR (400 MHz, DMSO-d6) δ 11.70 (s, 1H), 9.22 (d, J=1.8 Hz, 1H), 8.46 (d, J=1.9 Hz, 1H), 8.38 (s, 1H), 7.70 (s, 1H), 5.71 (d, J=7.3 Hz, 1H), 4.69 (s, 2H), 3.46 (s, 3H), 2.70 (d, J=1.1 Hz, 3H), 2.16 (s, 3H), 1.85 (d, J=7.3 Hz, 3H). Retention time (LC-MS): 2.023 min. MH$^+$536.

Compound 99. (S)-2-(3-methyl-2,6-dioxo-1-(2-oxobutyl)-2,3-dihydro-1H-purin-7(6H)-yl)-N-(2-(6-methyl-5-(trifluoromethyl)pyridin-3-yl)thiazol-4-yl)propanamide

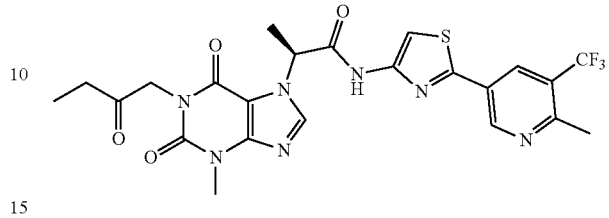

This compound was prepared using the method described for compound 2 with appropriate starting materials and purified via preparative HPLC, 54.7% yield as a light yellow solid. $^1$H NMR (400 MHz, DMSO-d6) δ 11.70 (s, 1H), 9.21 (s, 1H), 8.45 (s, 1H), 8.38 (s, 1H), 7.70 (s, 1H), 5.72 (q, J=7.1 Hz, 1H), 4.69 (d, J=2.2 Hz, 2H), 3.45 (s, 3H), 2.70 (s, 3H), 2.56-2.51 (m, 2H), 1.85 (d, J=7.3 Hz, 3H), 0.94 (t, J=7.3 Hz, 3H). Retention time (LC-MS): 2.195 min. MH$^+$550.

Compound 100. (S)-N-(2-(5-fluoro-6-methylpyridin-3-yl)thiazol-4-yl)-2-(3-methyl-1-((5-methylisoxazol-3-yl)methyl)-2,6-dioxo-2,3-dihydro-1H-purin-7(6H)-yl)propanamide

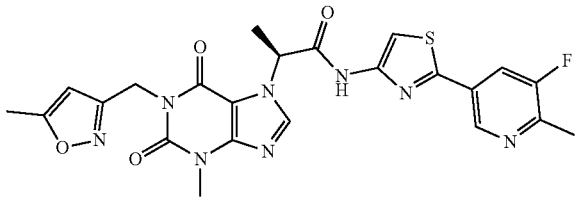

This compound was prepared using the method described for compound 2 with appropriate starting materials in 13.9% yield as a white solid. $^1$H NMR (400 MHz, DMSO-d6) δ 11.71 (s, 1H), 8.86 (s, 1H), 8.40 (s, 1H), 8.12-8.05 (m, 1H), 7.68 (s, 1H), 6.09 (s, 1H), 5.75 (q, J=7.6 Hz, 1H), 5.02 (s, 2H), 3.47 (s, 3H), 2.51 (s, 3H), 2.31 (s, 3H), 1.85 (d, J=7.2 Hz, 3H). Retention time (LC-MS): 1.306 min. MH$^+$525.

Compound 101. (S)-N-(2-(5-fluoro-6-methylpyridin-3-yl)thiazol-4-yl)-2-(3-methyl-2,6-dioxo-1-(2-oxobutyl)-2,3-dihydro-1H-purin-7(6H)-yl)propanamide

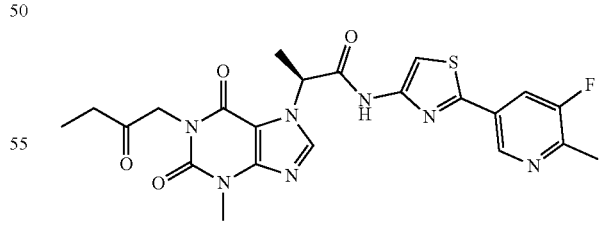

This compound was prepared using the method described for compound 2 with appropriate starting materials in 16.7% yield as a white solid. $^1$H NMR (400 MHz, DMSO-d6) δ 11.70 (s, 1H), 8.87 (s, 1H), 8.40 (s, 1H), 8.08 (dd, J=10.0, 1.8 Hz, 1H), 7.68 (s, 1H), 5.72 (d, J=7.2 Hz, 1H), 4.79-4.61 (m, 2H), 3.46 (s, 3H), 2.52 (m, 5H), 1.85 (d, J=7.2 Hz, 3H), 0.94 (t, J=7.2 Hz, 3H). Retention time (LC-MS): 1.807 min. MH$^+$500.

Compound 102. (2S)-N-(2-(2-(3-azabicyclo[3.1.0]hexan-3-yl)pyrimidin-5-yl)thiazol-4-yl)-2-(3-methyl-2,6-dioxo-1-(2,2,2-trifluoroethyl)-2,3-dihydro-1H-purin-7(6H)-yl)propanamide

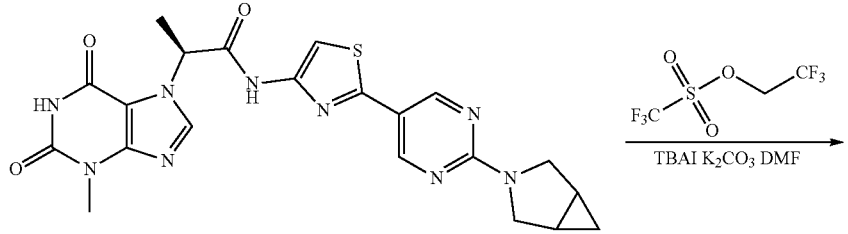

A mixture of (2S)-N-(2-(2-(3-azabicyclo[3.1.0]hexan-3-yl)pyrimidin-5-yl)thiazol-4-yl)-2-(3-methyl-2,6-dioxo-2,3-dihydro-1H-purin-7(6H)-yl)propanamide (50 mg, 0.104 mmol), 2,2,2-trifluoroethyl trifluoromethanesulfonate (24 mg, 0.104 mmol), potassium carbonate (14 mg, 0.104 mmol) and a catalytic amount of TBAI in DMF (1 mL) was stirred at 50° C. for 2 hrs. The mixture was diluted with EA and washed with water, brine successively, dried and concentrated to give crude product, which was purified via preparative HPLC to give (2S)-N-(2-(2-(3-azabicyclo[3.1.0]hexan-3-yl)pyrimidin-5-yl)thiazol-4-yl)-2-(3-methyl-2,6-dioxo-1-(2,2,2-trifluoroethyl)-2,3-dihydro-1H-purin-7(6H)-yl)propanamide (8.7 mg, 14.9% yield) as a white solid. $^1$H NMR (400 MHz, DMSO-d6) δ 11.63 (s, 1H), 8.80 (s, 2H), 8.38 (m, 1H), 7.45 (s, 1H), 5.70 (m, J=7.3 Hz, 1H), 4.62 (m, 2H), 3.82 (m, J=11.4 Hz, 2H), 3.54 (m, J=10.1 Hz, 2H), 3.47 (s, 3H), 1.83 (m, J=7.3 Hz, 3H), 1.68 (m, 2H), 0.77 (m, J=12.4, 7.9 Hz, 1H), 0.15 (m, 1H). Retention time (LC-MS): 2.335 min. MH$^+$561.

Compound 103. (2S)-N-(2-(2-(3-azabicyclo[3.1.0]hexan-3-yl)pyrimidin-5-yl)thiazol-4-yl)-2-(3-methyl-2,6-dioxo-1-(3,3,3-trifluoropropyl)-2,3-dihydro-1H-purin-7(6H)-yl)propanamide

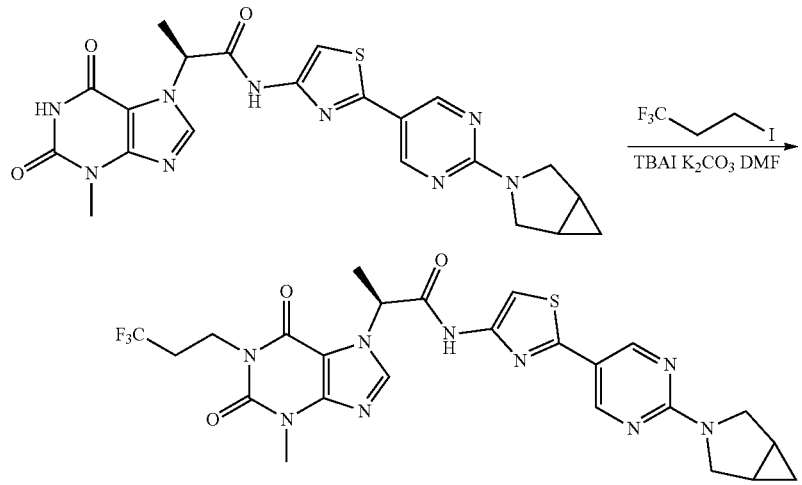

A mixture of (2S)-N-(2-(2-(3-azabicyclo[3.1.0]hexan-3-yl)pyrimidin-5-yl)thiazol-4-yl)-2-(3-methyl-2,6-dioxo-2,3-dihydro-1H-purin-7(6H)-yl)propanamide (50 mg, 0.104 mmol), 1,1,1-trifluoro-3-iodopropane (23 mg, 0.104 mmol), potassium carbonate (14 mg, 0.104 mmol) and a catalytic amount of TBAI in DMF (1 mL) was stirred at 50° C. for 2 hrs. The mixture was diluted with EA and washed with water, brine successively, dried and concentrated to give crude product, which was purified via preparative HPLC to give (2S)-N-(2-(2-(3-azabicyclo[3.1.0]hexan-3-yl)pyrimidin-5-yl)thiazol-4-yl)-2-(3-methyl-2,6-dioxo-1-(3,3,3-trifluoropropyl)-2,3-dihydro-1H-purin-7(6H)-yl)propanamide (12.1 mg, 20% yield) as a white solid. 1H NMR (400 MHz, DMSO-d6) δ 11.62 (s, 1H), 8.81 (s, 2H), 8.36 (s, 1H), 7.46 (s, 1H), 5.75 (m, J=7.3 Hz, 1H), 4.06 (m, 2H), 3.83 (m, J=11.4 Hz, 2H), 3.55 (m, J=11.0 Hz, 2H), 3.45 (s, 3H), 2.55 (m, 2H), 1.83 (m, J=7.3 Hz, 3H), 1.68 (m, 2H), 0.77 (m, 1H), 0.16 (m, 1H). Retention time (LC-MS): 2.427 min. MH+575.

Compound 104 (S)-2-(3-methyl-1-((3-methyl-1,2,4-oxadiazol-5-yl)methyl)-2,6-dioxo-2,3-dihydro-1H-purin-7(6H)-yl)-N-(6-(2-(trifluoromethyl)pyrimidin-5-yl)pyridin-2-yl)propanamide

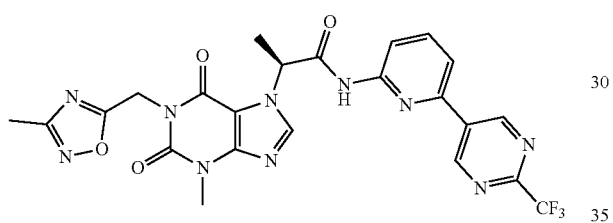

This compound was prepared using the method described for Compound 2 with appropriate starting materials in 18% yield as a white solid. 1H NMR (400 MHz, DMSO) δ 11.29 (s, 1H), 9.66 (s, 2H), 8.46 (s, 1H), 8.11 (d, J=7.5 Hz, 1H), 8.06-7.97 (m, 2H), 5.82 (s, 1H), 5.33-5.21 (m, 2H), 3.49 (s, 3H), 2.26 (s, 3H), 1.89 (d, J=7.3 Hz, 3H). Retention time (LC-MS): 2.333 min. MH+557.

Compound 105. (2S)-N-(2-(2-(3-azabicyclo[3.1.0]hexan-3-yl)pyrimidin-5-yl)thiazol-4-yl)-2-(1-(3-methoxy-2-oxopropyl)-3-methyl-2,6-dioxo-2,3-dihydro-1H-purin-7(6H)-yl)propanamide This compound was prepared using the method described for compound 2 with appropriate starting materials in 11.6% yield as a yellow solid. 1H NMR (400 MHz, DMSO-d6) δ 11.58 (s, 1H), 8.81 (s, 2H), 8.38 (s, 1H), 7.47 (s, 1H), 5.71 (m, J=7.3 Hz, 1H), 4.74 (s, 2H), 4.21 (s, 2H), 3.84 (m, J=11.4 Hz, 2H), 3.56 (m, J=11.6 Hz, 2H), 3.46 (s, 3H), 3.32 (s, 3H), 1.84 (m, J=7.2 Hz, 3H), 1.71 (s, 2H), 0.78 (m, J=4.5 Hz, 1H), 0.16 (m, J=4.3 Hz, 1H). Retention time (LC-MS): 1.918 min. MH+565.

Compound 106. (2S)-N-(2-(2-(3-azabicyclo[3.1.0]hexan-3-yl)pyrimidin-5-yl)thiazol-4-yl)-2-(1-(2-hydroxy-3-methoxypropyl)-3-methyl-2,6-dioxo-2,3-dihydro-1H-purin-7(6H)-yl)propanamide

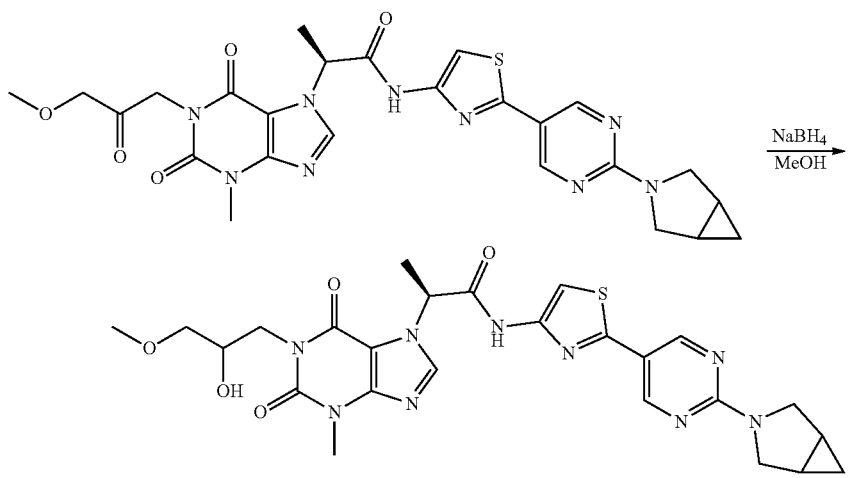

To a solution of (2S)-N-(2-(2-(3-azabicyclo[3.1.0]hexan-3-yl)pyrimidin-5-yl)thiazol-4-yl)-2-(1-(3-methoxy-2-oxopropyl)-3-methyl-2,6-dioxo-2,3-dihydro-1H-purin-7(6H)-yl)propanamide (50 mg, 0.088 mmol) in MeOH (1 mL) was added sodium borohydride (334 mg, 0.088 mmol) at 0° C. and the mixture was stirred at -10° C. for 2 hrs. The mixture was quenched with diluted hydrochloride acid (0.2 mL, 1N) and the mixture was concentrated to dryness to give a residue, which was purified via preparative HPLC to afford (2S)-N-(2-(2-(3-azabicyclo[3.1.0]hexan-3-yl)pyrimidin-5-yl)thiazol-4-yl)-2-(1-(2-hydroxy-3-methoxypropyl)-3-methyl-2,6-dioxo-2,3-dihydro-1H-purin-7(6H)-yl)propanamide (28.3 mg, 56.6% yield) as a white solid. $^1$H-NMR (400 MHz, DMSO-d6) δ 11.60 (s, 1H), 8.81 (s, 2H), 8.32 (s, 1H), 7.46 (m, J=1.1 Hz, 1H), 5.75 (m, J=7.0 Hz, 1H), 4.87 (m, J=4.7 Hz, 1H), 3.92 (m, 2H), 3.83 (m, J=11.4 Hz, 2H), 3.75 (m, J=7.2 Hz, 1H), 3.55 (m, J=11.1 Hz, 2H), 3.44 (s, 3H), 3.21 (m, J=5.3 Hz, 2H), 3.16 (m, 3H), 1.82 (m, J=7.3 Hz, 3H), 1.67 (m, 2H), 0.77 (m, J=12.6, 7.8 Hz, 1H), 0.15 (m, 1H). Retention time (LC-MS): 1.773 min. MH$^+$567.

Compound 107. (S)-2-(3-methyl-1-((3-methyl-1,2,4-oxadiazol-5-yl)methyl)-2,6-dioxo-2,3-dihydro-1H-purin-7(6H)-yl)-N-(2-(5-methyl-6-(trifluoromethyl)pyridin-3-yl)thiazol-4-yl)propanamide

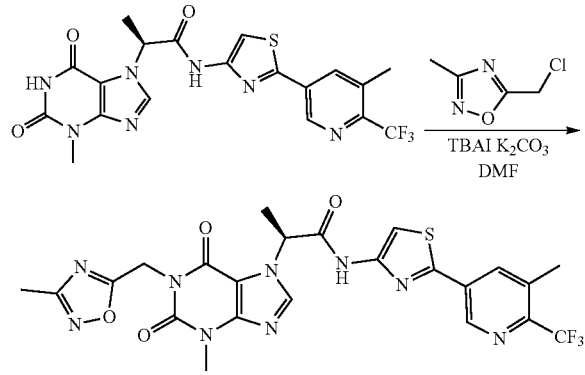

A mixture of (S)-2-(3-methyl-2,6-dioxo-2,3-dihydro-1H-purin-7(6H)-yl)-N-(2-(5-methyl-6-(trifluoromethyl)pyridin-3-yl)thiazol-4-yl)propanamide (50 mg, 0.104 mmol), 5-(chloromethyl)-3-methyl-1,2,4-oxadiazole (14 mg, 0.104 mmol), potassium carbonate (14 mg, 0.104 mmol) and a catalytic amount of TBAI in N,N-dimethyl formamide (1 mL) was stirred at 50° C. for 2 hrs. The mixture was concentrated to dryness and purified via preparative HPLC to afford (S)-2-(3-methyl-1-((3-methyl-1,2,4-oxadiazol-5-yl)methyl)-2,6-dioxo-2,3-dihydro-1H-purin-7(6H)-yl)-N-(2-(5-methyl-6-(trifluoromethyl)pyridin-3-yl)thiazol-4-yl)propanamide (12.1 mg, 20.2% yield) as a white solid. 1H NMR (400 MHz, DMSO-d6) δ 11.81 (s, 1H), 9.07 (s, 1H), 8.43 (m, 2H), 7.78 (s, 1H), 5.75 (m, J=7.1 Hz, 1H), 5.21 (m, 2H), 3.49 (s, 3H), 2.56 (s, 3H), 2.27 (s, 3H), 1.87 (m, J=7.3 Hz, 3H). Retention time (LC-MS): 2.321 min. MH$^+$575.

Compound 108. (S)-2-(3-methyl-1-((3-methyl-1,2,4-oxadiazol-5-yl)methyl)-2,6-dioxo-2,3-dihydro-1H-purin-7(6H)-yl)-N-(2-(6-methyl-5-(trifluoromethyl)pyridin-3-yl)thiazol-4-yl)propanamide

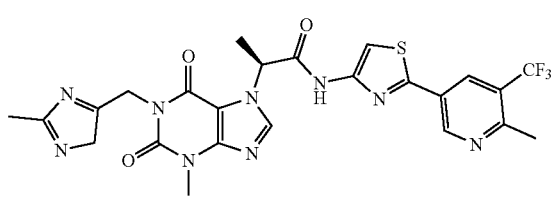

This compound was prepared using the method described for compound 1 with appropriate starting materials in 9.2% yield as a white solid. 1H NMR (400 MHz, DMSO-d6) δ 11.76 (s, 1H), 9.24 (m, J=1.8 Hz, 1H), 8.45 (m, 2H), 7.72 (s, 1H), 5.74 (m, J=7.1 Hz, 1H), 5.27 (m, 2H), 3.49 (s, 3H), 2.71 (m, J=1.2 Hz, 3H), 2.27 (s, 3H), 1.87 (m, J=7.3 Hz, 3H). Retention time (LC-MS): 2.183min. MH$^+$575.

Compound 109. (S)-2-(3-methyl-2,6-dioxo-1-(2-oxopropyl)-2,3-dihydro-1H-purin-7(6H)-yl)-N-(6-(6-methyl-5-(trifluoromethyl)pyridin-3-yl)pyrazin-2-yl)propanamide

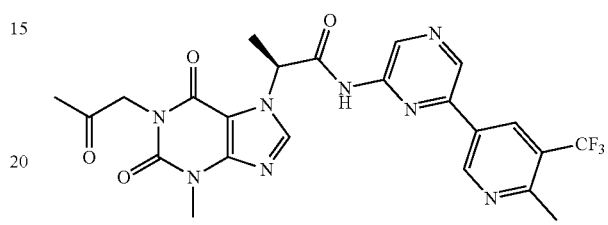

This compound was prepared using the method described for compound 2 with appropriate starting materials in 11% yield as a white solid. $^1$H NMR (400 MHz, DMSO-d6) δ 11.53 (s, 1H), 9.48 (s, 1H), 9.28 (s, 1H), 9.21 (s, 1H), 8.74 (s, 1H), 8.43 (s, 1H), 5.81 (s, 1H), 4.70 (s, 2H), 3.47 (s, 3H), 2.74 (s, 3H), 2.16 (s, 3H), 1.90 (d, J=7.2 Hz, 3H). Retention time (LC-MS): 1.440 min. MH$^+$531.

Compound 110. (S)-2-(3-methyl-1-((5-methylisoxazol-3-yl)methyl)-2,6-dioxo-2,3-dihydro-1H-purin-7(6H)-yl)-N-(2-(6-methyl-5-(trifluoromethyl)pyridin-3-yl)pyrimidin-4-yl)propanamide

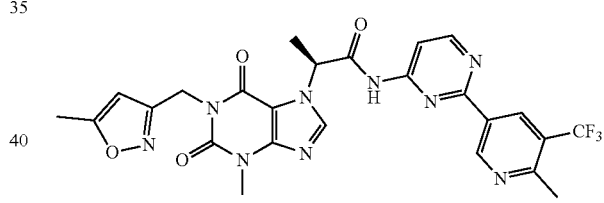

This compound was prepared using the method described for compound 2 with appropriate starting materials in 9.36% yield as a white solid. $^1$H NMR (400 MHz, DMSO-d6) δ 11.62 (s, 1H), 9.59 (s, 1H), 8.88-8.80 (m, 2H), 8.40 (s, 1H), 7.98 (d, J=5.7 Hz, 1H), 6.08 (s, 1H), 5.82 (d, J=7.3 Hz, 1H), 5.02 (s, 2H), 3.48 (s, 3H), 2.74 (s, 3H), 2.30 (s, 3H), 1.89 (d, J=7.2 Hz, 3H). Retention time (LC-MS): 1.975 min. MH$^+$570.

Compound 111. (S)-N-(2-(5-chloro-6-methylpyridin-3-yl)thiazol-4-yl)-2-(3-methyl-2,6-dioxo-1-(2-oxopropyl)-2,3-dihydro-1H-purin-7(6H)-yl)propanamide

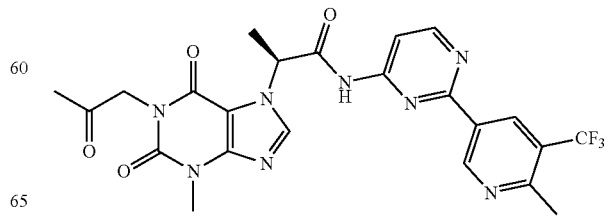

This compound was prepared using the method described for compound 2 with appropriate starting materials in 7.5% yield as a white solid. $^1$H NMR (400 MHz, DMSO-d6) δ 11.63 (s, 1H), 9.59 (s, 1H), 8.85 (d, 2H), 8.42 (s, 1H), 7.97 (d, J=5.8 Hz, 1H), 5.77 (d, J=7.3 Hz, 1H), 4.67 (d, 2H), 3.46 (s, 3H), 2.75 (s, 3H), 2.16 (s, 3H), 1.89 (d, J=7.2 Hz, 3H). Retention time (LC-MS): 2.022 min. MH$^+$531.

Compound 112. (S)-2-(3-methyl-1-((5-methylisoxazol-3-yl)methyl)-2,6-dioxo-2,3-dihydro-1H-purin-7(6H)-yl)-N-(2-(6-methyl-5-(trifluoromethyl)pyridin-3-yl)thiazol-4-yl)propanamide

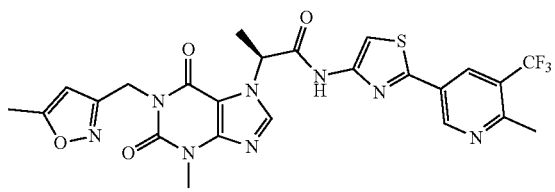

This compound was prepared using the method described for compound 2 with appropriate starting materials in 31.6% yield as a yellow solid. $^1$H NMR (400 MHz, DMSO-D6) δ 11.76 (s, 1H), 9.23 (s, 1H), 8.47 (s, 1H), 8.40 (s, 1H), 7.72 (s, 1H), 6.09 (s, 1H), 5.76 (d, J=7.4 Hz, 1H), 5.02 (s, 2H), 3.48 (s, 3H), 2.71 (s, 3H), 2.31 (s, 3H), 1.86 (d, J=7.2 Hz, 3H). Retention time (LC-MS): 2.254min. MH$^+$575.

Compound 113. (2S)-N-(6-(5-(3-azabicyclo[3.1.0]hexan-3-yl)pyrazin-2-yl)pyridin-2-yl)-2-(3-methyl-2,6-dioxo-1-(2-oxobutyl)-2,3-dihydro-1H-purin-7(6H)-yl)propanamide To a solution of (S)-2-(3-methyl-2,6-dioxo-1-(2-oxobutyl)-2,3-dihydro-1H-purin-7(6H)-yl)propanoic acid (61 mg, 0.2 mmol) and 6-(5-(3-azabicyclo[3.1.0]hexan-3-yl)pyrazin-2-yl)pyridin-2-amine(50 mg, 0.20 mmol) in dichloromethane (4 mL) was added HOAt (30 mg, 0.22 mmol) at room temperature. The reaction mixture was cooled in an ice-water bath to 0° C., and pyridine (0.03 mL, 0.30 mmol) was added drop-wise followed by drop-wise addition of DIC (0.04 mL, 0.40 mmol) under N$_2$ protection. The ice-water bath was removed after the addition and the mixture was stirred at 30° C. overnight. The resulting mixture was washed with water (5 mL) and saturated aq.NH$_4$Cl (5 mL), dried over anhydrous Na$_2$SO$_4$ and filtered. The filtrate was concentrated under reduced pressure and the residue was purified via preparative HPLC to afford (2S)-N-(6-(5-(3-azabicyclo[3.1.0]hexan-3-yl)pyrazin-2-yl)pyridin-2-yl)-2-(3-methyl-2,6-dioxo-1-(2-oxobutyl)-2,3-dihydro-1H-purin-7(6H)-yl)propanamide (5 mg, 5% yield) as a white solid. Retention time (LC-MS): 1.409 min. MH$^+$544. $^1$H NMR (400 MHz, DMSO-D6) δ 10.99 (s, 1H), 8.93 (d, J=1.2 Hz, 1H), 8.39 (s, 1H), 8.03 (s, J=1.2 Hz, 1H), 7.95 (s, 1H), 7.83 (m, 2H)5.79 (q, J=6.4 Hz 1H), 4.70 (s, 2H), 3.78 (d, J=11.2 Hz, 2H), 3.52 (d, J=10.4 Hz, 3H), 3.46 (s, 3H), 2.55 (m, 2H) 1.86 (d, J=6.4 Hz, 3H), 1.74 (m, 2H), 0.93 (m, 3H), 0.77 (m, 1H), 0.20 (m, 1H).

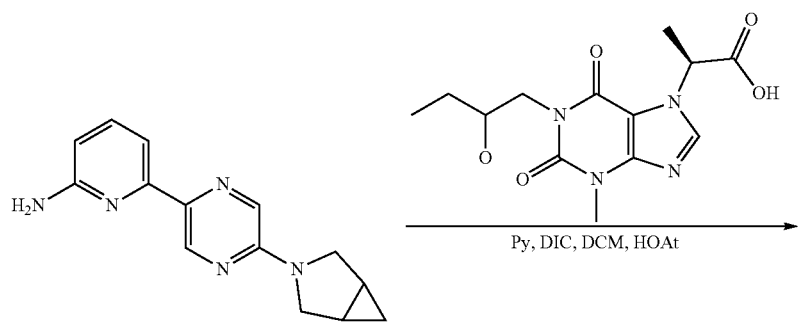

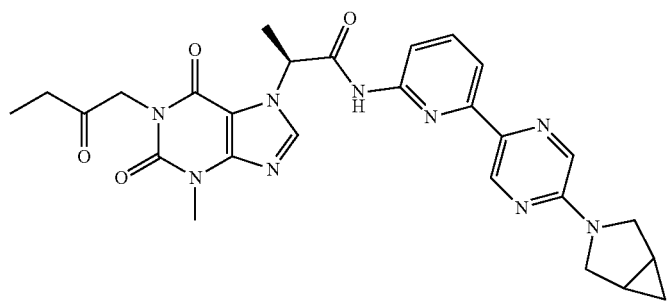

Compound 114. (S)-2-(3-methyl-1-((5-methylisox-azol-3-yl)methyl)-2,6-dioxo-2,3-dihydro-1H-purin-7(6H)-yl)-N-(2'-((S)-2-(trifluoromethyl)pyrrolidin-1-yl)-[2,5'-bipyrimidin]-4-yl)propanamide

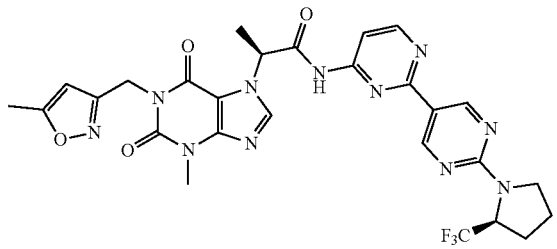 [SMILES: Cc1cc(Cn2c(=O)c3c(ncn3[C@@H](C)C(=O)Nc3ccnc(-c4cnc(N5CCC[C@H]5C(F)(F)F)nc4)n3)n(C)c2=O)no1]

This compound was prepared using the method described for compound 1 with appropriate starting materials in 77% yield as a white solid. $^1$H NMR (400 MHz, DMSO-D6) δ 11.46 (s, 1H), 9.23 (s, 2H), 8.70 (d, J=5.7 Hz, 1H), 8.39 (s, 1H), 7.83 (d, J=5.7 Hz, 1H) 6.06 (s, 1H), 5.81 (d, J=7.1 Hz, 1H), 5.13 (m, 1 H), 5.00 (s, 2H), 3.69 (m, 2 H), 3.46 (s, 3H), 2.29 (s, 3H), 2.08-2.20 (m, 4H), 1.87 (d, J=7.2 Hz, 3H). MH$^+$626.

Compound 115. (S)-2-(3-methyl-1-((5-methylisox-azol-3-yl)methyl)-2,6-dioxo-2,3-dihydro-1H-purin-7(6H)-yl)-N-(6-(24(S)-2-(trifluoromethyl)pyrrolidin-1-yl)pyrimidin-5-yl)pyridin-2-yl)propanamide

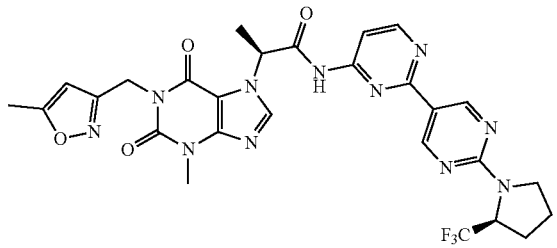 [SMILES: Cc1cc(Cn2c(=O)c3c(ncn3[C@@H](C)C(=O)Nc3ccnc(-c4cnc(N5CCC[C@H]5C(F)(F)F)nc4)n3)n(C)c2=O)no1]

This compound was prepared using the method described for compound 1 with appropriate starting materials in 55% yield as a white solid. $^1$H NMR (400 MHz, DMSO-D6) δ 11.02 (s, 1H), 9.09 (s, 2H), 8.38 (s, 1H), 7.82-7.92 (m, 2H), 7.76 (m, 1 H), 6.06 (s, 1H), 5.81 (d, J=7.1 Hz, 1H), 5.10 (m, 1 H), 5.01 (s, 2H), 3.68 (m, 2 H), 3.46 (s, 3H), 2.29 (s, 3H), 2.08-2.20 (m, 4H), 1.85 (d, J=7.2 Hz, 3H). MH$^+$625.

Compound 116 (S)-2-(3-methyl-2,6-dioxo-1-(2-oxobutyl)-2,3-dihydro-1H-purin-7(6H)-yl)-N-(6'-(trifluoromethyl)-[2,3'-bipyridin]-6-yl)propanamide

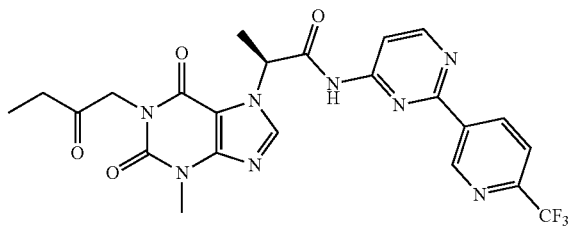 [SMILES: CCC(=O)Cn1c(=O)c2c(ncn2[C@@H](C)C(=O)Nc2ccnc(-c3ccc(C(F)(F)F)nc3)n2)n(C)c1=O]

This compound was prepared using the method described for compound 1 with appropriate starting materials in 29% yield as a white solid. $^1$H NMR (400 MHz, DMSO-D6) δ 11.18 (s, 1H), 9.43 (s, 1H), 8.69 (d, J=7.3 Hz, 1H), 8.39 (s, 1H), 7.90-8.01 (m, 3H), 5.78 (m, 1H), 5.54 (m, 1H), 4.69 (m, 2H), 3.46 (s, 3H), 1.87 (d, J=7.3 Hz, 3H), 1.73 (d, J=7.3 Hz, 1H), 0.84 (m, 3H). MH$^+$530.

Compound 117. (S)-2-(1-(isoxazol-3-ylmethyl)-3-methyl-2,6-dioxo-2,3-dihydro-1H-purin-7(6H)-yl)-N-(6-(2-(trifluoromethyl)pyrimidin-5-yl)pyridin-2-yl)propanamide

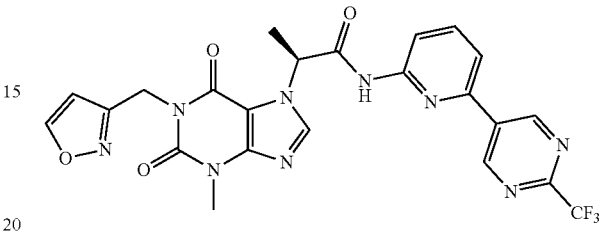

This compound was prepared using the method described for compound 1 with appropriate starting materials as a white solid. $^1$HNMR (400 MHz, DMSO-d$_6$) δ 11.26 (s, 1H), 9.66 (s, 2H), 8.79 (s, 1 H), 8.40 (s, 1H), 7.98-8.02 (m, 3H), 6.45 (s, 1H), 5.83 (m, 1H), 5.10 (s, 2H), 3.48 (s, 3H), 1.88 (d, J=7.2 Hz, 3H). MH$^+$542.

Compound 118. (S)-2-(3-methyl-1-((5-methylisox-azol-3-yl)methyl)-2,6-dioxo-2,3-dihydro-1H-purin-7(6H)-yl)-N-(6-(6-(trifluoromethyl)pyridin-3-yl)pyrazin-2-yl)propanamide

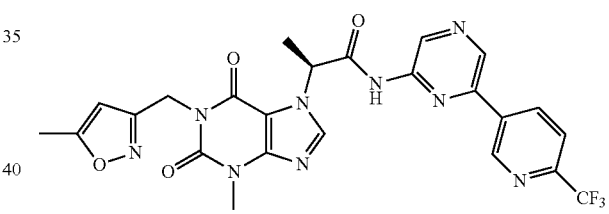

This compound was prepared using the method described for compound 1 with appropriate starting materials as a white solid. $^1$HNMR (400 MHz, DMSO-d$_6$) δ 11.57 (s, 1H), 9.48 (s, 1H), 9.31(s, H), 9.17 (s, 1H), 8.76 (d, J=8.0 Hz, 1 H), 8.41 (s, 1H), 8.13 (d, J=8.2 Hz, 1 H), 6.08 (s, 1H), 5.84 (m, 1H), 5.02 (s, 2H), 3.48 (s, 3H), 2.30 (s, 3H), 1.90 (d, J=7.3 Hz, 3H). MH$^+$556.

Compound 119. (S)-2-(1-(isoxazol-3-ylmethyl)-3-methyl-2,6-dioxo-2,3-dihydro-1H-purin-7(6H)-yl)-N-(6-(6-(trifluoromethyl)pyridin-3-yl)pyrazin-2-yl)propanamide

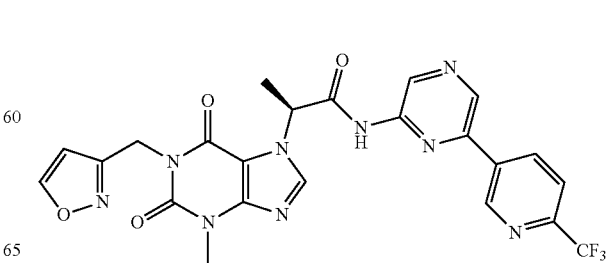

This compound was prepared using the method described for compound 1 with appropriate starting materials as a white solid. ¹HNMR (400 MHz, DMSO-d$_6$) δ 11.57 (s, 1H), 9.48 (s, 1H), 9.31(s, H), 9.18 (s, 1H), 8.76 (m, 2 H), 8.42 (s, 1H), 8.13 (d, J=8.3 Hz, 1 H), 6.46 (s, 1H), 5.84 (m, 1H), 5.10 (s, 2H), 3.48 (s, 3H), 1.90 (d, J=7.3 Hz, 3H). MH⁺542.

Compound 120. (S)-2-(1-(isoxazol-3-ylmethyl)-3-methyl-2,6-dioxo-2,3-dihydro-1H-purin-7(6H)-yl)-N-(6-(2-(trifluoromethyl)pyrimidin-5-yl)pyrazin-2-yl)propanamide

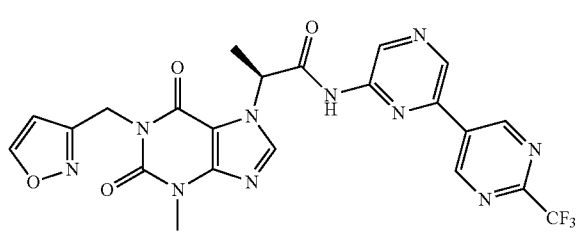 [SMILES: C[C@@H](C(=O)Nc1cncc(-c2cnc(C(F)(F)F)nc2)n1)n1cnc2c1c(=O)n(Cc1ccon1)c(=O)n2C]

This compound was prepared using the method described for compound 1 with appropriate starting materials as a white solid. ¹HNMR (400 MHz, DMSO-d$_6$) δ 11.61 (s, 1H), 9.68 (s, 2H), 9.33 (s, 1H), 9.19 (s, 1H), 8.78 (s, 1 H), 8.41 (s, 1H), 6.44 (s, 1H), 5.82 (m, 1H), 5.09 (s, 2H), 3.47 (s, 3H), 1.89 (d, J=7.2 Hz, 3H). MH⁺543.

Compound 121. (S)-N-(6'-methoxy-5'-(trifluoromethyl)-[2,3'-bipyridin]-6-yl)-2-(3-methyl-1-((5-methylisoxazol-3-yl)methyl)-2,6-dioxo-2,3-dihydro-1H-purin-7(6H)-yl)propanamide

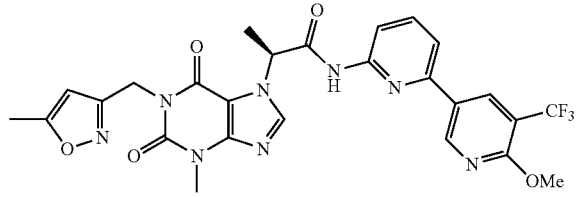 [SMILES: COc1ncc(-c2cccc(NC(=O)[C@H](C)n3cnc4c3c(=O)n(Cc3cc(C)on3)c(=O)n4C)n2)cc1C(F)(F)F]

This compound was prepared using the method described for compound 1 with appropriate starting materials as a white solid. ¹HNMR (400 MHz, DMSO-d$_6$) δ 11.09 (s, 1H), 9.13 (s, 1H), 8.71 (s, 1 H), 8.39 (s, 1H), 7.83-7.99 (m, 3H), 6.07 (s, 1H), 5.81 (m, 1H), 5.01 (s, 2H), 4.06 (s, 3H), 3.46 (s, 3H), 2.29 (s, 3H), 1.86 (d, J=7.3 Hz, 3H). MH⁺585.

Compound 122. (S)-N-(6'-ethoxy-5'-(trifluoromethyl)-[2,3'-bipyridin]-6-yl)-2-(3-methyl-1-((5-methylisoxazol-3-yl)methyl)-2,6-dioxo-2,3-dihydro-1H-purin-7(6H)-yl)propanamide

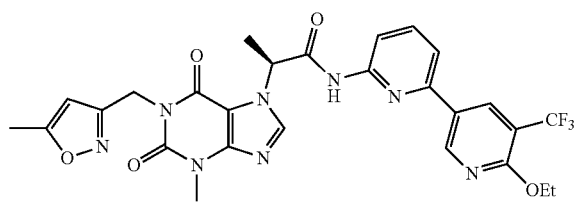 [SMILES: CCOc1ncc(-c2cccc(NC(=O)[C@H](C)n3cnc4c3c(=O)n(Cc3cc(C)on3)c(=O)n4C)n2)cc1C(F)(F)F]

This compound was prepared using the method described for compound 1 with appropriate starting materials as a white solid. ¹HNMR (400 MHz, DMSO-d$_6$) δ 11.08 (s, 1H), 9.11 (s, 1H), 8.70 (s, 1 H), 8.38 (s, 1H), 7.82-7.96 (m, 3H), 6.06 (s, 1H), 5.82 (m, 1H), 5.01 (s, 2H), 4.52 (m, 2H), 3.46 (s, 3H), 2.28 (s, 3H), 1.86 (d, J=7.3 Hz, 3H), 1.35 (t, 3H). MH⁺599.

Compound 123. (S)-N-(6'-chloro-5'-(trifluoromethyl)-[2,3'-bipyridin]-6-yl)-2-(3-methyl-1-((5-methylisoxazol-3-yl)methyl)-2,6-dioxo-2,3-dihydro-1H-purin-7(6H)-yl)propanamide

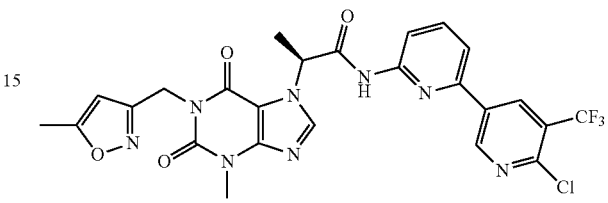

This compound was prepared using the method described for compound 1 with appropriate starting materials as a white solid. ¹HNMR (400 MHz, DMSO-d$_6$) δ 11.19 (s, 1H), 9.38 (s, 1H), 8.89 (s, 1 H), 8.39 (s, 1H), 7.85-8.06 (m, 3H), 6.07 (s, 1H), 5.82 (m, 1H), 5.01 (s, 2H), 3.46 (s, 3H), 2.29 (s, 3H), 1.86 (d, J=7.3 Hz, 3H), 1.35 (t, 3H). MH⁺589.

Compound 124. (S)-N-(6'-methoxy-5'-(trifluoromethyl)-[2,3'-bipyridin]-6-yl)-2-(3-methyl-2,6-dioxo-1-(2-oxobutyl)-2,3-dihydro-1H-purin-7(6H)-yl)propanamide

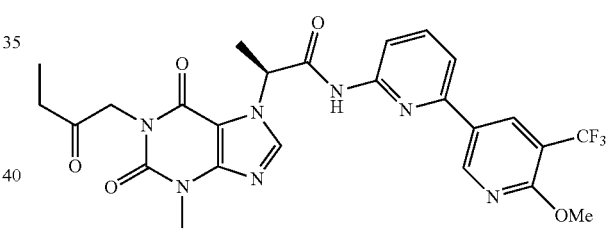

This compound was prepared using the method described for compound 1 with appropriate starting materials as a white solid. ¹HNMR (400 MHz, DMSO-d$_6$) δ 11.07 (s, 1H), 9.15 (s, 1H), 8.72 (s, 1 H), 8.39 (s, 1H), 7.83-7.99 (m, 3H), 5.81 (m, 1H), 4.69 (t, 2H), 4.06 (s, 3H), 3.45 (s, 3H), 2.50 (m, 2H), 1.86 (d, J=7.3 Hz, 3H), 0.93 (t, 3H). MH⁺560.

Compound 125. (S)-N-(6'-ethoxy-5'-(trifluoromethyl)-[2,3'-bipyridin]-6-yl)-2-(3-methyl-2,6-dioxo-1-(2-oxobutyl)-2,3-dihydro-1H-purin-7(6H)-yl)propanamide

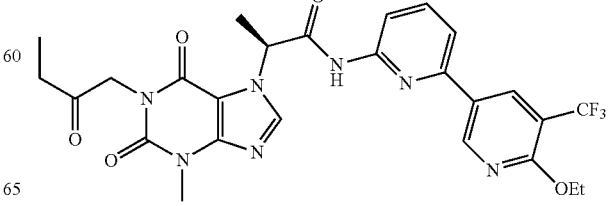

This compound was prepared using the method described for compound 1 with appropriate starting materials as a white solid. $^1$HNMR (400 MHz, DMSO-d$_6$) δ 11.07 (s, 1H), 9.12 (s, 1H), 8.71 (s, 1 H), 8.38 (s, 1H), 7.83-7.99 (m, 3H), 5.78 (m, 1H), 4.69 (t, 2H), 4.52 (q, 2H), 3.45 (s, 3H), 2.50 (m, 2H), 1.86 (d, J=7.3 Hz, 3H), 1.36 (t, 3H), 0.93 (t, 3H). MH$^+$574.

Compound 126. (S)-2-(3-methyl-1-((5-methylisoxazol-3-yl)methyl)-2,6-dioxo-2,3-dihydro-1H-purin-7(6H)-yl)-N-(6'-methyl-5'-(trifluoromethyl)-[2,3'-bipyridin]-6-yl)propanamide

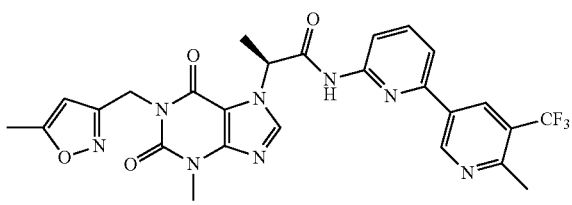 [SMILES: Cc1cc(Cn2c(=O)c3c(ncn3[C@@H](C)C(=O)Nc3cccc(-c4cnc(C)c(C(F)(F)F)c4)n3)n(C)c2=O)no1]

This compound was prepared using the method described for compound 1 with appropriate starting materials as a white solid. $^1$HNMR (400 MHz, DMSO-d$_6$) δ 11.15 (s, 1H), 9.40 (s, 1H), 8.70 (s, 1 H), 8.26 (s, 1H), 7.90-8.03 (m, 3H), 6.07 (s, 1H), 5.82 (m, 1H), 5.01 (s, 2H), 3.46 (s, 3H), 2.70 (s, 3H), 2.29 (s, 3H), 1.86 (d, J=7.3 Hz, 3H). MH$^+$569.

Compound 127. (S)-N-(5',6'-dimethyl-[2,3'-bipyridin]-6-yl)-2-(3-methyl-1-((5-methylisoxazol-3-yl)methyl)-2,6-dioxo-2,3-dihydro-1H-purin-7(6H)-yl)propanamide

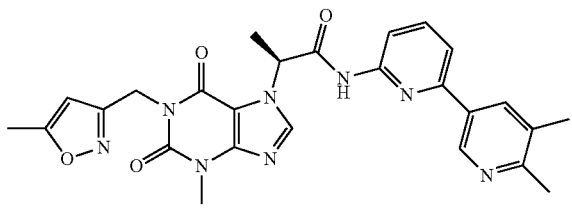

This compound was prepared using the method described for compound 1 with appropriate starting materials as a white solid. $^1$HNMR (400 MHz, DMSO-d$_6$) δ 11.08 (s, 1H), 8.94 (s, 1H), 8.38 (s, 1H), 8.17 (s, 1H), 7.72-7.96 (m, 3H), 6.07 (s, 1H), 5.82 (m, 1H), 5.01 (s, 2H), 3.46 (s, 3H), 2.33 (s, 3H), 2.29 (s, 3H), 1.86 (d, J=7.3 Hz, 3H). MH$^+$515.

Compound 128. (S)-2-(3-methyl-1-((5-methylisoxazol-3-yl)methyl)-2,6-dioxo-2,3-dihydro-1H-purin-7(6H)-yl)-N-(6-(6-methyl-5-(trifluoromethyl)pyridin-3-yl)pyrazin-2-yl)propanamide

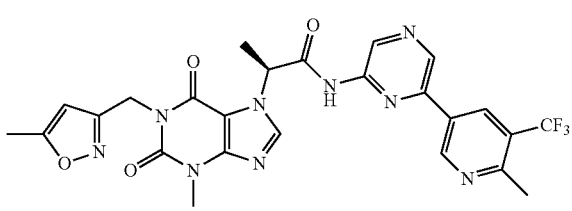 [SMILES: Cc1cc(Cn2c(=O)c3c(ncn3[C@@H](C)C(=O)Nc3cncc(-c4cnc(C)c(C(F)(F)F)c4)n3)n(C)c2=O)no1]

This compound was prepared using the method described for compound 1 with appropriate starting materials as a white solid. $^1$HNMR (400 MHz, DMSO-d$_6$) δ 11.49 (s, 1H), 9.46 (s, 1H), 9.27 (s, 1H), 9.19 (s, 1H), 8.72 (s, 1 H), 8.40 (s, 1H), 6.07 (s, 1H), 5.82 (m, 1H), 5.01 (s, 2H), 3.47 (s, 3H), 2.72 (s, 3H), 2.29 (s, 3H), 1.89 (d, J=7.3 Hz, 3H). MH$^+$570.

Compound 129. (S)-2-(3-methyl-1-((5-methylisoxazol-3-yl)methyl)-2,6-dioxo-2,3-dihydro-1H-purin-7(6H)-yl)-N-(5'-methyl-6'-(trifluoromethyl)-[2,3'-bipyridin]-6-yl)propanamide

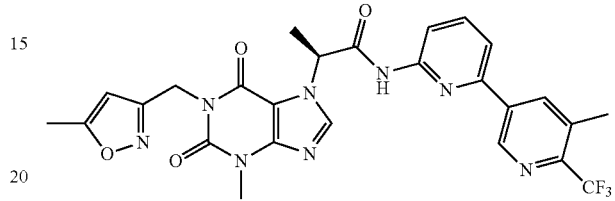

This compound was prepared using the method described for compound 1 with appropriate starting materials as a white solid. $^1$HNMR (400 MHz, DMSO-d$_6$) δ 11.19 (s, 1H), 9.20 (s, 1H), 8.55 (s, 1 H), 8.39 (s, 1H), 7.86-8.07 (m, 3H), 6.07 (s, 1H), 5.82 (m, 1H), 5.01 (s, 2H), 3.46 (s, 3H), 2.55 (s, 3H), 2.29 (s, 3H), 1.87 (d, J=7.3 Hz, 3H). MH$^+$569.

Compound 130. (S)-2-(3-methyl-1-((5-methylisoxazol-3-yl)methyl)-2,6-dioxo-2,3-dihydro-1H-purin-7(6H)-yl)-N-(6-(5-methyl-6-(trifluoromethyl)pyridin-3-yl)pyrazin-2-yl)propanamide

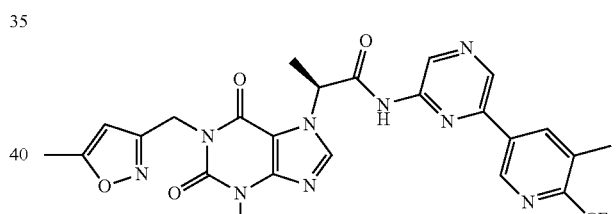

This compound was prepared using the method described for compound 1 with appropriate starting materials as a white solid. $^1$HNMR (400 MHz, DMSO-d$_6$) δ 11.55 (s, 1H), 9.29 (s, 1H), 9.24 (s, 1H), 9.14 (s, 1H), 8.61 (s, 1 H), 8.40 (s, 1H), 6.07 (s, 1H), 5.82 (m, 1H), 5.01 (s, 2H), 3.47 (s, 3H), 2.56 (s, 3H), 2.29 (s, 3H), 1.89 (d, J=7.3 Hz, 3H). MH$^+$570.

Compound 131. (S)-2-(3-methyl-1-((3-methyl-1,2,4-oxadiazol-5-yl)methyl)-2,6-dioxo-2,3-dihydro-1H-purin-7(6H)-yl)-N-(5'-methyl-6'-(trifluoromethyl)-[2,3'-bipyridin]-6-yl)propanamide

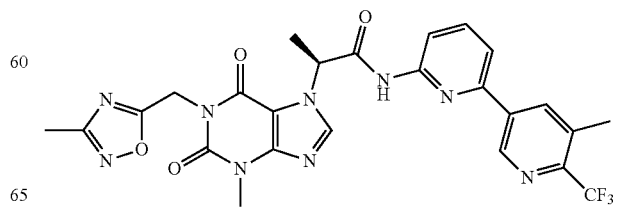

This compound was prepared using the method described for compound 1 with appropriate starting materials as a white solid. ¹HNMR (400 MHz, DMSO-d₆) δ 11.20 (s, 1H), 9.19 (s, 1H), 8.55 (s, 1 H), 8.44 (s, 1H), 7.86-8.07 (m, 3H), 5.81 (m, 1H), 5.26 (q, 2H), 3.48 (s, 3H), 2.55 (s, 3H), 2.25 (s, 3H), 1.88 (d, J=7.3 Hz, 3H). MH⁺570.

Compound 132. (S)-2-(3-methyl-1-((3-methyl-1,2,4-oxadiazol-5-yl)methyl)-2,6-dioxo-2,3-dihydro-1H-purin-7(6H)-yl)-N-(6-(6-methyl-5-(trifluoromethyl)pyridin-3-yl)pyrazin-2-yl)propanamide

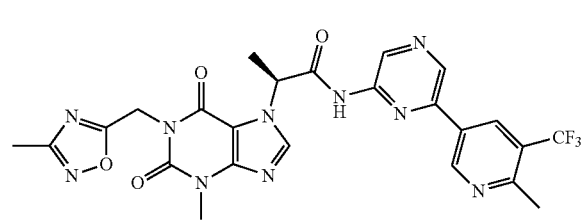 [SMILES: Cc1noc(Cn2c(=O)c3c(ncn3[C@@H](C)C(=O)Nc3cncc(-c4cnc(C)c(C(F)(F)F)c4)n3)n(C)c2=O)n1]

This compound was prepared using the method described for compound 1 with appropriate starting materials as a white solid. ¹HNMR (400 MHz, DMSO-d₆) δ 11.51 (s, 1H), 9.45 (s, 1H), 9.26 (s, 1H), 9.19 (s, 1H), 8.71 (s, 1 H), 8.45 (s, 1H), 5.82 (m, 1H), 5.25 (q, 2H), 3.48 (s, 3H), 2.72 (s, 3H), 2.25 (s, 3H), 1.89 (d, J=7.3 Hz, 3H). MH⁺571.

Compound 133. (S)-2-(3-methyl-1-((3-methyl-1,2,4-oxadiazol-5-yl)methyl)-2,6-dioxo-2,3-dihydro-1H-purin-7(6H)-yl)-N-(6-(5-methyl-6-(trifluoromethyl)pyridin-3-yl)pyrazin-2-yl)propanamide

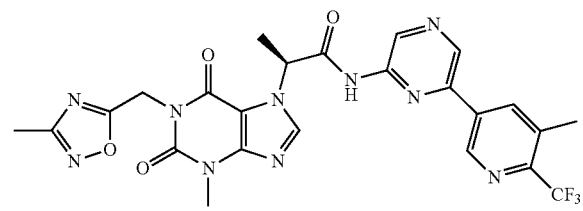

This compound was prepared using the method described for compound 1 with appropriate starting materials as a white solid. ¹HNMR (400 MHz, DMSO-d₆) δ 11.57 (s, 1H), 9.09-9.28 (m, 3H), 8.60 (s, 1 H), 8.45 (s, 1H), 5.82 (m, 1H), 5.25 (q, 2H), 3.48 (s, 3H), 2.56 (s, 3H), 2.25 (s, 3H), 1.90 (d, J=7.3 Hz, 3H). MH⁺571.

Compound 134. (S)-2-(3-methyl-1-((3-methyl-1,2,4-oxadiazol-5-yl)methyl)-2,6-dioxo-2,3-dihydro-1H-purin-7(6H)-yl)-N-(5'-methyl-6'-(trifluoromethyl)-[2,3'-bipyridin]-6-yl)propanamide

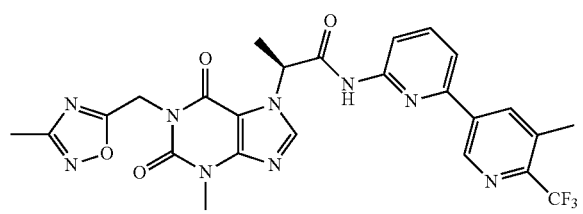

This compound was prepared using the method described for compound 1 with appropriate starting materials as a white solid. ¹HNMR (400 MHz, DMSO-d₆) δ 11.16 (s, 1H), 9.40 (s, 1H), 8.69 (s, 1 H), 8.44 (s, 1H), 7.92-8.01 (m, 3H), 5.80 (m, 1H), 5.25 (q, 2H), 3.48 (s, 3H), 2.70 (s, 3H), 2.24 (s, 3H), 1.87 (d, J=7.3 Hz, 3H). MH⁺570.

Compound 135. (S)-2-(3-methyl-2,6-dioxo-1-(2-oxobutyl)-2,3-dihydro-1H-purin-7(6H)-yl)-N-(6'-methyl-5'-(trifluoromethyl)-[2,3'-bipyridin]-6-yl)propanamide

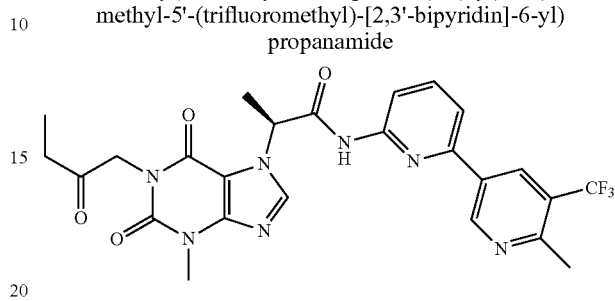

This compound was prepared using the method described for compound 1 with appropriate starting materials as a white solid. ¹HNMR (400 MHz, DMSO-d₆) δ 11.13 (s, 1H), 9.40 (s, 1H), 8.70 (s, 1 H), 8.39 (s, 1H), 7.93-8.02 (m, 3H), 5.79 (m, 1H), 4.69 (t, 2H), 3.45 (s, 3H), 2.71 (s, 3H), 2.50 (m, 2H), 1.86 (d, J=7.3 Hz, 3H), 0.93 (t, 3H). MH⁺544.

Compound 136. (S)-2-(1-(isoxazol-3-ylmethyl)-3-methyl-2,6-dioxo-2,3-dihydro-1H-purin-7(6H)-yl)-N-(6'-methyl-5'-(trifluoromethyl)-[2,3'-bipyridin]-6-yl)propanamide

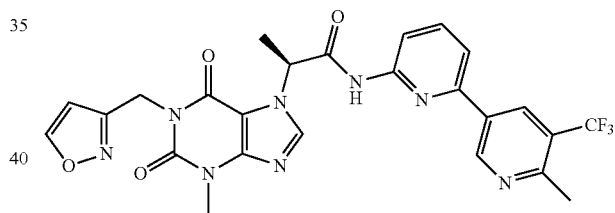

This compound was prepared using the method described for compound 1 with appropriate starting materials as a white solid. ¹HNMR (400 MHz, DMSO-d₆) δ 11.14 (s, 1H), 9.40 (s, 1H), 8.78 (s, 1 H), 8.69 (s, 1 H), 8.39 (s, 1H), 7.92-8.01 (m, 3H), 6.45 (s, 1H), 5.82 (m, 1H), 5.09 (s, 2H), 3.47 (s, 3H), 2.70 (s, 3H), 1.86 (d, J=7.3 Hz, 3H). MH⁺555.

Compound 137. (S)-2-(1-(isoxazol-3-ylmethyl)-3-methyl-2,6-dioxo-2,3-dihydro-1H-purin-7(6H)-yl)-N-(6-(5-methyl-6-(trifluoromethyl)pyridin-3-yl)pyrazin-2-yl)propanamide

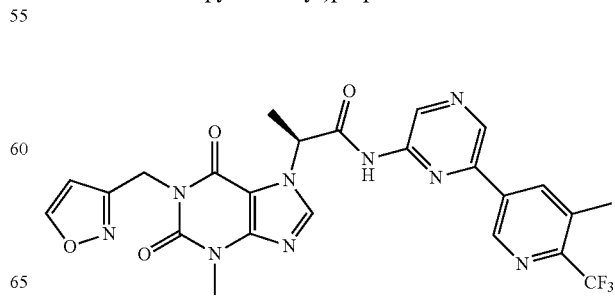

This compound was prepared using the method described for compound 1 with appropriate starting materials as a white solid. ¹HNMR (400 MHz, DMSO-d$_6$) δ 11.56 (s, 1H), 9.29 (s, 1H), 9.24 (s, 1H), 9.14 (s, 1H), 8.78 (s, 1 H), 8.60 (s, 1 H), 8.41 (s, 1H), 6.45 (s, 1H), 5.83 (m, 1H), 5.09 (s, 2H), 3.47 (s, 3H), 2.56 (s, 3H), 1.89 (d, J=7.3 Hz, 3H). MH⁺556.

Compound 139 (S)-N-(6-(5-chloro-6-methylpyridin-3-yl)pyrazin-2-yl)-2-(3-methyl-1-((5-methylisoxazol-3-yl)methyl)-2,6-dioxo-2,3-dihydro-1H-purin-7(6H)-yl)propanamide

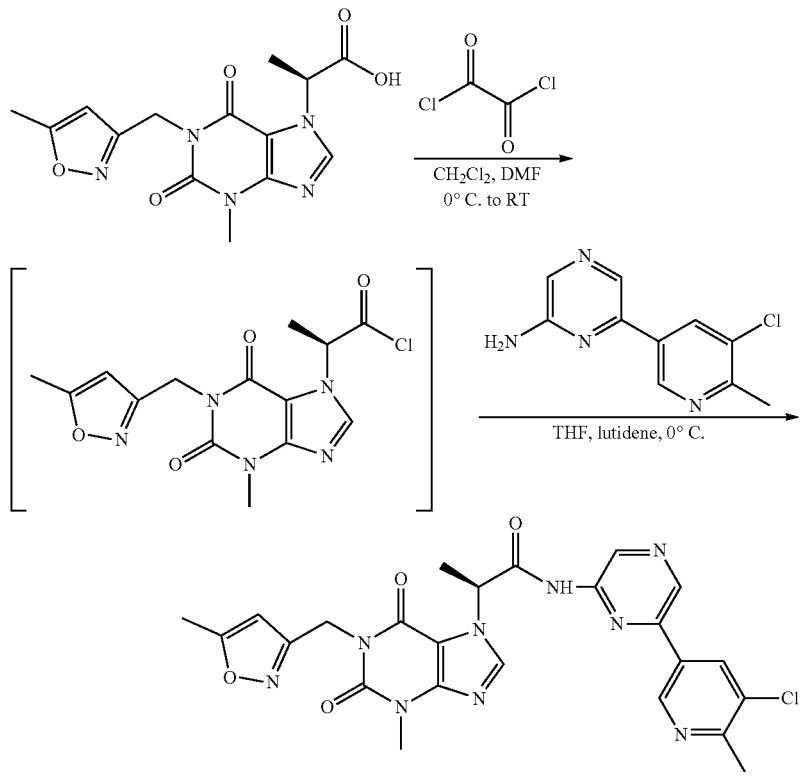

To a suspension of (S)-2-(3-methyl-1-((5-methylisoxazol-3-yl)methyl)-2,6-dioxo-2,3-dihydro-1H-purin-7(6H)-yl)propanoic acid (58 mg, 0.172 mmol) in DCM (2 mL) was added oxalyl chloride (0.035 mL, 0.413 mmol). The reaction was cooled to 0° C. then DMF (1 drop) was added. The mixture was stirred at 0° C. for 5 min, warmed to RT for 1 h, evaporated to dryness then diluted with THF (2 mL) and cooled to 0° C. Next 6-(5-chloro-6-methylpyridin-3-yl) pyrazin-2-amine (38 mg, 0.172 mmol) was added and the reaction was stirred at 0° C. for 1 h, diluted with 0.2N HCl (10 mL) and water (30 ml) then extracted with EA (3×25 mL). The combined organic layers were dried with MgSO$_4$ and concentrated to a residue which was purified by chromatography eluted with MeOH/DCM (2:98 to 3:97) to give (S)-N-(6-(5-chloro-6-methylpyridin-3-yl)pyrazin-2-yl)-2-(3-methyl-1-((5-methylisoxazol-3-yl)methyl)-2,6-dioxo-2,3-dihydro-1H-purin-7(6H)-yl)propanamide (37 mg, 40% yield) as an off-white solid. ¹H NMR (CDCl$_3$) δ: 9.92 (s, 1H), 9.22 (s, 1H), 8.84 (s,1H), 8.72 (s, 1H), 8.10 (s, 1H), 7.93 (s, 1H), 5.95 (s, 1H), 5.88 (q, J=4 and 8 Hz, 1H), 5.28 (d, J=4 Hz, 2H), 3.63 (s, 3H), 2.69 (s, 3H), 2.15 (s, 3H), 1.98 (d, J=8 Hz, 3H). LCMS: MH⁺536 and T$_R$=2.837 min.

Compound 140 (S)-N-(6-(5-chloro-6-methylpyridin-3-yl)pyrazin-2-yl)-2-(3-methyl-1-((5-methylisoxazol-3-yl)methyl)-2,6-dioxo-2,3-dihydro-1H-purin-7(6H)-yl)propanamide

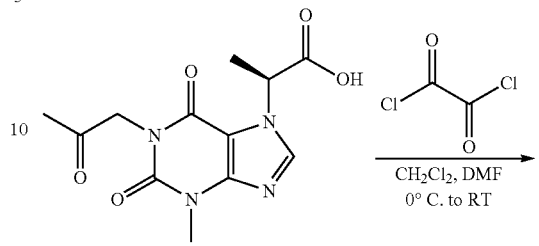

-continued

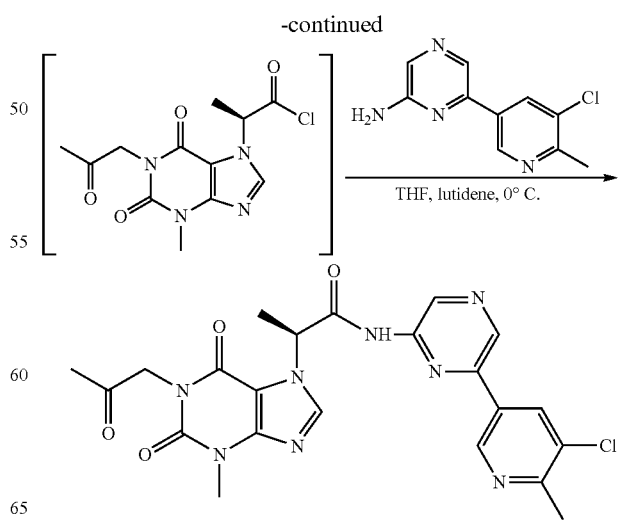

To a suspension of (S)-2-(3-methyl-2,6-dioxo-1(2-oxopropyl)-2,3-dihydro-1H-purin-7(6H)-yl)propanoic acid (0.067 mg, 0.227 mmol) in DCM (3 mL) was added oxalyl chloride (0.046 mL, 0.545 mmol). The reaction was cooled to 0° C. then DMF (2 drops) was added. The mixture was stirred at 0° C. for 5 min, stirred at RT for 1 h, evaporated to dryness then diluted with THF (3 mL) and cooled to 0° C. Next 6-(5-chloro-6-methylpyridin-3-yl)pyrazin-2-amine (50 mg, 0.227 mmol) was added and the reaction was stirred at 0° C. for 1 h, diluted with water (30 ml) then extracted with EA (3×25 mL). The combined organic layers were dried with MgSO$_4$ and concentrated to a residue which was purified by Prep TLC eluted with EA to give (S)-N-(6-(5-chloro-6-methylpyridin-3-yl)pyrazin-2-yl)-2-(3-methyl-2,6-dioxo-1(2-oxopropyl)-2,3-dihydro-1H-purin-7(6H)-yl)propanamide (30 mg, 26.5% yield) as an off-white solid. $^1$H NMR (CDCl$_3$) δ: 9.80 (s, 1H), 9.40 (s, 1H), 8.97 (s, 1H), 8.79 (s, 1H), 8.24 (s, 1H), 7.91 (s, 1H), 5.70 (q, J=8 and 16 Hz, 1H), 4.90 (d, J=4 Hz, 2H), 3.59 (s, 3H), 2.70 (s, 3H), 2.32 (s, 3H), 1.93 (d, J=4 Hz, 3H). LCMS: MH$^+$497 and T$_R$=2.560 min.

Compound 141 2-(3-methyl-2,6-dioxo-1-(pyridin-2-ylmethyl)-2,3-dihydro-1H-purin-7(6H)-yl)-N-(2'-(trifluoromethyl)-2,5'-bipyrimidin-4-yl)propanamide

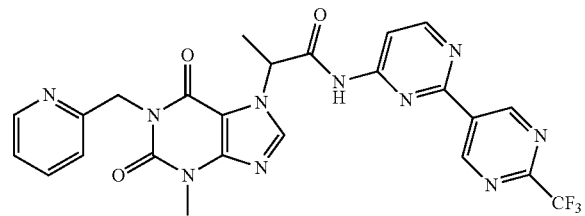 [SMILES: CC(C(=O)Nc1ccnc(-c2cnc(C(F)(F)F)nc2)n1)n1cnc2c1c(=O)n(Cc1ccccn1)c(=O)n2C]

This compound was prepared using the method described for compound 10 with appropriate starting materials as a white solid. $^1$H NMR (400 MHz, DMSO-d$_6$) δ 11.74 (s, 1H), 9.76 (s, 2H), 8.89 (d, J=5.6 Hz, 1H), 8.42-8.36 (m, 2H), 8.04 (d, J=5.6 Hz, 1H), 7.69 (t, J=7.6 Hz, 1H), 7.20 (t, J=6.8 Hz, 2H), 5.81 (d, J=7.2 Hz, 1H), 5.12 (s, 2H), 3.48 (s, 3H), 1.89 (d, J=7.2 Hz, 3H). Retention time (LC-MS): 2.190 min. MH$^+$553.

Compound 142 (2S)-N-(6-(2-(3-azabicyclo[3.1.0]hexan-3-yl)pyrimidin-5-yl)pyridin-2-yl)-2-(3-methyl-2,6-dioxo-1-(2-oxopropyl)-2,3-dihydro-1H-purin-7(6H)-yl)propanamide

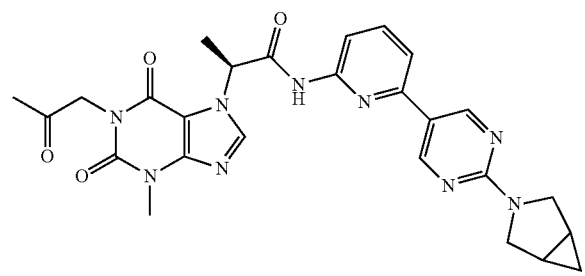 [SMILES: CC(=O)Cn1c(=O)c2c(ncn2[C@@H](C)C(=O)Nc2cccc(-c3cnc(N4CC5CC5C4)nc3)n2)n(C)c1=O]

This Compound was prepared using the similar method described in Compound 2 with appropriate starting materials as a white solid. $^1$H NMR (400 MHz, DMSO-d$_6$) δ 10.82 (s, 1H), 8.82 (s, 2H), 8.21 (s, 1H), 7.65 (m, 2H), 7.43 (d, J=7.6 Hz, 1H), 5.58 (s, 1H), 4.53 (s, 2H), 3.67 (d, J=11.2 Hz, 2H), 3.37 (d, J=10.8 Hz, 2H), 3.28 (s, 3H), 1.99 (s, 3H), 1.69 (d, J=7.2 Hz, 3H), 1.52 (s, 2H), 0.60 (d, J=4.8 Hz, 1H), 0.00 (d, J=4.0 Hz, 1H). Retention time (LC-MS): 2.273 min. MH$^+$530.

Compound 143 (2S)-N-(2'-(3-azabicyclo[3.1.0]hexan-3-yl)-2,5'-bipyrimidin-4-yl)-2-(3-methyl-2,6-dioxo-1-(2-oxopropyl)-2,3-dihydro-1H-purin-7(6H)-yl)propanamide

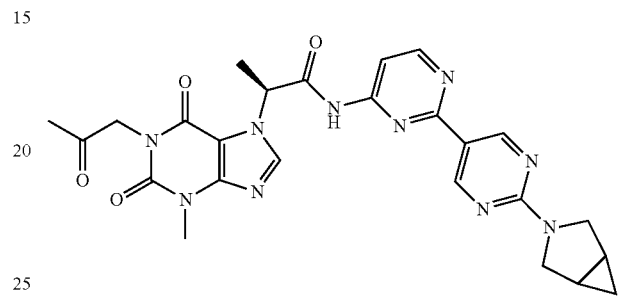

This compound was prepared using the method described for compound 2 with appropriate starting materials as a white solid. $^1$H NMR (400 MHz, DMSO-d$_6$) δ 11.24 (s, 1H), 8.99 (s, 2H), 8.51 (d, J=5.6 Hz, 1H), 8.22 (s, 1H), 7.62 (d, J=5.6 Hz, 1H), 5.60 (d, J=7.2 Hz, 1H), 4.53 (s, 2H), 3.70 (d, J=11.2 Hz, 2H), 3.40 (d, J=10.4 Hz, 2H), 3.29 (s, 3H), 1.99 (s, 3H), 1.70 (d, J=7.2 Hz, 3H), 1.53 (s, 2H), 0.61 (d, J=4.4 Hz, 1H), 0.00 (d, J=4.4 Hz, 1H). Retention time (LC-MS): 2.167 min. MH$^+$531.

Compound 144 (2S)-N-(2'-(3-azabicyclo[3.1.0]hexan-3-yl)-2,5'-bipyrimidin-4-yl)-2-(3-methyl-2,6-dioxo-1-(2-oxopropyl)-2,3-dihydro-1H-purin-7(6H)-yl)propanamide

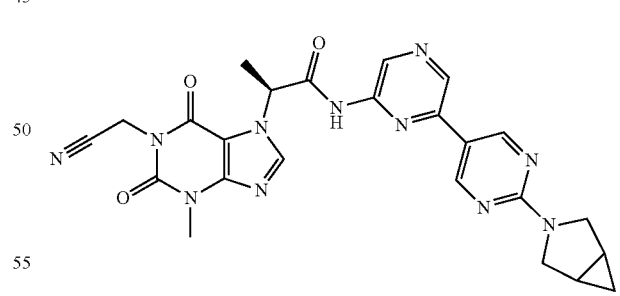

This compound was prepared using the method described for compound 10 with appropriate starting materials and separated via preparative Chiral HPLC in 33.94% yield to form a white solid. $^1$H NMR (400 MHz, DMSO-d$_6$) δ 11.40 (s, 1H), 9.11 (s, 1H), 9.04 (s, 2H), 8.91 (s, 1H), 8.44 (s, 1H), 5.82 (s, 1H), 4.84 (s, 2H), 3.86 (d, J=11.2 Hz, 2H), 3.56 (d, J=11.6 Hz, 2H), 3.49 (s, 3H), 1.89 (d, J=7.2 Hz, 3H), 1.70 (s, 2H), 0.78 (d, J=4.6 Hz, 1H), 0.17 (d, J=4.2 Hz, 1H). Retention time (LC-MS): 1.567 min. MH$^+$514.

Compound 145 (2S)-N-(2-(2-(3-azabicyclo[3.1.0]hexan-3-yl)pyrimidin-5-yl)thiazol-4-yl)-2-(1-(but-2-ynyl)-3-methyl-2,6-dioxo-2,3-dihydro-1H-purin-7(6H)-yl)propanamide

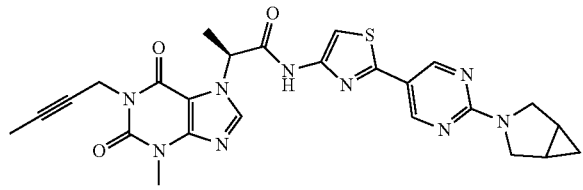 [SMILES: CC#CCn1c(=O)c2c(ncn2[C@@H](C)C(=O)Nc2csc(-c3cnc(N4CC5CC5C4)nc3)n2)n(C)c1=O]

This compound was prepared using the method described for compound 1 with appropriate starting materials in 22.64% yield as a yellow solid. ¹H NMR (400 MHz, DMSO-d6) δ 11.64 (s, 1H), 8.82 (s, 2H), 8.36 (s, 1H), 7.48 (s, 1H), 5.83-5.63 (m, 1H), 4.52 (s, 2H), 3.84 (d, J=11.2 Hz, 2H), 3.56 (d, J=10.8 Hz, 2H), 3.46 (s, 3H), 1.84 (d, J=7.2 Hz, 3H), 1.70 (m, 5H), 0.78 (d, J=4.8 Hz, 1H), 0.17 (d, J=4.4 Hz, 1H). Retention time (LC-MS): 2.260 min. MH⁺532.

Compound 146 (2S)-N-(6-(2-(6,6-difluoro-3-azabicyclo[3.1.0]hexan-3-yl)pyrimidin-5-yl)pyridin-2-yl)-2-(1-(3-methoxy-2-oxopropyl)-3-methyl-2,6-dioxo-2,3-dihydro-1H-purin-7(6H)-yl)propanamide

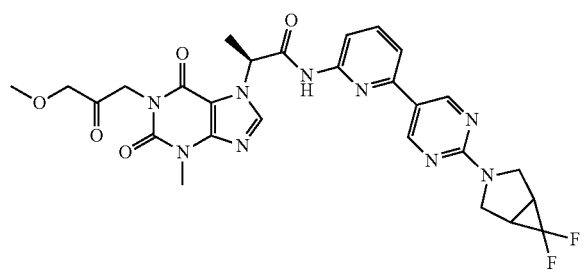 [SMILES: COCC(=O)Cn1c(=O)c2c(ncn2[C@@H](C)C(=O)Nc2cccc(-c3cnc(N4CC5C(C4)C5(F)F)nc3)n2)n(C)c1=O]

This compound was prepared using the method described for compound 2 with appropriate starting materials in 6.7% yield. White solid.¹H-NMR (400 MHz, DMSO-d6) δ 11.01 (s, 1H), 9.03 (s, 2H), 8.40 (s, 1H), 7.84 (m, 2H), 7.63 (d, J=7.6 Hz, 1H), 5.79 (s, 1H), 4.89-4.64 (m, 2H), 4.21 (s, 2H), 3.99 (d, J=12.0 Hz, 2H), 3.84 (d, J=10.4 Hz, 2H), 3.46 (s, 3H), 3.31 (s, 3H), 2.70 (d, J=10.4 Hz, 2H), 1.86 (d, J=7.2 Hz, 3H). Retention time (LC-MS): 1.510 min. MH⁺596.

Compound 147 (2S)-N-(6-(2-(3-azabicyclo[3.1.0]hexan-3-yl)pyrimidin-5-yl)pyridin-2-yl)-2-(3-methyl-2,6-dioxo-1-(2-oxobutyl)-2,3-dihydro-1H-purin-7(6H)-yl)propanamide

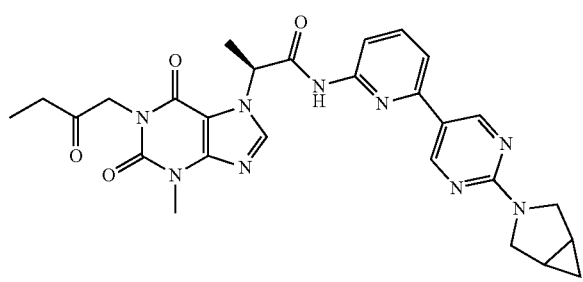 [SMILES: CCC(=O)Cn1c(=O)c2c(ncn2[C@@H](C)C(=O)Nc2cccc(-c3cnc(N4CC5CC5C4)nc3)n2)n(C)c1=O]

This compound was prepared using the method described for compound 2 with appropriate starting materials in 49.6% yield. White solid.¹HNMR (400 MHz, DMSO-d6) S. 10.98 (s, 1H), 8.97 (s, 2H), 8.37 (s, 1H), 7.85 (d, J=8.2 Hz, 1H), 7.79 (t, J=7.9 Hz, 1H), 7.59 (d, J=7.8 Hz, 1H), 5.78 (s, 1H), 4.75-4.61 (m, 2H), 3.83 (d, J=11.3 Hz, 2H), 3.52 (d, J=11.0 Hz, 2H), 3.44 (s, 3H), 2.55-2.50 (m, 2H), 1.85 (d, J=7.3 Hz, 3H), 1.71-1.64 (m, 2H), 0.92 (t, J=7.3 Hz, 3H), 0.75 (dd, J=12.4, 7.6 Hz, 1H), 0.19-0.10 (m, 1H). Retention time (LC-MS): 2.43 min. MH⁺544.

Compound 148 (2R)-N-(6-(2-(3-azabicyclo[3.1.0]hexan-3-yl)pyrimidin-5-yl)pyridin-2-yl)-2-(1-(cyanomethyl)-3-methyl-2,6-dioxo-2,3-dihydro-1H-purin-7(6H)-yl)propanamide

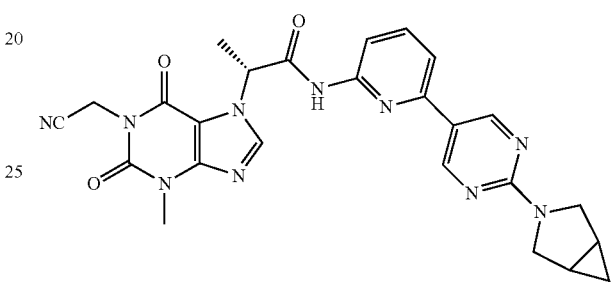

This compound was prepared using the method described for compound 10 with appropriate starting materials and separated via preparative Chiral HPLC in 22.9% yield as a white solid. ¹H NMR (400 MHz, DMSO-d6) δ 11.03 (s, 1H), 9.00 (s, 2H), 8.43 (s, 1H), 7.88 (d, J=7.7 Hz, 1H), 7.82 (t, J=7.9 Hz, 1H), 7.61 (d, J=8.1 Hz, 1H), 5.83 (s, 1H), 4.85 (s, 2H), 3.86 (d, J=11.3 Hz, 2H), 3.55 (d, J=11.1 Hz, 2H), 3.49 (s, 3H), 1.88 (d, J=7.3 Hz, 3H), 1.73-1.66 (m, 2H), 0.78 (dt, J=12.3, 6.2 Hz, 1H), 0.18 (dd, J=8.4, 4.2 Hz, 1H). Retention time (LC-MS): 1.89 min. MH⁺513.

Compound 149 (2S)-N-(6-(2-(3-azabicyclo[3.1.0]hexan-3-yl)pyrimidin-5-yl)pyridin-2-yl)-2-(1-(cyanomethyl)-3-methyl-2,6-dioxo-2,3-dihydro-1H-purin-7(6H)-yl)propanamide

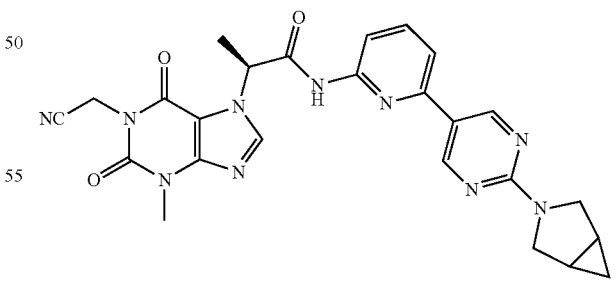

This compound was prepared using the method described for compound 10 with appropriate starting materials and separated via preparative Chiral HPLC in 34.2% yield as a white solid. ¹H NMR (400 MHz, DMSO-d6) δ 11.06 (s, 1H), 9.00 (s, 2H), 8.43 (s, 1H), 7.88 (d, J=8.0 Hz, 1H), 7.81 (t, J=7.9 Hz, 1H), 7.61 (d, J=7.6 Hz, 1H), 5.81 (s, 1H), 4.84 (s, 2H), 3.85 (d, J=11.2 Hz, 2H), 3.54 (d, J=10.6 Hz, 2H), 3.48

(s, 3H), 1.87 (d, J=7.2 Hz, 3H), 1.69 (s, 2H), 0.77 (d, J=4.8 Hz, 1H), 0.17 (d, J=4.0 Hz, 1H). Retention time (LC-MS): 1.89 min. MH+513.

Compound 150 (S)-2-(3-methyl-1-((3-methyl-1,2,4-oxadiazol-5-yl)methyl)-2,6-dioxo-2,3-dihydro-1H-purin-7(6H)-yl)-N-(2-(5-methyl-6-(trifluoromethyl)pyridin-3-yl)pyrimidin-4-yl)propanamide

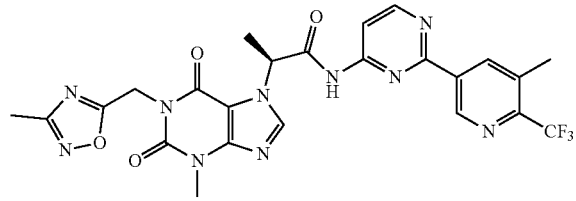 [SMILES: Cc1noc(Cn2c(=O)c3c(ncn3[C@@H](C)C(=O)Nc3ccnc(-c4cnc(C(F)(F)F)c(C)c4)n3)n(C)c2=O)n1]

This compound was prepared using the method described for compound 2 with appropriate starting materials and separated via preparative HPLC as a white solid. ¹H NMR (400 MHz, DMSO-d6) δ 11.70 (s, 1H), 9.38 (s, 1H), 8.86 (d, J=5.7 Hz, 1H), 8.73 (s, 1H), 8.46 (s, 1H), 7.99 (d, J=5.7 Hz, 1H), 5.80 (d, J=7.0 Hz, 1H), 5.32-5.21 (m, 2H), 3.49 (s, 3H), 2.58 (d, J=1.6 Hz, 3H), 2.26 (s, 3H), 1.90 (d, J=7.3 Hz, 3H). Retention time (LC-MS): 2.147 min. MH+571.

Compound 151 (S)-2-(3-methyl-1-((5-methyl-1,2,4-oxadiazol-3-yl)methyl)-2,6-dioxo-2,3-dihydro-1H-purin-7(6H)-yl)-N-(6'-methyl-5'-(trifluoromethyl)-2,3'-bipyridin-6-yl)propanamide

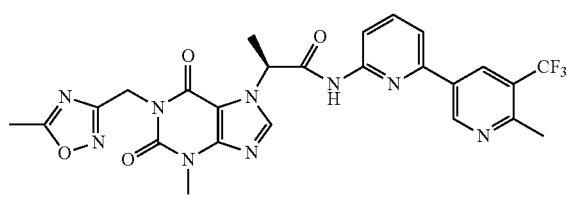 [SMILES: Cc1nc(Cn2c(=O)c3c(ncn3[C@@H](C)C(=O)Nc3cccc(-c4cnc(C)c(C(F)(F)F)c4)n3)n(C)c2=O)no1]

This compound was prepared using the method described for compound 1 with appropriate starting materials in 24.5% yield as a white solid. ¹HNMR (400 MHz, DMSO-d₆) δ 11.16 (s, 1H), 9.41 (s, 1H), 8.70 (d, J=1.8 Hz, 1H), 8.43 (s, 1H), 8.03 (s, 1H), 7.99-7.91 (m, 2H), 5.83 (d, J=6.6 Hz, 1H), 5.17-5.05 (m, 2H), 3.48 (s, 3H), 2.72 (d, J=1.3 Hz, 3H), 1.89 (d, J=7.3 Hz, 3H). Retention time (LC-MS): 2.411 min. MH+570.

Compound 152 (2S)-N-(6-(2-(3-azabicyclo[3.1.0]hexan-3-yl)pyrimidin-5-yl)pyrazin-2-yl)-2-(3-methyl-2,6-dioxo-1-(2-oxopropyl)-2,3-dihydro-1H-purin-7(6H)-yl)propanamide

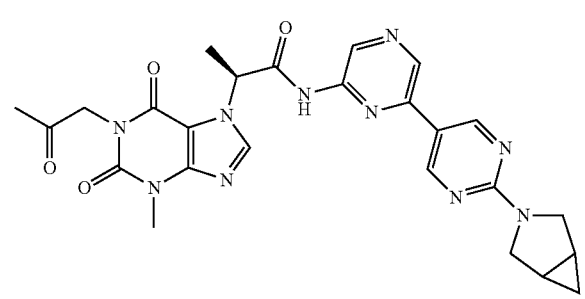 [SMILES: CC(=O)Cn1c(=O)c2c(ncn2[C@@H](C)C(=O)Nc2cncc(-c3cnc(N4CC5CC5C4)nc3)n2)n(C)c1=O]

This compound was prepared using the method described for compound 2 with appropriate starting materials in 22.1% yield. White solid. ¹H NMR (400 MHz, DMSO-d₆)δ 11.33 (s, 1H), 9.10 (s, 1H), 9.02 (s, 2H), 8.90 (s, 1H), 8.40 (s, 1H), 5.78 (d, J=6.9 Hz, 1H), 4.69 (s, 2H), 3.85 (d, J=11.4 Hz, 2H), 3.56 (d, J=11.0 Hz, 2H), 3.46 (s, 3H), 2.16 (s, 3H), 1.88 (d, J=7.2 Hz, 3H), 1.70 (s, 2H), 0.77 (d, J=4.8 Hz, 1H), 0.16 (d, J=4.3 Hz, 1H). Retention time (LC-MS): 2.072 min. MH+531.

Compound 153 (2S)-N-(2-(2-(3-azabicyclo[3.1.0]hexan-3-yl)pyrimidin-5-yl)thiazol-4-yl)-2-(3-methyl-2,6-dioxo-1-(2-oxopropyl)-2,3-dihydro-1H-purin-7(6H)-yl)propanamide

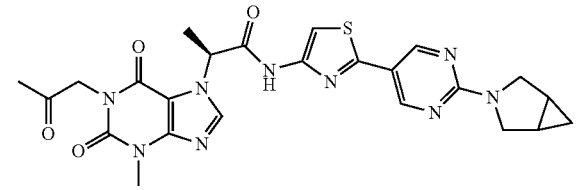 [SMILES: CC(=O)Cn1c(=O)c2c(ncn2[C@@H](C)C(=O)Nc2csc(-c3cnc(N4CC5CC5C4)nc3)n2)n(C)c1=O]

This compound was prepared using the method described for compound 2 with appropriate starting materials in 54.5% yield as a yellow solid. ¹H NMR (400 MHz, DMSO-d6) δ 11.60 (s, 1H), 8.81 (s, 2H), 8.39 (s, 1H), 7.47 (s, 1H), 5.70 (d, J=7.3 Hz, 1H), 4.70 (d, J=1.2 Hz, 2H), 3.84 (d, J=11.4 Hz, 2H), 3.56 (d, J=11.2 Hz, 2H), 3.46 (s, 3H), 2.17 (s, 3H), 1.84 (d, J=7.3 Hz, 3H), 1.73-1.67 (m, 2H), 0.78 (d, J=4.7 Hz, 1H), 0.17 (d, J=4.3 Hz, 1H). Retention time (LC-MS): 2.303 min. MH+536.

Compound 154 (S)-2-(3-methyl-2,6-dioxo-1-(2-oxopropyl)-2,3-dihydro-1H-purin-7(6H)-yl)-N-(5-(2-(trifluoromethyl)pyrimidin-5-yl)thiazol-4-yl)propanamide

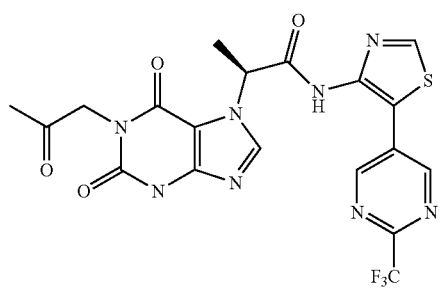 [SMILES: CC(=O)Cn1c(=O)[nH]c2ncn([C@@H](C)C(=O)Nc3ncsc3-c3cnc(C(F)(F)F)nc3)c2c1=O]

This compound was prepared using the method described for compound 2 with appropriate starting materials in 45.0% yield as a yellow solid. ¹H NMR (DMSO-d6) δ 11.18 (s, 1H), 9.26 (s, 1H), 9.05 (s, 2H), 8.27 (s, 1H), 5.58-5.61 (m, 1H), 4.69-4.84 (m, 2H), 3.49 (s, 3H), 2.20 (s, 3H), 1.81 (d, J=7.20 Hz, 3H). Retention time (LC-MS): 1.658 min. MH+523.

Compound 155 (2S)-N-(2'-(3-azabicyclo[3.1.0]
hexan-3-yl)-2,5'-bipyrimidin-4-yl)-2-(1-(cyanom-
ethyl)-3-methyl-2,6-dioxo-2,3-dihydro-1H-purin-7
(6H)-yl)propanamide

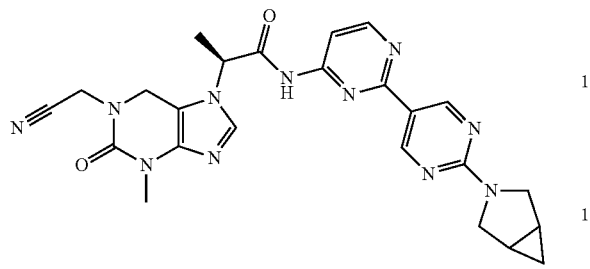

This compound was prepared using the method described for compound 10 with appropriate starting materials and separated via preparative Chiral HPLC in 40.3% yield as a white solid. ¹H NMR (DMSO-d$_6$) δ 11.49 (s, 1H), 9.17 (s, 2H), 8.68 (d, J=5.6 Hz , 1H), 8.44 (s, 1H), 7.80 (d, J=6.0 Hz , 1H), 5.79-5.82 (m, 1H), 4.85 (s, 2H), 3.87 (d, J=11.2 Hz , 2H), 3.57 (d, J=11.2 Hz, 2H), 3.49 (s, 3H), 1.88 (d, J=7.2 Hz , 3H), 1.69-1.72 (m, 2H), 0.76-0.81 (m, 1H), 0.16-0.20 (m, 1H). Retention time (LC-MS): 1.739 min. MH$^+$514.

Compound 156 (S)-2-(3-methyl-1-((5-methylisox-
azol-3-yl)methyl)-2,6-dioxo-2,3-dihydro-1H-purin-7
(6H)-yl)-N-(5'-(trifluoromethyl)-2,3'-bipyridin-6-yl)
propanamide

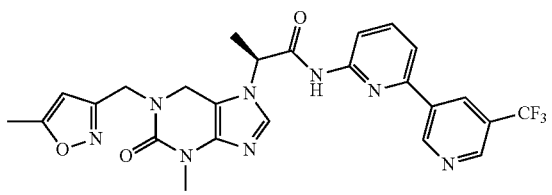 [SMILES: Cc1cc(CN2Cc3c(ncn3[C@@H](C)C(=O)Nc3cccc(-c4cncc(C(F)(F)F)c4)n3)N(C)C2=O)no1]

This compound was prepared using the method described for compound 2 with appropriate starting materials in 18.1% yield as awhite solid. ¹H NMR (400 MHz, DMSO-d6) δ 11.20 (s, 1H), 9.59 (s, 1H), 9.07 (s, 1H), 8.81 (s, 1H), 8.41 (s, 1H), 8.07 (d, J=6.7 Hz, 1H), 8.03-7.94 (m, 2H), 6.08 (s, 1H), 5.82 (d, J=7.0 Hz, 1H), 5.02 (s, 2H), 3.47 (s, 3H), 2.30 (s, 3H), 1.88 (d, J=7.3 Hz, 3H). Retention time (LC-MS): 2.406 min. MH$^+$555.

Compound 157 (S)-2-(1-(but-2-ynyl)-3-methyl-2,6-
dioxo-2,3-dihydro-1H-purin-7(6H)-yl)-N-(2-(24(R)-
2-(trifluoromethyl)pyrrolidin-1-yl)pyrimidin-5-yl)
thiazol-4-yl)propanamide

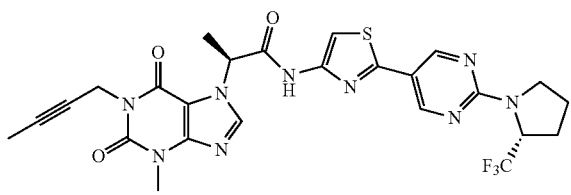 [SMILES: CC#CCn1c(=O)c2c(ncn2[C@@H](C)C(=O)Nc2csc(-c3cnc(N4CCC[C@@H]4C(F)(F)F)nc3)n2)n(C)c1=O]

This compound was prepared using the method described for compound 2 with appropriate starting materials in 30% yield as a yellow solid. ¹H-NMR (400 MHz, DMSO-d$_6$) δ 11.68 (s, 1H), 8.95(s, 2H), 8.37 (s, 1H), 7.55(s, 1H), 5.74(d, J=7.2 Hz, 1H), 5.10(t, J=8.0 Hz, 1H), 4.51(m, 2H), 3.71(m, 2H), 3.47 (s, 3H), 2.17(m, 4H), 1.83(m, 3H), 1.71 (d, J=7.2 Hz, 3H). Retention time (LC-MS): 2.066 min. MH$^+$588.

Compound 158 (2S)-N-(5'-(3-azabicyclo[3.1.0]
hexan-3-yl)-[2,2'-bipyrazin]-6-yl)-2-(3-methyl-2,6-
dioxo-1-(2-oxobutyl)-2,3-dihydro-1H-purin-7(6H)-
yl)propanamide

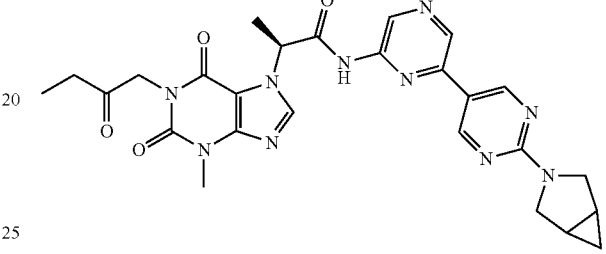

This compound was prepared using the method described for compound 2 with appropriate starting materials in 20.3% yield as a yellow solid. 1H NMR (400 MHz, DMSO-d6) δ 11.34 (s, 1H), 9.13 (s, 1H), 9.01 (s, 1H), 8.87 (d, J=1.2 Hz, 1H), 8.41 (s, 1H), 8.09 (d, J=1.2 Hz, 1H), 5.82 (d, J=7.0 Hz, 1H), 4.79-4.60 (m, 2H), 3.80 (d, J=10.8 Hz, 2H), 3.55 (d, J=10.7 Hz, 2H), 3.47 (s, 3H), 2.57-2.52 (m, 2H), 1.89 (d, J=7.3 Hz, 3H), 1.80-1.67 (m, 2H), 0.94 (t, J=7.3 Hz, 3H), 0.80 (m, 1H), 0.21 (m, 1H). Retention time (LC-MS): 1.873 min. MH$^+$545.

Compound 159 (2S)-N-(5'-(6,6-difluoro-3-azabicy-
clo[3.1.0]hexan-3-yl)-[2,2'-bipyrazin]-6-yl)-2-(3-
methyl-2,6-dioxo-1-(2-oxobutyl)-2,3-dihydro-1H-
purin-7(6H)-yl)propanamide

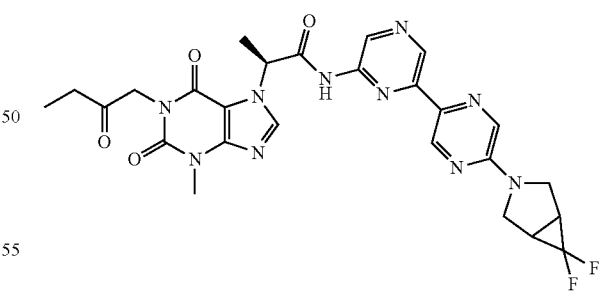

This compound was prepared using the method described for compound 2 with appropriate starting materials in 25.0% yield as a yellow solid. ¹H NMR (400 MHz, DMSO-d6) δ 9.15 (s, 1H), 9.02 (s, 1H), 8.90 (d, J=1.1 Hz, 1H), 8.41 (s, 1H), 8.30 (s, 1H), 8.14 (s, 1H), 5.82 (s,1H), 4.70 (s, 2H), 3.96 (d, J=11.4 Hz, 2H), 3.86 (d, J=9.9 Hz, 2H), 3.46 (s, 3H), 2.78 (d, J=10.7 Hz, 2H), 2.58-2.52 (m, 2H), 1.89 (d, J=7.3 Hz,3H), 0.93 (m, 3H). Retention time (LC-MS): 1.845 min. MH$^+$581.

Compound 160 (S)-2-(3-methyl-1-((3-methyl-1,2,4-oxadiazol-5-yl)methyl)-2,6-dioxo-2,3-dihydro-1H-purin-7(6H)-yl)-N-(6-(2-(trifluoromethyl)pyrimidin-5-yl)pyrazin-2-yl)propanamide

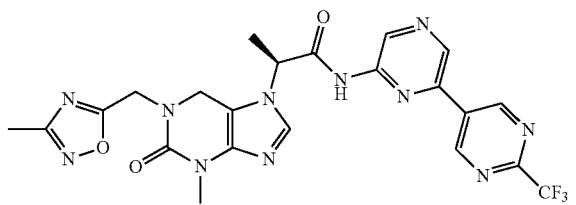 [SMILES: Cc1noc(CN2Cc3c(ncn3[C@@H](C)C(=O)Nc3cncc(-c4cnc(C(F)(F)F)nc4)n3)N(C)C2=O)n1]

This compound was prepared using the method described for compound 1 with appropriate starting materials in 12.9% yield as awhite solid. $^1$H NMR (400 Hz, DMSO-d$_6$) δ 11.66 (s, 1H), 9.70 (s, 2H), 9.35 (s, 1H), 9.23 (s, 1H), 8.47 (s, 1H), 5.82 (m, 1H), 5.29 (m, 2H), 3.49 (s, 3H), 2.26 (s, 3H), 1.91 (d, J=7.3 Hz, 3H). Retention time (LC-MS): 1.707 min. MH$^+$558.

Compound 161 (S)-2-(3-methyl-2,6-dioxo-1-(2,2,2-trifluoroethyl)-2,3-dihydro-1H-purin-7(6H)-yl)-N-(2-(5-methyl-6-(trifluoromethyl)pyridin-3-yl)thiazol-4-yl)propanamide

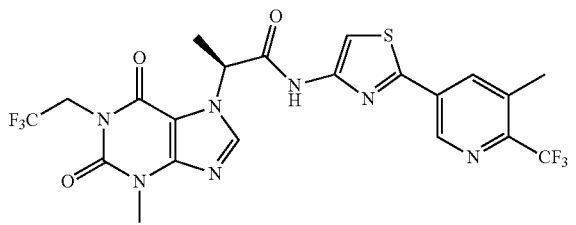 [SMILES: Cc1cc(-c2nc(NC(=O)[C@H](C)n3cnc4c3c(=O)n(CC(F)(F)F)c(=O)n4C)cs2)cnc1C(F)(F)F]

This compound was prepared using the method described for compound 102 with appropriate starting materials in 35.4% yield as awhite solid. $^1$H NMR (400 Hz, DMSO-d$_6$) δ 11.81 (s, 1H), 9.08 (s, 1H), 8.44 (s, 1H), 8.41 (s, 1H), 7.77 (s, 1H), 5.74 (m, 1H), 4.64 (m, 2H), 3.49 (s, 3H), 2.56 (s, 3H), 1.87 (d, J=7.2 Hz, 3H). Retention time (LC-MS): 2.473 min. MH$^+$562.

Compound 162 (S)-2-(3-methyl-2,6-dioxo-1-(2,2,2-trifluoroethyl)-2,3-dihydro-1H-purin-7(6H)-yl)-N-(2-(6-methyl-5-(trifluoromethyl)pyridin-3-yl)thiazol-4-yl)propanamide

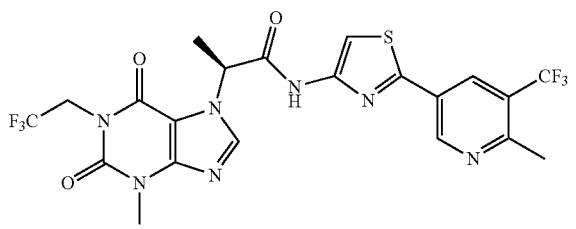 [SMILES: Cc1ncc(-c2nc(NC(=O)[C@H](C)n3cnc4c3c(=O)n(CC(F)(F)F)c(=O)n4C)cs2)cc1C(F)(F)F]

This compound was prepared using the method described for compound 1 with appropriate starting materials in 14.8% yield as a white solid. $^1$H NMR (400 Hz, DMSO-d$_6$) δ 11.75 (s, 1H), 9.24 (s, 1H), 8.47 (s, 1H), 8.42 (s, 1H), 7.71 (s, 1H), 5.74 (m, 1H), 4.71-4.59 (m, 2H), 3.49 (s, 3H), 2.71 (s, 3H), 1.86 (d, J=7.6 Hz, 3H). Retention time (LC-MS): 2.676 min. MH$^+$562.

Compound 163 (S)-2-(3-methyl-1-((5-methyl-1,2,4-oxadiazol-3-yl)methyl)-2,6-dioxo-2,3-dihydro-1H-purin-7(6H)-yl)-N-(2-(6-methyl-5-(trifluoromethyl)pyridin-3-yl)thiazol-4-yl)propanamide

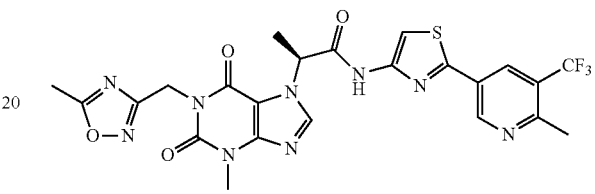

This compound was prepared using the method described for compound 1 with appropriate starting materials in 17.6% yield as a white solid. $^1$H NMR (400 Hz, DMSO-d$_6$) δ 11.75 (s, 1H), 9.23 (d, J=1.7 Hz, 1H), 8.46 (d, J=1.7 Hz, 1H), 8.42 (s, 1H), 7.71 (s, 1H), 5.75 (q, J=7.3 Hz, 1H), 5.11 (s, 2H), 3.47 (s, 3H), 2.70 (s, 3H), 2.53 (s, 3H), 1.86 (d, J=7.3 Hz, 3H). Retention time (LC-MS): 2.309 min. MH$^+$576.

Compound 164 (2S)-N-(5'-(6,6-difluoro-3-azabicyclo[3.1.0]hexan-3-yl)-[2,2'-bipyrazin]-6-yl)-2-(3-methyl-2,6-dioxo-1-(2-oxopropyl)-2,3-dihydro-1H-purin-7(6H)-yl)propanamide

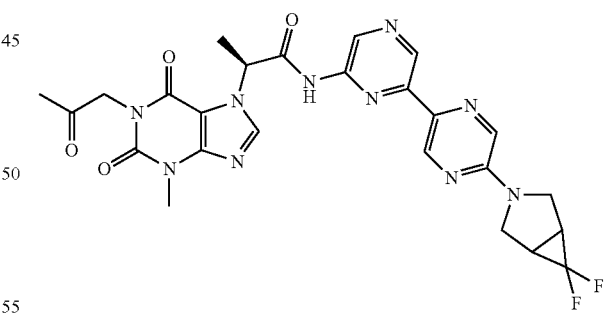

This compound was prepared using the method described for compound 2 with appropriate starting materials in 14.3% yield as a yellow solid. $^1$H NMR (400 MHz, DMSO-d6) δ 11.37 (s, 1H), 9.15 (s, 1H), 9.02 (s, 1H), 8.91 (d, J=1.2 Hz, 1H), 8.41 (s, 1H), 8.14 (d, J=1.6 Hz, 1H), 5.80 (m, 1H), 4.70 (s, 2H), 3.96 (d, J=11.6 Hz, 2H), 3.86 (d, J=9.4 Hz, 2H), 3.46 (s, 3H), 2.78 (d, J=10.6 Hz, 2H), 2.16 (s, 3H), 1.89 (d, J=7.3 Hz, 3H). Retention time (LC-MS): 1.663 min. MH$^+$567.

Compound 165 (2S)-N-(6-(2-(3-azabicyclo[3.1.0]
hexan-3-yl)pyrimidin-5-yl)pyridin-2-yl)-2-(1-(3-
methoxy-2-oxopropyl)-3-methyl-2,6-dioxo-2,3-di-
hydro-1H-purin-7(6H)-yl)propanamide

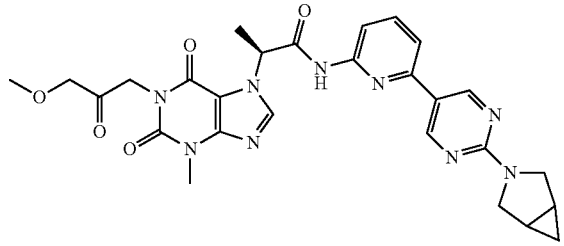 [SMILES: COCC(=O)Cn1c(=O)c2c(ncn2[C@@H](C)C(=O)Nc2cccc(-c3cnc(N4CC5CC5C4)nc3)n2)n(C)c1=O]

This compound was prepared using the method described for compound 2 with appropriate starting materials in 19.1% yield as a yellow solid. ¹H NMR (400 MHz, DMSO-d6) δ 11.01 (s, 1H), 8.99 (s, 2H), 8.39 (d, J=6.9 Hz, 1H), 7.88-7.78 (m, 2H), 7.60 (d, J=7.8 Hz, 1H), 5.79 (s, 1H), 4.74 (d, J=3.7 Hz, 2H), 4.21 (s, 2H), 3.85 (d, J=11.2 Hz, 2H), 3.55 (s, 3H), 3.46 (s, 3H), 3.31 (s, 3H), 1.86 (d, J=7.3 Hz, 3H), 1.68 (m, 2H), 0.77 (m, 1H), 0.17 (m, 1H). Retention time (LC-MS): 1.975 min. MH⁺560.

Compound 166 (2S)-N-(2-(2-(3-azabicyclo[3.1.0]
hexan-3-yl)pyrimidin-5-yl)thiazol-4-yl)-2-(3-methyl-
1-((3-methyl-1,2,4-oxadiazol-5-yl)methyl)-2,6-di-
oxo-2,3-dihydro-1H-purin-7(6H)-yl)propanamide

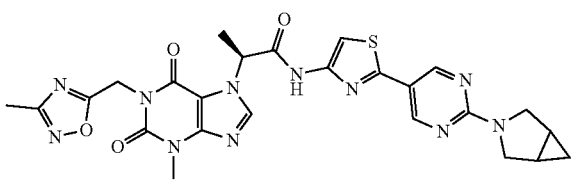 [SMILES: Cc1noc(Cn2c(=O)c3c(ncn3[C@@H](C)C(=O)Nc3csc(-c4cnc(N5CC6CC6C5)nc4)n3)n(C)c2=O)n1]

This compound was prepared using the method described for compound 107 with appropriate starting materials in 12.2% yield as a white solid. ¹H NMR (400 MHz, DMSO-d6) δ 11.63 (s, 1H), 8.81 (s, 2H), 8.43 (s, 1H), 7.47 (s, 1H), 5.72 (d, J=7.3 Hz, 1H), 5.25 (m, 2H), 3.83 (d, J=11.4 Hz, 2H), 3.55 (d, J=10.9 Hz, 2H), 3.48 (s, 3H), 2.26 (s, 3H), 1.84 (d, J=7.3 Hz, 3H), 1.67 (m, 2H), 0.76 (m, 1H), 0.17 (d, J=4.3 Hz, 1H). Retention time (LC-MS): 2.361 min. MH⁺576.

Compound 167 (2S)-N-(6-(2-(3-azabicyclo [3.1.0]
hexan-3-yl)pyrimidin-5- yl)pyridin-2-yl)-2-(3-
methyl-1-((3-methyl-1,2,4-oxadiazol-5-yl)methyl)-2,
6-dioxo-2,3- dihydro-1H-purin-7(6H)-yl)propana-
mide

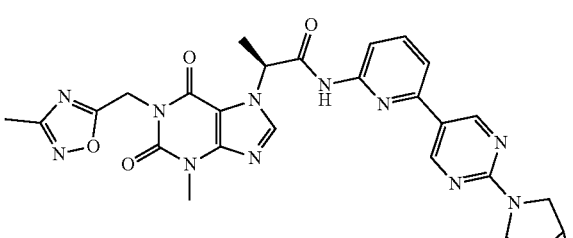

This compound was prepared using the method described for compound 1 with appropriate starting materials in 10.4% yield as a white solid. ¹H NMR (400 MHz, DMSO-d6) δ 11.02 (s, 1H), 8.99 (s, 2H), 8.44 (s, 1H), 7.82 (m, 2H), 7.61 (d, J=8.2 Hz, 1H), 5.80 (s, 1H), 5.27 (m, 2H), 3.84 (d, J=11.3 Hz, 2H), 3.54 (d, J=11.2 Hz, 2H), 3.48 (s, 3H), 2.26 (s, 3H), 1.87 (d, J=7.6 Hz, 3H), 1.69 (m, 2H), 0.752 (m, 1H), 0.16 (m, 1H). Retention time (LC-MS): 2.298 min. MH⁺570.

Compound 168 (2S)-N-(6-(2-(3-azabicyclo[3.1.0]
hexan-3-yl)pyrimidin-5- yl)pyridin-2-yl)-2-(1-(but-
2-yn-1-yl)-3-methyl-2,6-dioxo-2,3-dihydro-1H-pu-
rin-7(6H)- yl)propanamide

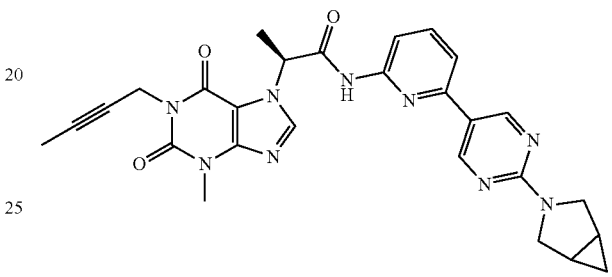

This compound was prepared using the method described for compound 1 with appropriate starting materials in 7.6% yield as a white solid. ¹H NMR (400 MHz, DMSO-d6) δ 11.04 (s, 1H), 9.00 (s, 2H), 8.37 (s, 1H), 7.81 (m, 2H), 7.61 (d, J=8.3 Hz, 1H), 5.83 (s, 1H), 4.52 (m, 2H), 3.85 (d, J=11.6 Hz, 2H), 3.55 (d, J=11.1 Hz, 2H), 3.46 (d, J=4.7 Hz, 3H), 1.86 (d, J=7.3 Hz, 3H), 1.70 (m, 5H), 0.76 (m, 1H), 0.17 (m, 1H). Retention time (LC-MS): 2.312 min. MH⁺526.

Compound 169 (2S)-2-(1-(but-2-yn-1-yl)-3-methyl-
2,6-dioxo-2,3-dihydro-1H - purin-7(6H)-yl)-N-(6-
(2-(6,6-difluoro-3-azabicyclo[3.1.0]hexan-3-yl)py-
rimidin-5-yl)pyridin- 2-yl)propanamide

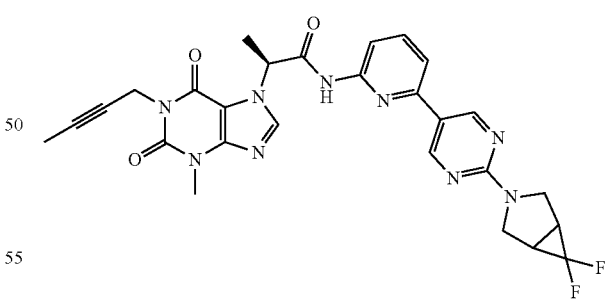

This compound was prepared using the method described for compound 1 with appropriate starting materials and separated via preparative HPLC in 3.9% yield as a white solid. ¹H NMR (400 MHz, DMSO-d6) δ 11.05 (s, 1H), 9.04 (s, 2H), 8.37 (s, 1H), 7.84 (m, 2H), 7.64 (d, J=8.4 Hz, 1H), 5.83 (s, 1H), 4.52 (m, 2H), 3.99 (d, J=12 Hz, 2H), 3.87 (d, J=10.4 Hz, 2H), 3.46 (s, 3H), 2.70 (d, J=10.4 Hz, 2H), 1.86 (d, J=7.6 Hz, 3H), 1.69 (m, 3H). Retention time (LC-MS): 2.379 min. MH⁺562.

Compound 170 (S)-2-(3-methyl-1-((5-methyl-1,2,4-oxadiazol-3-yl)methyl)-2,6-dioxo-2,3-dihydro-1H-purin-7(6H)-yl)-N-(6-(6-methyl-5-(trifluoromethyl)pyridin-3-yl)pyrazin-2-yl)propanamide

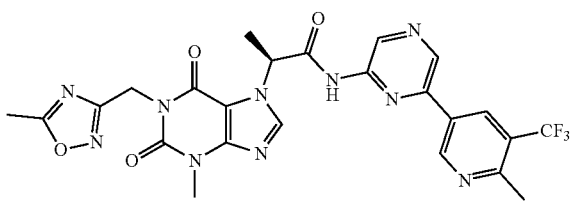 [SMILES: Cc1nc(Cn2c(=O)c3c(ncn3[C@@H](C)C(=O)Nc3cncc(-c4cnc(C)c(C(F)(F)F)c4)n3)n(C)c2=O)no1]

This compound was prepared using the method described for compound 1 with appropriate starting materials in 13.4% yield as a white solid. ¹H NMR (400 MHz, DMSO-d6) δ 11.54 (s, 1H), 9.47 (s, 1H), 9.27 (s, 1H), 9.21 (s, 1H), 8.73 (s, 1H), 8.45 (s, 1H), 5.86-5.78 (m, 1H), 5.11 (s, 2H), 3.48 (s, 3H), 2.73 (s, 3H), 2.52 (s, 3H), 1.90 (d, J=7.3 Hz, 3H). Retention time (LC-MS): 1.817 min. MH⁺571.

Compound 171 (S)-2-(3-methyl-1-((5-methyl-1,2,4-oxadiazol-3-yl)methyl)-2,6-dioxo-2,3-dihydro-1H-purin-7(6H)-yl)-N-(6-(2-(trifluoromethyl)pyrimidin-5-yl)pyridin-2-yl)propanamide

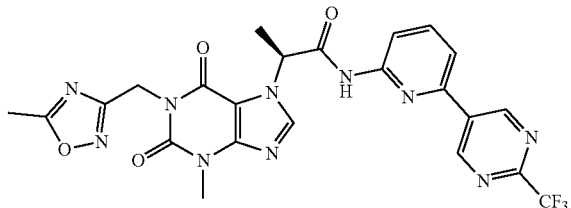

This compound was prepared using the method described for compound 1 with appropriate starting materials in 20.4% yield as a white solid. ¹H NMR (400 MHz, DMSO-d6) δ 11.29 (s, 1H), 9.66 (s, 2H), 8.43 (s, 1H), 8.11 (d, J=7.5 Hz, 1H), 8.06-7.96 (m, 2H), 5.83 (s, 1H), 5.16-5.05 (m, 2H), 3.48 (s, 3H), 2.51 (s, 3H), 1.89 (d, J=7.3 Hz, 3H). Retention time (LC-MS): 1.876 min. MH⁺557.

Compound 172 (S)-2-(3-methyl-1-((5-methyl-1,2,4-oxadiazol-3-yl)methyl)-2,6-dioxo-2,3-dihydro-1H-purin-7(6H)-yl)-N-(2-(6-methyl-5-(trifluoromethyl)pyridin-3-yl)pyrimidin-4-yl)propanamide

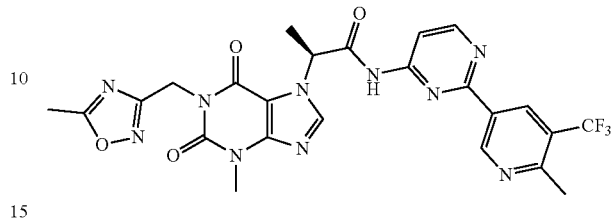

This compound was prepared using the method described for compound 1 with appropriate starting materials in 15.0% yield as a white solid. ¹H NMR (400 MHz, DMSO-d6) δ 11.60 (s, 1H), 9.59 (s, 1H), 8.88-8.81 (m, 2H), 8.44 (s, 1H), 7.97 (d, J=5.6 Hz, 1H), 5.81 (s, 1H), 5.10 (s, 2H), 3.48 (s, 3H), 2.74 (s, 3H), 2.52 (s, 3H), 1.90 (d, J=7.3 Hz, 3H). Retention time (LC-MS): 1.305 min. MH⁺571.

Compound 173 (2S)-N-(2'-(3-azabicyclo[3.1.0]hexan-3-yl)-[2,5'-bipyrimidin]-4-yl)-2-(1-(but-2-yn-1-yl)-3-methyl-2,6-dioxo-2,3-dihydro-1H-purin-7(6H)-yl)propanamide

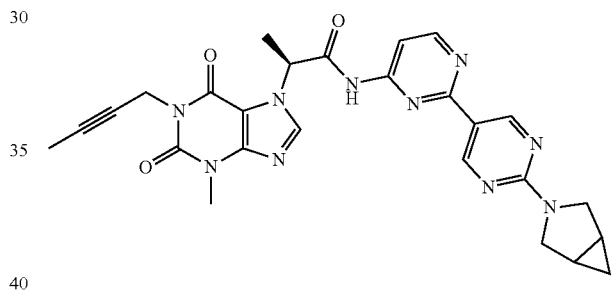

This compound was prepared using the method described for compound 1 with appropriate starting materials and separated via preparative HPLC in 13.8% yield as a white solid. ¹H NMR (400 MHz, DMSO-d6) δ 11.46 (s, 1H), 9.17 (s, 2H), 8.68 (d, J=6 Hz, 1H), 8.37 (s, 1H), 7.80 (d, J=5.6 Hz, 1H), 5.81 (s, 1H), 4.51 (m, 2H), 3.87 (d, J=11.2 Hz, 2H), 3.59 (d, J=12 Hz, 2H), 3.46 (s, 3H), 1.88 (d, J=7.2 Hz, 3H), 1.70 (m, 5H), 0.78 (m, 1H), 0.17 (m, 1H). Retention time (LC-MS): 2.225 min. MH⁺527.

Compound 174 N-(6-(4-chlorophenyl)pyridin-2-yl)-2-(3,8-dimethyl-2,6-dioxo-1-(pyridin-2-ylmethyl)-2,3-dihydro-1H-purin-7(6H)-yl)acetamide

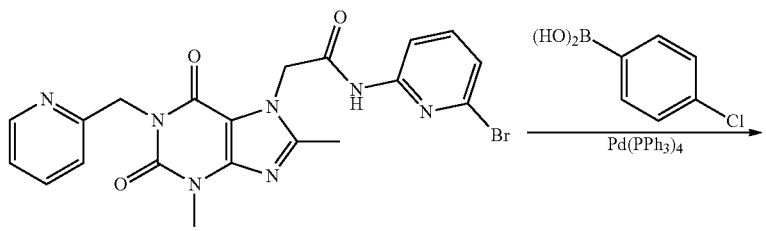

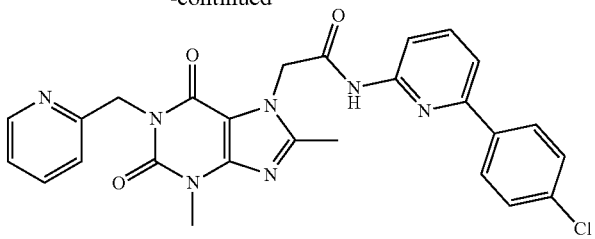

To a mixture of N-(6-bromopyridin-2-yl)-2-(3,8-dimethyl-2,6-dioxo-1-(pyridin-2-ylmethyl)-2,3-dihydro-1H-purin-7(6H)-yl)acetamide (140 mg, 0.29 mmol) and 4-chlorophenylboronic acid (68 mg, 0.43 mmol) in toluene/ethanol/2N aq. Na$_2$CO$_3$ (2 mL/1 mL/0.5 mL) was added Pd(PPh$_3$)$_4$ (48 mg, 0.04 mmol) after degassed three times under N$_2$ atmosphere. The mixture was then heated to 100° C. for 2 h. The reaction mixture was cooled to RT and filtered through Celite. The filtrate was extracted with EA (3×20 mL). Combined organic layers were dried over Na$_2$SO$_4$ and filtered. The filtrate was concentrated and the residue was purified via prep-HPLC to give N-(6-(4-chlorophenyl)pyridin-2-yl)-2-(3,8-dimethyl-2,6-dioxo-1-(pyridin-2-ylmethyl)-2,3-dihydro-1H-purin-7(6H)-yl)acetamide (100 mg, 67.1% yield) as a white solid. H-NMR (400 MHz, DMSO-d$_6$) δ 11.09 (s, 1H), 8.42 (dd, J=5.1, 1.7 Hz, 1H), 8.12 (t, J=8.7 Hz, 2H), 7.95 (s, 1H), 7.89 (t, J=7.9 Hz, 1H), 7.76-7.65 (m, 2H), 7.57 (d, J=8.6 Hz, 2H), 7.22 (d, J=9.7 Hz, 2H), 5.33 (s, 2H), 5.13 (s, 2H), 3.45 (s, 3H), 2.45 (s, 3H). Retention time (LC-MS): 2.160 min. MH$^+$516.

Compound 175 N-(6-(3,4-difluorophenyl)pyridin-2-yl)-2-(3,8-dimethyl-2,6-dioxo-1-(pyridin-2-ylmethyl)-2,3-dihydro-1H-purin-7(6H)-yl)acetamide

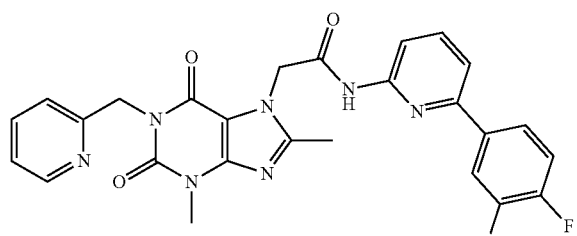

This compound was prepared using the method described for compound 174 with appropriate starting materials. $^1$H-NMR (400 MHz, DMSO-d$_6$) δ 11.08 (s, 1H), 8.42 (d, J=3.5 Hz, 1H), 8.22 -8.08 (m, 1H), 7.96 (s, 2H), 7.90 (t, J=7.9 Hz, 1H), 7.72 (m, 2H), 7.58 (m, 1H), 7.22 (d, J=7.9 Hz, 2H), 5.33 (s, 2H), 5.13 (s, 2H), 3.44 (d, J=7.1 Hz, 3H), 2.45 (s, 3H). Retention time (LC-MS): 2.040 min. MH$^+$518.

Compound 176 (S)-2-(3,8-dimethyl-2,6-dioxo-1-(pyridin-2-ylmethyl)-2,3-dihydro-1H-purin-7(6H)-yl)-N-(6-(2-(2-(trifluoromethyl)pyrrolidin-1-yl)pyrimidin-5-yl)pyridin-2-yl)acetamide

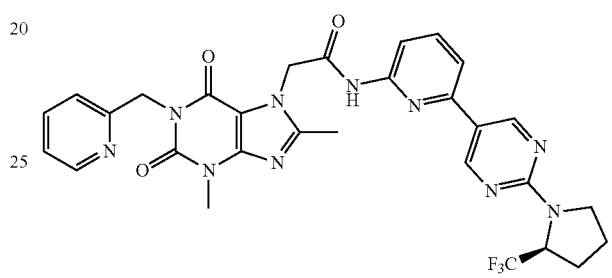

This compound was prepared using the method described for compound 1 with appropriate starting materials. $^1$H-NMR (400 MHz, DMSO-d$_6$) δ 11.03 (s, 1H), 9.10 (s, 2H), 8.42 (dd, J=5.1, 1.7 Hz, 1H), 7.91 (s, 1H), 7.86 (t, J=7.9 Hz, 1H), 7.74-7.63 (m, 2H), 7.22 (d, J=9.9 Hz, 2H), 5.33 (s, 2H), 5.16-5.05 (m, 3H), 3.77-3.63 (m, 2H), 3.45 (s, 3H), 2.45 (s, 3H), 2.23-2.02 (m, 4H). Retention time (LC-MS): 2.247 min. MH$^+$419.2.

Compound 177 2-(3,8-dimethyl-2,6-dioxo-1-(pyridin-2-ylmethyl)-2,3-dihydro-1H-purin-7(6H)-yl)-N-(6-(2-(trifluoromethyl)pyrimidin-5-yl)pyridin-2-yl)acetamide

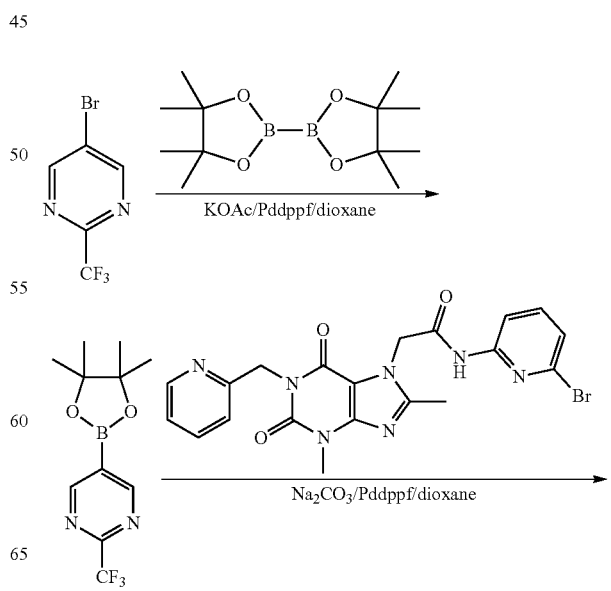

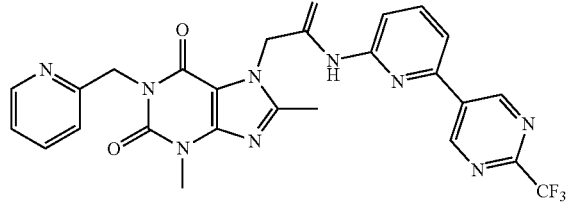

A mixture of 5-bromo-2-(trifluoromethyl)pyrimidine (113 mg, 0.50 mmol), 4,4,5,5-tetramethyl-2-(4,4,5,5-tetramethyl-1,3,2-dioxaborolan-2-yl)-1,3,2-dioxaborolane (153 mg, 0.60 mmol), potassium acetate (148 mg, 1.51 mmol) and [1,1'-bis(diphenylphos-phino)ferrocene]dichloropalladium(II) (15 mg) in a dioxane (5 mL) was degassed under $N_2$ for three times and stirred at 100° C. for 2 h under $N_2$ atmosphere. The mixture was cooled to RT. N-(6-bromopyridin-2-yl)-2-(3,8-dimethyl-2,6-dioxo-1-(pyridin-2-ylmethyl)-2,3-dihydro-1H-purin-7(6H)-yl)acetamide (140 mg, 0.29 mmol), aqueous $Na_2CO_3$ solution (1 mL, 2 M) and [1,1'-bis(diphenylphosphino)ferrocene]dichloropalladium(II) (15 mg) were added to the above mixture under $N_2$ atmosphere. The mixture was stirred at 100° C. under $N_2$ for 2 h and cooled to RT. The reaction mixture was extracted with DCM (2×30 mL). Combined organic layers were washed with brine, dried over $Na_2SO_4$, and concentrated and the residue was purified prep-HPLC to give 2-(3,8-dimethyl-2,6-dioxo-1-(pyridin-2-ylmethyl)-2,3-dihydro-1H-purin-7(6H)-yl)-N-(6-(2-(trifluoromethyl)pyrimidin-5-yl)pyridin-2-yl)acetamide (40 mg, 25.1% yield) as a white solid. $^1$H NMR (400 MHz, DMSO-$d_6$) δ 11.26 (s, 1H), 9.66 (s, 2H), 8.42 (d, J=3.6 Hz, 1H), 8.10 (s, 1H), 8.07-7.96 (m, 2H), 7.70 (td, J=7.7, 1.6 Hz, 1H), 7.22 (d, J=7.7 Hz, 2H), 5.35 (s, 2H), 5.13 (s, 2H), 3.45 (s, 3H), 2.46 (s, 3H). Retention time (LC-MS): 1.640 min. MH$^+$552.

Compound 178 N-(2-(3,4-difluorophenyl)thiazol-4-yl)-2-(3-methyl-2,6-dioxo-1-(pyridin-2-ylmethyl)-2,3-dihydro-1H-purin-7(6H)-yl)acetamide

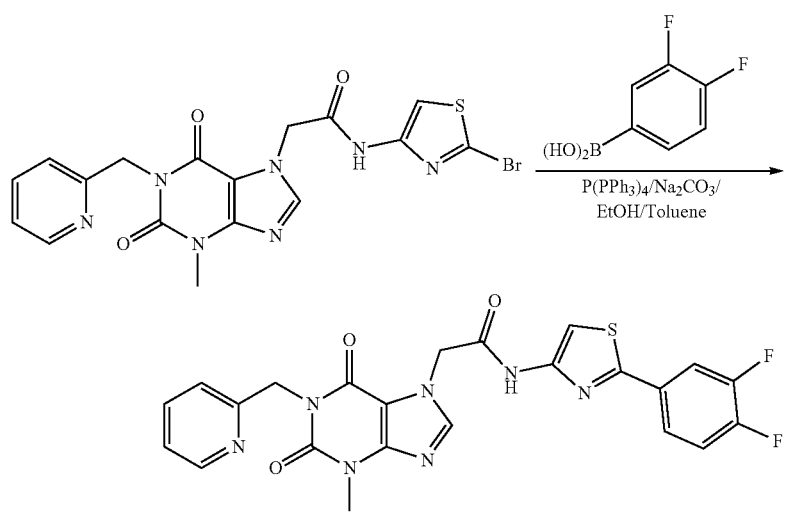

A mixture of N-(2-bromothiazol-4-yl)-2-(3-methyl-2,6-dioxo-1-(pyridin-2-ylmethyl)-2,3-dihydro-1H-purin-7(6H)-yl)acetamide (70 mg, 0.15 mmol), 4-chlorophenylboronic acid (35 mg, 0.22 mmol) in a mixed solution (toluene: ethanol: aq $Na_2CO_3$ (2 M)=4:2:1, 7 mL) was degassed under $N_2$ atmosphere, followed by addition of tetrakis(triphenylphosphine)palladium (10 mg). The mixture was stirred under $N_2$ at 100° C. for 2 h and cooled to RT. The mixture was extracted with DCM (3×10 mL). Combined organic layers were washed with brine, dried over $Na_2SO_4$, and concentrated and the residue was purified prep-HPLC to give N-(2-(3,4-difluorophenyl)thiazol-4-yl)-2-(3-methyl-2,6-dioxo-1-(pyridin-2-ylmethyl)-2,3-dihydro-1H-purin-7(6H)-yl)acetamide (20 mg, 27.8% yield) as a white solid. $^1$H NMR (400 MHz, DMSO-$d_6$) δ 11.60 (s, 1H), 8.42 (d, J=4.1 Hz, 1H), 8.14 (s, 1H), 7.94 (d, J=9.1 Hz, 1H), 7.82-7.68 (m, 2H), 7.64-7.54 (m, 2H), 7.26-7.19 (m, 2H), 5.27 (s, 2H), 5.13 (s, 2H), 3.48 (s, 3H). Retention time (LC-MS): 2.160 min. MH$^+$510.

Compound 181 N-(6-(4-chlorophenyl)pyridin-2-yl)-2-(3-methyl-2,6-dioxo-1-(2-oxopropyl)-1,2,3,6-tetrahydropurin-7-yl)acetamide

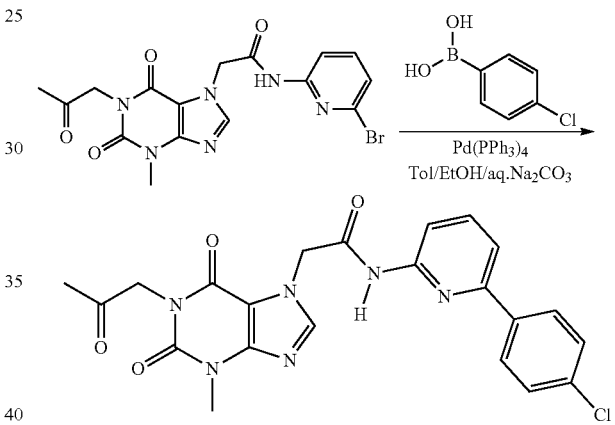

To a solution of N-(6-bromopyridin-2-yl)-2-(3-methyl-2,6-dioxo-1-(2-oxopropyl)-1,2,3,6-tetrahydropurin-7-yl)acetamide (150 mg, 0.34 mmol) in toluene/ethanol (4 mL/2 mL) was added aqueous Na$_2$CO$_3$ solution and the mixture was degassed under N$_2$ for three times. To the above mixture, 4-chlorophenylboronic acid (80 mg, 0.52 mmol) and tetrakis (triphenylphosphine)palladium (19.6 mg, 0.017 mmol) were added under N$_2$ atmosphere. The rsulting mixture was stirred at 100° C. under N$_2$ for 2 h. The mixture was diluted with DCM, washed with brine, dried over Na$_2$SO$_4$, and concentrated and the residue was purified via prep-HPLC to give N-(6-(4-chlorophenyl)pyridin-2-yl)-2-(3-methyl-2,6-dioxo-1-(2-oxopropyl)-1,2,3,6-tetrahydropurin -7-yl)acetamide (30 mg, 20.0% yield) as a white solid. $^1$H-NMR (400 MHz, DMSO-d$_6$) δ 11.08 (s, 1H), 8.13 (d, J=10.4 Hz, 3H), 7.95 (s, 1H), 7.89 (t, J=7.9 Hz, 1H), 7.73 (d, J=7.8 Hz, 1H), 7.59 (d, J=8.5 Hz, 2H), 5.30 (s, 2H), 4.70 (s, 2H), 3.46 (s, 4H), 2.17 (s, 3H). Retention time (LC-MS): 1.375 min. MH$^+$467.

Compound 182 N-(6-(3,4-difluorophenyl)pyridin-2-yl)-2-(3-methyl-2,6-dioxo-1-(2-oxopropyl)-1,2,3,6-tetrahydropurin-7-yl)acetamide

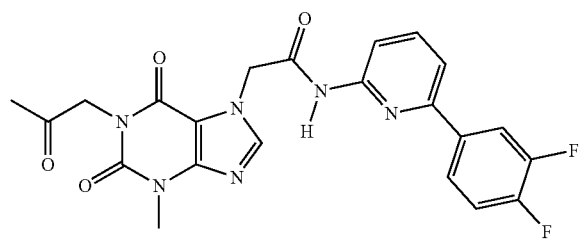 [SMILES: CC(=O)Cn1c(=O)c2c(ncn2CC(=O)Nc2cccc(-c3ccc(F)c(F)c3)n2)n(C)c1=O]

This compound was prepared using the method described for compound 181 with appropriate starting materials. $^1$H-NMR (400 MHz, DMSO-d$_6$) δ 11.04 (s, 1H), 8.13 (s, 1H), 7.93 (d, J=29.1 Hz, 2H), 7.76 (s, 1H), 7.57 (s, 1H), 5.31 (s, 1H), 4.69 (s, 1H), 3.46 (s, 2H), 2.50 (s, 2H), 2.16 (s, 2H), 2.07 (s, 1H). Retention time (LC-MS): 2.141 min. MH$^+$469.

Compound 183 (S)-2-(3-methyl-2,6-dioxo-1-(2-oxopropyl)-1,2,3,6-tetrahydropurin-7-yl)-N-(6-(2-(2-(trifluo romethyl)pyrrolidin-1-yl)pyrimidin-5-yl) pyridin-2-yl)acetamide

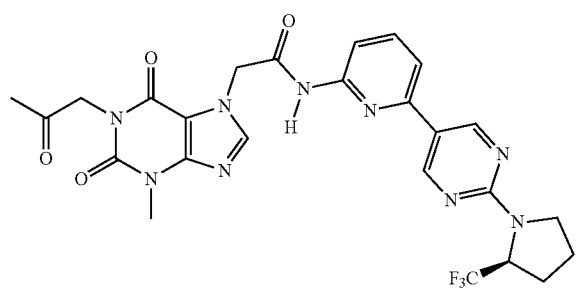 [SMILES: CC(=O)Cn1c(=O)c2c(ncn2CC(=O)Nc2cccc(-c3cnc(N4CCC[C@H]4C(F)(F)F)nc3)n2)n(C)c1=O]

This compound was prepared using the method described for compound 181 with appropriate starting materials. $^1$H NMR (400 MHz, DMSO-d$_6$) δ 11.01 (s, 1H), 9.11 (s, 2H), 8.14 (s, 1H), 7.87 (dd, J=16.4, 8.8 Hz, 2H), 7.68 (d, J=8.0 Hz, 1H), 5.30 (s, 2H), 5.20-5.01 (m, 1H), 4.70 (s, 2H), 3.71 (t, J=6.7 Hz, 2H), 3.46 (s, 3H), 2.21 (d, J=9.3 Hz, 1H), 2.16-2.13 (m, 1H), 2.09 (d, J=13.6 Hz, 2H). Retention time (LC-MS): 2.405 min. MH$^+$572.

Compound 184 2-(1-(2-hydroxypropyl)-3-methyl-2,6-dioxo-1,2,3,6-tetrahydro purin-7-yl)-N-(6-(2-((S)-2-(trifluoromethyl)pyrrolidin-1-yl)pyrimidin-5-yl) pyridin-2-yl)acetamide

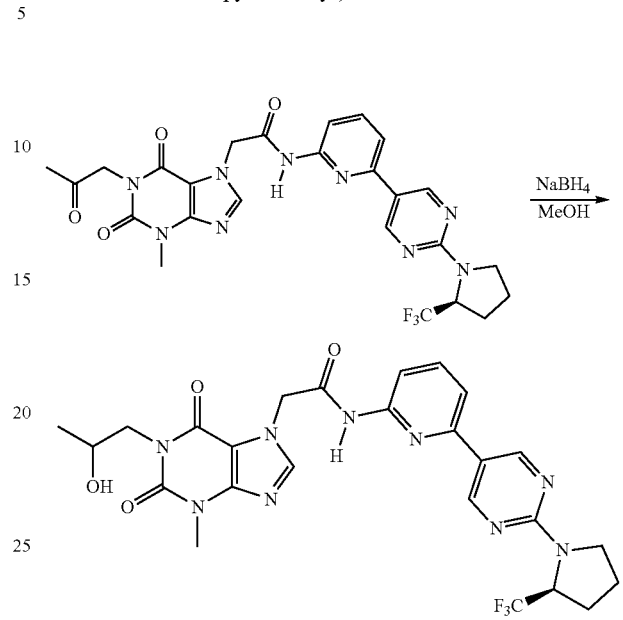

To a solution of (S)-2-(3-methyl-2,6-dioxo-1-(2-oxopropyl)-1,2,3,6-tetrahydropurin-7-yl)-N-(6-(2-(2-(trifluoromethyl) pyrrolidin-1-yl)pyrimidin-5-yl)pyridin-2-yl)acetamide (25 mg, 43.90 μmol) in MeOH (2 mL) was added sodium borohydride (3 mg, 65.84 μmol) and the mixture was stirred at RT for 2 h. The reaction was poured into ice water, and extracted with EA. Combined organic layers were dried over Na$_2$SO$_4$ and filtered. The filtrate was concentrated under reduced pressure and the residue was purified via prep-HPLC to give 2-(1-(2-hydroxypropyl)-3-methyl-2,6-dioxo-1,2,3,6-tetrahydropurin-7-yl)-N-(6-(2-((S)-2-(trifluoromethyl)pyrrolidin-1-yl)pyrimidin-5-yl)pyridin-2-yl) acetamide (20 mg, 79.7% yield) as a white solid. $^1$H NMR (400 MHz, DMSO-d$_6$) δ 11.01 (s, 1H), 9.12 (s, 2H), 8.08 (s, 1H), 7.88 (dd, J=17.2, 9.5 Hz, 2H), 7.68 (d, J=8.0 Hz, 1H), 5.31 (s, 2H), 5.18-5.03 (m, 1H), 4.67 (d, J=4.4 Hz, 1H), 3.97-3.85 (m, 2H), 3.69 (dt, J=12.1, 7.4 Hz, 3H), 3.45 (s, 4H), 2.29-2.01 (m, 4H), 1.00 (d, J=5.8 Hz, 3H). Retention time (LC-MS): 2.090 min. MH$^+$574.

Compound 185 2-(3-methyl-2,6-dioxo-1-(2-oxopropyl)-2,3-dihydro-1H-purin-7(6H)-yl)-N-(6-(2-(trifluoromethyl)pyrimidin-5-yl)pyridin-2-yl)acetamide

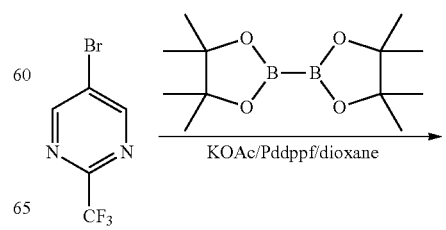

381

-continued

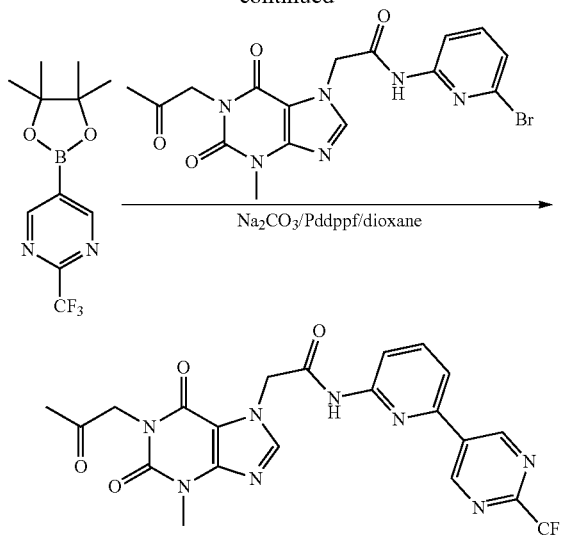

A mixture of 5-bromo-2-(trifluoromethyl)pyrimidine (113 mg, 0.50 mmol), 4,4,5,5-tetramethyl-2-(4,4,5,5-tetramethyl-1,3,2-dioxaborolan-2-yl)-1,3,2-dioxaborolane (153 mg, 0.60 mmol), potassium acetate (148 mg, 1.51 mmol) and [1,1'-bis(diphenylphos-phino)ferrocene]dichloropalladium(II) (15 mg) in a dioxane (5 mL) was degassed under $N_2$ for three times and stirred at 100° C. for 2 h under $N_2$ atmosphere. The mixture was cooled to RT. N-(6-bromopyridin-2-yl)-2-(3-methyl-2,6-dioxo-1-(2-oxopropyl)-1,2,3,6-tetrahydropurin-7-yl)acetamide (150 mg, 0.34 mmol), aqueous $Na_2CO_3$ solution (1 mL, 2 M) and [1,1'-bis(diphenylphosphino)ferrocene]dichloropalladium(II) (15 mg) were added to the above mixture under $N_2$ atmosphere. The mixture was stirred at 100° C. under $N_2$ for 2 h and cooled to RT. The reaction mixture was extracted with DCM (2×10 mL). Combined organic layers were washed with brine, dried over $Na_2SO_4$, and concentrated and the residue was purified prep-HPLC to give 2-(3-methyl-2,6-dioxo-1-(2-oxopropyl)-1,2,3,6-tetrahydropurin-7-yl)-N-(6-(2-(trifluoromethyl)pyrimidin-5-yl)pyridin-2-yl)acetamide (10 mg, 10.0% yield) as a white solid. $^1$H NMR (400 MHz, DMSO-$d_6$) δ 11.23 (s, 4H), 9.67 (s, 9H), 8.15 (s, 5H), 8.05 (d, J=7.5 Hz, 6H), 8.01 (t, J=5.8 Hz, 6H), 5.33 (s, 8H), 4.70 (s, 9H), 3.47 (s, 14H), 2.17 (s, 14H). Retention time (LC-MS): 1.968 min. MH$^+$503.

Compound 186 2-(3-methyl-2,6-dioxo-1-(pyridin-2-ylmethyl)-2,3-dihydro-1H-purin-7(6H)-yl)-N-(6-(2-(trifluoromethyl)pyrimidin-5-yl)pyridin-2-yl)acetamide

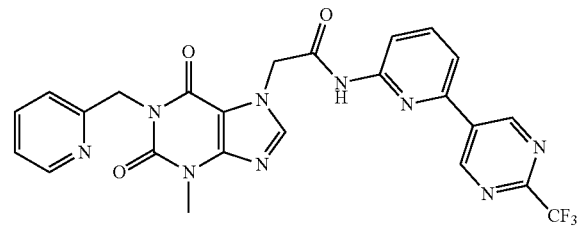 [SMILES: Cn1c(=O)n(Cc2ccccn2)c(=O)c2c1ncn2CC(=O)Nc1cccc(-c2cnc(C(F)(F)F)nc2)n1]

This compound was prepared using the method described for compound 185 with appropriate starting materials. $^1$H NMR (400 MHz, DMSO-$d_6$) 611.22 (s, 1H) 9.66 (s, 2H), 8.42-8.41 (d, 1H), 8.15 (s, 1H), 7.98-8.05 (m, 3H), 7.68-7.72 (m, 2H), 7.20-7.23 (t, 2H), 5.34 (s, 2H), 5.13 (s, 2H) 3.717-3.644 (m, 2H), 3.49 (s, 3H). Retention time (LC-MS): 1.938 min. MH$^+$538.

Compound 187 N-(6-(3,4-difluorophenyl)pyridin-2-yl)-2-(3-methyl-2,6-dioxo-1-(pyridin-2-ylmethyl)-2,3-dihydro-1H-purin-7(6H)-yl)acetamide

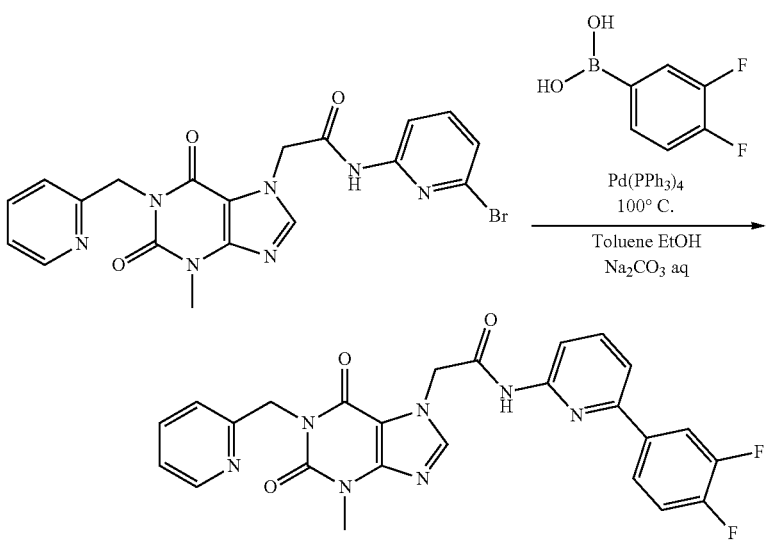

To a mixture of N-(6-bromopyridin-2-yl)-2-(3-methyl-2,6-dioxo-1-(pyridin-2-ylmethyl)-2,3-dihydro-1H-purin-7(6H)-yl)acetamide (150 mg, 0.32 mmol) in toluene (2 mL) was added 3,4-difluorophenylboronic acid (75.64 mg, 0.479 mmol), ethanol (1 mL), aq. sodium carbonate (0.5 mL, 2 N solution) and tetrakis(triphenylphosphine)palladium under $N_2$ atmosphere. After the addition, the mixture was stirred at Compound 188 N-(6-(4-chlorophenyl)pyridin-2-yl)-2-(3-methyl-2,6-dioxo-1-(pyridin-2-ylmethyl)-2,3-dihydro-1H-purin-7(6H)-yl)acetamide

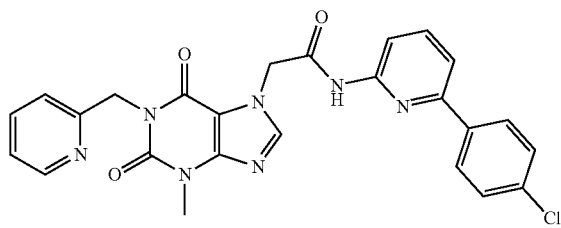 [SMILES: Cn1c(=O)n(Cc2ccccn2)c(=O)c2c1ncn2CC(=O)Nc1cccc(-c2ccc(Cl)cc2)n1]

This compound was prepared using the method described for compound 187 with appropriate starting materials. $^1$H NMR (MeOH-d4) δ 11.060 (m, 1H) 8.426-8.415 (d, 1H), 8.142-8.098 (m, 3H), 7.947-7.866 (m, 2H), 7.628-7.683 (m, 2H), 7.583-7.561 (d, 2H), 7.236-7.204 (m,2H), 5.317 (s, 2H), 5.134 (s, 2H), 3.476 (s, 3H). Retention time (LC-MS): 2.490 min. MH$^+$502.

Compound 189 (S)-2-(3-methyl-2,6-dioxo-1-(pyridin-2-ylmethyl)-2,3-dihydro-1H-purin-7(6H)-yl)-N-(6-(2-(2-(trifluoromethyl)pyrrolidin-1-yl)pyrimidin-5-yl)pyridin-2-yl)acetamide

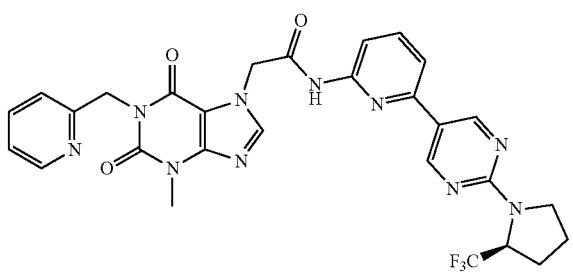 [SMILES: Cn1c(=O)n(Cc2ccccn2)c(=O)c2c1ncn2CC(=O)Nc1cccc(-c2cnc(N3CCC[C@H]3C(F)(F)F)nc2)n1]

This compound was prepared using the method described for compound 187 with appropriate starting materials. $^1$H NMR (MeOH-d4) M1.010 (s, 1H) 9.095 (s, 2H), 8.423-8.412 (d, 1H), 8.143 (s, 1H), 7.904-7.838 (m, 2H), 7.729-7.661 (m, 2H), 7.239-7.208 (m, 2H), 5.314 (s, 2H), 5.135-5.081 (m, 3H) 3.717-3.644 (m, 2H), 3.597-3.518 (m, 3H), 2.216-2.069 (m, 4H). Retention time (LC-MS): 2.258 min. MH$^+$607.

Compound 190 (S)-2-(3-methyl-2,6-dioxo-1-(pyridin-2-ylmethyl)-1,2,3,6-tetra hydropurin-7-yl)-N-(2-(2-(2-(trifluoromethyl)pyrrolidin-1-yl)pyrimidin-5-yl)thiazol-4-yl)acetamide

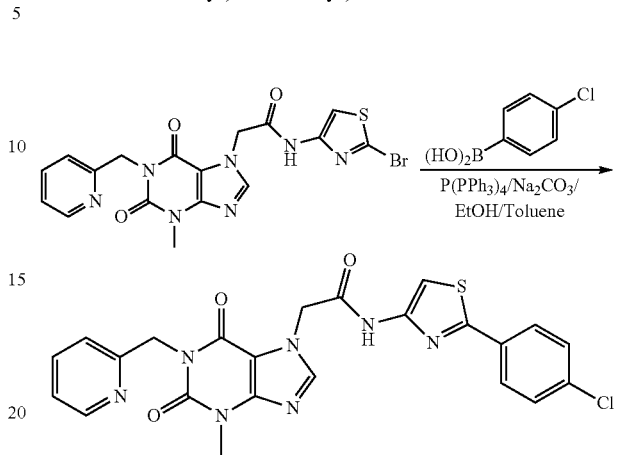

A mixture of N-(2-bromothiazol-4-yl)-2-(3-methyl-2,6-dioxo-1-(pyridin-2-ylmethyl)-2,3-dihydro-1H-purin-7(6H)-yl)acetamide (70 mg, 0.15 mmol), 4-chlorophenylboronic acid (35 mg, 0.22 mmol) in a mixed solution (toluene: ethanol: aq Na$_2$CO$_3$ (2 M)=4:2:1, 7 mL) was degassed under N$_2$ and tetrakis(triphenylphosphine)palladium (10 mg) was added. The mixture was stirred under N$_2$ at100° C. for 2 h and cooled to RT. The mixture was extracted with DCM (3×10 mL). Combined organic layers were washed with brine, dried over Na$_2$SO$_4$, and concentrated and the residue was purified prep-HPLC to give N-(2-(4-chlorophenyl)thiazol-4-yl)-2-(3-methyl-2,6-dioxo-1-(pyridin-2-ylmethyl)-2,3-dihydro-1H-purin-7(6H)-yl)acetamide (20 mg, 28.0% yield) as a white solid. $^1$H NMR (400 MHz, DMSO-d$_6$) δ 11.60 (s, 1H), 8.42 (d, J=4.3 Hz, 1H), 8.14 (s, 1H), 7.92 (d, J=8.5 Hz, 2H), 7.71 (t, J=7.7 Hz, 1H), 7.63-7.54 (m, 3H), 7.29-7.16 (m, 2H), 5.27 (s, 2H), 5.13 (s, 2H), 3.47 (s, 3H). Retention time (LC-MS): 2.117 min. MH$^+$508.

Compound 191 2-(3-methyl-2,6-dioxo-1-(pyridin-2-ylmethyl)-2,3-dihydro-1H-purin-7(6H)-yl)-N-(2-(2-(trifluoromethyl)pyrimidin-5-yl)thiazol-4-yl)acetamide

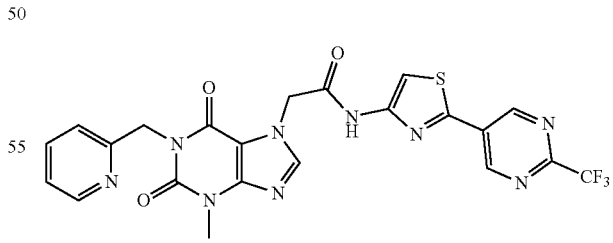

This compound was prepared using the method described for compound 190 with appropriate starting materials. $^1$H NMR (400 MHz, DMSO-d$_6$) δ 11.80 (s, 1H), 9.51 (s, 2H), 8.42 (d, J=4.2 Hz, 1H), 8.15 (s, 1H), 7.85 (s, 1H), 7.72 (dd, J=10.7, 4.6 Hz, 1H), 7.32-7.15 (m, 2H), 5.29 (s, 2H), 5.14 (d, J=7.2 Hz, 2H), 3.47 (d, J=6.1 Hz, 4H). Retention time (LC-MS): 1.808 min. MH$^+$544.

Compound 192 N-(6-(4-chlorophenyl)pyridin-2-yl)-2-(3,8-dimethyl-2,6-dioxo-1-(2-oxopropyl)-1,2,3,6-tetrahydropurin-7-yl)acetamide

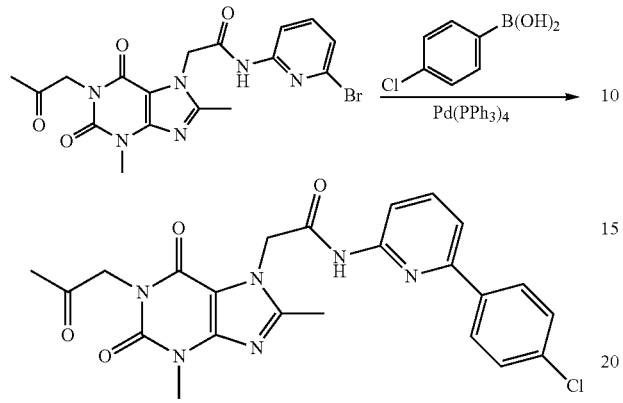

To a mixture of N-(6-bromopyridin-2-yl)-2-(3,8-dimethyl-2,6-dioxo-1-(2-oxopropyl)-1,2,3,6-tetrahydropurin-7-yl)acetamide (7, 150 mg, 0.334 mmol) and 4-chlorophenylboronic acid (62 mg, 0.4 mmol) in toluene/EtOH/2N aq. Na$_2$CO$_3$ (1.6 mL/0.8 mL/0.4 mL) was added Pd(PPh$_3$)$_4$ (38 mg, 0.034 mmol) after degassed three times under N$_2$ atmosphere, then the mixture was heated to 100° C. for 2 h. The mixture was cooled to RT and filtered through Celite. The filtrate was extracted with EA (3×5 mL). Combined organic layers were dried over Na$_2$SO$_4$ and filtered. The filtrate was concentrated and the residue was purified by chromatography (eluted with PE/acetone =3/1) to give N-(6-(4-chlorophenyl)pyridin-2-yl)-2-(3,8-dimethyl-2,6-dioxo-1-(2-oxopropyl)-1,2,3,6-tetrahydropurin-7-yl)acetamide (100 mg, 62.5% yield) as a white solid. 1H-NMR (400 MHz, DMSO-d$_6$) δ 11.09 (s, 1H), 8.12-8.14 (d, J=8.8 Hz, 2H), 7.94-7.95 (d, J=1.6 Hz, 1H), 7.87-7.91 (t, J=14.6 Hz, 1H), 7.72-7.74 (d, J=8.0 Hz, 1H), 7.58-7.60 (d, J=8.4 Hz, 1H), 5.30 (s, 2H), 4.49 (s, 2H), 3.42 (s, 3H), 2.50 (s, 3H), 2.17 (s, 3H). Retention time (LC-MS): 1.551 min. MH$^+$481.

Compound 193 N-(6-(3,4-difluorophenyl)pyridin-2-yl)-2-(3,8-dimethyl-2,6-dioxo-1-(2-oxopropyl)-1,2,3,6-tetrahydropurin-7-yl)acetamide

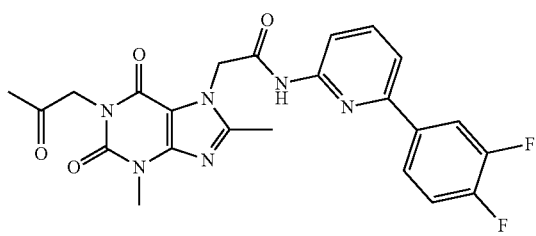 [SMILES: CC(=O)Cn1c(=O)c2c(nc(C)n2CC(=O)Nc2cccc(-c3ccc(F)c(F)c3)n2)n(C)c1=O]

This compound was prepared using the method described for compound 192 with appropriate starting materials. $^1$H-NMR (400 MHz, DMSO-d$_6$) δ 11.09 (s, 1H), 8.16-8.18 (m, 1H), 8.13-8.15 (m, 2H), 7.92-7.99 (m, 1H), 7.76-7.78 (d, J=8.4 Hz, 1H), 7.56-7.63 (m, 1H), 5.31 (s, 2H), 4.69 (s, 2H), 3.46 (s, 3H), 2.50 (s, 3H), 2.17 (s, 3H). Retention time (LC-MS): 1.414 min. MH$^+$483.

Compound 194 2-(3,8-dimethyl-2,6-dioxo-1-(2-oxopropyl)-1,2,3,6-tetrahydropurin-7-yl)-N-(6-(2-(trifluo-romethyl)pyrimidin-5-yl)pyridin-2-yl)acetamide

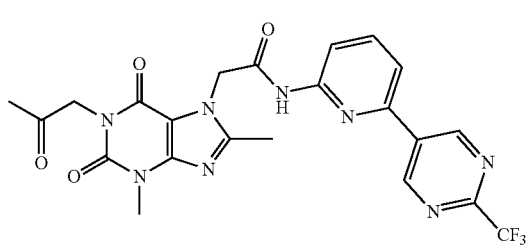 [SMILES: CC(=O)Cn1c(=O)c2c(nc(C)n2CC(=O)Nc2cccc(-c3cnc(C(F)(F)F)nc3)n2)n(C)c1=O]

This compound was prepared using the method described for compound 192 with appropriate starting materials. $^1$H-NMR (400 MHz, DMSO-d$_6$) δ 11.26 (s, 1H), 9.68 (s, 2H), 8.13-8.16 (d, J=12.4 Hz, 1H), 8.01-8.04 (t, J=10.0 Hz, 2H), 5.33 (s, 2H), 4.69 (s, 2H), 3.42 (s, 3H), 2.50 (s, 3H), 2.17 (s, 3H). Retention time (LC-MS): 1.431 min. MH$^+$517.

Compound 195 2-(3,8-dimethyl-2,6-dioxo-1-(2-oxopropyl)-1,2,3,6-tetrahydropurin-7-yl)-N-(6-(2-(trifluoro methyl)pyrimidin-5-yl)pyridin-2-yl)acetamide

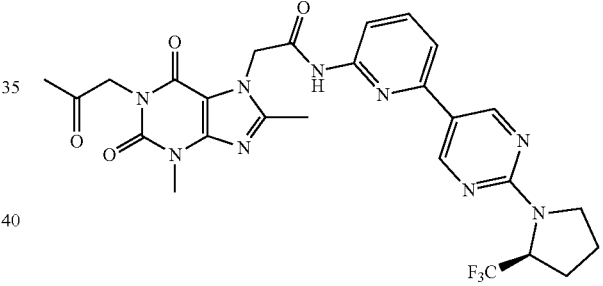

This compound was prepared using the method described for compound 192 with appropriate starting materials. $^1$H-NMR (400 MHz, DMSO-d$_6$) δ 11.02 (s, 1H), 9.11 (s, 2H), 7.84-7.88 (m, 2H), 7.67-7.69 (d, J=8.0 Hz, 1H), 5.30 (s, 2H), 5.09-5.13 (m, 1H), 4.69 (s, 2H), 3.68-3.72 (m, 2H), 3.43 (s, 3H), 2.43 (s, 3H), 2.30 (s, 5H), 2.02-2.08 (m, 2H). Retention time (LC-MS): 1.501 min. MH$^+$586.

Compound 196 N-(6-(4,4-difluoropiperidin-1-yl)pyridin-2-yl)-2-(3-methyl-1-((5-methyl isoxazol-3-yl)methyl)-2,6-dioxo-2,3-dihydro-1H-purin-7(6H)-yl)acetamide

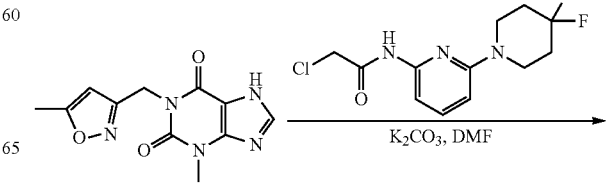

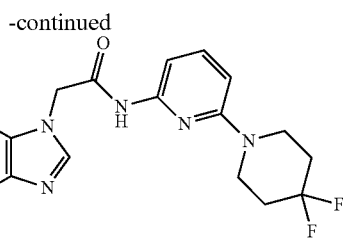

A mixture of 3-methyl-1-((5-methylisoxazol-3-yl)methyl)-1H-purine-2,6 (3H,7H)-dione (80 mg, 306.24 μmol), 2-chloro-N-(6-(4,4-difluoropiperidin -1-yl)pyridin-2-yl)acetamide (133 mg, 459.35 μmol), TBAI (68 mg, 18 μmol) and POTASSIUM CARBONATE (106 mg, 765.59 μmol) in DMF (5 mL) was stirred at 50° C. for 2 h. The reaction mixture was quenched by water (40 mL), and then extracted with EA (3×10 mL). Combined organic layers were dried over $Na_2SO_4$ and filtered. The filtrate was concentrated and the residue was purified by chromatography (eluted with PE:EA=1:1) to afford N-(6-(4,4-difluoropiperidin-1-yl)pyridin-2-yl)-2-(3-methyl-1-((5-methylisoxazol-3-yl) methyl)-2,6-dioxo-2,3-dihydro-1H-purin-7(6H)-yl)acetamide (40 mg, 25.4% yield) as a white solid. $^1$H-NMR (400 MHz, DMSO-$d_6$) δ 10.52 (s, 1H), 8.10 (s, 1H), 7.53 (t, J=8.1 Hz, 1H), 7.27 (s, 1H), 6.65 (d, J=8.3 Hz, 1H), 6.09 (s, 1H), 5.28 (m, 2H), 5.01 (s, 2H), 3.74-3.64 (m, 4H), 3.46 (s, 3H), 2.32 (s, 3H), 2.06-1.89 (m, 4H). Retention time (LC-MS): 2.363 min. MH$^+$515.2.

Compound 197 N-(6-(3,3-difluoroazetidin-1-yl) pyridin-2-yl)-2-(3-methyl-1-((5-methylisoxazol-3-yl) methyl)-2,6-dioxo-2,3-dihydro-1H-purin-7(6H)-yl) acetamide

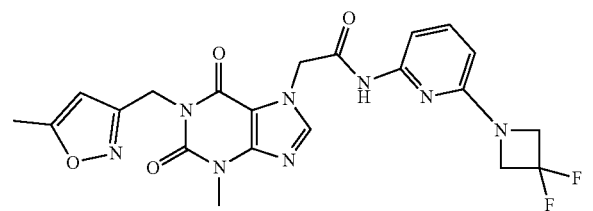 [SMILES: Cc1cc(Cn2c(=O)c3c(ncn3CC(=O)Nc3cccc(N4CC(F)(F)C4)n3)n(C)c2=O)no1]

This compound was prepared using the method described for compound 196 with appropriate starting materials. $^1$H NMR (400 MHz, CDCl$_3$) δ 9.93 (s, 1H), 8.00 (d, J=8.5 Hz, 1H), 7.84 (d, J=8.8 Hz, 1H), 7.77 (s, 1H), 5.99 (s, 1H), 5.28 (d, J=8.8 Hz, 4H), 3.65 (s, 3H), 2.23 (s, 3H). Retention time (LC-MS): 2.19 min. MH$^+$487.

Compound 198 N-(5-(4-isopropylpiperidin-1-yl) pyridin-2-yl)-2-(3-methyl-1-((5-methylisoxazol-3-yl) methyl)-2,6-dioxo-2,3-dihydro-1H-purin-7(6H)-yl) acetamide

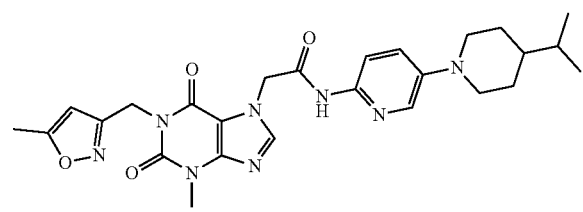 [SMILES: Cc1cc(Cn2c(=O)c3c(ncn3CC(=O)Nc3ccc(N4CCC(C(C)C)CC4)cn3)n(C)c2=O)no1]

This compound was prepared using the method described for compound 196 with appropriate starting materials. $^1$H-NMR (400 MHz, DMSO-$d_6$) δ 10.70 (s, 1H), 8.09 (s, 1H), 8.00 (d, J=2.8 Hz, 1H), 7.80 (d, J=9.1 Hz, 1H), 7.36 (dd, J=9.1, 2.7 Hz, 1H), 6.08 (s, 1H), 5.20 (s, 2H), 5.00 (s, 2H), 3.68 (m, 2H), 3.45 (s, 3H), 2.56 (t, J=11.4 Hz, 2H), 2.31 (s, 3H), 1.69 (m, 2H), 1.42 (m, 1H), 1.26 (m, 2H), 1.14 (d, J=11.5 Hz, 1H), 0.86 (d, J=6.7 Hz, 6H). Retention time (LC-MS): 2.506 min. MH$^+$519.2.

Compound 199 2-(3-Methyl-1-((5-methylisoxazol-3-yl)methyl)-2,6-dioxo-2,3-dihydro-1H-purin-7(6H)-yl)-N-(quinolin-2-yl)acetamide

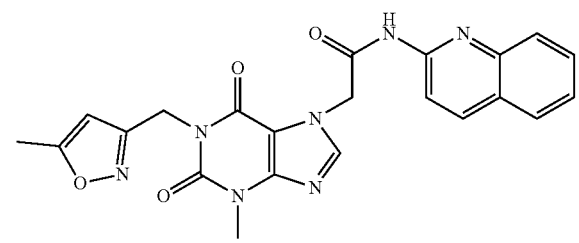 [SMILES: Cc1cc(Cn2c(=O)c3c(ncn3CC(=O)Nc3ccc4ccccc4n3)n(C)c2=O)no1]

This compound was prepared using the method described for compound 196 with appropriate starting materials. $^1$H NMR (400 MHz, DMSO-$d_6$) δ 11.34 (s, 1H), 8.37 (d, J=8.9 Hz, 1H), 8.15 (s, 2H), 7.93 (d, J=7.8 Hz, 1H), 7.85 (d, J=8.5 Hz, 1H), 7.74 (t, J=7.7 Hz, 1H), 7.52 (t, J=7.5 Hz, 1H), 6.10 (s, 1H), 5.35 (s, 2H), 5.02 (s, 2H), 3.48 (s, 3H), 2.32 (s, 3H). Retention time (LC-MS): 1.992 min. MH$^+$446.

Compound 200 N-(5-bromo-6-(trifluoromethyl) pyridin-2-yl)-2-(3-methyl-1-((5-methyl-isoxazol-3-yl)methyl)-2,6-dioxo-2,3-dihydro-1H-purin-7(6H)-yl)acetamide

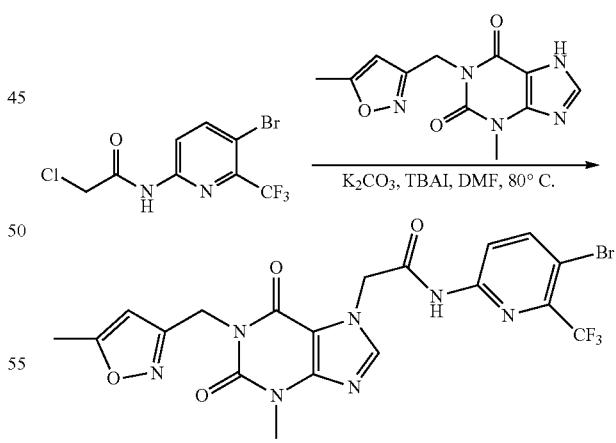

A mixture of N-(5-bromo-6-(trifluoromethyl)pyridin-2-yl)-2-chloroacetamide (70.5 mg, 0.27 mmol), potassium carbonate (74.6 mg, 0.54 mmol), TBAI (10.0 mg, 0.03 mmol) and 3-methyl-1-((5-methylisoxazol-3-yl)methyl)-1H-purine-2,6(3H,7H)-dione (85.0 mg, 0.27 mmol) in DMF (3 mL) was stirred at 80° C. overnight. The reaction mixture was diluted with EA, washed in sequence with water, aq. NH$_4$Cl and brine, dried over Na$_2$SO$_4$, and concentrated under reduced pressure. The residue was purified by chromatography (eluted with PE:EA=1:1) to give the title compound (100.0 mg, 68.7% yield) as a white solid. $^1$HNMR (400 MHz, CDCl$_3$) δ 9.93 (s, 1H), 7.99 (d, J=8.5 Hz, 1H), 7.84 (d, J=8.8 Hz, 1H), 7.77 (s, 1H), 5.99 (s, 1H), 5.29 (t, J=6.9 Hz, 4H), 3.65 (s, 3H), 2.23 (s, 3H). Retention time (LC-MS): 2.59 min. MH$^+$542.

Compound 201 N-(5-cyano-6-(trifluoromethyl)pyridin-2-yl)-2-(3- methyl-1-((5-methyl isoxazol-3-yl) methyl)-2,6-dioxo-2,3-dihydro-1H-purin-7(6H)-yl) acetamide

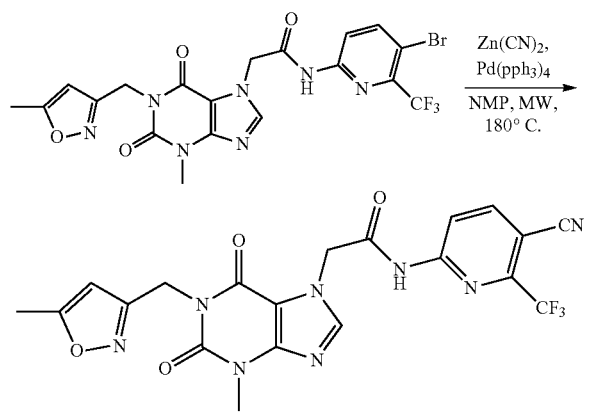

N-(5-bromo-6-(trifluoromethyl)pyridin-2-yl)-2-(3-methyl-1-((5-methylisoxazol-3-yl) methyl)-2,6-dioxo-2,3-dihydro-1H-purin-7(6H)-yl)acetamide (27.1 mg, 0.05 mmol) and Zn(CN)$_2$ (5.9 mg, 0.05 mmol) was dissolved in NMP in a microwave oven vessel, followed by addition of Pd(PPh$_3$)$_4$ (5.8 mg, 0.005 mmol). The reaction mixture was heated under nitrogen in a Biotage Initiator device at 180° C. and high absorbance for 30 min. The reaction mixture was poured into EA. The mixture was washed with water and brine, dried over Na$_2$SO$_4$ and filtered. The filtrate was concentrated under reduced pressure. The residue was purified prep-TLC to afford the title compound (15 mg, 61.4% yield) as a white solid. $^1$HNMR (400 MHz, DMSO-d$_6$) δ 12.01 (s, 1H), 8.62 (d, J=8.8 Hz, 1H), 8.42 (d, J=8.8 Hz, 1H), 8.19 (s, 1H), 6.17 (s, 1H), 5.41 (s, 2H), 5.08 (s, 2H), 3.54 (s, 3H), 2.39 (s, 3H).Retention time (LC-MS): 2.18 min. MH$^+$489.

Compound 202 2-(3-methyl-1-((5-methylisoxazol-3-yl)methyl)-2,6-dioxo-2,3-dihydro-1H-purin-7(6H)-yl)-N-(6-(4-(trifluoromethyl)piperidin-1-yl)pyridin-2-yl)acetamide

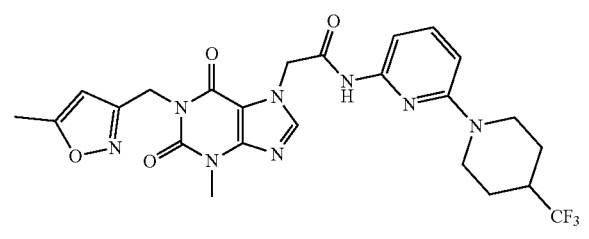 [SMILES: Cc1cc(Cn2c(=O)c3c(ncn3CC(=O)Nc3cccc(N4CCC(C(F)(F)F)CC4)n3)n(C)c2=O)no1]

This compound was prepared using the method described for compound 196 with appropriate starting materials. $^1$HNMR (400 Hz, DMSO-d$_6$,) δ 10.49 (s, 1H), 8.11 (s, 1H), 7.51 (t, J=8.1 Hz, 1H), 7.24 (d, J=6.7 Hz, 1H), 6.58 (d, J=8.4 Hz, 1H), 6.10 (s, 1H), 5.23 (s, 2H), 5.02 (s, 2H), 4.41 (dd, J=12.1, 7.1 Hz, 2H), 3.46 (d, J=4.1 Hz, 3H), 2.84 (t, J=12.1 Hz, 2H), 2.61 (d, J=8.6 Hz, 1H), 2.32 (s, 3H), 1.87 (d, J=11.0 Hz, 2H), 1.48-1.34 (m, 2H). Retention time (LC-MS): 2.457 min. MH$^+$547.3.

Compound 203 N-(4-ethyl-6-(trifluoromethyl)pyridin-2-yl)-2-(3-methyl-1-((5-methylisoxazol-3-yl)methyl)-2,6-dioxo-2,3-dihydro-1H-purin-7(6H)-yl) acetamide

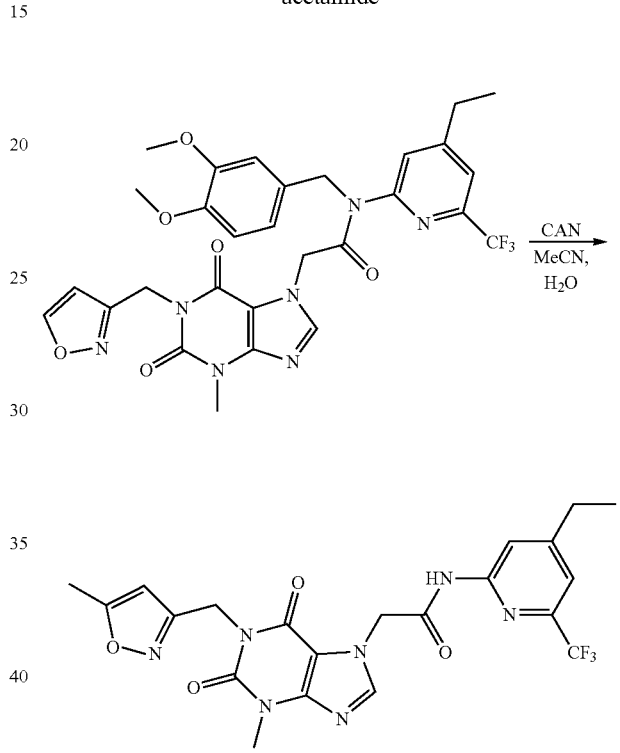

To a solution of N-(3,4-dimethoxybenzyl)-N-(4-ethyl-6-(trifluoromethyl)pyridin-2- yl)-2-(1-(isoxazol-3-ylmethyl)-3-methyl-2,6-dioxo-2,3-dihydro-1H-purin-7(6H)-yl)acetamide (50 mg, 0.078 mmol) in MeCN (3 mL) and H$_2$O (3 mL) was added portionwise CAN (128.29 mg, 0.23 mmol) at 0° C. After the addition, the mixture was warmed to r.t. and stirred for 3 h. The reaction mixture was diluted with EA, washed with water, brine, dried over Na$_2$SO$_4$ and filtered. The filtrate was purified via prep-TLC twice (eluted with PE:EA=1:2 and then DCM:MeOH=10:1) to afford N-(4-ethyl -6-(trifluoromethyl)pyridin-2-yl)-2-(3-methyl-1-((5-methylisoxazol-3-yl)methyl)-2,6-dioxo-2,3-dihydro-1H-purin-7(6H)-yl)acetamide (5 mg, 13% yield) as a white solid. $^1$HNMR (400 MHz, DMSO-d$_6$) δ 11.41 (s, 1H), 8.13 (d, J=11.9 Hz, 2H), 7.53 (s, 1H), 6.10 (s, 1H), 5.29 (s, 2H), 5.01 (s, 2H), 3.47 (s, 3H), 2.76-2.67 (m, 2H), 2.32 (s, 3H), 1.18 (t, J=7.6 Hz, 3H). MH$^+$492.

Compound 204 N-(4-methoxy-6-(trifluoromethyl)pyridin-2-yl)-2-(3-methyl-1-((5-methylisoxazol-3-yl)methyl)-2,6-dioxo-2,3-dihydro-1H-purin-7(6H)-yl)acetamide

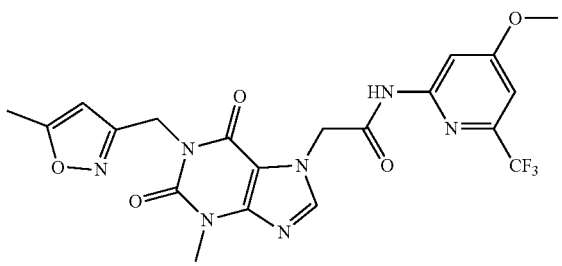

This compound was prepared using the method described for compound 203 with appropriate starting materials. ¹HNMR (400 MHz, DMSO-$d_6$) δ 11.42 (s, 1H), 8.11 (s, 1H), 7.82 (s, 1H), 7.21 (d, J=2.0 Hz, 1H), 6.10 (s, 1H), 5.29 (s, 2H), 5.02 (s, 2H), 3.88 (s, 3H), 3.47 (s, 3H), 2.32 (s, 3H). MH⁺494.

Compound 211 N-(4-(ethyl(trifluoromethyl)amino)phenyl)-2-(3-me-thyl-1-((5-methylisoxazol-3-yl)methyl)-2,6-dioxo-2,3-dihydro-1H-purin-7(6H)-yl)acetamide

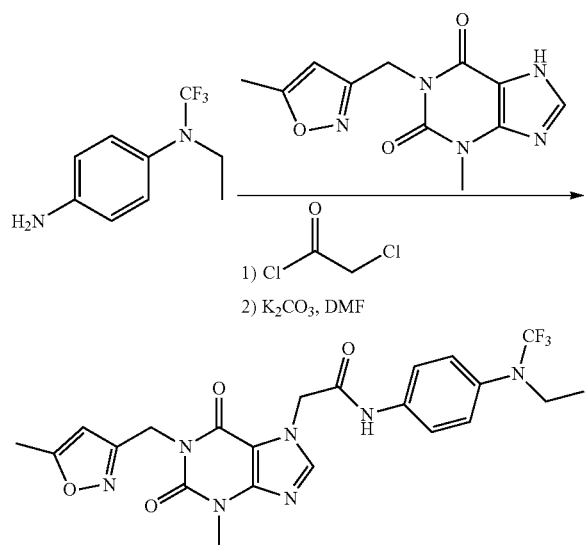

To a solution of N1-ethyl-N1-(trifluoromethyl)benzene-1,4-diamine (35.2 mg, 0.156 mmol) in DMF (1 mL) was added drop-wise chloroacetyl chloride (35 mg, 0.31 mmol) at 0° C. The mixture was stirred at r.t. for 1 hr, then poured into aqueous NaHCO₃ solution and extracted with EA twice. Combined organic layers were concentrated under reduced pressure. The residue was dissolved in DMF (2 mL), followed by addition of 3-methyl-1-((5-methylisoxazol-3-yl)methyl)-1H-purine-2,6(3H,7H)-dione (50 mg, 0.156 mmol) and POTASSIUM CARBONATE (43.2 mg, 0.313 mmol). The mixture was then stirred at 60° C. for 4 h and diluted with EA (10 mL) and brine (10 mL). The organic layers was separated, washed with S. aq. NH₄Cl, dried over Na₂SO₄ and concentrated under reduced pressure. The residue was purified via preparative TLC (DCM:MeOH=30:1) to give N-(4-(ethyl (trifluorom ethyl) amino)phenyl)-2-(3-methyl-1-((5-methylisoxazol-3-yl)methyl)-2,6-dioxo-2,3-dihydro-1H-purin-7(6H)-yl)acetamide (11.2 mg, 14.2% yield) as a white solid. ¹H-NMR (400 MHz, DMSO-$d_6$) δ 11.61 (s, 1H), 8.13 (s, 1H), 7.61-7.63 (d, J=8.8 Hz, 2H), 7.31-7.33 (d, J=8.8 Hz, 2H), 6.09 (s, 1H), 5.21 (s, 2H), 5.02 (s, 2H), 3.61-3.63 (m, 2H), 3.47 (s, 3H), 2.32 (s, 3H), 1.06-1.09 (t, 3H). Retention time (LC-MS): 2.028 min. MH⁺506.

Compound 212 N-(6-(3-azabicyclo [3.1.0] hexan-3-yl)pyridin-2-yl)-2-(3-methyl-1-((5-methylisoxazol-3-yl)methyl)-2,6-dioxo-2,3-dihydro-1H-purin-7(6H)-yl)acetamide

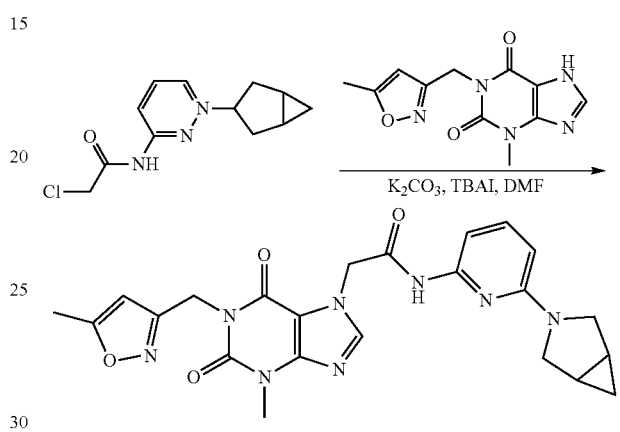

A solution of N-(6-(3-azabicyclo[3.1.0]hexan-3-yl)pyridin-2-yl)-2-chloroacetamide (30 mg, 0.12 mmol), POTASSIUM CARBONATE (32.95 mg, 0.24 mmol), 3-methyl-1-((5-methylisoxazol-3-yl)methyl)-1H-purine-2,6(3H,7H)-dione (31.14 mg, 0.12 mmol) and TBAI (4.40 mg, 0.012 mmol) in DMF (3 mL) was stirred at 50° C. for 3 hrs. The mixture was diluted with EA, washed with water, brine, dried over Na₂SO₄ and filtered. The filtrate was concentrated and purified with preparative TLC (DCM/ MeOH=20:1) to afford N-(6-(3-azabicyclo[3.1.0]hexan-3-yl)pyridin-2-yl)-2-(3-methyl-1-((5-methylisoxazol-3-yl)methyl)-2,6-dioxo-2,3-dihydro-1H-purin-7(6H)-yl)acetamide (15 mg, 26.3% yield) as a white solid. ¹H NMR (400 MHz, DMSO) δ 10.40 (s, 1H), 8.10 (s, 1H), 7.42 (t, J=8.0 Hz, 1H), 7.19 (s, 1H), 6.16 (d, J=8.2 Hz, 1H), 6.09 (s, 1H), 5.23 (s, 2H), 5.01 (s, 2H), 3.64 (d, J=10.2 Hz, 2H), 3.46 (s, 3H), 3.34-3.30 (m, 2H), 2.32 (s, 3H), 1.74 -1.55 (m, 2H), 0.72 (d, J=4.4 Hz, 1H), 0.17 (d, J=4.0 Hz, 1H). Retention time (LC-MS): 1.965 min. MH⁺477.

Compound 213 N-(6-(6,6-difluoro-3-azabicyclo[3.1.0]hexan-3-yl)pyridin-2-yl)-2-(3-methyl-1-((5-methylisoxazol-3-yl)methyl)-2,6-dioxo-2,3-dihydro-1H-purin-7(6H)-yl)acetamide

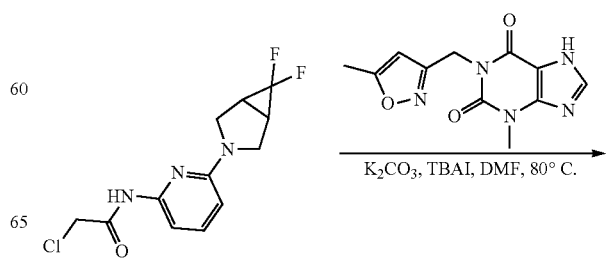

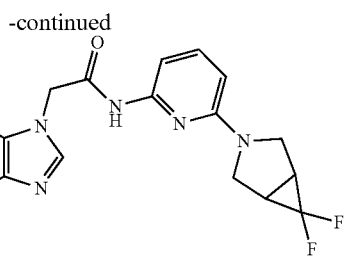

A mixture of 2-chloro-N-(6-(6,6-difluoro-3-azabicyclo[3.1.0]hexan-3-yl)pyridin-2-yl)acetamide (6, 200.0 mg, 0.7 mmol), potassium carbonate (145.1 mg, 1.1 mmol), 3-methyl-1-((5-methylisoxazol-3-yl)methyl)-1H-purine-2,6(3H,7H)-dione (7, 182.8 mg, 0.7 mmol) and TBAI (25.9 mg, 0.07 mmol) in DMF (5 mL) was stirred at 80° C. overnight. The mixture was diluted with EA and washed with water, saturated aqueous NH$_4$Cl solution and brine, dried over Na$_2$SO$_4$, and evaporated. The residue was purified by preparative TLC to give N-(6-(6,6-difluoro-3-azabicyclo[3.1.0]hexan-3-yl)pyridin-2-yl)-2-(3-methyl-1-((5-methylisoxazol-3-yl)methyl)-2,6-dioxo-2,3-dihydro-1H-purin-7(6H)-yl)acetamide (15.0 mg, 4.2% yield) as a white solid. $^1$H NMR (400 MHz, DMSO) δ 10.46 (s, 1H), 8.11 (s, 1H), 7.48 (t, J=7.9 Hz, 1H), 7.24 (s, 1H), 6.19 (d, J=8.1 Hz, 1H), 6.10 (s, 1H), 5.24 (s, 2H), 5.02 (s, 2H), 3.78 (d, J=10.8 Hz, 2H), 3.67 (d, J=9.7 Hz, 2H), 3.47 (s, 3H), 2.68 (d, J=10.8 Hz, 2H), 2.32 (s, 3H). Retention time (LC-MS): 2.26 min. MH$^+$513.

Compound 214 2-(3-methyl-1-((5-methylisoxazol-3-yl)methyl)-2,6-dioxo-2,3-dihydro-1H-purin-7(6H)-yl)-N-(6-(4-(2,2,2-trifluoroethyl)piperazin-1-yl)pyridin-2-yl)acetamide

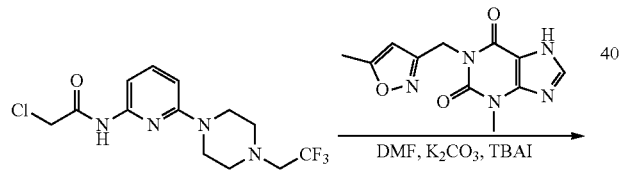

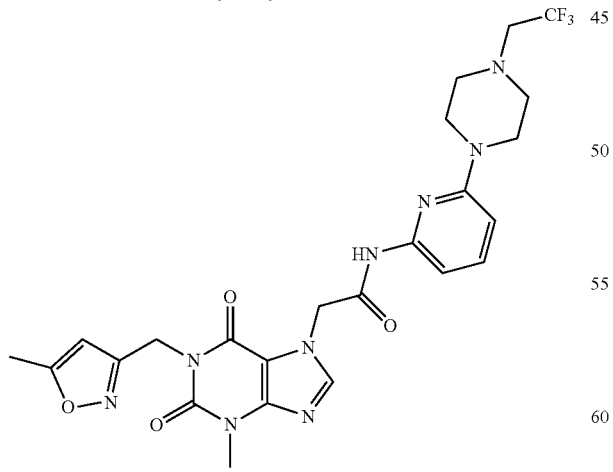

A mixture of 2-chloro-N-(6-(4-(2,2,2-trifluoroethyl)piperazin-1-yl)pyridin-2-yl)acetamide (15 mg, 0.045 mmol), potassium carbonate (12.30 mg, 0.089 mmol), 3-methyl-1-((5-methylisoxazol-3-yl)methyl)-1H-purine-2,6(3H,7H)-dione (11.62 mg, 0.045 mmol) and TBAI (1.64 mg, 0.0045 mmol) in DMF (3 mL) was stirred at 70° C. for 3h. The mixture was diluted with EA, washed with water, brine, dried over Na$_2$SO$_4$ and filtered. The filtrate was purified via prep HPLC to afford 2-(3-methyl-1-((5-methylisoxazol-3-yl)methyl)-2,6-dioxo-2,3-dihydro-1H-purin-7(6H)-yl)-N-(6-(4-(2,2,2-trifluoroethyl)piperazin-1-yl)pyridin-2-yl)acetamide (10 mg, 40% yield) as a white solid. 1H NMR (400 MHz, DMSO) δ 10.55 (s, 1H), 8.17 (s, 1H), 7.57 (t, J=7.9 Hz, 1H), 7.32 (s, 1H), 6.61 (d, J=8.4 Hz, 1H), 6.16 (s, 1H), 5.29 (s, 2H), 5.08 (s, 2H), 3.57 (s, 4H), 3.53 (s, 3H), 3.30 (d, J=10.5 Hz, 2H), 2.77 (s, 4H), 2.39 (s, 3H). Retention time (LC-MS): 2.362 min. MH$^+$562.

Compound 215 2-(3-methyl-1-((5-methylisoxazol-3-yl)methyl)-2,6-dioxo-2,3-dihydro-1H-purin-7(6H)-yl)-N-(6'-(trifluoromethyl)-2,3'-bipyridin-6-yl)acetamide

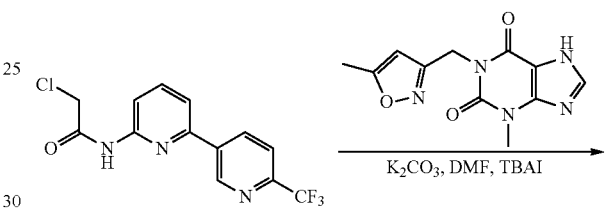

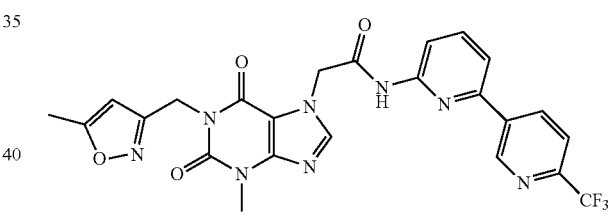

A mixture of 3-methyl-1-((5-methylisoxazol-3-yl)methyl)-1H-purine-2,6(3H,7H)-dione (33 mg, 0.126 mmol), 2-chloro-N-(6'-(trifluoromethyl)-2,3'-bipyridin-6-yl)acetamide (40 mg, 0.126 mmol), POTASSIUM CARBONATE (34 mg, 0.252 mmol), and TBAI (4.5 mg, 0.012 mmol) in DMF (5 mL) was stirred at 50° C. for 3hrs. The reaction mixture was then diluted with EA. The reaction mixture was washed in sequence with water, saturated NH$_4$Cl solution and brine, dried over Na$_2$SO$_4$ and filtered. The filtrate was concentrated under reduced pressure and the residue was purified prep-HPLC to give 2-(3-methyl-1-((5-methylisoxazol-3-yl)methyl)-2,6-dioxo-2,3-dihydro-1H-purin-7(6H)-yl)-N-(6'-(trifluoromethyl)-2,3'-bipyridin-6-yl)acetamide (14 mg, 20.4% yield) as a white solid. Retention time (LC-MS): 2.347 min. MH$^+$541. $^1$H NMR (400 MHz, DMSO) δ 11.21 (s, 1H), 9.45 (s, 1H), 8.72 (d, J=7.6 Hz, 1H), 8.15 (s, 1H), 8.04 (m, 3H), 7.93 (d, J=8.0 Hz, 1H), 6.10 (s, 1H), 5.34 (s, 2H), 5.02 (s, 2H), 3.48 (s, 3H), 2.32 (s, 3H).

Compound 216 2-(3-methyl-2,6-dioxo-1-(2-oxopropyl)-2,3-dihydro-1H-purin-7(6H)-yl)-N-(2-(5-methyl-6-(trifluoromethyl)pyridin-3-yl)thiazol-4-yl)acetamide

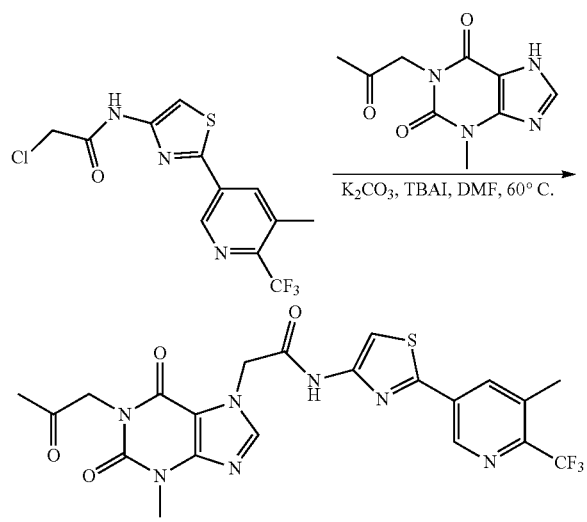

To a solution of 2-chloro-N-(2-(5-methyl-6-(trifluoromethyl)pyridin-3-yl)thiazol-4-yl)acetamide (35 mg, 0.1 mmol) and 8-isopropyl-1,3-dimethyl-1H-purine-2,6(3H,7H)-dione (23.2 mg, 0.1 mmol) in DMF (3 mL) was added TBAI (3.8 mg, 0.01 mmol) and POTASSIUM CARBONATE (28.9 mg, 0.2 mmol) under $N_2$ protection. The mixture was stirred at 60° C. for 2 hrs. The reaction was quenched by water (5 mL) and extracted with EA (2*5 mL). The combined organic layer was washed with saturated aq. LiCl (2*5 mL), dried over $Na_2SO_4$ and filtered. The filtrate was concentrated. The crude product was purified via Prep-HPLC to afford 2-(3-methyl-1-((5-methylisoxazol-3-yl)methyl)-2,6-dioxo-2,3-dihydro-1H-purin-7(6H)-yl)-N-(2-(5-methyl-6-(trifluoromethyl)pyridin-3-yl)thiazol-4-yl)acetamide (30 mg, 55.1% yield) as a white solid. Retention time (LC-MS): 1.931 min. MH+522. $^1$H NMR (400 MHz, DMSO-d6) δ 11.74 (s, 1H), 9.07 (s, 1H), 8.40 (s, 1H), 8.14 (s, 1H), 7.76 (s, 1H), 5.26 (s, 2H), 4.70 (s, 2H), 3.46 (s, 3H), 2.56 (d, J=1.8 Hz, 3H), 2.17 (s, 3H).

Compound 217 2-(3-methyl-1-((5-methylisoxazol-3-yl)methyl)-2,6-dioxo-2,3-dihydro-1H-purin-7(6H)-yl)-N-(2-(5-methyl-6-(trifluoromethyl)pyridin-3-yl)thiazol-4-yl)acetamide

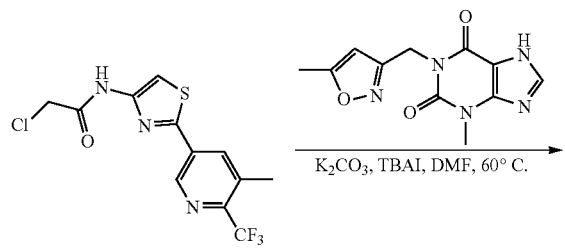

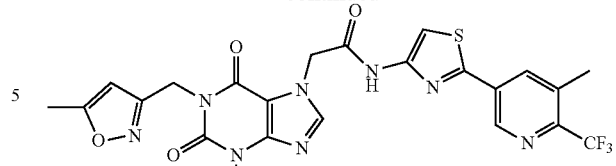

This compound was prepared using the method described for compound 43 with appropriate starting materials and purified via preparative HPLC, 73.4% yield as a light yellow solid. Retention time (LC-MS): 2.202 min. MH+561. $^1$H NMR (400 MHz, DMSO-d6) δ 11.72 (s, 1H), 9.06 (s, 1H), 8.39 (s, 1H), 8.14 (s, 1H), 7.76 (s, 1H), 6.10 (s, 1H), 5.28 (s, 2H), 5.02 (s, 2H), 3.48 (s, 3H), 2.55 (d, J=1.6 Hz, 3H), 2.32 (s, 3H).

Compound 218 2-(3-methyl-2,6-dioxo-1-(2-oxopropyl)-2,3-dihydro-1H-purin-7(6H)-yl)-N-(2-(6-methyl-5-(trifluoromethyl)pyridin-3-yl)thiazol-4-yl)acetamide

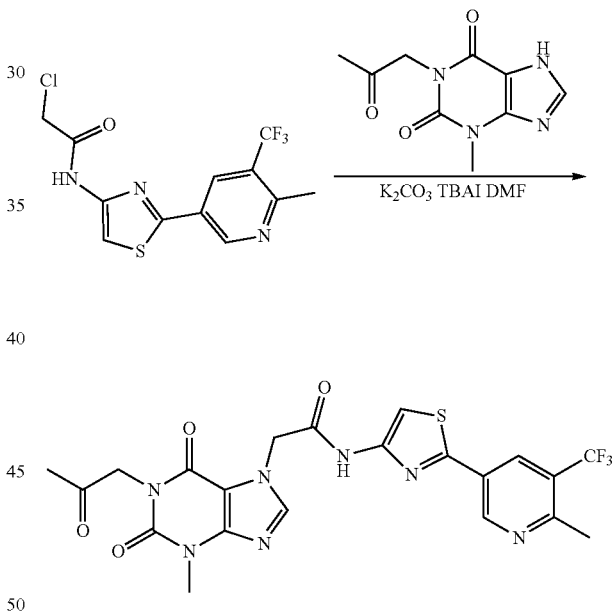

A mixture of (2-chloro-N-(2-(6-methyl-5-(trifluoromethyl)pyridin-3-yl)thiazol-4-yl)acetamide (3, 45 mg, 0.135 mmol), 3-methyl-1-(2-oxopropyl)-1H-purine-2,6(3H,7H)-dione (30 mg, 0.135 mmol), potassium carbonate (18 mg, 0.135 mmol) and a catalytic amount of TBAI in DMF (1 mL) was stirred at 50° C. for 2 hrs. The mixture was diluted with EA and washed with water, brine successively, dried and concentrated to give crude product, which was purified via preparative HPLC to give 2-(3-methyl-2,6-dioxo-1-(2-oxopropyl)-2,3-dihydro-1H-purin-7(6H)-yl)-N-(2-(6-methyl-5-(trifluoromethyl)pyridin-3-yl)thiazol-4-yl)acetamide (17.6 mg, 25.5% yield) as a white solid. Retention time (LC-MS): 1.910 min. MH+521. $^1$H-NMR (400 MHz, DMSO-d6) δ 11.71 (s, 1H), 9.24 (s, 1H), 8.44 (m, 1H), 8.14 (s, 1H), 7.70 (s, 1H), 5.25 (s, 2H), 4.70 (s, 2H), 3.46 (s, 3H), 2.71 (s, 3H), 2.17 (s, 3H).

Compound 219 N-(6-(4-(2-fluoropropan-2-yl)piperidin-1-yl)pyridin-2-yl)-2-(3-methyl-1-((5-methylisoxazol-3-yl)methyl)-2,6-dioxo-2,3-dihydro-1H-purin-7(6H)-yl)acetamide

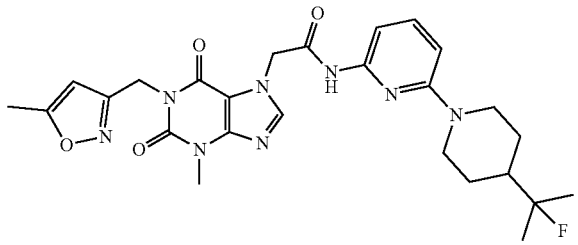 [SMILES: Cc1cc(Cn2c(=O)c3c(ncn3CC(=O)Nc3cccc(N4CCC(C(C)(C)F)CC4)n3)n(C)c2=O)no1]

This compound was prepared using the method described for compound 196 with appropriate starting materials. ¹HNMR (400 Hz, DMSO-$d_6$,) δ 10.42 (s, 1H), 8.76 (d, J=3.1 Hz, 1H), 8.51 (d, J=8.4 Hz, 1H), 8.09 (s, 1H), 7.44-7.48 (m, 2H), 7.19 (bs, 1H), 6.52 (d, J=6.4 Hz, 1H), 6.08(s, 1H), 5.22 (s, 2H), 5.01 (s, 2H), 4.39 (d, J=12.8 Hz, 2H), 3.45 (s, 3H), 2.71 (t, J=12.1 Hz, 3H), 2.31 (s, 3H), 1.73 (d, J=11.5 Hz, 2H), 1.29 (s, 3H), 1.24 (s, 3H). MH⁺539.

Compound 220 N-(5-(4-(2-fluoropropan-2-yl)piperidin-1-yl)pyridin-2-yl)-2-(3-methyl-1-((5-methylisoxazol-3-yl)methyl)-2,6-dioxo-2,3-dihydro-1H-purin-7(6H)-yl)acetamide

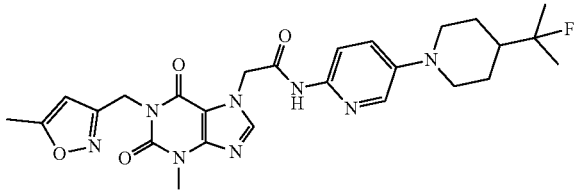 [SMILES: Cc1cc(Cn2c(=O)c3c(ncn3CC(=O)Nc3ccc(N4CCC(C(C)(C)F)CC4)cn3)n(C)c2=O)no1]

This compound was prepared using the method described for compound 196 with appropriate starting materials. ¹HNMR (400 Hz, DMSO-$d_6$,) δ 10.73 (s, 1H), 8.11 (s, 1H), 8.04 (s, 1H), 7.82 (d, J=8.1 Hz, 1H), 7.40 (d, J=6.7 Hz, 1H), 6.10 (s, 1H), 5.22 (s, 2H), 5.02 (s, 2H), 3.76 (d, J=4.1 Hz, 2H), 3.47 (s, 3H), 2.60 (t, J=12.1 Hz, 3H), 2.32 (s, 3H), 1.75 (d, J=11.0 Hz, 2H), 1.64 (m, 2H), 1.26-1.43 (m, 8H). MH⁺539.

Compound 221 2-(3-methyl-1-((5-methylisoxazol-3-yl)methyl)-2,6-dioxo-2,3-dihydro-1H-purin-7(6H)-yl)-N-(5'-methyl-6'-(trifluoromethyl)-[2,3'-bipyridin]-6-yl)acetamide

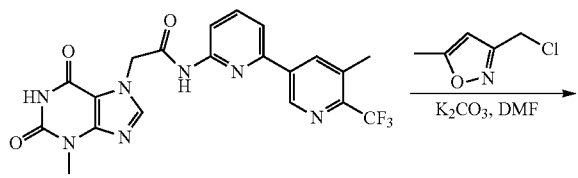

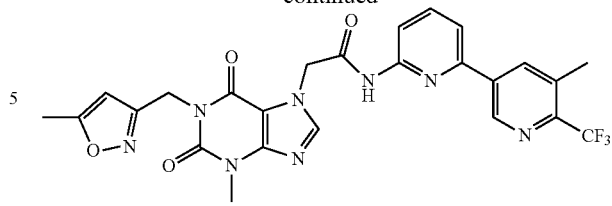

3-(Chloromethyl)-5-methylisoxazole (6.5 mg, 0.05 mmol) and potassium carbonate (8.5 mg, 0.06 mmol) were added to 2-(3-methyl-2,6-dioxo-2,3-dihydro-1H-purin-7(6H)-yl)-N-(5'-methyl-6'-(trifluoromethyl)-[2,3'-bipyridin]-6-yl)acetamide (19 mg, 0.041 mmol) in DIVlF (4 mL). The mixture was stirred at RT overnight. The mixture was diluted with water and extracted with EA twice. The combined organic phases were concentrated and purified by silica gel column chromatography (0-3% MeOH/DCM) to afford title compound (13.4 mg, 59% yield) as a white solid. ¹H-NMR (400 MHz, DMSO-$d_6$) δ 11.15 (s, 1H), 9.20 (s, 1H), 8.55 (s, 1H), 7.87-8.13 (m, 4H), 6.09 (s, 1H), 5.33 (s, 2H), 5.01 (s, 2H), 3.46 (s, 3H), 2.55 (s, 3H), 2.31 (s, 3H). MH⁺555.

Compound 222 2-(3-methyl-1-((3-methyl-1,2,4-oxadiazol-5-yl)methyl)-2,6-dioxo-2,3-dihydro-1H-purin-7(6H)-yl)-N-(5'-methyl-6'-(trifluoromethyl)-[2,3'-bipyridin]-6-yl)acetamide

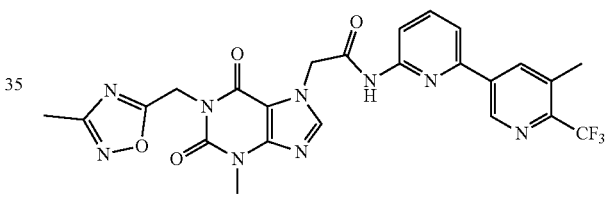

This compound was prepared using the method described for compound 221 with appropriate starting materials as a white solid. ¹H-NMR (400 MHz, DMSO-$d_6$) δ 11.16 (s, 1H), 9.20 (s, 1H), 8.55 (s, 1H), 8.17 (s, 1H) 7.87-8.06 (m, 3H), 5.33 (s, 2H), 5.26 (s, 2H), 3.48 (s, 3H), 2.54 (s, 3H), 2.26 (s, 3H). MH⁺556.

Compound 223 2-(3-methyl-1-((5-methyl-1,2,4-oxadiazol-3-yl)methyl)-2,6-dioxo-2,3-dihydro-1H-purin-7(6H)-yl)-N-(5'-methyl-6'-(trifluoromethyl)-[2,3'-bipyridin]-6-yl)acetamide

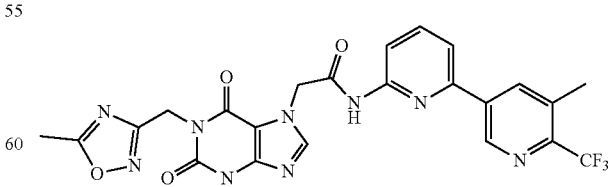

This compound was prepared using the method described for compound 221 with appropriate starting materials as a white solid. ¹H-NMR (400 MHz, DMSO-$d_6$) δ 11.16 (s, 1H), 9.20 (s, 1H), 8.55 (s, 1H), 8.15 (s, 1H) 7.87-8.06 (m, 3H), 5.33 (s, 2H), 5.10 (s, 2H), 3.47 (s, 3H), 2.54 (m, 6H). MH+556.

Compound 224 2-(1-(isoxazol-3-ylmethyl)-3-methyl-2,6-dioxo-2,3-dihydro-1H-purin-7(6H)-yl)-N-(5'-methyl-6'-(trifluoromethyl)-[2,3'-bipyridin]-6-yl)acetamide

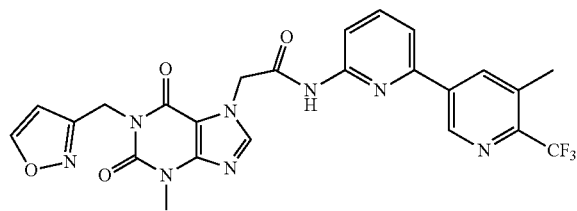 [SMILES: Cc1cc(-c2cccc(NC(=O)Cn3cnc4c3c(=O)n(Cc3ccon3)c(=O)n4C)n2)cnc1C(F)(F)F]

This compound was prepared using the method described for compound 221 with appropriate starting materials as a white solid. $^1$H-NMR (400 MHz, DMSO-$d_6$) δ 11.15 (s, 1H), 9.20 (s, 1H), 8.80 (s, 1H), 8.55 (s, 1H), 8.14 (s, 1H) 7.87-8.06 (m, 3H), 6.46 (s, 1H), 5.33 (s, 2H), 5.10 (s, 2H), 3.47 (s, 3H), 2.55 (m, 6H). MH+541.

Compound 225 2-(3-methyl-1-((3-methylisoxazol-5-yl)methyl)-2,6-dioxo-2,3-dihydro-1H-purin-7(6H)-yl)-N-(5'-methyl-6'-(trifluoromethyl)-[2,3'-bipyridin]-6-yl)acetamide

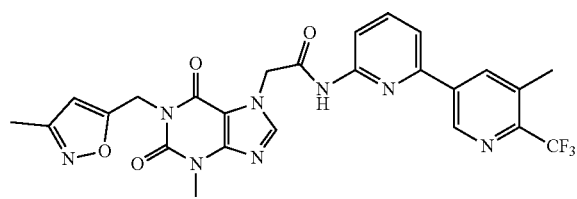 [SMILES: Cc1cc(Cn2c(=O)c3c(ncn3CC(=O)Nc3cccc(-c4cnc(C(F)(F)F)c(C)c4)n3)n(C)c2=O)on1]

This compound was prepared using the method described for compound 221 with appropriate starting materials as a white solid. $^1$H-NMR (400 MHz, DMSO-$d_6$) δ 11.15 (s, 1H), 9.20 (s, 1H), 8.55 (s, 1H), 8.14 (s, 1H), 7.87-8.06 (m, 3H), 6.19 (s, 1H), 5.33 (s, 2H), 5.09 (s, 2H), 3.47 (s, 3H), 2.55 (s, 3H), 2.14 (s, 3H). MH+555.

Compound 226 2-(3-methyl-2,6-dioxo-1-(2-oxobutyl)-2,3-dihydro-1H-purin-7(6H)-yl)-N-(5'-methyl-6'-(trifluoromethyl)-[2,3'-bipyridin]-6-yl)acetamide

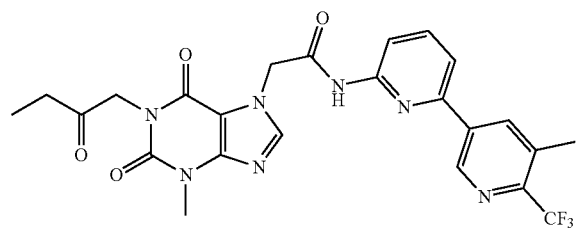 [SMILES: CCC(=O)Cn1c(=O)c2c(ncn2CC(=O)Nc2cccc(-c3cnc(C(F)(F)F)c(C)c3)n2)n(C)c1=O]

This compound was prepared using the method described for compound 221 with appropriate starting materials as a white solid. $^1$H-NMR (400 MHz, DMSO-$d_6$) δ 11.14 (s, 1H), 9.20 (s, 1H), 8.55 (s, 1H), 8.13 (s, 1H), 7.87-8.06 (m, 3H), 5.31 (s, 2H), 4.68 (s, 2H), 3.45 (s, 3H), 2.51 (m, 5H), 0.93 (t, 3H). MH+530.

Compound 227 2-(3-methyl-2,6-dioxo-1-(2-oxopropyl)-2,3-dihydro-1H-purin-7(6H)-yl)-N-(5'-methyl-6'-(trifluoromethyl)-[2,3'-bipyridin]-6-yl)acetamide

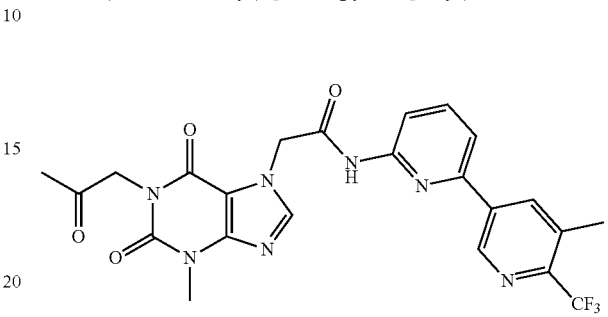

This compound was prepared using the method described for compound 221 with appropriate starting materials as a white solid. $^1$H-NMR (400 MHz, DMSO-$d_6$) δ 11.14 (s, 1H), 9.20 (s, 1H), 8.55 (s, 1H), 8.13 (s, 1H), 7.87-8.04 (m, 3H), 5.31 (s, 2H), 4.69 (s, 2H), 3.45 (s, 3H), 2.55 (s, 3H), 2.16 (s, 3H). MH+516.

Compound 228 N-(5'-fluoro-6'-methyl-[2,3'-bipyridin]-6-yl)-2-(3-methyl-1-((5-methylisoxazol-3-yl)methyl)-2,6-dioxo-2,3-dihydro-1H-purin-7(6H)-yl)acetamide

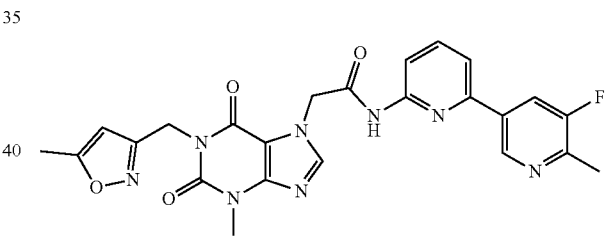

This compound was prepared using the method described for compound 221 with appropriate starting materials as a white solid. $^1$H-NMR (400 MHz, DMSO-$d_6$) δ 11.08 (s, 1H), 9.04 (s, 1H), 8.25 (d, J=10.9 Hz, 1 H), 8.13 (s, 1H), 7.80-8.04 (m, 3H), 6.09 (s, 1H), 5.32 (s, 2H), 5.01 (s, 2H), 3.47 (s, 3H), 2.50 (s, 3H), 2.31 (s, 3H). MH+505.

Compound 229 2-(3-methyl-1-((5-methylisoxazol-3-yl)methyl)-2,6-dioxo-2,3-dihydro-1H-purin-7(6H)-yl)-N-(6-(5-methyl-6-(trifluoromethyl)pyridin-3-yl)pyrazin-2-yl)acetamide

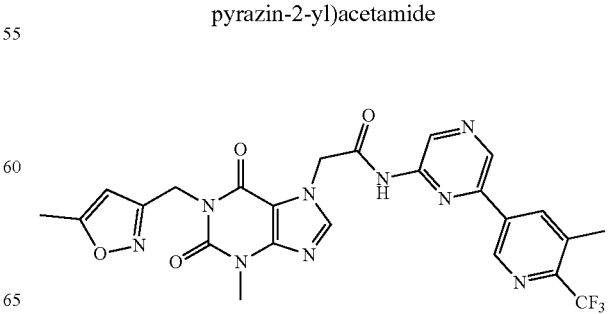

This compound was prepared using the method described for compound 221 with appropriate starting materials as a white solid. $^1$H-NMR (400 MHz, DMSO-d$_6$) δ 11.53 (s, 1H), 9.28 (bs, 1H), 9.24 (s, 1H), 9.15 (s, 1H), 8.61 (s, 1H), 8.14 (s, 1H), 6.09 (s, 1H), 5.37 (s, 2H), 5.01 (s, 2H), 3.47 (s, 3H), 2.56 (s, 3H), 2.31 (s, 3H). MH$^+$556.

Compound 230 2-(3-methyl-1-((3-methyl-1,2,4-oxadiazol-5-yl)methyl)-2,6-dioxo-2,3-dihydro-1H-purin-7(6H)-yl)-N-(6-(5-methyl-6-(trifluoromethyl)pyridin-3-yl)pyrazin-2-yl)acetamide

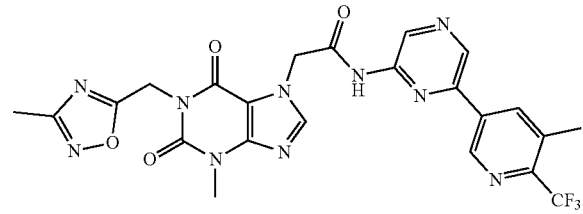

This compound was prepared using the method described for compound 221 with appropriate starting materials as a white solid. $^1$H-NMR (400 MHz, DMSO-d$_6$) δ 11.53 (s, 1H), 9.28 (bs, 1H), 9.24 (s, 1H), 9.15 (s, 1H), 8.61 (s, 1H), 8.19 (s, 1H), 5.38 (s, 2H), 5.26 (s, 2H), 3.48 (s, 3H), 2.56 (s, 3H), 2.27 (s, 3H). MH$^+$557.

Compound 231 N-(5'-fluoro-6'-methyl-[2,3'-bipyridin]-6-yl)-2-(3-methyl-1-((3-methyl-1,2,4-oxadiazol-5-yl)methyl)-2,6-dioxo-2,3-dihydro-1H-purin-7(6H)-yl)acetamide

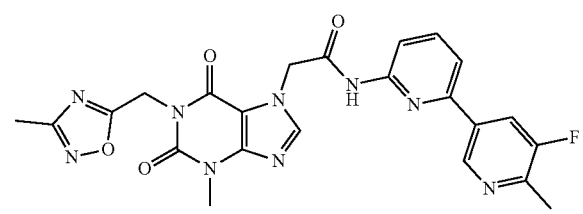 [SMILES: Cc1noc(Cn2c(=O)c3c(ncn3CC(=O)Nc3cccc(-c4cnc(C)c(F)c4)n3)n(C)c2=O)n1]

This compound was prepared using the method described for compound 221 with appropriate starting materials as a white solid. $^1$H-NMR (400 MHz, DMSO-d$_6$) δ 11.08 (s, 1H), 9.04 (s, 1H), 8.24 (d, J=10.9 Hz, 1 H), 8.17 (s, 1H), 7.80-8.00 (m, 3H), 5.32 (s, 2H), 5.26 (s, 2H), 3.48 (s, 3H), 2.51 (s, 3H), 2.26 (s, 3H). MH$^+$506.

Compound 232 2-(3-methyl-2,6-dioxo-1-(2-oxopropyl)-2,3-dihydro-1H-purin-7(6H)-yl)-N-(6-(5-methyl-6-(trifluoromethyl)pyridin-3-yl)pyrazin-2-yl)acetamide

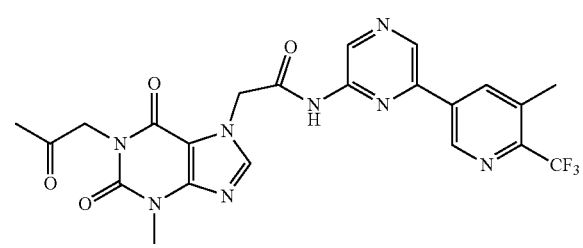 [SMILES: CC(=O)Cn1c(=O)c2c(ncn2CC(=O)Nc2cncc(-c3cnc(C(F)(F)F)c(C)c3)n2)n(C)c1=O]

This compound was prepared using the method described for compound 221 with appropriate starting materials as a white solid. $^1$H-NMR (400 MHz, DMSO-d$_6$) δ 11.51 (s, 1H), 9.28 (s, 1H), 9.24 (s, 1H), 9.15 (s, 1H), 8.61 (s, 1H), 8.14 (s, 1H), 5.35 (s, 2H), 4.67 (s, 2H), 3.46 (s, 3H), 2.56 (s, 3H), 2.16 (s, 3H). MH$^+$517.

Compound 233 2-(3-methyl-2,6-dioxo-1-(2-oxobutyl)-2,3-dihydro-1H-purin-7(6H)-yl)-N-(6-(5-methyl-6-(trifluoromethyl)pyridin-3-yl)pyrazin-2-yl)acetamide

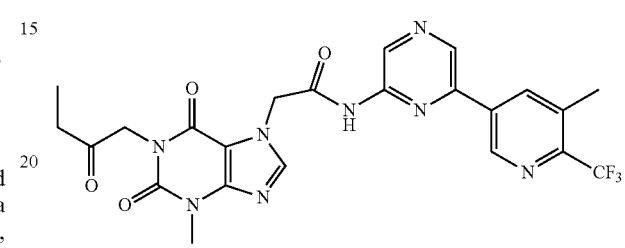

This compound was prepared using the method described for compound 221 with appropriate starting materials as a white solid. $^1$H-NMR (400 MHz, DMSO-d$_6$) δ 11.51 (s, 1H), 9.28 (s, 1H), 9.24 (s, 1H), 9.15 (s, 1H), 8.61 (s, 1H), 8.14 (s, 1H), 5.36 (s, 2H), 4.69 (s, 2H), 3.46 (s, 3H), 2.56 (m, 5H), 0.93 (t, 3H). MH$^+$531.

Compound 234 2-(3-methyl-2,6-dioxo-1-(2-oxopropyl)2,3-dihydro-1H-purin-7(6H)-yl)-N-(6'-methyl-5'-(trifluoromethyl)-[2,3'-bipyridin]-6-yl)acetamide

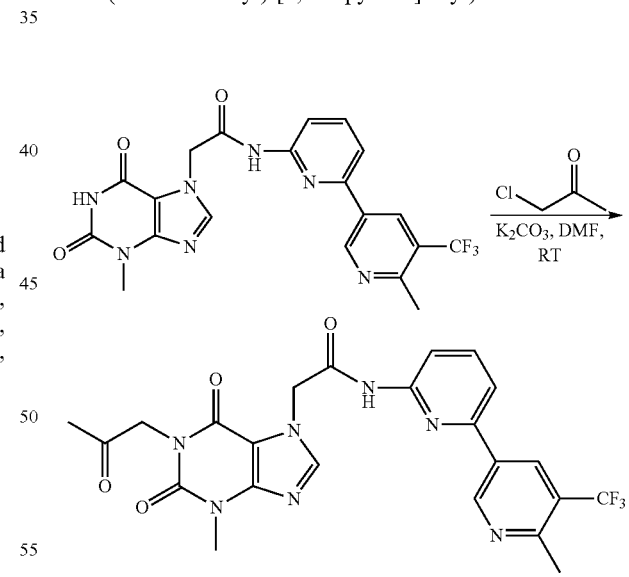

2-(3-methyl-2,6-dioxo-2,3-dihydro-1H-purin-7(6H)-yl)-N-(6'-methyl-5'-(trifluoromethyl)-[2,3-bipyridin]-6-yl)acetamide (50 mg, 0.109 mmol) and potassium carbonate (23 mg, 0.164 mmol) were combined in DMF (4 mL) then chloroacetone (0.010 mL, 0.120 mmol) was added drop wise. The reaction was stirred at RT for 18 h, diluted with water (10 mL) and extracted with EA (3×10 ml). The combined organic layers were washed with aq. 1 N LiCl (2×10 ml), dried with MgSO$_4$ and concentrated to a residue which was purified by chromatography eluted with MeOH/

DCM (1:99 to 1:97) to give 2-(3-methyl-2,6-dioxo-1-(2-oxopropyl)2,3-dihydro-1H-purin-7(6H)-yl)-N-(6'-methyl-5'-(trifluoromethyl)-[2,3'-bipyridin]-6-yl)acetamide (19 mg, 33.9% yield) as an off-white solid. $^1$H NMR (CDCl$_3$) δ: 9.44 (brd s, 1H), 9.18 (s, 1H), 8.51 (s, 1H), 8.11 (s, 1H), 7.82 (s, 1H), 7.79 (s, 1H), 7.55 (d, 1H, J=8 Hz), 5.10 (s,2H), 4.88 (s, 2H), 3.60 (s, 3H), 2.78 (s, 3H), 2.29 (s, 3H). LCMS: MH$^+$516 and T$_R$=2.897 min.

Compound 235 2-(3-methyl-2,6-dioxo-1-(2-oxobutyl)-2,3-dihydro-1H-purin-7(6H)-yl)-N-(6'-methyl-5'-(trifluoromethyl)-[2,3-bipyridin]-6-yl)acetamide

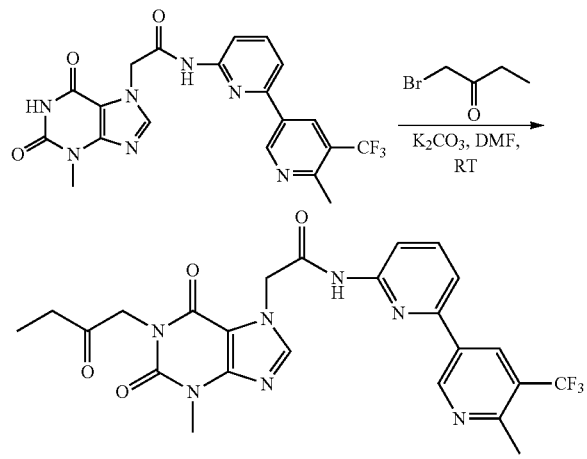

2-(3-methyl-2,6-dioxo-2,3-dihydro-1H-purin-7(6H)-yl)-N-(6'-methyl-5'-(trifluoromethyl)-[2,3-bipyridin]-6-yl)acetamide (50 mg, 0.109 mmol) and potassium carbonate (23 mg, 0.164 mmol) were combined in DMF (4 mL) then 1-bromobutan-2-one (0.012 mL, 0.120 mmol) was added drop wise. The reaction was heated at 55° C. for 18 h then concentrated to a residue which was purified by chromatography eluted with MeOH/DCM (1:99 to 1:97) to give 2-(3-methyl-2,6-dioxo-1-(2-oxobutyl)-2,3-dihydro-1H-purin-7(6H)-yl)-N-(6'-methyl-5'-(trifluoromethyl)-[2,3'-bipyridin]-6-yl)acetamide (18 mg, 31.2% yield) as a white solid. $^1$H NMR (CDCl$_3$) δ: 9.44 (brd s, 1H), 9.21 (s, 1H), 8.55 (s, 1H), 8.13 (d, J=4 Hz, 1H), 7.87-7.81 (m, 2H), 7.58 (d, 1H, J=8 Hz), 5.13 (s, 2H), 4.89 (s, 2H), 3.62 (s, 3H), 2.81 (s, 3H), 2.61 (q, J=8 Hz and 12 Hz, 2H), 1.14 (t, J=8 Hz, 3H). LCMS: MH$^+$530 and T$_R$=3.091 min.

Compound 236 2-(1-(3-hydroxypropyl)-3-methyl-2,6-dioxo-2,3-dihydro-1H-purin-7(6H)-yl)-N-(6%methyl-5'-(trifluoromethyl)-[2,3-bipyridin]-6-yl) acetamide

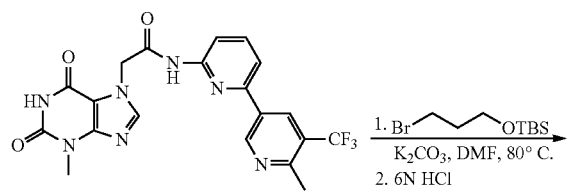

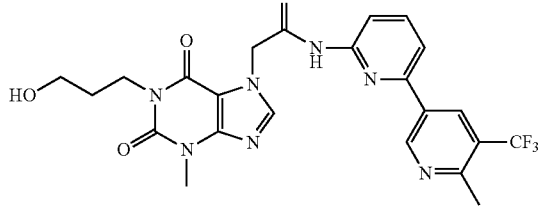

2-(3-methyl-2,6-dioxo-2,3-dihydro-1H-purin-7(6H)-yl)-N-(6'-methyl-5' -(trifluoromethyl)-[2,3-bipyridin]-6-yl)acetamide (50 mg, 0.109 mmol) and potassium carbonate (23 mg, 0.164 mmol) were combined in DMF (4 mL) then (3-bromopropoxy)(tert-butyl)dimethylsilane (30 mg, 0.120 mmol) was added. The reaction was heated at 80° C. for 18 h, cooled to RT then enough aq. 6N HCl was added until PH =1. The reaction was stirred at RT for 1 h, diluted with water (20 mL) and extracted with EA (3×20 mL). The combined organic layers were dried with MgSO$_4$ and concentrated to a residue which was purified by Prep TLC eluted with MeOH/DCM (1:9) to give 2-(1-(3-hydroxypropyl)-3-methyl-2,6-dioxo-2,3-dihydro-1H-purin-7(6H)-yl)-N-(6'-methyl-5'-(trifluoromethyl)-[2,3'-bipyridin]-6-yl)acetamide (15 mg, 26.8% yield) as a white solid. $^1$H NMR (CDCl$_3$) δ: 9.80 (brd s, 1H), 9.30 (s, 1H), 8.45 (s, 1H), 7.82 (t, J=8 Hz, 1H), 7.78 (s, 1H), 7.55 (d, J=8 Hz, 1H), 5.13 (s, 2H), 5.12 (s, 2H), 4.24 (t, J=8 Hz, 2H), 3.91-3.84 (m, 1H), 3.66-3.56 (m, 5H), 2.78 (s, 3H), 2.00-1.90 (m, 2H). LCMS: MH$^+$518 and T$_R$=2.682 min.

Compound 237 2-(1-(3-hydroxyethoxy)-3-methyl-2,6-dioxo-2,3-dihydro-1H-purin-7(6H)-yl)-N-(6%methyl-5'-(trifluoromethyl)-[2,3-bipyridin]-6-yl) acetamide

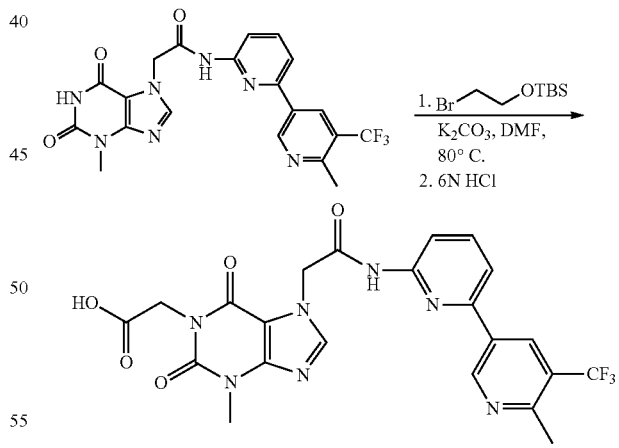

2-(3-methyl-2,6-dioxo-2,3-dihydro-1H-purin-7(6H)-yl)-N-(6'-methyl-5' -(trifluoromethyl)-[2,3-bipyridin]-6-yl)acetamide (100 mg, 0.218 mmol) and potassium carbonate (45 mg, 0.327 mmol) were combined in DMF (5 mL) then (3-bromoethoxy)(tert-butyl)dimethylsilane (57 mg, 0.240 mmol) was added. The reaction was heated at 80° C. for 18 h, cooled to RT then enough aq. 6N HCl was added until PH=1. The reaction was stirred at RT for 1 h and concentrated to a residue which was purified by chromatography eluted with MeOH/DCM (2:98 to 8:92) to give 2-(1-(3- hydroxyethoxy)-3-methyl-2,6-dioxo-2,3-dihydro-1H-purin-7(6H)-yl)-N-(6'-methyl-5'-(trifluoromethyl)-[2,3'-bipyridin]-6-yl)acetamide (28 mg, 25.5% yield) as a white solid. $^1$H NMR (CDCl$_3$) δ: 9.66 (brd s, 1H), 9.24 (s, 1H), 8.54 (s, 1H), 7.87-7.80 (m, 2H), 7.58 (d, J=8 Hz, 1H), 5.15 (s, 2H), 4.37 (t, J=8 Hz, 2H), 3.93 (t, J=4 Hz, 1H), 3.64 (s, 3H), 2.81 (s, 3H). LCMS: MH$^+$504 and T$_R$=2.607 min.

Compound 238 2-(3-methyl-1-((5-methylisoxazol-3-yl)methyl)-2,6-dioxo-2,3-dihydro-1H-purin-7(6H)-yl)-N-(6'-methyl-5'-(trifluoromethyl)-[2,3-bipyridin]-6-yl)acetamide

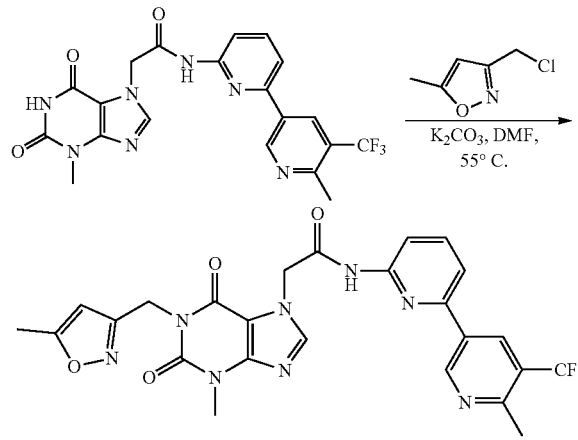

2-(3-methyl-2,6-dioxo-2,3-dihydro-1H-purin-7(6H)-yl)-N-(6'-methyl-5'-(trifluoromethyl)-[2,3-bipyridin]-6-yl)acetamide (50 mg, 0.109 mmol) and potassium carbonate (25 mg, 0.327 mmol) were combined in DMF (3 mL) then 3-(chloromethyl)-5-methylisoxazole (16 mg, 0.120 mmol) was added. The reaction was heated at 55° C. for 18 h, cooled to RT then concentrated to a residue which was purified by chromatography eluted with MeOH/DCM (1:99 to 3:97) to give 2-(3-methyl-1-((5-methylisoxazol-3-yl)methyl)-2,6-dioxo-2,3-dihydro-1H-purin-7(6H)-yl)-N-(6'-methyl-5'-(trifluoromethyl)-[2,3'-bipyridin]-6-yl)acetamide (19 mg, 31.7% yield) as a white solid. $^1$H NMR (CDCl$_3$) δ: 9.53 (brd s, 1H), 9.17 (s, 1H), 8.51 (s, 1H), 8.08 (brd s, 1H), 7.84-7.75 (m, 2H), 7.55 (d, J=8 Hz, 1H), 6.02 (s, 1H), 5.30 (s, 2H), 5.20 (s, 2H) 3.64 (s, 3H), 2.80 (s, 3H), 2.28 (s, 3H). LCMS: MH$^+$555 and T$_R$=3.108 min.

Compound 239 2-(1-(isoxazol-3-ylmethyl)-3-methyl-2,6-dioxo-2,3-dihydro-1H-purin-7(6H)-yl)-N-(6'-methyl-5'-(trifluoromethyl)-[2,3-bipyridin]-6-yl)acetamide

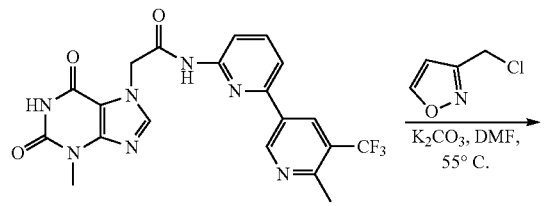

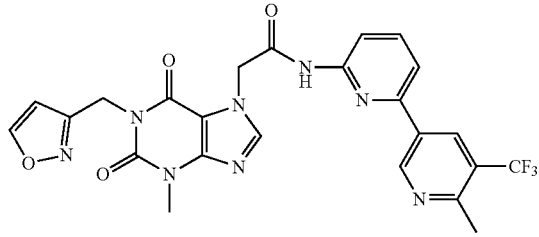

2-(3-methyl-2,6-dioxo-2,3-dihydro-1H-purin-7(6H)-yl)-N-(6'-methyl-5'-(trifluoromethyl)-[2,3-bipyridin]-6-yl)acetamide (50 mg, 0.109 mmol) and potassium carbonate (25 mg, 0.327 mmol) were combined in DMF (3 mL) then 3-(chloromethyl)isoxazole (16 mg, 0.120 mmol) was added. The reaction was heated at 55° C. for 18 h, cooled to RT then concentrated to a residue which was purified by chromatography eluted with MeOH/DCM (1:99 to 3:97) to give 2-(1-(isoxazol-3-ylmethyl)-3-methyl-2,6-dioxo-2,3-dihydro-1H-purin-7(6H)-yl)-N-(6'-methyl-5'-(trifluoromethyl)-[2,3'-bipyridin]-6-yl)acetamide (29 mg, 49.2% yield) as a white solid. $^1$H NMR (CDCl$_3$) δ: 9.45 (brd s, 1H), 9.14 (s, 1H), 8.48 (s, 1H), 8.23 (s, 1H), 8.07 (brd s, 1H), 7.82-7.73 (m, 2H), 7.53 (d, J=8 Hz, 1H), 6.40 (s, 1H), 5.35 (s, 2H), 5.17 (s, 2H) 3.61 (s, 3H), 2.77 (s, 3H). LCMS: MH$^+$541 and T$_R$=3.005 min.

Compound 240 2-(3-methyl-1-((5-methyl-1,2,4-oxadiazol-3-yl)methyl-2,6-dioxo-2,3-dihydro-1H-purin-7(6H)-yl)-N-(6'-methyl-5'-(trifluoromethyl)-[2,3-bipyridin]-6-yl)acetamide

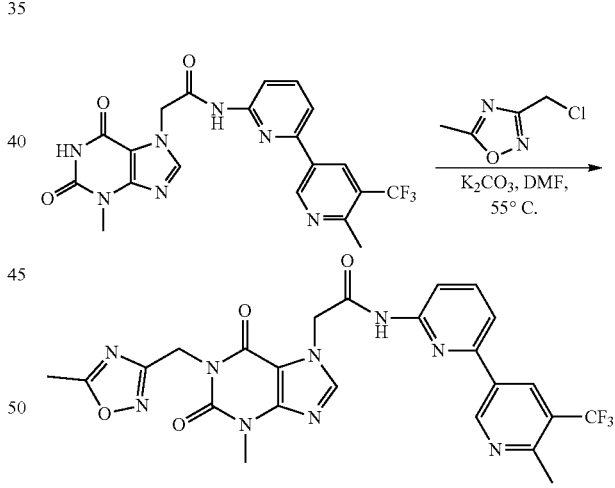

2-(3-methyl-2,6-dioxo-2,3-dihydro-1H-purin-7(6H)-yl)-N-(6'-methyl-5'-(trifluoromethyl)-[2,3-bipyridin]-6-yl)acetamide (50 mg, 0.109 mmol) and potassium carbonate (25 mg, 0.327 mmol) were combined in DMF (3 mL) then 3-(chloromethyl)-5-methyl-1,2,4-oxadiazole (16 mg, 0.120 mmol) was added. The reaction was heated at 55° C. for 18 h, cooled to RT then concentrated to a residue which was purified by chromatography eluted with MeOH/DCM (1:99 to 3:97) to give 2-(3-methyl-1-((5-methyl-1,2,4-oxadiazol-3-yl)methyl)-2,6-dioxo-2,3-dihydro-1H-purin-7 (6H)-yl)-N-(6'-methyl-5'-(trifluoromethyl)-[2,3'-bipyridin]-6-yl)acetamide (18 mg, 29.5% yield) as a light tan solid. $^1$H NMR (CDCl$_3$) δ: 9.26 (brd s, 1H), 9.14 (s, 1H), 8.47 (s, 1H), 8.08

(brd s, 1H), 7.84-7.75 (m, 2H), 7.54 (d, J=8 Hz, 1H), 5.35 (s, 2H), 5.16 (s, 2H) 3.62 (s, 3H), 2.77 (s, 3H), 2.47 (s, 3H). LCMS: MH+556 and $T_R$=2.962 min.

Compound 241 2-(3-methyl-1-((3-methyl-1,2,4-oxadiazol-5-yl)methyl-2,6-dioxo-2,3-dihydro-1H-purin-7(6H)-yl)-N-(6'-methyl-5'-(trifluoromethyl)-[2,3'-bipyridin]-6-yl)acetamide

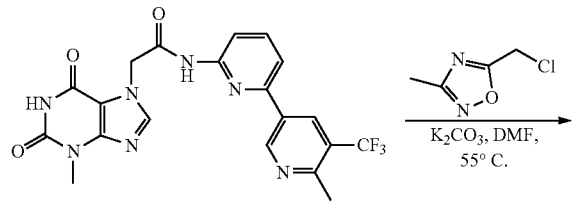

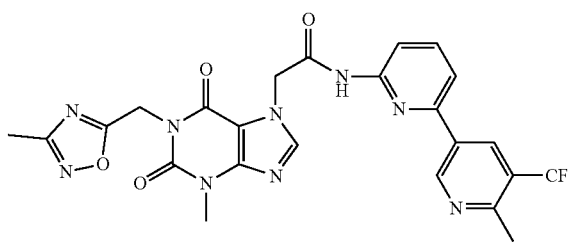

2-(3-methyl-2,6-dioxo-2,3-dihydro-1H-purin-7(6H)-yl)-N-(6'-methyl-5'-(trifluoromethyl)-[2,3-bipyridin]-6-yl)acetamide (50 mg, 0.109 mmol) and potassium carbonate (25 mg, 0.327 mmol) were combined in DMF (3 mL) then 5-(chloromethyl)-3-methyl-1,2,4-oxadiazole (16 mg, 0.120 mmol) was added. The reaction was heated at 55° C. for 18 h, cooled to RT then concentrated to a residue which was purified by chromatography eluted with MeOH/DCM (1:99 to 3:97) to give 2-(3-methyl-1-((3-methyl-1,2,4-oxadiazol-5-yl)methyl-2,6-dioxo-2,3-dihydro-1H-purin-7 (6H)-yl)-N-(6' -methyl-5' -(trifluoromethyl)-[2,3'-bipyridin]-6-yl)acetamide (28 mg, 45.9% yield) as a white solid. $^1$H NMR (CDCl$_3$) δ: 9.14 (s, 2H), 8.47 (s, 1H), 8.08 (brd s, 1H), 7.88-7.77 (m, 2H), 7.55 (d, J=8 Hz, 1H), 5.42 (s, 2H), 5.15 (s, 2H) 3.53 (s, 3H), 2.77 (s, 3H), 2.27 (s, 3H). LCMS: MH+556 and $T_R$=3.032 min.

Compound 242 2-(3-methyl-2,6-dioxo-1-(3-oxobutyl)-2,3-dihydro-1H-purin-7(6H)-yl)-N-(6'-methyl-5'-(trifluoromethyl)-[2,3'-bipyridin]-6-yl)acetamide

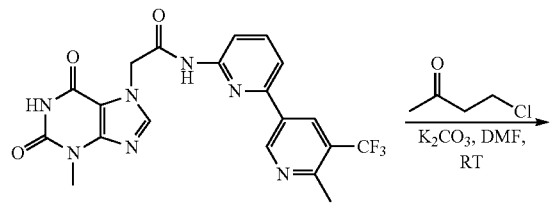

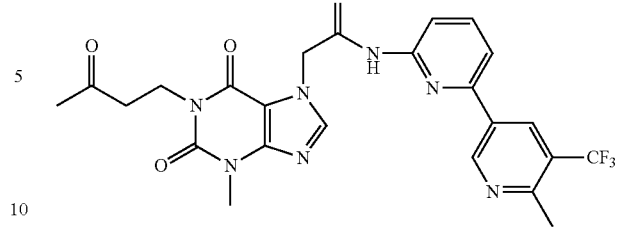

2-(3-methyl-2,6-dioxo-2,3-dihydro-1H-purin-7(6H)-yl)-N-(6'-methyl-5'-(trifluoromethyl)-[2,3-bipyridin]-6-yl)acetamide (50 mg, 0.109 mmol) and potassium carbonate (23 mg, 0.164 mmol) were combined in DMF (3 mL) then 4-chlorobutane-2-one (12 mg, 0.109 mmol) was added. The reaction was stirred at RT for 18 h and concentrated to a residue which was purified by chromatography eluted with MeOH/DCM (1:99 to 3:97) to give 2-(3-methyl-2,6-dioxo-1-(3-oxobutyl)-2,3-dihydro-1H-purin-7(6H)-yl)-N-(6'-methyl-5'-(trifluoromethyl)-[2,3-bipyridin]-6-yl)acetamide (11 mg) as a white solid. $^1$H NMR (CDCl$_3$) δ: 9.69 (brd s, 1H), 9.30 (s, 1H), 8.68 (s, 1H), 8.14 (d, J=8 Hz, 1H), 7.83 (t, J=8 Hz, 1H), 7.76 (s, 1H), 7.55 (d, J=4 Hz, 1H), 5.22 (brd s, 2H), 4.27 (t, J=8 Hz, 2H), 3.59 (s, 3H), 2.92 (s, 3H), 2.80 (t, J=8 Hz, 2H), 2.12 (s, 3H), 2.12 (s, 3H). LCMS: MH+530 and $T_R$=2.906 min.

Compound 243 2-(3-methyl-2,6-dioxo-1-(2-oxobutyl)-2,3-dihydro-1H-purin-7(6H)-yl)-N-(6-(6-methyl-5-(trifluoromethyl)pyridin-3-yl)pyrazin-2-yl)acetamide

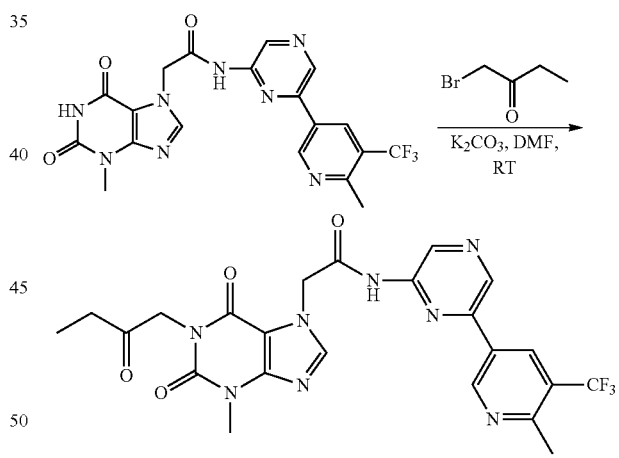

2-(3-methyl-2,6-dioxo-2,3-dihydro-1H-purin-7(6H)-yl)-N-(6-(6-methyl-5-(trifluoromethyl) pyridin-3-yl)pyrazin-2-yl) acetamide (50 mg, 0.109 mmol) and potassium carbonate (23 mg, 0.164 mmol) were combined in DMF (4 mL) then 1-bromobutan-2-one (0.012 mL, 0.120 mmol) was added drop wise. The reaction was stirred at RT for 18 h then concentrated to a residue which was purified by chromatography eluted with MeOH/DCM (1:99 to 1:97) to give 2-(3-methyl-2,6-dioxo-1-(2-oxobutyl)-2,3-dihydro-1H-purin-7(6H)-yl)-N-(6-(6-methyl-5-(trifluoromethyl)pyridin-3-yl)pyrazin-2-yl)acetamide (14 mg, 24.1% yield) as a white solid. $^1$H NMR (CDCl$_3$) δ: 9.93 (brd s, 1H), 9.43 (s, 1H), 9.29 (s, 1H), 8.87 (s, 1H), 8.58 (s, 1H), 7.82 (s, 1H), 5.17 (s, 2H), 4.95 (s, 2H), 3.59 (s, 3H), 2.87 (s, 3H), 2.59 (q, J=8 Hz and 12 Hz, 2H), 1.09 (t, J=8 Hz, 3H). LCMS: MH+531 and $T_R$=2.821 min.

Compound 245 2-(3-methyl-2,6-dioxo-1-(2-oxopropyl)-2,3-dihydro-1H-purin-7(6H)-yl)-N-(6-(6-methyl-5-(trifluoromethyl)pyridin-3-yl)pyrazin-2-yl)acetamide

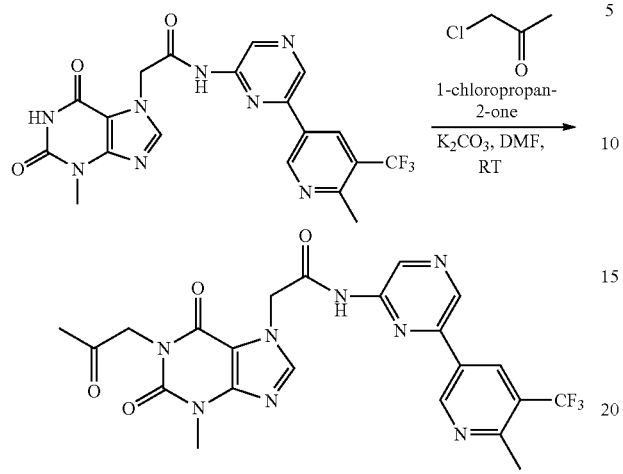

2-(3-methyl-2,6-dioxo-2,3-dihydro-1H-purin-7(6H)-yl)-N-(6-(6-methyl-5-(trifluoromethyl) pyridin-3-yl)pyrazin-2-yl) acetamide (100 mg, 0.217 mmol) and potassium carbonate (45 mg, 0.326 mmol) were combined in DIVIF (5 mL) then 1-chloropropan-2-one (0.017 mL, 0.217 mmol) was added drop wise. The reaction was stirred at RT for 18 h then concentrated to a residue which was purified by chromatography eluted with MeOH/DCM (1:99 to 1:97) to give 2-(3-methyl-2,6-dioxo-1-(2-oxopropyl)-2,3-dihydro-1H-purin-7(6H)-yl)-N-(6-(6-methyl-5-(trifluoromethyl)pyridin-3-yl)pyrazin-2-yl)acetamide (16 mg, 14.3% yield) as a white solid. $^1$H NMR (CDCl$_3$) δ: 9.91 (brd s, 1H), 9.45 (s, 1H), 9.29 (s, 1H), 8.88 (s, 1H), 8.60 (s, 1H), 7.81 (s, 1H), 5.14 (s, 2H), 4.88 (s, 2H), 3.60 (s, 3H), 2.88 (s, 3H), 2.30 (s, 3H). LCMS: MH$^+$517 and T$_R$=2.635 min.

Compound 246 2-(3-methyl-1-((5-methylisoxazol-3-yl)methyl)-2,6-dioxo-2,3-dihydro-1H-purin-7(6H)-yl)-N-(2-(6-methyl-5-(trifluoromethyl)pyridin-3-yl)thiazol-4-yl)acetamide A mixture of 3-methyl-1-((5-methylisoxazol-3-yl)methyl)-1H-purine-2,6(3H,7H)-dione (31 mg, 0.12 mmol), 2-chloro-N-(2-(6-methyl-5-(trifluoromethyl)pyridin-3-yl)thiazol-4-yl)acetamide (40 mg, 0.12 mmol), potassium carbonate (33 mg, 0.24 mmol) and a catalytic amount of TBAI in N,N-dimethylformamide (1 mL) was stirred at 50° C. overnight. The mixture was diluted with EA and washed with water, brine successively, dried and concentrated to give a crude product, which was purified via preparative HPLC to give 2-(3-methyl-1-((5-methylisoxazol-3- yl)methyl)-2,6-dioxo-2,3-dihydro-1H-purin-7(6H)-yl)-N-(2-(6-methyl-5-(trifluoromethyl)pyridin-3-yl)thiazol-4-yl)acetamide (25 mg, 37.3% yield) as a white solid. $^1$H NMR (400 MHz, DMSO) δ 11.71 (s, 1H), 9.24 (s, 1H), 8.46 (s, 1H), 8.14 (s, 1H), 7.71 (s, 1H), 6.10 (s, 1H), 5.27 (s, 2H), 5.02 (s, 2H), 3.47 (s, 3H), 2.71 (s, 3H), 2.32 (s, 3H). Retention time (LC-MS): 1.415 min. MH$^+$561.

Compound 247 2-(3-methyl-2,6-dioxo-1-(2-oxobutyl)-2,3-dihydro-1H-purin- 7(6H)-yl)-N-(2-(6-methyl-5-(trifluoromethyl)pyridin-3-yl)thiazol-4-yl)acetamide

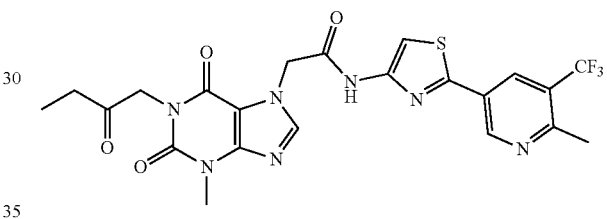

This compound was prepared using the method described for compound 246 with appropriate starting materials in 29.7% yield as a white solid. 1H NMR (400 MHz, DMSO-d6) δ 11.69 (s, 1H), 9.24 (s, 1H), 8.46 (s, 1H), 8.14 (s, 1H), 7.70 (s, 1H), 5.26 (s, 2H), 4.69 (s, 2H), 3.46 (s, 3H), 2.71 (s, 3H), 2.54 (s, 2H), 0.95 (t, J=6 Hz, 3H). Retention time (LC-MS): 2.069 min. MH$^+$536.

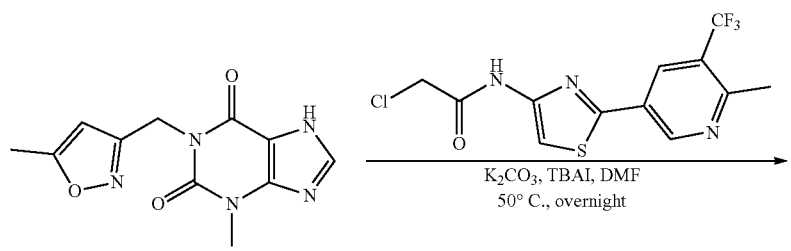

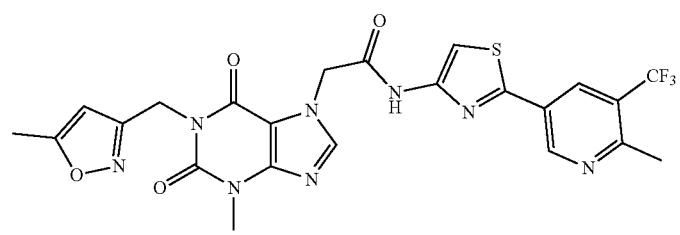

Compound 248 2-(3-methyl-1-((5-methyl-1,2,4-oxadiazol-3-yl)methyl)-2,6-dioxo-2,3-dihydro-1H-purin-7(6H)-yl)-N-(2-(6-methyl-5-(trifluoromethyl)pyridin-3-yl)thiazol-4-yl)acetamide

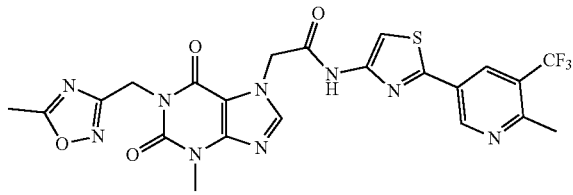

This compound was prepared using the method described for compound 246 with appropriate starting materials in 18.4% yield as a white solid. ¹H NMR (400 MHz, DMSO-d6) δ 11.72 (s, 1H), 9.23 (d, J=4 Hz, 1H), 8.46 (d, J=4 Hz, 1H), 8.16 (s, 1H), 7.70 (s, 1H), 5.28 (s, 2H), 5.11 (s, 2H), 3.48 (s, 3H), 2.71 (s, 3H), 2.53 (s, 3H). Retention time (LC-MS): 2.280 min. MH⁺562.

Compound 249 2-(3-methyl-2,6-dioxo-1-(2-oxobutyl)-2,3-dihydro-1H-purin-7(6H)-yl)-N-(2-(5-methyl-6-(trifluoromethyl)pyridin-3-yl)thiazol-4-yl)acetamide

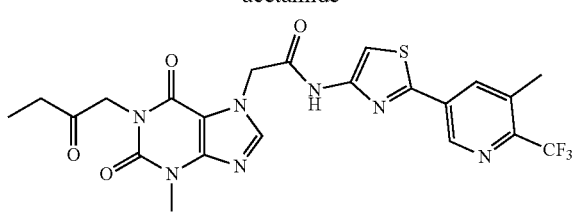

This compound was prepared using the method described for compound 246 with appropriate starting materials in 39.2% yield as a white solid. ¹H NMR (400 MHz, DMSO-d6) δ11.74 (s, 1H), 9.07 (s, 1H), 8.39 (s, 1H), 8.15 (s, 1H), 7.76 (s, 1H), 5.27 (s, 2H), 4.70 (s, 2H), 3.46 (s, 3H), 2.51 (s, 5H), 0.95 (t, J=6.4 Hz, 3H). Retention time (LC-MS): 2.424 min. MH⁺536.

Compound 250 2-(3-methyl-1-((3-methyl-1,2,4-oxadiazol-5-yl)methyl)-2,6-dioxo-2,3-dihydro-1H-purin-7(6H)-yl)-N-(2-(5-methyl-6-(trifluoromethyl)pyridin-3-yl)thiazol-4-yl)acetamide To a solution of 2-(3-methyl-2,6-dioxo-2,3-dihydro-1H-purin-7(6H)-yl)-N-(2-(5-methyl-6-(trifluoromethyl)pyridin-3-yl)thiazol-4-yl)acetamide (20 mg, 0.043 mmol) and 5-(chloromethyl)-3-methyl-1,2,4-oxadiazole (6.27 mg, 0.047 mmol) in DMF (1 mL) was added TBAI (1.59 mg, 0.0043 mmol) and potassium carbonate (11.88 mg, 0.086 mmol) under N₂ protection. The mixture was stirred at 40° C. for 1 hrs. The reaction was quenched by water (5 mL) and extracted with EA (2×5 mL). The combined organic layer was washed with saturated brine (2×5 mL), dried over Na₂SO₄ and filtered. The filtrate was concentrated. The crude product was purified via Preparative-TLC (DCM:MeOH=20:1) to afford 2-(3-methyl-1-((3-methyl-1,2,4-oxadiazol-5-yl)methyl)-2,6-dioxo-2,3-dihydro-1H-purin-7(6H)-yl)-N-(2-(5-methyl-6-(trifluoromethyl)pyridin-3-yl)thiazol-4-yl)acetamide (10 mg, 41.4% yield) as a white solid. ¹H NMR (400 MHz, DMSO-d6) δ 11.76 (s, 1H), 9.07 (s, 1H), 8.40 (s, 1H), 8.19 (s, 1H), 7.76 (s, 1H), 5.28 (d, J=6.2 Hz, 4H), 3.49 (s, 3H), 2.55 (s, 3H), 2.28 (s, 3H). Retention time (LC-MS): 2.104 min. MH⁺562.

Compound 251 2-(3-methyl-2,6-dioxo-1-(2,2,2-trifluoroethyl)-2,3-dihydro-1H-purin-7(6H)-yl)-N-(2-(5-methyl-6-(trifluoromethyl)pyridin-3-yl)thiazol-4-yl)acetamide

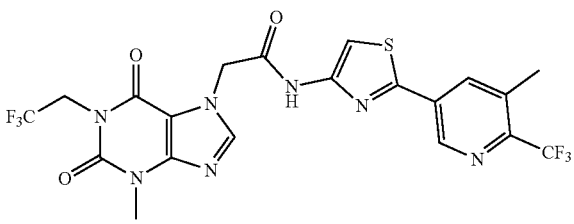 [SMILES: Cc1cc(-c2nc(NC(=O)Cn3cnc4c3c(=O)n(CC(F)(F)F)c(=O)n4C)cs2)cnc1C(F)(F)F]

This compound was prepared using the method described for compound 250 with appropriate starting materials and separated via preparative-TLC in 42.5% yield as a white solid. ¹H NMR (400 MHz, DMSO-d6) δ 11.76 (s, 1H), 9.07 (s, 1H), 8.40 (s, 1H), 8.18 (s, 1H), 7.76 (s, 1H), 5.29 (s, 2H), 4.65 (q, J=9.1 Hz, 2H), 3.49 (s, 3H), 2.56 (d, J=1.5 Hz, 3H). Retention time (LC-MS): 2.355 min. MH⁺548.

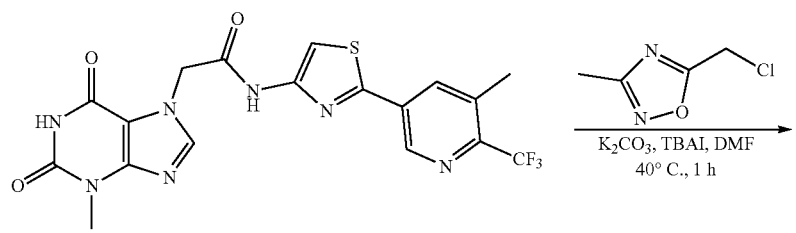

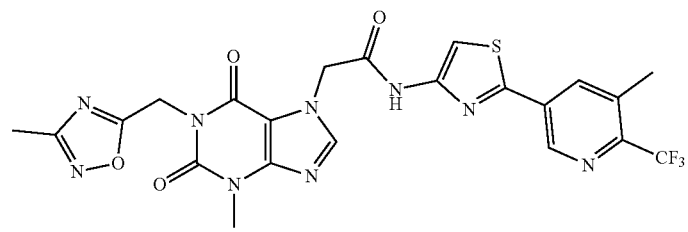

Compound 252 2-(3-methyl-1-((3-methyl-1,2,4-oxadiazol-5-yl)methyl)-2,6-dioxo-2,3-dihydro-1H-purin-7(6H)-yl)-N-(2-(6-methyl-5-(trifluoromethyl)pyridin-3-yl)thiazol-4-yl)acetamide

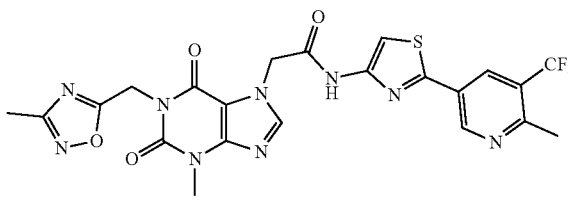

This compound was prepared using the method described for compound 250 with appropriate starting materials and separated via preparative-HPLC in 16.3% yield as a white solid. $^1$H NMR (400 MHz, DMSO-d6) δ 11.71 (s, 1H), 9.23 (d, J=1.6 Hz, 1H), 8.45 (d, 1H), 8.18 (s, 1H), 7.70 (s, 1H), 5.27 (s, 4H), 3.48 (s, 3H), 2.70 (d, J=1.2 Hz, 3H), 2.27 (s, 3H). Retention time (LC-MS): 2.252 min. MH$^+$562.

Compound 253 2-(3-methyl-1-((5-methyl-1,2,4-oxadiazol-3-yl)methyl)-2,6-dioxo-2,3-dihydro-1H-purin-7(6H)-yl)-N-(2-(5-methyl-6-(trifluoromethyl)pyridin-3-yl)thiazol-4-yl)acetamide

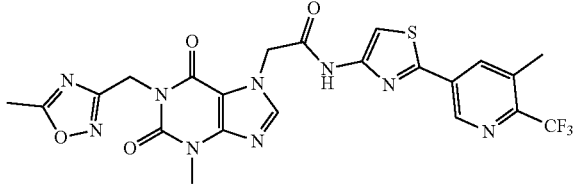 [SMILES: Cc1nc(Cn2c(=O)c3c(ncn3CC(=O)Nc3csc(-c4cnc(C(F)(F)F)c(C)c4)n3)n(C)c2=O)no1]

This compound was prepared using the method described for compound 250 with appropriate starting materials and separated via preparative-TLC in 49.7% yield as a white solid. $^1$H NMR (400 MHz, DMSO-d6) δ 11.75 (s, 1H), 9.07 (s, 1H), 8.40 (s, 1H), 8.17 (s, 1H), 7.76 (s, 1H), 5.29 (s, 2H), 5.11 (s, 2H), 3.48 (s, 3H), 2.55 (d, J=1.4 Hz, 3H), 2.53 (s, 3H). Retention time (LC-MS): 2.286 min. MH$^+$562.

Compound 254 2-(1-(3-methoxy-2-oxopropyl)-3-methyl-2,6-dioxo-2,3-dihydro-1H-purin-7(6H)-yl)-N-(2-(6-methyl-5-(trifluoromethyl)pyridin-3-yl)thiazol-4-yl)acetamide

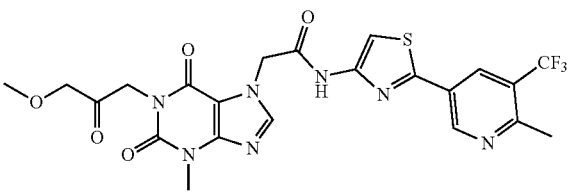

This compound was prepared using the method described for compound 246 with appropriate starting materials and separated via preparative-HPLC in 8.9% yield as a white solid. $^1$H NMR (400 MHz, DMSO-d6) δ 1.71 (s, 1H), 9.24 (s, 1H), 8.46 (s, 1H), 8.15 (s, 1H), 7.70 (s, 1H), 5.26 (s, 2H), 4.75 (s, 2H), 4.22 (s, 2H), 3.46 (s, 3H), 3.32 (s, 3H), 2.71 (s, 3H). Retention time (LC-MS): 1.990 min. MH$^+$552.

Compound 255 2-(1-(3-methoxy-2-oxopropyl)-3-methyl-2,6-dioxo-2,3-dihydro-1H-purin-7(6H)-yl)-N-(2-(5-methyl-6-(trifluoromethyl)pyridin-3-yl)thiazol-4-yl)acetamide

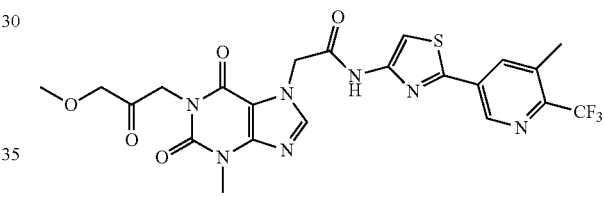

This compound was prepared using the method described for compound 246 with appropriate starting materials in 30.4% yield. White solid. $^1$H NMR (400 MHz, DMSO-d6) 611.72 (s, 1H), 9.07 (s, 1H), 8.40 (s, 1H), 8.15 (s, 1H), 7.75 (s, 1H), 5.26 (s, 2H), 4.74 (s, 2H), 4.22 (s, 2H), 3.46 (s, 3H), 3.32 (s, 3H), 2.55 (s, 3H). Retention time (LC-MS): 2.065 min. MH$^+$552.

Compound 256 (2S)-N-(6-(5-(6,6-difluoro-3-azabicyclo[3.1.0]hexan-3-yl)pyrazin-2-yl)pyridin-2-yl)-2-(3-methyl-2,6-dioxo-1-(2-oxobutyl)-2,3-dihydro-1H-purin-7(6H)-yl)propanamide

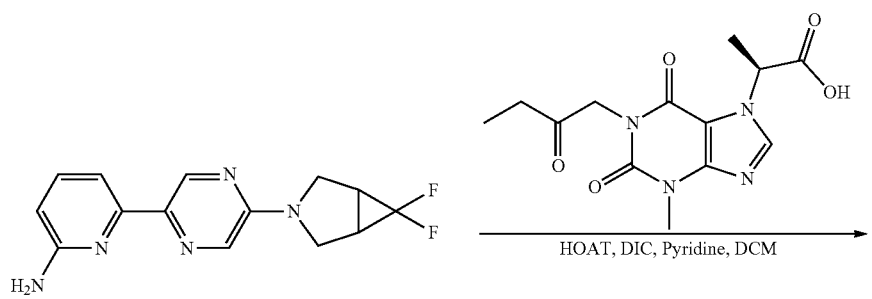

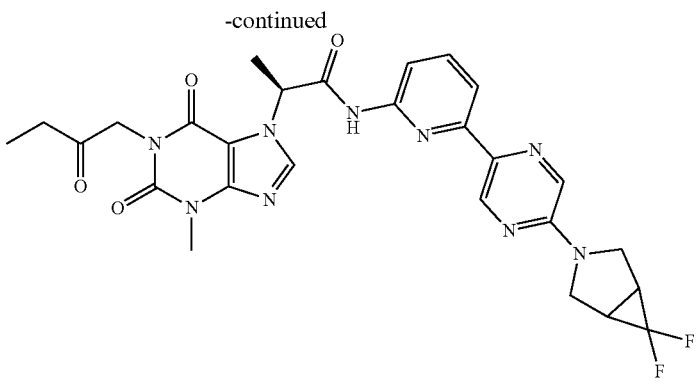

To a solution of 6-(5-(6,6-difluoro-3-azabicyclo[3.1.0]hexan-3-yl)pyrazin-2-yl)pyridin-2-amine (40 mg, 0.138 mmol) and (S)-2-(3-methyl-2,6-dioxo-1-(2-oxobutyl)-2,3-dihydro-1H-purin-7(6H)-yl)propanoic acid (47 mg, 0.151 mmol) in DCM (4 mL) was added HOAt (19 mg, 0.138 mmol) at RT. The reaction mixture was cooled under ice-water bath to 0° C., followed by drop-wise addition of pyridine (0.02 mL, 0.27 mmol) and DIC (0.03 mL, 0.21 mmol) under $N_2$ protection. The ice-water bath was removed after the addition and the mixture was stirred at RT overnight. The reaction mixture was washed with brine. The organic layer was separated, dried over $Na_2SO_4$ and filtered. The filtrate was concentrated under reduced pressure and the residue was purified via preparative HPLC to give (2S)-N-(6-(5-(6,6-difluoro-3-azabicyclo[3.1.0]hexan-3-yl)pyrazin-2-yl)pyridin-2-yl)-2-(3-methyl-2,6-dioxo-1-(2-oxobutyl)-2,3-dihydro-1H-purin-7(6H)-yl)propanamide (16 mg, 20.1% yield) as a white solid. Retention time (LC-MS): 1.842 min. MH$^+$580. $^1$H NMR (400 MHz, DMSO) δ 11.00 (s, 1H), 8.96 (s, 1H), 8.39 (s, 1H), 8.08 (s, 1H), 7.92 (s, 1H), 7.83-7.87 (m, 2H), 5.79-5.81 (m, 1H), 4.69 (s, 2H), 3.94 (d, J=11.2 Hz, 2H), 3.83 (d, J=9.2 Hz, 2H), 3.46 (s, 3H), 2.76 (d, J=11.2 Hz, 2H), 2.50-2.55 (m, 2H), 1.87 (d, J=7.2 Hz, 3H), 0.93 (t, J=7.2 Hz, 3H).

Compound 257 (2S)-N-(6-(5-(6,6-difluoro-3-azabicyclo[3.1.0]hexan-3-yl)pyrazin-2-yl)pyridin-2-yl)-2-(3-methyl-2,6-dioxo-1-(2-oxopropyl)-2,3-dihydro-1H-purin-7(6H)-yl)propanamide

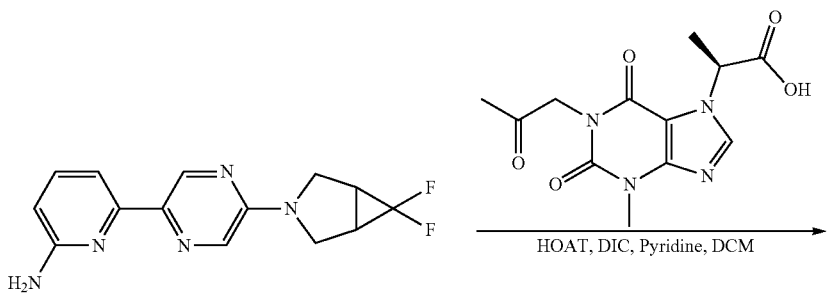

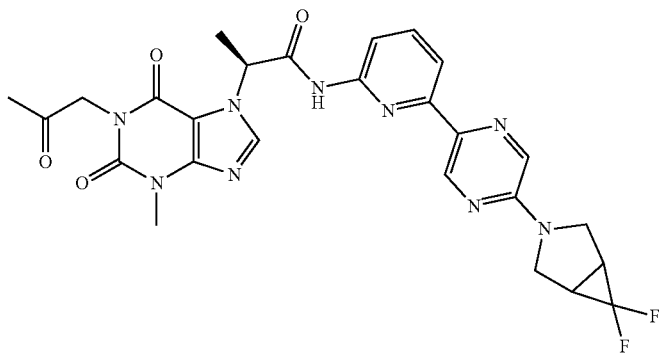

The title compound was prepared as described for Compound 256 in 15.3% yield as a white solid. Retention time (LC-MS): 1.844 min. MH$^+$566. $^1$H NMR (400 MHz, DMSO) δ 11.01 (s, 1H), 8.96 (s, 1H), 8.40 (s, 1H), 8.08 (s, 1H), 7.91 (s, 1H), 7.84-7.87 (m, 2H), 5.79-5.81 (m, 1H), 4.69 (s, 2H), 3.93 (d, J=11.2 Hz, 2H), 3.83 (d, J=9.2 Hz, 2H), 3.46 (s, 3H), 2.76 (d, J=10.8 Hz, 2H), 2.16 (s, 3H), 1.87 (d, J=7.2 Hz, 3H).

Compound 258 (2S)-N-(6'-(6,6-difluoro-3-azabicyclo[3.1.0]hexan-3-yl)-[2,3'-bipyridin]-6-yl)-2-(1-(3-methoxy-2-oxopropyl)-3-methyl-2,6-dioxo-2,3-dihydro-1H-purin-7(6H)-yl)propanamide

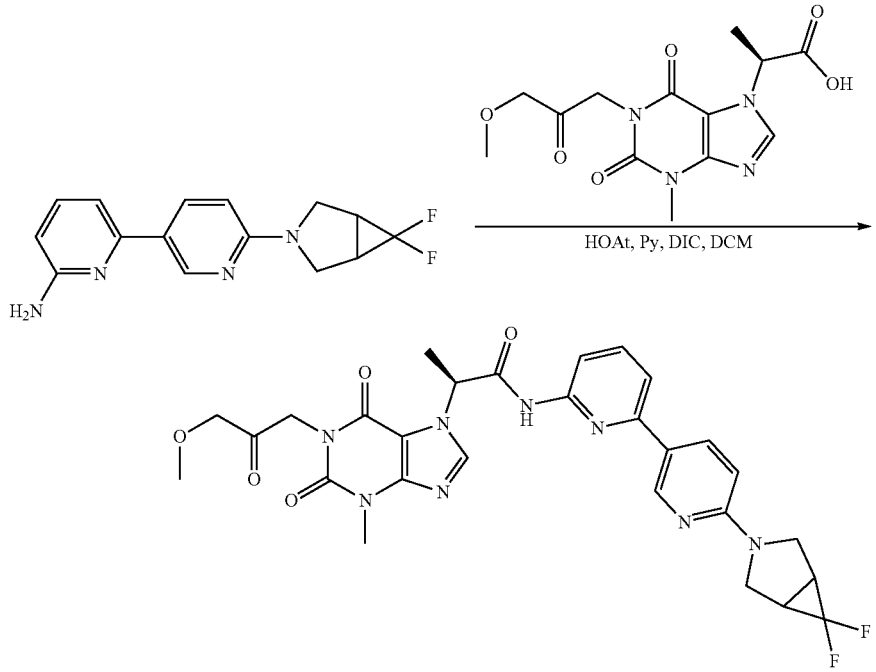

To a mixture of 6'-(6,6-difluoro-3-azabicyclo[3.1.0]hexan-3-yl)-[2,3'-bipyridin]-6-amine (45 mg, 0.156 mmol) and (S)-2-(1-(3-methoxy-2-oxopropyl)-3-methyl-2,6-dioxo-2,3-dihydro-1H-purin-7(6H)-yl)propanoic acid (55.7 mg, 0.172 mmol) in dichloromethane (4 mL) was added HOAt (21.2 mg, 0.156 mmol) at room temperature. The reaction mixture was cooled under ice-water bath to 0° C., and pyridine (0.025 mL, 0.312 mmol) was added drop-wise followed by drop-wise addition of DIC (0.036 mL, 0.234 mmol) under $N_2$ protection. The ice-water bath was removed after the addition and the mixture was stirred at room temperature overnight. The resulting mixture was poured into ice water (5 mL) and extracted with ethyl acetate. The organic layer was separated, dried over anhydrous $Na_2SO_4$ and filtered. The filtrate was concentrated under reduced pressure and the residue was purified via preparative HPLC to afford (2S)-N-(6'-(6,6-difluoro-3-azabicyclo[3.1.0]hexan-3-yl)-[2,3'-bipyridin]-6-yl)-2-(1-(3-methoxy-2-oxopropyl)-3-methyl-2,6-dioxo-2,3-dihydro-1H-purin-7(6H)-yl)propanamide (27.9 mg, 30.0% yield) as a white solid. Retention time (LC-MS): 0.994 min. MH+595. $^1$H NMR (400 MHz, DMSO-d6) δ 10.96 (s, 1H), 8.81 (d, J=2.0 Hz, 1H), 8.40 (s, 1H), 8.23-8.17 (m, 1H), 7.85-7.76 (m, 2H), 7.60 (d, J=8.4 Hz, 1H), 6.60 (d, J=9.2 Hz, 1H), 5.79-5.78 (m, 1H), 4.79-4.69 (m, 2H), 4.21 (s, 2H), 3.86 (d, J=10.8 Hz, 2H), 3.76 (d, J=9.2 Hz, 2H), 3.46-3.44 (m, 3H), 3.29 (d, J=14.8 Hz, 3H), 2.72 (d, J=10.8 Hz, 2H), 1.86 (d, J=6.8 Hz, 3H).

Compound 259 2-(3-methyl-1-((5-methylisoxazol-3-yl)methyl)-2,6-dioxo-2,3-dihydro-1H-purin-7(6H)-yl)-N-(2-(2-(trifluoromethyl)pyrimidin-5-yl)thiazol-4-yl)acetamide

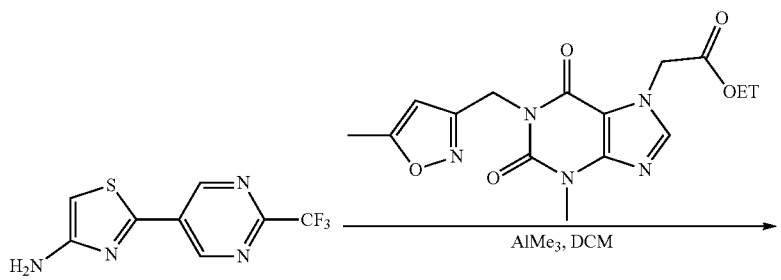

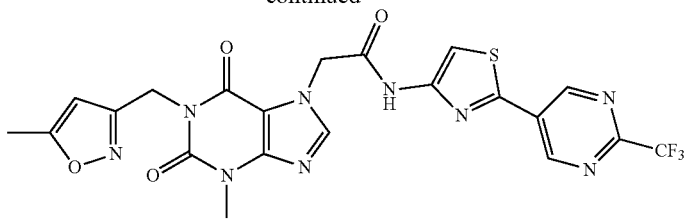

To a solution of 2-(2-(trifluoromethyl)pyrimidin-5-yl)thiazol-4-amine (40 mg, 0.16 mmol) in DCM (3 mL) was added drop-wise trimethylaluminum (0.48 mL, 0.48 mmol) at 0° C. After the addition, the mixture was warmed to RT and stirred for 0.5 h. Then a solution of (S)-methyl ethyl 2-(3-methyl-1-((5-methylisoxazol-3-yl)methyl)-2,6-dioxo-2,3-dihydro-1H-purin-7(6H)-yl)acetate (56 mg, 0.16 mmol) in DCM (1 mL) was added drop-wise and the reaction mixture was stirred at 30° C. overnight. The reaction was quenched by addition of several drops of MeOH. The mixture was concentrated under reduced pressure and the residue was purified by chromatography (DCM:MeOH=100:1 to 40:1) to afford a crude product, which was further purified via preparative HPLC to afford 2-(3-methyl-1-((5-methylisoxazol-3-yl)methyl)-2,6-dioxo-2,3-dihydro-1H-purin-7(6H)-yl)-N-(2-(2-(trifluoromethyl)pyrimidin-5-yl)thiazol-4-yl)acetamide (25 mg, 28.4% yield) as a yellow solid. Retention time (LC-MS): 1.679 min. MH$^+$548. $^1$H NMR (400 MHz, DMSO) δ 11.82 (s, 1H), 9.52 (s, 2H), 8.14 (s, 1H), 7.85 (s, 1H), 6.10 (s, 1H), 5.29 (s, 2H), 5.02 (s, 2H), 3.47 (s, 3H), 2.32 (s, 3H).

Compound 260 2-(3-methyl-1-((3-methyl-1,2,4-oxadiazol-5-yl)methyl)-2,6-dioxo-2,3-dihydro-1H-purin-7(6H)-yl)-N-(2-(2-(trifluoromethyl)pyrimidin-5-yl)thiazol-4-yl)acetamide

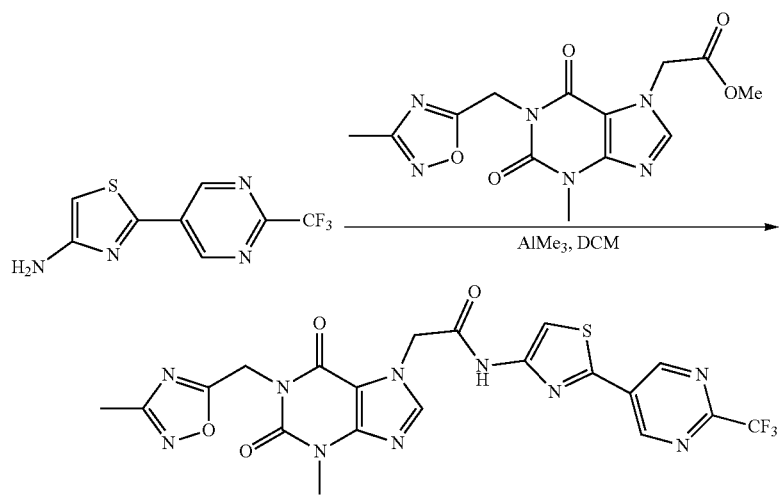

The title compound was prepared as described for Compound 259 in 20.2% yield as a yellow solid. Retention time (LC-MS): 1.528 min. MH$^+$549. $^1$H NMR (400 MHz, DMSO) δ 11.83 (s, 1H), 9.52 (s, 2H), 8.19 (s, 1H), 7.85 (s, 1H), 5.28 (d, J=8.8 Hz, 4H), 3.48 (s, 3H), 2.29 (s, 3H).

Compound 261 ((2S)-N-(2'-(3-azabicyclo[3.1.0]hexan-3-yl)-2,5'-bipyrimidin-4-yl)-2-(1-(but-2-ynyl)-3-methyl-2,6-dioxo-2,3-dihydro-1H-purin-7(6H)-yl)propanamide

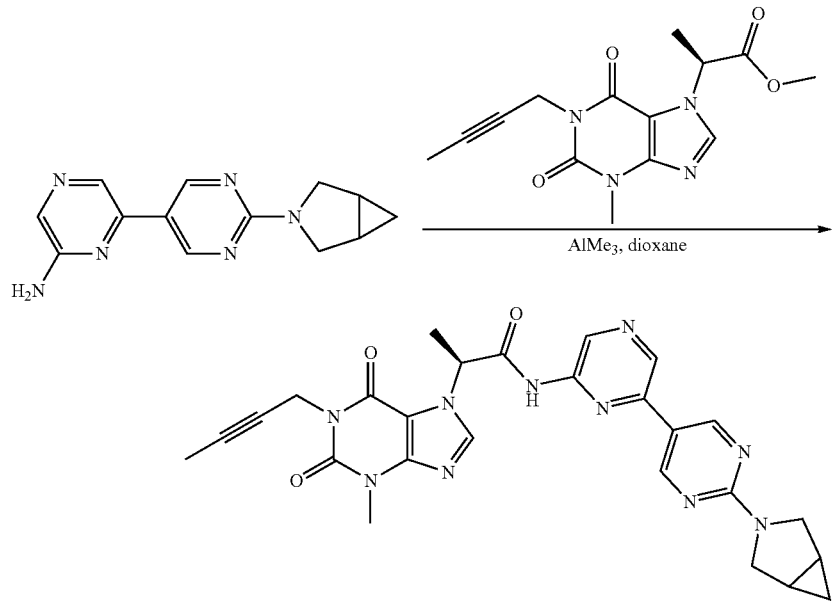

To a solution of 6-(2-(3-azabicyclo[3.1.0]hexan-3-yl)pyrimidin-5-yl)pyrazin-2-amine (42.0 mg, 0.164 mmol) in DCM (4 mL) was added drop-wise trimethylaluminum (0.66 mL, 0.657 mmol) at 0° C. After the addition, the mixture was warmed to RT and stirred for 0.5 h. Then a solution of (S)-methyl 2-(1-(but-2-ynyl)-3-methyl-2,6-dioxo-2,3-dihydro-1H-purin-7(6H)-yl)propanoate (50 mg, 0.164 mmol) in DCM (1 mL) was added drop-wise and the reaction mixture was stirred at 30° C. overnight. The reaction was quenched by addition of several drops of MeOH. The mixture was concentrated under reduced pressure and the residue was purified by chromatography (DCM:MeOH=100:1 to 40:1) to afford a crude product, which was further purified via preparative HPLC to afford (2S)-N-(6-(2-(3-azabicyclo[3.1.0]hexan-3-yl)pyrimidin-5-yl)pyrazin-2-yl)-2-(1-(but-2-ynyl)-3-methyl-2,6-dioxo-2,3-dihydro-1H-purin-7(6H)-yl)propanamide (30 mg, 34.67% yield) as a white solid. Retention time (LC-MS): 1.534 min. MH+527. $^1$H NMR (400 MHz, DMSO) δ 11.38 (s, 1H), 9.11 (s, 1H), 9.04 (s, 2H), 8.91 (s, 1H), 8.39 (s, 1H), 5.82 (m, 1H), 4.53-4.50 (m, 2H), 3.86 (d, J=11.2 Hz, 2H), 3.56 (d, J=11.2 Hz, 2H), 3.47 (s, 3H), 1.88 (d, J=7.6 Hz, 3H), 1.71-1.69 (m, 5H), 0.78-0.77 (m, 1H), 0.18-0.17 (m, 1H).

Compound 262 (2S)-2-(1-(but-2-yn-1-yl)-3-methyl-2,6-dioxo-2,3-dihydro-1H-purin-7(6H)-yl)-N-(2-(6-(6,6-difluoro-3-azabicyclo[3.1.0]hexan-3-yl)pyridin-3-yl)thiazol-4-yl)propanamide

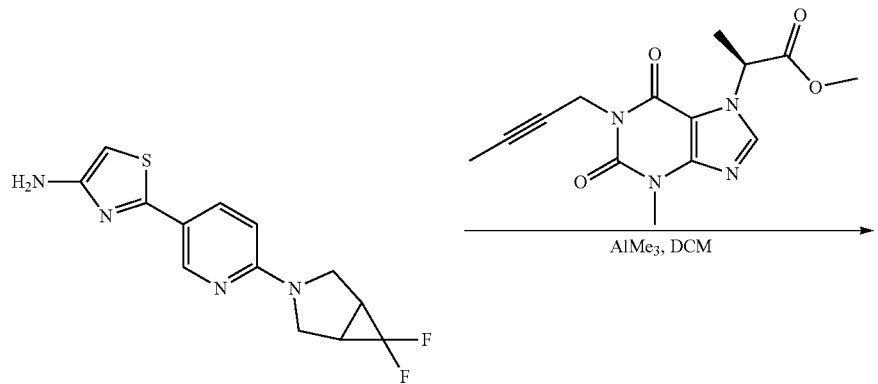

-continued

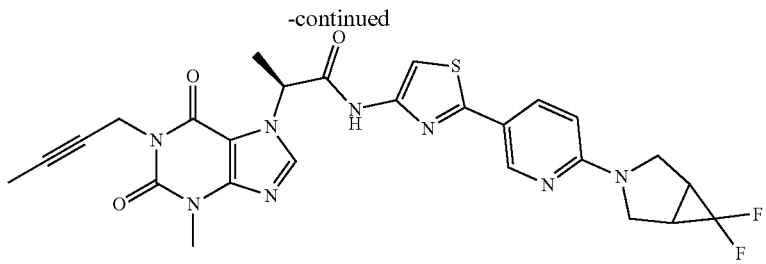

To a solution of 2-(6-(6,6-difluoro-3-azabicyclo[3.1.0]hexan-3-yl)pyridin-3-yl)thiazol-4-amine (70 mg, 0.238 mmol) in dry DCM (3 mL) was added drop-wise trimethylaluminum (0.95 mL, 0.952 mmol) at 0 oC. After the addition, the mixture was warmed to RT and stirred for 0.5 h. Then a solution of (S)-methyl 2-(1-(but-2-yn-1-yl)-3-methyl-2,6-dioxo-2,3-dihydro-1H-purin-7(6H)-yl)propanoate (5, 72 mg, 0.238 mmol) in dry DCM (0.5 mL) was added drop-wise and the reaction mixture was stirred at RT overnight. The reaction was quenched by addition of several drops of MeOH. The mixture was concentrated under reduced pressure and the residue was purified by chromatography (DCM:MeOH=80:1) to afford a crude product, which was further purified via preparative HPLC to afford (2S)-2-(1-(but-2-yn-1-yl)-3-methyl-2,6-dioxo-2,3-dihydro-1H-purin-7(6H)-yl)-N-(2-(6-(6,6-difluoro-3-azabicyclo[3.1.0]hexan-3-yl)pyridin-3-yl)thiazol-4-yl)propanamide (5.6 mg, 3.73% yield) as a white solid. Retention time (LC-MS): 1.333 min. MH+567. 1H NMR (400 MHz, DMSO-d6) δ 11.59 (s, 1H), 8.65 (s, 1H), 8.37 (s, 1H), 7.99-7.96 (m, 1H), 7.43 (s, 1H), 6.61 (d, J=8.8 Hz, 1H), 5.77-5.73 (m, 1H), 4.52 (d, J=2.4 Hz, 2H), 3.86 (d, J=11.2 Hz, 2H), 3.77 (d, J=10.0 Hz, 2H), 3.46 (s, 3H), 2.73 (d, J=10.8 Hz, 2H), 1.84 (d, J=7.6 Hz, 3H), 1.70 (s, 3H).

Compound 263 (2S)-N-(2-(6-(3-azabicyclo[3.1.0]hexan-3-yl)pyridin-3-yl)thiazol-4-yl)-2-(1-(but-2-yn-1-yl)-3-methyl-2,6-dioxo-2,3-dihydro-1H-purin-7(6H)-yl)propanamide To a solution of 2-(6-(3-azabicyclo[3.1.0]hexan-3-yl)pyridin-3-yl)thiazol-4-amine (70 mg, 0.238 mmol) in dry DCM (3 mL) was added drop-wise trimethylaluminum (1.1 mL, 1.084 mmol) at 0° C. After the addition, the mixture was warmed to RT and stirred for 0.5 h. Then a solution of (S)-methyl 2-(1-(but-2-yn-1-yl)-3-methyl-2,6-dioxo-2,3-dihydro-1H-purin-7(6H)-yl)propanoate (82 mg, 0.271 mmol) in dry DCM (0.5 mL) was added drop-wise and the reaction mixture was stirred at RT overnight. The reaction was quenched by addition of several drops of MeOH. The mixture was concentrated under reduced pressure and the residue was purified by chromatography (DCM:MeOH=80:1) to afford a crude product, which was further purified via preparative HPLC to afford (2S)-N-(2-(6-(3-azabicyclo[3.1.0]hexan-3-yl)pyridin-3-yl)thiazol-4-yl)-2-(1-(but-2-yn-1-yl)-3-methyl-2,6-dioxo-2,3-dihydro-1H-purin-7(6H)-yl)propanamide (3.3 mg, 2% yield) as a pale yellow solid. Retention time (LC-MS): 1.273 min. MH+531. $^1$H NMR (400 MHz, DMSO-d6) δ 11.58 (s, 1H), 8.62 (s, 1H), 8.36 (s, 1H), 7.94-7.91 (m, 1H), 7.40 (s, 1H), 6.56 (d, J=8.8 Hz, 1H), 5.75-5.73 (m, 1H), 4.53-4.51 (m, 2H), 3.70 (d, J=10.8 Hz, 2H), 3.45 (d, J=10.0 Hz, 5H), 1.84 (d, J=7.2 Hz, 3H), 1.72-1.70 (m, 5H), 0.78-0.76 (m, 1H), 0.20-0.17 (m, 1H).

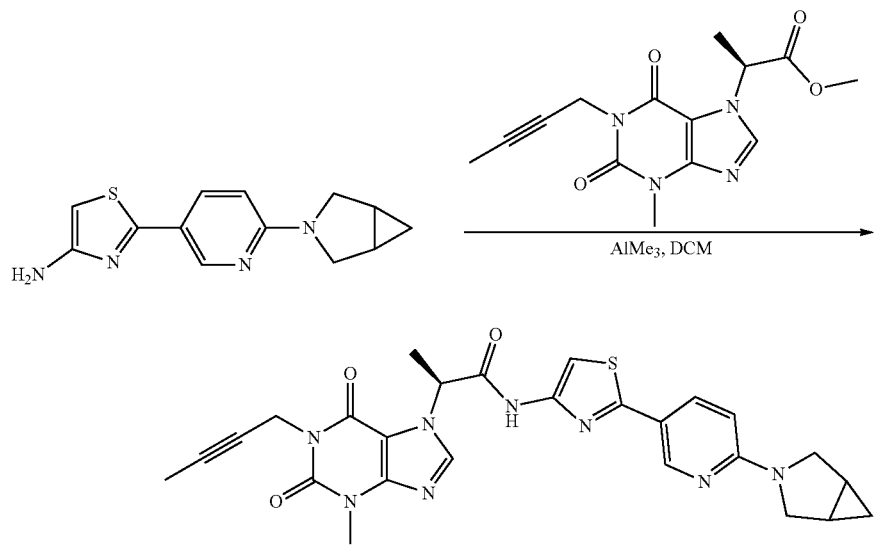

Compound 264 (2S)-N-(2-(5-(3-azabicyclo[3.1.0]hexan-3-yl)pyrazin-2-yl)thiazol-4-yl)-2-(1-(3-methoxy-2-oxopropyl)-3-methyl-2,6-dioxo-2,3-dihydro-1H-purin-7(6H)-yl)propanamide

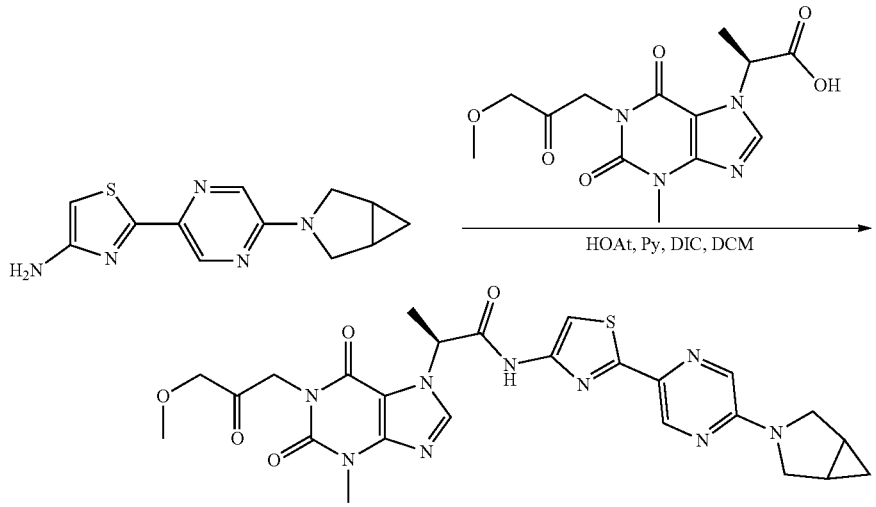

To a mixture of 2-(5-(3-azabicyclo[3.1.0]hexan-3-yl)pyrazin-2-yl)thiazol-4-amine (40 mg, 0.155 mmol) and (S)-2-(1-(3-methoxy-2-oxopropyl)-3-methyl-2,6-dioxo-2,3-dihydro-1H-purin-7(6H)-yl)propanoic acid (2, 56 mg, 0.171 mmol) in DCM (3 mL) was added HOAt (21 mg, 0.155 mmol) at RT. The reaction mixture was cooled under ice-water bath to 0° C., and pyridine (0.025 mL, 0.310 mmol) was added drop-wise followed by drop-wise addition of DIC (0.036 mL, 0.233 mmol) under $N_2$ protection. The ice-water bath was removed after the addition and the mixture was stirred at RT overnight. The reaction mixture was poured into ice water (5 mL) and extracted with DCM. The organic layer was separated, dried over $Na_2SO_4$ and filtered. The filtrate was concentrated under reduced pressure and the residue was purified via preparative HPLC to afford (2S)-N-(2-(5-(3-azabicyclo[3.1.0]hexan-3-yl)pyrazin-2-yl)thiazol-4-yl)-2-(1-(3-methoxy-2-oxopropyl)-3-methyl-2,6-dioxo-2,3-dihydro-1H-purin-7(6H)-yl)propanamide (6.5 mg, 7.4% yield) as a yellow solid. Retention time (LC-MS): 1.485 min. MH+566. $^1$H NMR (400 MHz, DMSO-d6) δ 11.58 (s, 1H), 8.66 (s, 1H), 8.39 (s, 1H), 8.01 (s, 1H), 7.47 (s, 1H), 5.76-5.70 (m, 1H), 4.74 (s, 2H), 4.21 (s, 2H), 3.77 (d, J=10.8 Hz, 2H), 3.53 (d, J=10.4 Hz, 2H), 3.50-3.48 (m, 3H), 3.31 (s, 3H), 1.84 (d, J=7.6 Hz, 3H), 1.75 (d, J=4.4 Hz, 2H), 0.85-0.78 (m, 1H), 0.20 (d, J=4.0 Hz, 1H)

Compound 265 (2S)-N-(2-(2-(6,6-difluoro-3-azabicyclo[3.1.0]hexan-3-yl)pyrimidin-5-yl)thiazol-4-yl)-2-(1-(3-methoxy-2-oxopropyl)-3-methyl-2,6-dioxo-2,3-dihydro-1H-purin-7(6H)-yl)propanamide

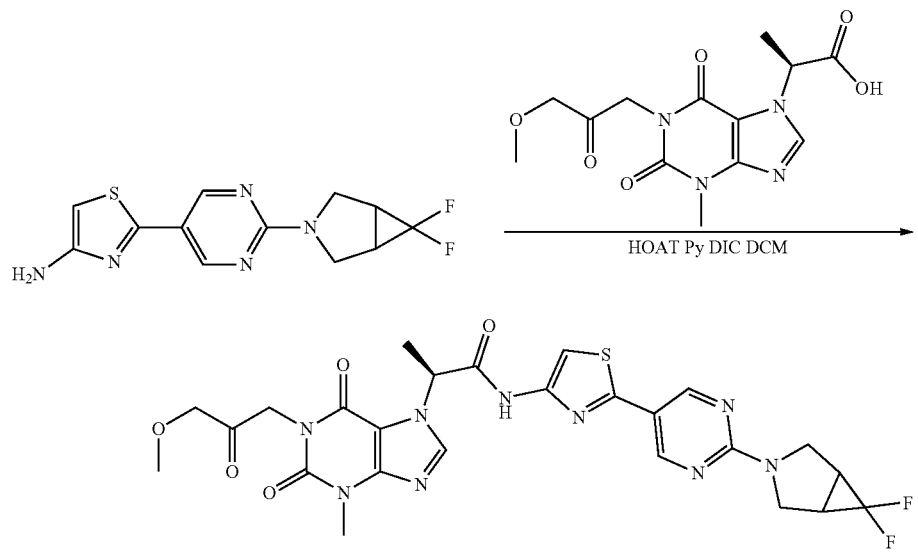

To a mixture of 2-(2-(6,6-difluoro-3-azabicyclo[3.1.0]hexan-3-yl)pyrimidin-5-yl)thiazol-4-amine (50 mg, 0.169 mmol) and (S)-2-(1-(3-methoxy-2-oxopropyl)-3-methyl-2,6-dioxo-2,3-dihydro-1H-purin-7(6H)-yl)propanoic acid (2, 60.3 mg, 0.186 mmol) in DCM (3 mL) was added HOAt (23 mg, 0.169 mmol) at RT. The reaction mixture was cooled under ice-water bath to 0° C., and pyridine (0.027 mL, 0.338 mmol) was added drop-wise followed by drop-wise addition of DIC (0.039 mL, 0.254 mmol) under $N_2$ protection. The ice-water bath was removed after the addition and the mixture was stirred at RT overnight. The reaction mixture was poured into ice water (5 mL) and extracted with DCM. The organic layer was separated, dried over $Na_2SO_4$ and filtered. The filtrate was concentrated under reduced pressure and the residue was purified via preparative HPLC to afford (2S)-N-(2-(2-(6,6-difluoro-3-azabicyclo[3.1.0]hexan-3-yl)pyrimidin-5-yl)thiazol-4-yl)-2-(1-(3-methoxy-2-oxopropyl)-3-methyl-2,6-dioxo-2,3-dihydro-1H-purin-7(6H)-yl)propanamide (28.7 mg, 28.2% yield) as a white solid. Retention time (LC-MS): 1.979 min. MH$^+$602. $^1$H NMR (400 MHz, DMSO-d6) δ 11.62 (s, 1H), 8.85 (s, 2H), 8.39 (s, 1H), 7.49 (s, 1H), 5.71-5.69 (m, 1H), 4.74 (s, 2H), 4.22 (s, 2H), 3.98 (d, J=12.0 Hz, 2H), 3.85 (d, J=10.4 Hz, 2H), 3.51 (s, 3H), 3.33 (d, J=13.2, 3H), 2.71 (d, J=10.8, 2H), 1.84 (d, J=7.2, 3H).

Compound 266 (2S)-N-(6-(5-(3-azabicyclo[3.1.0]hexan-3-yl)pyrazin-2-yl)pyridin-2-yl)-2-(1-(3-methoxy-2-oxopropyl)-3-methyl-2,6-dioxo-2,3-dihydro-1H-purin-7(6H)-yl)propanamide To a solution of S)-2-(1-(3-methoxy-2-oxopropyl)-3-methyl-2,6-dioxo-2,3-dihydro-1H-purin-7(6H)-yl)propanoic acid(61 mg,0.2 mmol) and 6-(5-(3-azabicyclo[3.1.0]hexan-3-yl)pyrazin-2-yl)pyridin-2-amine(50 mg, 0.20 mmol) in DCM (4 mL) was added HOAt (30 mg, 0.22 mmol) at RT. The reaction mixture was cooled under ice-water bath to 0° C., and pyridine (0.03 mL, 0.40 mmol) was added drop-wise followed by drop-wise addition of DIC (0.04 mL, 0.30 mmol) under $N_2$ protection. The ice-water bath was removed after the addition and the mixture was stirred at 30 ° C. overnight. The reaction mixture was washed with water (5 mL) and saturated aq.NH$_4$Cl (5 mL), dried over $Na_2SO_4$ and filtered. The filtrate was concentrated under reduced pressure and the residue was purified via preparative HPLC to afford (2S)-N-(6-(5-(3-azabicyclo[3.1.0]hexan-3-yl)pyrazin-2-yl)pyridin-2-yl)-2-(1-(3-methoxy-2-oxopropyl)-3-methyl-2,6-dioxo-2,3-dihydro-1H-purin-7(6H)-yl)propanamide (18.3 mg,15.2% yield) as a white solid. Retention time (LC-MS): Retention 1.539 min. MH$^+$560. $^1$H NMR δ 10.99 (s, 1H), 8.93 (d, J=0.8 Hz, 1H),8.40 (s, 1H), 8.03 (s, J=0.8 Hz, 1H), 7.83 (m, 3H), 5.80 (d, J=6.0 Hz, 1H), 4.75(s, J=3.2 Hz, 2H), 4.21 (s, 2H), 3.78 (d, J=10.4 Hz, 2H), 3.52 (s, 2H), 3.46 (s, 3H), 3.32 (s, 3H), 1.87 (d, J=7.2 Hz, 3H), 1.74 (t, J=3.6 Hz, 2H), 0.77 (m, 1H),0.20 (m, 1H).

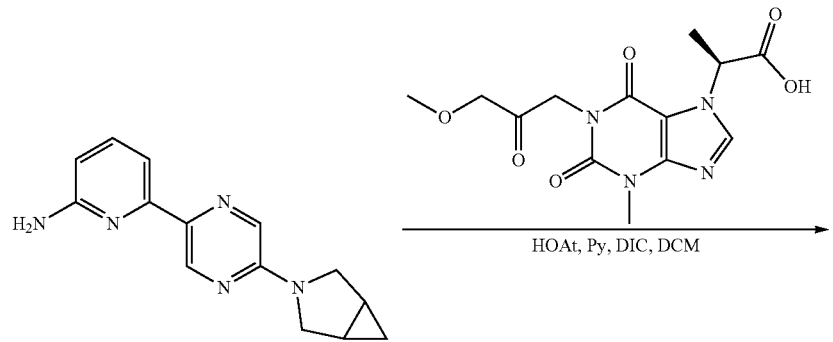

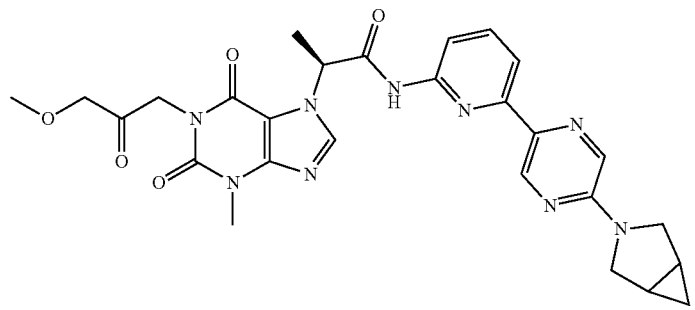

Compound 267 (2S)-2-(1-(but-2-ynyl)-3-methyl-2,6-dioxo-2,3-dihydro-1H-purin-7(6H)-yl)-N-(2-(2-(6,6-difluoro-3-azabicyclo[3.1.0]hexan-3-yl)pyrimidin-5-yl)thiazol-4-yl)propanamide

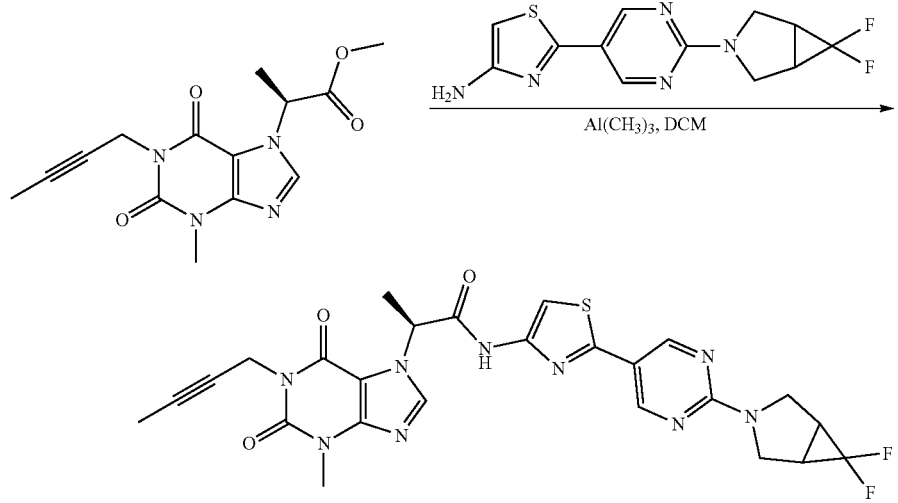

To a solution of 2-(2-(6,6-difluoro-3-azabicyclo[3.1.0]hexan-3-yl)pyrimidin-5-yl)thiazol-4-amine (50 mg, 0.17 mmol) in DCM (8 mL) was added drop-wise trimethylaluminum (0.68 mL, 0.68 mmol) at 0° C. After the addition, the mixture was warmed to RT and stirred for 0.5 h. Then a solution of (S)-methyl 2-(1-(but-2-ynyl)-3-methyl-2,6-dioxo-2,3-dihydro-1H-purin-7(6H)-yl)propanoate (51.52 mg, 0.17 mmol) in DCM (2 mL) was added drop-wise and the reaction mixture was stirred at RT overnight. The reaction was quenched by addition of several drops of MeOH. The mixture was concentrated under reduced pressure and the residue was purified via Pre.HPLC to give (2S)-2-(1-(but-2-ynyl)-3-methyl-2,6-dioxo-2,3-dihydro-1H-purin-7(6H)-yl)-N-(2-(2-(6,6-difluoro-3-azabicyclo[3.1.0]hexan-3-yl)pyrimidin-5-yl)thiazol-4-yl)propanamide (5 mg, 5.2% yield) as a yellow solid. Retention time (LC-MS): 2.285min.

MH$^+$568. $^1$H NMR (400 MHz, DMSO) δ 11.66 (s, 1H), 8.86 (s, 2H), 8.37 (s, 1H), 7.50 (s, 1H), 5.74 (q, J=6.8 Hz, 1H), 4.53-4.52 (m, 2H), 4.00-3.97 (m, 2H), 3.87-3.84 (d, J=11.6 Hz, 2H), 3.46 (s, 3H), 2.73-2.71 (m, J=10.8 Hz, 2H), 1.85-1.83 (d, J=7.6 Hz, 3H), 1.71 (s, 3H).

Compound 268 (S)-2-(1-(but-2-ynyl)-3-methyl-2,6-dioxo-2,3-dihydro-1H-purin-7(6H)-yl)-N-(2-(24(S)-2-(trifluoromethyl)pyrrolidin-1-yl)pyrimidin-5-yl)thiazol-4-yl)propanamide

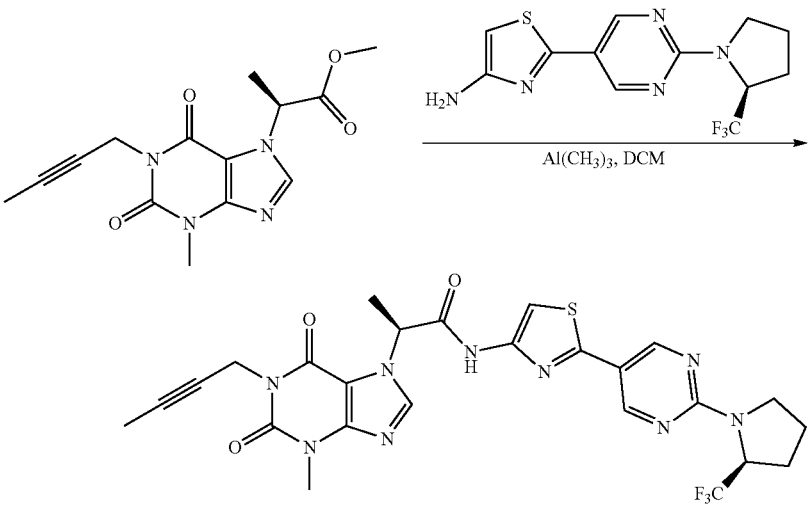

To a solution of (S)-2-(2-(2-(trifluoromethyl)pyrrolidin-1-yl)pyrimidin-5-yl)thiazol-4-amine (50 mg, 0.16 mmol) in DCM (8 mL) was added drop-wise trimethylaluminum (0.63 mL, 0.63 mmol) at 0° C. After the addition, the mixture was warmed to RT and stirred for 0.5 h. Then a solution of (S)-methyl 2-(1-(but-2-ynyl)-3-methyl-2,6-dioxo-2,3-dihydro-1H-purin-7(6H)-yl)propanoate (48.25 mg, 0.16 mmol) in DCM (2 mL) was added drop-wise and the reaction mixture was stirred at RT overnight. The reaction was quenched by addition of several drops of MeOH. The mixture was concentrated under reduced pressure and the residue was purified via Prep HPLC to give (S)-2-(1-(but-2-ynyl)-3-methyl-2,6-dioxo-2,3-dihydro-1H-purin-7(6H)-yl)-N-(2-(2-((S)-2-(trifluoromethyl)pyrrolidin-1-yl)pyrimidin-5-yl)thiazol-4-yl)propanamide (10 mg, 10.7% yield) as a yellow solid. Retention time (LC-MS): 2.034min. MH$^+$588. $^1$H NMR (400 MHz, DMSO) δ 11.67 (s, 1H), 8.95 (s, 1H), 8.37 (s, 1H), 7.55 (s, 1H), 5.75 (s, 1H), 5.12-5.08 (m, 1H), 4.51 (m, 2H), 3.71 (m, 2H), 3.47 (s, 3H), 2.25-2.04 (m, 4H), 1.85 (d, J=7.2 Hz, 3H), 1.71 (s, 3H).

Compound 269 (2S)-N-(2-(6-(6,6-difluoro-3-azabicyclo[3.1.0]hexan-3- yl)pyridin-3-yl)thiazol-4-yl)-2-(1-(3-methoxy-2-oxopropyl)-3-methyl-2,6-dioxo-2, 3-dihydro- 1H-purin-7(6H)-yl)propanamide

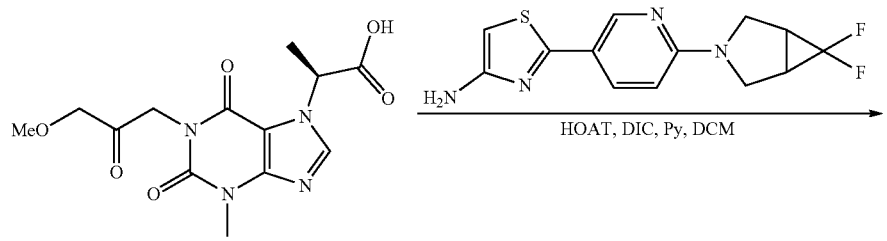

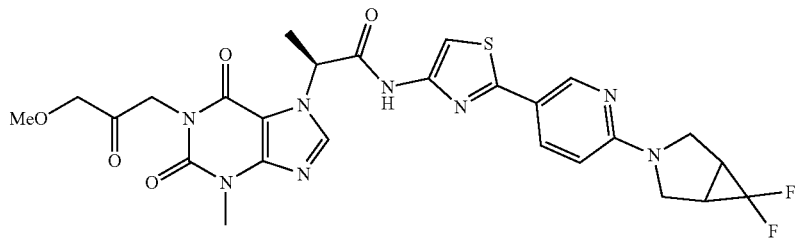

To a solution of 2-(6-(6,6-difluoro-3-azabicyclo[3.1.0] hexan-3-yl)pyridin-3-yl)thiazol-4-amine (25 mg, 0.085 mmol) and (S)-2-(1-(3-methoxy-2-oxopropyl)-3-methyl-2, 6-dioxo-2,3-dihydro-1H-purin-7(6H)-yl)propanoic acid (30.31 mg, 0.094 mmol) in DCM (10 mL) was added HOAT (13.89 mg, 0.10 mmol) at RT. The reaction mixture was cooled under ice-water bath to 0° C., followed by slow dropwise addition of pyridine (0.01 mL, 0.17 mmol) and DIC (0.02 mL, 0.13 mmol) under N$_2$ protection. The ice-water bath was removed after the addition and the mixture was stirred at RT. overnight. The reaction mixture was washed with water (10 mL), and. aq. HCl (10 mL, 0.5M). The organic layer was separated, dried over Na$_2$SO$_4$ and filtered. The filtrate was concentrated under reduced pressure and the residue was purified via Prep-HPLC to give (2S)-N-(2-(6-(6,6-difluoro-3-azabicyclo[3.1.0]hexan-3-yl) pyridin-3-yl)thiazol-4-yl)-2-(1-(3-methoxy-2-oxopropyl)-3-methyl-2,6-dioxo-2,3-dihydro-1H-purin-7(6H)-yl)propanamide (20 mg, 39.1% yield) as a yellow solid. Retention time (LC-MS): 2.050min. MH$^+$601. $^1$H NMR (400 MHz, DMSO) δ 11.55 (s, 1H), 8.64 (d, J=2.4 Hz, 1H), 8.39 (s, 1H), 7.97 (m, 1H), 7.42 (s, 1H), 6.60 (d, J=9.2 Hz, 1H), 5.71 (m, 1H), 4.74 (m, 2H), 4.21 (s, 2H), 3.85 (d, J=10.8 Hz, 2H), 3.76 (d, J=9.2 Hz, 2H), 3.46 (s, 3H), 3.31 (s, 3H), 2.72 (m, 2H), 1.84 (d, J=7.2 Hz, 3H).

Compound 270 (2S)-N-(2-(5-(3-azabicyclo[3.1.0]hexan-3-yl)pyrazin-2-yl)thiazol-4-yl)-2-(3-methyl-2,6-dioxo-1-(2-oxobutyl)-2,3-dihydro-1H-purin-7(6H)-yl)propanamide

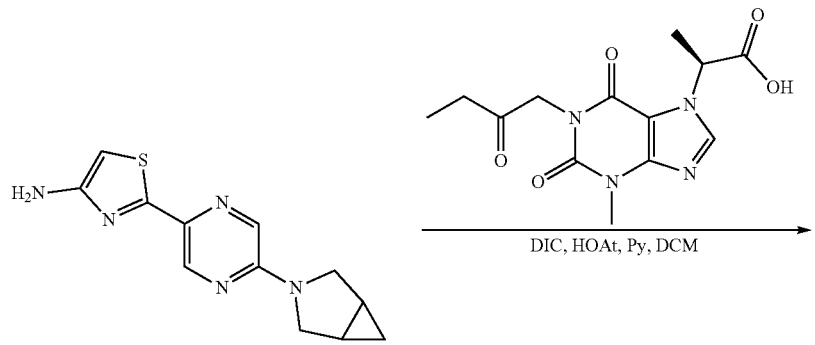

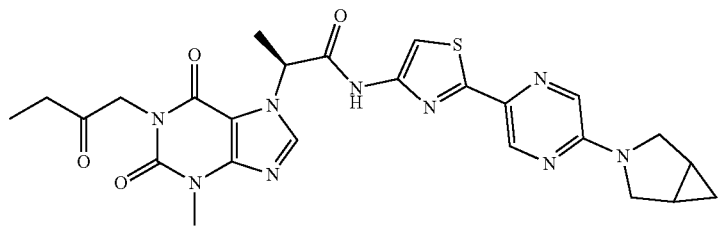

To a solution of 2-(5-(3-azabicyclo[3.1.0]hexan-3-yl)pyrazin-2-yl)thiazol-4-amine (40 mg, 0.15 mmol) and (S)-2-(3-methyl-2,6-dioxo-1-(2-oxobutyl)-2,3-dihydro-1H-purin-7(6H)-yl)propanoic acid (47.5 mg, 0.15 mmol) in dichloromethane (4 mL) was added HOAt (20.9 mg, 0.15 mmol) at room temperature. The reaction mixture was cooled under ice-water bath to 0° C., and pyridine (24.3 mg, 0.32 mmol) was added drop-wise followed by drop-wise addition of DIC (29.0 mg, 0.23 mmol) under N₂ protection. The ice-water bath was removed after the addition and the mixture was stirred at 30° C. overnight. The resulting mixture was washed with water (3 mL) and saturated aq.NH₄Cl (3 mL). The organic layer was separated, dried over anhydrous Na₂SO₄ and filtered. The filtrate was concentrated under reduced pressure and the residue was purified via preparative HPLC to afford (2S)-N-(2-(5-(3-azabicyclo[3.1.0]hexan-3-yl)pyrazin-2-yl)thiazol-4-yl)-2-(3-methyl-2,6-dioxo-1-(2-oxobutyl)-2,3-dihydro-1H-purin-7(6H)-yl)propanamide (25.1 mg, 29.5% yield) as yellow solid. Retention time (LC-MS): 1.637 min. MH⁺550. ¹H NMR (400 MHz, DMSO) δ 11.57 (s, 1H), 8.66 (s, 1H), 8.38 (s, 1H), 8.01 (s, 1H), 7.47 (s, 1H), 5.69-5.71 (m, 1H), 4.69 (s, 2H), 3.76 (d, J=10.8 Hz, 2H),3.53 (d, J=10.4 Hz, 2H), 3.45 (s, 3H), 2.52-2.56 (m, 2H), 1.84 (d, J=7.2 Hz, 3H), 1.71-1.76 (m, 2H), 0.94 (t, J=7.2 Hz, 3H), 0.77-0.80 (m, 1H), 0.18-0.21 (m, 1H).

Compound 271 (2S)-N-(6-(6-(3-azabicyclo[3.1.0]hexan-3-yl)pyridin-3-yl)pyrazin-2-yl)-2-(1-(3-methoxy-2-oxopropyl)-3-methyl-2,6-dioxo-2,3-dihydro-1H-purin-7(6H)-yl)propanamide

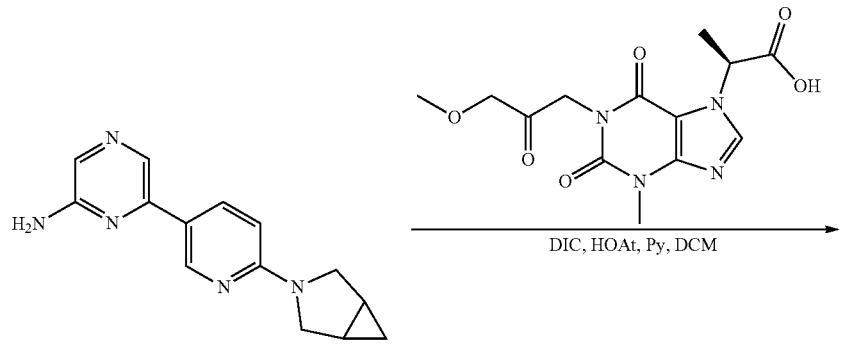

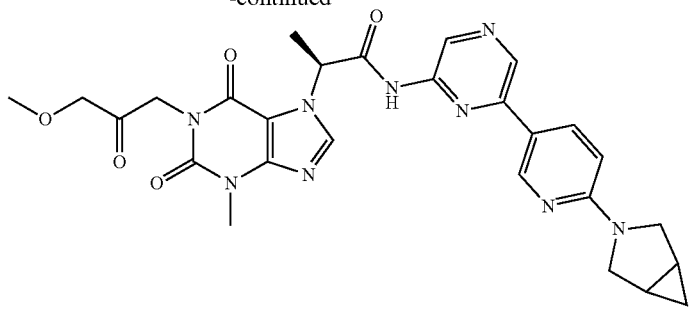

To a solution of 6-(6-(3-azabicyclo[3.1.0]hexan-3-yl)pyridin-3-yl)pyrazin-2-amine (50 mg, 0.197 mmol) and (S)-2-(1-(3-methoxy-2-oxopropyl)-3-methyl-2,6-dioxo-2,3-dihydro-1H-purin-7(6H)-yl)propanoic acid (64 mg, 0.197 mmol) in dichloromethane (4 mL) was added HOAt (26.8 mg, 0.197 mmol) at room temperature. The reaction mixture was cooled under ice-water bath to 0° C., and pyridine (31 mg, 0.394 mmol) was added drop-wise followed by drop-wise addition of DIC (37 mg, 0.296 mmol) under $N_2$ protection. The ice-water bath was removed after the addition and the mixture was stirred at 30° C. overnight. The resulting mixture was washed with water (3 mL) and saturated aq.$NH_4Cl$ (3 mL). The organic layer was separated, dried over anhydrous $Na_2SO_4$ and filtered. The filtrate was concentrated under reduced pressure and the residue was purified via preparative HPLC to afford (2S)-N-(6-(6-(3-azabicyclo[3.1.0]hexan-3-yl)pyridin-3-yl)pyrazin-2-yl)-2-(1-(3-methoxy-2-oxopropyl)-3-methyl-2,6-dioxo-2,3-dihydro-1H-purin-7(6H)-yl)propanamide (27.8 mg, 25.2% yield) as light yellow solid. Retention time (LC-MS): 0.735 min. MH$^+$560. $^1$E1 NMR (400 MHz, DMSO) δ 11.31 (s, 1H), 9.04 (s, 1H), 8.88 (s, 1H), 8.84-8.85 (d, J=2.4 Hz, 1H), 8.41 (s, 1H), 8.17-8.20 (dd, J=8.8 Hz, 2.4 Hz, 1H), 6.59-6.61 (d, J=8.8 Hz, 1H), 5.78-5.80 (m, 1H), 4.73-4.74 (d, J=2 Hz, 2H), 4.20 (s, 2H), 3.71-3.73 (d, J=10.4 Hz, 2H), 3.46 (s, 3H), 3.44-3.46 (d, J=10.4 Hz, 2H), 3.30 (s, 3H), 1.87-1.89 (d, J=7.2 Hz, 2H), 1.70-1.72 (m, 2H), 0.74-0.79 (m, 2H), 0.17-0.20 (m, 1H).

Compound 272 (2S)-N-(6-(5-(6,6-difluoro-3-azabicyclo[3.1.0]hexan-3-yl)pyrazin-2-yl)pyridin-2-yl)-2-(3-methyl-2,6-dioxo-1-(2-oxopropyl)-2,3-dihydro-1H-purin-7(6H)-yl)propanamide

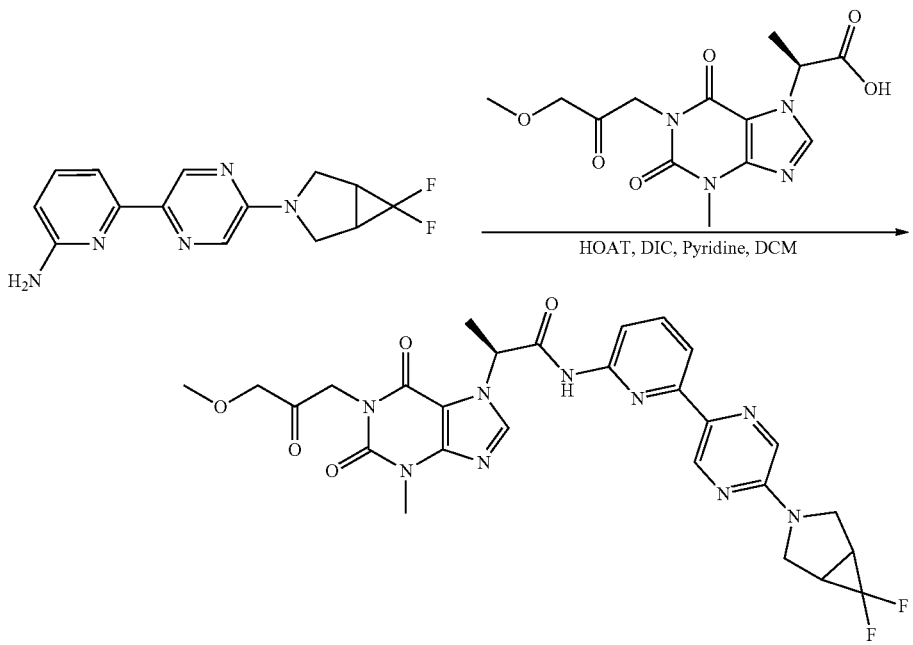

The title compound was prepared as Compound 256, 30.4% yield as a white solid. Retention time (LC-MS): 1.555 min. MH$^+$596. $^1$H NMR (400 MHz, DMSO) δ 11.02 (s, 1H), 8.96 (s, 1H), 8.41 (s, 1H), 8.08 (s, 1H), 7.92 (s, 1H), 7.83-7.87 (m, 2H), 5.79-5.81 (m, 1H), 4.74 (s, 2H), 4.21 (s, 2H), 3.93 (d, J=10.8 Hz, 2H), 3.83 (d, J=9.2 Hz, 2H), 3.46 (s, 3H), 3.31 (s, 3H), 2.76 (d, J=10.4 Hz, 2H), 1.87 (d, J=7.2 Hz, 3H).

Equivalents

While this invention has been disclosed with reference to specific aspects, it is apparent that other aspects and variations of this invention may be devised by others skilled in the art without departing from the true spirit and scope of the invention. The appended claims are intended to be construed to include all such aspects and equivalent variations.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference.

While this invention has been particularly shown and described with references to preferred embodiments thereof, it will be understood by those skilled in the art that various changes in form and details may be made therein without departing from the scope of the invention encompassed by the appended claims.

The invention claimed is:
1. A compound of Formula (I):

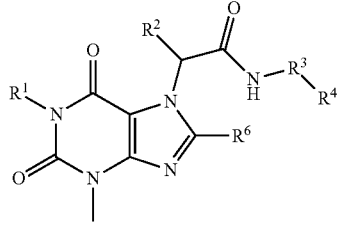

or a pharmaceutically acceptable salt thereof, wherein:
$R^1$ is

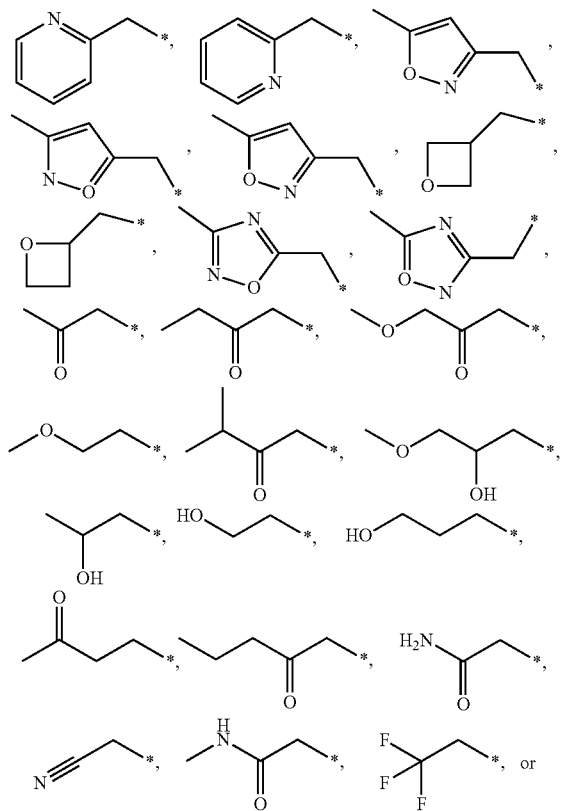

-continued

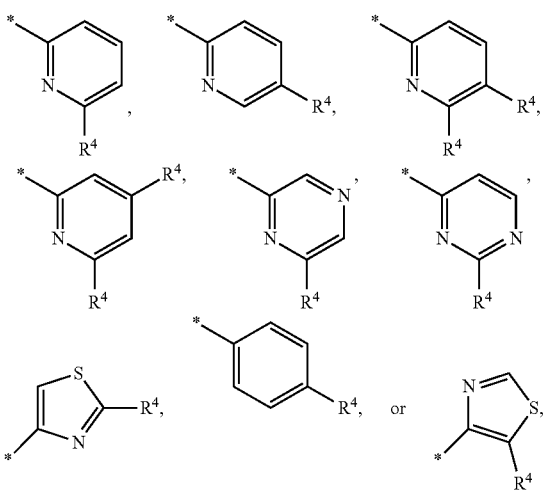

$R^2$ is is methyl;
$R^3$ is

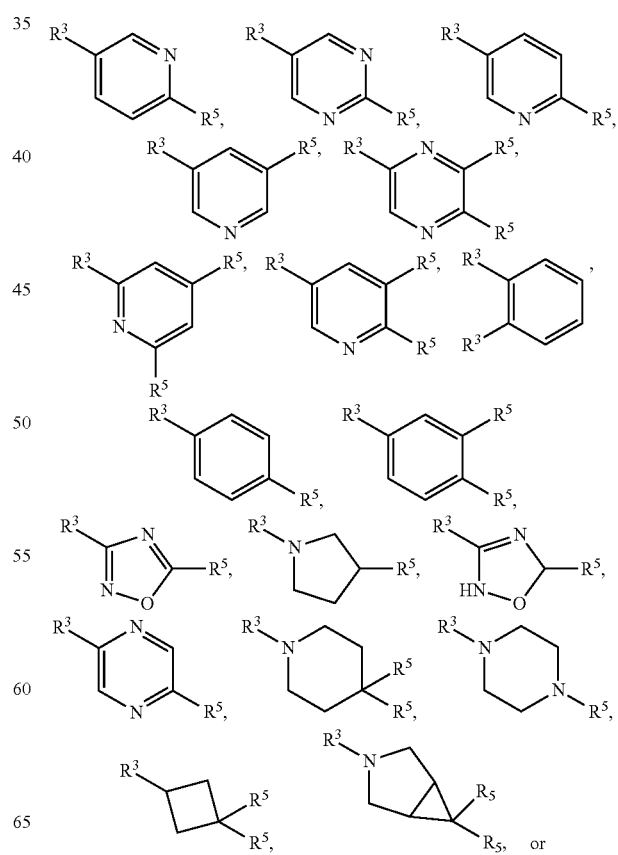

$R^4$ is independently H, methyl, ethyl, propyl, cyano, methoxy, chlorine, fluorine, bromine, —$CF_3$, —$CF_2$, -continued

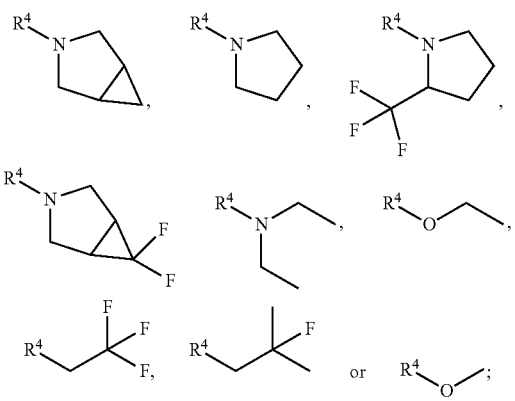

$R^5$ is independently H, —$CF_3$, cyanomethyl, bromine, chlorine, fluorine, methyl, ethyl, isopropyl, cyano, keto, $R^6$ is H; and
$R^8$ is H, methyl, ethyl, or $CF_3$.

2. The compound of claim 1, wherein $R^1$ is

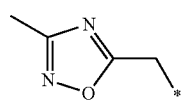

3. The compound of claim 1 wherein $R^1$ is

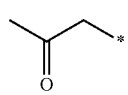 [SMILES: *CC(C)=O]

4. The compound of claim 2 wherein $R^3$ is

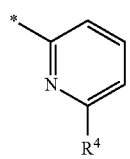

5. The compound of claim 2 wherein $R^3$ is

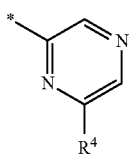

6. A compound of the formula:

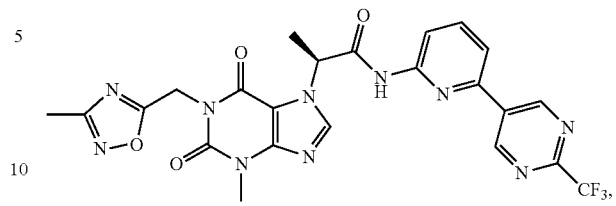

or a pharmaceutically acceptable salt thereof.

7. The compound according to claim 6 which is:

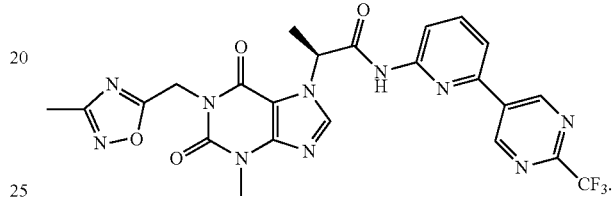

8. A compound of the formula:

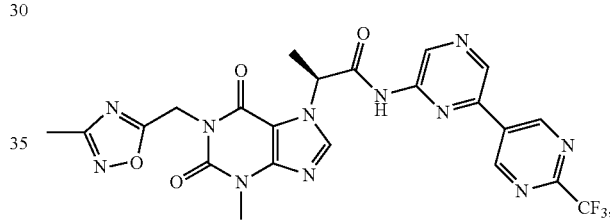

or a pharmaceutically acceptable salt thereof.

9. The compound according to claim 8 which is:

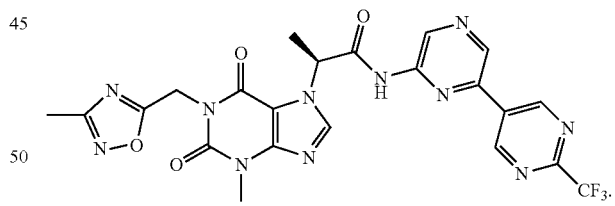

10. A compound of the formula:

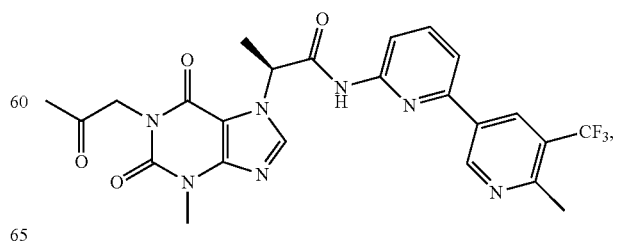

or a pharmaceutically acceptable salt thereof.

11. The compound according to claim 10 which is:

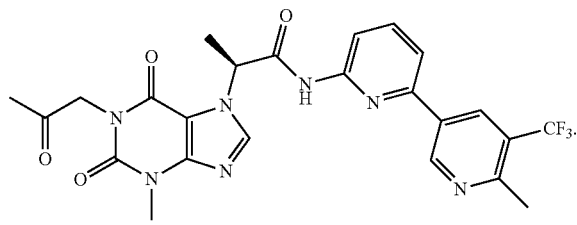 [SMILES: CC(=O)Cn1c(=O)c2c(ncn2[C@@H](C)C(=O)Nc2cccc(-c3cnc(C)c(C(F)(F)F)c3)n2)n(C)c1=O]

12. A pharmaceutical composition comprising a compound according to claim 6 or a pharmaceutically acceptable salt thereof in a mixture with a pharmaceutically acceptable excipient, diluent, or carrier.

13. A pharmaceutical composition comprising a compound according to claim 8 or a pharmaceutically acceptable salt thereof in a mixture with a pharmaceutically acceptable excipient, diluent, or carrier.

14. A pharmaceutical composition comprising a compound according to claim 10 or a pharmaceutically acceptable salt thereof in a mixture with a pharmaceutically acceptable excipient, diluent, or carrier.

15. A method of treating chronic pain in a subject comprising administering an effective amount of a compound according to claim 6, or a pharmaceutically acceptable salt thereof.

16. A method of treating chronic pain in a subject comprising administering an effective amount of a compound according to claim 8, or a pharmaceutically acceptable salt thereof.

17. A method of treating chronic pain in a subject comprising administering an effective amount of a compound according to claim 10, or a pharmaceutically acceptable salt thereof.

18. A method of treating neuropathic pain in a subject comprising administering an effective amount of a compound according to claim 6, or a pharmaceutically acceptable salt thereof.

19. A method of treating neuropathic pain in a subject comprising administering an effective amount of a compound according to claim 8, or a pharmaceutically acceptable salt thereof.

20. A method of treating neuropathic pain in a subject comprising administering an effective amount of a compound according to claim 10, or a pharmaceutically acceptable salt thereof.

* * * * *